US008299233B2

(12) United States Patent
Andre et al.

(10) Patent No.: US 8,299,233 B2
(45) Date of Patent: Oct. 30, 2012

(54) MOLECULAR IN VITRO DIAGNOSIS OF BREAST CANCER

(75) Inventors: Fabrice Andre, Sceaux (FR); Stefan Michiels, Paris (FR); Suzette Delaloge, Longjumeau (FR); Marc Spielmann, Cachan (FR); Philippe Dessen, Ivry sur Seine (FR); Philippe Vielh, Sceaux (FR)

(73) Assignees: Centre National de la Recherche Scientifique, Paris (FR); Institut Gustave Roussy, Villejuif (FR)

( * ) Notice: Subject to any disclaimer, the term of this patent is extended or adjusted under 35 U.S.C. 154(b) by 0 days.

(21) Appl. No.: 12/811,792

(22) PCT Filed: Jan. 5, 2009

(86) PCT No.: PCT/EP2009/050060
§ 371 (c)(1),
(2), (4) Date: Sep. 29, 2010

(87) PCT Pub. No.: WO2009/087139
PCT Pub. Date: Jul. 16, 2009

(65) Prior Publication Data
US 2011/0009286 A1 Jan. 13, 2011

(30) Foreign Application Priority Data
Jan. 4, 2008 (EP) .................................... 08100106

(51) Int. Cl.
C07H 21/04 (2006.01)
(52) U.S. Cl. ................... 536/24.31; 536/24.3; 536/23.1
(58) Field of Classification Search .................. None
See application file for complete search history.

(56) References Cited

U.S. PATENT DOCUMENTS

| 6,881,571 | B1 * | 4/2005 | Schweighoffer et al. | .. 435/287.2 |
| 2001/0053519 | A1 * | 12/2001 | Fodor et al. | ............. 435/6 |
| 2002/0048763 | A1 * | 4/2002 | Penn et al. | ............. 435/6 |
| 2003/0219741 | A1 | 11/2003 | Isogai et al. | |

FOREIGN PATENT DOCUMENTS

| WO | 01/57270 A | 8/2001 |
| WO | 03/106648 A | 12/2003 |
| WO | 2004/106495 A | 12/2004 |

OTHER PUBLICATIONS

GenBank Accession AC004505.1 GI:2996633 (http://www.ncbi.nlm.nih.gov/nucleotide/2996633?report=genbank&log$=nuclalign&blast_rank=12&RID=EYKP3F0H01N, Jun. 20, 1998).*
Affymetrix: "GeneChip exon array system for human, mouse, and rat", Affymetrix Data Sheet, 2006, XP002480421.
"Affymetrix GeneChip Human Genome U133 Array Set HG-U133A", GEO, Mar. 11, 2002, XP002355386.
Miao Lixia et al: "Alternative splicing of breast cancer associated gene BRCA1 from breast cancer cell line" Journal of Biochemistry and Molecular Biology, Jan. 1, 2007, pp. 15-21, vol. 40, No. 1, XP008091534.
Mandusic Vesna et al, "Expression of estrogen receptor beta wt isoform (ER beta 1) and ER beta Delta 5 splice variant mRNAs in sporadic breast cancer", Journal of Cancer Research and Clinical Oncology, Aug. 2007, pp. 571-579, vol. 133, No. 8, XP 002480405.
Span Paul N et al: "Do the survivin (BIRC5) splice variants modulate or add to the prognostic value of total survivin in breast cancer?", Clinical Chemistry, Sep. 2006, pp. 1693-1700, vol. 52, No. 9, XP002480406.
Agrawal Shirpa et al: Differential expression of PTEN and its splice variants in heritable and sporadic breast cancer, Proceedings of American Association for Cancer Research Annual Meeting, Apr. 2006, pp. 841, XP001536928.
Landi Stefano et al: "Interleukin-4 and interleukin-4 receptor polymorphisms and colorectal cancer risk", European Journal of Cancer, Mar. 2007, pp. 762-768, vol. 43, No. 4, XP002480876.
European Search Report in Corresponding Application No. EP 08 10 0106 Dated May 20, 2008.
International Search Report in Corresponding Application No. PCT/EP2009/050060 Dated May 4, 2009.

* cited by examiner

Primary Examiner — Steven Pohnert
(74) Attorney, Agent, or Firm — Young & Thompson

(57) ABSTRACT

The invention relates to the use of a multiplicity of polynucleotide probe sets, the multiplicity of polynucleotide probe sets consisting in a combination of pools of polynucleotide probe sets, each polynucleotide probe set containing at least one polynucleotide probe chosen among a library of nucleic acid sequences, the polynucleotide probes involved in the combination of pools of polynucleotide probe sets of the multiplicity of polynucleotide probe sets being such that each polynucleotide probe specifically hybridizes with one gene, and/or at least one of its variants when present, for determining the variation of expression at least 12 genes, and their variants when present, in order to diagnose the benign or malignant state of a breast tumor.

12 Claims, 7 Drawing Sheets

3A

3B

3C

3D

3E

3F

3G

MOLECULAR IN VITRO DIAGNOSIS OF BREAST CANCER

The present invention describes a molecular in vitro diagnosis of breast cancers. More particularly, the invention relates to the use of molecular probes for the diagnosis evaluation of breast tumors.

Breast Cancer is the most frequent cancer in women in western countries (40,000 new cases in France/year). Although several advances have been achieved in the last 10 years the mortality rates remain high (11,000 death/year in France). There is therefore a need for a new generation of advances in this disease. Two axes have allowed improvement of breast cancer survival rates: i. an earlier and more accurate diagnosis, ii. the development of adjuvant therapies.

Breast Cancer diagnosis is currently performed in a vast majority of cases by a preoperative core needle biopsy. This exam is currently considered as a level 1 recommendation in France (www.has-sante.fr). In selected centers that are experts in this field, a fine needle aspiration is used to perform breast cancer diagnosis. Overall, the preoperative diagnosis of breast cancer is currently allowed by microscopic assessment of samples obtained either fine needle aspiration (FNA) or core needle biopsy (CNB). Each of this approach presents some limitations that hamper the quality of care in patients who present a breast lesion. FNA is associated with an unacceptable rate of misdiagnosis. The rate of uncertain diagnosis is indeed around 30% (Oyama T, Koibuchi Y, McKee G. Core needle biopsy (CNB) as a diagnostic method for breast lesions: comparison with fine needle aspiration cytology (FNA). Breast Cancer. 2004; 11(4):339-42; Orell S R, Farshid G. False-positive reports in fine needle biopsy of breast lesions. Pathology. 2001 November; 33(4):428-36; Meunier M, Clough K. Fine needle aspiration cytology versus percutaneous biopsy of nonpalpable breast lesions. Eur J Radiol. 2002 April; 42(1):10-6). CNB exhibits better performance for diagnosis but is associated with some major limitations. First, since CNB is a complex procedure, the appointments are usually given several weeks after detection of breast lesions. This induces a delayed diagnosis and therefore treatment. With the increase of mass screening, this delay will probably increase over time. Second, the CNB is associated with clinical side effects. The rate of hematoma related to the procedure indeed range between 0.6 and 4% (Barreau B, Tastet S, Lakdja F, Henriques C, Valentin F, Labat M J, Dilhuydy M H. [Patients' information in percutaneous core breast biopsy] Bull Cancer. 2005 March; 92(3):257-65). In addition, CNB is associated is a more painful procedure as compared to FNA. Finally, CNB is an expensive procedure for a frequent disease (200 Euros/procedure). Overall, from these considerations rises the need for a diagnostic test performed on FNA samples that would be accurate, quick and cost-saving. This test could either substitute cytological exam of FNA sample or be performed in complement to this one. This test would allow an earlier, safer and cost-saving diagnosis procedure.

Regarding mass screening, mammogram is currently considered as the gold standard for mass screening. Nevertheless, this approach is limited by a high rate of false negative results, especially in young women and in aggressive tumors. In addition, mammogram is limited by the fact that a significant proportion of women do not perform the test. These considerations point out the need for a screening test that would be better or complementary to mammogram and that would be based on an easier procedure.

So, there is a need to provide test for the patients to diagnose and give a diagnosis of the status of the breast tumor detected.

Many methods based on the knowledge of the molecular mechanism of the breast tumor evolution have been extensively described. These methods describe in particular large-scale process for the determination of variation of expression of genes, or proteins, which can define a hallmark of the breast tumor evolution.

WO 2007/048978 describes methods and compositions for the detection of molecular markers in order to diagnose cancer. In particular, this document describes methods and compositions that can be used to detect the presence or evolution of a breast tumor in a patient.

However, this document discloses in particular micro-arrays for the evaluation of miss-regulated expressed genes, without interest for the expression of variants of genes.

WO 2004/065545 discloses a diagnostic and prognostic method of the breast cancer tumor status, wherein said method consists to compare the expression profile of at least 5 genes of a determined list of 70 genes to the expression profile of said at least 5 genes of a determined list of 70 genes of a control tumor.

However, this document never teaches that the disclosed method can detect splicing variant of the mentioned at least 5 genes chosen among the list of 70 genes to determine the breast cancer status of a tumor.

The setting-up of new arrays to analyse the large-scale expression of exons allows a highly accurate identification of differential molecular events between two conditions. This approach not only analyzes genes differentially expressed (as it is the case with conventional DNA array) but also the differential splicing events. Applied to breast cancer, this large scale analysis could identify differential expression of gene sequences between cancer and benign lesions. Based on these data, it would be possible to set-up molecular assays that could allow a molecular diagnosis of breast cancer based on FNA samples, that would allow a quick, accurate and cost-saving diagnosis. In addition, this approach could allow to set-up a molecular test for breast cancer screening based on blood samples, ductal lavage or breast sampling by FNA.

One aim of the invention is to provide a molecular diagnosis to determine the status of a breast tumor.

Another aim of the invention provides micro-arrays to determine the benign or malignant status of a breast tumor.

Another aim of the invention provides a method using the micro-array to determine the benign or malignant status of a breast tumor.

The invention also provides a kit for the breast cancer diagnosis.

The invention discloses the use of a multiplicity of polynucleotide probe sets, said multiplicity of polynucleotide probe sets consisting in a combination of pools of polynucleotide probe sets, each polynucleotide probe set containing at least one polynucleotide probe chosen among a library of nucleic acid sequences, each nucleic acid sequence specifically hybridizing with a gene, and/or at least one of its variants when present, said gene being chosen among the group of genes consisting in SEQ ID NO 5419 to SEQ ID NO 5693, each given gene, when it presents NO variant, comprising at least one target region, the nucleic acid sequence of which is chosen among SEQ ID NO 2939 TO SEQ ID NO 4578, said target region characterizing said gene, each given gene, when it presents at least one variant, comprising at least two target regions such that:

at least one of the respective nucleic acid sequences of said target region chosen among SEQ ID NO 2939 to SEQ ID NO 4578 is present in a given variant of said gene, at least one of the respective nucleic acid sequences of said target region chosen among SEQ ID NO 2939 to SEQ ID NO 4578 is either absent in a given variant or is present in a configuration that differs from the one of said gene, said two target regions characterizing said gene, each variant of a given gene presenting at least one target region, said target region being such that its respective nucleic acid sequence is chosen among SEQ ID NO 2939 to SEQ ID NO 4578, each variant is characterized by:
  either the combination of the presence of at least one target region also present in the gene, the respective nucleic acid sequence of which being chosen among SEQ ID NO 2939 to SEQ ID NO 4578, and the absence of at least one target region present in the gene the respective nucleic acid sequence of which being chosen among SEQ ID NO 2939 to SEQ ID NO 4578,
  or the presence of a target region, the respective nucleic acid sequence of which being chosen among SEQ ID NO 2939 to SEQ ID NO 4578, said target region presenting a configuration that does not naturally exist in the gene, each polynucleotide probe of a polynucleotide probe set hybridizes with a specific nucleic acid sequence contained in a given target region of the target regions characterizing a given gene, and/or at least one of its variants when present, each given gene, and its variants when present, is specifically recognized by the polynucleotide probes of at least a given polynucleotide probe set, each polynucleotide probe of a given pool of polynucleotide probe set being such that it hybridizes with a given gene, and/or at least one of its variants when present, and cannot hybridize with any other gene different from said given gene, and cannot hybridize with any other variants of a gene different from said given gene, the polynucleotide probes involved in the combination of pools of polynucleotide probe sets of said multiplicity of polynucleotide probe sets being such that each polynucleotide probe specifically hybridizes with one gene, and/or at least one of its variants when present, of a sub-group comprising 12 genes among the genes of the group consisting in SEQ ID NO 5419 to SEQ ID NO 5693, for determining the variation of expression a gene, and its variants when present, of said sub-group in order to diagnose the benign or malignant state of a breast tumor.

The invention discloses the use of a multiplicity of polynucleotide probe sets, each polynucleotide probe set containing at least one polynucleotide probe chosen among a library of nucleic acid sequences, said library comprising or consisting of at least one copy each of the nucleic acids consisting of SEQ ID NO 1 to SEQ ID NO 2938, said polynucleotide probes being such that the nucleic acid sequence of each polynucleotide probe specifically hybridizes with the nucleotidic sequence of one target region of one gene, and/or of at least one of its variants when present, for determining the variation of the expression of
  at least 12 determined genes belonging to a group of determined genes represented by the nucleotidic sequences SEQ ID NO: 5419 to SEQ ID NO: 5693 and
  at least one variant of said genes at least 12 determined genes, when they exist,
  said 12 determined genes being represented by the following nucleotidic sequences:
  SEQ ID NOs 5421; 5423; 5432; 5434; 5486; 5491; 5525; 5552; 5599; 5652; 5654 and 5683,
in order to diagnose in vitro or ex vivo the benign or malignant state of a breast tumor,
  wherein
  a) each given gene,
    a. when it presents no variant, comprises at least one target region, said target region characterizing said gene,
    b. when it presents one variant, comprises at least one target region, said target region characterizing said gene and its variant, and preferably said variant being characterized by the fact that its nucleic acid sequence is shorter than the nucleic acid sequence of said gene,
    c. when it presents at least two variants, comprises at least two target regions, said two target regions characterizing said gene, such that:
      i. at least one of the respective polynucleotidic sequences of said target region is present in a given variant of said gene, and
      ii. at least one of the respective polynucleotidic sequences of said target region is either
        absent in a given variant, or
        present in a given variant in a configuration that differs from the one of said gene,
        preferably said variant being characterized such that its nucleic acid sequence is shorter than the nucleic acid of said gene,
  b) each variant of a given gene presents at least one target region,
  and
    if said variant is the unique variant of a gene, said variant has the same target as said gene, and
    if said variant is one of the variants of a gene that has at least two variants, each variant of said gene is characterized by either:
      a. the combination of the presence of at least one target region also present in the gene, and the absence of at least one target region present in the gene, or
      b. the combination of the presence of at least one target region also present in the gene, and the presence of a target region, said target region presenting a configuration that does not naturally exist in the gene,
  c) the nucleotidic sequence of each given gene, and its variants when present, is specifically recognized by the nucleic acid sequences of polynucleotide probes contained in at least one given polynucleotide probe set,
  d) the nucleic acid sequence of each polynucleotide probe of a polynucleotide probe set hybridizes with a specific polynucleotidic sequence contained in a given target region of the target regions which characterize a given gene, and/or at least one of its variants when present,
  e) the nucleic acid sequence of each polynucleotide probe of a given pool of polynucleotide probe set being such that
    a. it hybridizes with the nucleotidic sequence of a given gene, and/or of at least one of its variants when present, and b. cannot hybridize with
   i. the nucleotidic sequence of any other gene different from said given gene, and
   ii. the nucleotidic sequence of any other variants of a gene different from said given gene,
   with the proviso that said gene, and its variants when present, is not KRT17, LOC440421, KRT6C and KRT6A, said genes being respectively represented by SEQ ID NO 5431; 5689; 5651 and 5682.

In the case of KRT17, LOC440421, KRT6C and KRT6A genes, said genes being respectively represented by SEQ ID NO 5431; 5689; 5651 and 5682, the above mentioned definition of the nucleic acid sequence of each polynucleotide probe of a given pool of polynucleotide probe set applies with the exception that:

1—polynucleotide probes of a given pool of polynucleotide probe set recognizing KRT17 can hybridize with LOC440421 and at least one of its variant when present, 2—polynucleotide probes of a given pool of polynucleotide probe set recognizing LOC440421 can hybridize with KRT17 and at least one of its variant when present, 3—polynucleotide probes of a given pool of polynucleotide probe set recognizing KRT6C can hybridize with KRT6A and at least one of its variant when present, and 4—polynucleotide probes of a given pool of polynucleotide probe set recognizing KRT6A can hybridize with KRT6C and at least one of its variant when present.

The invention is based on the unexpected observation made by the inventors that the variation of expression of some genes, and their variants when they exist, may characterize the evolution of a diagnosed breast tumor. More particularly, the variants of the invention are the products of a differential splicing, or alternative splicing.

The inventors have demonstrated that the variation of expression of at least 12 determined genes of a group of 275 determined genes, and of variants of said at least 12 determined genes when they exist, hallmarks the benign or malignant status of a breast tumor.

Then, the invention describes the use of polynucleotide probes to characterize a benign versus malignant hallmark of a breast tumor, each polynucleotide probe hybridizing specifically with one gene, and at least one of its splicing variants when they exist, said gene splicing variant being able to be recognized by at least one polynucleotide probe.

In genetics, splicing is a modification of genetic information after transcription, in which introns of precursor messenger RNA (pre-mRNA) are removed and exons of precursor messenger RNA are joined. The splicing prepares the pre-mRNA to produce the mature messenger RNA (mRNA), which then undergoes translation as part of the protein synthesis to produce proteins.

Alternative splicing, in the sense of the invention, is the RNA splicing variation mechanism, in which the exons of the pre-mRNA are separated and reconnected so as to produce alternative ribonucleotide arrangements. In this way, alternative splicing uses genetic expression to facilitate the synthesis of a greater variety of transcripts.

When the pre-mRNA has been transcribed from the DNA, it includes several introns and exons. The exons which are retained in the mRNA are determined during the splicing process. The use of alternative splicing factors leads to a modification of the definition of a "gene" and imposes the variant notion.

For example a pre-mRNA containing 3 exons, if it is considered that variants must contain at least one exon of the gene and at least one exon missing of said gene, can hypothetically produce 6 different variants, as the result of alternative splicing.

In the invention, a gene is defined by the fact that it comprises the deoxyribonucleic acid sequence corresponding to the mRNA which results of the transcription of the DNA sequence, and after the splicing process. Then, the gene is characterized in that it comprises all the exons present in the genomic sequence of said gene.

All the 275 genes considered in the invention present a nucleic acid sequence chosen among the group consisting in SEQ ID NO 5419 to SEQ ID NO 5693.

In the invention, there are two alternatives for a gene:
said gene is not submitted to alternative splicing, and presents no variants, or
said gene presents at least one variant.

In the case of a gene having no variant, this gene can is characterized in the invention by the presence of a target region. This target region corresponds to a nucleic acid sequence contained in the total nucleic acid sequence of the said gene.

In the case of a gene having one variant, this gene is defined by a target region, and its variant is defined by the same target region. The difference between the gene and its variant is preferably determined by the fact that the nucleic acid sequence of said gene is longer than the nucleic acid sequence of its variant.

This recognizing by one target region allows a redundancy of the representativity of said gene. Indeed, the target region contained in a gene having one variant is thus recognized at least twice, i.e. when the gene is present and when the variant of this gene is present. This redundancy enhances the specificity of detection of the gene expression variation.

In the case of a gene having at least two variants, this gene is defined by at least two regions, these two regions characterizing the gene. These regions are therefore present in gene. These regions, also called target regions correspond to nucleic acid sequences contained in the total nucleic acid sequence of said gene. Moreover, these target regions of said gene are located at a different position in the sequence of said gene.

The targets regions that are involved in the invention present a nucleic acid sequence chosen among the group consisting in SEQ ID NO 2939 to SEQ ID NO 4578.

According to the invention, a "variant" is defined as a polynucleotide molecule that differs from the reference polynucleotide molecule (the gene), but retains essential properties. The gene and its variants share similar polynucleotide sequences with, for example, 70% of nucleic acids identity, preferably 80% of nucleic acids identity, preferably 90% of nucleic acids identity and more preferably 95% of nucleic acids identity. The variants of the invention can be also considered as isoforms.

To be considered as a variant of a given gene, a polynucleotide sequence must contain at least one nucleotide sequence present in the said gene, this sequence corresponding to the target sequence defined above.

If a variant is the unique variant of a gene, this variant has the same target region as its gene, preferably with a nucleic acid sequence with a size that is shorter than the size of the nucleic acid sequence of said gene. Since said variant corresponds to a splicing product of a gene, it generally has one or more exons lacking that are present in said gene. Nevertheless, it is possible, in some rare examples, that a variant of a gene has a nucleic acid sequence with a size which is higher than the size of the nucleic acid sequence of said gene.

If a variant is a variant of a gene that has at least two variants, said variant has at least one difference in the presence of a nucleic acid sequence with respect to the given gene nucleic acid sequence. The specific combination of the presence of at least one target sequence and the absence of at least one target sequence defines the specific characteristic of a given variant. Therefore, each variant is defined by a "bar code" corresponding to the diversity of the presence and absence of all the target sequences present in a gene.

For example, if a gene contains 3 exons, all the nucleic acid sequences consisting in least one exon of said gene, and missing at least one of the other 2 exons of the said given gene, are considered as variants of said given gene.

FIG. 1A illustrates this example.

In the invention, a variant of a gene is characterized in that it comprises at least on target region. These target regions corresponds to polynucleotidic sequences chosen among the group consisting in SEQ ID NO 2939 to SEQ ID NO 4578.

So, a given variant of a gene can be characterized with respect to the target sequence by the fact it contains at least a target region, present in the gene corresponding to said variant, and must is devoid of at least one target region, present in the gene corresponding to said variant, only in the case of a gene that has at least two variants.

As defined above, a variant of a gene having at least two variants is then characterized by a bar code which corresponds to a combination of the presence of at least one target region of the gene, corresponding to the variant, and the absence of at least one target region of the gene corresponding to the variant.

A variant can also be alternatively defined. This other definition is supported by the feature of the invention: the alternative splicing.

When a gene, constituted by at least 3 exons, is differentially spliced, in the corresponding variants, some exons are fused to exons which are not naturally fused in the sequence of the gene. For example, in a gene constituted by 3 exons E1, E2 and E3, one variant can be constituted by the fusion of E1 and E3. In the gene, the natural configuration corresponds to the sequence E1-E2-E3. Then the configuration observed in the variant, E1-E3, is considered as a non natural configuration.

In this case, variant presents a sequence that does not exist in the natural configuration of the gene. It generally corresponds to a junction of to distant exons, separated by at least one other exon. If the target region characterizing the variant corresponds to the junction between two exons, naturally distant in the normal configuration in the gene, said target region characterizes specifically said variant. This example is illustrated by FIG. 1B.

Example of genes having, or not, at least one variant are represented in FIG. 3.

According to the invention, polynucleotide probes are used to detect the variation of expression of a gene, and/or its variants when they exist, to determine the status of a breast tumor.

Artificially, polynucleotide probes are grouped to form a polynucleotide probe set. The term "polynucleotide probe set" used in the invention defines a group of polynucleotide probes as described above. A given set of polynucleotide probe contains from one polynucleotide probe to several polynucleotide probes. Preferably, the polynucleotide probe set of the invention contains one polynucleotide probe to three or four polynucleotide probes. Thereby, polynucleotide probes regrouped in a polynucleotide probe set of the invention are able to hybridize to the same target region.

The polynucleotides probes are also brought together to form a "pool of polynucleotide probe sets". The polynucleotides probes contained in the polynucleotide probe sets of a pool are able to specifically hybridize with nucleic acid sequences of a gene, and/or variants of said gene when they exist.

Alternatively, the polynucleotide probes contained in the polynucleotide probe sets of a pool are able to specifically hybridize neither with nucleic acid sequences of a different gene, nor with nucleic acid sequences of variants of said different gene, when they exist.

However, in few cases, the above definition should be modulated. In the case of genes KRT17 (SEQ ID NO 5431) and LOC440421 (SEQ ID NO 5689), these genes are two different genes, but share a high similarity/identity in their nucleic acid sequence. Thus, these two genes present some gene regions in their nucleic acid sequence which can be identical. If a target region is present in said gene region, therefore, the polynucleotide probe that recognize the target region contained in said gene region will be able to recognize the two genes.

A similar example applies with genes KRT6A (SEQ ID NO 5682) and KRT6C (SEQ ID NO 5651).

Then, polynucleotide probes of a pool of polynucleotide probe sets are able to characterize a gene and its variants. Moreover, a given gene, and its variants when they exist, can be detected only by the polynucleotide probes of the same pool of polynucleotide probe sets.

According to the invention, each gene, and its variants when present, can be detected by all the polynucleotide probes of a probe set. Moreover, each gene can be recognized by all the polynucleotide probes of at least one polynucleotide probe set, i.e. each gene and its variants can be defined by at least one polynucleotide probe set.

A variant can be detected by two polynucleotide probes belonging to two different polynucleotide probe sets, provided that they belong to the same pool of polynucleotide probe set.

The multiplicity, pool, polynucleotide probe set, and polynucleotide probe interconnection are represented in FIG. 2.

Terms "library comprising or consisting of at least one copy each of the nucleic acids consisting of SEQ ID NO 1 to SEQ ID NO 2938" means that the library can contain one, or two, or three, or four, or five or six or seven or eight, or nine or ten copies of each polynucleotide probes represented by the nucleic acids consisting of SEQ ID NO 1 to SEQ ID NO 2938. Thus, the minimal library contains 2938 polynucleotides probes, and the maximal library contains 29380 polynucleotides probes. Preferably the preferred library of the invention contains 4582 polynucleotides probes.

In the invention, a "benign breast tumor" is any non-cancerous breast abnormality. Some (not all) benign conditions can signal an increased risk for breast cancer. The most common benign breast conditions include fibrocystic breast condition, benign breast tumors, and breast inflammation. Depending on the type of benign breast condition and the patient's medical situation, treatment may or may not be necessary.

In the invention, a "malignant breast tumor refers" to a malignant tumor that has developed from cells in the breast. Malignant tumors penetrate and destroy healthy body tissues. A group of cells within a tumor may also break away and spread to other parts of the body. Cells that spread from one region of the body into another are called metastases.

The term "base" is used to define the components of the DNA or RNA, i.e. deoxyribonucleotides and ribonucleotides respectively.

Terms "nucleic acids", "nucleic acid molecule", "nucleic acid sequence", "polynucleotidic sequence", and "polynucleotide" are uniformly used to define a chain of bases that characterizing a DNA or an RNA molecule.

In the invention, "polynucleotide probe" represent a fragment of nucleic acid molecule, corresponding to DNA or RNA, with a variable length. The length of the polynucleotide probe is commonly comprised between 15 bases to 1000 bases, and preferably between 20 bases to 500 bases. Advantageously, the polynucleotide probes defined in the invention comprise from 20 bases to 30 bases. These polynucleotide probes are defined by their nucleic acid sequence.

In the invention, terms "multiplicity" and "combination" are used to define a group of polynucleotide probes sets and polynucleotide probes, respectively. Theses groups correspond to an ensemble of probes, or sets of probes, characterized in that they contains similar information.

According to the invention, each nucleic acid sequence corresponding to nucleic acid probe "specifically hybridizes with" a target region of the said gene. These terms mean that each polynucleotide probe is able to hybridize with a gene, and/or its variants when they exist, defined above. The polynucleotide probe thereby hybridizes to single-stranded nucleic acid molecule (gene and/or its variants, which are DNA or RNA) whose nucleic acid sequence allows base pairing due to complementarity between the nucleic acid sequence of the probe and the nucleic acid sequence of the gene and/or variants of said gene. The base pairing (A-T;G-C) is a concept well known by the skilled man in the art.

Each polynucleotide probe is able to hybridize with one gene and/or at least one variant of said gene, in a specific region of said variant called target region.

Said target region is then defined as the region allowing the base pairing between polynucleotide probe and a gene and/or its variants, when they exist.

Thereby, each polynucleotide probe is able to define a gene and/or at least one variant of said gene, when they exist.

According to the invention, each polynucleotide probe specifically hybridizes with a specific nucleic acid sequence contained in the target region. Moreover, each polynucleotide probes can recognizes a sequence overlapping partially with the sequence recognized by another probe of the same polynucleotide probe set.

To sum up, in the invention each gene, or reference transcript, can be expressed differentially in the form of variants. These variants differ from each other by the presence or absence or the variation of a sequence of a specific region: the target region. This region is liable to be recognized by one to three polynucleotide probes, said polynucleotide probes hybridizing with the same target region being brought together in a polynucleotide probe set.

Then, the use of the multiplicity of polynucleotide probe sets of the invention allows to detect the variation of expression of at least 12 determined genes consisting in SEQ ID NO 5421, SEQ ID NO 5423, SEQ ID NO 5432, SEQ ID NO 5434, SEQ ID NO 5486, SEQ ID NO 5491, SEQ ID NO 5525, SEQ ID NO 5552, SEQ ID NO 5599, SEQ ID NO 5652, SEQ ID NO 5654 and SEQ ID NO 5683, and their variants when they exist, of the group of determined genes constituted by genes of the group constituted by SEQ ID NO 5419 to SEQ ID NO 5693, and a skill man in the art can determine if the breast tumor is malignant or benign.

Thereby, if the expression of a given gene and/or at least one of its variants belonging to the group of 12 determined genes corresponds to a "profile" similar to that of a benign tumor, the tumor of the patient will be considered as evolving to a benign status. In contrast, the expression of a gene and/or at least one of its variant belonging to the group of 12 genes corresponds to that of a "profile" similar to a malignant tumor, it will be considered that the tumor is a malignant tumor.

In one embodiment, the invention discloses the use of a multiplicity of polynucleotide probe sets, wherein the multiplicity of polynucleotide probe sets consisting in a combination of pools of polynucleotide probe sets chosen among 1640 probe sets of polynucleotides, each polynucleotide probe set containing at least one polynucleotide probe chosen among a library of nucleic acid sequences consisting in SEQ ID NO 1 to SEQ ID NO 2938, each nucleic acid sequence hybridizing with a gene, and/or at least one of its variants when present, said gene being chosen among the group of genes consisting in SEQ ID NO 5419 to SEQ ID NO 5693, each given gene, when it presents NO variant, comprising at least one target region, the nucleic acid sequence of which is chosen among SEQ ID NO 2939 TO SEQ ID NO 4578, said target region characterizing said gene, each given gene, when it presents at least one variant, comprising at least two target regions such that:
at least one of the respective nucleic acid sequences of said target region chosen among SEQ ID NO 2939 to SEQ ID NO 4578 is present in a given variant of said gene,
at least one of the respective nucleic acid sequences of said target region chosen among SEQ ID NO 2939 to SEQ ID NO 4578 is either absent in a given variant or is present in a configuration that differs from the one of said gene,
said two target regions characterizing said gene, each variant of a given gene presenting at least one target region, said target region being such that its respective nucleic acid sequence is chosen among SEQ ID NO 2939 to SEQ ID NO 4578, each variant is characterized by:
either the combination of the presence of at least one target region also present in the gene, the respective nucleic acid sequence of which being chosen among SEQ ID NO 2939 to SEQ ID NO 4578, and the absence of at least one target region present in the gene the respective nucleic acid sequence of which being chosen among SEQ ID NO 2939 to SEQ ID NO 4578,
or the presence of a target region, the respective nucleic acid sequence of which being chosen among SEQ ID NO 2939 to SEQ ID NO 4578, said target region presenting a configuration that does not naturally exist in the gene, each polynucleotide probe of a polynucleotide probe set hybridizes with a specific nucleic acid sequence contained in a given target region of the target regions which characterize a given gene, and/or at least one of its variants when present, each given gene, and its variants when present, is specifically recognized by at least a given polynucleotide probe set, each polynucleotide probe of a given pool of polynucleotide probe set being such that it hybridizes with a given gene, and/or at least one of its variants when present, and cannot hybridize with any other gene different from said given gene, and cannot hybridize with any other variants of a gene different from said given gene, the polynucleotide probes involved in the combination of pools of polynucleotide probe sets of said multiplicity of polynucleotide probe sets being such that each polynucleotide probe specifically hybridizes with one gene, and/or at least one of its variants when present, of a sub-group comprising 12 genes among the genes of the group consisting in SEQ ID NO 5419 to SEQ ID NO 5693, for determining the variation of expression a gene, and its variants when present, of said sub-group in order to diagnose the benign or malignant state of a breast tumor.

In one preferred embodiment, the invention discloses the use of a multiplicity of polynucleotide probe sets defined above, for determining the variation of the expression of at least 20 determined genes of a group of genes represented by the nucleotidic sequences SEQ ID NO: 5419 to SEQ ID NO: 5693, said 20 determined genes being represented by the following nucleotidic sequences:
SEQ ID Nos 5421; 5423; 5432; 5434; 5457; 5486; 5491; 5513; 5516; 5525; 5532; 5552; 5599; 5616; 5624; 5643; 5652; 5654; 5673 and 5683.

The invention resides in the unexpected observation that the variation of expression of a group of at least 20 determined genes chosen among 275 determined genes is sufficient to determine the malignant or the benign status of a breast tumor.

In another preferred embodiment the invention discloses the use of a multiplicity of polynucleotide probe sets as above defined, for determining the variation of the expression of at least 35 determined genes of a group of determined genes represented by the nucleotidic sequences SEQ ID NO: 5419 to SEQ ID NO: 5693 said 35 determined genes being represented by the following nucleotidic sequences: SEQ ID Nos 5421; 5423; 5431; 5432; 5434; 5440; 5457; 5462; 5470; 5486; 5491; 5505; 5513; 5516; 5525; 5532; 5546; 5552; 5594; 5599; 5601; 5603; 5616; 5618; 5624; 5627; 5630; 5643; 5645; 5652; 5654; 5660; 5669; 5673 and 5683.

The invention also resides in the unexpected observation that the variation of expression of a group of at least 35 determined genes chosen among 275 determined genes is sufficient to determine the malignant or the benign status of a breast tumor.

In another preferred embodiment the invention discloses the use of a multiplicity of polynucleotide probe sets previously defined, for determining the variation of the expression of at least 43 determined genes of a group of determined genes represented by the nucleotidic sequences SEQ ID NO: 5419 to SEQ ID NO: 5693, said 43 determined genes being represented by the following nucleotidic sequences:
SEQ ID Nos 5421; 5423; 5431; 5432; 5434; 5440; 5455; 5457; 5462; 5470; 5475; 5486; 5491; 5499; 5505; 5513; 5516; 5520; 5525; 5532; 5546; 5549; 5552; 5594; 5599; 5601; 5603; 5616; 5618; 5623; 5624; 5627; 5630; 5643; 5645; 5651; 5652; 5654; 5660; 5669; 5673; 5683 and 5686.

The invention also resides in the unexpected observation that the variation of expression of a group of at least 43 determined genes chosen among 275 determined genes is sufficient to determine the malignant or the benign status of a breast tumor.

In another preferred embodiment the invention discloses the use of a multiplicity of polynucleotide probe sets such as defined above, for determining the variation of the expression of at least 206 determined genes of a group of determined genes represented by the nucleotidic sequences SEQ ID NO: 5419 to SEQ ID NO: 5693 said 206 determined genes being represented by the following nucleotidic sequences: SEQ ID Nos 5420; 5421; 5422; 5423; 5425; 5426; 5427; 5428; 5429; 5430; 5431; 5432; 5434; 5435; 5436; 5437; 5438; 5439; 5440; 5441; 5442; 5443; 5444; 5445; 5446; 5447; 5449; 5450; 5451; 5452; 5453; 5454; 5455; 5456; 5457; 5459; 5460; 5461; 5462; 5463; 5465; 5467; 5468; 5470; 5473; 5475; 5476; 5479; 5480; 5482; 5484; 5485; 5486; 5487; 5488; 5489; 5490; 5491; 5492; 5493; 5495; 5496; 5497; 5498; 5499; 5502; 5503; 5505; 5506; 5507; 5508; 5509; 5511; 5512; 5513; 5515; 5516; 5517; 5518; 5519; 5520; 5523; 5524; 5525; 5526; 5528; 5529; 5530; 5531; 5532; 5533; 5534; 5536; 5538; 5539; 5540; 5543; 5544; 5545; 5546; 5547; 5549; 5550; 5552; 5553; 5554; 5556; 5558; 5559; 5560; 5562; 5563; 5564; 5565; 5566; 5567; 5568; 5569; 5570; 5571; 5573; 5574; 5575; 5576; 5577; 5578; 5581; 5582; 5585; 5587; 5588; 5590; 5591; 5593; 5594; 5595; 5597; 5598; 5599; 5600; 5601; 5602; 5603; 5604; 5605; 5606; 5608; 5609; 5610; 5611; 5612; 5613; 5615; 5616; 5617; 5618; 5622; 5623; 5624; 5625; 5627; 5629; 5630; 5631; 5632; 5633; 5634; 5635; 5637; 5638; 5639; 5640; 5641; 5642; 5643; 5644; 5645; 5647; 5648; 5649; 5651; 5652; 5653; 5654; 5656; 5657; 5658; 5660; 5661; 5665; 5667; 5669; 5672; 5673; 5675; 5676; 5677; 5678; 5680; 5681; 5683; 5684; 5686; 5687; 5689 and 5692.

The invention also resides in the unexpected observation that the variation of expression of a group of at least 206 determined genes chosen among 275 determined genes is sufficient to determine the malignant or the benign status of a breast tumor, and provide the best results.

In another preferred embodiment the invention discloses the use of a multiplicity of polynucleotide probe sets such as above defined, for determining the variation of the expression of 275 determined genes represented by the nucleotidic sequences SEQ ID NO: 5419 to SEQ ID NO: 5693.

The invention also resides in the unexpected observation that the variation of expression of 275 determined genes is sufficient to determine the malignant or the benign status of a breast tumor.

Then, in an advantageous embodiment, the invention describes the use of a multiplicity of polynucleotide probe sets that allow the detection of variation of expression 12 genes, and their variants when they exist, said variation defining the benign or malignant hallmark of the breast tumor.

More particularly, the 12 genes, and their variants when they exist, are represented by their nucleic acid sequences consisting in SEQ ID NO 5421, SEQ ID NO 5423, SEQ ID NO 5432, SEQ ID NO 5434, SEQ ID NO 5486, SEQ ID NO 5491, SEQ ID NO 5525, SEQ ID NO 5552, SEQ ID NO 5599, SEQ ID NO 5652, SEQ ID NO 5654 and SEQ ID NO 5683 and are specifically recognized by their target sequences.

In one preferred embodiment, the invention relates to the use of a multiplicity of polynucleotide probe sets for determining the variation the gene expression as defined above, and of at least one variant of said genes when present, said variant being represented by the nucleic acid sequences SEQ ID NO 4579 to SEQ ID NO 5418 and SEQ ID NO 5694, the correspondence between each variant and its corresponding gene being represented in Table 1A-E and in Table 6.

Thus, according to the invention the inventors have demonstrated that the determination of the variation of expression of at least 12 genes chosen among a group of 275 genes, and of at least one variant of each at least 12 genes give a good information about the benign or malignant status of a breast tumor, without important false positives.

Also, others aspects of the invention demonstrate that the study of the variation of expression of:
at least 20 determined genes, or
at least 35 determined genes, or
at least 43 determined genes or
at least 206 determined genes
of a group of 275 determined genes, and the expression of at least one variant of said at least 20 determined genes, or
of said at least 35 determined genes, or
of said at least 43 determined genes, or
of said at least 206 determined genes
allows to the pathologist to clearly and without ambiguity determine if a breast tumor is, or will be, benign or malignant.

In one particular embodiment, the variation of expression of all the 275 determined genes and at least one of their variant allows the diagnostic.

In another particular embodiment, the invention relates to the use as defined above, for the determination of the variation of expression of at least 12 determined genes of the group of 275 determined genes represented by SEQ ID NO 5419 to SEQ ID NO 5693, and of at least one of the variants of said at least 12 determined genes, wherein the correspondence between genes and their variants is indicated in the following table 1A.

Table 1A represents the correspondences between the group of 12 determined genes and their corresponding variants.

| Gene Name | Gene SEQ ID | Variants SEQ ID |
| --- | --- | --- |
| AK5 | SEQ ID NO 5654 | SEQ ID NO 4620 |
| COL17A1 | SEQ ID NO 5683 | SEQ ID NO 4739; SEQ ID NO 4784; SEQ ID NO 5242; SEQ ID NO 5384 |
| DMD | SEQ ID NO 5421 | SEQ ID NO 4664; SEQ ID NO 4860; SEQ ID NO 5058; SEQ ID NO 5095; SEQ ID NO 5150; SEQ ID NO 5381; SEQ ID NO 5410; |
| KIT | SEQ ID NO 5423 | SEQ ID NO 5107 |
| KRT14 | SEQ ID NO 5434 | SEQ ID NO 4819; SEQ ID NO 4825; SEQ ID NO 4845; SEQ ID NO 4877; SEQ ID NO 4891; SEQ ID NO 4969 |
| KRT16 | SEQ ID NO 5525 | SEQ ID NO 4826; SEQ ID NO 4881 |
| KRT5 | SEQ ID NO 5432 | SEQ ID NO 5279 |
| MYH11 | SEQ ID NO 5599 | SEQ ID NO 4697; SEQ ID NO 4870; SEQ ID NO 5361; SEQ ID NO 5365 |
| NRG1 | SEQ ID NO 5552 | SEQ ID NO 5084 |
| PTN | SEQ ID NO 5486 | SEQ ID NO 4666 |
| SFRP1 | SEQ ID NO 5491 | SEQ ID NO 5161 |
| TSHZ2 | SEQ ID NO 5652 | SEQ ID NO 4962 |

In another particular embodiment, the invention relates to the use as defined above, for the determination of the variation of expression of at least 20 determined genes of the group of 275 genes represented by SEQ ID NO 5419 to SEQ ID NO 5693, and of at least one of the variants of said at least 20 determined genes, wherein the correspondence between genes and their variants is indicated in the following table 1B.

Table 1B represents the correspondences between the group of 20 determined genes and their corresponding variants.

| Gene Name | Gene SEQ ID | Variants SEQ ID |
| --- | --- | --- |
| AK5 | SEQ ID NO 5654 | SEQ ID NO 5224 |
| C2orf40 | SEQ ID NO 5616 | SEQ ID NO 4832 |
| C9orf61 | SEQ ID NO 5516 | SEQ ID NO 4661 |
| CNN1 | SEQ ID NO 5457 | SEQ ID NO 5181; SEQ ID NO 4666 |
| COL17A1 | SEQ ID NO 5683 | SEQ ID NO 4739; SEQ ID NO 4784; SEQ ID NO 5242; SEQ ID NO 5384 |
| DMD | SEQ ID NO 5421 | SEQ ID NO 4664; SEQ ID NO 4860; SEQ ID NO 4908; SEQ ID NO 5058; SEQ ID NO 5095; SEQ ID NO 5150; SEQ ID NO 5381; SEQ ID NO 5410; SEQ ID NO 5107 |
| DMN | SEQ ID NO 5643 | SEQ ID NO 4610; SEQ ID NO 5120 |
| EDN3 | SEQ ID NO 5673 | SEQ ID NO 5405 |
| IL33 | SEQ ID NO 5624 | SEQ ID NO 4927 |
| KIT | SEQ ID NO 5423 | SEQ ID NO 5177; SEQ ID NO 4748; SEQ ID NO 4817; SEQ ID NO 4821; SEQ ID NO 5152 |
| KRT14 | SEQ ID NO 5434 | SEQ ID NO 4969 |
| KRT16 | SEQ ID NO 5525 | SEQ ID NO 4826; SEQ ID NO 4881 |
| KRT5 | SEQ ID NO 5432 | SEQ ID NO 5279; SEQ ID NO 4740; SEQ ID NO 4819; SEQ ID NO 4825; SEQ ID NO 4845; SEQ ID NO 4877; SEQ ID NO 4878; SEQ ID NO 4891 |
| MYH11 | SEQ ID NO 5599 | SEQ ID NO 4697; SEQ ID NO 4870; SEQ ID NO 4972; SEQ ID NO 5103; SEQ ID NO 5323; SEQ ID NO 5361; SEQ ID NO 5365 |
| NRG1 | SEQ ID NO 5552 | SEQ ID NO 5084; SEQ ID NO 5413 |
| NTRK2 | SEQ ID NO 5532 | SEQ ID NO 5121 |
| PIK3C2G | SEQ ID NO 5513 | SEQ ID NO 5109 |
| PTN | SEQ ID NO 5486 | SEQ ID NO 5317; SEQ ID NO 4909 |
| SFRP1 | SEQ ID NO 5491 | SEQ ID NO 5161 |
| TSHZ2 | SEQ ID NO 5652 | SEQ ID NO 4962; SEQ ID NO 4620; SEQ ID NO 4694; SEQ ID NO 4786; SEQ ID NO 4794 |

In another preferred embodiment, the invention relates to the use as defined above, for the determination of the variation of expression of at least 35 determined genes of the group of 275 determined genes represented by SEQ ID NO 5419 to SEQ ID NO 5693, and of at least one of the variants of said at least 35 determined genes, wherein the correspondence between genes and their variants is indicated in the following table 1C.

Table 1C represents the correspondences between the group of 35 determined genes and their corresponding variants.

| Gene Name | Gene SEQ ID | Variants SEQ ID |
| --- | --- | --- |
| ACTA2 | SEQ ID NO 5462 | — |
| AK5 | SEQ ID NO 5654 | SEQ ID NO 4586; SEQ ID NO 4620; SEQ ID NO 4658; SEQ ID NO 4694; SEQ ID NO 4786; SEQ ID NO 4794; SEQ ID NO 4856; SEQ ID NO 5078; SEQ ID NO 5224; SEQ ID NO 5391 |
| C2orf40 | SEQ ID NO 5616 | SEQ ID NO 4832 |
| C9orf61 | SEQ ID NO 5516 | SEQ ID NO 4661 |
| CNN1 | SEQ ID NO 5457 | SEQ ID NO 5181 |
| CNTNAP3 | SEQ ID NO 5627 | SEQ ID NO 4675 |
| COL14A1 | SEQ ID NO 5594 | SEQ ID NO 5102 |
| COL17A1 | SEQ ID NO 5683 | SEQ ID NO 4739; SEQ ID NO 4784; SEQ ID NO 5242; SEQ ID NO 5384 |
| CRYAB | SEQ ID NO 5470 | SEQ ID NO 4858 |
| DMD | SEQ ID NO 5421 | SEQ ID NO 4664; SEQ ID NO 4860; SEQ ID NO 4908; SEQ ID NO 5058; SEQ ID NO 5095; SEQ ID NO 5150; SEQ ID NO 5381; SEQ ID NO 5387; SEQ ID NO 5410 |
| DMN | SEQ ID NO 5643 | SEQ ID NO 4610; SEQ ID NO 5120 |
| DST | SEQ ID NO 5660 | SEQ ID NO 5309 |
| EDN3 | SEQ ID NO 5673 | SEQ ID NO 5405 |
| FAM126A | SEQ ID NO 5618 | SEQ ID NO 5157 |
| FBXL7 | SEQ ID NO 5546 | SEQ ID NO 4932 |
| GRAMD3 | SEQ ID NO 5601 | SEQ ID NO 4857 |
| IL33 | SEQ ID NO 5624 | SEQ ID NO 4927 |
| IRX1 | SEQ ID NO 5603 | SEQ ID NO 5140 |
| KIT | SEQ ID NO 5423 | SEQ ID NO 5107; SEQ ID NO 5177 |
| KRT14 | SEQ ID NO 5434 | SEQ ID NO 4740; SEQ ID NO 4819; SEQ ID NO 4825; SEQ ID NO 4845; SEQ ID NO 4877; SEQ ID NO 4878; SEQ ID NO 4891; SEQ ID NO 4969 |
| KRT16 | SEQ ID NO 5525 | SEQ ID NO 4826; SEQ ID NO 4881 |

-continued

| Gene Name | Gene SEQ ID | Variants SEQ ID |
|---|---|---|
| KRT17 | SEQ ID NO 5431 | SEQ ID NO 4876; SEQ ID NO 4992 |
| KRT5 | SEQ ID NO 5432 | SEQ ID NO 4748; SEQ ID NO 4817; SEQ ID NO 4821; SEQ ID NO 4919; SEQ ID NO 5152; SEQ ID NO 5279 |
| MME | SEQ ID NO 5440 | SEQ ID NO 4579; SEQ ID NO 5054 |
| MYH11 | SEQ ID NO 5599 | SEQ ID NO 4697; SEQ ID NO 4870; SEQ ID NO 4972; SEQ ID NO 5053; SEQ ID NO 5103; SEQ ID NO 5323; SEQ ID NO 5361; SEQ ID NO 5365 |
| MYLK | SEQ ID NO 5630 | SEQ ID NO 5376 |
| NDRG2 | SEQ ID NO 5669 | SEQ ID NO 4868; SEQ ID NO 4911 |
| NRG1 | SEQ ID NO 5552 | SEQ ID NO 5084; SEQ ID NO 5148; SEQ ID NO 5413 |
| NTRK2 | SEQ ID NO 5532 | SEQ ID NO 5121 |
| PIK3C2G | SEQ ID NO 5513 | SEQ ID NO 5109 |
| PTN | SEQ ID NO 5486 | SEQ ID NO 4666; SEQ ID NO 5317 |
| SFRP1 | SEQ ID NO 5491 | SEQ ID NO 4909; SEQ ID NO 5161 |
| TANK | SEQ ID NO 5505 | SEQ ID NO 5069 |
| TSHZ2 | SEQ ID NO 5652 | SEQ ID NO 4962 |
| WIF1 | SEQ ID NO 5645 | SEQ ID NO 5397 |

In other preferred embodiment, the invention relates to the use as defined above, for the determination of the variation of expression of at least 43 determined genes of the group of 275 determined genes represented by SEQ ID NO 5419 to SEQ ID NO 5693, and of at least one of the variants of said at least 43 determined genes, wherein the correspondence between genes and their variants is indicated in the following table 1D.

Table 1D represents the correspondences between the group of 43 determined genes and their corresponding variants.

| Gene Name | Gene SEQ ID | Variants SEQ ID |
|---|---|---|
| ACTA2 | SEQ ID NO 5462 | SEQ ID NO 4633; SEQ ID NO 4795; SEQ ID NO 4956; SEQ ID NO 5052; SEQ ID NO 5093; SEQ ID NO |
| AK5 | SEQ ID NO 5654 | SEQ ID NO 4586; SEQ ID NO 4620; SEQ ID NO 4658; SEQ ID NO 4694; SEQ ID NO 4786; SEQ ID NO 4794; SEQ ID NO 4856; SEQ ID NO 5078; SEQ ID NO 5224; SEQ ID NO 5391 |
| C2orf40 | SEQ ID NO 5616 | SEQ ID NO 4832; SEQ ID NO 4862 |
| C9orf61 | SEQ ID NO 5516 | SEQ ID NO 4661 |
| CNN1 | SEQ ID NO 5457 | SEQ ID NO 5181; SEQ ID NO 5185 |
| CNTNAP3 | SEQ ID NO 5627 | SEQ ID NO 4597; SEQ ID NO 4675 |
| COL14A1 | SEQ ID NO 5594 | SEQ ID NO 5102 |
| COL17A1 | SEQ ID NO 5683 | SEQ ID NO 4739; SEQ ID NO 4784; SEQ ID NO 5242; SEQ ID NO 5384 |
| CRYAB | SEQ ID NO 5470 | SEQ ID NO 4858 |
| DKK3 | SEQ ID NO 5549 | SEQ ID NO 4933; SEQ ID NO 5208 |
| DMD | SEQ ID NO 5421 | SEQ ID NO 4664; SEQ ID NO 4860; SEQ ID NO 4908; SEQ ID NO 5058; SEQ ID NO 5095; SEQ ID NO 5150; SEQ ID NO 5381; SEQ ID NO 5387; SEQ ID NO 5410 |
| DMN | SEQ ID NO 5643 | SEQ ID NO 4610; SEQ ID NO 5120; SEQ ID NO 5396 |
| DST | SEQ ID NO 5660 | SEQ ID NO 5309 |
| EDN3 | SEQ ID NO 5673 | SEQ ID NO 4629 |
| FAM126A | SEQ ID NO 5618 | SEQ ID NO 5126; SEQ ID NO 5157 |
| FBXL7 | SEQ ID NO 5546 | SEQ ID NO 4932 |
| GRAMD3 | SEQ ID NO 5601 | SEQ ID NO 4857 |
| IL33 | SEQ ID NO 5624 | SEQ ID NO 4927 |
| IRX1 | SEQ ID NO 5603 | SEQ ID NO 5140 |
| KIT | SEQ ID NO 5423 | SEQ ID NO 5107; SEQ ID NO 5177 |
| KRT14 | SEQ ID NO 5434 | SEQ ID NO 4740; SEQ ID NO 4819; SEQ ID NO 4825; SEQ ID NO 4845; SEQ ID NO 4877; SEQ ID NO 4878; SEQ ID NO 4891; SEQ ID NO 4969 |
| KRT15 | SEQ ID NO 5475 | SEQ ID NO 4619; SEQ ID NO 4867; SEQ ID NO 4967 |
| KRT16 | SEQ ID NO 5525 | SEQ ID NO 4826; SEQ ID NO 4881 |

-continued

| Gene Name | Gene SEQ ID | Variants SEQ ID |
|---|---|---|
| KRT17 | SEQ ID NO 5431 | SEQ ID NO 4876; SEQ ID NO 4992; SEQ ID NO 5036 |
| KRT5 | SEQ ID NO 5432 | SEQ ID NO 4748; SEQ ID NO 4782; SEQ ID NO 4817; SEQ ID NO 4821; SEQ ID NO 4827; SEQ ID NO 4919; SEQ ID NO 4970; SEQ ID NO 5323; SEQ ID NO 5279; SEQ ID NO 5406 |
| KRT6C | SEQ ID NO 5651 | SEQ ID NO 4840 |
| MGC70870 | SEQ ID NO 5686 | SEQ ID NO 5201 |
| MID1 | SEQ ID NO 5623 | SEQ ID NO 4706 |
| MME | SEQ ID NO 5440 | SEQ ID NO 4579; SEQ ID NO 4607; SEQ ID NO 5054 |
| MYH11 | SEQ ID NO 5599 | SEQ ID NO 4697; SEQ ID NO 4870; SEQ ID NO 4972; SEQ ID NO 5053; SEQ ID NO 5103; SEQ ID NO 5323; SEQ ID NO 5361; SEQ ID NO 5365 |
| MYLK | SEQ ID NO 5630 | SEQ ID NO 5376 |
| NDRG2 | SEQ ID NO 5669 | SEQ ID NO 4868; SEQ ID NO 4898; SEQ ID NO 4911; SEQ ID NO 5010 |
| NRG1 | SEQ ID NO 5552 | SEQ ID NO 5084; SEQ ID NO 5085; SEQ ID NO 5148; SEQ ID NO 5395; SEQ ID NO 5412; SEQ ID NO 5413 |
| NTRK2 | SEQ ID NO 5532 | SEQ ID NO 5121 |
| PDE1C | SEQ ID NO 5520 | SEQ ID NO 4657 |
| PIK3C2G | SEQ ID NO 5513 | SEQ ID NO 5109 |
| PTN | SEQ ID NO 5486 | SEQ ID NO 4666; SEQ ID NO 5317 |
| SFRP1 | SEQ ID NO 5491 | SEQ ID NO 4909; SEQ ID NO 5161 |
| TANK | SEQ ID NO 5505 | SEQ ID NO 5069 |
| TOP2A | SEQ ID NO 5455 | SEQ ID NO 5153 |
| TP63 | SEQ ID NO 5499 | SEQ ID NO 4588 |
| TSHZ2 | SEQ ID NO 5652 | SEQ ID NO 4962 |
| WIF1 | SEQ ID NO 5645 | SEQ ID NO 5397 |

In another preferred embodiment, the invention relates to the use as defined above, for the determination of the variation of expression of at least 206 determined genes of the group of 275 determined genes represented by SEQ ID NO 5419 to SEQ ID NO 5693, and of at least one of the variants of said at least 206 determined genes, wherein the correspondence between genes and their variants is indicated in the following table 1E.

Table 1E represents the correspondences between the group of 206 determined genes and their corresponding variants.

| Gene Name | Gene SEQ ID | Variants SEQ ID |
|---|---|---|
| A2M | SEQ ID NO 5420 | SEQ ID NO 4855; SEQ ID NO 4945; SEQ ID NO 5092; SEQ ID NO 5248; SEQ ID NO 5328; SEQ ID NO 5363; SEQ ID NO 5364 |
| ACTA2 | SEQ ID NO 5462 | SEQ ID NO 4632; SEQ ID NO 4633; SEQ ID NO 4795; SEQ ID NO 4956; SEQ ID NO 4959; SEQ ID NO 4981; SEQ ID NO 5052; SEQ ID NO 5057; SEQ ID NO 5093; SEQ ID NO 5316; SEQ ID NO 5350; SEQ ID NO 5369 |
| ACTG2 | SEQ ID NO 5463 | SEQ ID NO 4774; SEQ ID NO 4777; SEQ ID NO 4940 |
| ADD3 | SEQ ID NO 5588 | SEQ ID NO 4629 |
| AK5 | SEQ ID NO 5654 | SEQ ID NO 4586; SEQ ID NO 4620; SEQ ID NO 4658; SEQ ID NO 4694; SEQ ID NO 4786; SEQ ID NO 4794; SEQ ID NO 4856; SEQ ID NO 5071; SEQ ID NO 5078; SEQ ID NO 5224; SEQ ID NO 5391 |
| ALDH7A1 | SEQ ID NO 5456 | SEQ ID NO 4836 |
| ALKBH3 | SEQ ID NO 5641 | SEQ ID NO 4756 |
| ANLN | SEQ ID NO 5587 | SEQ ID NO 4734; SEQ ID NO 4792; SEQ ID NO 5210 |
| ANXA1 | SEQ ID NO 5436 | SEQ ID NO 4651; SEQ ID NO 4760; SEQ ID NO 4888; SEQ ID NO 5066; SEQ ID NO 5343 |

| Gene Name | Gene SEQ ID | Variants SEQ ID |
|---|---|---|
| ANXA8L2 | SEQ ID NO 5465 | SEQ ID NO 4901; SEQ ID NO 5018; SEQ ID NO 5246 |
| APCDD1 | SEQ ID NO 5647 | SEQ ID NO 4871; SEQ ID NO 5001; SEQ ID NO 5081; SEQ ID NO 5182 |
| AQP1 | SEQ ID NO 5661 | SEQ ID NO 4676; SEQ ID NO 4865 |
| ARHGAP26 | SEQ ID NO 5560 | SEQ ID NO 5215 |
| ARL4A | SEQ ID NO 5453 | SEQ ID NO 4793; SEQ ID NO 5002; SEQ ID NO 5004 |
| ARRDC3 | SEQ ID NO 5591 | SEQ ID NO 4642; SEQ ID NO 4973 |
| ASPM | SEQ ID NO 5581 | SEQ ID NO 5050 |
| ASPN | SEQ ID NO 5573 | SEQ ID NO 4854 |
| ATP8B4 | SEQ ID NO 5608 | SEQ ID NO 4814 |
| B4GALNT4 | SEQ ID NO 5656 | SEQ ID NO 5007 |
| BCL11A | SEQ ID NO 5577 | SEQ ID NO 5204 |
| BUB1 | SEQ ID NO 5509 | SEQ ID NO 5082 |
| C1orf112 | SEQ ID NO 5582 | SEQ ID NO 5268 |
| C2orf40 | SEQ ID NO 5616 | SEQ ID NO 4832; SEQ ID NO 4862 |
| C3orf64 | SEQ ID NO 5653 | SEQ ID NO 4626 |
| C9orf61 | SEQ ID NO 5516 | SEQ ID NO 4661; SEQ ID NO 4788; SEQ ID NO 5034; SEQ ID NO 5290 |
| CCNB1 | SEQ ID NO 5615 | SEQ ID NO 5138 |
| CCNE2 | SEQ ID NO 5631 | SEQ ID NO 4656 |
| CDKN3 | SEQ ID NO 5523 | SEQ ID NO 4837 |
| CENPA | SEQ ID NO 5467 | SEQ ID NO 4637 |
| CENPE | SEQ ID NO 5468 | SEQ ID NO 5097 |
| CENPF | SEQ ID NO 5568 | SEQ ID NO 4843; SEQ ID NO 5130 |
| CFI | SEQ ID NO 5422 | SEQ ID NO 4719; SEQ ID NO 5105 |
| CHST9 | SEQ ID NO 5613 | SEQ ID NO 4582 |
| CLDN8 | SEQ ID NO 5667 | SEQ ID NO 4720; SEQ ID NO 4953 |
| CLIP4 | SEQ ID NO 5606 | SEQ ID NO 5314 |
| CNN1 | SEQ ID NO 5457 | SEQ ID NO 5079; SEQ ID NO 5181; SEQ ID NO 5185 |
| CNTNAP3 | SEQ ID NO 5627 | SEQ ID NO 4597; SEQ ID NO 4675 |
| CNTNAP3B | SEQ ID NO 5692 | SEQ ID NO 5399 |
| COL14A1 | SEQ ID NO 5594 | SEQ ID NO 4727; SEQ ID NO 4936; SEQ ID NO 5102; SEQ ID NO 5326; SEQ ID NO 5382; SEQ ID NO 5418 |
| COL17A1 | SEQ ID NO 5683 | SEQ ID NO 4739; SEQ ID NO 4747; SEQ ID NO 4784; SEQ ID NO 4897; SEQ ID NO 5008; SEQ ID NO 5242; SEQ ID NO 5384 |
| CRK | SEQ ID NO 5571 | SEQ ID NO 4757 |
| CRYAB | SEQ ID NO 5470 | SEQ ID NO 4611; SEQ ID NO 4685; SEQ ID NO 4688; SEQ ID NO 4689; SEQ ID NO 4773; SEQ ID NO 4858; SEQ ID NO 4863; SEQ ID NO 4894; SEQ ID NO 4975; SEQ ID NO 5407; SEQ ID NO 5416 |
| CTHRC1 | SEQ ID NO 5639 | SEQ ID NO 4598 |
| CX3CL1 | SEQ ID NO 5490 | SEQ ID NO 4630; SEQ ID NO 4951 |
| DHCR7 | SEQ ID NO 5459 | SEQ ID NO 5025; SEQ ID NO 5339 |
| DKK3 | SEQ ID NO 5549 | SEQ ID NO 4624; SEQ ID NO 4831; SEQ ID NO 4933; SEQ ID NO 4989; SEQ ID NO 5049; SEQ ID NO 5184; SEQ ID NO 5205; SEQ ID NO 5207; SEQ ID NO 5208; SEQ ID NO 5378 |
| DMD | SEQ ID NO 5421 | SEQ ID NO 4593; SEQ ID NO 4664; SEQ ID NO 4860; SEQ ID NO 4908; SEQ ID NO 5058; SEQ ID NO 5095; SEQ ID NO 5150; SEQ ID NO 5381; SEQ ID NO 5387; SEQ ID NO 5388; SEQ ID NO 5389; SEQ ID NO 5410 |
| DMN | SEQ ID NO 5643 | SEQ ID NO 4610; SEQ ID NO 5120; SEQ ID NO 5396 |
| DOCK8 | SEQ ID NO 5672 | SEQ ID NO 4623; SEQ ID NO 4728; SEQ ID NO 5118 |
| DST | SEQ ID NO 5660 | SEQ ID NO 4587; SEQ ID NO 4679; SEQ ID NO 5236; SEQ ID NO 5309; SEQ ID NO 5336 |
| EDN3 | SEQ ID NO 5673 | SEQ ID NO 4714; SEQ ID NO 5405 |
| EGR2 | SEQ ID NO 5429 | SEQ ID NO 4020; SEQ ID NO 5356 |
| ETV1 | SEQ ID NO 5518 | SEQ ID NO 4730; SEQ ID NO 5080; SEQ ID NO 5197; SEQ ID NO 5209; SEQ ID NO 5214; SEQ ID NO 5218; SEQ ID NO 5241; SEQ ID NO 5329; SEQ ID NO 5417 |
| ETV5 | SEQ ID NO 5511 | SEQ ID NO 4999; SEQ ID NO 5330 |
| FAM126A | SEQ ID NO 5618 | SEQ ID NO 4641; SEQ ID NO 4646; SEQ ID NO 5126; SEQ ID NO 5157 |
| FAM130A2 | SEQ ID NO 5609 | SEQ ID NO 5149; SEQ ID NO 5281 |
| FAM13A1 | SEQ ID NO 5559 | SEQ ID NO 4680; SEQ ID NO 4804; SEQ ID NO 5293 |
| FBXL7 | SEQ ID NO 5546 | SEQ ID NO 4932 |
| FDXR | SEQ ID NO 5503 | SEQ ID NO 5318 |
| FLJ25770 | SEQ ID NO 5684 | SEQ ID NO 4735 |
| FMO2 | SEQ ID NO 5460 | SEQ ID NO 4600; SEQ ID NO 5065 |
| FN1 | SEQ ID NO 5675 | SEQ ID NO 4608; SEQ ID NO 4609; SEQ ID NO 4636; SEQ ID NO 4649; SEQ ID NO 4842; SEQ ID NO 5015; SEQ ID NO 5022; SEQ ID NO 5098; SEQ ID NO 5141; SEQ ID NO 5164; SEQ ID NO 5165; SEQ ID NO 5183; SEQ ID NO 5186; SEQ ID NO 5258; SEQ ID NO 5307 |
| FRZB | SEQ ID NO 5461 | SEQ ID NO 5174 |
| FTO | SEQ ID NO 5687 | SEQ ID NO 4971; SEQ ID NO 5151; SEQ ID NO 5257 |
| FZD1 | SEQ ID NO 5497 | SEQ ID NO 4652 |
| GABRP | SEQ ID NO 5554 | SEQ ID NO 4614; SEQ ID NO 5031; SEQ ID NO 5061; SEQ ID NO 5067; SEQ ID NO 5347 |
| GALE | SEQ ID NO 5446 | SEQ ID NO 4618 |
| GJB3 | SEQ ID NO 5602 | SEQ ID NO 5262 |
| GLTSCR2 | SEQ ID NO 5566 | SEQ ID NO 4775; SEQ ID NO 4834; SEQ ID NO 4872 |
| GPM6B | SEQ ID NO 5443 | SEQ ID NO 5104 |
| GPR177 | SEQ ID NO 5444 | SEQ ID NO 5051; SEQ ID NO 5267; SEQ ID NO 5298 |
| GRAMD3 | SEQ ID NO 5601 | SEQ ID NO 4587; SEQ ID NO 4857; SEQ ID NO 4926; SEQ ID NO 4934; SEQ ID NO 5087; SEQ ID NO 5088; SEQ ID NO 5240; SEQ ID NO 5291; SEQ ID NO 5354 |
| GRIA4 | SEQ ID NO 5437 | SEQ ID NO 4772; SEQ ID NO 5238 |
| GSTA1 | SEQ ID NO 5644 | SEQ ID NO 4655 |
| GUCY1A3 | SEQ ID NO 5438 | SEQ ID NO 4716; SEQ ID NO 4886; SEQ ID NO 4913; SEQ ID NO 5044; SEQ ID NO 5070 |
| GYPC | SEQ ID NO 5473 | SEQ ID NO 5133 |
| HNRNPA1 | SEQ ID NO 5612 | SEQ ID NO 5273 |
| HOXA7 | SEQ ID NO 5538 | SEQ ID NO 5005 |
| IFNGR1 | SEQ ID NO 5430 | SEQ ID NO 4925 |
| IGF1 | SEQ ID NO 5435 | SEQ ID NO 5414 |
| IL33 | SEQ ID NO 5624 | SEQ ID NO 4927 |
| IMPAD1 | SEQ ID NO 5574 | SEQ ID NO 5360 |
| INTS8 | SEQ ID NO 5575 | SEQ ID NO 4724 |
| IRX1 | SEQ ID NO 5603 | SEQ ID NO 5140 |
| ITM2A | SEQ ID NO 5517 | SEQ ID NO 4592 |
| KCTD12 | SEQ ID NO 5638 | SEQ ID NO 5162 |
| KIAA0101 | SEQ ID NO 5556 | SEQ ID NO 4648; SEQ ID NO 4808; SEQ ID NO 4809; SEQ ID NO 4904 |
| KIAA2013 | SEQ ID NO 5637 | SEQ ID NO 4990 |
| KIF11 | SEQ ID NO 5512 | SEQ ID NO 4988 |
| KIF23 | SEQ ID NO 5640 | SEQ ID NO 4725; SEQ ID NO 4732; SEQ ID NO 4899 |
| KIF4A | SEQ ID NO 5547 | SEQ ID NO 4964 |
| KIT | SEQ ID NO 5423 | SEQ ID NO 5107; SEQ ID NO 5177 |
| KLHL13 | SEQ ID NO 5625 | SEQ ID NO 4979 |
| KMO | SEQ ID NO 5498 | SEQ ID NO 4653 |
| KRT13 | SEQ ID NO 5648 | SEQ ID NO 5261; SEQ ID NO 5351 |
| KRT14 | SEQ ID NO 5434 | SEQ ID NO 4740; SEQ ID NO 4818; SEQ ID NO 4819; SEQ ID NO 4825; SEQ ID NO 4845; SEQ ID NO 4877; SEQ ID NO 4878; SEQ ID NO 4891; SEQ ID NO 4969 |
| KRT15 | SEQ ID NO 5475 | SEQ ID NO 4619; SEQ ID NO 4645; SEQ ID NO 4737; SEQ ID NO 4844; SEQ ID NO 4849; SEQ ID NO 4866; SEQ ID NO 4867; SEQ ID NO 4869; SEQ ID NO 4882; SEQ ID NO 4890; SEQ ID NO 4967; SEQ ID NO 4978; SEQ ID NO 5147 |

| Gene Name | Gene SEQ ID | Variants SEQ ID |
| --- | --- | --- |
| KRT16 | SEQ ID NO 5525 | SEQ ID NO 4826; SEQ ID NO 4881 |
| KRT17 | SEQ ID NO 5431 | SEQ ID NO 4820; SEQ ID NO 4824; SEQ ID NO 4873; SEQ ID NO 4876; SEQ ID NO 4920; SEQ ID NO 4992; SEQ ID NO 5036; SEQ ID NO 5048 |
| KRT19 | SEQ ID NO 5476 | SEQ ID NO 4750; SEQ ID NO 4941 |
| KRT28 | SEQ ID NO 5657 | SEQ ID NO 5154 |
| KRT5 | SEQ ID NO 5432 | SEQ ID NO 4748; SEQ ID NO 4782; SEQ ID NO 4817; SEQ ID NO 4821; SEQ ID NO 4823; SEQ ID NO 4827; SEQ ID NO 4919; SEQ ID NO 4970; SEQ ID NO 5152; SEQ ID NO 5179; SEQ ID NO 5277; SEQ ID NO 5279; SEQ ID NO 5406 |
| KRT6C | SEQ ID NO 5651 | SEQ ID NO 4840; SEQ ID NO 5310 |
| KRT7 | SEQ ID NO 5524 | SEQ ID NO 4896; SEQ ID NO 4995 |
| KRT72 | SEQ ID NO 5633 | SEQ ID NO 5311 |
| LGR4 | SEQ ID NO 5585 | SEQ ID NO 4764; SEQ ID NO 5116 |
| LMOD1 | SEQ ID NO 5544 | SEQ ID NO 4710 |
| LMOD1 | SEQ ID NO | SEQ ID NO 5280 |
| LMOD1 | SEQ ID NO | SEQ ID NO 5302 |
| LOC147804 | SEQ ID NO 5680 | SEQ ID NO 5211 |
| LOC440421 | SEQ ID NO 5689 | SEQ ID NO 5006 |
| LPHN2 | SEQ ID NO 5545 | SEQ ID NO 4625; SEQ ID NO 5160 |
| LPHN3 | SEQ ID NO 5562 | SEQ ID NO 5187 |
| MAF | SEQ ID NO 5451 | SEQ ID NO 4850; SEQ ID NO 5390 |
| MAGED4B | SEQ ID NO 5611 | SEQ ID NO 5284 |
| MAML2 | SEQ ID NO 5617 | SEQ ID NO 4862; SEQ ID NO 5156 |
| MAP2K6 | SEQ ID NO 5485 | SEQ ID NO 4722; SEQ ID NO 4917 |
| MATN2 | SEQ ID NO 5479 | SEQ ID NO 4677; SEQ ID NO 4861; SEQ ID NO 5017; SEQ ID NO 5100 |
| MED20 | SEQ ID NO 5507 | SEQ ID NO 4830 |
| MERTK | SEQ ID NO 5536 | SEQ ID NO 5124 |
| MFGE8 | SEQ ID NO 5530 | SEQ ID NO 4580; SEQ ID NO 4711; SEQ ID NO 4765; SEQ ID NO 4839; SEQ ID NO 5301 |
| MGC70870 | SEQ ID NO 5686 | SEQ ID NO 5201 |
| MID1 | SEQ ID NO 5623 | SEQ ID NO 4698; SEQ ID NO 4699; SEQ ID NO 4700; SEQ ID NO 4701; SEQ ID NO 4702; SEQ ID NO 4703; SEQ ID NO 4705; SEQ ID NO 4706; SEQ ID NO 5074 |
| MKI67 | SEQ ID NO 5480 | SEQ ID NO 4754; SEQ ID NO 4790; SEQ ID NO 4884; SEQ ID NO 4921; SEQ ID NO 4954 |
| MME | SEQ ID NO 5440 | SEQ ID NO 4579; SEQ ID NO 4607; SEQ ID NO 5054 |
| MXI1 | SEQ ID NO 5635 | SEQ ID NO 5269 |
| MYH11 | SEQ ID NO 5599 | SEQ ID NO 4602; SEQ ID NO 4697; SEQ ID NO 4870; SEQ ID NO 4972; SEQ ID NO 5053; SEQ ID NO 5103; SEQ ID NO 5323; SEQ ID NO 5361; SEQ ID NO 5365 |
| MYLK | SEQ ID NO 5630 | SEQ ID NO 4682; SEQ ID NO 4687; SEQ ID NO 4931; SEQ ID NO 5358; SEQ ID NO 5376; SEQ ID NO 5400; SEQ ID NO 5401 |
| MYO18A | SEQ ID NO 5632 | SEQ ID NO 4907 |
| NCAPG | SEQ ID NO 5597 | SEQ ID NO 4630 |
| NDRG2 | SEQ ID NO 5669 | SEQ ID NO 4601; SEQ ID NO 4715; SEQ ID NO 4766; SEQ ID NO 4781; SEQ ID NO 4822; SEQ ID NO 4859; SEQ ID NO 4868; SEQ ID NO 4898; SEQ ID NO 4911; SEQ ID NO 4914; SEQ ID NO 4947; SEQ ID NO 4977; SEQ ID NO 4986; SEQ ID NO 5010; SEQ ID NO 5027; SEQ ID NO 5028; SEQ ID NO 5030; SEQ ID NO 5062; SEQ ID NO 5194; SEQ ID NO 5198; SEQ ID NO 5200; SEQ ID NO 5212; SEQ ID NO 5222; SEQ ID NO 5227; SEQ ID NO 5229; SEQ ID NO 5234; SEQ ID NO 5235; SEQ ID NO 5252; SEQ ID NO 5256; SEQ ID NO 5292; SEQ ID NO 5304; SEQ ID NO 5342; SEQ ID NO 5344; SEQ ID NO 5346; SEQ ID NO 5348; SEQ ID NO 5367 |
| NECAB1 | SEQ ID NO 5598 | SEQ ID NO 4797 |
| NEFH | SEQ ID NO 5593 | SEQ ID NO 4976; SEQ ID NO 5266 |
| NEK2 | SEQ ID NO 5482 | SEQ ID NO 4976 |
| NFIB | SEQ ID NO 5526 | SEQ ID NO 4628; SEQ ID NO 4767; SEQ ID NO 4833; SEQ ID NO 5271; SEQ ID NO 5370; SEQ ID NO 5371 |
| NME4 | SEQ ID NO 5519 | SEQ ID NO 4806; SEQ ID NO 5372 |
| NR3C2 | SEQ ID NO 5439 | SEQ ID NO 4606 |
| NRG1 | SEQ ID NO 5552 | SEQ ID NO 4713; SEQ ID NO 5084; SEQ ID NO 5085; SEQ ID NO 5086; SEQ ID NO 5148; SEQ ID NO 5393; SEQ ID NO 5394; SEQ ID NO 5395; SEQ ID NO 5412; SEQ ID NO 5413 |
| NTRK2 | SEQ ID NO 5532 | SEQ ID NO 4946; SEQ ID NO 5056; SEQ ID NO 5121; SEQ ID NO 5178; SEQ ID NO 5385; SEQ ID NO 5386 |
| NUSAP1 | SEQ ID NO 5570 | SEQ ID NO 4639; SEQ ID NO 4768; SEQ ID NO 4929; SEQ ID NO 5335 |
| ODZ2 | SEQ ID NO 5677 | SEQ ID NO 4665; SEQ ID NO 5176 |
| OGFRL1 | SEQ ID NO 5605 | SEQ ID NO 5040 |
| OSR1 | SEQ ID NO 5642 | SEQ ID NO 4937 |
| P2RY13 | SEQ ID NO 5600 | SEQ ID NO 4993 |
| PDE1C | SEQ ID NO 5520 | SEQ ID NO 4657 |
| PDGFRA | SEQ ID NO 5533 | SEQ ID NO 4918; SEQ ID NO 4938 |
| PELI1 | SEQ ID NO 5590 | SEQ ID NO 5014 |
| PFKM | SEQ ID NO 5425 | SEQ ID NO 5380 |
| PIGR | SEQ ID NO 5484 | SEQ ID NO 4663; SEQ ID NO 4916; SEQ ID NO 5345 |
| PIK3C2G | SEQ ID NO 5513 | SEQ ID NO 5109; SEQ ID NO 5345 |
| PKD2 | SEQ ID NO 5426 | SEQ ID NO 5111; SEQ ID NO 5128 |
| PPP1R14A | SEQ ID NO 5622 | SEQ ID NO 4592; SEQ ID NO 4721; SEQ ID NO 5137 |
| PRC1 | SEQ ID NO 5502 | SEQ ID NO 4631; SEQ ID NO 4744; SEQ ID NO 4785; SEQ ID NO 4994; SEQ ID NO 5075; SEQ ID NO 5188; SEQ ID NO 5191; SEQ ID NO 5312 |
| PRNP | SEQ ID NO 5427 | SEQ ID NO 4644; SEQ ID NO 4915 |
| PROS1 | SEQ ID NO 5428 | SEQ ID NO 5206 |
| PTN | SEQ ID NO 5486 | SEQ ID NO 4666; SEQ ID NO 5317 |
| PTPRZ1 | SEQ ID NO 5487 | SEQ ID NO 5064; SEQ ID NO 5112; SEQ ID NO 5125 |
| PTTG1 | SEQ ID NO 5506 | SEQ ID NO 4885; SEQ ID NO 5073; SEQ ID NO 5136 |
| PZP | SEQ ID NO 5488 | SEQ ID NO 4673; SEQ ID NO 4738; SEQ ID NO 4851; SEQ ID NO 5313 |
| RACGAP1 | SEQ ID NO 5550 | SEQ ID NO 4589; SEQ ID NO 5237; SEQ ID NO 5283; SEQ ID NO 5288; SEQ ID NO 5322 |
| RBMS3 | SEQ ID NO 5445 | SEQ ID NO 4980 |
| RIC3 | SEQ ID NO 5604 | SEQ ID NO 4612; SEQ ID NO 5140; SEQ ID NO 5155; SEQ ID NO 5270 |
| ROPN1B | SEQ ID NO 5447 | SEQ ID NO 4718; SEQ ID NO 5144 |
| RPL3 | SEQ ID NO 5441 | SEQ ID NO 4763; SEQ ID NO 4963 |
| RRM2 | SEQ ID NO 5452 | SEQ ID NO 4691; SEQ ID NO 4798 |
| S100B | SEQ ID NO 5534 | SEQ ID NO 4798; SEQ ID NO 4948; SEQ ID NO 4974 |
| S100P | SEQ ID NO 5531 | SEQ ID NO 4835 |
| SAA1 | SEQ ID NO 5665 | SEQ ID NO 4690; SEQ ID NO 4813 |
| SAA2 | SEQ ID NO 5610 | SEQ ID NO 4584; SEQ ID NO 4813; SEQ ID NO 4816; SEQ ID NO 5170; SEQ ID NO 5409 |
| SAMD5 | SEQ ID NO 5450 | SEQ ID NO 5158 |
| SATB1 | SEQ ID NO 5489 | SEQ ID NO 4709; SEQ ID NO 4815; SEQ ID NO 4852; SEQ ID NO 4950; SEQ ID NO 5249; SEQ ID NO 5337 |
| SFRP1 | SEQ ID NO 5491 | SEQ ID NO 4674; SEQ ID NO 4909; SEQ ID NO 5161 |
| SFTPD | SEQ ID NO 5492 | SEQ ID NO 4674 |
| SIRPA | SEQ ID NO 5634 | SEQ ID NO 4880; SEQ ID NO 4997; SEQ ID NO 5131; SEQ ID NO 5379 |
| SLC25A27 | SEQ ID NO 5508 | SEQ ID NO 5253 |
| SLC26A8 | SEQ ID NO 5629 | SEQ ID NO 4672 |
| SMARCA2 | SEQ ID NO 5493 | SEQ ID NO 4810 |
| SMC4 | SEQ ID NO 5678 | SEQ ID NO 4998; SEQ ID NO 5244; SEQ ID NO 5320 |

-continued

| Gene Name | Gene SEQ ID | Variants SEQ ID |
|---|---|---|
| SORBS1 | SEQ ID NO 5564 | SEQ ID NO 4681 |
| SPARCL1 | SEQ ID NO 5515 | SEQ ID NO 4585; SEQ ID NO 4693; SEQ ID NO 4832; SEQ ID NO 4910; SEQ ID NO 4924; SEQ ID NO 4935; SEQ ID NO 4939; SEQ ID NO 4960; SEQ ID NO 4961; SEQ ID NO 5029; SEQ ID NO 5035; SEQ ID NO 5055; SEQ ID NO 5059; SEQ ID NO 5090; SEQ ID NO 5127; SEQ ID NO 5199; SEQ ID NO 5202; SEQ ID NO 5228; SEQ ID NO 5230; SEQ ID NO 5232; SEQ ID NO 5254; SEQ ID NO 5276; SEQ ID NO 5325; SEQ ID NO 5353 |
| SPG3A | SEQ ID NO 5567 | SEQ ID NO 4966 |
| SPRY2 | SEQ ID NO 5529 | SEQ ID NO 4742; SEQ ID NO 4982; SEQ ID NO 5233 |
| TAGLN | SEQ ID NO 5442 | SEQ ID NO 4594; SEQ ID NO 4662; SEQ ID NO 4906; SEQ ID NO 5024; SEQ ID NO 5082; SEQ ID NO 5355 |
| TANK | SEQ ID NO 5505 | SEQ ID NO 4895; SEQ ID NO 5069 |
| TESC | SEQ ID NO 5576 | SEQ ID NO 5360 |
| TF | SEQ ID NO 5454 | SEQ ID NO 4654; SEQ ID NO 4668; SEQ ID NO 4669; SEQ ID NO 4758; SEQ ID NO 4892; SEQ ID NO 5032; SEQ ID NO 5099; SEQ ID NO 5411 |
| TLE4 | SEQ ID NO 5539 | SEQ ID NO 4595; SEQ ID NO 4616; SEQ ID NO 4635; SEQ ID NO 4729; SEQ ID NO 4733; SEQ ID NO 4889; SEQ ID NO 5122 |
| TMEM16A | SEQ ID NO 5578 | SEQ ID NO 4708 |
| TMPRSS2 | SEQ ID NO 5528 | SEQ ID NO 5231; SEQ ID NO 5247; SEQ ID NO 5296 |
| TOP2A | SEQ ID NO 5455 | SEQ ID NO 4686; SEQ ID NO 5153 |
| TP63 | SEQ ID NO 5499 | SEQ ID NO 4588; SEQ ID NO 4590; SEQ ID NO 4653; SEQ ID NO 4828; SEQ ID NO 5043 |
| TPM1 | SEQ ID NO 5449 | SEQ ID NO 5319 |
| TPM2 | SEQ ID NO 5676 | SEQ ID NO 4581; SEQ ID NO 4638; SEQ ID NO 4789; SEQ ID NO 4800; SEQ ID NO 4983; SEQ ID NO 5366 |
| TPM3 | SEQ ID NO 5649 | SEQ ID NO 4634; SEQ ID NO 4741; SEQ ID NO 4769; SEQ ID NO 4771; SEQ ID NO 4799; SEQ ID NO 4800; SEQ ID NO 4803; SEQ ID NO 4875; SEQ ID NO 4985; SEQ ID NO 4987; SEQ ID NO 5264; SEQ ID NO 5265; SEQ ID NO 5274; SEQ ID NO 5299; SEQ ID NO 5308; SEQ ID NO 5315 |
| TPX2 | SEQ ID NO 5543 | SEQ ID NO 4596; SEQ ID NO 5129 |
| TRIM2 | SEQ ID NO 5563 | SEQ ID NO 5119 |
| TRIM29 | SEQ ID NO 5681 | SEQ ID NO 4847; SEQ ID NO 4848; SEQ ID NO 5333; SEQ ID NO 5357; SEQ ID NO 5392 |
| TSHZ2 | SEQ ID NO 5652 | SEQ ID NO 4962 |
| UBAP2L | SEQ ID NO 5558 | SEQ ID NO 5072 |
| UBE2C | SEQ ID NO 5658 | SEQ ID NO 5077; SEQ ID NO 5172; SEQ ID NO 5173; SEQ ID NO 5403; SEQ ID NO 5404 |
| UBE2T | SEQ ID NO 5553 | SEQ ID NO 4660; SEQ ID NO 5041 |
| UTRN | SEQ ID NO 5540 | SEQ ID NO 5091 |
| VIM | SEQ ID NO 5495 | SEQ ID NO 4643 |
| WIF1 | SEQ ID NO 5645 | SEQ ID NO 5142; SEQ ID NO 5397; SEQ ID NO 5415 |
| YWHAZ | SEQ ID NO 5496 | SEQ ID NO 4749 |
| ZDHHC2 | SEQ ID NO 5569 | SEQ ID NO 4768; SEQ ID NO 5106; SEQ ID NO 5260 |
| ZNF462 | SEQ ID NO 5595 | SEQ ID NO 4851 |
| ZNF521 | SEQ ID NO 5565 | SEQ ID NO 4723; SEQ ID NO 5195; SEQ ID NO 5196; SEQ ID NO 5219; SEQ ID NO 5321; SEQ ID NO 5359 |

In another particular embodiment, the invention relates to the use as defined above, for the determination of the variation of expression of 275 determined genes represented by SEQ ID NO 5419 to SEQ ID NO 5693, and of at least one of their variants when they exist, wherein the correspondence between genes and their variants is indicated in the following table 6.

Table 6 summarizes the correspondence between all the sequences disclosed in the invention. In this table:
    SEQ ID NOs 1-2938 represent polynucleotide probes, and targets, variants and genes they can recognize,
    SEQ ID NOs 2939-4578 represent target regions, and variant and genes containing them, and polynucleotide probes recognizing them,
    SEQ ID NOs 4579-5418 and SEQ ID NO 5694 represent variants and their corresponding gene, and target they comprises, and also polynucleotide probes recognizing them,
    SEQ ID NOs 5419-5493 represent genes.

In another preferred embodiment, the invention relates to the use of a multiplicity of polynucleotide probe sets for determining the variation of the gene expression as defined above, and of its variants when present, wherein target regions are characterized by the polynucleotide sequences SEQ ID NO 2939 to 4578, each target region of each gene, and of each variant when they exist, being represented in Table 6.

For example, in the invention, for detecting the variation of expression of the group of at least 12 determined genes of the group of 275 genes, each of the 12 genes has the following target region:
    AK5 (SEQ ID NO 5654) contains the following target regions: SEQ ID NO 2979 and 2988
    COL17A1 (SEQ ID NO 5683) contains the following target regions: SEQ ID NO 2944; 2955; 2971; 2973 and 2974,
    DMD (SEQ ID NO 5421) contains the following target regions: SEQ ID NO 2939; 2940; 2941; 2942; 2943; 2945; 2947; 2949; 2950; 2952; 2953; 2957; 2961; 2962; 2963; 2964; 2970 and 2980,
    KIT (SEQ ID NO 5423) contains the following target regions: SEQ ID NO 2984; 2946; 2951; 2954; 2958; 2960; 2965; 2969; 2975 and 2978
    KRT16 (SEQ ID NO 5525) contains the following target regions: SEQ ID NO 2966 and 2972,
    KRT14 (SEQ ID NO 5434) contains the following target regions: SEQ ID NO 2946; 2951; 2954; 2958; 2960; 2965; 2969; 2975 and 2978,
    KRT5 (SEQ ID NO 5432) contains the following target regions: SEQ ID NO 2985,
    MYH11 (SEQ ID NO 5599) contains the following target regions: SEQ ID NO 2948; 2956; 2959; 2967; 2976; 2981; 2982 and 2986,
    NRG1 (SEQ ID NO 5552) contains the following target regions: SEQ ID NO 2977,
    PTN (SEQ ID NO 5486) contains the following target regions: SEQ ID NO 2983,
    SFRP1 (SEQ ID NO 5491) contains the following target regions: SEQ ID NO 2968, and
    TSHZ2 (SEQ ID NO 5652) contains the following target regions: SEQ ID NO 2987.

With Table 6, knowing gene and variants, it is easy to identify the sequence of the corresponding target region.

In another particular embodiments, the invention discloses the use of a multiplicity of polynucleotide probe sets for determining the variation of the gene expression as defined above, and/or of their variants when present, wherein each polynucleotide probe contained in a polynucleotide probe set is represented by the nucleic acid sequence of the library consisting in SEQ ID NO 1 to SEQ ID NO 2938, the correspondence between each polynucleotide probe and its corresponding target region, said target region corresponding to a gene and its variants when present, being represented in Table 6.

For example, in the invention, for detecting the variation of expression of the group of at least 12 determined genes of the group of 275 genes, each of the 12 genes is recognized by the following polynucleotide probes:

AK5 (SEQ ID NO 5654) is recognized by the polynucleotide probes SEQ ID NO 790; 791; 792; 793; 794 and 795, COL17A1 (SEQ ID NO 5683) is recognized by the polynucleotide probes SEQ ID NO 157; 158; 159; 167; 168; 169; 171; 172; 173 and 177, DMD (SEQ ID NO 5421) is recognized by the polynucleotide probes SEQ ID NO 312; 313; 314; 315; 316; 317; 324; 325; 326; 327; 328; 329; 330; 331; 333; 334; 335; 336; 339; 340; 341; 345; 346; 347; 348; 353; 360; 361; 364; 365; 366; 367; 368; 369; 370; 374 and 375, KIT (SEQ ID NO 5423) is recognized by the polynucleotide probes SEQ ID NO 1081; 1082 and 1083, KRT14 (SEQ ID NO 5434) is recognized by the polynucleotide probes SEQ ID NO 1165; 1158; 1159; 1160; 1161; 1162; 1166; 1167; 1168; 1169; 1170; 1171; 1185; 1186; 1194; 1198; 1199; 1200 and 1203, KRT16 (SEQ ID NO 5525) is recognized by the polynucleotide probes SEQ ID NO 1262; 1263; 1264; 1267; 1268 and 1269, KRT5 (SEQ ID NO 5432) is recognized by the polynucleotide probes SEQ ID NO 1129; 1140 and 1141, MYH11 (SEQ ID NO 5599) is recognized by the polynucleotide probes SEQ ID NO 1522; 1519; 1520; 1521; 1523; 1524; 1534; 1535; 1536; 1544; 1545; 1546; 1551; 1552; 1553; 1554; 1555; 1556 and 1557, NRG1 (SEQ ID NO 5552) is recognized by the polynucleotide probes SEQ ID NO 969; 972 and 981, PTN (SEQ ID NO 5486) is recognized by the polynucleotide probes SEQ ID NO 2026; 2027 and 2028, SFRP1 (SEQ ID NO 5491) is recognized by the polynucleotide probes SEQ ID NO 2179; 2180 and 2181, and TSHZ2 (SEQ ID NO 5652) is recognized by the polynucleotide probes SEQ ID NO 136; 137 and 138.

To summarize, for the same example of at least 12 determined genes of the group of 275 genes, the correspondences are the following ones:

NRG1 (SEQ ID NO 5552) and one of its variants (SEQ ID 5084) both contain the target region SEQ ID 2977, said target region being recognized by polynucleotide probes SEQ ID NO 969, 972 and 981, PTN (SEQ ID NO 5486) and one of its variants (SEQ ID 4666) both contain the target region SEQ ID 2983, said target region being recognized by polynucleotide probes SEQ ID NO 2026, 2027 and 2028, SFRP1 (SEQ ID NO 5491) and one of its variants (SEQ ID 5161) both contain the target region SEQ ID 2968, said target region being recognized by polynucleotide probes SEQ ID NO 2179, 2180 and 2181, TSHZ2 (SEQ ID NO 5652) and one of its variants (SEQ ID 4962) both contain the target region SEQ ID 2987, said target region being recognized by polynucleotide probes SEQ ID NO 136, 137 and 138, KIT (SEQ ID NO 5423) and one of its variants (SEQ ID 5107) both contain the target region SEQ ID 2984, said target region being recognized by polynucleotide probes SEQ ID NO 1081, 1082 and 1083, KRT16 (SEQ ID NO 5525) and two of its variants (SEQ ID 4826 and 4881) are such as KRT5 and SEQ ID 4826 both contain the target region SEQ ID 2972, said target region being recognized by polynucleotide probes SEQ ID NO 1267, 1268 and 1269, and KRT5 and SEQ ID 4881 both contain the target region SEQ ID 2966, said target region being recognized by polynucleotide probes SEQ ID NO 1262, 1263 and 1264, KRT5 (SEQ ID NO 5432) and one of its variants (SEQ ID 5279) both contain the target region SEQ ID 2985, said target region being recognized by polynucleotide probes SEQ ID NO 1129, 1140 and 1141, KRT14 (SEQ ID NO 5434) and six of its variants (SEQ ID 4819, 4825, 4845, 4877, 4891 and 4969) are such as:

KRT14 and SEQ ID 4819 both contain the target regions SEQ ID 2954, 2960 and 2969, said target regions being recognized respectively by polynucleotide probes SEQ ID NO 116 and 1166, SEQ ID NO 1158 and SEQ ID NO 1159, 1160 and 1161

KRT14 and SEQ ID 4825 both contain the target regions SEQ ID 2975 and 2978, said target regions being recognized respectively by polynucleotide probes SEQ ID NO 1167, 1168 and 1169 and SEQ ID NO 1162, 1170 and 1171, KRT14 and SEQ ID 4845 both contain the target region SEQ ID 2965, said target region being recognized by polynucleotide probes SEQ ID NO 1203, KRT14 and SEQ ID 4877 both contain the target region SEQ ID 2946, said target region being recognized by polynucleotide probes SEQ ID NO 1198, 1199 and 1200, KRT14 and SEQ ID 4891 both contain the target region SEQ ID 2958, said target region being recognized by polynucleotide probes SEQ ID NO 1185, 1186 and 1194, and KRT14 and SEQ ID 4969 both contain the target region SEQ ID 2951, said target region being recognized by polynucleotide probes SEQ ID NO 1185, 1186 and 1194, MYH11 (SEQ ID NO 5599) and four of its variants (SEQ ID 4697, 4870, 5361 and 5365) are such as:

MYH11 and SEQ ID 4697 both contain the target regions SEQ ID NO 2948 and 2986, said target regions being recognized respectively by polynucleotide probes SEQ ID NO 1522; 1523 and 1524, and SEQ ID NO 1519; 1520 and 1521

MYH11 and SEQ ID 4870 both contain the target regions SEQ ID NO 2956, 2959, 2981 and 2982, said target regions being recognized respectively by polynucleotide probes SEQ ID 1551, 1552 and 1553, SEQ ID NO 1523, 1524 and 1557, SEQ ID NO 1551, 1552 and 1553 and SEQ ID NO 1554, 1555 and 1556, MYH11 and SEQ ID 5361 both contain the target region SEQ ID 2967, said target region being recognized by polynucleotide probes SEQ ID NO 1534, 1535 and 1536, MYH11 and SEQ ID 5365 both contain the target region SEQ ID 2976, said target region being recognized by polynucleotide probes SEQ ID NO 1544, 1545 and 1546, AK5 (SEQ ID NO 5654) and one of its variants (SEQ ID 4654) both contain the target regions SEQ ID 2979 and 2988, said target regions being respectively recognized by polynucleotide probes SEQ ID NO 790, 791 and 792, and SEQ ID NO 793, 794 and 795, COL17A1 (SEQ ID NO 5599) and four of its variants (SEQ ID 4739, 4784, 5242 and 5384) are such as:

COL17A1 and SEQ ID 4739 both contain the target regions SEQ ID NO 2944 and 2955, said target regions being recognized respectively by polynucleotide probes SEQ ID NO 171; 172 and 173, and SEQ ID NO 177, COL17A1 and SEQ ID 4784 both contain the target region SEQ ID NO 2973, said target region being recognized by polynucleotide probes SEQ ID NO 167, 168 and 169, COL17A1 and SEQ ID 5242 both contain the target region SEQ ID 2974, said target region being recognized by polynucleotide probes SEQ ID NO 167, 168 and 177, COL17A1 and SEQ ID 5384 both contain the target region SEQ ID 2971, said target region being recognized by polynucleotide probes SEQ ID NO 157, 158 and 159, DMD (SEQ ID NO 5421) and seven of its variants (SEQ ID NO 4664, 4860, 5058, 5095, 5150, 5381 and 5410) are such as:

DMD and SEQ ID 4664 both contain the target regions SEQ ID NO 294 and 2947, said target regions being recognized respectively by polynucleotide probes SEQ ID NO 312, 313 and 314, and SEQ ID NO 315, 316 and 317

DMD and SEQ ID 4860 both contain the target region SEQ ID 2940, said target region being recognized by polynucleotide probes SEQ ID NO 364, 365 and 366, DMD and SEQ ID 5058 both contain the target region SEQ ID 2950, said target region being recognized by polynucleotide probes SEQ ID NO 353, 360 and 361, DMD and SEQ ID 5095 both contain the target regions SEQ ID 2939, 2942, 2945, 2949, 2953, 2961, 2963, 2964 and 2970, said target region being respectively recognized by polynucleotide probes
SEQ ID NO 333, 334 and 335,
SEQ ID NO 312, 313 and 348,
SEQ ID NO 315, 331 and 336,
SEQ ID NO 339, 340 and 341,
SEQ ID NO 324, 325 and 326,
SEQ ID NO 345, 346 and 347,
SEQ ID NO 315, 330 and 331,
SEQ ID NO 327, 328 and 329, and
SEQ ID NO 327, 328 and 329, DMD and SEQ ID 5150 both contain the target region SEQ ID 2980, said target region being recognized by polynucleotide probes SEQ ID NO 368, 374 and 375, DMD and SEQ ID 5381 both contain the target regions SEQ ID 2941, 2952 and 2962, said target regions being respectively recognized by polynucleotide probes SEQ ID NO 364, 365 and 366, SEQ ID NO 315, 316 and 370, and SEQ ID NO 367, 368 and 369, DMD and SEQ ID 5410 both contain the target region SEQ ID 2957, said target region being recognized by polynucleotide probes SEQ ID NO 315, 316 and 370.

Using Table 6, and knowing genes and variants, it is easy to identify the sequence of the corresponding target region and probes.

The invention also relates to the use of a multiplicity of at least 50 polynucleotide probe sets chosen among 1640 polynucleotide probe sets, the nucleic acid sequences of the polynucleotide probes contained in said 50 polynucleotide probe sets being the following nucleic acid sequences: SEQ ID NOs 136; 137; 138; 157; 158; 159; 167; 168; 169; 171; 172; 173; 177; 312; 313; 313; 314; 315; 316; 317; 324; 325; 326; 327; 328; 329; 330; 331; 333; 334; 335; 336; 339; 340; 341; 345; 346; 347; 348; 353; 360; 361; 364; 365; 366; 367; 368; 369; 370; 374; 375; 790; 791; 792; 793; 794; 795; 969; 972; 981; 1081; 1082; 1083; 1129; 1140; 1141; 1158; 1159; 1160; 1161; 1162; 1165; 1166; 1167; 1168; 1169; 1170; 1171; 1185; 1186; 1194; 1198; 1199; 1200; 1203; 1262; 1263; 1264; 1267; 1268; 1269; 1519; 1520; 1521; 1522; 1523; 1524; 1534; 1535; 1536; 1544; 1545; 1546; 1551; 1552; 1553; 1554; 1555; 1556; 1557; 2026; 2027; 2028; 2179; 2180 and 2181, each polynucleotide probe set containing from 1 to 4 of said polynucleotide probes, for the determination of the variation of expression of:
at least 12 determined genes belonging to a group of genes represented by the nucleotidic sequences SEQ ID NO: 5419 to SEQ ID NO: 5693 and
at least one variant of said genes of at least 12 determined genes, when they exist,
said 12 determined genes being represented by the following nucleotidic sequences:
SEQ ID NOs 5421; 5423; 5432; 5434; 5486; 5491; 5525; 5552; 5599; 5652; 5654 and 5683 and the corresponding variants being represented in table 1A in order to diagnose in vitro or ex vivo the benign or malignant state of a breast tumor.

In one preferred embodiment, the invention relates to the use as defined above, wherein the polynucleotide probes contained in said at least 50 polynucleotide probe sets are as mentioned above and wherein SEQ ID NOs 167; 168; 177; 312; 313; 327; 328; 329; 331; 364; 365; 366; 368; 370; 1185; 1186; 1194; 1523; 1524; 1551; 1552 and 1553 are present twice, SEQ ID NO 316 is present in three copies and SEQ ID NO 315 is present in 5 copies.

Thus, in all the 50 polynucleotide probe sets mentioned above, 143 polynucleotide probes are present, the above mentioned polynucleotide probes being present at least once, and in particular SEQ ID NOs 167; 168; 177; 312; 313; 327; 328; 329; 331; 364; 365; 366; 368; 370; 1185; 1186; 1194; 1523; 1524; 1551; 1552 and 1553 are present twice, SEQ ID NO 316 is present in three copies and SEQ ID NO 315 is present in 5 copies.

The above mentioned polynucleotide probes contained in the 50 nucleotides probe sets specifically recognized the above mentioned gene and their variant when present via target region, the correspondence being deduced from Table 6.

In one preferred embodiment, the invention relates to the use of a multiplicity of at least 100 polynucleotide probe sets as defined above, the nucleic acid sequence of the polynucleotides probes contained in said 100 polynucleotide probe sets being the following nucleic acid sequences: SEQ ID NO 120; 136; 137; 138; 154; 155; 156; 157; 158; 159; 167; 168; 169; 171; 172; 173; 174; 175; 176; 177; 312; 313; 314; 315; 316; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 363; 364; 365; 366; 367; 368; 369; 370; 371; 374; 375; 376; 378; 379; 380; 381; 555; 556; 557; 558; 560; 561; 562; 566; 567; 788; 789; 790; 791; 792; 793; 794; 795; 800; 801; 802; 821; 822; 823; 969; 971; 972; 981; 1056; 1057; 1058; 1075; 1076; 1077; 1081; 1082; 1083; 1087; 1088; 1089; 1103; 1104; 1105; 1114; 1115; 1116; 1123; 1124; 1125; 1129; 1130; 1131; 1140; 1141; 1158; 1159; 1160; 1161; 1162; 1163; 1164; 1165; 1166; 1167; 1168; 1169; 1170; 1171; 1172; 1180; 1181; 1185; 1186; 1187; 1188; 1189; 1190; 1191; 1192; 1193; 1194; 1195; 1196; 1198; 1199; 1200; 1201; 1202; 1203; 1207; 1262; 1263; 1264; 1267; 1268; 1269; 1509; 1510; 1511; 1519; 1520; 1521; 1522; 1523; 1524; 1528; 1529; 1534; 1535; 1536; 1544; 1545; 1546; 1551;

1552; 1553; 1554; 1555; 1556; 1557; 1561; 1562; 1682; 1683; 1684; 1776; 1777; 1778; 2023; 2024; 2025; 2026; 2027; 2028; 2173; 2174; 2175; 2176; 2177; 2178; 2179; 2180; 2181; 2762; 2763; 2764; 2860; 2861; 2862; 2883; 2884 and 2885, each polynucleotide probe set containing from 1 to 4 of said polynucleotide probes, for the determination of the variation of expression of
  at least 20 determined genes belonging to a group of determined genes represented by the nucleotidic sequences SEQ ID NO: 5419 to SEQ ID NO: 5693 and
  at least one variant of said genes at least 20 determined genes, when they exist,
  said 20 determined genes being represented by the following nucleotidic sequences:
    SEQ ID Nos 5421; 5423; 5432; 5434; 5457; 5486; 5491; 5513; 5516; 5525; 5532; 5552; 5599; 5616; 5624; 5643; 5652; 5654; 5673 and 5683 and the corresponding variants being represented in table 1B
in order to diagnose in vitro or ex vivo the benign or malignant state of a breast tumor.

In one preferred embodiment, the invention relates to the use as defined above, wherein the polynucleotide probes contained in said at least 100 polynucleotide probe sets are as mentioned above and wherein SEQ ID NOs 167; 168; 177; 312; 313; 316; 317; 327; 329; 330; 353; 361; 364; 365; 366; 367; 368; 369; 370; 821; 822; 823; 1129; 1164; 1185; 1186; 1187; 1188; 1189; 1203; 1523; 1551; 1552 and 1553 are present twice, SEQ ID NOs 328; 331; 1162; 1194; 1519; 1520; 1521 and 1524 are present in three copies and SEQ ID NO 315 is present in 6 copies.

Thus, in all the 100 polynucleotide probe sets mentioned above, 282 polynucleotide probes are present, the above mentioned polynucleotide probes being present at least once, and in particular SEQ ID NOs 167; 168; 177; 312; 313; 316; 317; 327; 329; 330; 353; 361; 364; 365; 366; 367; 368; 369; 370; 821; 822; 823; 1129; 1164; 1185; 1186; 1187; 1188; 1189; 1203; 1523; 1551; 1552 and 1553 are present twice, SEQ ID NOs 328; 331; 1162; 1194; 1519; 1520; 1521 and 1524 are present in three copies and SEQ ID NO 315 is present in 6 copies.

The above mentioned polynucleotide probes contained in the 100 nucleotides probe sets specifically recognized the above mentioned gene and their variant when present via target region, the correspondence being deduced from Table 6.

In another preferred embodiment, the invention relates to the use of a multiplicity of at least 150 polynucleotide probe sets as previously defined, the nucleic acid sequence of the polynucleotides probes contained in said 150 polynucleotide probe sets being the following nucleic acid sequences: SEQ ID NOs 4; 5; 6; 120; 136; 137; 138; 154; 155; 156; 157; 158; 159; 167; 168; 169; 171; 172; 173; 174; 175; 176; 177; 197; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 367; 368; 369; 370; 371; 374; 375; 376; 377; 378; 379; 380; 381; 513; 514; 515; 552; 553; 554; 555; 556; 557; 558; 559; 560; 561; 562; 566; 567; 783; 784; 785; 788; 789; 790; 791; 792; 793; 794; 795; 796; 797; 798; 799; 800; 801; 802; 803; 804; 805; 806; 807; 808; 812; 813; 814; 818; 821; 822; 823; 968; 969; 970; 971; 972; 981; 1056; 1057; 1058; 1061; 1062; 1063; 1064; 1065; 1066; 1067; 1068; 1069; 1070; 1071; 1075; 1076; 1077; 1080; 1081; 1082; 1083; 1087; 1088; 1089; 1103; 1104; 1105; 1114; 1115; 1116; 1123; 1124; 1125; 1129; 1130; 1131; 1139; 1140; 1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1262; 1263; 1264; 1267; 1268; 1269; 1284; 1285; 1315; 1469; 1470; 1471; 1509; 1510; 1511; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1580; 1581; 1582; 1671; 1682; 1683; 1684; 1685; 1686; 1690; 1691; 1692; 1776; 1777; 1778; 1788; 1789; 1790; 1890; 1891; 1892; 1952; 1953; 1954; 1963; 2023; 2024; 2025; 2026; 2027; 2028; 2065; 2067; 2088; 2089; 2090; 2091; 2173; 2174; 2175; 2176; 2177; 2178; 2179; 2180; 2181; 2196; 2201; 2229; 2230; 2231; 2536; 2537; 2538; 2576; 2577; 2578; 2599; 2600; 2762; 2763; 2764; 2774; 2775; 2776; 2860; 2861; 2862; 2883; 2884 and 2885, each polynucleotide probe set containing from 1 to 4 of said polynucleotide probes, for the determination of the variation of expression of
  at least 35 determined genes belonging to a group of determined genes represented by the nucleotidic sequences SEQ ID NO: 5419 to SEQ ID NO: 5693 and
  at least one variant of said genes at least 35 determined genes, when they exist,
  said 35 determined genes being represented by the following nucleotidic sequences:
    SEQ ID Nos 5421; 5423; 5431; 5432; 5434; 5440; 5457; 5462; 5470; 5486; 5491; 5505; 5513; 5516; 5525; 5532; 5546; 5552; 5594; 5599; 5601; 5603; 5616; 5618; 5624; 5627; 5630; 5643; 5645; 5652; 5654; 5660; 5669; 5673 and 5683, and the corresponding variants being represented in table 1C
in order to diagnose in vitro or ex vivo the benign or malignant state of a breast tumor.

In one preferred embodiment, the invention relates to the use as defined above, wherein the polynucleotide probes contained in said at least 150 polynucleotide probe sets are as mentioned above and wherein SEQ ID NOs 167; 168; 177; 312; 313; 317; 327; 329; 330; 353; 361; 363; 364; 365; 366; 369; 370; 371; 558; 567; 796; 797; 801; 806; 807; 808; 813; 814; 821; 822; 823; 969; 1056; 1057; 1058; 1129; 1141; 1163; 1164; 1185; 1186; 1187; 1188; 1189; 1199; 1203; 1469; 1470; 1471; 1523; 1551; 1552 and 1553 are present twice, SEQ ID NOs 316; 328; 331; 368; 788; 1194; 1519; 1520; 1521; 1524 are present in three copies, SEQ ID NO 1162 is present in 4 copies and SEQ ID NO 315 is present in 6 copies.

Thus, in all the 150 polynucleotide probe sets mentioned above, 422 polynucleotide probes are present, the above mentioned polynucleotide probes being present at least once, and in particular SEQ ID NOs 167; 168; 177; 312; 313; 317; 327; 329; 330; 353; 361; 363; 364; 365; 366; 369; 370; 371; 558; 567; 796; 797; 801; 806; 807; 808; 813; 814; 821; 822; 823; 969; 1056; 1057; 1058; 1129; 1141; 1163; 1164; 1185; 1186; 1187; 1188; 1189; 1199; 1203; 1469; 1470; 1471; 1523; 1551; 1552 and 1553 are present twice, SEQ ID NOs 316; 328; 331; 368; 788; 1194; 1519; 1520; 1521; 1524 are present in three copies, SEQ ID NO 1162 is present in 4 copies and SEQ ID NO 315 is present in 6 copies.

The above mentioned polynucleotide probes contained in the 150 nucleotides probe sets specifically recognized the above mentioned gene and their variant when present via target region, the correspondence being deduced from Table 6.

A preferred embodiment of the invention relates to the use of a multiplicity of at least 200 polynucleotide probe sets as defined above, the nucleic acid sequence of the polynucleotide probes contained in said 200 polynucleotide probe sets being the following nucleic acid sequences: SEQ ID NOs 4; 5; 6; 120; 121; 122; 123; 130; 131; 132; 136; 137; 138; 154; 155; 156; 157; 158; 159; 167; 168; 169; 171; 172; 173; 174; 175; 176; 177; 195; 196; 197; 198; 199; 200; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 368; 369; 370; 371; 374; 375; 376; 377; 378; 379; 380; 381; 513; 514; 515; 552; 553; 554; 555; 556; 557; 558; 559; 560; 561; 562; 563; 564; 565; 566; 567; 783; 784; 785; 788; 789; 790; 791; 792; 793; 794; 795; 796; 797; 798; 799; 800; 801; 802; 803; 804; 805; 806; 807; 808; 809; 810; 811; 812; 813; 814; 815; 816; 817; 818; 821; 822; 823; 824; 825; 826; 840; 841; 845; 846; 847; 868; 968; 969; 970; 971; 972; 973; 974; 975; 976; 977; 981; 1056; 1057; 1058; 1059; 1060; 1061; 1062; 1063; 1064; 1065; 1066; 1067; 1068; 1069; 1070; 1071; 1075; 1076; 1077; 1080; 1081; 1082; 1083; 1084; 1085; 1086; 1087; 1088; 1089; 1094; 1095; 1096; 1103; 1104; 1105; 1110; 1111; 1112; 1114; 1115; 1116; 1123; 1124; 1125; 1126; 1127; 1128; 1129; 1130; 1131; 1139; 1140; 1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1229; 1230; 1242; 1243; 1244; 1245; 1250; 1251; 1252; 1262; 1263; 1264; 1265; 1266; 1267; 1268; 1269; 1270; 1271; 1272; 1284; 1285; 1315; 1335; 1407; 1408; 1469; 1470; 1471; 1509; 1510; 1511; 1512; 1513; 1514; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1563; 1564; 1580; 1581; 1582; 1586; 1587; 1588; 1671; 1682; 1683; 1684; 1685; 1686; 1687; 1688; 1689; 1690; 1691; 1692; 1743; 1744; 1745; 1776; 1777; 1778; 1788; 1789; 1790; 1890; 1891; 1892; 1896; 1897; 1898; 1952; 1953; 1954; 1963; 1974; 2023; 2024; 2025; 2026; 2027; 2028; 2061; 2062; 2063; 2065; 2067; 2068; 2072; 2083; 2084; 2085; 2088; 2089; 2090; 2091; 2092; 2173; 2174; 2175; 2176; 2177; 2178; 2179; 2180; 2181; 2196; 2201; 2229; 2230; 2231; 2381; 2382; 2383; 2536; 2537; 2538; 2576; 2577; 2578; 2599; 2600; 2601; 2602; 2603; 2762; 2763; 2764; 2774; 2775; 2776; 2778; 2779; 2783; 2794; 2860; 2861; 2862; 2883; 2884 and 2885,
for the determination of the variation of expression of
    at least 43 determined genes belonging to a group of determined genes represented by the nucleotidic sequences SEQ ID NO: 5419 to SEQ ID NO: 5693 and
    at least one variant of said determined genes at least 43 genes, when they exist,
    said 43 determined genes being represented by the following nucleotidic sequences:
    SEQ ID Nos 5421; 5423; 5431; 5432; 5434; 5440; 5455; 5457; 5462; 5470; 5475; 5486; 5491; 5499; 5505; 5513; 5516; 5520; 5525; 5532; 5546; 5549; 5552; 5594; 5599; 5601; 5603; 5616; 5618; 5623; 5624; 5627; 5630; 5643; 5645; 5651; 5652; 5654; 5660; 5669; 5673; 5683 and 5686, and the corresponding variants being represented in table 1D,
in order to diagnose in vitro or ex vivo the benign or malignant state of a breast tumor.

In one preferred embodiment, the invention relates to the use as defined above, wherein the polynucleotide probes contained in said at least 200 polynucleotide probe sets are as mentioned above and wherein SEQ ID NOs 167; 168; 177; 312; 313; 317; 327; 329; 330; 353; 361; 363; 364; 365; 366; 367; 369; 370; 371; 558; 567; 796; 797; 801; 806; 807; 808; 813; 814; 821; 822; 823; 845; 968; 970; 972; 1056; 1057; 1058; 1085; 1114; 1115; 1116; 1123; 1124; 1125; 1129; 1141; 1163; 1164; 1185; 1186; 1187; 1188; 1189; 1199; 1203; 1523; 1551; 1552; 1553; 1557; 1586; 1587; 1588; 1952; 1953; 1954; 2088; 2090; 2091; 2762; 2763 and 2764 are present twice, SEQ ID NOs 316; 328; 331; 368; 788; 1284; 1285; 1469; 1470; 1471; 1519; 1520; 1521; 1524; 2065; 2067 and 2089 are present in three copies, SEQ ID NO 1194 is present in 4 copies and SEQ ID NOs 315 and 1162 are present in 6 copies.

Thus, in all the 200 polynucleotide probe sets mentioned above, 565 polynucleotide probes are present, the above mentioned polynucleotide probes being present at least once, and in particular SEQ ID NOs 167; 168; 177; 312; 313; 317; 327; 329; 330; 353; 361; 363; 364; 365; 366; 367; 369; 370; 371; 558; 567; 796; 797; 801; 806; 807; 808; 813; 814; 821; 822; 823; 845; 968; 970; 972; 1056; 1057; 1058; 1085; 1114; 1115; 1116; 1123; 1124; 1125; 1129; 1141; 1163; 1164; 1185; 1186; 1187; 1188; 1189; 1199; 1203; 1523; 1551; 1552; 1553; 1557; 1586; 1587; 1588; 1952; 1953; 1954; 2088; 2090; 2091; 2762; 2763 and 2764 are present twice, SEQ ID NOs 316; 328; 331; 368; 788; 1284; 1285; 1469; 1470; 1471; 1519; 1520; 1521; 1524; 2065; 2067 and 2089 are present in three copies, SEQ ID NO 1194 is present in 4 copies and SEQ ID NOs 315 and 1162 are present in 6 copies.

The above mentioned polynucleotide probes contained in the 200 nucleotides probe sets specifically recognized the above mentioned gene and their variant when present via target region, the correspondence being deduced from Table 6.

The multiplicities mentioned above are considered as the "Top Polynucleotide Probe Sets".

In another preferred embodiment, the invention relates to the use of a multiplicity of at least 1228 polynucleotide probe sets as defined above, containing 3985 polynucleotide probes, the nucleic acid sequence of the polynucleotide probes contained in said 1228 polynucleotide probe sets being represented in the first 1228 lines of the Table 7, for the determination of the variation of expression of for determining the variation of the expression of
    at least 206 determined genes belonging to a group of determined genes represented by the nucleotidic sequences SEQ ID NO: 5419 to SEQ ID NO: 5693 and
    at least one variant of said genes at least 206 genes, when they exist,
    said 206 genes being represented by the following nucleotidic sequences:
    SEQ ID Nos 5420; 5421; 5422; 5423; 5425; 5426; 5427; 5428; 5429; 5430; 5431; 5432; 5434; 5435; 5436; 5437; 5438; 5439; 5440; 5441; 5442; 5443; 5444; 5445; 5446; 5447; 5449; 5450; 5451; 5452; 5453; 5454; 5455; 5456; 5457; 5459; 5460; 5461; 5462; 5463; 5465; 5467; 5468; 5470; 5473; 5475; 5476; 5479; 5480; 5482; 5484; 5485; 5486; 5487; 5488; 5489; 5490; 5491; 5492; 5493; 5495; 5496; 5497; 5498; 5499; 5502; 5503; 5505; 5506; 5507; 5508; 5509; 5511; 5512; 5513; 5515; 5516; 5517; 5518; 5519; 5520; 5523; 5524; 5525; 5526; 5528; 5529; 5530; 5531; 5532; 5533; 5534; 5536; 5538; 5539; 5540; 5543; 5544; 5545; 5546; 5547; 5549; 5550; 5552; 5553; 5554; 5556; 5558; 5559; 5560; 5562; 5563; 5564; 5565; 5566; 5567; 5568; 5569; 5570; 5571; 5573; 5574; 5575; 5576;

5577; 5578; 5581; 5582; 5585; 5587; 5588; 5590; 5591; 5593; 5594; 5595; 5597; 5598; 5599; 5600; 5601; 5602; 5603; 5604; 5605; 5606; 5608; 5609; 5610; 5611; 5612; 5613; 5615; 5616; 5617; 5618; 5622; 5623; 5624; 5625; 5627; 5629; 5630; 5631; 5632; 5633; 5634; 5635; 5637; 5638; 5639; 5640; 5641; 5642; 5643; 5644; 5645; 5647; 5648; 5649; 5651; 5652; 5653; 5654; 5656; 5657; 5658; 5660; 5661; 5665; 5667; 5669; 5672; 5673; 5675; 5676; 5677; 5678; 5680; 5681; 5683; 5684; 5686; 5687; 5689 and 5692, and the corresponding variants being represented in table 1E, in order to diagnose in vitro or ex vivo the benign or malignant state of a breast tumor.

Thus, in all the 1228 polynucleotide probe sets mentioned above, 3427 polynucleotide probes are present.

Also, a preferred embodiment of the invention discloses the use of a multiplicity of 1640 polynucleotide probe sets as defined above, the nucleic acid sequence of the polynucleotide probes contained in said 1640 polynucleotide probe sets being represented in Table 7, for the determination of the variation of expression of
  275 determined genes represented by the nucleotidic sequences SEQ ID NO: 5419 to SEQ ID NO: 5693 and
  at least one variant of said genes 275 determined genes, when they exist, the correspondence being mentioned in table 6,
  in order to diagnose in vitro or ex vivo the benign or malignant state of a breast tumor.

Thus, in all the 1640 polynucleotide probe sets mentioned above, 4586 polynucleotide probes are present.

In another embodiment, the invention discloses the use of a multiplicity of polynucleotide probe sets, wherein the sub-group of genes is constituted by 12 to 259 genes chosen among the group of genes consisting in SEQ ID NO 5419 to SEQ ID NO 5677.

The sub-groups of genes contain at least 12 genes, as described above. The sub-group of genes can also contain advantageously 19 genes, or advantageously 32 genes, or advantageously 40 genes, or advantageously 214 genes or more advantageously 259 genes.

According to the invention, each gene of the sub-groups of genes, and/or its variants when they exist, are specifically recognized by at least one polynucleotide probe belonging to a polynucleotide probe set of a pool of polynucleotide probe sets.

In a more particular embodiment, the invention relates to the use of a multiplicity of polynucleotide probe sets, wherein the sub-group of genes is constituted by the 259 genes of the group consisting in SEQ ID NO 5419 to SEQ ID NO 5693.

The inventors have unexpectedly demonstrated that a group of 259 genes, and/or their variants when they exist, give some powerful information to precisely determine the benign or malignant status of a breast tumor.

In the group of 259 genes, each gene, and its variants when they exist is specifically recognized by at least one polynucleotide probe belonging to a polynucleotide probe set of a pool of polynucleotide probe sets.

In another advantageous embodiment, the invention discloses the use of a multiplicity of polynucleotide probe sets, wherein the polynucleotide probe sets are chosen among at least 50 polynucleotide probe sets, particularly at least 100 polynucleotide probe sets, more particularly at least 150 polynucleotide probe sets, more particularly at least 200 polynucleotide probe sets, more particularly at least 1228 polynucleotide probe sets, and more particularly 1640 polynucleotide probe sets of the library of nucleic acid sequences consisting in SEQ ID NO 1 to SEQ ID NO 2938.

The multiplicity of polynucleotide probe sets is of at least 50 polynucleotide probe sets, and particularly at least 100 polynucleotide probe sets, more particularly at least 150 polynucleotide probe sets, and more advantageously at least 200 polynucleotide probe sets.

These multiplicities are considered as the "Top Polynucleotide Probe Sets".

The Top 50 polynucleotide probe sets contains a combination of polynucleotide probes characterized by SEQ ID NO 138, SEQ ID NO 140, SEQ ID NO 157, SEQ ID NO 159, SEQ ID NO 167, SEQ ID NO 168, SEQ ID NO 169, SEQ ID NO 171, SEQ ID NO 173, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 329, SEQ ID NO 330, SEQ ID NO 331 SEQ ID NO 333, SEQ ID NO 335, SEQ ID NO 336, SEQ ID NO 339, SEQ ID NO 341, SEQ ID NO 345, SEQ ID NO 347, SEQ ID NO 353, SEQ ID NO 360, SEQ ID NO 361, SEQ ID NO 364, SEQ ID NO 366, SEQ ID NO 367, SEQ ID NO 369, SEQ ID NO 790, SEQ ID NO 792, SEQ ID NO 793, SEQ ID NO 795, SEQ ID NO 969, SEQ ID NO 972, SEQ ID NO 981, SEQ ID NO 1081, SEQ ID NO 1083, SEQ ID NO 1129, SEQ ID NO 1140, SEQ ID NO 1141, SEQ ID NO 1151, SEQ ID NO 1158, SEQ ID NO 1159, SEQ ID NO 1162, SEQ ID NO 1165, SEQ ID NO 1166, SEQ ID NO 1167, SEQ ID NO 1169, SEQ ID NO 1170, SEQ ID NO 1171, SEQ ID NO 1185, SEQ ID NO 1186, SEQ ID NO 1194, SEQ ID NO 1198, SEQ ID NO 1200, SEQ ID NO 1203, SEQ ID NO 1262, SEQ ID NO 1264, SEQ ID NO 1267, SEQ ID NO 1269, SEQ ID NO 1520, SEQ ID NO 1522, SEQ ID NO 1523, SEQ ID NO 1524, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 2026, SEQ ID NO 2028, SEQ ID NO 2179 and SEQ ID NO 2181.

The Top 100 polynucleotide probe set contains a combination of polynucleotide probes characterized by SEQ ID NO 120, SEQ ID NO 138, SEQ ID NO 140, SEQ ID NO 154, SEQ ID NO 155, SEQ ID NO 156, SEQ ID NO 157, SEQ ID NO 159, SEQ ID NO 166, SEQ ID NO 167, SEQ ID NO 168, SEQ ID NO 169, SEQ ID NO 171, SEQ ID NO 173, SEQ ID NO 174, SEQ ID NO 175, SEQ ID NO 176, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 328, SEQ ID NO 329, SEQ ID NO 330, SEQ ID NO 331, SEQ ID NO 331, SEQ ID NO 332, SEQ ID NO 333, SEQ ID NO 335, SEQ ID NO 336, SEQ ID NO 337, SEQ ID NO 338, SEQ ID NO 339, SEQ ID NO 341, SEQ ID NO 345, SEQ ID NO 347, SEQ ID NO 349, SEQ ID NO 350, SEQ ID NO 351, SEQ ID NO 352, SEQ ID NO 353, SEQ ID NO 354, SEQ ID NO 355, SEQ ID NO 356, SEQ ID NO 360, SEQ ID NO 361, SEQ ID NO 363, SEQ ID NO 364, SEQ ID NO 364, SEQ ID NO 366, SEQ ID NO 367, SEQ ID NO 369, SEQ ID NO 369, SEQ ID NO 371, SEQ ID NO 376, SEQ ID NO 378, SEQ ID NO 379, SEQ ID NO 380, SEQ ID NO 381, SEQ ID NO 555, SEQ ID NO 556, SEQ ID NO 557, SEQ ID NO 558, SEQ ID NO 560, SEQ ID NO 561, SEQ ID NO 562, SEQ ID NO 566, SEQ ID NO 567, SEQ ID NO 788, SEQ ID NO 789, SEQ ID NO 790, SEQ ID NO 792, SEQ ID NO 793, SEQ ID NO 795, SEQ ID NO 800, SEQ ID NO 801, SEQ ID NO 802, SEQ ID NO 821, SEQ ID NO 822, SEQ ID NO 823, SEQ ID NO 969, SEQ ID NO 971, SEQ ID NO 972, SEQ ID NO 981, SEQ ID NO 1056, SEQ ID NO 1057, SEQ ID NO 1058, SEQ ID NO 1075, SEQ ID NO 1076, SEQ ID NO 1077, SEQ ID NO 1081, SEQ ID NO 1083, SEQ ID NO 1087, SEQ ID NO 1088, SEQ ID NO 1089, SEQ ID NO 1103, SEQ ID NO 1104, SEQ ID NO 1105, SEQ ID NO 1114, SEQ ID NO 1115, SEQ ID NO 1116, SEQ ID NO 1123, SEQ ID NO 1124, SEQ ID NO 1125, SEQ ID NO 1129, SEQ ID NO 1130, SEQ ID NO 1131, SEQ ID NO 1140, SEQ ID NO 1141, SEQ ID NO 1142, SEQ ID NO 1143, SEQ ID NO 1151, SEQ ID NO 1158, SEQ ID NO 1159, SEQ ID NO 1162, SEQ ID NO 1163, SEQ ID NO 1163, SEQ ID NO 1164, SEQ ID NO 1165, SEQ ID NO 1166, SEQ ID NO 1167, SEQ ID NO 1169, SEQ ID NO 1170, SEQ ID NO 1171, SEQ ID NO 1172, SEQ ID NO 1172, SEQ ID NO 1180, SEQ ID NO 1181, SEQ ID NO 1185, SEQ ID NO 1186, SEQ ID NO 1187, SEQ ID NO 1188, SEQ ID NO 1189, SEQ ID NO 1189, SEQ ID NO 1190, SEQ ID NO 1191, SEQ ID NO 1192, SEQ ID NO 1193, SEQ ID NO 1194, SEQ ID NO 1195, SEQ ID NO 1196, SEQ ID NO 1198, SEQ ID NO 1200, SEQ ID NO 1201, SEQ ID NO 1202, SEQ ID NO 1203, SEQ ID NO 1207, SEQ ID NO 1262, SEQ ID NO 1264, SEQ ID NO 1267, SEQ ID NO 1269, SEQ ID NO 1509, SEQ ID NO 1510, SEQ ID NO 1511, SEQ ID NO 1519, SEQ ID NO 1520, SEQ ID NO 1520, SEQ ID NO 1521, SEQ ID NO 1522, SEQ ID NO 1523, SEQ ID NO 1524, SEQ ID NO 1524, SEQ ID NO 1528, SEQ ID NO 1529, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 1561, SEQ ID NO 1562, SEQ ID NO 1682, SEQ ID NO 1683, SEQ ID NO 1684, SEQ ID NO 1776, SEQ ID NO 1777, SEQ ID NO 1778, SEQ ID NO 2023, SEQ ID NO 2024, SEQ ID NO 2025, SEQ ID NO 2026, SEQ ID NO 2028, SEQ ID NO 2173, SEQ ID NO 2174, SEQ ID NO 2175, SEQ ID NO 2176, SEQ ID NO 2177, SEQ ID NO 2178, SEQ ID NO 2179, SEQ ID NO 2181, SEQ ID NO 2762, SEQ ID NO 2763, SEQ ID NO 2764, SEQ ID NO 2860, SEQ ID NO 2861, SEQ ID NO 2862, SEQ ID NO 2883, SEQ ID NO 2884 and SEQ ID NO 2885.

The Top 150 polynucleotide probe set contains a combination of polynucleotide probes characterized by polynucleotide probes chosen among SEQ ID NO 1 to SEQ ID NO 2938.

The Top 200 polynucleotide probe set contains a combination of polynucleotide probes characterized by polynucleotide probes chosen among SEQ ID NO 1 to SEQ ID NO 2938.

According to the invention, the multiplicities used can also be represented by a number of at least 300 polynucleotide probe sets, more particularly at least 400 polynucleotide probe sets, more particularly at least 500 polynucleotide probe sets, more particularly at least 600 polynucleotide probe sets, more particularly at least 700 polynucleotide probe sets, more particularly at least 800 polynucleotide probe sets, more particularly at least 900 polynucleotide probe sets, more particularly at least 1000 polynucleotide probe sets, more particularly at least 1100 polynucleotide probe sets, more particularly at least 1228 polynucleotide probe sets, more particularly at least 1400 polynucleotide probe sets, and more particularly 1640 polynucleotide probe sets.

All the above-mentioned multiplicities of polynucleotide probe sets contain polynucleotides probes chosen among the library of nucleic acid sequences consisting in SEQ ID NO 1 to SEQ ID NO 2938.

According to the invention, the 1228 polynucleotide probe sets are an advantageous multiplicity of probe sets defined to diagnose the benign versus malignant status of a breast tumor.

In another embodiment, the invention also relates to the use of a multiplicity of polynucleotide probe sets, wherein polynucleotide probe sets are chosen among at least 50 polynucleotide probe sets, particularly at least 100 polynucleotide probe sets, more particularly at least 150 polynucleotide probe sets, more particularly at least 200 polynucleotide probe sets, more particularly at least 1228 polynucleotide probe sets, and more particularly 1640 polynucleotide probe sets of the library of nucleic acid sequences consisting in SEQ ID NO 1 to SEQ ID NO 2938, and wherein the sub-group of genes is constituted by the 259 genes of the group consisting in SEQ ID NO 5419 to SEQ ID NO 5677.

According to the invention, the benign versus malignant status of a breast tumor can be determined by the use of 2938 polynucleotide probes.

In an advantageous embodiment, the invention describes the use of a multiplicity of polynucleotide probe sets, wherein a variant of a given gene is chosen among the group of variants consisting in SEQ ID NO 4579 to SEQ ID NO 5418.

According to the invention, each gene can have:
no variant
at least one variant, as defined above.

In an advantageous embodiment, the invention discloses the use of a multiplicity of polynucleotide probe sets, each polynucleotide probe set containing at least one polynucleotide probe, each probe being able to specifically hybridize with at least one gene, and/or its variants when they exist, to determine the benign or malignant status of a breast tumor.

More particularly, the invention discloses the use of 2938 polynucleotides probes, assembled in polynucleotide probe sets, said polynucleotides probes being able to detect the variation of expression of at least one gene chosen among 259 genes, and/or its variants when present. According to the invention, the variation of expression of at least 839 variants and the variation of expression 259 genes can be detected by the use of the multiplicities of polynucleotide probe sets described above.

The invention also discloses a library of nucleic acid sequences consisting in SEQ ID NO 1 to SEQ ID NO 2938.

This library consists in all the polynucleotide probes that can be regrouped in 1640 representative probe sets of the invention. Then, the library consists in a group that contains 2938 polynucleotide probes.

The invention advantageously discloses a multiplicity of polynucleotide probes sets chosen among the nucleic acid sequences of the library described above, wherein the multiplicity of polynucleotide probe sets represents a combination of pool of polynucleotide probe sets able to specifically hybridize with 214 genes, and/or their variants when they exist, chosen among SEQ ID NO 5419 to SEQ ID NO 5677.

The group of polynucleotide probes represents a combination of 1228 polynucleotide probe sets. The group allows to detect the variation of expression of 214 genes and/or their variants when they exist.

The invention advantageously discloses a multiplicity of polynucleotide probe sets chosen among the nucleic acid sequences of the library according to claim 8, wherein the multiplicity of polynucleotide probe sets represents a combination of pool of polynucleotide probe sets able to specifically hybridize with 40 genes, and/or their variants when they exist, chosen among SEQ ID NO 5419 to SEQ ID NO 5677.

The group of polynucleotide probes represents a combination of 200 polynucleotide probe sets. The group allows to detect the variation of expression of 40 genes and/or their variants when they exist.

The invention more advantageously discloses a multiplicity of polynucleotide probe sets chosen among the nucleic acid sequences of the library according to claim 8, wherein the multiplicity of polynucleotide probe sets represents a combination of pool of polynucleotide probe sets able to specifically hybridize with 32 genes, and/or their variants when they exist, chosen among SEQ ID NO 5419 to SEQ ID NO 5677.

The group of polynucleotide probes represents a combination of 150 polynucleotide probe sets. The group allows to detect the variation of expression of 32 genes and/or their variants when they exist.

The invention more advantageously discloses multiplicity of polynucleotide probe sets chosen among the nucleic acid sequences of the library according to claim 8, wherein the multiplicity of polynucleotide probe sets represents a combination of pool of polynucleotide probe sets able to specifically hybridize with 19 genes, and/or their variants when they exist, chosen among SEQ ID NO 5419 to SEQ ID NO 5677.

According to the invention, the set of polynucleotide probe being able to specifically hybridize with 19 genes, and/or their variants when they exist, comprises the polynucleotide probes consisting in SEQ ID NO 120, SEQ ID NO 138, SEQ ID NO 140, SEQ ID NO 154, SEQ ID NO 155, SEQ ID NO 156, SEQ ID NO 157, SEQ ID NO 159, SEQ ID NO 166, SEQ ID NO 167, SEQ ID NO 168, SEQ ID NO 169, SEQ ID NO 171, SEQ ID NO 173, SEQ ID NO 174, SEQ ID NO 175, SEQ ID NO 176, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 328, SEQ ID NO 329, SEQ ID NO 330, SEQ ID NO 331, SEQ ID NO 331, SEQ ID NO 332, SEQ ID NO 333, SEQ ID NO 335, SEQ ID NO 336, SEQ ID NO 337, SEQ ID NO 338, SEQ ID NO 339, SEQ ID NO 341, SEQ ID NO 345, SEQ ID NO 347, SEQ ID NO 349, SEQ ID NO 350, SEQ ID NO 351, SEQ ID NO 352, SEQ ID NO 353, SEQ ID NO 354, SEQ ID NO 355, SEQ ID NO 356, SEQ ID NO 360, SEQ ID NO 361, SEQ ID NO 363, SEQ ID NO 364, SEQ ID NO 364, SEQ ID NO 366, SEQ ID NO 367, SEQ ID NO 369, SEQ ID NO 369, SEQ ID NO 371, SEQ ID NO 376, SEQ ID NO 378, SEQ ID NO 379, SEQ ID NO 380, SEQ ID NO 381, SEQ ID NO 555, SEQ ID NO 556, SEQ ID NO 557, SEQ ID NO 558, SEQ ID NO 560, SEQ ID NO 561, SEQ ID NO 562, SEQ ID NO 566, SEQ ID NO 567, SEQ ID NO 788, SEQ ID NO 789, SEQ ID NO 790, SEQ ID NO 792, SEQ ID NO 793, SEQ ID NO 795, SEQ ID NO 800, SEQ ID NO 801, SEQ ID NO 802, SEQ ID NO 821, SEQ ID NO 822, SEQ ID NO 823, SEQ ID NO 969, SEQ ID NO 971, SEQ ID NO 972, SEQ ID NO 981, SEQ ID NO 1056, SEQ ID NO 1057, SEQ ID NO 1058, SEQ ID NO 1075, SEQ ID NO 1076, SEQ ID NO 1077, SEQ ID NO 1081, SEQ ID NO 1083, SEQ ID NO 1087, SEQ ID NO 1088, SEQ ID NO 1089, SEQ ID NO 1103, SEQ ID NO 1104, SEQ ID NO 1105, SEQ ID NO 1114, SEQ ID NO 1115, SEQ ID NO 1116, SEQ ID NO 1123, SEQ ID NO 1124, SEQ ID NO 1125, SEQ ID NO 1129, SEQ ID NO 1130, SEQ ID NO 1131, SEQ ID NO 1140, SEQ ID NO 1141, SEQ ID NO 1142, SEQ ID NO 1143, SEQ ID NO 1151, SEQ ID NO 1158, SEQ ID NO 1159, SEQ ID NO 1162, SEQ ID NO 1163, SEQ ID NO 1163, SEQ ID NO 1164, SEQ ID NO 1165, SEQ ID NO 1166, SEQ ID NO 1167, SEQ ID NO 1169, SEQ ID NO 1170, SEQ ID NO 1171, SEQ ID NO 1172, SEQ ID NO 1172, SEQ ID NO 1180, SEQ ID NO 1181, SEQ ID NO 1185, SEQ ID NO 1186, SEQ ID NO 1187, SEQ ID NO 1188, SEQ ID NO 1189, SEQ ID NO 1189, SEQ ID NO 1190, SEQ ID NO 1191, SEQ ID NO 1192, SEQ ID NO 1193, SEQ ID NO 1194, SEQ ID NO 1195, SEQ ID NO 1196, SEQ ID NO 1198, SEQ ID NO 1200, SEQ ID NO 1201, SEQ ID NO 1202, SEQ ID NO 1203, SEQ ID NO 1207, SEQ ID NO 1262, SEQ ID NO 1264, SEQ ID NO 1267, SEQ ID NO 1269, SEQ ID NO 1509, SEQ ID NO 1510, SEQ ID NO 1511, SEQ ID NO 1519, SEQ ID NO 1520, SEQ ID NO 1520, SEQ ID NO 1521, SEQ ID NO 1522, SEQ ID NO 1523, SEQ ID NO 1524, SEQ ID NO 1528, SEQ ID NO 1529, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 1561, SEQ ID NO 1562, SEQ ID NO 1682, SEQ ID NO 1683, SEQ ID NO 1684, SEQ ID NO 1776, SEQ ID NO 1777, SEQ ID NO 1778, SEQ ID NO 2023, SEQ ID NO 2024, SEQ ID NO 2025, SEQ ID NO 2026, SEQ ID NO 2028, SEQ ID NO 2173, SEQ ID NO 2174, SEQ ID NO 2175, SEQ ID NO 2176, SEQ ID NO 2177, SEQ ID NO 2178, SEQ ID NO 2179, SEQ ID NO 2181, SEQ ID NO 2762, SEQ ID NO 2763, SEQ ID NO 2764, SEQ ID NO 2860, SEQ ID NO 2861, SEQ ID NO 2862, SEQ ID NO 2883, SEQ ID NO 2884 and SEQ ID NO 2885

The group of polynucleotide probes represents a combination of 100 polynucleotide probe sets. The group allows to detect the variation of expression of 19 genes and/or their variants when they exist.

The invention advantageously discloses a multiplicity of polynucleotide probe sets chosen among the nucleic acid sequences of the library according to claim 8, wherein the multiplicity of polynucleotide probe sets represents a combination of pool of polynucleotide probe sets able to specifically hybridize with 12 genes, and/or their variants when they exist, chosen among SEQ ID NO 5419 to SEQ ID NO 5677.

According to the invention, the set of polynucleotide probe being able to specifically hybridize with 12 genes, and/or their variants when they exist, comprises the polynucleotide probes consisting in SEQ ID NO 138, SEQ ID NO 140, SEQ ID NO 157, SEQ ID NO 159, SEQ ID NO 167, SEQ ID NO 168, SEQ ID NO 169, SEQ ID NO 171, SEQ ID NO 173, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 329, SEQ ID NO 330, SEQ ID NO 331 SEQ ID NO 333, SEQ ID NO 335, SEQ ID NO 336, SEQ ID NO 339, SEQ ID NO 341, SEQ ID NO 345, SEQ ID NO 347, SEQ ID NO 353, SEQ ID NO 360, SEQ ID NO 361, SEQ ID NO 364, SEQ ID NO 366, SEQ ID NO 367, SEQ ID NO 369, SEQ ID NO 790, SEQ ID NO 792, SEQ ID NO 793, SEQ ID NO 795, SEQ ID NO 969, SEQ ID NO 972, SEQ ID NO 981, SEQ ID NO 1081, SEQ ID NO 1083, SEQ ID NO 1129, SEQ ID NO 1140, SEQ ID NO 1141, SEQ ID NO 1151, SEQ ID NO 1158, SEQ ID NO 1159, SEQ ID NO 1162, SEQ ID NO 1165, SEQ ID NO 1166, SEQ ID NO 1167, SEQ ID NO 1169, SEQ ID NO 1170, SEQ ID NO 1171, SEQ ID NO 1185, SEQ ID NO 1186, SEQ ID NO 1194, SEQ ID NO 1198, SEQ ID NO 1200, SEQ ID NO 1203, SEQ ID NO 1262, SEQ ID NO 1264, SEQ ID NO 1267, SEQ ID NO 1269, SEQ ID NO 1520, SEQ ID NO 1522, SEQ ID NO 1523, SEQ ID NO 1524, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 2026, SEQ ID NO 2028, SEQ ID NO 2179 and SEQ ID NO 2181.

The group of polynucleotide probes represents a combination of 50 polynucleotide probe sets. The group allows to detect the variation of expression of 12 genes and/or their variants when they exist.

The invention also discloses a multiplicity of 50 polynucleotide probe sets chosen among 1640 polynucleotide probe sets as defined above.

Also, the invention relates to a multiplicity of at least 50 polynucleotide probe sets chosen among 1640 polynucleotide probe sets, the nucleic acid sequences of the polynucleotide probes contained in said 50 polynucleotide probe sets being the following nucleic acid sequences: SEQ ID NOs 136; 137; 138; 157; 158; 159; 167; 168; 169; 171; 172; 173; 177; 312; 313; 313; 314; 315; 316; 317; 324; 325; 326; 327; 328; 329; 330; 331; 333; 334; 335; 336; 339; 340; 341; 345; 346; 347; 348; 353; 360; 361; 364; 365; 366; 367; 368; 369; 370; 374; 375; 790; 791; 792; 793; 794; 795; 969; 972; 981;

1081; 1082; 1083; 1129; 1140; 1141; 1158; 1159; 1160; 1161; 1162; 1165; 1166; 1167; 1168; 1169; 1170; 1171; 1185; 1186; 1194; 1198; 1199; 1200; 1203; 1262; 1263; 1264; 1267; 1268; 1269; 1519; 1520; 1521; 1522; 1523; 1524; 1534; 1535; 1536; 1544; 1545; 1546; 1551; 1552; 1553; 1554; 1555; 1556; 1557; 2026; 2027; 2028; 2179; 2180 and 2181, each polynucleotide probe set containing from 1 to 4 of said polynucleotide probes, preferably, wherein SEQ ID NOs 167; 168; 177; 312; 313; 327; 328; 329; 331; 364; 365; 366; 368; 370; 1185; 1186; 1194; 1523; 1524; 1551; 1552 and 1553 are present twice, SEQ ID NO 316 is present in three copies and SEQ ID NO 315 is present in 5 copies.

In one preferred embodiment, the invention also discloses a multiplicity of 100 polynucleotide probe sets chosen among 1640 polynucleotide probe sets as defined above.

Also, the invention relates to a multiplicity of at least 100 polynucleotide probe sets as above defined, the nucleic acid sequences of the polynucleotides probes contained in said 100 polynucleotide probe sets being the following nucleic acid sequences: SEQ ID NO 120; 136; 137; 138; 154; 155; 156; 157; 158; 159; 167; 168; 169; 171; 172; 173; 174; 175; 176; 177; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 363; 364; 365; 366; 367; 368; 369; 370; 371; 374; 375; 376; 378; 379; 380; 381; 555; 556; 557; 558; 560; 561; 562; 566; 567; 788; 789; 790; 791; 792; 793; 794; 795; 800; 801; 802; 821; 822; 823; 969; 971; 972; 981; 1056; 1057; 1058; 1075; 1076; 1077; 1081; 1082; 1083; 1087; 1088; 1089; 1103; 1104; 1105; 1114; 1115; 1116; 1123; 1124; 1125; 1129; 1130; 1131; 1140; 1141; 1158; 1159; 1160; 1161; 1162; 1163; 1164; 1165; 1166; 1167; 1168; 1169; 1170; 1171; 1172; 1180; 1181; 1185; 1186; 1187; 1188; 1189; 1190; 1191; 1192; 1193; 1194; 1195; 1196; 1198; 1199; 1200; 1201; 1202; 1203; 1207; 1262; 1263; 1264; 1267; 1268; 1269; 1509; 1510; 1511; 1519; 1520; 1521; 1522; 1523; 1524; 1528; 1529; 1534; 1535; 1536; 1544; 1545; 1546; 1551; 1552; 1553; 1554; 1555; 1556; 1557; 1561; 1562; 1682; 1683; 1684; 1776; 1777; 1778; 2023; 2024; 2025; 2026; 2027; 2028; 2173; 2174; 2175; 2176; 2177; 2178; 2179; 2180; 2181; 2762; 2763; 2764; 2860; 2861; 2862; 2883; 2884 and 2885, each polynucleotide probe set containing from 1 to 4 of said polynucleotide probes, preferably, wherein SEQ ID NOs 167; 168; 177; 312; 313; 316; 317; 327; 329; 330; 353; 361; 364; 365; 366; 367; 368; 369; 370; 821; 822; 823; 1129; 1164; 1185; 1186; 1187; 1188; 1189; 1203; 1523; 1551; 1552 and 1553 are present twice, SEQ ID NOs 328; 331; 1162; 1194; 1519; 1520; 1521 and 1524 are present in three copies and SEQ ID NO 315 is present in 6 copies.

In another preferred embodiment, the invention also discloses a multiplicity of 150 polynucleotide probe sets chosen among 1640 polynucleotide probe sets as defined above.

In other word, the invention relates to a multiplicity of at least 150 polynucleotide probe sets previously defined, the nucleic acid sequences of the polynucleotides probes contained in said 150 polynucleotide probe sets being the following nucleic acid sequences: SEQ ID NOs 4; 5; 6; 120; 136; 137; 138; 154; 155; 156; 157; 158; 159; 167; 168; 169; 171; 172; 173; 174; 175; 176; 177; 197; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 367; 368; 369; 370; 371; 374; 375; 376; 377; 378; 379; 380; 381; 513; 514; 515; 552; 553; 554; 555; 556; 557; 558; 559; 560; 561; 562; 566; 567; 783; 784; 785; 788; 789; 790; 791; 792; 793; 794; 795; 796; 797; 798; 799; 800; 801; 802; 803; 804; 805; 806; 807; 808; 812; 813; 814; 818; 821; 822; 823; 968; 969; 970; 971; 972; 981; 1056; 1057; 1058; 1061; 1062; 1063; 1064; 1065; 1066; 1067; 1068; 1069; 1070; 1071; 1075; 1076; 1077; 1080; 1081; 1082; 1083; 1087; 1088; 1089; 1103; 1104; 1105; 1114; 1115; 1116; 1123; 1124; 1125; 1129; 1130; 1131; 1139; 1140; 1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1262; 1263; 1264; 1267; 1268; 1269; 1284; 1285; 1315; 1469; 1470; 1471; 1509; 1510; 1511; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1580; 1581; 1582; 1671; 1682; 1683; 1684; 1685; 1686; 1690; 1691; 1692; 1776; 1777; 1778; 1788; 1789; 1790; 1890; 1891; 1892; 1952; 1953; 1954; 1963; 2023; 2024; 2025; 2026; 2027; 2028; 2065; 2067; 2088; 2089; 2090; 2091; 2173; 2174; 2175; 2176; 2177; 2178; 2179; 2180; 2181; 2196; 2201; 2229; 2230; 2231; 2536; 2537; 2538; 2576; 2577; 2578; 2599; 2600; 2762; 2763; 2764; 2774; 2775; 2776; 2860; 2861; 2862; 2883; 2884 and 2885, each polynucleotide probe set containing from 1 to 4 of said polynucleotide probes, preferably, wherein SEQ ID NOs 167; 168; 177; 312; 313; 317; 327; 329; 330; 353; 361; 363; 364; 365; 366; 369; 370; 371; 558; 567; 796; 797; 801; 806; 807; 808; 813; 814; 821; 822; 823; 969; 1056; 1057; 1058; 1129; 1141; 1163; 1164; 1185; 1186; 1187; 1188; 1189; 1199; 1203; 1469; 1470; 1471; 1523; 1551; 1552 and 1553 are present twice, SEQ ID NOs 316; 328; 331; 368; 788; 1194; 1519; 1520; 1521; 1524 are present in three copies, SEQ ID NO 1162 is present in 4 copies and SEQ ID NO 315 is present in 6 copies.

Another preferred embodiment of the invention relates to a multiplicity of 200 polynucleotide probe sets chosen among 1640 polynucleotide probe sets as defined above.

Indeed, a preferred embodiment of the invention discloses a multiplicity of at least 200 polynucleotide probe sets defined above, the nucleic acid sequences of the polynucleotide probes contained in said 200 polynucleotide probe sets being the following nucleic acid sequences: SEQ ID NOs 4; 5; 6; 120; 121; 122; 123; 130; 131; 132; 136; 137; 138; 154; 155; 156; 157; 158; 159; 167; 168; 169; 171; 172; 173; 174; 175; 176; 177; 195; 196; 197; 198; 199; 200; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 368; 369; 370; 371; 374; 375; 376; 377; 378; 379; 380; 381; 513; 514; 515; 552; 553; 554; 555; 556; 557; 558; 559; 560; 561; 562; 563; 564; 565; 566; 567; 783; 784; 785; 788; 789; 790; 791; 792; 793; 794; 795; 796; 797; 798; 799; 800; 801; 802; 803; 804; 805; 806; 807; 808; 809; 810; 811; 812; 813; 814; 815; 816; 817; 818; 821; 822; 823; 824; 825; 826; 840; 841; 845; 846; 847; 868; 968; 969; 970; 971; 972; 973; 974; 975; 976; 977; 981; 1056; 1057; 1058; 1059; 1060; 1061; 1062; 1063; 1064; 1065; 1066; 1067; 1068; 1069; 1070; 1071; 1075; 1076; 1077; 1080; 1081; 1082; 1083; 1084; 1085; 1086; 1087; 1088; 1089; 1094; 1095; 1096; 1103; 1104; 1105; 1110; 1111; 1112; 1114; 1115; 1116; 1123; 1124; 1125; 1126; 1127; 1128; 1129; 1130; 1131; 1139; 1140;

1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1229; 1230; 1242; 1243; 1244; 1245; 1250; 1251; 1252; 1262; 1263; 1264; 1265; 1266; 1267; 1268; 1269; 1270; 1271; 1272; 1284; 1285; 1315; 1335; 1407; 1408; 1469; 1470; 1471; 1509; 1510; 1511; 1512; 1513; 1514; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1563; 1564; 1580; 1581; 1582; 1586; 1587; 1588; 1671; 1682; 1683; 1684; 1685; 1686; 1687; 1688; 1689; 1690; 1691; 1692; 1743; 1744; 1745; 1776; 1777; 1778; 1788; 1789; 1790; 1890; 1891; 1892; 1896; 1897; 1898; 1952; 1953; 1954; 1963; 1974; 2023; 2024; 2025; 2026; 2027; 2028; 2061; 2062; 2063; 2065; 2067; 2068; 2072; 2083; 2084; 2085; 2088; 2089; 2090; 2091; 2092; 2173; 2174; 2175; 2176; 2177; 2178; 2179; 2180; 2181; 2196; 2201; 2229; 2230; 2231; 2381; 2382; 2383; 2536; 2537; 2538; 2576; 2577; 2578; 2599; 2600; 2601; 2602; 2603; 2762; 2763; 2764; 2774; 2775; 2776; 2778; 2779; 2783; 2794; 2860; 2861; 2862; 2883; 2884 and 2885, each polynucleotide probe set containing from 1 to 4 of said polynucleotide probes, preferably, wherein SEQ ID NOs 167; 168; 177; 312; 313; 317; 327; 329; 330; 353; 361; 363; 364; 365; 366; 367; 369; 370; 371; 558; 567; 796; 797; 801; 806; 807; 808; 813; 814; 821; 822; 823; 845; 968; 970; 972; 1056; 1057; 1058; 1085; 1114; 1115; 1116; 1123; 1124; 1125; 1129; 1141; 1163; 1164; 1185; 1186; 1187; 1188; 1189; 1199; 1203; 1523; 1551; 1552; 1553; 1557; 1586; 1587; 1588; 1952; 1953; 1954; 2088; 2090; 2091; 2762; 2763 and 2764 are present twice, SEQ ID NOs 316; 328; 331; 368; 788; 1284; 1285; 1469; 1470; 1471; 1519; 1520; 1521; 1524; 2065; 2067 and 2089 are present in three copies, SEQ ID NO 1194 is present in 4 copies and SEQ ID NOs 315 and 1162 are present in 6 copies.

Another particular embodiment of the invention relates to a multiplicity of 1228 polynucleotide probe sets chosen among 1640 polynucleotide probe sets as defined above.

The invention, in a particular embodiment, relates to a multiplicity of at least 1228 polynucleotide probe sets as defined above, containing 3985 polynucleotide probes, the nucleic acid sequences of the polynucleotide probes contained in said 1228 polynucleotide probe sets being represented in the first 1228 lines of the Table 7.

The invention discloses, in another preferred embodiment, a multiplicity 1640 polynucleotide probe sets as defined above.

The invention related to a multiplicity of 1640 polynucleotide probe sets as previously defined, the nucleic acid sequences of the polynucleotide probes contained in said 1640 polynucleotide probe sets being represented in Table 7.

The invention also discloses a micro-array comprising or consisting in a multiplicity of polynucleotide probe sets as defined above.

Thus, the invention discloses a micro-array comprising the library of nucleic acid sequences consisting in SEQ ID NO 1 to SEQ ID NO 2938, or a multiplicity of polynucleotide probe sets:

corresponding to a multiplicity of 1228 polynucleotide probe sets comprising nucleic acid sequences chosen among the group consisting in SEQ ID NO 1 to SEQ ID NO 2938, or corresponding to a multiplicity of 200 polynucleotide probe sets comprising nucleic acid sequences consisting in SEQ ID NO 1 to SEQ ID NO 2938, or corresponding to a multiplicity of 150 polynucleotide probe sets comprising nucleic acid sequences consisting in SEQ ID NO 1 to SEQ ID NO 2938, or corresponding to a multiplicity of 100 polynucleotide probe sets comprising nucleic acid sequences consisting in SEQ ID NO 1 to SEQ ID NO 2938, and in particular consisting in SEQ ID NO 120, SEQ ID NO 138, SEQ ID NO 140, SEQ ID NO 154, SEQ ID NO 155, SEQ ID NO 156, SEQ ID NO 157, SEQ ID NO 159, SEQ ID NO 166, SEQ ID NO 167, SEQ ID NO 168, SEQ ID NO 169, SEQ ID NO 171, SEQ ID NO 173, SEQ ID NO 174, SEQ ID NO 175, SEQ ID NO 176, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 328, SEQ ID NO 329, SEQ ID NO 330, SEQ ID NO 331, SEQ ID NO 331, SEQ ID NO 332, SEQ ID NO 333, SEQ ID NO 335, SEQ ID NO 336, SEQ ID NO 337, SEQ ID NO 338, SEQ ID NO 339, SEQ ID NO 341, SEQ ID NO 345, SEQ ID NO 347, SEQ ID NO 349, SEQ ID NO 350, SEQ ID NO 351, SEQ ID NO 352, SEQ ID NO 353, SEQ ID NO 354, SEQ ID NO 355, SEQ ID NO 356, SEQ ID NO 360, SEQ ID NO 361, SEQ ID NO 363, SEQ ID NO 364, SEQ ID NO 364, SEQ ID NO 366, SEQ ID NO 367, SEQ ID NO 369, SEQ ID NO 369, SEQ ID NO 371, SEQ ID NO 376, SEQ ID NO 378, SEQ ID NO 379, SEQ ID NO 380, SEQ ID NO 381, SEQ ID NO 555, SEQ ID NO 556, SEQ ID NO 557, SEQ ID NO 558, SEQ ID NO 560, SEQ ID NO 561, SEQ ID NO 562, SEQ ID NO 566, SEQ ID NO 567, SEQ ID NO 788, SEQ ID NO 789, SEQ ID NO 790, SEQ ID NO 792, SEQ ID NO 793, SEQ ID NO 795, SEQ ID NO 800, SEQ ID NO 801, SEQ ID NO 802, SEQ ID NO 821, SEQ ID NO 822, SEQ ID NO 823, SEQ ID NO 969, SEQ ID NO 971, SEQ ID NO 972, SEQ ID NO 981, SEQ ID NO 1056, SEQ ID NO 1057, SEQ ID NO 1058, SEQ ID NO 1075, SEQ ID NO 1076, SEQ ID NO 1077, SEQ ID NO 1081, SEQ ID NO 1083, SEQ ID NO 1087, SEQ ID NO 1088, SEQ ID NO 1089, SEQ ID NO 1103, SEQ ID NO 1104, SEQ ID NO 1105, SEQ ID NO 1114, SEQ ID NO 1115, SEQ ID NO 1116, SEQ ID NO 1123, SEQ ID NO 1124, SEQ ID NO 1125, SEQ ID NO 1129, SEQ ID NO 1130, SEQ ID NO 1131, SEQ ID NO 1140, SEQ ID NO 1141, SEQ ID NO 1142, SEQ ID NO 1143, SEQ ID NO 1151, SEQ ID NO 1158, SEQ ID NO 1159, SEQ ID NO 1162, SEQ ID NO 1163, SEQ ID NO 1163, SEQ ID NO 1164, SEQ ID NO 1165, SEQ ID NO 1166, SEQ ID NO 1167, SEQ ID NO 1169, SEQ ID NO 1170, SEQ ID NO 1171, SEQ ID NO 1172, SEQ ID NO 1172, SEQ ID NO 1180, SEQ ID NO 1181, SEQ ID NO 1185, SEQ ID NO 1186, SEQ ID NO 1187, SEQ ID NO 1188, SEQ ID NO 1189, SEQ ID NO 1189, SEQ ID NO 1190, SEQ ID NO 1191, SEQ ID NO 1192, SEQ ID NO 1193, SEQ ID NO 1194, SEQ ID NO 1195, SEQ ID NO 1196, SEQ ID NO 1198, SEQ ID NO 1200, SEQ ID NO 1201, SEQ ID NO 1202, SEQ ID NO 1203, SEQ ID NO 1207, SEQ ID NO 1262, SEQ ID NO 1264, SEQ ID NO 1267, SEQ ID NO 1269, SEQ ID NO 1509, SEQ ID NO 1510, SEQ ID NO 1511, SEQ ID NO 1519, SEQ ID NO 1520, SEQ ID NO 1520, SEQ ID NO 1521, SEQ ID NO 1522, SEQ ID NO 1523, SEQ ID NO 1524, SEQ ID NO 1524, SEQ ID NO 1528, SEQ ID NO 1529, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 1561, SEQ ID NO 1562, SEQ ID NO 1682, SEQ ID NO 1683, SEQ ID NO 1684, SEQ ID NO 1776, SEQ ID NO 1777, SEQ ID NO 1778, SEQ ID NO 2023, SEQ ID NO 2024, SEQ ID NO 2025, SEQ ID NO 2026, SEQ ID NO 2028, SEQ ID NO 2173, SEQ ID NO 2174, SEQ ID NO 2175, SEQ ID NO 2176, SEQ ID NO 2177, SEQ ID NO 2178, SEQ ID NO 2179, SEQ ID NO 2181, SEQ ID NO 2762, SEQ ID NO 2763, SEQ ID NO 2764, SEQ ID NO 2860, SEQ ID NO 2861, SEQ ID NO 2862, SEQ ID NO 2883, SEQ ID NO 2884 and SEQ ID NO 2885, or corresponding to a multiplicity of 50 polynucleotide probe sets comprising nucleic acid sequences consisting in SEQ ID NO 1 to SEQ ID NO 2938, and in particular consisting in SEQ ID NO 138, SEQ ID NO 140, SEQ ID NO 157, SEQ ID NO 159, SEQ ID NO 167, SEQ ID NO 168, SEQ ID NO 169, SEQ ID NO 171, SEQ ID NO 173, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 329, SEQ ID NO 330, SEQ ID NO 331 SEQ ID NO 333, SEQ ID NO 335, SEQ ID NO 336, SEQ ID NO 339, SEQ ID NO 341, SEQ ID NO 345, SEQ ID NO 347, SEQ ID NO 353, SEQ ID NO 360, SEQ ID NO 361, SEQ ID NO 364, SEQ ID NO 366, SEQ ID NO 367, SEQ ID NO 369, SEQ ID NO 790, SEQ ID NO 792, SEQ ID NO 793, SEQ ID NO 795, SEQ ID NO 969, SEQ ID NO 972, SEQ ID NO 981, SEQ ID NO 1081, SEQ ID NO 1083, SEQ ID NO 1129, SEQ ID NO 1140, SEQ ID NO 1141, SEQ ID NO 1151, SEQ ID NO 1158, SEQ ID NO 1159, SEQ ID NO 1162, SEQ ID NO 1165, SEQ ID NO 1166, SEQ ID NO 1167, SEQ ID NO 1169, SEQ ID NO 1170, SEQ ID NO 1171, SEQ ID NO 1185, SEQ ID NO 1186, SEQ ID NO 1194, SEQ ID NO 1198, SEQ ID NO 1200, SEQ ID NO 1203, SEQ ID NO 1262, SEQ ID NO 1264, SEQ ID NO 1267, SEQ ID NO 1269, SEQ ID NO 1520, SEQ ID NO 1522, SEQ ID NO 1523, SEQ ID NO 1524, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 2026, SEQ ID NO 2028, SEQ ID NO 2179 and SEQ ID NO 2181.

The microarray refers to nucleic acid molecule covalently attached to an inert chemical surface, such as coated glass slides or gene chips, and to which a mobile DNA target is hybridized. All the commonly used surfaces can also serve as a support.

The invention discloses a method for the in vitro and/or ex vivo determination of the benign or malignant state of a breast tumor in a biological sample from a subject, by determining the variation of the expression of a gene, and/or at least one of its variants when present, of a sub-group comprising at least 12 genes among the genes of the group consisting in SEQ ID NO 5419 to SEQ ID NO 5677, comprising:

a) contacting nucleic acid molecules from said biological sample a multiplicity of polynucleotide probe sets, said multiplicity of polynucleotide probe sets consisting in a combination of pools of polynucleotide probe sets, each polynucleotide probe set containing at least one polynucleotide probe chosen among a library of nucleic acid sequences, each nucleic acid sequence specifically hybridizing with a gene, and/or at least one of its variants when present, said gene being chosen among the group of genes consisting in SEQ ID NO 5419 to SEQ ID NO 5677, each given gene, when it presents no variant, comprising at least one target region, the nucleic acid sequence of which is chosen among SEQ ID NO 2939 to SEQ ID NO 4578, said target region characterizing said gene, each given gene, when it presents at least one variant, comprising at least two target regions such that:
at least one of the respective nucleic acid sequences of said target region chosen among SEQ ID NO 2939 to SEQ ID NO 4578 is present in a given variant of said gene,
at least one of the respective nucleic acid sequences of said target region chosen among SEQ ID NO 2939 to SEQ ID NO 4578 is either absent in a given variant or is present in a configuration that differs from the one of said gene, said two target regions characterizing said gene,
each variant of a given gene presenting at least one target region, said target region being such that its respective nucleic acid sequence is chosen among SEQ ID NO 2939 to SEQ ID NO 4578, each variant is characterized by:
either the combination of the presence of at least one target region also present in the gene, the respective nucleic acid sequence of which being chosen among SEQ ID NO 2939 to SEQ ID NO 4578, and the absence of at least one target region present in the gene the respective nucleic acid sequence of which being chosen among SEQ ID NO 2939 to SEQ ID NO 4578,
or the presence of a target region, the respective nucleic acid sequence of which being chosen among SEQ ID NO 2939 to SEQ ID NO 4578, said target region presenting a configuration that does not naturally exist in the gene, each polynucleotide probe of a polynucleotide probe set hybridizes with a specific nucleic acid sequence contained in a given target region of the target regions which characterize a given gene, and/or at least one of its variants when present, each given gene, and its variants when present, is specifically recognized by at least a given polynucleotide probe set, each polynucleotide probe of a given pool of polynucleotide probe set being such that it hybridizes with a given gene, and/or at least one of its variants when present, and cannot hybridize with any other gene different from said given gene, and cannot hybridize with any other variants of a gene different from said given gene, b) determining a profile of expression variants of said genes from the detection of the nucleic acid complexes formed in the previous step, c) comparing said profile with a reference gene expression variant profile of a control subject, d) concluding, from the previous comparison, the benign or malignant state of the breast cancer in the subject.

Also, the invention relates to a method for the determination, preferably in vitro and/or ex vivo, of the benign or malignant state of a breast tumor in a biological sample from a subject, by determining the variation of the expression of
at least 12 determined genes belonging to a group of determined genes represented by the nucleotidic sequences SEQ ID NO: 5419 to SEQ ID NO: 5693 and
at least one variant of said genes at least 12 determined genes, when they exist, said 12 determined genes being represented by the following nucleotidic sequences:
SEQ ID NOs 5421; 5423; 5432; 5434; 5486; 5491; 5525; 5552; 5599; 5652; 5654 and 5683,
comprising:
(1) contacting nucleic acid molecules from said biological sample to a multiplicity of polynucleotide probe sets, said multiplicity of polynucleotide probe sets consisting in a combination of pools of polynucleotide probe sets, to allow the formation of a nucleic acid complex,
each polynucleotide probe set containing at least one polynucleotide probe chosen among a library of nucleic acid sequences, said library comprising or consisting of at least one copy each of the nucleic acids consisting of SEQ ID NO 1 to SEQ ID NO 2938,
said polynucleotide probes being such that the nucleic acid sequence of each polynucleotide probe specifically hybridizes with the nucleotidic sequence of one target region of one gene, and/or of at least one of its variants when present,
wherein
a) each given gene,
   a. when it presents no variant, comprises at least one target region, said target region characterizing said gene,
   b. when it presents one variant, comprises at least one target region, said target region characterizing said gene and its variant, and said variant being characterized by the fact that its nucleic acid sequence is shorter than the nucleic acid sequence of said gene,
   c. when it presents at least two variants, comprises at least two target regions, said two target regions characterizing said gene, such that:
      iii. at least one of the respective polynucleotidic sequences of said target region is present in a given variant of said gene, and
      iv. at least one of the respective polynucleotidic sequences of said target region is either
         absent in a given variant, or
         present in a given variant in a configuration that differs from the one of said gene,
         said variant being characterized by the fact that its nucleic acid sequence is shorter than the nucleic acid sequence of said gene,
b) each variant of a given gene presents at least one target region,
and
   if said variant is the unique variant of a gene, said variant has the same target than said gene, and
   if said variant is one of the variants of a gene that has at least two variants, each variant of said gene is characterized by either:
      a. the combination of the presence of at least one target region also present in the gene, and the absence of at least one target region present in the gene, or
      b. the combination of the presence of at least one target region also present in the gene, and the presence of a target region, said target region presenting a configuration that does not naturally exist in the gene,
c) the nucleotidic sequence of each given gene, and its variants when present, is specifically recognized by the nucleic acid sequences of polynucleotide probes contained in at least one given polynucleotide probe set,
d) the nucleic acid sequence of each polynucleotide probe of a polynucleotide probe set hybridizes with a specific polynucleotidic sequence contained in a given target region of the target regions which characterize a given gene, and/or at least one of its variants when present,
e) the nucleic acid sequence of each polynucleotide probe of a given pool of polynucleotide probe set being such that
   a. it hybridizes with the nucleotidic sequence of a given gene, and/or of at least one of its variants when present, and
   b. cannot hybridize with
      i. the nucleotidic sequence of any other gene different from said given gene, and
      ii. the nucleotidic sequence of any other variants of a gene different from said given gene,
(2) determining a profile of expression of said genes and of variants of said genes from the detection of the nucleic acid complexes formed in the previous step,
(3) comparing said profile with a reference expression profile of a control benign breast tumor, and/or a reference expression profile of a control malignant tumor, and
(4) concluding, from the previous comparison, that:
   if said profile of expression is similar to the reference expression profile of a control benign breast tumor, then the breast cancer is benign, and
   if said profile of expression is similar to the reference expression profile of a control malignant breast tumor, then the breast cancer is malignant,
   with the proviso that said gene, and its variants when present, is not KRT17, LOC440421, KRT6C and KRT6A, said genes being respectively represented by SEQ ID NO 5431; 5689; 5651 and 5682.

The invention also describes a method that allows the determination of the status, benign or malignant, of a breast tumor.

In the method of the invention, a biological sample corresponding to a breast tumor is used as a source of nucleic acid molecule. Said biological sample refers to a sample obtained from an organism or from components (e.g., cells) of an organism. The sample may be one of any biological tissue. Frequently the sample could be a "clinical sample" which is a sample derived from a patient. Such samples include, but are not limited to, FNA sample, CNB sample, ductal lavage and blood sample. Biological samples may also include sections of tissues such as frozen sections taken for histological purposes.

The subject from which biological sample is provided is commonly a woman, afflicted, or suspected to be afflicted by a breast tumor. The subject can also be a man, with, or suspected to have, a breast cancer. By extension, all the mammals can be diagnosed by the method provides by the invention, with the proviso that they could develop a breast tumor.

The extraction of the nucleic acid molecules of the samples is managed by a routine protocol used in the art. Advantageously, nucleic acid molecules extracted from the biological sample are RNA.

Then, the method of the invention consists in contacting nucleic acid molecules extracted from the biological sample of a subject, with a multiplicity of polynucleotide probe sets. Each polynucleotide probe set contains at least one polynucleotide probe.

The contact between the polynucleotide probe set, and more particularly the polynucleotide probes contained in each polynucleotide probe set, allows to form a nucleic acid complex between the nucleic acid molecule corresponding to a gene, and/or its variants when they exist, and a polynucleotide probe.

Preferably, before contacting the polynucleotide probes with the nucleic acid molecules, nucleic acid molecules are labeled with any know labeling agents (radioisotopes, enzymes, fluorescent molecule . . . ). The hybridization is made according a standard procedure, by modulating if necessary saline concentration and temperature. The protocol used for hybridization is well known by the skilled man in the art.

The presence and amount of the formed nucleic acid complex is detected, by the detection of hybridized nucleic acid molecules which have been labeled with labeling agent, with a specific detection method fitting to the used labeled agent.

According to the invention, each probe set that have hybridized with labeled nucleic acid molecules allows to attribute a value of hybridization. The given value is dependant of the labeling agent.

The compilation of all the values of hybridization allows to establish a profile that corresponds to the specific feature of the tumor assayed. This result is considered as a hallmark of the tumor assayed.

The tumor profile is compared to a reference profile, in particular profile of tumors deriving from biological sample of non afflicted by breast cancer subjects, or derived from biological sample of a subject afflicted by a benign or a malignant breast tumor. Alternatively, the tumor profile assayed can be compared with tumor profile of patients afflicted by benign breast tumor or malignant breast tumor. Typically, the comparison is made by using software commonly used in this type of comparison, and well known and described in the art.

From the comparison between tumor profile and reference profile, it is possible to determine if the breast tumor derived from the biological sample of a patient is a benign tumor or a malignant tumor.

In an advantageous embodiment, the invention discloses a method for the in vitro and/or ex vivo determination of the benign or malignant state of a breast tumor in a biological sample from a subject, wherein the determination of the variation of the expression of a gene, and/or at least one of its variants when present, of a sub-group comprising at least 12 genes among the genes of the group consisting in SEQ ID NO 5419 to SEQ ID NO 5677, comprises:

a) contacting nucleic acid molecules from said biological sample with a multiplicity of polynucleotide probe sets consisting in a combination of pools of polynucleotide probe sets chosen among 1640 probe sets of polynucleotides, each polynucleotide probe set containing at least one polynucleotide probe chosen among a library of nucleic acid sequences consisting in SEQ ID NO 1 to SEQ ID NO 2938, each nucleic acid sequence hybridizing with a gene, and/or at least one of its variants when present, said gene being chosen among the group of genes consisting in SEQ ID NO 5419 to SEQ ID NO 5677, each given gene, when it presents NO variant, comprising at least one target region, the nucleic acid sequence of which is chosen among SEQ ID NO 2939 TO SEQ ID NO 4578, said target region characterizing said gene, each given gene, when it presents at least one variant, comprising at least two target regions such that:

at least one of the respective nucleic acid sequences of said target region chosen among SEQ ID NO 2939 to SEQ ID NO 4578 is present in a given variant of said gene, at least one of the respective nucleic acid sequences of said target region chosen among SEQ ID NO 2939 to SEQ ID NO 4578 is either absent in a given variant or is present in a configuration that differs from the one of said gene, said two target regions characterizing said gene, each variant of a given gene presenting at least one target region, said target region being such that its respective nucleic acid sequence is chosen among SEQ ID NO 2939 to SEQ ID NO 4578, each variant is characterized by:

either the combination of the presence of at least one target region also present in the gene, the respective nucleic acid sequence of which being chosen among SEQ ID NO 2939 to SEQ ID NO 4578, and the absence of at least one target region present in the gene the respective nucleic acid sequence of which being chosen among SEQ ID NO 2939 to SEQ ID NO 4578, or the presence of a target region, the respective nucleic acid sequence of which being chosen among SEQ ID NO 2939 to SEQ ID NO 4578, said target region presenting a configuration that does not naturally exist in the gene, each polynucleotide probe of a polynucleotide probe set hybridizes with a specific nucleic acid sequence contained in a given target region of the target regions which characterize a given gene, and/or at least one of its variants when present, each given gene, and its variants when present, is specifically recognized by at least a given polynucleotide probe set, each polynucleotide probe of a given pool of polynucleotide probe set being such that it hybridizes with a given gene, and/or at least one of its variants when present, and cannot hybridize with any other gene different from said given gene, and cannot hybridize with any other variants of a gene different from said given gene, b) determining a profile of expression variants of said genes from the detection of the nucleic acid complexes formed in the previous step, c) comparing said profile with a reference gene expression variant profile of a control subject, d) concluding, from the previous comparison, the benign or malignant state of the breast cancer in the subject.

In one preferred embodiment, the invention relates to a method for the in vitro and/or ex vivo determination of the benign or malignant state of a breast tumor in a biological sample from a subject as defined above, by determining the variation of the expression of at least 20 determined genes of a group of determined genes represented by the nucleotidic sequences SEQ ID NO: 5419 to SEQ ID NO: 5693
said 20 determined genes being represented by the following nucleotidic sequences: SEQ ID Nos 5421; 5423; 5432; 5434; 5457; 5486; 5491; 5513; 5516; 5525; 5532; 5552; 5599; 5616; 5624; 5643; 5652; 5654; 5673 and 5683.

In one other preferred embodiment, the invention relates to a method for the in vitro and/or ex vivo determination of the benign or malignant state of a breast tumor in a biological sample from a subject such as defined above, by 35 determined genes of a group of determined genes represented by the nucleotidic sequences SEQ ID NO: 5419 to SEQ ID NO: 5693
  said 35 determined genes being represented by the following nucleotidic sequences:
  SEQ ID Nos 5421; 5423; 5431; 5432; 5434; 5440; 5457; 5462; 5470; 5486; 5491; 5505; 5513; 5516; 5525; 5532; 5546; 5552; 5594; 5599; 5601; 5603; 5616; 5618; 5624; 5627; 5630; 5643; 5645; 5652; 5654; 5660; 5669; 5673 and 5683.

Another preferred embodiment of the invention relates to a method for the in vitro and/or ex vivo determination of the benign or malignant state of a breast tumor in a biological sample from a subject as previously defined, by determining the variation of the expression of at least 43 determined genes of a group of determined genes represented by the nucleotidic sequences SEQ ID NO: 5419 to SEQ ID NO: 5693
  said 43 determined genes being represented by the following nucleotidic sequences:
  5486; 5491; 5499; 5505; 5513; 5516; 5520; 5525; 5532; 5546; 5549; 5552; 5594; 5599; 5601; 5603; 5616; 5618; 5623; 5624; 5627; 5630; 5643; 5645; 5651; 5652; 5654; 5660; 5669; 5673; 5683 and 5686.

Another particular embodiment of the invention relates to a method for the in vitro and/or ex vivo determination of the benign or malignant state of a breast tumor in a biological sample from a subject as defined above, by determining the variation of the expression of at least 206 determined genes of a group of determined genes represented by the nucleotidic sequences SEQ ID NO: 5419 to SEQ ID NO: 5693
  said 206 determined genes being represented by the following nucleotidic sequences:
  SEQ ID Nos 5420; 5421; 5422; 5423; 5425; 5426; 5427; 5428; 5429; 5430; 5431; 5432; 5434; 5435; 5436; 5437; 5438; 5439; 5440; 5441; 5442; 5443; 5444; 5445; 5446; 5447; 5449; 5450; 5451; 5452; 5453; 5454; 5455; 5456; 5457; 5459; 5460; 5461; 5462; 5463; 5465; 5467; 5468; 5470; 5473; 5475; 5476; 5479; 5480; 5482; 5484; 5485; 5486; 5487; 5488; 5489; 5490; 5491; 5492; 5493; 5495; 5496; 5497; 5498; 5499; 5502; 5503; 5505; 5506; 5507; 5508; 5509; 5511; 5512; 5513; 5515; 5516; 5517; 5518; 5519; 5520; 5523; 5524; 5525; 5526; 5528; 5529; 5530; 5531; 5532; 5533; 5534; 5536; 5538; 5539; 5540; 5543; 5544; 5545; 5546; 5547; 5549; 5550; 5552; 5553; 5554; 5556; 5558; 5559; 5560; 5562; 5563; 5564; 5565; 5566; 5567; 5568; 5569; 5570; 5571; 5573; 5574; 5575; 5576; 5577; 5578; 5581; 5582; 5585; 5587; 5588; 5590; 5591; 5593; 5594; 5595; 5597; 5598; 5599; 5600; 5601; 5602; 5603; 5604; 5605; 5606; 5608; 5609; 5610; 5611; 5612; 5613; 5615; 5616; 5617; 5618; 5622; 5623; 5624; 5625; 5627; 5629; 5630; 5631; 5632; 5633; 5634; 5635; 5637; 5638; 5639; 5640; 5641; 5642; 5643; 5644; 5645; 5647; 5648; 5649; 5651; 5652; 5653; 5654; 5656; 5657; 5658; 5660; 5661; 5665; 5667; 5669; 5672; 5673; 5675; 5676; 5677; 5678; 5680; 5681; 5683; 5684; 5686; 5687; 5689 and 5692.

In another preferred embodiment, the invention discloses a method for the in vitro and/or ex vivo determination of the benign or malignant state of a breast tumor in a biological sample from a subject such as defined above, by determining the variation of the expression of 275 determined genes represented by the nucleotidic sequences SEQ ID NO: 5419 to SEQ ID NO: 5693.

Another particular embodiment of the invention relates to a method for the in vitro and/or ex vivo determination of the benign or malignant state of a breast tumor in a biological sample from a subject such as defined above, wherein said variant being represented by the nucleic acid sequences SEQ ID NO 4579 to SEQ ID NO 5418 and SEQ ID NO 5694, the correspondence between each variant and its corresponding gene being represented in Table 1A-E and Table 6.

In still another embodiment, the invention relates to a method for the in vitro and/or ex vivo determination of the benign or malignant state of a breast tumor in a biological sample from a subject as defined above, wherein target regions are characterized by the polynucleotide sequences SEQ ID NO 2939 to 4578, the each target region of each gene, and of each variant when they exist, being represented in Table 6.

In one other preferred embodiment, the invention relates to a method for the in vitro and/or ex vivo determination of the benign or malignant state of a breast tumor in a biological sample from a subject such as previously defined, wherein each polynucleotide probe contained in a polynucleotide probe set is represented by the nucleic acid sequence of the library consisting in SEQ ID NO 1 to SEQ ID NO 2938,
the correspondence between each polynucleotide probe and its corresponding target region, said target region corresponding to a gene and its variants when present, being represented in Table 6.

In another advantageous embodiment, the invention relates to a method for the in vitro and/or ex vivo determination of the benign or malignant state of a breast tumor in a biological sample from a subject, wherein the sub-group of genes is constituted by 12 to 259 genes chosen among the group consisting in SEQ ID NO 5419 to SEQ ID NO 5677.

In another embodiment, the invention discloses a method for the in vitro and/or ex vivo determination of the benign or malignant state of a breast tumor described above, wherein the sub-group of genes is constituted by the 259 genes of the group consisting in SEQ ID NO 5419 to SEQ ID NO 5677.

In a more particular embodiment, the invention relates to a method for the in vitro and/or ex vivo determination of the benign or malignant state of a breast tumor in a biological sample from a subject, wherein said set of polynucleotide probes are chosen among the group consisting in:

at least 50 polynucleotide probe sets, particularly at least 100 polynucleotide probe sets, more particularly at least 150 polynucleotide probes sets, more particularly at least 200 polynucleotide probe sets, more particularly at least 1228 polynucleotide probe sets and more particularly 1640 polynucleotide probe sets of the library of nucleic acid sequences consisting in SEQ ID NO 1 to SEQ ID NO 2938.

The sub-groups of 50, 100, 150, 200 polynucleotide probe sets are defined as the Top sub-groups allowing to determine the benign or malignant status of the tumor.

It is also disclosed in the invention that the multiplicity of probe sets can be constituted by at least 300 polynucleotide probe sets, more particularly at least 400 polynucleotide probe sets, more particularly at least 500 polynucleotide probe sets, more particularly at least 600 polynucleotide probe sets, more particularly at least 700 polynucleotide probe sets, more particularly at least 800 polynucleotide probe sets, more particularly at least 900 polynucleotide probe sets, more particularly at least 1000 polynucleotide probe sets, more particularly at least 1100 polynucleotide probe sets, more particularly at least 1228 polynucleotide probe sets, more particularly at least 1400 polynucleotide probe sets, and more particularly 1640 polynucleotide probe sets.

All the polynucleotide probes contained in the polynucleotide probe sets used in the method of the invention are chosen among a library of nucleic acid sequences consisting SEQ ID NO 1 to SEQ ID NO 2938.

In one embodiment, the invention discloses a method described above, wherein a variant of a given gene is chosen among the group of variants consisting in SEQ ID NO 4579 to SEQ ID NO 5418.

The method of the invention allows to detect the variation of expression genes, and their variants when they exist, said genes being characterized in that they consist in the nucleic acid sequences chosen among the group consisting in SEQ ID NO 5419 to SEQ ID NO 5677 and said variants being characterized in that they consist in the nucleic acid sequence chosen among the group consisting in SEQ ID NO 4579 to SEQ ID NO 5418.

In the invention, it is also disclosed a method for the in vitro and/or ex vivo determination of the benign or malignant state of a breast tumor, wherein the variation of expression of a gene, and/or at least one of its variants when present, said gene being chosen in the group consisting in SEQ ID NO 5419 to SEQ ID NO 5693, is Over represented (Up-regulated), or Under represented (Down-regulated).

Each gene expression, and expression of its variants if they exist, revealed by the method of the invention corresponds to an expression product of a gene of the group consisting in SEQ ID NO 5419 to SEQ ID NO 5693.

These variants are normally expressed in a subject non afflicted by breast cancer. These variants are also expressed in the biological of subject afflicted by benign breast cancer or malignant breast cancer. Each variant have a specific expression level corresponding to the state of the breast cancer. Each variant can then be overexpressed compare to the same variant expressed in a normal subject, or under expressed comparing to the same variant expressed in a normal subject.

The genes, and/or their variants are up-regulated, preferably when their expression levels are more than 1.7 fold higher than the expression levels of said genes in a patient non afflicted by a breast tumor, and significantly different (preferably with a significant coefficient value of less than 0.05). The genes, and/or their variants are down-regulated, preferably when their expression levels are less than 1.7 fold lower than the expression levels of said genes in a patient non afflicted by a breast tumor, and significantly different (preferably with a significant coefficient value of less than 0.05).

In a particular embodiment, the invention discloses a method described above, wherein the nucleic acid molecules from the biological sample of the subject are mRNA/or cDNA, said mRNA resulting from the expression of the genes consisting in SEQ ID NO 5419 to SEQ ID NO 5693, and/or at least one of their variants when present, represented by the nucleotidic sequences SEQ ID NO 4579 to SEQ ID NO 5418 and SEQ ID NO 5694.

In the invention, nucleic acid molecules are extracted from the biological sample of the subject, prior to be contacted with the set of polynucleotide probes, immobilized in a support.

The extraction and preparation of said nucleic acid molecules from the biological sample of the subject is made with a routine protocol commonly used by a skilled man in the art.

More particularly, the RNA are extracted from the biological sample, eventually, mRNA are isolated from the total RNA. In the case of the use of cDNA, mRNA are reverse-transcripted with a standard procedure.

The invention relates to a kit for the in vitro and/or ex vivo determination of benign or malignant status of a breast tumor, comprising:

a multiplicity as defined above, or a microarray as defined above.

The invention relates to a kit for the in vitro and/or ex vivo determination of benign or malignant status of a breast tumor, comprising the following group of polynucleotide probes:

SEQ ID NOs 136; 137; 138; 157; 158; 159; 167; 168; 169; 171; 172; 173; 177; 312; 313; 313; 314; 315; 316; 317; 324; 325; 326; 327; 328; 329; 330; 331; 333; 334; 335; 336; 339; 340; 341; 345; 346; 347; 348; 353; 360; 361; 364; 365; 366; 367; 368; 369; 370; 374; 375; 790; 791; 792; 793; 794; 795; 969; 972; 981; 1081; 1082; 1083; 1129; 1140; 1141; 1158; 1159; 1160; 1161; 1162; 1165; 1166; 1167; 1168; 1169; 1170; 1171; 1185; 1186; 1194; 1198; 1199; 1200; 1203; 1262; 1263; 1264; 1267; 1268; 1269; 1519; 1520; 1521; 1522; 1523; 1524; 1534; 1535; 1536; 1544; 1545; 1546; 1551; 1552; 1553; 1554; 1555; 1556; 1557; 2026; 2027; 2028; 2179; 2180 and 2181, preferably, wherein SEQ ID NOs 167; 168; 177; 312; 313; 327; 328; 329; 331; 364; 365; 366; 368; 370; 1185; 1186; 1194; 1523; 1524; 1551; 1552 and 1553 are present twice, SEQ ID NO 316 is present in three copies and SEQ ID NO 315 is present in 5 copies, or SEQ ID NO 120; 136; 137; 138; 154; 155; 156; 157; 158; 159; 167; 168; 169; 171; 172; 173; 174; 175; 176; 177; 312; 313; 314; 315; 316; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 363; 364; 365; 366; 367;

368; 369; 370; 371; 374; 375; 376; 378; 379; 380; 381; 555; 556; 557; 558; 560; 561; 562; 566; 567; 788; 789; 790; 791; 792; 793; 794; 795; 800; 801; 802; 821; 822; 823; 969; 971; 972; 981; 1056; 1057; 1058; 1075; 1076; 1077; 1081; 1082; 1083; 1087; 1088; 1089; 1103; 1104; 1105; 1114; 1115; 1116; 1123; 1124; 1125; 1129; 1130; 1131; 1140; 1141; 1158; 1159; 1160; 1161; 1162; 1163; 1164; 1165; 1166; 1167; 1168; 1169; 1170; 1171; 1172; 1180; 1181; 1185; 1186; 1187; 1188; 1189; 1190; 1191; 1192; 1193; 1194; 1195; 1196; 1198; 1199; 1200; 1201; 1202; 1203; 1207; 1262; 1263; 1264; 1267; 1268; 1269; 1509; 1510; 1511; 1519; 1520; 1521; 1522; 1523; 1524; 1528; 1529; 1534; 1535; 1536; 1544; 1545; 1546; 1551; 1552; 1553; 1554; 1555; 1556; 1557; 1561; 1562; 1682; 1683; 1684; 1776; 1777; 1778; 2023; 2024; 2025; 2026; 2027; 2028; 2173; 2174; 2175; 2176; 2177; 2178; 2179; 2180; 2181; 2762; 2763; 2764; 2860; 2861; 2862; 2883; 2884 and 2885, preferably, wherein SEQ ID NOs 167; 168; 177; 312; 313; 316; 317; 327; 329; 330; 353; 361; 364; 365; 366; 367; 368; 369; 370; 821; 822; 823; 1129; 1164; 1185; 1186; 1187; 1188; 1189; 1203; 1523; 1551; 1552 and 1553 are present twice, SEQ ID NOs 328; 331; 1162; 1194; 1519; 1520; 1521 and 1524 are present in three copies and SEQ ID NO 315 is present in 6 copies, or SEQ ID NOs 4; 5; 6; 120; 136; 137; 138; 154; 155; 156; 157; 158; 159; 167; 168; 169; 171; 172; 173; 174; 175; 176; 177; 197; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 367; 368; 369; 370; 371; 374; 375; 376; 377; 378; 379; 380; 381; 513; 514; 515; 552; 553; 554; 555; 556; 557; 558; 559; 560; 561; 562; 566; 567; 783; 784; 785; 788; 789; 790; 791; 792; 793; 794; 795; 796; 797; 798; 799; 800; 801; 802; 803; 804; 805; 806; 807; 808; 812; 813; 814; 818; 821; 822; 823; 968; 969; 970; 971; 972; 981; 1056; 1057; 1058; 1061; 1062; 1063; 1064; 1065; 1066; 1067; 1068; 1069; 1070; 1071; 1075; 1076; 1077; 1080; 1081; 1082; 1083; 1087; 1088; 1089; 1103; 1104; 1105; 1114; 1115; 1116; 1123; 1124; 1125; 1129; 1130; 1131; 1139; 1140; 1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1262; 1263; 1264; 1267; 1268; 1269; 1284; 1285; 1315; 1469; 1470; 1471; 1509; 1510; 1511; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1580; 1581; 1582; 1671; 1682; 1683; 1684; 1685; 1686; 1690; 1691; 1692; 1776; 1777; 1778; 1788; 1789; 1790; 1890; 1891; 1892; 1952; 1953; 1954; 1963; 2023; 2024; 2025; 2026; 2027; 2028; 2065; 2067; 2088; 2089; 2090; 2091; 2173; 2174; 2175; 2176; 2177; 2178; 2179; 2180; 2181; 2196; 2201; 2229; 2230; 2231; 2536; 2537; 2538; 2576; 2577; 2578; 2599; 2600; 2762; 2763; 2764; 2774; 2775; 2776; 2860; 2861; 2862; 2883; 2884 and 2885, preferably, wherein SEQ ID NOs 167; 168; 177; 312; 313; 317; 327; 329; 330; 353; 361; 363; 364; 365; 366; 369; 370; 371; 558; 567; 796; 797; 801; 806; 807; 808; 813; 814; 821; 822; 823; 969; 1056; 1057; 1058; 1129; 1141; 1163; 1164; 1185; 1186; 1187; 1188; 1189; 1199; 1203; 1469; 1470; 1471; 1523; 1551; 1552 and 1553 are present twice, SEQ ID NOs 316; 328; 331; 368; 788; 1194; 1519; 1520; 1521; 1524 are present in three copies, SEQ ID NO 1162 is present in 4 copies and SEQ ID NO 315 is present in 6 copies, or SEQ ID NOs 4; 5; 6; 120; 121; 122; 123; 130; 131; 132; 136; 137; 138; 154; 155; 156; 157; 158; 159; 167; 168; 169; 171; 172; 173; 174; 175; 176; 177; 195; 196; 197; 198; 199; 200; 248; 254; 255; 305; 306; 307; 312; 313; 314; 315; 316; 317; 324; 325; 326; 327; 328; 329; 330; 331; 332; 333; 334; 335; 336; 337; 338; 339; 340; 341; 345; 346; 347; 348; 349; 350; 351; 352; 353; 354; 355; 356; 360; 361; 362; 363; 364; 365; 366; 367; 368; 369; 370; 371; 374; 375; 376; 377; 378; 379; 380; 381; 513; 514; 515; 552; 553; 554; 555; 556; 557; 558; 559; 560; 561; 562; 563; 564; 565; 566; 567; 783; 784; 785; 788; 789; 790; 791; 792; 793; 794; 795; 796; 797; 798; 799; 800; 801; 802; 803; 804; 805; 806; 807; 808; 809; 810; 811; 812; 813; 814; 815; 816; 817; 818; 821; 822; 823; 824; 825; 826; 840; 841; 845; 846; 847; 868; 968; 969; 970; 971; 972; 973; 974; 975; 976; 977; 981; 1056; 1057; 1058; 1059; 1060; 1061; 1062; 1063; 1064; 1065; 1066; 1067; 1068; 1069; 1070; 1071; 1075; 1076; 1077; 1080; 1081; 1082; 1083; 1084; 1085; 1086; 1087; 1088; 1089; 1094; 1095; 1096; 1103; 1104; 1105; 1110; 1111; 1112; 1114; 1115; 1116; 1123; 1124; 1125; 1126; 1127; 1128; 1129; 1130; 1131; 1139; 1140; 1141; 1158; 1159; 1160; 1161; 1162; 1163; 1164; 1165; 1166; 1167; 1168; 1169; 1170; 1171; 1172; 1174; 1175; 1176; 1180; 1181; 1185; 1186; 1187; 1188; 1189; 1190; 1191; 1192; 1193; 1194; 1195; 1196; 1197; 1198; 1199; 1200; 1201; 1202; 1203; 1204; 1205; 1206; 1207; 1229; 1230; 1242; 1243; 1244; 1245; 1250; 1251; 1252; 1262; 1263; 1264; 1265; 1266; 1267; 1268; 1269; 1270; 1271; 1272; 1284; 1285; 1315; 1335; 1407; 1408; 1469; 1470; 1471; 1509; 1510; 1511; 1512; 1513; 1514; 1515; 1516; 1517; 1519; 1520; 1521; 1522; 1523; 1524; 1528; 1529; 1534; 1535; 1536; 1537; 1538; 1539; 1544; 1545; 1546; 1550; 1551; 1552; 1553; 1554; 1555; 1556; 1557; 1558; 1559; 1560; 1561; 1562; 1563; 1564; 1580; 1581; 1582; 1586; 1587; 1588; 1671; 1682; 1683; 1684; 1685; 1686; 1687; 1688; 1689; 1690; 1691; 1692; 1743; 1744; 1745; 1776; 1777; 1778; 1788; 1789; 1790; 1890; 1891; 1892; 1896; 1897; 1898; 1952; 1953; 1954; 1963; 1974; 2023; 2024; 2025; 2026; 2027; 2028; 2061; 2062; 2063; 2065; 2067; 2068; 2072; 2083; 2084; 2085; 2088; 2089; 2090; 2091; 2092; 2173; 2174; 2175; 2176; 2177; 2178; 2179; 2180; 2181; 2196; 2201; 2229; 2230; 2231; 2381; 2382; 2383; 2536; 2537; 2538; 2576; 2577; 2578; 2599; 2600; 2601; 2602; 2603; 2762; 2763; 2764; 2774; 2775; 2776; 2778; 2779; 2783; 2794; 2860; 2861; 2862; 2883; 2884 and 2885, preferably, wherein SEQ ID NOs 167; 168; 177; 312; 313; 317; 327; 329; 330; 353; 361; 363; 364; 365; 366; 367; 369; 370; 371; 558; 567; 796; 797; 801; 806; 807; 808; 813; 814; 821; 822; 823; 845; 968; 970; 972; 1056; 1057; 1058; 1085; 1114; 1115; 1116; 1123; 1124; 1125; 1129; 1141; 1163; 1164; 1185; 1186; 1187; 1188; 1189; 1199; 1203; 1523;

1551; 1552; 1553; 1557; 1586; 1587; 1588; 1952; 1953; 1954; 2088; 2090; 2091; 2762; 2763 and 2764 are present twice, SEQ ID NOs 316; 328; 331; 368; 788; 1284; 1285; 1469; 1470; 1471; 1519; 1520; 1521; 1524; 2065; 2067 and 2089 are present in three copies, SEQ ID NO 1194 is present in 4 copies and SEQ ID NOs 315 and 1162 are present in 6 copies, or
- the polynucleotide probes contained in said 1228 polynucleotide probe sets being represented in the first 1228 lines of the Table 7, or
- the nucleic acid sequence of the polynucleotide probes contained in said 1640 polynucleotide probe sets being represented in Table 7.

The invention also relates to
- a micro-array comprising the library of nucleic acid sequences consisting in SEQ ID NO 1 to SEQ ID NO 2938, or
- a multiplicity of polynucleotide probe sets chosen among the group consisting in:
  - a multiplicity of 1228 polynucleotide probe sets comprising nucleic acid sequences chosen among the group consisting in SEQ ID NO 1 to SEQ ID NO 2938, or
- a multiplicity of 200 polynucleotide probe sets comprising nucleic acid sequences consisting in SEQ ID NO 1 to SEQ ID NO 2938, or
- a multiplicity of 150 polynucleotide probe sets comprising nucleic acid sequences consisting in SEQ ID NO 1 to SEQ ID NO 2938, or
- a multiplicity of 100 polynucleotide probe sets comprising nucleic acid sequences consisting in SEQ ID NO 1 to SEQ ID NO 2938, and in particular consisting in SEQ ID NO 120, SEQ ID NO 138, SEQ ID NO 140, SEQ ID NO 154, SEQ ID NO 155, SEQ ID NO 156, SEQ ID NO 157, SEQ ID NO 159, SEQ ID NO 166, SEQ ID NO 167, SEQ ID NO 168, SEQ ID NO 169, SEQ ID NO 171, SEQ ID NO 173, SEQ ID NO 174, SEQ ID NO 175, SEQ ID NO 176, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 328, SEQ ID NO 329, SEQ ID NO 330, SEQ ID NO 331, SEQ ID NO 331, SEQ ID NO 332, SEQ ID NO 333, SEQ ID NO 335, SEQ ID NO 336, SEQ ID NO 337, SEQ ID NO 338, SEQ ID NO 339, SEQ ID NO 341, SEQ ID NO 345, SEQ ID NO 347, SEQ ID NO 349, SEQ ID NO 350, SEQ ID NO 351, SEQ ID NO 352, SEQ ID NO 353, SEQ ID NO 354, SEQ ID NO 355, SEQ ID NO 356, SEQ ID NO 360, SEQ ID NO 361, SEQ ID NO 363, SEQ ID NO 364, SEQ ID NO 364, SEQ ID NO 366, SEQ ID NO 367, SEQ ID NO 369, SEQ ID NO 369, SEQ ID NO 371, SEQ ID NO 376, SEQ ID NO 378, SEQ ID NO 379, SEQ ID NO 380, SEQ ID NO 381, SEQ ID NO 555, SEQ ID NO 556, SEQ ID NO 557, SEQ ID NO 558, SEQ ID NO 560, SEQ ID NO 561, SEQ ID NO 562, SEQ ID NO 566, SEQ ID NO 567, SEQ ID NO 788, SEQ ID NO 789, SEQ ID NO 790, SEQ ID NO 792, SEQ ID NO 793, SEQ ID NO 795, SEQ ID NO 800, SEQ ID NO 801, SEQ ID NO 802, SEQ ID NO 821, SEQ ID NO 822, SEQ ID NO 823, SEQ ID NO 969, SEQ ID NO 971, SEQ ID NO 972, SEQ ID NO 981, SEQ ID NO 1056, SEQ ID NO 1057, SEQ ID NO 1058, SEQ ID NO 1075, SEQ ID NO 1076, SEQ ID NO 1077, SEQ ID NO 1081, SEQ ID NO 1083, SEQ ID NO 1087, SEQ ID NO 1088, SEQ ID NO 1089, SEQ ID NO 1103, SEQ ID NO 1104, SEQ ID NO 1105, SEQ ID NO 1114, SEQ ID NO 1115, SEQ ID NO 1116, SEQ ID NO 1123, SEQ ID NO 1124, SEQ ID NO 1125, SEQ ID NO 1129, SEQ ID NO 1130, SEQ ID NO 1131, SEQ ID NO 1140, SEQ ID NO 1141, SEQ ID NO 1142, SEQ ID NO 1143, SEQ ID NO 1151, SEQ ID NO 1158, SEQ ID NO 1159, SEQ ID NO 1162, SEQ ID NO 1163, SEQ ID NO 1163, SEQ ID NO 1164, SEQ ID NO 1165, SEQ ID NO 1166, SEQ ID NO 1167, SEQ ID NO 1169, SEQ ID NO 1170, SEQ ID NO 1171, SEQ ID NO 1172, SEQ ID NO 1172, SEQ ID NO 1180, SEQ ID NO 1181, SEQ ID NO 1185, SEQ ID NO 1186, SEQ ID NO 1187, SEQ ID NO 1188, SEQ ID NO 1189, SEQ ID NO 1189, SEQ ID NO 1190, SEQ ID NO 1191, SEQ ID NO 1192, SEQ ID NO 1193, SEQ ID NO 1194, SEQ ID NO 1195, SEQ ID NO 1196, SEQ ID NO 1198, SEQ ID NO 1200, SEQ ID NO 1201, SEQ ID NO 1202, SEQ ID NO 1203, SEQ ID NO 1207, SEQ ID NO 1262, SEQ ID NO 1264, SEQ ID NO 1267, SEQ ID NO 1269, SEQ ID NO 1509, SEQ ID NO 1510, SEQ ID NO 1511, SEQ ID NO 1519, SEQ ID NO 1520, SEQ ID NO 1520, SEQ ID NO 1521, SEQ ID NO 1522, SEQ ID NO 1523, SEQ ID NO 1524, SEQ ID NO 1524, SEQ ID NO 1528, SEQ ID NO 1529, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 1561, SEQ ID NO 1562, SEQ ID NO 1682, SEQ ID NO 1683, SEQ ID NO 1684, SEQ ID NO 1776, SEQ ID NO 1777, SEQ ID NO 1778, SEQ ID NO 2023, SEQ ID NO 2024, SEQ ID NO 2025, SEQ ID NO 2026, SEQ ID NO 2028, SEQ ID NO 2173, SEQ ID NO 2174, SEQ ID NO 2175, SEQ ID NO 2176, SEQ ID NO 2177, SEQ ID NO 2178, SEQ ID NO 2179, SEQ ID NO 2181, SEQ ID NO 2762, SEQ ID NO 2763, SEQ ID NO 2764, SEQ ID NO 2860, SEQ ID NO 2861, SEQ ID NO 2862, SEQ ID NO 2883, SEQ ID NO 2884 and SEQ ID NO 2885, or
- a multiplicity of 50 polynucleotide probe sets comprising nucleic acid sequences consisting in SEQ ID NO 1 to SEQ ID NO 2938, and in particular consisting in SEQ ID NO 138, SEQ ID NO 140, SEQ ID NO 157, SEQ ID NO 159, SEQ ID NO 167, SEQ ID NO 168, SEQ ID NO 169, SEQ ID NO 171, SEQ ID NO 173, SEQ ID NO 177, SEQ ID NO 312, SEQ ID NO 314, SEQ ID NO 315, SEQ ID NO 317, SEQ ID NO 324, SEQ ID NO 326, SEQ ID NO 327, SEQ ID NO 329, SEQ ID NO 330, SEQ ID NO 331 SEQ ID NO 333, SEQ ID NO 335, SEQ ID NO 336, SEQ ID NO 339, SEQ ID NO 341, SEQ ID NO 345, SEQ ID NO 347, SEQ ID NO 353, SEQ ID NO 360, SEQ ID NO 361, SEQ ID NO 364, SEQ ID NO 366, SEQ ID NO 367, SEQ ID NO 369, SEQ ID NO 790, SEQ ID NO 792, SEQ ID NO 793, SEQ ID NO 795, SEQ ID NO 969, SEQ ID NO 972, SEQ ID NO 981, SEQ ID NO 1081, SEQ ID NO 1083, SEQ ID NO 1129, SEQ ID NO 1140, SEQ ID NO 1141, SEQ ID NO 1151, SEQ ID NO 1158, SEQ ID NO 1159, SEQ ID NO 1162, SEQ ID NO 1165, SEQ ID NO 1166, SEQ ID NO 1167, SEQ ID NO 1169, SEQ ID NO 1170, SEQ ID NO 1171, SEQ ID NO 1185, SEQ ID NO 1186, SEQ ID NO 1194, SEQ ID NO 1198, SEQ ID NO 1200, SEQ ID NO 1203, SEQ ID NO 1262, SEQ ID NO 1264, SEQ ID NO 1267, SEQ ID NO 1269, SEQ ID NO 1520, SEQ ID NO 1522, SEQ ID NO 1523, SEQ ID NO 1524, SEQ ID NO 1534, SEQ ID NO 1536, SEQ ID NO 1544, SEQ ID NO 1546, SEQ ID NO 1551, SEQ ID NO 1553, SEQ ID NO 1554, SEQ ID NO 1556, SEQ ID NO 1557, SEQ ID NO 2026, SEQ ID NO 2028, SEQ ID NO 2179 and SEQ ID NO 2181.

Preferably in the kit of the invention, the micro-array comprises 1228 polynucleotide probe sets that represent the best multiplicity of polynucleotide probe sets to characterize efficiently the benign or malignant status of the breast tumor of a subject.

Optionally, the kit of the invention may contain protocol and molecules to label nucleic acid molecules used to be contacted with the micro-array. Also, the kit of the invention may contain protocol and material for the extraction and purification of the nucleic acid molecules from the biological sample of a subject.

The contain of the kit is not limited to the described materials and protocols described above, and may contain any other material or procedures that can help a skilled man in the art to use the kit of the invention.

FIGS. 1 TO 6 ILLUSTRATE THE INVENTION

FIG. 1A represents a gene containing 3 exons, and its variants that lack at least one exon. T represents a Target region. The "bar code" associated to the presence or absence of a target region is indicated: 1=present; 0=absent.

FIG. 1B represents a gene containing 3 exons, and its variant that lacks one exon. T represents a Target region. The "bar code" associated to the presence or absence of a target region is indicated: 1=present; 0=absent.

FIG. 3A represents a gene having no variant and having one target region.

FIG. 3B represents a gene having no variant and having two target regions.

FIG. 3C represents a gene having one variant and having one target region.

FIG. 3D represents a gene having one variant and having two target regions.

FIG. 3E represents a gene having two variants and having two target regions.

FIG. 3F represents a gene having two variants and having three target regions.

FIG. 3G represents a gene having two variants and having three target regions, one of its target regions being in a configuration different in variant and gene.

Figure 4:
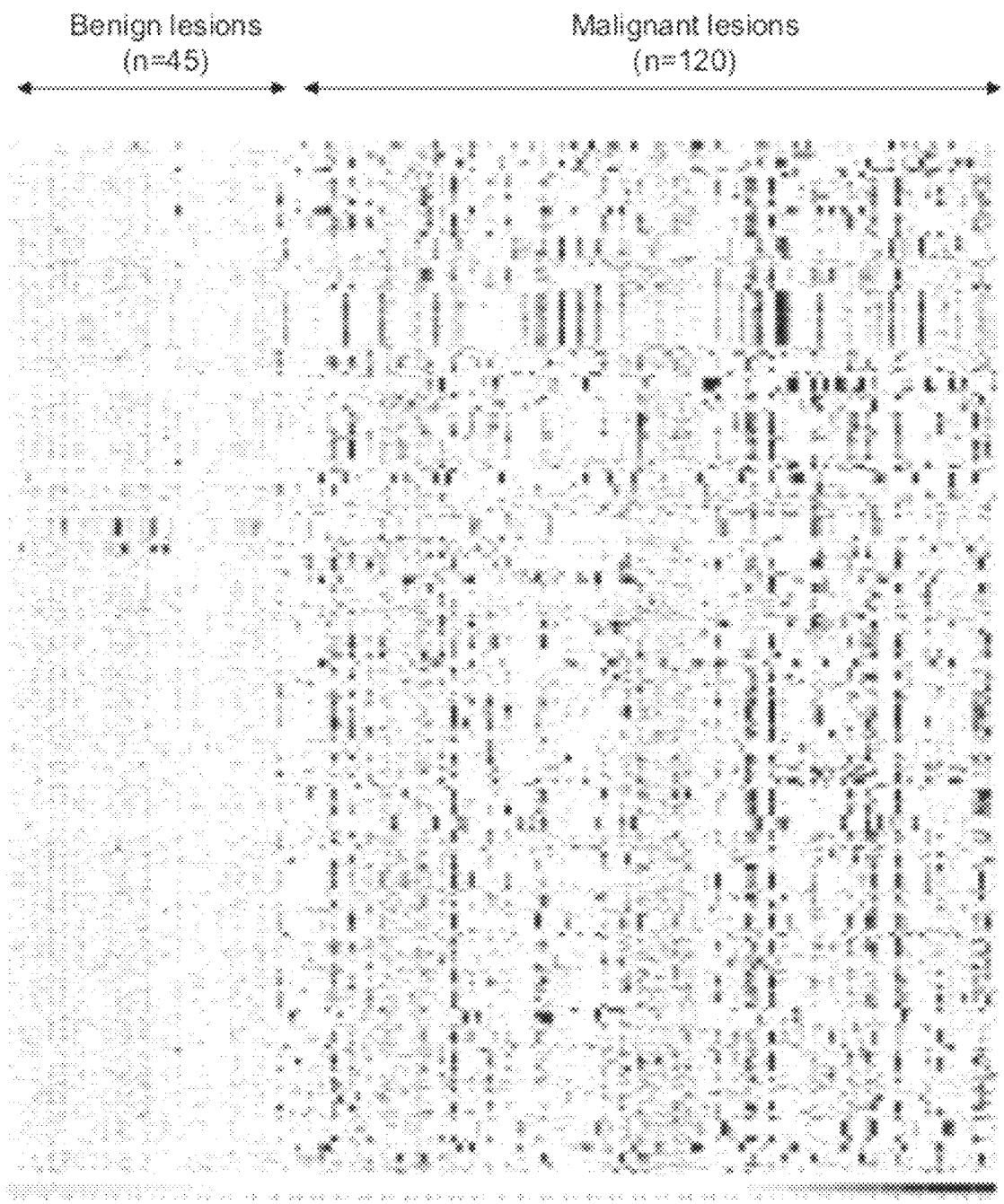

FIG. 4 represents Heatmap of the 1656 exon-probes that present a more than two fold higher intensity in malignant condition. The FIG. 4 reports the intensities of exon-probes that present more than a two-fold higher intensity in malignant tumors. Each column represents a sample, and each raw represent an exon-probe.

Figure 5:
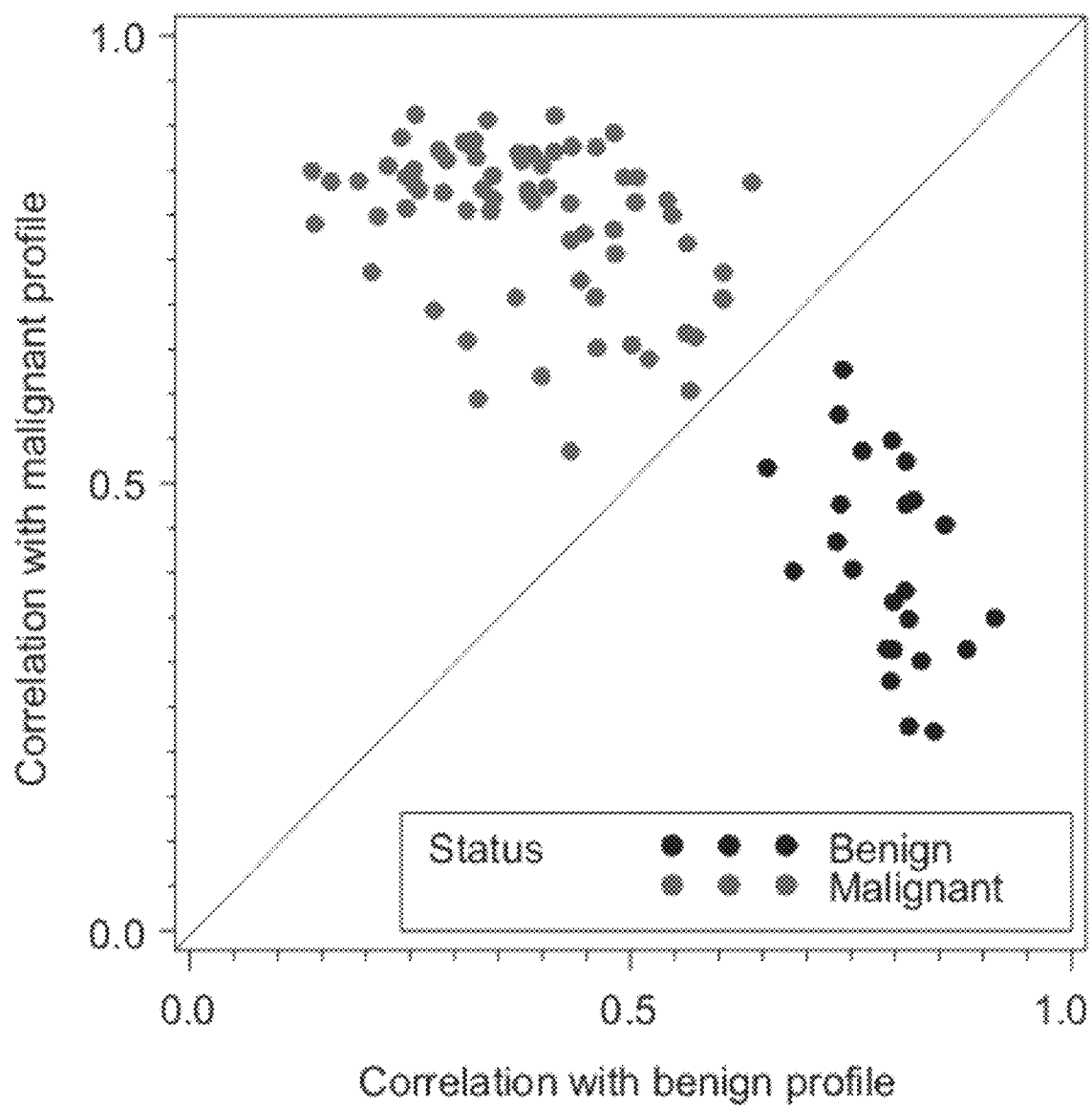

FIG. 5 represents the correlation of each specimen with the average benign and malignant profiles. Each tumor is classified according to its correlation with the average expressions of the probes in the benign and malignant group respectively during one leave-one-out-step. The bisecting line defines a region of benign prediction (bottom right triangle) and malignant prediction (upper left triangle). Tumors from the benign group are depicted in black, and those from the malignant group, in grey. Any misclassifications correspond to benign samples located in the malignant prediction area and vice versa. Training set included 94 samples (benign tumor, n=24, malignant tumor, n=70).

Figure 6:
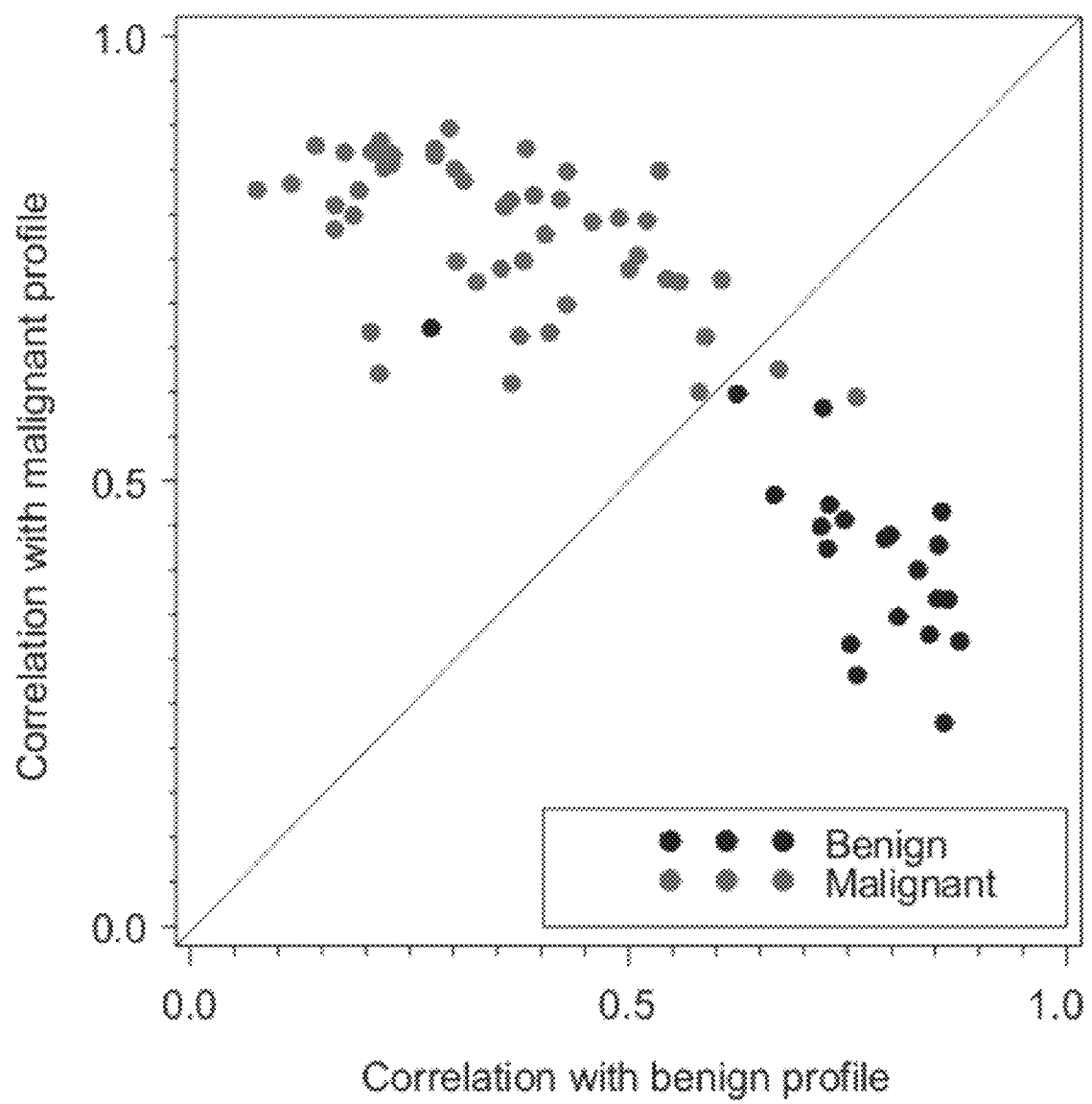

FIG. 6 represents the correlation of each specimen in the validation set with the average benign and malignant profiles of the preferred 1,228 signature polynucleotide probe sets obtained on the patients in the training set. Validation set included 71 samples (benign tumor, n=21, malignant tumor, n=50). Each tumor is classified according to its correlation with the average expressions of the probes in the benign and malignant profiles. The bisecting line defines a region of benign prediction (bottom right triangle) and malignant prediction (upper left triangle). Tumors from the benign group are depicted in black, and those from the malignant group, in grey. Any misclassifications correspond to benign samples located in the malignant prediction area and vice versa.

The following examples illustrate the invention, but the invention is not limited to these examples.

EXAMPLE I

Differentially Expressed Genes and Exons Between Malignant and Benign Breast Diseases 56652 probes (8%) presented a different intensity between malignant and benign conditions (adjusted p value<0.05). Of these, 37858 were exon-probes (B, T, and F) and 18794 were junction-probes (C, D, E). Of the 37858 exon-probes (B, T, F), 17441 were higher in malignant as opposed to benign diseases. The 17441 exon-probes (B, T, F) that were found higher in malignant condition referred to 12091 exons and 3391 genes. Of the 17441 exon-probes increased in malignant tumors, 1656 presented more than a two fold increased intensity in malignant conditions as compared to benign tumors. Heatmap of intensities for these 1656 probes is reported in FIG. 4. These 1656 probe sets referred to 1178 exons and 363 genes.

Figure 1:
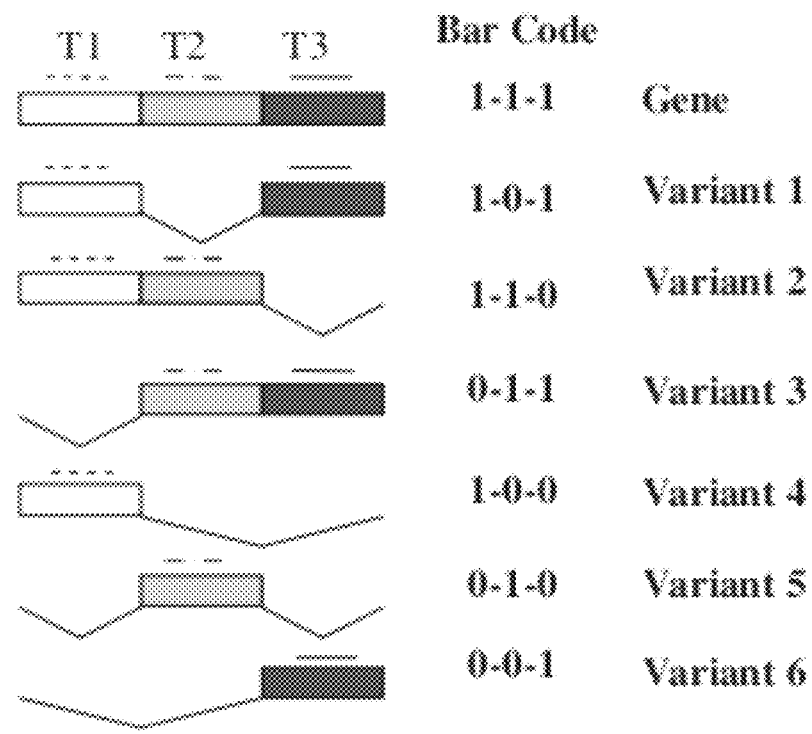
Figure 1:
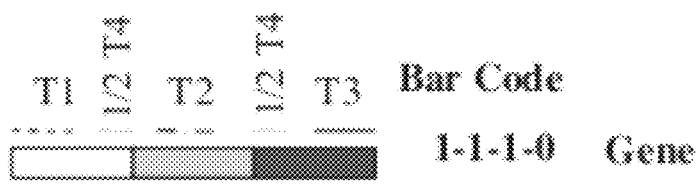
Figure 1:
Figure 2:
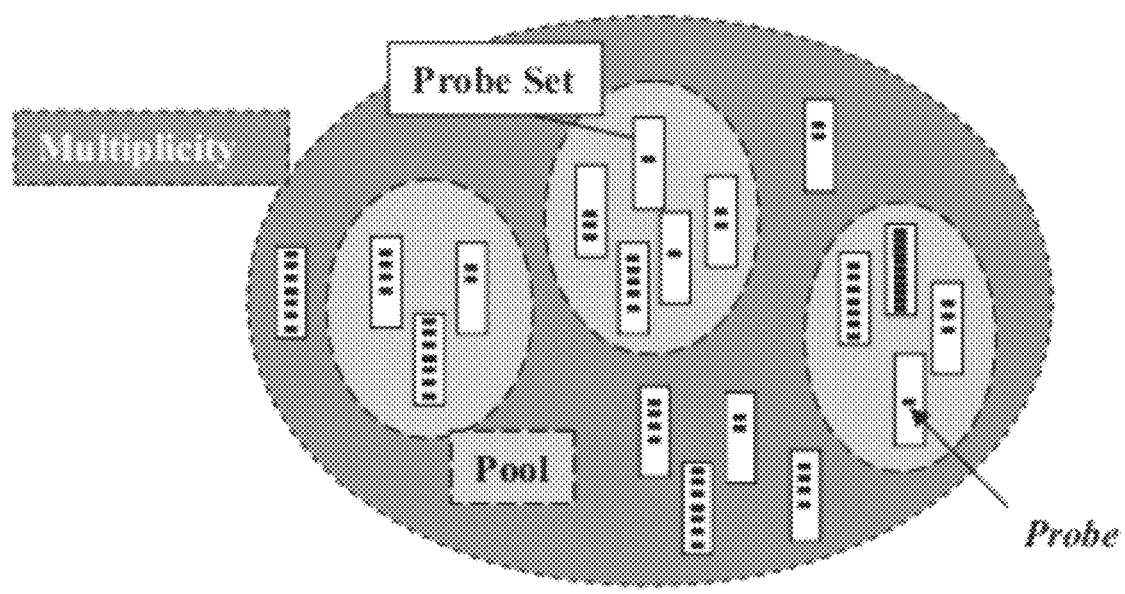
FIG. 2 represents the notions of multiplicity, pool, probe set and probes of the invention.
Figure 3:
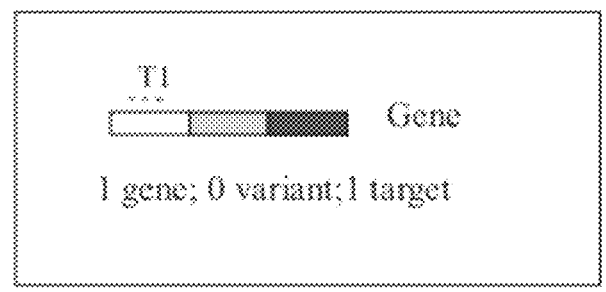
FIG. 3A to 3G represent the gene and its variant when they exist and the corresponding target region.
Figure 3:
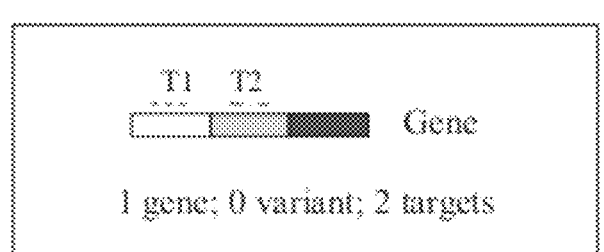
Figure 3:
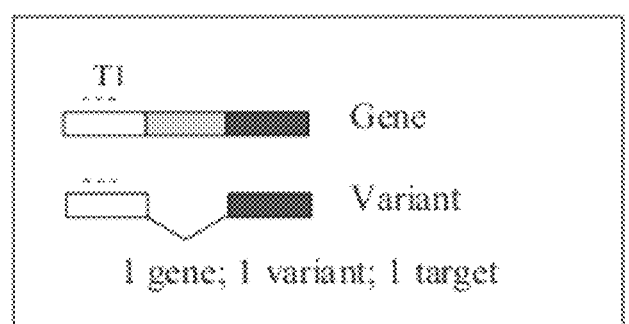
Figure 3:
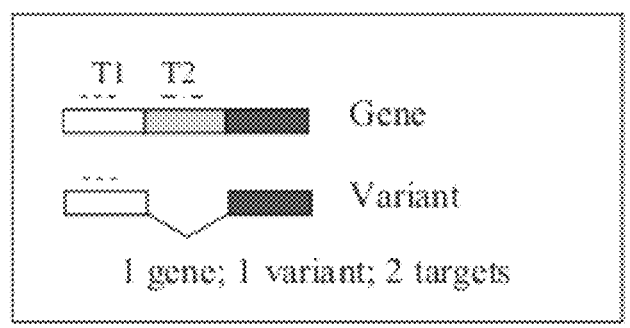
Figure 3:
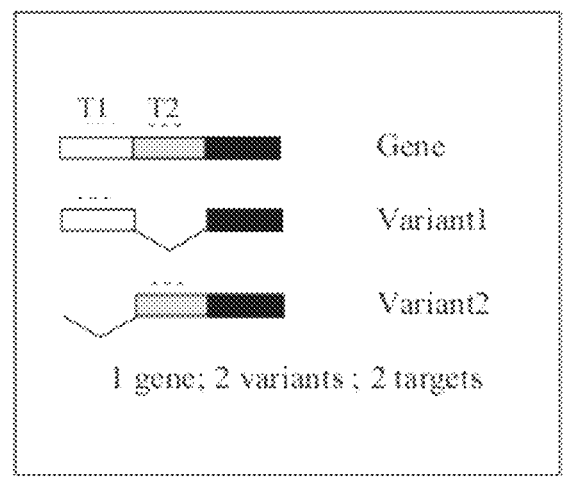
Figure 3:
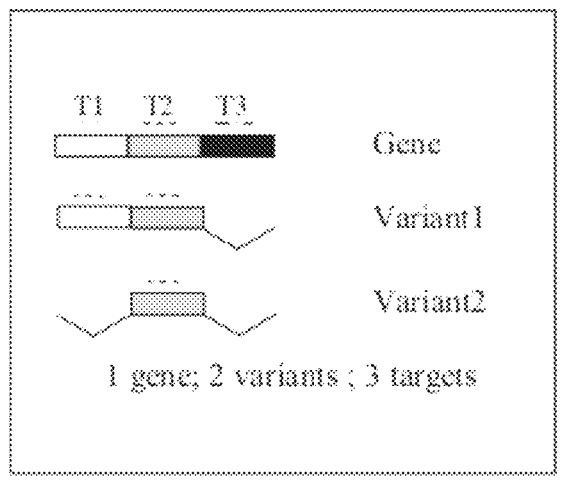
Figure 3:
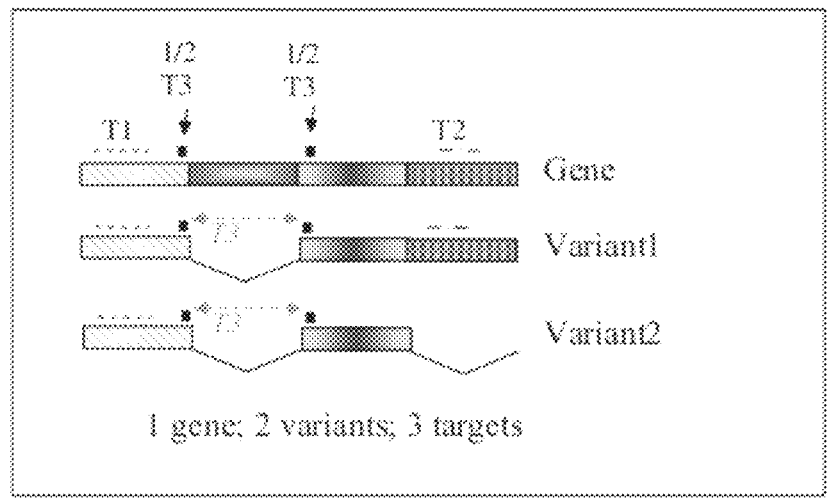

The level of gene expression was then determined as reported in patients and methods section. Among the 11921 filtered genes, 3733 were differentially expressed between cancer and benign conditions (adjusted p value <0.05). This accounts for 7% of the overall genes included in the array and 31% of the filtered genes. Of these, 1984 were overexpressed in malignant condition. Several of these genes are currently being targeted in therapeutics including TOP2A, VEGFA, AURKA, PARP1, RAS. Seventy-two genes presented more than a two fold increase of the mean value in breast cancer. As expected, a high proportion of these 72 highly overexpressed genes related to cell cycle activation and mitosis, including cyclins (CCNA2, CCNE2, CCNB2), cell division cycle family (CDC2, CKS1B, CKS2, NUF2), kinesin family members (KIF23, NDC80, KIF4A, KIF18A, MKLP2, KIF14) and centromere proteins (CENPF, CENPE). FIG. 3 reports the dotplots for gene expression of the top 10 overexpressed genes. Two (PTTG1, NET1) of the 10 most overexpressed genes were considered as potential new therapeutic targets given their oncogenic properties. Pathways analyses using Bio-Carta database identified 7 pathways that presented an enrichment of genes differentially expressed in one or the other condition. Interestingly, genes involved in spliceosome assembly were significantly enriched in malignant condition (LS permutations, p=0.001, KS permutations, p=0.002), suggesting an activation of this phenomenon in breast cancer.

Finally, the inventors identified 2675 exons (adjusted p value <0.05) overexpressed in malignant condition who were not located within the 1984 filtered genes whose geometric mean values differ between cancer and benign lesions. These 2675 exon-probes were located in 1559 genes. The splice index for the 2675 exon is reported in supplementary table 4. Numbers of these over-expressed exons located within unchanged genes have potential oncogenic properties. As illustration, probe sets for exon 9 casein kinase 1 delta (CSNK1D), exon 5-6 retinoblastoma binding protein 9 (RBBP9) and exon 21-22 Erbb2 interacting protein (ERBB2IP/LAP2) presented a 1.67 (adjusted p=0.005), 1.45 (adjusted p=0.006) and 1.6 (adjusted p=0.0005) fold increased intensity in malignant as compared to benign tumors. At the opposite, the geo mean ratio between cancer and benign tumors for gene expression levels were 1.09 (p=0.95), 1.04 (p=0.61) and 1.00 (p=0.96) for CSNK1D, RBBP9, ERBB2IP/LAP2 respectively. These findings suggest that a significant proportion of genes identified as unchanged may actually contain differentially expressed exons. These considerations suggest that analyses at exon level provide additional information to analyses at gene level, to decipher the transcriptional program of breast malignancy.

Based on the finding that breast cancer and benign tumors present widely different exonic profiles, the inventors developed a molecular classifier for breast cancer diagnosis on FNA samples.

EXAMPLE II

Development of a Molecular Classifier for Breast Cancer Diagnosis

Patients et Methods.

Patients.

94 patients have been included in the present study. These patients referred at the Institut Gustave Roussy for a clinical or radiological breast lesion in 2006. FNA was performed in all of these patients to assess the diagnosis of the breast lesion. A breast adenocarcinoma was diagnosed in 70 patients, and a benign lesion was diagnosed in 24 patients. Breast cancer diagnosis was based on the identification of cancer cells on the CNB or surgical specimen. The diagnosis of benign lesion was based on the identification of non-malignant epithelial cells on CNB and the identification of non-malignant epithelial cells in FNA sample together with lack of radiological change after 3 or 6 months follow-up. Patient characteristics are reported in Table 2.

TABLE 2

Table 2: patient characteristics

|  | Benign lesions (n = 24) | Malignant lesions (n = 70) |
|---|---|---|
| Median Age (range) | 41 (16-74) | 59 (30-92) |
| Median clinical size (range) | 17 mm (7-35) | 29 mm (7-110) |
| ACR classification | | |
| ACR3 | 14 (58%) | 0 |
| ACR4 | 9 (37%) | 13 (19%) |
| ACR5 | 1 (5%) | 56 (81%) |
| Not assessable | 1 | |
| Palpable lesion | | |
| Yes | 15 (65%) | 53 (78%) |
| NO | 8 (35%) | 15 (22%) |
| Not assessable | 1 | 2 |
| Pathological tumor size (range) | NA | 28 mm (6-60) |
| pTNM Stage | | |
| Node negative disease | | 27 (45%) |
| Node positive disease | NA | 20 (33%) |
| Stage IV disease | | 1 (2%) |
| Preoperative medical treatment | | 12 (20%) |
| Not assessable | | 10 |
| Tumor grade | | |
| Grade 1 | | 17 (27%) |
| Grade 2 | NA | 24 (37%) |
| Grade 3 | | 23 (36%) |
| Not Assessable | | 6 |
| Estogen receptor expression | | |
| ER negative | | 17 (25%) |
| ER positive | NA | 50 (75%) |
| Not assessable | | 3 |
| Progesteron receptor expression | | |
| PR negative | | 29 (43%) |
| PR positive | NA | 39 (57%) |
| Not assessable | | 3 |
| Her2 status | | |
| Overexpression | | 13 (20%) |
| Not overexpressed | NA | 53 (80%) |
| Not assessable | | 4 |

Sample Processing and Hybridization

RNA was extracted using RNEasy kit (Qiagen) from FNA specimen. Total RNA quality and quantity were evaluated using the RNA 6000 Nano LabChip kit with the Agilent 2100 Bioanalyzer.

Sample amplification and labeling was performed using the WT-Ovation Pico RNA Amplification System and the FL-Ovation cDNA Biotin Module v2 (NuGen, Inc., part #'s 3300-60 and 4200-60) according to manufacturer's instructions.

Standard methods following recommendations of the manufacturer were used to hybridize the samples. A pan-genomic array has been designed to detect 138,636 splicing events. 20,649 genes are analyzed using this array. The overall number of probes included in this array was 6,079,562. The present study was focused on 703,680 Evidenced probes. Once hybridized, the arrays were washed and stained using the FS450-0001 Fluidics protocol prior to scanning using the Affymetrix GeneChip® Scanner 3000 7G. .DAT and .CEL images were visually inspected for anomalies and accurate grid placement. The .CEL files were imported into Partek® Genomics Suite and the data were processed using the Robust Multichip Average (RMA) background correction method followed by GC content background correction. Quantile normalization was performed across all arrays, and then data was Log2 transformed and mean probe summarization was performed.

Normalization

Data were processed using the RMA background correction method followed by guanine-cytosine content background correction. Quantile normalization was performed across all arrays, and then data was log2 transformed and mean probe summarization was performed.

Pre-filtering

Starting from the 703,680 Evidenced probes, the inventors filtered out probes whose expression varied little across the 94 patient training set as follows: first the inventors floored the expression values at 10 (i.e. all expression values lower than 10 were replaced by 10), and secondly they deleted a probe from the data set if the ratio of the maximum by minimum intensity across the 94-patient set was higher or equal to 5 and if the difference between the maximum and minimum intensity was higher or equal to 100. In total 176,832 probes were retained for analysis after the pre-filtering step.

Statistical Analysis

The point biserial correlation coefficient was calculated for each probe between probe expression and a binary indicator which value was defined by the status of the patient (the indicator took the value 0 in patients who had benign tissue and the value 1 in tissues from patients with tumors) (Kraemer H C: Biserial correlation, in Encyclopedia of Statistical Science, Vol 1. Edited by Kotz S, Read C B. New York, Wiley, 1982, pp 276-280). The probes with the highest absolute correlation are those which are the most likely correlated with the occurrence of a tumor. The inventors used the t-test to test whether the point biserial correlation values were significantly different from 0 (Kraemer HC: Biserial correlation, in Encyclopedia of Statistical Science, Vol 1. Edited by Kotz S, Read C B. New York, Wiley, 1982, pp 276-280). In order to take the multiple testing issues into account they used a very stringent cut-off for statistical significance: 10e-8 (1 out of 100 million).

In order to develop a prediction rule to classify tissues from new patients with unknown status (benign vs. malignant), the inventors chose the nearest centroid prediction rule, which has been intensively studied on data from several microarray studies (S. Michiels, S. Koscielny, C. Hill. Prediction of cancer outcome with microarrays: a multiple random validation strategy. Lancet 2005; 365:488-92). This prediction rule classifies new patients according to the Pearson correlation between the expression of their signature probes and the average profiles in the two categories (the average benign and malignant profiles are defined as the vector of the average expression values of the signature probes in patients with benign and malignant tissues of the 94 patient training set), the predicted category being the one with the highest Pearson correlation. The signature probes were defined as those probes for which the p-value of test of significance of the point biserial correlation coefficient with the benign vs. malignant status was below a particular threshold.

Leave-one-out cross-validation was used to estimate the prediction accuracy of the prediction rule. One sample is left out, and the remaining samples are used to build the prediction rule, which is then used to classify the left-out sample. The entire model-building process was repeated for each leave-one-out training set to provide unbiased estimates of the prediction accuracy (Ntzani E E, Ioannidis J P. Predictive ability of DNA microarrays for cancer outcomes and correlates: an empirical assessment. Lancet 2003; 362: 1439-44; Simon R, Radmacher M D, Dobbin K, McShane L M. Pitfalls in the use of DNA microarray data for diagnostic and prognostic classification. J Natl Cancer Inst 2003; 95: 14-8): correlation coefficients were recalculated, ordered according to their absolute value, the signature probes defined and the nearest centroid prediction rule was constructed. Then, the inventors predicted the outcome of the one sample they left out in the first place based on the highest correlation coefficient it had with the average benign and the malignant profile from the 93 other samples. At the end of the leave-one-out cross-validation procedure, the inventors counted in how many cases the predictions were correct and in how many cases the predictions were incorrect.

The inventors repeated the above performance evaluation procedure based on leave-one-out cross-validation for different p-value thresholds for signature genes in order to find an optimal prediction rule yielding the lowest number of misclassified patients. They tried the following four p-values thresholds to define the signature genes: 10e-11, 10e-10, 10e-09 and 10e-8.

The inventors also provide subsets of 50, 100, 150 and 200 polynucleotide probe sets whose expression can be used to classify the benign and malignant status of tissues of new patients.

Results:

The inventors found 1,640 Evidenced polynucleotide probe sets that were significantly associated with malignancy at the stringent p-value cut-off of p<10e-8 (see Table 3). The polynucleotide probe sets with positive correlation are those which have increased expression in malignant tissues, those with negative correlation have increased expression in the benign tissues.

The inventors developed an optimal prediction rule based on the methodology explained above. The preferred p-value threshold for defining signature genes was p<10e-9. This p-value threshold corresponds to the first 1228 polynucleotide probe sets in Table 3 (with identifier no 1 to no 1228). When using leave-one-out cross-validation to estimated the prediction accuracy of the prediction rule with this particular threshold, they obtained 0 out of 24 patients (0%) with benign status that were misclassified and 0 out of 70 patients with malignant status that were misclassified (0%). This corresponds to a sensitivity of 100% and a specificity of 100%.

TABLE 3

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1 | 1756.022.2-C_at | −0.91151 | 0.91150698 | 21.25746 | <1e-16 | 1756.022. | NM_000109.2 | CQ714747.1 | GENBANK_PATENT | 1 |
| 2 | 1756.029.1-D_at | −0.89254 | 0.89253605 | 18.98306 | <1e-16 | 1756.029. | NM_000109.2 | BI551231.1 | EST | 1 |
| 3 | 1756.026.1-C_at | −0.89221 | 0.8922081 | 18.94884 | <1e-16 | 1756.026. | NM_000109.2 | M63075.1 | mRNA | 1 |
| 4 | 1756.022.4-T_at | −0.87666 | 0.87666398 | 17.47788 | <1e-16 | 1756.022. | NM_000109.2 | CQ714747.1 | GENBANK_PATENT | 1 |
| 5 | 1756.011.1-B_at | −0.87581 | 0.87581182 | 17.40484 | <1e-16 | 1756.011. | NM_000109.2 | AX114289.1 | GENBANK_PATENT | 1 |
| 6 | 1308.008.1-C_at | −0.86492 | 0.86492412 | 16.52922 | <1e-16 | 1308.008. | NM_130778.1 | BE148646.1 | EST | 1 |
| 7 | 1756.022.3-F_at | −0.84937 | 0.84936983 | 15.43558 | <1e-16 | 1756.022. | NM_000109.2 | CQ714747.1 | GENBANK_PATENT | 1 |
| 8 | 3861.020.1-D_at | −0.84359 | 0.84358795 | 15.06806 | <1e-16 | 3861.020. | NM_000526.3 | BM018298.1 | EST | 1 |
| 9 | 1756.011.1-F_at | −0.83903 | 0.83903098 | 14.7913 | <1e-16 | 1756.011. | NM_000109.2 | AX114289.1 | GENBANK_PATENT | 1 |
| 10 | 4629.007.1-F_at | −0.83653 | 0.83653075 | 14.64397 | <1e-16 | 4629.007. | NM_022844.1 | AY520817.1 | mRNA | 16 |
| 11 | 1756.022.4-B_at | −0.83558 | 0.83557952 | 14.58872 | <1e-16 | 1756.022. | NM_000109.2 | CQ714747.1 | GENBANK_PATENT | 1 |
| 12 | 1756.024.1-F_at | −0.83305 | 0.83304555 | 14.44365 | <1e-16 | 1756.024. | NM_000109.2 | CD299688.1 | EST | 1 |
| 13 | 3861.019.1-T_at | −0.83092 | 0.83091678 | 14.32409 | <1e-16 | 3861.019. | NM_000526.3 | BQ359236.1 | EST | 1 |
| 14 | 1756.026.1-T_at | −0.83005 | 0.83004684 | 14.27581 | <1e-16 | 1756.026. | NM_000109.2 | M63075.1 | mRNA | 1 |
| 15 | 1756.022.1-B_at | −0.82986 | 0.8298586 | 14.26541 | <1e-16 | 1756.022. | NM_000109.2 | CQ714747.1 | GENBANK_PATENT | 1 |
| 16 | 3861.013.1-T_at | −0.82888 | 0.82888471 | 14.21185 | <1e-16 | 3861.013. | NM_000526.3 | BG677893.1 | EST | 1 |
| 17 | 3861.001.1-B_at | −0.82731 | 0.82731458 | 14.12635 | <1e-16 | 3861.001. | NM_130778.1 | BE148646.1 | EST | 1 |
| 18 | 4629.020.1-C_at | −0.82454 | 0.82453945 | 13.97781 | <1e-16 | 4629.020. | NM_022844.1 | BI819760.1 | EST | 1 |
| 19 | 1756.027.1-T_at | −0.82281 | 0.82280868 | 13.88676 | <1e-16 | 1756.027. | NM_000109.2 | S60971.1 | mRNA | 1 |
| 20 | 3861.013.1-T_at | −0.82153 | 0.82153279 | 13.82042 | <1e-16 | 3861.013. | NM_000526.3 | BM563823.1 | EST | 1 |
| 21 | 4629.020.1-D_at | −0.8194 | 0.81940128 | 13.71099 | <1e-16 | 4629.020. | NM_022844.1 | BI819760.1 | EST | 1 |
| 22 | 3861.001.1-B_at | −0.81782 | 0.8178189 | 13.63089 | <1e-16 | 3861.001. | NM_000526.3 | BG677893.1 | EST | 1 |
| 23 | 1756.022.4-F_at | −0.81687 | 0.81686612 | 13.5831 | <1e-16 | 1756.022. | NM_000109.2 | CQ714747.1 | GENBANK_PATENT | 1 |
| 24 | 1756.026.1-F_at | −0.81627 | 0.81626518 | 13.55314 | <1e-16 | 1756.026. | NM_000109.2 | M63075.1 | mRNA | 1 |
| 25 | 1756.022.2-T_at | −0.81571 | 0.815705 | 13.52532 | <1e-16 | 1756.022. | NM_000109.2 | CQ714747.1 | GENBANK_PATENT | 1 |
| 26 | 1756.022.2-F_at | −0.81498 | 0.8149825 | 13.48962 | <1e-16 | 1756.022. | NM_000109.2 | CQ714747.1 | GENBANK_PATENT | 1 |
| 27 | 3861.022.1-B_at | −0.81494 | 0.81494272 | 13.48766 | <1e-16 | 3861.022. | NM_000526.3 | BI085500.1 | EST | 1 |
| 28 | 3868.004.1-D_at | −0.81412 | 0.81412336 | 13.4474 | <1e-16 | 3868.004. | NM_055557.2 | BM045170.1 | EST | 1 |
| 29 | 4629.015.1-C_at | −0.81348 | 0.81347687 | 13.41581 | <1e-16 | 4629.015. | NM_022844.1 | DB284318.1 | EST | 1 |
| 30 | 6422.002.1-E_at | −0.81346 | 0.81346311 | 13.41514 | <1e-16 | 6422.002. | NM_003012.3 | AX565729.1 | GENBANK_PATENT | 3 |
| 31 | 3861.001.1-D_at | −0.81115 | 0.81115184 | 13.30339 | <1e-16 | 3861.001. | NM_000526.3 | BG677893.1 | EST | 1 |
| 32 | 1756.022.1-F_at | −0.81112 | 0.81111566 | 13.30165 | <1e-16 | 1756.022. | NM_000109.2 | CQ714747.1 | GENBANK_PATENT | 1 |
| 33 | 1308.003.1-T_at | −0.80635 | 0.80635142 | 13.07706 | <1e-16 | 1308.003. | NM_130778.1 | NM_000494.2 | REFSEQ | 19 |
| 34 | 3868.005.1-B_at | −0.8061 | 0.80610095 | 13.06545 | <1e-16 | 3868.005. | NM_055557.2 | BG682632.1 | EST | 1 |
| 35 | 1308.007.1-F_at | −0.8044 | 0.80440011 | 12.98719 | <1e-16 | 1308.007. | NM_130778.1 | BF916393.1 | EST | 1 |
| 36 | 1308.009.1-F_at | −0.8039 | 0.80390038 | 12.96437 | <1e-16 | 1308.009. | NM_130778.1 | DA425187.1 | EST | 1 |
| 37 | 3861.007.1-E_at | −0.8038 | 0.80380368 | 12.95997 | <1e-16 | 3861.007. | NM_000526.3 | BG682207.1 | EST | 11 |
| 38 | 4629.016.1-D_at | −0.80378 | 0.80377953 | 12.95887 | <1e-16 | 4629.016. | NM_022844.1 | DB289769.1 | EST | 1 |
| 39 | 3084.007.1-F_at | −0.80131 | 0.80130924 | 12.84728 | <1e-16 | 3084.007. | NM_013957.1 | CN603653.1 | EST | 3 |
| 40 | 3861.007.1-F_at | −0.79968 | 0.79968463 | 12.77489 | <1e-16 | 3861.007. | NM_000526.3 | BG682207.1 | EST | 11 |
| 41 | 26289.003.1-E_at | −0.79508 | 0.7950811 | 12.57397 | <1e-16 | 26289.003. | NM_174858.1 | AK090967.1 | mRNA | 3 |
| 42 | 1756.028.1-T_at | −0.79389 | 0.79388677 | 12.52282 | <1e-16 | 1756.028. | NM_000109.2 | CQ733377.1 | GENBANK_PATENT | 1 |
| 43 | 4629.021.1-E_at | −0.7935 | 0.79350334 | 12.50648 | <1e-16 | 4629.021. | NM_022844.1 | CQ717811.1 | GENBANK_PATENT | 1 |
| 44 | 4629.020.1-D_at | −0.78948 | 0.78947575 | 12.33726 | <1e-16 | 4629.020. | NM_022844.1 | BI819760.1 | EST | 1 |
| 45 | 5764.001.1-F_at | −0.78733 | 0.78733221 | 12.24894 | <1e-16 | 5764.001. | NM_002825.5 | AX135902.1 | GENBANK_PATENT | 3 |
| 46 | 3815.002.3-F_at | −0.78506 | 0.78505901 | 12.15655 | <1e-16 | 3815.002. | NM_000222.1 | CQ719901.1 | GENBANK_PATENT | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 47 | 3852.020.1-T_at | −0.78181 | 0.78181405 | 12.02688 | <1e-16 | 3852.020. | NM_000424.2 | DA764792.1 | EST | 1 |
| 48 | 4629.007.1-E_at | −0.78063 | 0.78063131 | 11.98024 | <1e-16 | 4629.007. | NM_022844.1 | AY520817.1 | mRNA | 16 |
| 49 | 128553.003.1-F | −0.78062 | 0.78061872 | 11.97975 | <1e-16 | 128553.00 | NM_173485.2 | BP394387.1 | EST | 1 |
| 50 | 26289.003.1-F_at | −0.78004 | 0.78004 | 11.95705 | <1e-16 | 26289.003 | NM_174858.1 | AK090967.1 | GENBANK_PATENT | 3 |
| 51 | 3815.002.2-F_at | −0.77826 | 0.77825678 | 11.88761 | <1e-16 | 3815.002. | NM_000222.1 | CQ719901.1 | EST | 1 |
| 52 | 1756.029.1-B_at | −0.77795 | 0.77795132 | 11.87578 | <1e-16 | 1756.029. | NM_000109.2 | BI551231.1 | EST | 1 |
| 53 | 4629.005.1-E_at | −0.7779 | 0.77790413 | 11.87396 | <1e-16 | 4629.005. | NM_022844.1 | CB963138.1 | EST | 3 |
| 54 | 4629.010.1-B_at | −0.77786 | 0.77786129 | 11.8723 | <1e-16 | 4629.010. | NM_022844.1 | AI285326.1 | EST | 1 |
| 55 | 6422.001.1-T_at | −0.77686 | 0.77685589 | 11.83356 | <1e-16 | 6422.001. | NM_003012.3 | CQ850220.1 | GENBANK_PATENT | 2 |
| 56 | 5764.001.1-E_at | −0.77561 | 0.77560627 | 11.78573 | <1e-16 | 5764.001. | NM_002825.5 | AX135902.1 | GENBANK_PATENT | 3 |
| 57 | 3861.008.1-F_at | −0.77548 | 0.77547795 | 11.78084 | <1e-16 | 3861.008. | NM_000526.3 | BE184532.1 | EST | 1 |
| 58 | 1756.030.2-T_at | −0.77479 | 0.77478755 | 11.75458 | <1e-16 | 1756.030. | NM_000109.2 | BM929495.1 | EST | 2 |
| 59 | 3084.009.1-B_at | −0.77277 | 0.77277347 | 11.67858 | <1e-16 | 3084.009. | NM_013957.1 | U02327.1 | mRNA | 2 |
| 60 | 26289.002.1-T_at | −0.7720 | 0.7720739 | 11.65239 | <1e-16 | 26289.002 | NM_174858.1 | BF966377.1 | EST | 1 |
| 61 | 1756.022.5-B_at | −0.77137 | 0.77136743 | 11.62604 | <1e-16 | 1756.022. | NM_000109.2 | CQ714747.1 | GENBANK_PATENT | 16 |
| 62 | 4629.007.1-D_at | −0.77091 | 0.77091122 | 11.60908 | <1e-16 | 4629.007. | NM_022844.1 | AY520817.1 | mRNA | 1 |
| 63 | 23336.001.1-C_at | −0.76979 | 0.76978838 | 11.56754 | <1e-16 | 23336.001 | NM_145728.1 | AJ697971.1 | mRNA | 19 |
| 64 | 1308.003.1-D_at | −0.76831 | 0.7683088 | 11.5132 | <1e-16 | 1308.003. | NM_130778.1 | NM_000494.2 | REFSEQ | 1 |
| 65 | 1756.022.3-T_at | −0.76731 | 0.76730759 | 11.47668 | <1e-16 | 1756.022. | NM_000109.2 | CQ714747.1 | GENBANK_PATENT | 1 |
| 66 | 3861.020.1-T_at | −0.76715 | 0.76714705 | 11.47084 | <1e-16 | 3861.020. | NM_000526.3 | BM018298.1 | EST | 1 |
| 67 | 3861.022.1-C_at | −0.76448 | 0.76448457 | 11.37481 | <1e-16 | 3861.022. | NM_000526.3 | BI085500.1 | EST | 1 |
| 68 | 3852.012.2-B_at | −0.76294 | 0.76294046 | 11.31975 | <1e-16 | 3861.012. | NM_000424.2 | CQ733668.1 | GENBANK_PATENT | 1 |
| 69 | 26289.012.1-E_at | −0.76192 | 0.76191947 | 11.28361 | <1e-16 | 26289.012 | NM_174858.1 | BG189938.1 | EST | 1 |
| 70 | 23336.003.1-T_at | −0.76122 | 0.76122392 | 11.2591 | <1e-16 | 23336.003 | NM_145728.1 | CQ723645.1 | GENBANK_PATENT | 1 |
| 71 | 26289.007.1-B_at | −0.76082 | 0.76081931 | 11.24888 | <1e-16 | 26289.007 | NM_174858.1 | DA259560.1 | EST | 1 |
| 72 | 84417.001.1-T_at | −0.76076 | 0.76075848 | 11.24275 | <1e-16 | 84417.001 | NM_032411.1 | BI561114.1 | EST | 1 |
| 73 | 3861.018.1-D_at | −0.7605 | 0.76050387 | 11.23382 | <1e-16 | 3861.018. | NM_000526.3 | BM019687.1 | EST | 1 |
| 74 | 3852.004.1-B_at | −0.76039 | 0.76038766 | 11.22975 | <1e-16 | 3852.004. | NM_000424.2 | BE715131.1 | EST | 1 |
| 75 | 90865.006.1-B_at | −0.76035 | 0.76035315 | 11.22855 | <1e-16 | 90865.006 | NM_033439.2 | AV707946.1 | EST | 1 |
| 76 | 4629.021.1-F_at | −0.76012 | 0.7601167 | 11.22027 | <1e-16 | 4629.021. | NM_022844.1 | CQ717811.1 | GENBANK_PATENT | 16 |
| 77 | 3861.018.1-T_at | −0.76002 | 0.76001693 | 11.21679 | <1e-16 | 3861.018. | NM_000526.3 | BM019687.1 | EST | 1 |
| 78 | 1756.022.1-T_at | −0.75998 | 0.75998388 | 11.21563 | <1e-16 | 1756.022. | NM_000109.2 | CQ714747.1 | GENBANK_PATENT | 1 |
| 79 | 1264.003.1-B_at | −0.75956 | 0.75955538 | 11.20068 | <1e-16 | 1264.003. | NM_001299.4 | CV811526.1 | EST | 1 |
| 80 | 26289.010.1-E_at | −0.7591 | 0.75909546 | 11.18467 | <1e-16 | 26289.010 | NM_174858.1 | AX988359.1 | GENBANK_PATENT | 1 |
| 81 | 3861.001.1-F_at | −0.75842 | 0.75842235 | 11.16131 | <1e-16 | 3861.001. | NM_000526.3 | BG677893.1 | EST | 1 |
| 82 | 1908.002.1-T_at | −0.75841 | 0.75841175 | 11.16094 | <1e-16 | 1908.002. | NM_207032.1 | NM_207033.1 | REFSEQ | 8 |
| 83 | 4629.007.1-C_at | −0.75757 | 0.75757437 | 11.132 | <1e-16 | 4629.007. | NM_022844.1 | AY520817.1 | mRNA | 16 |
| 84 | 1756.022.5-T_at | −0.75733 | 0.75732729 | 11.12348 | <1e-16 | 1756.022. | NM_000109.2 | CQ714747.1 | GENBANK_PATENT | 1 |
| 85 | 3815.002.4-B_at | −0.75611 | 0.75610941 | 11.08167 | <1e-16 | 3815.002. | NM_000222.1 | CQ719901.1 | GENBANK_PATENT | 1 |
| 86 | 1756.022.2-B_at | −0.75476 | 0.75476064 | 11.03568 | <1e-16 | 1756.022. | NM_000109.2 | CQ714747.1 | GENBANK_PATENT | 1 |
| 87 | 1756.027.1-B_at | −0.75441 | 0.75441365 | 11.0239 | <1e-16 | 1756.027. | NM_000109.2 | S60971.1 | mRNA | 1 |
| 88 | 3852.008.2-T_at | −0.75435 | 0.75434944 | 11.02172 | <1e-16 | 3852.008. | NM_000424.2 | BG675837.1 | EST | 1 |
| 89 | 6422.001.1-E_at | −0.75383 | 0.75383168 | 11.00419 | <1e-16 | 6422.001. | NM_003012.3 | CQ850220.1 | GENBANK_PATENT | 2 |
| 90 | 3861.022.1-F_at | −0.75247 | 0.75247162 | 10.95837 | <1e-16 | 3861.022. | NM_000526.3 | BI085500.1 | EST | 1 |
| 91 | 4915.011.1-D_at | −0.75125 | 0.75124983 | 10.91748 | <1e-16 | 4915.011. | NM_006180.3 | CQ723929.1 | GENBANK_PATENT | 1 |
| 92 | 5288.001.1-F_at | −0.75114 | 0.75113721 | 10.91373 | <1e-16 | 5288.001. | NM_004570.2 | CQ720591.1 | GENBANK_PATENT | 1 |
| 93 | 3861.007.1-T_at | −0.75024 | 0.75024416 | 10.88402 | <1e-16 | 3861.007. | NM_000526.3 | BG682207.1 | EST | 2 |
| 94 | 3852.006.1-C_at | −0.74966 | 0.74965968 | 10.86465 | <1e-16 | 3852.006. | NM_000424.2 | BG679014.1 | EST | 11 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 95 | 9413.003.1-T_at | −0.74954 | 0.74953975 | 10.86069 | <1e-16 | 9413.003. | NM_004816.2 | BX641153.1 | mRNA | 10 |
| 96 | 3861.020.1-C_at | −0.74922 | 0.74922185 | 10.85018 | <1e-16 | 3861.020. | NM_000526.3 | BM018298.1 | EST | 1 |
| 97 | 1308.008.1-D_at | −0.7468 | 0.746803 | 10.77082 | <1e-16 | 1308.008. | NM_130778.1 | BE148646.1 | EST | 1 |
| 98 | 23336.001.1-T_at | −0.74666 | 0.74665951 | 10.76614 | <1e-16 | 23336.001. | NM_145728.1 | AJ697971.1 | mRNA | 1 |
| 99 | 3815.001.1-F_at | −0.74657 | 0.74656536 | 10.76307 | <1e-16 | 3815.001. | NM_000222.1 | CS237377.1 | GENBANK_PATENT | 1 |
| 100 | 1756.022.5-F_at | −0.74654 | 0.74654247 | 10.76233 | <1e-16 | 1756.022. | NM_000109.2 | CQ714747.1 | GENBANK_PATENT | 1 |
| 101 | 79937.001.1-T_at | −0.74608 | 0.74607796 | 10.74722 | <1e-16 | 79937.001. | NM_033655.2 | AF333769.2 | mRNA | 1 |
| 102 | 4915.012.1-E_at | −0.74575 | 0.74575052 | 10.73659 | <1e-16 | 4915.012. | NM_006180.3 | CD103051.1 | EST | 1 |
| 103 | 3861.022.1-T_at | −0.74356 | 0.74356005 | 10.66593 | <1e-16 | 3861.022. | NM_000526.3 | BI085500.1 | EST | 1 |
| 104 | 26289.005.1-T_at | −0.74355 | 0.74354601 | 10.66548 | <1e-16 | 26289.005. | NM_174858.1 | BI546738.1 | EST | 1 |
| 105 | 3815.002.3-B_at | −0.74306 | 0.74306109 | 10.64994 | <1e-16 | 3815.002. | NM_000222.1 | CQ719901.1 | GENBANK_PATENT | 1 |
| 106 | 4311.009.1-F_at | −0.74287 | 0.74287019 | 10.64383 | <1e-16 | 4311.009. | NM_000902.2 | A30431.1 | GENBANK_PATENT | 1 |
| 107 | 26289.006.1-T_at | −0.74283 | 0.74282989 | 10.64255 | <1e-16 | 26289.006. | NM_174858.1 | CN356131.1 | EST | 1 |
| 108 | 5288.003.1-F_at | −0.74231 | 0.74231399 | 10.62608 | <1e-16 | 5288.003. | NM_004570.2 | CQ721655.1 | GENBANK_PATENT | 1 |
| 109 | 4629.020.1-B_at | −0.7423 | 0.74230371 | 10.62575 | <1e-16 | 4629.020. | NM_022844.1 | BI819760.1 | EST | 1 |
| 110 | 26289.007.1-D_at | −0.74169 | 0.74168883 | 10.60617 | <1e-16 | 26289.007. | NM_174858.1 | DA259560.1 | EST | 1 |
| 111 | 3815.002.1-B_at | −0.74167 | 0.74166962 | 10.60556 | <1e-16 | 3815.002. | NM_000222.1 | CQ719901.1 | GENBANK_PATENT | 1 |
| 112 | 26289.004.1-T_at | −0.74153 | 0.74153045 | 10.60114 | <1e-16 | 26289.004. | NM_174858.1 | NM_012093.2 | REFSEQ | 7 |
| 113 | 79192.002.2-T_at | −0.74131 | 0.74131399 | 10.59427 | <1e-16 | 79192.002. | NM_024337.3 | CQ731489.1 | GENBANK_PATENT | 1 |
| 114 | 4638.006.1-D_at | −0.74126 | 0.74125872 | 10.59252 | <1e-16 | 4638.006. | NM_053025.2 | DR005817.1 | EST | 2 |
| 115 | 3084.008.1-F_at | −0.74052 | 0.74051659 | 10.56902 | <1e-16 | 3084.008. | NM_013957.1 | CQ733299.1 | GENBANK_PATENT | 1 |
| 116 | 4311.001.1-T_at | −0.7346 | 0.73459701 | 10.38463 | <1e-16 | 4311.001. | NM_000902.2 | CB988534.1 | EST | 1 |
| 117 | 3815.002.1-D_at | −0.73458 | 0.73457702 | 10.38401 | <1e-16 | 3815.002. | NM_000222.1 | CQ719901.1 | GENBANK_PATENT | 1 |
| 118 | 4629.020.1-T_at | −0.73906 | 0.73905518 | 10.523 | <1e-16 | 4629.020. | NM_022844.1 | BI819760.1 | EST | 1 |
| 119 | 1756.026.1-B_at | −0.739 | 0.73899721 | 10.52119 | <1e-16 | 1756.026. | NM_000109.2 | M63075.1 | mRNA | 1 |
| 120 | 3852.022.1-E_at | −0.73857 | 0.73856714 | 10.50771 | <1e-16 | 3852.022. | NM_000424.2 | BP226135.1 | EST | 1 |
| 121 | 4629.015.1-D_at | −0.73849 | 0.73848689 | 10.5052 | <1e-16 | 4629.015. | NM_022844.1 | DB284318.1 | EST | 1 |
| 122 | 26289.007.1-C_at | −0.73826 | 0.73825579 | 10.49797 | <1e-16 | 26289.007. | NM_174858.1 | DA259560.1 | EST | 1 |
| 123 | 23194.003.1-C_at | −0.73638 | 0.73638084 | 10.43964 | <1e-16 | 23194.003. | NM_012304.3 | BP290286.1 | EST | 1 |
| 124 | 3815.002.1-B_at | −0.73534 | 0.73534271 | 10.40757 | <1e-16 | 3815.002. | NM_000222.1 | CQ719901.1 | GENBANK_PATENT | 1 |
| 125 | 26289.007.1-T_at | −0.7346 | 0.73459701 | 10.38463 | <1e-16 | 26289.007. | NM_174858.1 | DA259560.1 | EST | 1 |
| 126 | 65983.009.1-B_at | −0.73458 | 0.73457702 | 10.38401 | <1e-16 | 65983.009. | NM_023927.1 | CQ413222.1 | GENBANK_PATENT | 2 |
| 127 | 23336.001.1-F_at | −0.73393 | 0.73392505 | 10.36403 | <1e-16 | 23336.001. | NM_145728.1 | AJ697971.1 | mRNA | 1 |
| 128 | 1410.007.2-B_at | −0.73346 | 0.73346173 | 10.34986 | <1e-16 | 1410.007. | NM_001885.1 | BI548180.1 | EST | 1 |
| 129 | 1756.029.1-F_at | −0.73299 | 0.73298982 | 10.33546 | <1e-16 | 1756.029. | NM_000109.2 | BI551231.1 | EST | 1 |
| 130 | 7373.003.6-C_at | −0.73258 | 0.73257952 | 10.32297 | <1e-16 | 7373.003. | NM_021110.1 | CQ716670.1 | GENBANK_PATENT | 1 |
| 131 | 10010.002.1-E_at | −0.7322 | 0.73219822 | 10.31139 | <1e-16 | 10010.002. | NM_004180.2 | CF242863.1 | EST | 1 |
| 132 | 59.026.1-B_at | −0.73215 | 0.73215036 | 10.30993 | <1e-16 | 59.026.1 | — | — | — | — |
| 133 | 4915.011.1-F_at | −0.73192 | 0.73191927 | 10.30292 | <1e-16 | 4915.011. | NM_006180.3 | CQ723929.1 | GENBANK_PATENT | 1 |
| 134 | 3872.007.1-D_at | −0.73192 | 0.73191502 | 10.30279 | <1e-16 | 3872.007. | NM_000422.1 | BU155457.1 | EST | 1 |
| 135 | 26289.002.1-D_at | −0.73171 | 0.73171045 | 10.2966 | <1e-16 | 26289.002. | NM_174858.1 | BF966377.1 | EST | 1 |
| 136 | 84668.002.1-C_at | −0.73162 | 0.73162167 | 10.29391 | <1e-16 | 84668.002. | NM_032581.2 | AL833296.1 | mRNA | 20 |
| 137 | 1756.002.2-T_at | −0.73157 | 0.73156873 | 10.2923 | <1e-16 | 1756.002. | NM_000109.2 | NM_004016.1 | REFSEQ | 30 |
| 138 | 57447.033.1-C_at | −0.73085 | 0.73084864 | 10.27055 | <1e-16 | 57447.033 | NM_201535.1 | DA135222.1 | EST | 1 |
| 139 | 26289.009.1-E_at | −0.7304 | 0.73039812 | 10.25697 | <1e-16 | 26289.009. | NM_174858.1 | AA393277.1 | EST | 1 |
| 140 | 3872.006.1-F_at | −0.73024 | 0.73023988 | 10.25221 | <1e-16 | 3872.006. | NM_000422.1 | BM017443.1 | EST | 1 |
| 141 | 3861.022.1-D_at | −0.72983 | 0.72982952 | 10.23988 | <1e-16 | 3861.022. | NM_000526.3 | BI085500.1 | EST | 1 |
| 142 | 3861.020.1-B_at | −0.72921 | 0.72920518 | 10.22116 | <1e-16 | 3861.020. | NM_000526.3 | BM018298.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 143 | 667.021.1-B_at | −0.72908 | 0.72907922 | 10.21739 | <1e-16 | 667.021.1 | NM_183380.1 | DB134537.1 | EST | 1 |
| 144 | 57447.027.1-F_at | −0.72812 | 0.72812186 | 10.18881 | <1e-16 | 57447.027 | NM_201535.1 | BM810623.1 | EST | 9 |
| 145 | 56477.001.1-D_at | −0.72775 | 0.72774687 | 10.17766 | <1e-16 | 56477.001 | NM_148672.1 | NM_019846.3 | REFSEQ | 13 |
| 146 | 26289.008.1-F_at | −0.72745 | 0.72744814 | 10.16878 | <1e-16 | 26289.008 | NM_174858.1 | AV721097.1 | EST | 1 |
| 147 | 59.024.2-D_at | −0.72739 | 0.72738851 | 10.16701 | <1e-16 | 59.024.2 | — | — | — | — |
| 148 | 4629.005.1-T_at | −0.72738 | 0.7273826 | 10.16683 | <1e-16 | 4629.005. | NM_022844.1 | CB963138.1 | EST | 3 |
| 149 | 3815.002.1-T_at | −0.72727 | 0.72727235 | 10.16356 | <1e-16 | 3815.002. | NM_000222.1 | CQ719901.1 | GENBANK_PATENT | 1 |
| 150 | 23336.001.1-B_at | −0.72692 | 0.7269191 | 10.15309 | <1e-16 | 23336.001 | NM_145728.1 | AJ697971.1 | mRNA | 1 |
| 151 | 3084.004.2-F_at | −0.72617 | 0.72616697 | 10.13085 | <1e-16 | 3084.004. | NM_013957.1 | NM_013964.1 | REFSEQ | 5 |
| 152 | 27122.014.2-T_at | −0.72585 | 0.72585166 | 10.12156 | 1E-16 | 27122.014 | NM_013253.4 | DA180412.1 | EST | 1 |
| 153 | 26289.008.1-C_at | −0.72537 | 0.72537026 | 10.10738 | 1E-16 | 26289.008 | NM_174858.1 | AV721097.1 | EST | 1 |
| 154 | 286887.003.2-B | −0.72458 | 0.72457637 | 10.08408 | 1E-16 | 286887.00 | NM_173086.2 | BG876719.1 | EST | 1 |
| 155 | 4629.005.1-F_at | −0.72437 | 0.72437411 | 10.07816 | 1E-16 | 4629.005. | NM_022844.1 | CB963138.1 | EST | 3 |
| 156 | 3872.009.1-T_at | −0.72329 | 0.72328551 | 10.04637 | 1E-16 | 3872.009. | NM_000422.1 | BX647923.1 | mRNA | 91 |
| 157 | 59.014.2-D_at | −0.72287 | 0.72287431 | 10.0344 | 1E-16 | 59.014.2 | NM_001613.1 | CB962422.1 | EST | 1 |
| 158 | 403340.001.2-B | −0.72269 | 0.72269253 | 10.02912 | 1E-16 | 403340.00 | NM_203481.1 | DA145754.1 | EST | 1 |
| 159 | 3852.014.1-F_at | −0.72194 | 0.72194027 | 10.0073 | 1E-16 | 3852.014. | NM_000424.2 | BF826002.1 | EST | 1 |
| 160 | 27122.001.1-T_at | −0.72089 | 0.72088962 | 9.976959 | 1E-16 | 27122.001 | NM_013253.4 | BP290952.1 | EST | 1 |
| 161 | 26289.008.1-T_at | −0.72077 | 0.72076825 | 9.973463 | 1E-16 | 26289.008 | NM_000222.1 | CQ719901.1 | GENBANK_PATENT | 1 |
| 162 | 3815.002.3-T_at | −0.72074 | 0.72073551 | 9.97252 | 1E-16 | 3815.002. | NM_000424.2 | BG675837.1 | EST | 1 |
| 163 | 3852.008.1-E_at | −0.72072 | 0.72072375 | 9.972181 | 1E-16 | 3852.008. | NM_174858.1 | BG189938.1 | EST | 1 |
| 164 | 26289.012.1-T_at | −0.72026 | 0.72026202 | 9.958901 | 1E-16 | 26289.012 | NM_174858.1 | DA259560.1 | EST | 1 |
| 165 | 4638.006.1-F_at | −0.72019 | 0.72019094 | 9.956859 | 1E-16 | 4638.006. | NM_053205.2 | DR005817.1 | EST | 2 |
| 166 | 8626.005.1-B_at | −0.71997 | 0.71997497 | 9.950658 | 1E-16 | 8626.005. | NM_003722.3 | AB042841.1 | mRNA | 1 |
| 167 | 3815.002.4-T_at | −0.71955 | 0.71955195 | 9.938531 | 1E-16 | 3815.002. | NM_000222.1 | CQ719901.1 | GENBANK_PATENT | 1 |
| 168 | 84668.004.1-T_at | −0.71918 | 0.71917508 | 9.927746 | 1E-16 | 84668.004 | NM_032581.2 | AL597549.1 | EST | 1 |
| 169 | 3872.007.1-F_at | −0.71916 | 0.71915759 | 9.927246 | 1E-16 | 3872.007. | NM_000422.1 | BU155457.1 | EST | 1 |
| 170 | 57447.031.1-F_at | −0.7189 | 0.71889801 | 9.919829 | 1E-16 | 57447.031 | NM_201535.1 | AI272253.1 | EST | 1 |
| 171 | 3084.012.3-T_at | −0.71856 | 0.71855665 | 9.910088 | 2E-16 | 3084.012. | NM_013957.1 | U02325.1 | mRNA | 1 |
| 172 | 3852.005.1-T_at | −0.71827 | 0.71827136 | 9.901958 | 2E-16 | 3852.005. | NM_000424.2 | R47851.1 | EST | 1 |
| 173 | 84417.001.2-T_at | −0.71816 | 0.71816117 | 9.898821 | 2E-16 | 84417.001 | NM_032411.1 | BI561114.1 | EST | 1 |
| 174 | 3866.003.2-T_at | −0.71746 | 0.71745931 | 9.878874 | 2E-16 | 3866.003. | NM_022275.2 | AK090604.1 | mRNA | 22 |
| 175 | 3866.008.1-C_at | −0.71716 | 0.71715783 | 9.870325 | 2E-16 | 3866.008. | NM_022275.2 | BI771363.1 | EST | 1 |
| 176 | 3852.009.1-F_at | −0.71671 | 0.71671024 | 9.857654 | 3E-16 | 3852.009. | NM_000424.2 | BQ378037.1 | EST | 1 |
| 177 | 59.015.1-B_at | −0.71663 | 0.7166277 | 9.85532 | 3E-16 | 59.015.1. | NM_001613.1 | BP372009.1 | EST | 1 |
| 178 | 79937.002.1-F_at | −0.71652 | 0.71651832 | 9.852229 | 3E-16 | 79937.002 | NM_033655.2 | AB051501.2 | mRNA | 9 |
| 179 | 7153.002.6-F_at | −0.716462 | 0.71646227 | 9.850645 | 3E-16 | 7153.002. | NM_001067.2 | CQ735949.1 | GENBANK_PATENT | 114 |
| 180 | 4281.010.1-B_at | −0.71619 | 0.71619361 | 9.84306 | 3E-16 | 4281.010. | NM_033290.1 | AY540016.1 | mRNA | 1 |
| 181 | 59.008.1-B_at | −0.71578 | 0.7157817 | 9.831448 | 2E-16 | 59.008.1 | NM_001613.1 | BP373197.1 | EST | 1 |
| 182 | 1264.007.1-T_at | −0.71577 | 0.71576716 | 9.831038 | 3E-16 | 1264.007. | NM_001299.4 | CX761868.1 | EST | 1 |
| 183 | 3868.004.1-T_at | −0.7156 | 0.71560057 | 9.826348 | 3E-16 | 3868.004. | NM_005557.2 | BM045170.1 | EST | 1 |
| 184 | 3084.002.1-F_at | −0.71513 | 0.71512815 | 9.813066 | 3E-16 | 3084.002. | NM_013957.1 | CN603657.1 | EST | 1 |
| 185 | 5137.004.2-T_at | −0.71508 | 0.71508204 | 9.811771 | 3E-16 | 5137.004. | NM_005020.1 | BP226298.1 | EST | 1 |
| 186 | 4629.022.1-F_at | −0.71428 | 0.71427853 | 9.789249 | 3E-16 | 4629.022. | NM_022844.1 | AX898971.1 | GENBANK_PATENT | 1 |
| 187 | 4915.011.1-T_at | −0.71337 | 0.71336654 | 9.763782 | 3E-16 | 4915.011. | NM_006180.3 | CQ723929.1 | GENBANK_PATENT | 1 |
| 188 | 3852.013.1-E_at | −0.71333 | 0.71332619 | 9.762657 | 4E-16 | 3852.013. | NM_000424.2 | BG682634.1 | EST | 1 |
| 189 | 59.012.2-T_at | −0.71189 | 0.71189085 | 9.722787 | 4E-16 | 59.012.2 | NM_001613.1 | AL546033.3 | EST | 1 |
| 190 | 59.015.1-F_at | −0.71184 | 0.71184354 | 9.721477 | 4E-16 | 59.015.1 | NM_001613.1 | BP372009.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 191 | 4638.006.2-T_at | −0.7112 | 0.71119714 | 9.703606 | 4E-16 | 4638.006. | NM_053025.2 | DR005817.1 | EST | 2 |
| 192 | 23336.002.1-B_at | −0.7108 | 0.71079772 | 9.692588 | 6E-16 | 23336.002 | NM_145728.1 | NM_015286.4 | REFSEQ | 6 |
| 193 | 3868.005.1-C_at | −0.70987 | 0.7098711 | 9.6671 | 6E-16 | 3868.005. | NM_005557.2 | BG682632.1 | EST | 1 |
| 194 | 3866.011.2-D_at | −0.7087 | 0.70870117 | 9.635065 | 7E-16 | 3866.011. | NM_002275.2 | BQ218433.1 | EST | 1 |
| 195 | 56477.001.1-T_at | −0.70868 | 0.70868235 | 9.634551 | 7E-16 | 56477.001 | NM_148672.1 | NM_019846.3 | REFSEQ | 13 |
| 196 | 3815.001.1-T_at | −0.70825 | 0.70824726 | 9.622678 | 7E-16 | 3815.001. | NM_000222.1 | CS237377.1 | GENBANK_PATENT | 1 |
| 197 | 4311.001.1-T_at | −0.70821 | 0.70820529 | 9.621535 | 7E-16 | 4311.001. | NM_000902.2 | CB988534.1 | EST | 1 |
| 198 | 1264.003.1-D_at | −0.70785 | 0.70785219 | 9.611918 | 8E-16 | 1264.003. | NM_001299.4 | CV811526.1 | EST | 1 |
| 199 | 59.031.1-T_at | −0.70756 | 0.70755684 | 9.603885 | 8E-16 | 59.031.1 | NM_001613.1 | BG197213.1 | EST | 19 |
| 200 | 57447.030.1-B_at | −0.70751 | 0.70750665 | 9.60252 | 8E-16 | 57447.030 | NM_201535.1 | BM783465.1 | EST | 5 |
| 201 | 1410.003.2-B_at | −0.70746 | 0.70745636 | 9.601154 | 8E-16 | 1410.003. | NM_001885.1 | AX899079.1 | GENBANK_PATENT | 1 |
| 202 | 3866.009.2-D_at | −0.70722 | 0.70721526 | 9.594607 | 8E-16 | 3866.009. | NM_002275.2 | BI457146.1 | EST | 1 |
| 203 | 59.026.1-T_at | −0.70717 | 0.70717265 | 9.59345 | 8E-16 | 59.026.1 | — | — | — | — |
| 204 | 440421.001.1-T | −0.70711 | 0.70711453 | 9.591873 | 8E-16 | 440421.00 | XM_496202.2 | XM_934894.1 | REFSEQ | 2 |
| 205 | 1756.022.4-D_at | −0.70675 | 0.70675086 | 9.582014 | 9E-16 | 1756.022. | NM_000109.2 | CQ714747.1 | GENBANK_PATENT | 1 |
| 206 | 65983.009.1-D_at | −0.7066 | 0.70660056 | 9.577944 | 9E-16 | 65983.009 | NM_023927.1 | CQ413222.1 | GENBANK_PATENT | 2 |
| 207 | 57447.041.1-T_at | −0.70624 | 0.70624401 | 9.5683 | 9E-16 | 57447.041 | NM_201535.1 | DA295124.1 | EST | 1 |
| 208 | 3872.010.2-D_at | −0.70603 | 0.7060339 | 9.562622 | 1E-15 | 3872.010. | NM_000422.1 | BM008795.1 | EST | 1 |
| 209 | 4629.006.2-T_at | −0.70601 | 0.70600879 | 9.561944 | 1E-15 | 4629.006. | NM_022844.1 | DB079784.1 | EST | 1 |
| 210 | 3861.018.1-F_at | −0.70592 | 0.70592127 | 9.559582 | 1E-15 | 3861.018. | NM_000526.3 | BM019687.1 | EST | 1 |
| 211 | 3815.002.1-T_at | −0.70576 | 0.70576231 | 9.555292 | 1E-15 | 3815.002. | NM_000222.1 | CQ719901.1 | GENBANK_PATENT | 1 |
| 212 | 3866.012.2-D_at | −0.70556 | 0.70555782 | 9.549778 | 1E-15 | 3866.012. | NM_002275.2 | BI772438.1 | EST | 1 |
| 213 | 57447.021.1-D_at | −0.70548 | 0.70548085 | 9.547704 | 1E-15 | 57447.021 | NM_201535.1 | BQ954948.1 | EST | 28 |
| 214 | 59.015.1-T_at | −0.70494 | 0.7049442 | 9.533261 | 1E-15 | 59.015.1 | NM_001613.1 | BP372009.1 | EST | 1 |
| 215 | 8626.007.1-F_at | −0.70484 | 0.70483534 | 9.530036 | 1E-15 | 8626.007. | NM_003722.3 | BG698723.1 | EST | 1 |
| 216 | 5288.001.1-B_at | −0.70452 | 0.70452172 | 9.521914 | 1E-15 | 5288.001. | NM_004570.2 | CQ720591.1 | GENBANK_PATENT | 1 |
| 217 | 72.001.1-B_at | −0.70441 | 0.70440953 | 9.518904 | 1E-15 | 72.001.1 | NM_001615.3 | BP330025.1 | EST | 1 |
| 218 | 3866.006.2-D_at | −0.70383 | 0.70382789 | 9.503322 | 2E-15 | 3866.006. | NM_002275.2 | BQ641523.1 | EST | 1 |
| 219 | 3852.004.1-T_at | −0.70371 | 0.70371224 | 9.500228 | 2E-15 | 3852.004. | NM_000424.2 | BE715131.1 | EST | 1 |
| 220 | 4629.016.2-T_at | −0.70364 | 0.70363752 | 9.49823 | 2E-15 | 4629.016. | NM_022844.1 | DB289769.1 | EST | 1 |
| 221 | 4629.007.1-T_at | −0.70359 | 0.70358925 | 9.49694 | 2E-15 | 4629.007. | NM_022844.1 | AY520817.1 | mRNA | 16 |
| 222 | 65983.008.1-T_at | −0.70354 | 0.70353523 | 9.495496 | 2E-15 | 65983.008 | NM_023927.1 | BI547735.1 | EST | 2 |
| 223 | 65983.013.1-F_at | −0.70278 | 0.7027824 | 9.475409 | 2E-15 | 65983.013 | NM_023927.1 | AA610396.1 | EST | 1 |
| 224 | 3084.004.1-F_at | −0.70205 | 0.70204717 | 9.455852 | 2E-15 | 3084.004. | NM_013957.1 | NM_013964.1 | REFSEQ | 5 |
| 225 | 27122.007.1-F_at | −0.70181 | 0.70180898 | 9.449529 | 2E-15 | 27122.007 | NM_013253.4 | DA177251.1 | EST | 1 |
| 226 | 3866.008.1-D_at | −0.70143 | 0.70142639 | 9.439386 | 2E-15 | 3866.008. | NM_002275.2 | BI771363.1 | EST | 1 |
| 227 | 26289.009.1-T_at | −0.70109 | 0.70108634 | 9.430384 | 2E-15 | 26289.009 | NM_174858.1 | AA393277.1 | EST | 1 |
| 228 | 59.009.1-B_at | −0.70065 | 0.7006532 | 9.418936 | 2E-15 | 59.009.1 | NM_001613.1 | CD299238.1 | EST | 1 |
| 229 | 4629.010.1-D_at | −0.70044 | 0.70044198 | 9.413361 | 2E-15 | 4629.010. | NM_022844.1 | AI285326.1 | EST | 1 |
| 230 | 59.023.1-B_at | −0.70011 | 0.70010609 | 9.404505 | 2E-15 | 59.023.1 | NM_001613.1 | DB248573.1 | EST | 1 |
| 231 | 26289.002.1-F_at | −0.69973 | 0.6997339 | 9.394706 | 3E-15 | 26289.002 | NM_174858.1 | BF966377.1 | EST | 1 |
| 232 | 1908.001.1-T_at | −0.69949 | 0.69948609 | 9.388191 | 3E-15 | 1908.001. | NM_207032.1 | BC008876.2 | mRNA | 3 |
| 233 | 4915.008.1-F_at | −0.69917 | 0.69916784 | 9.379833 | 3E-15 | 4915.008. | NM_006180.3 | NM_001007097 | REFSEQ | 4 |
| 234 | 23336.002.1-B_at | −0.69904 | 0.69903724 | 9.376406 | 3E-15 | 23336.002 | NM_145728.1 | NM_015286.4 | REFSEQ | 6 |
| 235 | 3861.008.1-C_at | −0.69903 | 0.69902539 | 9.376095 | 3E-15 | 3861.008. | NM_000526.3 | BE184532.1 | EST | 1 |
| 236 | 3861.008.1-D_at | −0.69889 | 0.69889457 | 9.372664 | 3E-15 | 3861.008. | NM_000526.3 | BE184532.1 | EST | 1 |
| 237 | 57447.035.1-E_at | −0.69855 | 0.69855253 | 9.363704 | 3E-15 | 57447.035 | NM_201535.1 | BQ636638.1 | EST | 1 |
| 238 | 3861.018.1-C_at | −0.69848 | 0.69848178 | 9.361852 | 3E-15 | 3861.018. | NM_000526.3 | BM019687.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 239 | 1308.003.1-B_at | −0.69839 | 0.69838688 | 9.359369 | 3E-15 | 1308.003. | NM_130778.1 | NM_000494.2 | REFSEQ | 19 |
| 240 | 667.022.1-B_at | −0.69713 | 0.69712975 | 9.326564 | 3E-15 | 667.022.1 | NM_183380.1 | AX683196.1 | GENBANK_PATENT | 1 |
| 241 | 3866.011.2-T_at | −0.69701 | 0.69700959 | 9.323438 | 3E-15 | 3866.011. | NM_002275.2 | BQ218433.1 | EST | 1 |
| 242 | 2115.001.2-F_at | −0.69674 | 0.69674446 | 9.316544 | 3E-15 | 2115.001. | NM_004956.3 | X87175.1 | mRNA | 1 |
| 243 | 3866.011.2-B_at | −0.69651 | 0.69651246 | 9.310518 | 3E-15 | 3866.011. | NM_002275.2 | BQ218433.1 | EST | 1 |
| 244 | 26289.010.1-T_at | −0.69627 | 0.69627463 | 9.304346 | 3E-15 | 26289.010 | NM_174858.1 | AX988359.1 | GENBANK_PATENT | 1 |
| 245 | 27303.004.1-F_at | −0.69571 | 0.69571431 | 9.28983 | 4E-15 | 27303.004 | NM_001003793. | BQ876639.1 | EST | 1 |
| 246 | 59.003.1-B_at | −0.69503 | 0.69503447 | 9.27226 | 4E-15 | 59.003.1 | NM_001613.1 | DD218797.1 | GENBANK_PATENT | 1 |
| 247 | 4311.009.1-C_at | −0.69487 | 0.69486903 | 9.267992 | 4E-15 | 4311.009. | NM_000902.2 | A30431.1 | GENBANK_PATENT | 1 |
| 248 | 7373.003.6-B_at | −0.69405 | 0.69404745 | 9.246838 | 4E-15 | 7373.003. | NM_021110.1 | CQ716670.1 | GENBANK_PATENT | 1 |
| 249 | 65983.004.1-T_at | −0.69339 | 0.69339166 | 9.230003 | 5E-15 | 65983.004 | NM_023927.1 | BP262020.1 | EST | 1 |
| 250 | 26289.013.1-D_at | −0.69304 | 0.69304425 | 9.221102 | 5E-15 | 26289.013 | NM_174858.1 | CK024190.1 | EST | 1 |
| 251 | 3866.004.1-F_at | −0.69262 | 0.6926248 | 9.210372 | 5E-15 | 3866.004. | NM_002275.2 | BC110649.1 | mRNA | 1 |
| 252 | 56477.001.1-F_at | −0.69247 | 0.69247193 | 9.206466 | 5E-15 | 56477.001 | NM_148672.1 | NM_019846.3 | REFSEQ | 13 |
| 253 | 57447.037.1-F_at | −0.69228 | 0.69227756 | 9.201453 | 5E-15 | 57447.037 | NM_201535.1 | BF793156.1 | EST | 1 |
| 254 | 59.022.2-T_at | −0.69208 | 0.69207912 | 9.19644 | 6E-15 | 59.022.2 | — | — | — | — |
| 255 | 147495.008.1-F | −0.69208 | 0.69207819 | 9.196417 | 6E-15 | 147495.00 | NM_153000.3 | BU541433.1 | EST | 1 |
| 256 | 2.018.1-T_at | −0.69207 | 0.69207481 | 9.196331 | 6E-15 | 2.018.1 | NM_000014.4 | DB090657.1 | EST | 1 |
| 257 | 140807.003.1-E | −0.69207 | 0.69207171 | 9.196251 | 6E-15 | 140807.00 | NM_080747.1 | DB022590.1 | EST | 1 |
| 258 | 65983.009.1-T_at | −0.69206 | 0.69205534 | 9.195834 | 6E-15 | 65983.009 | NM_023927.1 | CQ413222.1 | GENBANK_PATENT | 2 |
| 259 | 84668.002.1-F_at | −0.69156 | 0.69155609 | 9.183115 | 6E-15 | 84668.002 | NM_032581.2 | AL833296.1 | mRNA | 20 |
| 260 | 3872.007.1-C_at | −0.69153 | 0.69153411 | 9.182556 | 6E-15 | 3872.007. | NM_000422.1 | BU155457.1 | EST | 1 |
| 261 | 2115.008.1-T_at | −0.69097 | 0.6909716 | 9.168257 | 6E-15 | 2115.008. | NM_004956.3 | BC045776.1 | mRNA | 3 |
| 262 | 65983.004.2-T_at | −0.69096 | 0.69095787 | 9.167908 | 6E-15 | 65983.004 | NM_023927.1 | BP262020.1 | EST | 1 |
| 263 | 57447.034.1-D_at | −0.69053 | 0.69052533 | 9.156935 | 7E-15 | 57447.034 | NM_201535.1 | BC011240.1 | mRNA | 1 |
| 264 | 3866.001.1-F_at | −0.69016 | 0.69016212 | 9.147735 | 7E-15 | 3866.001. | NM_002275.2 | CQ733235.1 | GENBANK_PATENT | 23 |
| 265 | 3866.008.1-F_at | −0.69014 | 0.69014281 | 9.147247 | 7E-15 | 3866.008. | NM_002275.2 | BI771363.1 | EST | 1 |
| 266 | 1959.003.1-C_at | −0.68985 | 0.68984796 | 9.139789 | 7E-15 | 1959.003. | NM_000399.2 | BX414563.2 | EST | 3 |
| 267 | 389432.002.1-T | −0.68963 | 0.6896308 | 9.134301 | 8E-15 | 389432.00 | NM_001030060. | CQ751492.1 | GENBANK_PATENT | 1 |
| 268 | 389734.001.1-T | −0.68953 | 0.68953203 | 9.131807 | 8E-15 | 389734.00 | XM_928572.1 | NM_033655.2 | REFSEQ | 1 |
| 269 | 3855.001.2-D_at | −0.68928 | 0.68928425 | 9.125555 | 8E-15 | 3855.001. | NM_005556.3 | BM754696.1 | EST | 1 |
| 270 | 3866.003.1-T_at | −0.68911 | 0.68910803 | 9.121111 | 8E-15 | 3866.003. | NM_002275.2 | AK090604.1 | mRNA | 22 |
| 271 | 3084.006.1-F_at | −0.689 | 0.68900076 | 9.118408 | 8E-15 | 3084.006. | NM_013957.1 | NM_013956.1 | REFSEQ | 3 |
| 272 | 4915.008.1-B_at | −0.68884 | 0.68884477 | 9.114479 | 8E-15 | 4915.008. | NM_006180.3 | NM_001007097 | REFSEQ | 4 |
| 273 | 2115.011.1-T_at | −0.68881 | 0.68880926 | 9.113585 | 8E-15 | 2115.011. | NM_004956.3 | DB093597.1 | EST | 1 |
| 274 | 65983.005.1-T_at | −0.68876 | 0.68875602 | 9.112245 | 8E-15 | 65983.005 | NM_023927.1 | CQ471280.1 | GENBANK_PATENT | 6 |
| 275 | 84668.004.1-T_at | −0.68808 | 0.68807773 | 9.095195 | 9E-15 | 84668.004 | NM_032581.2 | AL597549.1 | EST | 1 |
| 276 | 59.015.2-T_at | −0.68802 | 0.68801589 | 9.093643 | 9E-15 | 59.015.2 | NM_001613.1 | BP372009.1 | EST | 1 |
| 277 | 2119.006.1-B_at | −0.6878 | 0.687801 | 9.088252 | 9E-15 | 2119.006. | NM_004454.1 | DB094869.1 | EST | 1 |
| 278 | 4638.006.2-F_at | −0.68764 | 0.6876412 | 9.084246 | 1E-14 | 4638.006. | NM_053025.2 | DR005817.1 | EST | 2 |
| 279 | 3866.007.2-D_at | −0.68699 | 0.68699646 | 9.068108 | 1E-14 | 3866.007. | NM_002275.2 | BM548942.1 | EST | 1 |
| 280 | 59.014.1-F_at | −0.68691 | 0.68691236 | 9.066007 | 1E-14 | 59.014.1 | NM_001613.1 | CB962422.1 | EST | 1 |
| 281 | 3866.001.2-F_at | −0.68681 | 0.68680934 | 9.063433 | 1E-14 | 3866.001. | NM_002275.2 | CQ733235.1 | GENBANK_PATENT | 23 |
| 282 | 1308.008.1-B_at | −0.68652 | 0.68652289 | 9.056281 | 1E-14 | 1308.008. | NM_130778.1 | BE148646.1 | EST | 1 |
| 283 | 59.026.1-F_at | −0.68647 | 0.68647292 | 9.055034 | 1E-14 | 59.026.1 | — | — | — | — |
| 284 | 3866.013.1-T_at | −0.68626 | 0.68625953 | 9.049713 | 1E-14 | 3866.013. | NM_002275.2 | BI769443.1 | EST | 1 |
| 285 | 1264.001.2-F_at | −0.68577 | 0.68577484 | 9.037643 | 1E-14 | 1264.001. | NM_001299.4 | CX761868.1 | EST | 1 |
| 286 | 3866.007.2-T_at | −0.68566 | 0.68566296 | 9.034861 | 1E-14 | 3866.007. | NM_002275.2 | BM548942.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 287 | 27122.013.1-T_at | −0.68541 | 0.68541178 | 9.028617 | 1E−14 | 27122.013 | NM_013253.4 | DR155720.1 | EST | 1 |
| 288 | 27122.006.2-T_at | −0.68531 | 0.68531032 | 9.026097 | 1E−14 | 27122.006 | NM_013253.4 | DA171350.1 | EST | 1 |
| 289 | 3866.006.2-T_at | −0.68509 | 0.68508881 | 9.020598 | 1E−14 | 3866.006. | NM_002275.2 | BQ641523.1 | EST | 1 |
| 290 | 3866.009.2-T_at | −0.68506 | 0.68506091 | 9.019906 | 1E−14 | 3866.009. | NM_002275.2 | BI457146.1 | EST | 1 |
| 291 | 4240.004.1-D_at | −0.68504 | 0.68503667 | 9.019305 | 1E−14 | 4240.004. | NM_005928.1 | BC003610.2 | mRNA | 448 |
| 292 | 3866.010.1-C_at | −0.68501 | 0.68500991 | 9.018641 | 1E−14 | 3866.010. | NM_002275.2 | BM045201.1 | EST | 1 |
| 293 | 3866.009.2-B_at | −0.68464 | 0.68464309 | 9.009548 | 1E−14 | 3866.009. | NM_002275.2 | BI457146.1 | EST | 1 |
| 294 | 3866.009.1-T_at | −0.68457 | 0.68456652 | 9.007652 | 1E−14 | 3866.009. | NM_002275.2 | BI457146.1 | EST | 1 |
| 295 | 4629.006.1-T_at | −0.68451 | 0.68450911 | 9.00623 | 1E−14 | 4629.006. | NM_022844.1 | DB079784.1 | EST | 1 |
| 296 | 7018.029.1-B_at | −0.68388 | 0.68388329 | 8.990755 | 2E−14 | 7018.029. | NM_001063.2 | AV656085.1 | EST | 1 |
| 297 | 1410.002.2-B_at | −0.68375 | 0.8837454 | 8.987351 | 2E−14 | 1410.002. | NM_001885.1 | AX899073.1 | GENBANK_PATENT | 4 |
| 298 | 3866.012.1-T_at | −0.68307 | 0.68306583 | 8.970598 | 2E−14 | 3866.012. | NM_002275.2 | BI772438.1 | EST | 1 |
| 299 | 59.034.2-D_at | −0.68305 | 0.68305272 | 8.970275 | 2E−14 | 59.034.2 | — | — | — | — |
| 300 | 27122.019.1-F_at | −0.68293 | 0.68293177 | 8.967298 | 2E−14 | 27122.019 | NM_013253.4 | CX758435.1 | EST | 1 |
| 301 | 5156.001.1-T_at | −0.68292 | 0.6829222 | 8.967063 | 2E−14 | 5156.001. | NM_006206.3 | BC015186.1 | mRNA | 1 |
| 302 | 389734.001.2-T | −0.68274 | 0.68273641 | 8.962493 | 2E−14 | 389734.00 | XM_928572.1 | NM_033655.2 | REFSEQ | 1 |
| 303 | 27122.014.1-T_at | −0.68257 | 0.68256552 | 8.958292 | 2E−14 | 27122.014 | NM_013253.4 | DA180412.1 | EST | 1 |
| 304 | 57447.010.3-T_at | −0.68236 | 0.68236044 | 8.953255 | 2E−14 | 57447.010 | NM_201535.1 | BP349691.1 | EST | 1 |
| 305 | 358.018.1-F_at | −0.68232 | 0.68232244 | 8.952322 | 2E−14 | 358.018.1 | NM_198098.1 | BI765065.1 | EST | 1 |
| 306 | 3866.006.1-T_at | −0.68218 | 0.6821773 | 8.948759 | 2E−14 | 3866.006. | NM_002275.2 | BQ641523.1 | EST | 1 |
| 307 | 7373.001.1-T_at | −0.68199 | 0.68198548 | 8.944055 | 2E−14 | 7373.001. | NM_021110.1 | DB089175.1 | EST | 1 |
| 308 | 26289.012.1-B_at | −0.68184 | 0.68184048 | 8.940501 | 2E−14 | 26289.012 | NM_174858.1 | BG189938.1 | EST | 1 |
| 309 | 57447.029.1-T_at | −0.68178 | 0.68178369 | 8.939109 | 2E−14 | 57447.029 | NM_201535.1 | BX354120.2 | EST | 6 |
| 310 | 358.018.1-B_at | −0.68156 | 0.68155712 | 8.933561 | 2E−14 | 358.018.1 | NM_198098.1 | BI765065.1 | EST | 1 |
| 311 | 79068.010.1-B_at | −0.68149 | 0.68149173 | 8.93196 | 2E−14 | 79068.010 | XM_051200.8 | DA647247.1 | EST | 1 |
| 312 | 59.024.1-B_at | −0.68126 | 0.68126043 | 8.926302 | 2E−14 | 59.024.1 | — | — | — | — |
| 313 | 59.004.1-B_at | −0.68117 | 0.68116935 | 8.924076 | 2E−14 | 59.004.1 | NM_001613.1 | CQ696293.1 | GENBANK_PATENT | 1 |
| 314 | 3866.011.1-T_at | −0.68101 | 0.68100958 | 8.920172 | 2E−14 | 3866.011. | NM_002275.2 | BQ218433.1 | EST | 1 |
| 315 | 3866.013.1-E_at | −0.68096 | 0.68096121 | 8.91899 | 2E−14 | 3866.013. | NM_002275.2 | BI769443.1 | EST | 1 |
| 316 | 3866.010.1-D_at | −0.68032 | 0.68032145 | 8.903385 | 2E−14 | 3866.010. | NM_002275.2 | BM045201.1 | EST | 1 |
| 317 | 59.004.1-T_at | −0.68016 | 0.68016229 | 8.899508 | 2E−14 | 59.004.1 | NM_001613.1 | CQ696293.1 | GENBANK_PATENT | 37 |
| 318 | 2115.012.1-T_at | −0.68003 | 0.68003217 | 8.896341 | 2E−14 | 2115.012. | NM_021110.1 | DA407403.1 | EST | 1 |
| 319 | 2.018.1-D_at | −0.68003 | 0.68003048 | 8.8963 | 2E−14 | 2.018.1 | NM_004956.3 | DB090657.1 | EST | 1 |
| 320 | 2115.007.1-T_at | −0.67992 | 0.67991611 | 8.893517 | 2E−14 | 2115.007. | NM_004956.3 | DA189670.1 | EST | 1 |
| 321 | 59.040.1-T_at | −0.67978 | 0.67977663 | 8.890125 | 2E−14 | 59.040.1 | NM_001613.1 | EH_001613.6 | PREDICTED | 1 |
| 322 | 130497.001.2-T | −0.67974 | 0.67974133 | 8.889267 | 2E−14 | 130497.00 | NM_145260.2 | BP316395.1 | EST | 1 |
| 323 | 140885.014.1-T | −0.67971 | 0.67971161 | 8.888544 | 2E−14 | 140885.01 | NM_080792.2 | DR423079.1 | EST | 1 |
| 324 | 3866.005.1-F_at | −0.6797 | 0.67970122 | 8.888292 | 2E−14 | 3866.005. | NM_002275.2 | AL832226.1 | mRNA | 37 |
| 325 | 7373.003.3-F_at | −0.67961 | 0.67961087 | 8.886096 | 3E−14 | 7373.003. | NM_021110.1 | CQ716670.1 | GENBANK_PATENT | 1 |
| 326 | 8404.028.1-F_at | −0.67957 | 0.67957039 | 8.885112 | 3E−14 | 8404.028. | NM_004684.2 | CQ727530.1 | GENBANK_PATENT | 1 |
| 327 | 3860.007.1-D_at | −0.67955 | 0.67954786 | 8.884565 | 3E−14 | 3860.007. | NM_153490.1 | DB256579.1 | EST | 1 |
| 328 | 4638.003.1-C_at | −0.67882 | 0.678822 | 8.866957 | 3E−14 | 4638.003. | NM_053025.2 | BP289609.1 | EST | 2 |
| 329 | 3872.009.1-E_at | −0.67861 | 0.67861088 | 8.861844 | 3E−14 | 3872.009. | NM_000422.1 | BX647923.1 | mRNA | 91 |
| 330 | 59.004.2-T_at | −0.67859 | 0.67859272 | 8.861405 | 3E−14 | 59.004.2 | NM_001613.1 | CQ696293.1 | GENBANK_PATENT | 1 |
| 331 | 3872.006.1-C_at | −0.67843 | 0.67842819 | 8.857424 | 3E−14 | 3872.006. | NM_000422.1 | BM017443.1 | EST | 1 |
| 332 | 3866.005.1-C_at | −0.67822 | 0.67822035 | 8.852398 | 3E−14 | 3866.005. | NM_002275.2 | AL832226.1 | mRNA | 37 |
| 333 | 25925.008.1-T_at | −0.67797 | 0.6779714 | 8.846384 | 3E−14 | 25925.008 | NM_015461.1 | DA093254.1 | EST | 1 |
| 334 | 23650.011.2-T_at | −0.67792 | 0.67792361 | 8.84523 | 3E−14 | 23650.011 | NM_058193.1 | NM_012101.2 | REFSEQ | 11 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 335 | 3866.012.2-T_at | −0.67755 | 0.67754608 | 8.836122 | 3E-14 | 3866.012. | NM_002275.2 | BI772438.1 | EST | 1 |
| 336 | 3852.017.1-D_at | −0.6775 | 0.67750467 | 8.835124 | 3E-14 | 3852.017. | NM_000424.2 | CV575305.1 | EST | 1 |
| 337 | 4915.005.1-T_at | −0.67735 | 0.67734733 | 8.831332 | 3E-14 | 4915.005. | NM_006180.3 | BP348402.1 | EST | 1 |
| 338 | 4638.003.1-B_at | −0.67707 | 0.67706981 | 8.82465 | 3E-14 | 4638.003. | NM_053025.2 | BP289609.1 | EST | 2 |
| 339 | 1756.003.1-B_at | −0.67674 | 0.67673545 | 8.816608 | 4E-14 | 1756.003. | NM_000109.2 | AB208836.1 | mRNA | 1 |
| 340 | 4638.006.1-F_at | −0.67651 | 0.6765092 | 8.811172 | 4E-14 | 4638.006. | NM_053025.2 | DR005817.1 | EST | 2 |
| 341 | 57447.035.1-F_at | −0.67604 | 0.67604162 | 8.799953 | 4E-14 | 57447.035 | NM_201535.1 | BQ636638.1 | EST | 1 |
| 342 | 4638.014.1-T_at | −0.67585 | 0.67584646 | 8.795276 | 4E-14 | 4638.014. | NM_053025.2 | NM_053027.2 | REFSEQ | 2 |
| 343 | 7373.003.4-T_at | −0.67582 | 0.67582231 | 8.794697 | 4E-14 | 7373.003. | NM_021110.1 | CQ716670.1 | GENBANK_PATENT | 1 |
| 344 | 27122.014.2-D_at | −0.67579 | 0.67578648 | 8.793839 | 4E-14 | 27122.014 | NM_013253.4 | DA180412.1 | EST | 1 |
| 345 | 3866.007.1-T_at | −0.67504 | 0.67503748 | 8.775925 | 4E-14 | 3866.007. | NM_002275.2 | BM548942.1 | EST | 1 |
| 346 | 2707.002.1-E_at | −0.67499 | 0.67498884 | 8.774763 | 4E-14 | 2707.002. | NM_024009.2 | DA669405.1 | EST | 4 |
| 347 | 59.024.1-T_at | −0.67481 | 0.67480778 | 8.770441 | 4E-14 | 59.024.1 | — | — | — | |
| 348 | 23650.011.1-T_at | −0.6747 | 0.67469739 | 8.767807 | 4E-14 | 23650.011 | NM_058193.1 | NM_012101.2 | REFSEQ | 11 |
| 349 | 4638.011.1-F_at | −0.67462 | 0.67462378 | 8.766052 | 4E-14 | 4638.011. | NM_053025.2 | DB267860.1 | EST | 1 |
| 350 | 7373.002.1-F_at | −0.67455 | 0.67455304 | 8.764365 | 5E-14 | 7373.002. | NM_021110.1 | BC036192.1 | mRNA | 2 |
| 351 | 3866.013.1-F_at | −0.6745 | 0.6744968 | 8.763024 | 5E-14 | 3866.013. | NM_002275.2 | BI769443.1 | EST | 1 |
| 352 | 5608.002.1-T_at | −0.67444 | 0.67443693 | 8.761597 | 5E-14 | 5608.002. | NM_002758.2 | DA427998.1 | EST | 1 |
| 353 | 3866.001.1-C_at | −0.67411 | 0.67411218 | 8.753863 | 5E-14 | 3866.001. | NM_002275.2 | CQ733235.1 | GENBANK_PATENT | 23 |
| 354 | 1756.013.1-B_at | −0.67402 | 0.67402382 | 8.75176 | 5E-14 | 1756.013. | NM_000109.2 | NM_004019.1 | REFSEQ | 2 |
| 355 | 2115.006.1-E_at | −0.67381 | 0.67381491 | 8.746791 | 5E-14 | 2115.006. | NM_004956.3 | DA210177.1 | EST | 1 |
| 356 | 6376.001.2-F_at | −0.67341 | 0.6734055 | 8.737064 | 5E-14 | 6376.001. | NM_002996.3 | AK223351.1 | mRNA | 48 |
| 357 | 3084.004.1-B_at | −0.67338 | 0.67337698 | 8.736388 | 5E-14 | 3084.004. | NM_013957.1 | NM_013964.1 | REFSEQ | 5 |
| 358 | 3815.002.4F_at | −0.67334 | 0.67333838 | 8.735471 | 5E-14 | 3815.002. | NM_000222.1 | CQ719901.1 | GENBANK_PATENT | 1 |
| 359 | 8404.002.1-D_at | −0.6733 | 0.6733018 | 8.734603 | 5E-14 | 8404.002. | NM_004684.2 | BP383384.1 | EST | 1 |
| 360 | 1264.006.1-T_at | −0.67319 | 0.67318534 | 8.73184 | 5E-14 | 1264.006. | NM_001299.4 | CN366945.1 | EST | 1 |
| 361 | 59.022.2-D_at | −0.67316 | 0.67315986 | 8.731236 | 5E-14 | 59.022.2 | — | — | — | |
| 362 | 25925.001.1-T_at | −0.67306 | 0.67306029 | 8.728874 | 6E-14 | 25925.001 | NM_015461.1 | BC032869.2 | mRNA | 19 |
| 363 | 4638.006.2-B_at | −0.67278 | 0.67278344 | 8.722314 | 6E-14 | 4638.006. | NM_053025.2 | DR005817.1 | EST | 2 |
| 364 | 7373.003.5-B_at | −0.67271 | 0.67270981 | 8.72057 | 6E-14 | 7373.003. | NM_021110.1 | CQ716670.1 | GENBANK_PATENT | 1 |
| 365 | 8404.035.1-B_at | −0.6727 | 0.67269572 | 8.720236 | 6E-14 | 8404.035. | NM_004684.2 | BG716198.1 | EST | 1 |
| 366 | 59.012.1-T_at | −0.67254 | 0.67254112 | 8.716577 | 7E-14 | 59.012.1 | NM_001613.1 | AL546033.3 | EST | 1 |
| 367 | 3852.017.2-T_at | −0.67188 | 0.67188165 | 8.70099 | 7E-14 | 3852.017. | NM_000424.2 | CV575305.1 | EST | 1 |
| 368 | 3866.012.2-B_at | −0.67185 | 0.67184565 | 8.70014 | 7E-14 | 3866.012. | NM_002275.2 | BI772438.1 | EST | 1 |
| 369 | 2.022.1-B_at | −0.67169 | 0.67168628 | 8.69638 | 6E-14 | 2.022.1 | NM_000424.4 | BP343424.1 | EST | 1 |
| 370 | 27122.016.1-F_at | −0.67125 | 0.67124955 | 8.686085 | 7E-14 | 27122.016 | NM_013253.4 | BQ962557.1 | GENBANK_PATENT | 1 |
| 371 | 4311.009.1-B_at | −0.67109 | 0.67108684 | 8.682254 | 7E-14 | 4311.009. | NM_000902.2 | A30431.1 | EST | 1 |
| 372 | 59.031.2-T_at | −0.67084 | 0.67084085 | 8.676467 | 7E-14 | 59.031.2 | NM_001613.1 | BG197213.1 | EST | 19 |
| 373 | 4311.009.1-T_at | −0.67054 | 0.67053973 | 8.669389 | 7E-14 | 4311.009. | NM_000902.2 | A30431.1 | GENBANK_PATENT | 1 |
| 374 | 3866.006.2-B_at | −0.67045 | 0.67044748 | 8.667223 | 7E-14 | 3866.006. | NM_002275.2 | BQ641523.1 | EST | 1 |
| 375 | 57447.025.2-T_at | −0.67023 | 0.67022566 | 8.662016 | 7E-14 | 57447.025 | NM_201535.1 | DA646455.1 | EST | 2 |
| 376 | 1717.007.1-F_at | −0.67014 | 0.67013656 | 8.659925 | 8E-14 | 1717.007. | NM_001360.1 | BX438503.2 | GENBANK_PATENT | 1 |
| 377 | 59.004.2-D_at | −0.67008 | 0.67008376 | 8.658687 | 8E-14 | 59.004.2 | NM_001613.1 | CQ696293.1 | GENBANK_PATENT | 1 |
| 378 | 3866.007.2-B_at | −0.66995 | 0.66994537 | 8.655442 | 8E-14 | 3866.007. | NM_002275.2 | BM548942.1 | EST | 1 |
| 379 | 3866.010.1-F_at | −0.66945 | 0.66944797 | 8.643794 | 8E-14 | 3866.010. | NM_002275.2 | BM045201.1 | EST | 1 |
| 380 | 9768.001.1-T_at | −0.66933 | 0.66933125 | 8.641063 | 8E-14 | 9768.004. | NM_014736.4 | BG506365.1 | EST | 1 |
| 381 | 3084.012.2-T_at | −0.66928 | 0.66928297 | 8.639934 | 8E-14 | 3084.012. | NM_013957.1 | U02325.1 | mRNA | 2 |
| 382 | 1410.004.2-B_at | −0.66925 | 0.66925228 | 8.639216 | 8E-14 | 1410.004. | NM_001885.1 | AX888027.1 | GENBANK_PATENT | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 383 | 59.008.1-D_at | −0.66919 | 0.66919054 | 8.637773 | 8E-14 | 59.008.1 | NM_001613.1 | BP373197.1 | EST | 1 |
| 384 | 57447.030.1-C_at | −0.66908 | 0.66908366 | 8.635275 | 8E-14 | 57447.030 | NM_201535.1 | BM783465.1 | EST | 5 |
| 385 | 2327.002.1-D_at | −0.66908 | 0.66907887 | 8.635163 | 8E-14 | 2327.002. | NM_001460.2 | CD684429.1 | EST | 1 |
| 386 | 1308.004.1-B_at | −0.66865 | 0.66864754 | 8.625092 | 9E-14 | 1308.004. | NM_130778.1 | BF615666.1 | EST | 1 |
| 387 | 2568.005.2-B_at | −0.66838 | 0.66838113 | 8.61888 | 9E-14 | 2568.005. | NM_014211.1 | AK055205.1 | mRNA | 11 |
| 388 | 2568.001.1-T_at | −0.66811 | 0.66811257 | 8.612624 | 9E-14 | 2568.001. | NM_014211.1 | BX509618.1 | EST | 1 |
| 389 | 3084.004.2-T_at | −0.66789 | 0.66788994 | 8.607442 | 1E-13 | 3084.004. | NM_013957.1 | NM_013964.1 | REFSEQ | 5 |
| 390 | 7373.003.4-B_at | −0.66777 | 0.66776994 | 8.604651 | 1E-13 | 7373.003. | NM_021110.1 | CQ716670.1 | GENBANK_PATENT | 1 |
| 391 | 7153.002.2-D_at | −0.667642 | 0.66764203 | 8.601677 | 1E-13 | 7153.002. | NM_001067.2 | CQ735949.1 | GENBANK_PATENT | 114 |
| 392 | 2893.006.2-T_at | −0.66761 | 0.66760773 | 8.600829 | 1E-13 | 2893.006. | NM_000829.1 | BF669210.1 | EST | 1 |
| 393 | 3872.016.1-D_at | −0.66759 | 0.66758641 | 8.600384 | 1E-13 | 3872.016. | NM_000422.1 | CB127430.1 | EST | 1 |
| 394 | 9413.006.1-F_at | −0.6674 | 0.6674036 | 8.596137 | 1E-13 | 9413.006. | NM_004816.2 | BC021685.1 | mRNA | 2 |
| 395 | 59.023.2-B_at | −0.66731 | 0.6673108 | 8.593982 | 1E-13 | 59.023.2 | NM_001613.1 | DB248573.1 | EST | 1 |
| 396 | 72.005.1-B_at | −0.66711 | 0.66711142 | 8.589354 | 1E-13 | 72.005.1 | NM_001615.3 | CF130984.1 | EST | 20 |
| 397 | 4915.011.1-C_at | −0.66689 | 0.66688915 | 8.5842 | 1E-13 | 4915.011. | NM_006180.3 | CQ723929.1 | GENBANK_PATENT | 1 |
| 398 | 27122.018.1-F_at | −0.66662 | 0.6666247 | 8.578072 | 1E-13 | 27122.018 | NM_013253.4 | BG715341.1 | EST | 1 |
| 399 | 3852.006.1-B_at | −0.66652 | 0.66652184 | 8.57569 | 1E-13 | 3852.006. | NM_000424.2 | BG679014.1 | EST | 1 |
| 400 | 4638.006.2-D_at | −0.66649 | 0.66648584 | 8.574857 | 1E-13 | 4638.006. | NM_053025.2 | DR005817.1 | EST | 2 |
| 401 | 7153.005.1-E_at | −0.666056 | 0.66605623 | 8.56492 | 1E-13 | 7153.005. | NM_001067.2 | DB061604.1 | EST | 1 |
| 402 | 7373.001.2-T_at | −0.66587 | 0.66587031 | 8.560624 | 1E-13 | 7373.001. | NM_021110.1 | DB089175.1 | EST | 1 |
| 403 | 7018.026.1-B_at | −0.66537 | 0.66537209 | 8.549127 | 1E-13 | 7018.026. | NM_001063.2 | BM690655.1 | EST | 1 |
| 404 | 7402.014.1-B_at | −0.66525 | 0.66524627 | 8.546227 | 1E-13 | 7402.014. | NM_007124.1 | AL703969.1 | EST | 1 |
| 405 | 57447.010.3-D_at | −0.66513 | 0.66513034 | 8.543556 | 1E-13 | 57447.010 | NM_201535.1 | BP349691.1 | EST | 1 |
| 406 | 140446.004.1-T | −0.66502 | 0.66501858 | 8.540982 | 1E-13 | 140446.00 | NM_058242.1 | DB016079.1 | EST | 1 |
| 407 | 59.026.2-T_at | −0.66495 | 0.66494798 | 8.539356 | 1E-13 | 59.026.2 | — | — | — | — |
| 408 | 59.038.1-T_at | −0.66494 | 0.66493959 | 8.539163 | 1E-13 | 59.038.1 | NM_001613.1 | EH_001613.2 | PREDICTED | 1 |
| 409 | 4240.009.1-C_at | −0.66471 | 0.66470997 | 8.553879 | 1E-13 | 4240.009. | NM_005928.1 | BG829936.1 | EST | 2 |
| 410 | 57447.030.1-F_at | −0.66468 | 0.66468295 | 8.533258 | 1E-13 | 57447.030 | NM_201535.1 | BM783465.1 | EST | 5 |
| 411 | 9768.004.1-B_at | −0.664563 | 0.66456315 | 8.530503 | 1E-13 | 9768.004. | NM_014736.4 | BG506365.1 | EST | 2 |
| 412 | 57447.008.1-T_at | −0.66453 | 0.66453368 | 8.529826 | 1E-13 | 57447.008 | NM_201535.1 | DB195772.1 | EST | 1 |
| 413 | 59.014.2-T_at | −0.66423 | 0.66423397 | 8.52294 | 1E-13 | 59.014.2 | NM_001613.1 | CB962422.1 | EST | 1 |
| 414 | 4915.012.1-T_at | −0.66407 | 0.6640741 | 8.51927 | 1E-13 | 4915.012. | NM_006180.3 | CD103051.1 | EST | 1 |
| 415 | 3866.004.1-T_at | −0.66398 | 0.66397879 | 8.517083 | 1E-13 | 3866.004. | NM_002275.2 | BC110649.1 | mRNA | 1 |
| 416 | 2582.007.2-C_at | −0.66357 | 0.66357028 | 8.507718 | 2E-13 | 2582.007. | NM_001008216. | AK057302.1 | GENBANK_PATENT | 32 |
| 417 | 7153.002.5-T_at | 0.663259 | 0.66325931 | 8.500598 | 2E-13 | 7153.002. | NM_001067.2 | CQ735949.1 | GENBANK_PATENT | 114 |
| 418 | 4638.009.1-F_at | −0.66296 | 0.66295877 | 8.493725 | 2E-13 | 4638.009. | NM_053025.2 | AX885051.1 | GENBANK_PATENT | 39 |
| 419 | 3861.023.1-T_at | −0.66279 | 0.66279224 | 8.489919 | 2E-13 | 3861.023. | NM_000526.3 | BG676679.1 | EST | 1 |
| 420 | 5858.003.3-C_at | −0.66243 | 0.66242627 | 8.481564 | 2E-13 | 5858.003. | NM_002864.1 | AX512279.1 | GENBANK_PATENT | 2 |
| 421 | 3861.020.1-F_at | −0.66242 | 0.66241661 | 8.481344 | 2E-13 | 3861.020. | NM_000526.3 | BM018298.1 | EST | 1 |
| 422 | 147495.005.1-T | −0.66232 | 0.66231598 | 8.479048 | 2E-13 | 147495.00 | NM_153000.3 | BI822892.1 | EST | 1 |
| 423 | 4638.006.2-C_at | −0.66228 | 0.66227571 | 8.47813 | 2E-13 | 4638.006. | NM_053025.2 | DR005817.1 | EST | 2 |
| 424 | 1308.004.1-F_at | −0.66213 | 0.66212634 | 8.474725 | 2E-13 | 1308.004. | NM_130778.1 | BF615666.1 | EST | 1 |
| 425 | 4915.004.1-F_at | −0.66185 | 0.66184583 | 8.468335 | 2E-13 | 4915.004. | NM_006180.3 | NM_001018066 | REFSEQ | 28 |
| 426 | 3866.008.1-B_at | −0.66173 | 0.66172906 | 8.465676 | 2E-13 | 3866.008. | NM_002275.2 | BI771363.1 | EST | 1 |
| 427 | 8626.002.1-E_at | −0.66173 | 0.66172521 | 8.465589 | 2E-13 | 8626.002. | NM_000526.1 | AB016072.1 | mRNA | 16 |
| 428 | 1264.003.1-T_at | −0.66156 | 0.66156109 | 8.461855 | 2E-13 | 1264.003. | NM_037722.3 | CV811526.1 | EST | 1 |
| 429 | 59.042.1-F_at | −0.66151 | 0.66151227 | 8.460744 | 2E-13 | 59.042.1 | NM_001299.4 | EH_001613.8 | PREDICTED | 1 |
| 430 | 4833.004.1-C_at | 0.661269 | 0.66126853 | 8.455204 | 2E-13 | 4833.004. | NM_005009.2 | BG478602.1 | EST | 8 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 431 | 2568.006.1-B_at | −0.66106 | 0.661057 | 8.450399 | 2E-13 | 2568.006. | NM_014211.1 | CD385249.1 | EST | 1 |
| 432 | 57447.004.2-T_at | −0.66103 | 0.66102604 | 8.449696 | 2E-13 | 57447.004 | NM_201535.1 | CD515320.1 | EST | 2 |
| 433 | 59.014.2-B_at | −0.66085 | 0.66084763 | 8.445647 | 2E-13 | 59.014.2 | NM_001613.1 | CB962422.1 | EST | 1 |
| 434 | 3084.012.1-T_at | −0.66068 | 0.66068046 | 8.441855 | 2E-13 | 3084.012. | NM_013957.1 | U02325.1 | mRNA | 1 |
| 435 | 27122.017.1-T_at | −0.6605 | 0.66049978 | 8.43776 | 2E-13 | 27122.017 | NM_013253.4 | CB155251.1 | EST | 1 |
| 436 | 3852.012.2-T_at | −0.66039 | 0.66039403 | 8.435364 | 2E-13 | 3852.012. | NM_000424.2 | CQ733668.1 | GENBANK_PATENT | 1 |
| 437 | 59.033.1-T_at | −0.66029 | 0.66028879 | 8.43298 | 2E-13 | 59.033.1 | — | — | — | — |
| 438 | 27122.002.1-C_at | −0.66018 | 0.66018203 | 8.430563 | 2E-13 | 27122.002 | NM_013253.4 | AK098756.1 | mRNA | 1 |
| 439 | 3880.011.1-B_at | −0.65981 | 0.65981353 | 8.422227 | 2E-13 | 3880.011. | NM_002276.3 | BP330400.1 | EST | 1 |
| 440 | 65983.013.1-T_at | −0.65959 | 0.65958733 | 8.417116 | 2E-13 | 65983.013 | NM_023927.1 | AA610396.1 | EST | 1 |
| 441 | 3872.014.1-T_at | −0.65949 | 0.65948987 | 8.414915 | 2E-13 | 3872.014. | NM_000422.1 | BG678436.1 | EST | 1 |
| 442 | 162605.001.4-C | −0.65946 | 0.65945748 | 8.414184 | 2E-13 | 162605.00 | NM_181535.2 | CQ735954.1 | GENBANK_PATENT | 1 |
| 443 | 59.031.2-B_at | −0.65937 | 0.65937317 | 8.41228 | 2E-13 | 59.031.2 | NM_001613.1 | BG197213.1 | EST | 19 |
| 444 | 3084.012.2-B_at | −0.65926 | 0.65925637 | 8.409644 | 3E-13 | 3084.012. | NM_013957.1 | U02325.1 | mRNA | 1 |
| 445 | 5858.001.2-C_at | −0.65925 | 0.65925226 | 8.409552 | 3E-13 | 5858.001. | NM_002864.1 | BC111756.1 | mRNA | 2 |
| 446 | 65983.010.1-T_at | −0.65919 | 0.65918848 | 8.408113 | 3E-13 | 65983.010 | NM_023927.1 | DB261377.1 | EST | 1 |
| 447 | 7373.003.5-F_at | −0.65893 | 0.65892789 | 8.402237 | 3E-13 | 7373.003. | NM_021110.1 | CQ716670.1 | GENBANK_PATENT | 1 |
| 448 | 3866.010.1-T_at | −0.65871 | 0.65871193 | 8.397372 | 3E-13 | 3866.010. | NM_002275.2 | BM045201.1 | EST | 1 |
| 449 | 8404.005.1-B_at | −0.65871 | 0.65870759 | 8.397274 | 3E-13 | 8404.005. | NM_004684.2 | DA763956.1 | EST | 1 |
| 450 | 3866.005.1-T_at | −0.65866 | 0.65866359 | 8.396284 | 3E-13 | 3866.005. | NM_002275.2 | AL832226.1 | mRNA | 37 |
| 451 | 59.003.1-F_at | −0.65865 | 0.65864902 | 8.395956 | 3E-13 | 59.003.1 | NM_001613.1 | DD218797.1 | GENBANK_PATENT | 1 |
| 452 | 7153.002.5-F_at | 0.658561 | 0.65856119 | 8.393979 | 3E-13 | 7153.002. | NM_001067.2 | CQ735949.1 | GENBANK_PATENT | 114 |
| 453 | 2487.001.1-T_at | −0.65846 | 0.65846487 | 8.391811 | 3E-13 | 2487.001. | NM_001463.2 | CS141780.1 | GENBANK_PATENT | 7 |
| 454 | 3866.010.1-B_at | −0.6577 | 0.65770261 | 8.374683 | 3E-13 | 3866.010. | NM_002275.2 | BM045201.1 | EST | 1 |
| 455 | 147495.009.1-T | −0.65745 | 0.65745477 | 8.369124 | 3E-13 | 147495.00 | NM_153000.3 | CX164031.1 | EST | 1 |
| 456 | 65983.003.2-T_at | −0.65736 | 0.65735504 | 8.366888 | 3E-13 | 65983.003 | NM_023927.1 | BP292708.1 | EST | 1 |
| 457 | 59.040.1-D_at | −0.65731 | 0.65731134 | 8.365909 | 3E-13 | 59.040.1 | NM_001613.1 | EH_001613.6 | PREDICTED | 1 |
| 458 | 59.024.2-T_at | −0.6568 | 0.65679913 | 8.35444 | 3E-13 | 59.024.2 | — | — | — | — |
| 459 | 1717.009.2-B_at | −0.65673 | 0.65673229 | 8.352945 | 3E-13 | 1717.009. | NM_001360.1 | DB170498.1 | EST | 1 |
| 460 | 1756.027.1-F_at | −0.65672 | 0.6567193 | 8.352655 | 3E-13 | 1756.027. | NM_000109.2 | S60971.1 | mRNA | 1 |
| 461 | 59.042.1-B_at | −0.65672 | 0.65671619 | 8.352585 | 3E-13 | 59.042.1 | NM_001613.1 | EH_001613.8 | PREDICTED | 1 |
| 462 | 7153.002.5-D_at | 0.656687 | 0.65668727 | 8.351939 | 3E-13 | 7153.002. | NM_001067.2 | CQ735949.1 | GENBANK_PATENT | 114 |
| 463 | 57447.031.1-F_at | −0.6565 | 0.65650401 | 8.347842 | 4E-13 | 57447.031 | NM_201535.1 | AI272253.1 | EST | 1 |
| 464 | 140885.011.1-C | −0.65642 | 0.6564245 | 8.346065 | 4E-13 | 140885.01 | NM_080792.2 | BM041242.1 | EST | 1 |
| 465 | 59.003.1-T_at | −0.65633 | 0.65632979 | 8.34395 | 4E-13 | 59.003.1 | NM_001613.1 | DD218797.1 | GENBANK_PATENT | 1 |
| 466 | 3832.002.1-D_at | 0.655783 | 0.65578291 | 8.331747 | 4E-13 | 3832.002. | NM_004523.2 | BQ959682.1 | EST | 1 |
| 467 | 3880.005.1-D_at | −0.65576 | 0.65576275 | 8.331298 | 4E-13 | 3880.005. | NM_002276.3 | BE732853.1 | EST | 1 |
| 468 | 3084.012.1-F_at | −0.65533 | 0.65532867 | 8.32163 | 4E-13 | 3084.012. | NM_013957.1 | U02325.1 | mRNA | 1 |
| 469 | 6595.012.1-D_at | −0.65524 | 0.65523847 | 8.319622 | 4E-13 | 6595.012. | NM_003070.3 | DA368288.1 | EST | 1 |
| 470 | 59.012.2-D_at | −0.65512 | 0.65511987 | 8.316984 | 4E-13 | 59.012.2 | NM_001613.1 | AL546033.3 | EST | 1 |
| 471 | 57447.034.1-C_at | −0.655 | 0.65500441 | 8.314417 | 4E-13 | 57447.034 | NM_201535.1 | BC011240.1 | mRNA | 1 |
| 472 | 56477.001.1-B_at | −0.65493 | 0.65492856 | 8.312731 | 4E-13 | 56477.001 | NM_148672.1 | NM_019846.3 | REFSEQ | 13 |
| 473 | 57447.041.1-D_at | −0.65415 | 0.65415460 | 8.295552 | 4E-13 | 57447.041 | NM_201535.1 | DA295124.1 | EST | 1 |
| 474 | 9768.005.1-B_at | 0.653838 | 0.65383824 | 8.288543 | 5E-13 | 9768.005. | NM_014736.4 | BG529193.1 | EST | 13 |
| 475 | 285203.001.2-C | −0.65337 | 0.653374 | 8.278271 | 5E-13 | 285203.00 | NM_173654.1 | AK126187.1 | mRNA | 3 |
| 476 | 147495.006.1-B | −0.65324 | 0.6532398 | 8.275305 | 5E-13 | 147495.00 | NM_153000.3 | CN421888.1 | EST | 1 |
| 477 | 7018.029.1-D_at | −0.65323 | 0.65323377 | 8.275172 | 5E-13 | 7018.029. | NM_001063.2 | AV656085.1 | EST | 1 |
| 478 | 3852.009.1-T_at | −0.65315 | 0.65314811 | 8.273279 | 5E-13 | 3852.009. | NM_000424.2 | BQ378037.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 479 | 59.023.2-D_at | −0.65311 | 0.65311489 | 8.272545 | 5E-13 | 59.023.2 | NM_001613.1 | DB248573.1 | EST | 1 |
| 480 | 1959.002.1-D_at | −0.65279 | 0.65278556 | 8.265275 | 5E-13 | 1959.002. | NM_000399.2 | DB264199.1 | EST | 5 |
| 481 | 7018.014.1-D_at | −0.65274 | 0.65273731 | 8.264211 | 5E-13 | 7018.014. | NM_001063.2 | AX147483.1 | GENBANK_PATENT | 1 |
| 482 | 5858.004.1-F_at | −0.65256 | 0.65255793 | 8.260255 | 5E-13 | 5858.004. | NM_002864.1 | DB033417.1 | EST | 1 |
| 483 | 79192.002.2-D_at | −0.65251 | 0.65251201 | 8.259242 | 5E-13 | 79192.002 | NM_024337.3 | CQ731489.1 | GENBANK_PATENT | 1 |
| 484 | 59.008.2-B_at | −0.65248 | 0.65247737 | 8.258479 | 5E-13 | 59.008.2 | NM_001613.1 | BP373197.1 | EST | 1 |
| 485 | 8404.008.1-E_at | −0.65196 | 0.65195548 | 8.246986 | 6E-13 | 8404.008. | NM_004684.2 | DA342341.1 | EST | 1 |
| 486 | 59.008.1-F_at | −0.65193 | 0.65192656 | 8.24635 | 6E-13 | 59.008.1 | NM_001613.1 | BP373197.1 | EST | 1 |
| 487 | 4240.011.1-B_at | −0.65168 | 0.65168158 | 8.240963 | 6E-13 | 4240.011. | NM_005928.1 | DA921691.1 | EST | 1 |
| 488 | 94274.002.1-C_at | −0.65161 | 0.65161159 | 8.239425 | 6E-13 | 94274.002 | NM_033256.1 | CQ730829.1 | GENBANK_PATENT | 1 |
| 489 | 4638.015.1-T_at | −0.65116 | 0.65115703 | 8.229444 | 6E-13 | 4638.015. | NM_053025.2 | NM_053029.2 | REFSEQ | 2 |
| 490 | 6376.001.1-T_at | −0.65101 | 0.6510092 | 8.226201 | 6E-13 | 6376.001. | NM_002996.3 | AK223351.1 | mRNA | 48 |
| 491 | 57447.043.1-F_at | −0.65059 | 0.65059178 | 8.217053 | 6E-13 | 57447.043 | NM_201535.1 | DA829299.1 | EST | 1 |
| 492 | 59.039.1-T_at | −0.65045 | 0.65045393 | 8.214035 | 6E-13 | 59.039.1 | NM_001613.1 | EH_001613.4 | PREDICTED | 1 |
| 493 | 4638.006.1-B_at | −0.65024 | 0.65023997 | 8.209353 | 7E-13 | 4638.006. | NM_053025.2 | DR005817.1 | EST | 2 |
| 494 | 25802.003.1-F_at | −0.65011 | 0.65011381 | 8.206594 | 7E-13 | 25802.003 | NM_012134.1 | BC001755.1 | mRNA | 1 |
| 495 | 57447.025.1-T_at | −0.65004 | 0.65003729 | 8.204921 | 7E-13 | 57447.025 | NM_201535.1 | DA646455.1 | EST | 2 |
| 496 | 57447.017.1-T_at | −0.64984 | 0.64984134 | 8.20064 | 7E-13 | 57447.017 | NM_201535.1 | DA130260.1 | EST | 2 |
| 497 | 7018.026.1-C_at | −0.64969 | 0.64969118 | 8.19736 | 7E-13 | 7018.026. | NM_001063.2 | BM690655.1 | EST | 1 |
| 498 | 7018.028.1-E_at | −0.64913 | 0.64913076 | 8.185136 | 7E-13 | 7018.028. | NM_001063.2 | BX537660.1 | mRNA | 1 |
| 499 | 4915.008.1-C_at | −0.64904 | 0.64904081 | 8.183176 | 7E-13 | 4915.008. | NM_006180.3 | NM_001007097 | REFSEQ | 4 |
| 500 | 358.018.1-C_at | −0.64903 | 0.64902608 | 8.182855 | 7E-13 | 358.018.1 | NM_198098.1 | BT765065.1 | EST | 1 |
| 501 | 7153.002.6-B_at | −0.648669 | 0.648866924 | 8.175087 | 8E-13 | 7153.002. | NM_001067.2 | CQ735949.1 | GENBANK_PATENT | 114 |
| 502 | 57447.012.1-B_at | −0.6478 | 0.64780212 | 8.156247 | 9E-13 | 57447.012 | NM_201535.1 | DB294263.1 | EST | 1 |
| 503 | 59.040.1-T_at | −0.6477 | 0.64769503 | 8.153924 | 9E-13 | 59.040.1 | NM_001613.1 | EH_001613.6 | PREDICTED | 1 |
| 504 | 57447.006.1-T_at | −0.64719 | 0.64718891 | 8.142957 | 9E-13 | 57447.006 | NM_201535.1 | DA283861.1 | EST | 4 |
| 505 | 9493.006.1-A_at | −0.646558 | 0.646555111 | 8.129315 | 1E-12 | 9493.006. | NM_138555.1 | BF240578.1 | EST | 1 |
| 506 | 57447.004.1-T_at | −0.64628 | 0.64628054 | 8.123321 | 1E-12 | 57447.004 | NM_201535.1 | CD515320.1 | EST | 2 |
| 507 | 57447.004.2-B_at | −0.64619 | 0.64619175 | 8.121404 | 1E-12 | 57447.004 | NM_201535.1 | CD515320.1 | EST | 2 |
| 508 | 7373.001.2-D_at | −0.64567 | 0.64566532 | 8.110055 | 1E-12 | 7373.001. | NM_021110.1 | DB089175.1 | EST | 1 |
| 509 | 9493.004.1-B_at | −0.64562 | 0.64562012 | 8.109081 | 1E-12 | 9493.004. | NM_138555.1 | BM792243.1 | EST | 1 |
| 510 | 2568.005.2-C_at | −0.64555 | 0.64555051 | 8.107582 | 1E-12 | 2568.005. | NM_014211.1 | AK055205.1 | mRNA | 11 |
| 511 | 7018.029.1-F_at | −0.64542 | 0.64541955 | 8.104763 | 1E-12 | 7018.029. | NM_001063.2 | AV656085.1 | EST | 1 |
| 512 | 26289.013.1-B_at | −0.64525 | 0.64525015 | 8.101118 | 1E-12 | 26289.013 | NM_174858.1 | CK024190.1 | EST | 1 |
| 513 | 7169.015.1-B_at | −0.64523 | 0.64522581 | 8.100594 | 1E-12 | 7169.015. | NM_213674.1 | DB291177.1 | EST | 1 |
| 514 | 57451.001.3-F_at | −0.64518 | 0.64517957 | 8.0996 | 1E-12 | 57451.001 | XM_931456.1 | CS188752.1 | GENBANK_PATENT | 1 |
| 515 | 2568.005.2-F_at | −0.64485 | 0.64485248 | 8.092569 | 1E-12 | 2568.005. | NM_014211.1 | AK055205.1 | mRNA | 11 |
| 516 | 57447.004.2-F_at | −0.6444 | 0.6444048 | 8.082959 | 1E-12 | 57447.004 | NM_201535.1 | CD515320.1 | EST | 2 |
| 517 | 8404.004.1-B_at | −0.64434 | 0.6443376 | 8.081518 | 1E-12 | 8404.004. | NM_004684.2 | DA589023.1 | EST | 1 |
| 518 | 3855.004.2-D_at | −0.64418 | 0.64418264 | 8.078194 | 1E-12 | 3855.004. | NM_005556.3 | BU164293.1 | EST | 1 |
| 519 | 3872.014.1-F_at | −0.64417 | 0.64416831 | 8.077888 | 1E-12 | 3872.014. | NM_000422.1 | BG678436.1 | EST | 1 |
| 520 | 57447.033.1-F_at | −0.64416 | 0.64415874 | 8.077683 | 1E-12 | 57447.033 | NM_201535.1 | DA135222.1 | EST | 11 |
| 521 | 9452.001.1-T_at | −0.64405 | 0.64404914 | 8.075458 | 1E-12 | 9452.001. | NM_004867.3 | BG713980.1 | EST | 4 |
| 522 | 59.033.2-T_at | −0.64401 | 0.6440144 | 8.07459 | 1E-12 | 59.033.2 | NM_001613.1 | BQ881176.1 | EST | 6 |
| 523 | 3084.009.1-T_at | −0.64398 | 0.64398407 | 8.07394 | 1E-12 | 3084.009. | NM_013957.1 | U02327.1 | mRNA | 2 |
| 524 | 57447.040.1-T_at | −0.64395 | 0.6439477 | 8.073161 | 1E-12 | 57447.040 | NM_201535.1 | DA207862.1 | EST | 1 |
| 525 | 4833.004.1-T_at | 0.643936 | 0.64393608 | 8.072912 | 1E-12 | 4833.004. | NM_005009.2 | BG478602.1 | EST | 8 |
| 526 | 3426.001.1-F_at | −0.64388 | 0.64388211 | 8.071756 | 1E-12 | 3426.001. | NM_000204.1 | BC020718.1 | mRNA | 165 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 527 | 59.034.1-B_at | −0.64382 | 0.64381551 | 8.07033 | 1E-12 | 59.034.1 | — | — | — | — |
| 528 | 10253.001.1-E_at | −0.64381 | 0.64381114 | 8.070237 | 1E-12 | 10253.001 | NM_005842.2 | BE297407.1 | EST | 1 |
| 529 | 9073.001.1-C_at | −0.64379 | 0.64379361 | 8.069862 | 1E-12 | 9073.001. | NM_199328.1 | BC020866.1 | mRNA | 1 |
| 530 | 51201.005.1-T_at | −0.64366 | 0.64366016 | 8.067005 | 1E-12 | 51201.005 | NM_016353.2 | DA655803.1 | EST | 1 |
| 531 | 9477.006.1-C_at | −0.64347 | 0.64347364 | 8.063015 | 1E-12 | 9477.006. | NM_004275.3 | DA588860.1 | EST | 1 |
| 532 | 57447.028.1-T_at | −0.64334 | 0.64334257 | 8.060213 | 1E-12 | 57447.028 | NM_201535.1 | DA205446.1 | EST | 1 |
| 533 | 25925.007.1-T_at | −0.64319 | 0.64319062 | 8.056966 | 1E-12 | 25925.007 | NM_015461.1 | DA235718.1 | EST | 1 |
| 534 | 59.024.2-B_at | −0.64296 | 0.64295617 | 8.051959 | 1E-12 | 59.024.2 | — | — | — | — |
| 535 | 2.022.1-T_at | −0.64285 | 0.64285401 | 8.049778 | 1E-12 | 2.022.1 | NM_000014.4 | BP343424.1 | EST | 1 |
| 536 | 4281.008.2-B_at | −0.64283 | 0.64282648 | 8.04919 | 1E-12 | 4281.008. | NM_033984.1 | AY539984.1 | mRNA | 1 |
| 537 | 90231.001.1-C_at | −0.64281 | 0.64281469 | 8.048939 | 1E-12 | 90231.001 | NM_138346.1 | BQ673619.1 | EST | 1 |
| 538 | 358.012.1-D_at | −0.64281 | 0.64280918 | 8.048821 | 1E-12 | 358.012.1 | NM_198098.1 | AX597685.1 | GENBANK_PATENT | 1 |
| 539 | 3852.021.1-T_at | −0.64278 | 0.64278273 | 8.048257 | 1E-12 | 3852.021. | NM_000424.2 | DA764437.1 | EST | 1 |
| 540 | 7373.003.4-D_at | −0.64275 | 0.64274774 | 8.04751 | 1E-12 | 7373.003. | NM_021110.1 | CQ716670.1 | GENBANK_PATENT | 1 |
| 541 | 57447.048.1-T_at | −0.64264 | 0.64264124 | 8.045239 | 1E-12 | 57447.048 | NM_201535.1 | BX480398.1 | EST | 1 |
| 542 | 358.012.1-B_at | −0.6417 | 0.617015 | 8.025228 | 2E-12 | 358.012.1 | NM_198098.1 | AX597685.1 | GENBANK_PATENT | 1 |
| 543 | 7018.025.1-C_at | −0.64167 | 0.64166912 | 8.024539 | 2E-12 | 7018.025. | NM_001063.2 | BE971065.1 | EST | 1 |
| 544 | 5608.004.1-T_at | −0.64157 | 0.64157449 | 8.022528 | 2E-12 | 5608.004. | NM_002758.2 | AL709891.1 | EST | 1 |
| 545 | 3084.012.2-F_at | −0.64148 | 0.64148473 | 8.020621 | 2E-12 | 3084.012. | NM_013957.1 | U02325.1 | mRNA | 1 |
| 546 | 4306.002.1-C_at | −0.64137 | 0.64137229 | 8.018232 | 2E-12 | 4306.002. | NM_000901.1 | AJ315515.1 | EST | 1 |
| 547 | 4288.004.1-D_at | 0.641215 | 0.64121481 | 8.014889 | 2E-12 | 4288.004. | NM_002417.2 | BP232141.1 | EST | 2 |
| 548 | 57447.002.1-F_at | −0.6411 | 0.6411459 | 8.012549 | 2E-12 | 57447.002 | NM_201535.1 | BF526188.1 | EST | 1 |
| 549 | 4281.018.1-T_at | −0.64087 | 0.64086989 | 8.007571 | 2E-12 | 4281.018. | NM_033290.1 | AY539998.1 | mRNA | 1 |
| 550 | 10144.020.2-B_at | −0.64053 | 0.64053304 | 8.000433 | 2E-12 | 10144.020 | NM_014883.2 | DA864231.1 | EST | 1 |
| 551 | 6876.016.1-E_at | −0.64047 | 0.64046896 | 7.999075 | 2E-12 | 6876.016. | NM_001001522. | AB209555.1 | mRNA | 2 |
| 552 | 57447.008.2-T_at | −0.64046 | 0.64045856 | 7.998855 | 2E-12 | 57447.008 | NM_201535.1 | DB195772.1 | EST | 1 |
| 553 | 51203.004.1-T_at | −0.640272 | 0.64027205 | 7.994907 | 2E-12 | 51203.004 | NM_016359.2 | DB126040.1 | EST | 1 |
| 554 | 2335.028.1-B_at | 0.639825 | 0.63982479 | 7.985449 | 2E-12 | 2335.028. | NM_212482.1 | AJ320525.1 | mRNA | 1 |
| 555 | 7018.028.1-F_at | −0.63974 | 0.63973608 | 7.983575 | 2E-12 | 7018.028. | NM_001063.2 | BX537660.1 | mRNA | 1 |
| 556 | 7373.003.5-T_at | −0.63956 | 0.63955526 | 7.979756 | 2E-12 | 7373.003. | NM_021110.1 | CQ716670.1 | GENBANK_PATENT | 1 |
| 557 | 81557.006.1-C_at | −0.63955 | 0.63955366 | 7.979722 | 2E-12 | 81557.006 | NM_030801.2 | AK094541.1 | mRNA | 9 |
| 558 | 3866.002.1-D_at | −0.63923 | 0.63923163 | 7.972927 | 2E-12 | 3866.002. | NM_022275.2 | BG990007.1 | EST | 1 |
| 559 | 3866.001.1-B_at | −0.63865 | 0.63865251 | 7.960724 | 2E-12 | 3866.001. | NM_002275.2 | CQ733235.1 | GENBANK_PATENT | 23 |
| 560 | 55107.006.2-T_at | −0.63865 | 0.63864972 | 7.960666 | 2E-12 | 55107.006 | NM_018043.4 | CQ722042.1 | GENBANK_PATENT | 1 |
| 561 | 79068.010.1-D_at | −0.63836 | 0.63836198 | 7.954611 | 2E-12 | 79068.010 | XM_051200.8 | DA647247.1 | EST | 1 |
| 562 | 57447.009.1-T_at | −0.63836 | 0.63835821 | 7.954532 | 2E-12 | 57447.009 | NM_201535.1 | BI550962.1 | EST | 1 |
| 563 | 2115.015.1-T_at | 0.63799997 | 0.63799997 | 7.947002 | 2E-12 | 2115.015. | NM_004956.3 | DA220931.1 | EST | 1 |
| 564 | 1756.013.1-C_at | −0.638 | 0.63799967 | 7.946996 | 3E-12 | 1756.013. | NM_000109.2 | NM_004019.1 | REFSEQ | 448 |
| 565 | 7169.015.1-F_at | −0.63796 | 0.63796151 | 7.946194 | 3E-12 | 7169.015. | NM_213674.1 | DB291177.1 | EST | 1 |
| 566 | 65983.013.2-F_at | −0.63792 | 0.63792448 | 7.945416 | 3E-12 | 65983.013 | NM_023927.1 | AA610396.1 | EST | 1 |
| 567 | 8404.001.1-B_at | −0.63758 | 0.63757819 | 7.938148 | 3E-12 | 8404.001. | NM_004684.2 | DA132781.1 | EST | 1 |
| 568 | 4240.004.1-B_at | −0.63705 | 0.6370484 | 7.927043 | 3E-12 | 4240.004. | NM_005928.1 | BC003610.2 | mRNA | 1 |
| 569 | 57447.012.2-T_at | −0.63699 | 0.63699351 | 7.925894 | 3E-12 | 57447.012 | NM_201535.1 | DB294263.1 | EST | 1 |
| 570 | 57447.024.1-F_at | −0.63699 | 0.63698737 | 7.925765 | 3E-12 | 57447.024 | NM_201535.1 | DA566498.1 | EST | 1 |
| 571 | 358.018.1-T_at | −0.63696 | 0.63695985 | 7.925189 | 3E-12 | 358.018.1 | NM_198098.1 | BI765065.1 | EST | 1 |
| 572 | 59.031.1-C_at | −0.63688 | 0.6368768 | 7.92345 | 3E-12 | 59.031.1 | NM_001613.1 | BX480398.1 | EST | 19 |
| 573 | 59.031.1-C_at | −0.63685 | 0.63684644 | 7.922815 | 3E-12 | 59.031.1 | NM_001613.1 | BG197213.1 | EST | 19 |
| 574 | 3860.007.1-F_at | −0.63682 | 0.63682338 | 7.922332 | 3E-12 | 3860.007. | NM_153490.1 | DB256579.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 575 | 8404.028.1-C_at | −0.63664 | 0.63664266 | 7.918551 | 3E-12 | 8404.028. | NM_004684.2 | CQ727530.1 | GENBANK_PATENT | 1 |
| 576 | 4240.011.3-E_at | −0.63664 | 0.63664099 | 7.918517 | 3E-12 | 4240.011. | NM_005928.1 | DA921691.1 | EST | 1 |
| 577 | 59.022.2-B_at | −0.63634 | 0.63633565 | 7.912134 | 3E-12 | 59.022.2 | — | — | — | — |
| 578 | 3866.002.1-F_at | −0.63598 | 0.63598268 | 7.904763 | 3E-12 | 3866.002. | NM_002275.2 | BG990007.1 | EST | 1 |
| 579 | 3866.002.1-T_at | −0.63597 | 0.63596762 | 7.904448 | 3E-12 | 3866.002. | NM_002275.2 | BG990007.1 | EST | 1 |
| 580 | 4915.005.1-B_at | −0.63568 | 0.63568404 | 7.898533 | 3E-12 | 4915.005. | NM_006180.3 | BP348402.1 | EST | 1 |
| 581 | 8404.008.1-F_at | −0.63556 | 0.63555525 | 7.895848 | 3E-12 | 8404.008. | NM_004684.2 | DA342341.1 | EST | 1 |
| 582 | 79608.002.1-F_at | −0.63554 | 0.63553682 | 7.895464 | 3E-12 | 79608.002 | NM_024557.2 | AK021670.1 | mRNA | 3 |
| 583 | 8404.023.1-D_at | −0.63553 | 0.6355289 | 7.895299 | 3E-12 | 8404.023. | NM_004684.2 | BX463355.2 | EST | 1 |
| 584 | 3426.002.1-D_at | −0.63533 | 0.63533255 | 7.891208 | 3E-12 | 3426.002. | NM_000204.1 | CQ718881.1 | GENBANK_PATENT | 1 |
| 585 | 2335.027.1-T_at | −0.635297 | 0.63529691 | 7.890465 | 3E-12 | 2335.027. | NM_212482.1 | AJ320527.1 | mRNA | 1 |
| 586 | 11065.009.1-T_at | 0.635032 | 0.63503202 | 7.884951 | 3E-12 | 11065.009 | NM_181802.1 | CN354813.1 | EST | 1 |
| 587 | 140885.013.1-F | 0.63461 | 0.63461049 | 7.876186 | 3E-12 | 140885.01 | NM_080792.2 | BU180215.1 | EST | 1 |
| 588 | 57447.021.1-B_at | −0.6346 | 0.63459853 | 7.875938 | 3E-12 | 57447.021 | NM_201535.1 | BQ954948.1 | EST | 28 |
| 589 | 25802.004.1-C_at | −0.63457 | 0.63457163 | 7.875379 | 3E-12 | 25802.004 | NM_012134.1 | DA924386.1 | EST | 1 |
| 590 | 4638.014.1-F_at | −0.63442 | 0.63441678 | 7.872162 | 3E-12 | 4638.014. | NM_053025.2 | NM_053027.2 | REFSEQ | 2 |
| 591 | 9493.004.1-F_at | 0.634402 | 0.63440178 | 7.871851 | 3E-12 | 9493.004. | NM_138555.1 | BM792243.1 | EST | 1 |
| 592 | 8404.004.1-B_at | −0.63427 | 0.63426893 | 7.869093 | 3E-12 | 8404.004. | NM_004684.2 | DA589023.1 | EST | 1 |
| 593 | 8404.004.2-T_at | −0.63407 | 0.63407245 | 7.865016 | 3E-12 | 8404.004. | NM_004684.2 | DA589023.1 | EST | 1 |
| 594 | 57447.010.2-T_at | −0.63407 | 0.63406601 | 7.864882 | 3E-12 | 57447.010 | NM_201535.1 | BP349691.1 | EST | 1 |
| 595 | 57447.010.3-B_at | −0.634 | 0.6340009 | 7.863532 | 3E-12 | 57447.010 | NM_201535.1 | BP349691.1 | EST | 1 |
| 596 | 27122.006.1-T_at | −0.63398 | 0.63398053 | 7.863109 | 3E-12 | 27122.006 | NM_013253.4 | DA171350.1 | EST | 1 |
| 597 | 5156.005.1-T_at | −0.63358 | 0.63357822 | 7.854771 | 3E-12 | 5156.005. | NM_006206.3 | BP336054.1 | EST | 1 |
| 598 | 5858.004.1-E_at | −0.63354 | 0.63353969 | 7.853973 | 3E-12 | 5858.004. | NM_002864.1 | DB033417.1 | EST | 1 |
| 599 | 25802.008.1-D_at | −0.63342 | 0.63342256 | 7.851548 | 4E-12 | 25802.008 | NM_012134.1 | DA767597.1 | EST | 1 |
| 600 | 2327.002.2-T_at | −0.63326 | 0.63326081 | 7.848201 | 4E-12 | 2327.002. | NM_001460.2 | CD684429.1 | EST | 1 |
| 601 | 3852.004.1-C_at | −0.63298 | 0.63298294 | 7.842454 | 4E-12 | 3852.004. | NM_000424.2 | BE715131.1 | EST | 1 |
| 602 | 59.026.2-F_at | −0.63296 | 0.63295912 | 7.841961 | 4E-12 | 59.026.2 | — | — | — | — |
| 603 | 57447.029.1-C_at | −0.63295 | 0.63295354 | 7.841846 | 4E-12 | 57447.029 | NM_201535.1 | BX354120.2 | EST | 6 |
| 604 | 7169.022.1-D_at | −0.63293 | 0.63293098 | 7.84138 | 4E-12 | 7169.022. | NM_213674.1 | BG385598.1 | EST | 1 |
| 605 | 23266.001.3-B_at | −0.63277 | 0.63276519 | 7.837954 | 4E-12 | 23266.001 | NM_012302.1 | AK123422.1 | mRNA | 2 |
| 606 | 3084.012.1-B_at | −0.63235 | 0.63235255 | 7.829435 | 4E-12 | 3084.012. | NM_013957.1 | U02325.1 | mRNA | 1 |
| 607 | 29127.019.2-T_at | 0.632352 | 0.63235178 | 7.829419 | 4E-12 | 29127.019 | NM_013277.2 | DA779708.1 | EST | 1 |
| 608 | 10253.004.1-T_at | −0.63208 | 0.63208261 | 7.823868 | 4E-12 | 10253.004 | NM_005842.2 | BQ889545.1 | EST | 2 |
| 609 | 10124.002.1-D_at | −0.63205 | 0.63205489 | 7.823297 | 4E-12 | 10124.002 | NM_001037164. | BG178114.1 | EST | 6 |
| 610 | 3861.013.1-D_at | −0.63198 | 0.63198062 | 7.821766 | 4E-12 | 3861.013. | NM_000526.3 | BM563823.1 | EST | 1 |
| 611 | 8404.032.1-T_at | −0.63197 | 0.63197222 | 7.821593 | 4E-12 | 8404.032. | NM_004684.2 | CQ498058.1 | GENBANK_PATENT | 1 |
| 612 | 84441.002.1-E_at | −0.63188 | 0.63188122 | 7.819718 | 4E-12 | 84441.002 | NM_032427.1 | CQ739825.1 | GENBANK_PATENT | 1 |
| 613 | 2.013.1-E_at | −0.63181 | 0.63181031 | 7.818258 | 4E-12 | 2.013.1 | NM_000014.4 | DA467444.1 | EST | 1 |
| 614 | 3084.004.1-B_at | −0.63137 | 0.63136737 | 7.809141 | 4E-12 | 3084.004. | NM_013957.1 | NM_013964.1 | REFSEQ | 5 |
| 615 | 5288.001.2-F_at | −0.63124 | 0.63123725 | 7.806466 | 5E-12 | 5288.001. | NM_004570.2 | CQ720591.1 | GENBANK_PATENT | 1 |
| 616 | 57447.017.1-F_at | −0.63113 | 0.63113433 | 7.80435 | 5E-12 | 57447.017 | NM_201535.1 | DA130260.1 | EST | 1 |
| 617 | 3084.006.1-T_at | −0.63106 | 0.63105508 | 7.802721 | 5E-12 | 3084.006. | NM_013957.1 | NM_013956.1 | REFSEQ | 3 |
| 618 | 59.039.1-F_at | −0.63095 | 0.63094608 | 7.800482 | 5E-12 | 59.039.1 | NM_001613.1 | EH_001613.4 | PREDICTED | 1 |
| 619 | 2.024.1-T_at | −0.63086 | 0.63085582 | 7.798628 | 5E-12 | 2.024.1 | NM_000014.4 | DB286897.1 | EST | 1 |
| 620 | 3815.002.2-E_at | −0.63085 | 0.63085365 | 7.798584 | 5E-12 | 3815.002. | NM_000222.1 | CQ719901.1 | GENBANK_PATENT | 1 |
| 621 | 1756.009.1-D_at | −0.63082 | 0.63082241 | 7.797942 | 5E-12 | 1756.009. | NM_000109.2 | NM_004023.1 | REFSEQ | 1 |
| 622 | 7091.014.1-B_at | −0.63047 | 0.63046815 | 7.790673 | 5E-12 | 7091.014. | NM_007005.3 | BM480087.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 623 | 4629.015.1-F_at | −0.6304 | 0.6303903 | 7.789255 | 5E-12 | 4629.015. | NM_022844.1 | DB284318.1 | EST | 1 |
| 624 | 59.008.2-F_at | −0.63016 | 0.63015808 | 7.784317 | 5E-12 | 59.008.2 | NM_001613.1 | BP373197.1 | EST | 1 |
| 625 | 2568.005.2-T_at | −0.63012 | 0.6301238 | 7.783614 | 5E-12 | 2568.005. | NM_014211.1 | AK055205.1 | mRNA | 11 |
| 626 | 115207.002.1-T | −0.62994 | 0.62993556 | 7.779759 | 5E-12 | 115207.00 | NM_138444.2 | CQ851144.1 | GENBANK_PATENT | 1 |
| 627 | 4281.001.1-T_at | −0.62982 | 0.62981987 | 7.777391 | 5E-12 | 4281.001. | NM_033290.1 | AY539999.1 | mRNA | 1 |
| 628 | 84668.002.2-T_at | −0.62976 | 0.62975676 | 7.776099 | 5E-12 | 84668.002 | NM_032581.2 | AL833296.1 | mRNA | 20 |
| 629 | 4240.004.1-F_at | −0.6295 | 0.62950111 | 7.77087 | 5E-12 | 4240.004. | NM_005928.1 | BC003610.2 | mRNA | 448 |
| 630 | 8404.005.1-D_at | −0.62918 | 0.62917718 | 7.76425 | 6E-12 | 8404.005. | NM_004684.2 | DA763956.1 | EST | 1 |
| 631 | 8404.032.1-B_at | −0.62902 | 0.62902338 | 7.761109 | 6E-12 | 8404.032. | NM_004684.2 | CQ498058.1 | GENBANK_PATENT | 1 |
| 632 | 57447.044.1-E_at | −0.6289 | 0.62890008 | 7.758592 | 6E-12 | 57447.044 | NM_201535.1 | DB232855.1 | EST | 1 |
| 633 | 8626.006.2-F_at | −0.62867 | 0.6286676 | 7.753849 | 6E-12 | 8626.006. | NM_003722.3 | CB049427.1 | EST | 1 |
| 634 | 57447.051.2-B_at | −0.62855 | 0.62855194 | 7.751491 | 6E-12 | 57447.051 | NM_201535.1 | BX460053.2 | EST | 1 |
| 635 | 1063.001.1-T_at | −0.628003 | 0.62800305 | 7.74031 | 6E-12 | 1063.001. | NM_016343.3 | BG941308.1 | EST | 1 |
| 636 | 3426.002.1-T_at | −0.62796 | 0.62796276 | 7.73949 | 6E-12 | 3426.002. | NM_000204.1 | CQ718881.1 | GENBANK_PATENT | 1 |
| 637 | 1308.001.1-T_at | −0.62793 | 0.62793498 | 7.738925 | 6E-12 | 1308.001. | NM_130778.1 | BM773425.1 | EST | 1 |
| 638 | 389432.002.1-F | −0.62759 | 0.62758948 | 7.731899 | 6E-12 | 389432.00 | NM_001030060. | CQ751492.1 | GENBANK_PATENT | 1 |
| 639 | 57447.017.1-B_at | −0.62755 | 0.62754878 | 7.731072 | 7E-12 | 57447.017 | NM_201535.1 | DA130260.1 | EST | 1 |
| 640 | 2115.014.1-F_at | −0.62729 | 0.62729339 | 7.725883 | 7E-12 | 2115.014. | NM_004956.3 | CN396909.1 | EST | 1 |
| 641 | 5284.004.1-T_at | −0.62724 | 0.6272429 | 7.724858 | 7E-12 | 5284.004. | NM_002644.2 | DB225999.1 | EST | 1 |
| 642 | 57447.029.1-F_at | −0.62716 | 0.271633 | 7.723242 | 7E-12 | 57447.029 | NM_201535.1 | BX354120.2 | EST | 6 |
| 643 | 8626.006.1-F_at | −0.62697 | 0.62697054 | 7.71933 | 7E-12 | 8626.006. | NM_003722.3 | CB049427.1 | EST | 1 |
| 644 | 2982.002.1-C_at | −0.62686 | 0.62686245 | 7.717138 | 7E-12 | 2982.002. | NM_000856.2 | BP199345.1 | EST | 1 |
| 645 | 57447.047.1-C_at | −0.62685 | 0.62685067 | 7.716899 | 7E-12 | 57447.047 | NM_201535.1 | DA353543.1 | EST | 1 |
| 646 | 5803.006.1-E_at | −0.62682 | 0.62681659 | 7.716208 | 7E-12 | 5803.006. | NM_002851.1 | BM473091.1 | EST | 1 |
| 647 | 57447.021.1-F_at | −0.62659 | 0.62658775 | 7.71157 | 7E-12 | 57447.021 | NM_201535.1 | BQ954948.1 | EST | 28 |
| 648 | 57447.039.1-F_at | −0.62651 | 0.62651329 | 7.710061 | 7E-12 | 57447.039 | NM_201535.1 | DA356658.1 | EST | 1 |
| 649 | 4281.008.2-F_at | −0.62638 | 0.62637927 | 7.707347 | 7E-12 | 4281.008. | NM_033290.1 | AY539984.1 | mRNA | 1 |
| 650 | 57447.029.1-D_at | −0.62629 | 0.62629118 | 7.705563 | 7E-12 | 57447.029 | NM_201535.1 | BX354120.2 | EST | 6 |
| 651 | 65983.013.1-B_at | −0.62562 | 0.6256189 | 7.691968 | 8E-12 | 65983.013 | NM_023927.1 | AA610396.1 | EST | 1 |
| 652 | 5284.004.1-D_at | −0.62553 | 0.6255276 | 7.690123 | 8E-12 | 5284.004. | NM_002644.2 | DB225999.1 | EST | 1 |
| 653 | 4240.011.1-D_at | −0.62513 | 0.62512689 | 7.682036 | 8E-12 | 4240.011. | NM_005928.1 | DA921691.1 | EST | 1 |
| 654 | 57447.024.1-T_at | −0.62502 | 0.62502436 | 7.679968 | 8E-12 | 57447.024 | NM_201535.1 | DA566498.1 | EST | 1 |
| 655 | 6876.011.1-B_at | −0.625 | 0.62499658 | 7.679408 | 8E-12 | 6876.011. | NM_001001522. | AW956430.1 | EST | 1 |
| 656 | 7373.003.2-T_at | −0.62485 | 0.62484538 | 7.676359 | 8E-12 | 7373.003. | NM_021110.1 | CQ716670.1 | GENBANK_PATENT | 1 |
| 657 | 3852.014.1-D_at | −0.62476 | 0.62476477 | 7.674735 | 9E-12 | 3852.014. | NM_000424.2 | BF826002.1 | EST | 1 |
| 658 | 4915.005.1-D_at | −0.62473 | 0.62473239 | 7.674083 | 9E-12 | 4915.005. | NM_006180.3 | BP348402.1 | EST | 1 |
| 659 | 9768.002.2-B_at | −0.624527 | 0.62452688 | 7.669944 | 9E-12 | 9768.002. | NM_014736.4 | BM908225.1 | EST | 1 |
| 660 | 140885.010.1-D | −0.62442 | 0.62441747 | 7.667741 | 9E-12 | 140885.01 | NM_080792.2 | CQ728313.1 | GENBANK_PATENT | 1 |
| 661 | 4638.020.1-E_at | −0.62432 | 0.62431859 | 7.665751 | 9E-12 | 4638.020. | NM_053025.2 | DA694890.1 | EST | 1 |
| 662 | 57447.017.1-C_at | −0.62424 | 0.62423695 | 7.664109 | 9E-12 | 57447.017 | NM_201535.1 | DA130260.1 | EST | 1 |
| 663 | 7373.004.1-T_at | −0.62423 | 0.6242336 | 7.664041 | 9E-12 | 7373.004. | NM_021110.1 | M64109.1 | mRNA | 1 |
| 664 | 3852.008.2-E_at | −0.62396 | 0.62396244 | 7.658589 | 9E-12 | 3852.008. | NM_000424.2 | BG675837.1 | EST | 1 |
| 665 | 4281.015.1-E_at | −0.62376 | 0.62376072 | 7.654536 | 9E-12 | 4281.015. | NM_033290.1 | AY540009.1 | mRNA | 1 |
| 666 | 8404.013.1-C_at | −0.62375 | 0.62374788 | 7.654278 | 9E-12 | 8404.013. | NM_004684.2 | BP376616.1 | EST | 1 |
| 667 | 90293.001.3-T_at | −0.62357 | 0.62357218 | 7.65075 | 1E-11 | 90293.001 | NM_033495.2 | CQ714141.1 | GENBANK_PATENT | 9 |
| 668 | 57447.044.1-T_at | −0.62348 | 0.6234819 | 7.648937 | 1E-11 | 57447.044 | NM_201535.1 | DB232855.1 | EST | 1 |
| 669 | 23650.011.2-D_at | −0.62318 | 0.62317705 | 7.642822 | 1E-11 | 23650.011 | NM_058193.1 | NM_012101.2 | REFSEQ | 11 |
| 670 | 2335.006.1-D_at | −0.623003 | 0.62300327 | 7.639338 | 1E-11 | 2335.006. | NM_212482.1 | CX785805.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 671 | 57447.022.1-T_at | −0.6229 | 0.6290388 | 7.637347 | 1E−11 | 57447.022 | NM_201535.1 | DA079074.1 | EST | 2 |
| 672 | 8404.032.1-D_at | −0.62271 | 0.62271252 | 7.633514 | 1E−11 | 8404.032 | NM_004684.2 | CQ498058.1 | GENBANK_PATENT | 1 |
| 673 | 8404.030.1-F_at | −0.62267 | 0.62267432 | 7.632749 | 1E−11 | 8404.030. | NM_004684.2 | CD357736.1 | EST | 1 |
| 674 | 5803.002.2-T_at | −0.6225 | 0.62250014 | 7.629263 | 1E−11 | 5803.002. | NM_002851.1 | CQ725791.1 | GENBANK_PATENT | 24 |
| 675 | 8404.004.2-C_at | −0.62246 | 0.62245993 | 7.628459 | 1E−11 | 8404.004. | NM_004684.2 | DA589023.1 | EST | 1 |
| 676 | 84441.005.1-C_at | −0.62236 | 0.62236291 | 7.626518 | 1E−11 | 84441.005 | NM_032427.1 | CQ739827.1 | GENBANK_PATENT | 1 |
| 677 | 7091.015.1-F_at | −0.62201 | 0.62201208 | 7.619505 | 1E−11 | 7091.015. | NM_007005.3 | CQ724084.1 | GENBANK_PATENT | 1 |
| 678 | 2119.005.1-D_at | −0.62174 | 0.6217418 | 7.614107 | 1E−11 | 2119.005. | NM_004454.1 | BU197295.1 | EST | 1 |
| 679 | 7373.003.6-F_at | −0.6217 | 0.62170218 | 7.613316 | 1E−11 | 7373.003. | NM_021110.1 | CQ716670.1 | GENBANK_PATENT | 1 |
| 680 | 79608.008.1-T_at | −0.6214 | 0.62140438 | 7.607374 | 1E−11 | 79608.008 | NM_024557.2 | DA748988.1 | EST | 2 |
| 681 | 3852.008.1-T_at | −0.62129 | 0.62128908 | 7.605075 | 1E−11 | 3852.008. | NM_000424.2 | BG675837.1 | EST | 1 |
| 682 | 8626.007.1-T_at | −0.62113 | 0.62113254 | 7.601955 | 1E−11 | 8626.007. | NM_003722.3 | BG698723.1 | EST | 1 |
| 683 | 8404.022.1-T_at | −0.62104 | 0.62103797 | 7.60007 | 1E−11 | 8404.022. | NM_004684.2 | BP311988.1 | EST | 1 |
| 684 | 8404.034.1-T_at | −0.62101 | 0.62101196 | 7.599552 | 1E−11 | 8404.034. | NM_004684.2 | DA148306.1 | EST | 1 |
| 685 | 57447.049.1-T_at | −0.62097 | 0.62096556 | 7.598628 | 1E−11 | 57447.049 | NM_201535.1 | DB180733.1 | EST | 1 |
| 686 | 5311.002.1-B_at | −0.62092 | 0.62092128 | 7.597746 | 1E−11 | 5311.002. | NM_000297.2 | CQ727531.1 | GENBANK_PATENT | 1 |
| 687 | 2335.025.3-T_at | 0.620916 | 0.62091648 | 7.597651 | 1E−11 | 2335.025. | NM_212482.1 | CQ715726.1 | GENBANK_PATENT | 3 |
| 688 | 4147.012.1-T_at | −0.62076 | 0.62075962 | 7.594528 | 1E−11 | 4147.012. | NM_002380.3 | BX397573.2 | EST | 1 |
| 689 | 301.015.1-T_at | −0.62074 | 0.62074218 | 7.594181 | 1E−11 | 301.015.1 | NM_000700.1 | BM477702.1 | EST | 1 |
| 690 | 301.004.1-T_at | −0.62073 | 0.62073001 | 7.593939 | 1E−11 | 301.004.1 | NM_000700.1 | DB194639.1 | EST | 1 |
| 691 | 3426.002.2-F_at | −0.62048 | 0.62047946 | 7.588954 | 1E−11 | 3426.002. | NM_000204.1 | CQ718881.1 | GENBANK_PATENT | 24 |
| 692 | 7091.001.1-T_at | −0.62037 | 0.62037055 | 7.586788 | 1E−11 | 7091.001. | NM_007005.3 | BC045650.1 | EST | 2 |
| 693 | 8404.021.1-D_at | −0.62032 | 0.6203222 | 7.585827 | 1E−11 | 8404.021. | NM_004684.2 | DA291834.1 | mRNA | 17 |
| 694 | 7153.002.3-B_at | 0.620304 | 0.62030417 | 7.585469 | 1E−11 | 7153.002. | NM_001067.2 | CQ735949.1 | GENBANK_PATENT | 114 |
| 695 | 53335.002.1-E_at | −0.62026 | 0.62026302 | 7.584651 | 1E−11 | 53335.002 | NM_018014.2 | BU159551.1 | EST | 1 |
| 696 | 5284.003.2-T_at | −0.62002 | 0.62001653 | 7.579754 | 1E−11 | 5284.003. | NM_002644.2 | BP220016.1 | EST | 1 |
| 697 | 4306.002.1-F_at | 0.619996 | 0.61995574 | 7.578547 | 1E−11 | 4306.002. | NM_000901.1 | AJ315515.1 | mRNA | 1 |
| 698 | 5284.003.2-D_at | 0.61991 | 0.61991035 | 7.577646 | 1E−11 | 5284.003. | NM_002644.2 | BP220016.1 | EST | 1 |
| 699 | 5803.002.1-T_at | −0.61977 | 0.61977142 | 7.574888 | 1E−11 | 5803.002. | NM_002851.1 | CQ725791.1 | GENBANK_PATENT | 24 |
| 700 | 10253.004.1-F_at | −0.61973 | 0.61973277 | 7.574121 | 1E−11 | 10253.004 | NM_005842.2 | BQ889545.1 | EST | 2 |
| 701 | 23650.020.1-T_at | −0.61972 | 0.61971511 | 7.573771 | 1E−11 | 23650.020 | NM_058193.1 | DB266728.1 | EST | 1 |
| 702 | 57447.042.1-T_at | −0.61964 | 0.6196367 | 7.572215 | 1E−11 | 57447.042 | NM_201535.1 | DA937014.1 | EST | 1 |
| 703 | 6876.023.1-F_at | −0.6196 | 0.61960408 | 7.571568 | 1E−11 | 6876.023. | NM_001001522. | CN48209.1 | EST | 1 |
| 704 | 7169.015.1-C_at | −0.61949 | 0.61948888 | 7.569283 | 1E−11 | 7169.015. | NM_213674.1 | DB291177.1 | EST | 1 |
| 705 | 7153.002.4-F_at | 0.619203 | 0.61920323 | 7.563622 | 1E−11 | 7153.002. | NM_001067.2 | CQ735949.1 | GENBANK_PATENT | 114 |
| 706 | 4629.016.1-B_at | −0.61918 | 0.61917512 | 7.563065 | 1E−11 | 4629.016. | NM_022844.1 | DB289769.1 | EST | 1 |
| 707 | 6876.002.1-C_at | −0.61913 | 0.61912596 | 7.562091 | 1E−11 | 6876.002. | NM_001001522. | DB262921.1 | EST | 1 |
| 708 | 65983.007.1-T_at | −0.61906 | 0.61905788 | 7.560743 | 1E−11 | 65983.007 | NM_023927.1 | DA388235.1 | EST | 1 |
| 709 | 7373.003.2-F_at | −0.61891 | 0.61891452 | 7.557905 | 1E−11 | 7373.003. | NM_021110.1 | CQ716670.1 | GENBANK_PATENT | 1 |
| 710 | 152015.004.1-T | −0.61872 | 0.61872078 | 7.554071 | 2E−11 | 152015.00 | NM_001012337. | BC015413.1 | mRNA | 2 |
| 711 | 8404.004.2B_at | −0.61824 | 0.61823995 | 7.544566 | 2E−11 | 8404.004. | NM_004684.2 | DA589023.1 | EST | 1 |
| 712 | 6285.001.1-B_at | −0.61815 | 0.61815486 | 7.542886 | 2E−11 | 6285.001. | NM_006272.1 | BP349776.1 | EST | 1 |
| 713 | 2115.007.1-E_at | −0.61784 | 0.61784158 | 7.536702 | 2E−11 | 2115.007. | NM_004956.3 | DA189670.1 | EST | 1 |
| 714 | 2.013.1-T_at | −0.61782 | 0.61782175 | 7.536311 | 2E−11 | 2.013.1 | NM_000014.4 | DA467444.1 | EST | 1 |
| 715 | 6289.005.1-T_at | −0.61778 | 0.6177768 | 7.535424 | 2E−11 | 6289.005. | NM_030754.2 | BG618888.1 | EST | 39 |
| 716 | 9232.002.1-T_at | −0.61778 | 0.61774763 | 7.534848 | 2E−11 | 9232.002. | NM_004219.2 | BM459529.1 | EST | 2 |
| 717 | 59.014.1-B_at | −0.61765 | 0.61765007 | 7.532925 | 2E−11 | 59.014.1 | NM_001613.1 | CB962422.1 | EST | 1 |
| 718 | 59.031.1-F_at | −0.61751 | 0.61750627 | 7.53009 | 2E−11 | 59.031.1 | NM_001613.1 | BG197213.1 | EST | 19 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 719 | 3084.011.1-T_at | −0.61746 | 0.61746489 | 7.529274 | 2E−11 | 3084.011. | NM_013957.1 | CN603661.1 | EST | 1 |
| 720 | 3872.005.1-F_at | −0.61737 | 0.61737414 | 7.527486 | 2E−11 | 3872.005. | NM_000422.1 | BG682094.1 | EST | 1 |
| 721 | 3084.012.3-F_at | −0.6173 | 0.61730492 | 7.526122 | 2E−11 | 3084.012. | NM_013957.1 | U02325.1 | mRNA | 1 |
| 722 | 81704.008.1-F_at | −0.61719 | 0.61719009 | 7.523861 | 2E−11 | 81704.008 | NM_203447.1 | BC045629.1 | mRNA | 1 |
| 723 | 140885.010.2-C | −0.617 | 0.61700383 | 7.520194 | 2E−11 | 140885.01 | NM_080792.2 | CQ728313.1 | GENBANK_PATENT | 1 |
| 724 | 338707.006.1-E | −0.61688 | 0.61688739 | 7.517726 | 2E−11 | 338707.00 | NM_178537.3 | BX115728.1 | EST | 1 |
| 725 | 23266.008.2-T_at | −0.61684 | 0.61683767 | 7.516924 | 2E−11 | 23266.008 | NM_012302.2 | CQ799210.1 | GENBANK_PATENT | 1 |
| 726 | 120.005.2-E_at | −0.61665 | 0.61664987 | 7.513231 | 2E−11 | 120.005.2 | NM_019903.3 | AK223270.1 | mRNA | 78 |
| 727 | 4281.009.1-E_at | −0.61647 | 0.61647345 | 7.509764 | 2E−11 | 4281.009. | NM_033290.1 | AY540014.1 | mRNA | 1 |
| 728 | 4094.001.1-T_at | −0.61638 | 0.61638223 | 7.507972 | 2E−11 | 4094.001. | NM_001031804. | NM_005360.3 | REFSEQ | 17 |
| 729 | 2995.001.1-T_at | −0.61614 | 0.61614044 | 7.503223 | 2E−11 | 2995.001. | NM_002101.3 | CQ729268.1 | GENBANK_PATENT | 1 |
| 730 | 4638.011.1-T_at | −0.61607 | 0.61606684 | 7.501779 | 2E−11 | 4638.011. | NM_053025.2 | DB267860.1 | EST | 1 |
| 731 | 2335.017.1-T_at | −0.61595 | 0.61595485 | 7.499582 | 2E−11 | 2335.017. | NM_212482.1 | CQ896577.1 | GENBANK_PATENT | 4 |
| 732 | 5284.001.1-F_at | −0.61592 | 0.61592058 | 7.498909 | 2E−11 | 5284.001. | NM_002644.2 | AX012182.1 | GENBANK_PATENT | 1 |
| 733 | 8404.026.1-D_at | −0.61589 | 0.61588535 | 7.498218 | 2E−11 | 8404.026. | NM_004684.2 | BX647713.1 | mRNA | 141 |
| 734 | 2335.009.1-D_at | −0.615806 | 0.61580556 | 7.496653 | 2E−11 | 2335.009. | NM_212482.1 | BG927121.1 | EST | 51 |
| 735 | 10461.002.2-F_at | −0.61571 | 0.61570541 | 7.49469 | 2E−11 | 10461.002 | NM_006343.2 | CQ725500.1 | GENBANK_PATENT | 1 |
| 736 | 84441.002.1-T_at | −0.6157 | 0.61570234 | 7.494629 | 2E−11 | 84441.002 | NM_032427.1 | CQ739825.1 | GENBANK_PATENT | 1 |
| 737 | 147495.006.1-T | −0.61568 | 0.61567688 | 7.49413 | 2E−11 | 147495.00 | NM_153000.3 | CN421888.1 | EST | 1 |
| 738 | 7091.010.1-B_at | −0.61565 | 0.61564596 | 7.493524 | 2E−11 | 7091.010. | NM_007005.3 | AL551038.3 | EST | 1 |
| 739 | 8404.008.1-C_at | −0.61554 | 0.61554203 | 7.491488 | 2E−11 | 8404.008. | NM_004684.2 | DA342341.1 | EST | 1 |
| 740 | 6376.001.2-C_at | −0.61538 | 0.61538183 | 7.488349 | 2E−11 | 6376.001. | NM_002996.3 | AK223351.1 | mRNA | 48 |
| 741 | 3832.002.1-B_at | −0.61514 | 0.61501375 | 7.481144 | 2E−11 | 3832.002. | NM_004523.1 | BQ959682.1 | EST | 1 |
| 742 | 59.034.2-T_at | −0.61499 | 0.61498701 | 7.480621 | 2E−11 | 59.034.2 | — | BI822892.1 | EST | — |
| 743 | 147495.005.1-B | −0.61488 | 0.61488109 | 7.478549 | 2E−11 | 147495.00 | NM_153000.3 | BG682094.1 | EST | 1 |
| 744 | 3872.005.1-C_at | −0.61477 | 0.61477315 | 7.476439 | 2E−11 | 3872.005. | NM_000422.1 | AX575481.1 | GENBANK_PATENT | 5 |
| 745 | 79895.001.1-D_at | −0.61472 | 0.61471741 | 7.475349 | 2E−11 | 79895.001 | NM_024837.2 | DB238920.1 | EST | 1 |
| 746 | 57447.038.1-T_at | −0.61465 | 0.61464905 | 7.474013 | 2E−11 | 57447.038 | NM_201535.1 | CQ656872.1 | GENBANK_PATENT | 1 |
| 747 | 7373.008.1-T_at | −0.61439 | 0.61438569 | 7.468868 | 2E−11 | 7373.008. | NM_021110.1 | BQ636126.1 | EST | 1 |
| 748 | 4744.004.1-C_at | −0.61432 | 0.61431915 | 7.467569 | 2E−11 | 4744.004. | NM_021076.2 | CQ728313.1 | GENBANK_PATENT | 1 |
| 749 | 140885.010.1-T | −0.61432 | 0.61431838 | 7.467554 | 2E−11 | 140885.01 | NM_080792.2 | AB209555.1 | mRNA | 2 |
| 750 | 6876.016.2-E_at | −0.61423 | 0.61422523 | 7.465735 | 2E−11 | 6876.016. | NM_001001522. | BP194755.1 | EST | 4 |
| 751 | 8404.015.1-T_at | −0.61419 | 0.61419393 | 7.465124 | 2E−11 | 8404.015. | NM_004684.2 | AY539986.1 | mRNA | 1 |
| 752 | 4281.014.1-T_at | −0.61417 | 0.61416566 | 7.464573 | 2E−11 | 4281.014. | NM_033290.1 | BP363635.1 | EST | 1 |
| 753 | 4288.006.1-T_at | −0.614163 | 0.61416265 | 7.464514 | 2E−11 | 4288.006. | NM_002127.1 | DB064380.1 | EST | 1 |
| 754 | 25925.009.1-E_at | −0.61404 | 0.61403923 | 7.462106 | 2E−11 | 25925.009 | NM_015461.1 | BG829936.1 | mRNA | 2 |
| 755 | 4240.009.1-B_at | −0.61385 | 0.61385445 | 7.458502 | 2E−11 | 4240.009. | NM_005928.1 | DA361412.1 | EST | 1 |
| 756 | 667.010.1-E_at | −0.61376 | 0.61376087 | 7.456678 | 2E−11 | 667.010.1 | NM_183380.1 | AL832226.1 | mRNA | 37 |
| 757 | 3866.005.1-B_at | −0.61345 | 0.61345384 | 7.450696 | 2E−11 | 3866.005. | NM_002275.2 | BP199520.1 | EST | 1 |
| 758 | 57447.011.1-T_at | −0.61343 | 0.61343087 | 7.450249 | 2E−11 | 57447.011 | NM_201535.1 | BC011240.1 | EST | 1 |
| 759 | 57447.034.1-B_at | −0.61342 | 0.61342094 | 7.450055 | 2E−11 | 57447.034 | NM_201535.1 | DA924386.1 | EST | 1 |
| 760 | 25802.004.1-B_at | −0.61332 | 0.61331747 | 7.448041 | 2E−11 | 25802.004 | NM_0121134.1 | DB260047.1 | EST | 1 |
| 761 | 8404.024.1-T_at | −0.61318 | 0.6131717 | 7.44531 | 3E−11 | 8404.024. | NM_004684.2 | BI771628.1 | EST | 1 |
| 762 | 57447.032.1-T | −0.61307 | 0.61306529 | 7.443134 | 3E−11 | 57447.032 | NM_201535.1 | DB134537.1 | EST | 3 |
| 763 | 667.021.1-F_at | −0.61305 | 0.61304874 | 7.442812 | 3E−11 | 667.021.1 | NM_183380.1 | BC111756.1 | mRNA | 1 |
| 764 | 5858.001.2-F_at | −0.61258 | 0.6125845 | 7.433788 | 3E−11 | 5858.001. | NM_002864.1 | — | — | — |
| 765 | 51062.008.1-T_at | −0.61217 | 0.61217313 | 7.425802 | 3E−11 | 51062.008 | NM_015915.3 | CQ719775.1 | GENBANK_PATENT | 2 |
| 766 | 2335.013.1-F_at | −0.612162 | 0.61216233 | 7.425593 | 3E−11 | 2335.013. | NM_212482.1 | AL551632.3 | EST | 2 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 767 | 2568.001.2-T_at | -0.61211 | 0.61210705 | 7.424521 | 3E-11 | 2568.001. | NM_014211.1 | BX509618.1 | EST | 1 |
| 768 | 7170.005.2-D_at | -0.611952 | 0.61195174 | 7.421509 | 3E-11 | 7170.005. | NM_153649.2 | DA762962.1 | EST | 1 |
| 769 | 57447.034.1F_at | -0.61184 | 0.61184024 | 7.419347 | 3E-11 | 57447.034 | NM_201535.1 | BC011240.1 | mRNA | 1 |
| 770 | 7153.002.6-C_at | -0.611814 | 0.61181444 | 7.418847 | 3E-11 | 7153.002. | NM_001067.2 | CQ735949.1 | GENBANK_PATENT | 114 |
| 771 | 2568.003.1-T_at | -0.61165 | 0.61164713 | 7.415606 | 3E-11 | 2568.003. | NM_014211.1 | CD696885.1 | EST | 1 |
| 772 | 59.008.2-T_at | -0.61162 | 0.61161827 | 7.415046 | 3E-11 | 59.008.2 | NM_001613.1 | BP373197.1 | EST | 1 |
| 773 | 9898.015.2-B_at | -0.611466 | 0.61146611 | 7.4121 | 3E-11 | 9898.015. | NM_014847.2 | AI243670.2 | mRNA | 1 |
| 774 | 7018.013.1-T_at | -0.61122 | 0.6112152 | 7.407244 | 3E-11 | 7018.013. | NM_001063.2 | AX147484.1 | GENBANK_PATENT | 1 |
| 775 | 7170.034.2-D_at | -0.611012 | 0.61101246 | 7.403323 | 3E-11 | 7170.034. | NM_153649.2 | DA894441.1 | EST | 1 |
| 776 | 3866.004.1-E_at | -0.61074 | 0.61073542 | 7.397968 | 3E-11 | 3866.004. | NM_002275.2 | BC110649.1 | mRNA | 1 |
| 777 | 5284.001.1-T_at | -0.61068 | 0.61067717 | 7.396843 | 3E-11 | 5284.001. | NM_002644.2 | AX012182.1 | GENBANK_PATENT | 1 |
| 778 | 2.002.1-C_at | -0.61064 | 0.61064092 | 7.396143 | 3E-11 | 2.002.1 | NM_000014.4 | CQ672194.1 | GENBANK_PATENT | 1 |
| 779 | 57447.050.1-T_at | -0.61051 | 0.61050599 | 7.393537 | 3E-11 | 57447.050 | NM_201535.1 | DA257961.1 | EST | 17 |
| 780 | 7018.014.1-F_at | -0.61047 | 0.61046981 | 7.392839 | 3E-11 | 7018.014. | NM_001063.1 | AX147483.1 | GENBANK_PATENT | 1 |
| 781 | 2335.032.1-D_at | -0.610251 | 0.61025134 | 7.388623 | 3E-11 | 2335.032. | NM_212482.1 | DA647475.1 | EST | 1 |
| 782 | 3866.002.1-C_at | -0.61025 | 0.61024968 | 7.388591 | 3E-11 | 3866.002. | NM_002275.2 | BG990007.1 | EST | 1 |
| 783 | 57447.043.1-T_at | -0.61025 | 0.61024544 | 7.388509 | 3E-11 | 57447.043 | NM_201535.1 | DA829299.1 | EST | 1 |
| 784 | 51201.005.1-D_at | -0.61021 | 0.61021006 | 7.387827 | 3E-11 | 51201.005 | NM_016353.2 | DA655803.1 | EST | 1 |
| 785 | 51203.003.1-T_at | -0.610008 | 0.61000819 | 7.383934 | 3E-11 | 51203.003 | NM_016359.2 | BP283628.1 | EST | 1 |
| 786 | 9493.001.1-F_at | -0.609767 | 0.60976675 | 7.379281 | 3E-11 | 9493.001. | NM_138555.1 | BC051826.1 | mRNA | 1 |
| 787 | 57447.024.1-B_at | -0.60944 | 0.60943797 | 7.37295 | 3E-11 | 57447.024 | NM_201535.1 | DA566498.1 | EST | 1 |
| 788 | 80034.003.4-B_at | -0.60942 | 0.6094211 | 7.372625 | 4E-11 | 80034.003 | NM_024969.2 | CQ733306.1 | GENBANK_PATENT | 1 |
| 789 | 7170.016.3-C_at | -0.609237 | 0.60923665 | 7.369076 | 4E-11 | 7170.016. | NM_153649.2 | BF575596.1 | EST | 1 |
| 790 | 65983.003.1-T_at | -0.60914 | 0.60913896 | 7.367198 | 4E-11 | 65983.003 | NM_023927.1 | BP292708.1 | EST | 1 |
| 791 | 57447.026.1-T_at | -0.60891 | 0.60891356 | 7.362865 | 4E-11 | 57447.026 | NM_201535.1 | BP196338.1 | EST | 4 |
| 792 | 440421.001.1-F | -0.60867 | 0.6086702 | 7.35819 | 4E-11 | 440421.00 | XM_496202.2 | XM_934894.1 | REFSEQ | 2 |
| 793 | 301.008.1-D_at | -0.60853 | 0.60852747 | 7.355449 | 4E-11 | 301.008.1 | NM_000700.1 | CD688703.1 | EST | 1 |
| 794 | 80034.002.2-T_at | -0.60832 | 0.60831755 | 7.351421 | 4E-11 | 80034.002 | NM_024969.2 | DA769284.1 | EST | 1 |
| 795 | 7153.002.5-B_at | -0.608304 | 0.60830361 | 7.351154 | 4E-11 | 7153.002. | NM_001067.2 | CQ735949.1 | GENBANK_PATENT | 114 |
| 796 | 3852.008.2-F_at | -0.60821 | 0.60820967 | 7.349352 | 4E-11 | 3852.008. | NM_000424.2 | BG681715.1 | EST | 1 |
| 797 | 4288.006.2-T_at | -0.60812 | 0.60812437 | 7.347716 | 4E-11 | 4288.006. | NM_002417.2 | BP363635.1 | EST | 1 |
| 798 | 8404.013.1-F_at | -0.60779 | 0.60778896 | 7.341289 | 4E-11 | 8404.013. | NM_004684.2 | BP376616.1 | EST | 9 |
| 799 | 2.018.1-C_at | -0.60773 | 0.60772913 | 7.340143 | 4E-11 | 2.018.1 | NM_000014.4 | DB090657.1 | mRNA | 141 |
| 800 | 10124.003.1-B_at | -0.60757 | 0.60757027 | 7.337101 | 4E-11 | 10124.003 | NM_001037164. | BU664973.1 | EST | 1 |
| 801 | 3852.008.2-F_at | -0.60743 | 0.60743897 | 7.334588 | 4E-11 | 3852.008. | NM_000424.2 | BG675837.1 | EST | 1 |
| 802 | 8404.026.1-C_at | -0.60743 | 0.60742535 | 7.334327 | 4E-11 | 8404.026. | NM_004684.2 | BX647713.1 | mRNA | 1 |
| 803 | 23650.019.1-C_at | -0.6074 | 0.6073959 | 7.333764 | 4E-11 | 23650.019 | NM_058193.1 | BI224541.1 | EST | 1 |
| 804 | 7170.027.1-T_at | -0.607197 | 0.60719709 | 7.329961 | 5E-11 | 7170.027. | NM_153649.2 | BQ959117.1 | EST | 1 |
| 805 | 54928.003.1-E_at | -0.60719 | 0.60719005 | 7.329827 | 5E-11 | 54928.003 | NM_017813.2 | DB283344.1 | EST | 1 |
| 806 | 2335.025.1-B_at | -0.607111 | 0.60711088 | 7.328313 | 5E-11 | 2335.025. | NM_212482.1 | CQ715726.1 | GENBANK_PATENT | 3 |
| 807 | 3084.010.1-T_at | -0.60698 | 0.60697967 | 7.325805 | 5E-11 | 3084.010. | NM_013957.1 | BC007675.2 | mRNA | 7 |
| 808 | 57447.051.1-T_at | -0.60697 | 0.60697421 | 7.325701 | 5E-11 | 57447.051 | NM_201535.1 | BX460053.2 | EST | 1 |
| 809 | 80034.003.4-T_at | -0.60692 | 0.6069173 | 7.324613 | 5E-11 | 80034.003 | NM_024969.2 | CQ733306.1 | GENBANK_PATENT | 1 |
| 810 | 2568.005.1-D_at | -0.60678 | 0.6067777 | 7.321947 | 5E-11 | 2568.005. | NM_014211.1 | AK055205.1 | mRNA | 11 |
| 811 | 8404.032.1-F_at | -0.60677 | 0.60676941 | 7.321788 | 5E-11 | 8404.032. | NM_004684.2 | CQ498058.1 | GENBANK_PATENT | 1 |
| 812 | 2115.003.1-E_at | -0.60663 | 0.60662753 | 7.319079 | 5E-11 | 2115.003. | NM_004956.3 | DA128833.1 | EST | 1 |
| 813 | 57447.035.1-T_at | -0.60656 | 0.60656033 | 7.317796 | 5E-11 | 57447.035 | NM_201535.1 | BQ636638.1 | EST | 1 |
| 814 | 8404.009.1-T_at | -0.60613 | 0.60612981 | 7.309584 | 5E-11 | 8404.009. | NM_004684.2 | BP258993.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 815 | 8404.028.3-B_at | −0.60565 | 0.6056493939 | 7.300432 | 5E−11 | 8404.028. | NM_004684.2 | CQ727530.1 | GENBANK_PATENT | 1 |
| 816 | 6289.003.1-B_at | −0.60525 | 0.60524909 | 7.292816 | 5E−11 | 6289.003. | NM_030754.2 | R83510.1 | EST | 1 |
| 817 | 7170.025.1-F_at | 0.604985 | 0.6049846 | 7.287789 | 5E−11 | 7170.025. | NM_153649.2 | BE208737.1 | EST | 1 |
| 818 | 8404.030.1-D_at | −0.60498 | 0.60498368 | 7.287771 | 5E−11 | 8404.030. | NM_004684.2 | CD357736.1 | EST | 1 |
| 819 | 8404.009.1-F_at | −0.60494 | 0.6049439 | 7.287016 | 5E−11 | 8404.009. | NM_004684.2 | BP258993.1 | EST | 1 |
| 820 | 2335.009.1-T_at | 0.604716 | 0.60471597 | 7.282687 | 5E−11 | 2335.009. | NM_212482.1 | BG927121.1 | EST | 51 |
| 821 | 22974.007.1-F_at | 0.604647 | 0.60464714 | 7.28138 | 5E−11 | 22974.007 | NM_012112.4 | AF287265.1 | mRNA | 213 |
| 822 | 3426.002.1-B_at | −0.6044 | 0.60439543 | 7.276604 | 5E−11 | 3426.002. | NM_000204.1 | CQ718881.1 | GENBANK_PATENT | 1 |
| 823 | 4638.003.1-D_at | −0.60438 | 0.60437577 | 7.276231 | 5E−11 | 4638.003. | NM_053025.2 | BP289609.1 | EST | 1 |
| 824 | 4147.011.1-T_at | −0.6043 | 0.60430187 | 7.274829 | 6E−11 | 4147.011. | NM_002380.3 | BI559593.1 | EST | 2 |
| 825 | 6876.016.2-T_at | −0.60425 | 0.60425392 | 7.27392 | 6E−11 | 6876.016. | NM_0011001522. | AB209555.1 | mRNA | 2 |
| 826 | 23650.003.1-F_at | −0.60408 | 0.60408338 | 7.270687 | 6E−11 | 23650.003 | NM_058193.1 | BI333387.1 | EST | 1 |
| 827 | 4744.004.1-E_at | 0.60408 | 0.6040798 | 7.270619 | 6E−11 | 4744.004. | NM_021076.2 | BQ636126.1 | EST | 1 |
| 828 | 64168.010.1-F_at | −0.60405 | 0.60404978 | 7.270051 | 6E−11 | 64168.010 | NM_022351.2 | BM985162.1 | EST | 1 |
| 829 | 9073.001.1-F_at | −0.60404 | 0.60404345 | 7.269931 | 6E−11 | 9073.001. | NM_199328.1 | BC020866.1 | mRNA | 1 |
| 830 | 5288.001.3-B_at | −0.60399 | 0.60398504 | 7.268824 | 6E−11 | 5288.001. | NM_004570.2 | CQ720591.1 | GENBANK_PATENT | 1 |
| 831 | 3866.005.1-D_at | −0.60384 | 0.60383806 | 7.26604 | 6E−11 | 3866.005. | NM_002275.2 | AL832226.1 | mRNA | 37 |
| 832 | 8404.021.1-T_at | −0.6038 | 0.60380179 | 7.265353 | 6E−11 | 8404.021. | NM_004684.2 | DA291834.1 | EST | 1 |
| 833 | 25925.011.1-E_at | −0.60378 | 0.6037774 | 7.264891 | 6E−11 | 25925.011 | NM_015461.1 | DA105762.1 | EST | 1 |
| 834 | 23266.001.3-F_at | −0.60352 | 0.60352263 | 7.260069 | 6E−11 | 23266.001 | NM_012302.2 | AK123422.1 | mRNA | 2 |
| 835 | 9232.004.1-F_at | 0.603479 | 0.60347894 | 7.259242 | 6E−11 | 9232.004. | NM_004219.2 | BF983295.1 | EST | 1 |
| 836 | 4147.005.2-F_at | −0.60347 | 0.60346555 | 7.258989 | 6E−11 | 4147.005. | NM_002380.3 | CQ716197.1 | EST | 1 |
| 837 | 2335.025.3-B_at | 0.603394 | 0.60339429 | 7.257641 | 6E−11 | 2335.025. | NM_212482.1 | CQ715726.1 | GENBANK_PATENT | 3 |
| 838 | 4638.0061-C_at | −0.60335 | 0.60335253 | 7.256851 | 6E−11 | 4638.006. | NM_053025.2 | BC005817.1 | EST | 2 |
| 839 | 147804.004.1-T | 0.603318 | 0.60331792 | 7.256196 | 6E−11 | 147804.00 | NM_001010856. | DA204897.1 | GENBANK_PATENT | 1 |
| 840 | 81704.013.1-D_at | −0.60318 | 0.60318333 | 7.253652 | 6E−11 | 81704.013 | NM_203447.1 | CQ723361.1 | GENBANK_PATENT | 1 |
| 841 | 54443.013.1-B_at | −0.60317 | 0.60317758 | 7.253543 | 6E−11 | 54443.013 | NM_018685.2 | BX410228.2 | EST | 1 |
| 842 | 1410.005.1-T_at | −0.60301 | 0.60300785 | 7.250335 | 6E−11 | 1410.005. | NM_001885.1 | BM702557.1 | EST | 1 |
| 843 | 25925.009.1-T_at | −0.60288 | 0.60287704 | 7.247864 | 7E−11 | 25925.009 | NM_015461.1 | DB064380.1 | EST | 1 |
| 844 | 3204.001.1-T_at | −0.60272 | 0.60272058 | 7.24491 | 7E−11 | 3204.001. | NM_006896.3 | BX104300.1 | EST | 1 |
| 845 | 29997.012.1-F_at | −0.60268 | 0.60268472 | 7.244233 | 7E−11 | 29997.012 | NM_015710.3 | BG746448.1 | EST | 1 |
| 846 | 2.005.1-C_at | −0.60255 | 0.60254732 | 7.24164 | 7E−11 | 2.005.1 | NM_000014.4 | BI493707.1 | EST | 1 |
| 847 | 140885.011.1-F | −0.60254 | 0.60254281 | 7.241555 | 7E−11 | 140885.01 | NM_080792.2 | BM041242.1 | EST | 1 |
| 848 | 7153.002.3-F_at | 0.602528 | 0.60252816 | 7.241278 | 7E−11 | 7153.002. | NM_011067.2 | CQ735949.1 | GENBANK_PATENT | 114 |
| 849 | 1063.002.1-F_at | 0.602485 | 0.60248476 | 7.24046 | 7E−11 | 1063.002. | NM_016343.3 | CQ728087.1 | GENBANK_PATENT | 1 |
| 850 | 10144.021.1-F_at | −0.60221 | 0.60221389 | 7.235351 | 7E−11 | 10144.021 | NM_014883.2 | BG434219.1 | EST | 1 |
| 851 | 8404.025.1-E_at | −0.60217 | 0.60217399 | 7.234599 | 7E−11 | 8404.025. | NM_004684.2 | DB086831.1 | EST | 1 |
| 852 | 6876.020.1-B_at | −0.60216 | 0.60215903 | 7.234317 | 7E−11 | 6876.020. | NM_0011001522. | BM921237.1 | EST | 1 |
| 853 | 7170.006.1-C_at | 0.601994 | 0.6019941 | 7.231209 | 7E−11 | 7170.006. | NM_153649.2 | DB003864.1 | EST | 1 |
| 854 | 10051.016.1-T_at | 0.601783 | 0.60178293 | 7.227232 | 7E−11 | 10051.016 | NM_001002799. | DB062440.1 | GENBANK_PATENT | 1 |
| 855 | 5288.001.1-D_at | −0.60173 | 0.6017334 | 7.2263 | 7E−11 | 5288.001. | NM_004570.2 | CQ720591.1 | GENBANK_PATENT | 1 |
| 856 | 7018.029.1-T_at | −0.60153 | 0.60152604 | 7.222397 | 7E−11 | 7018.029. | NM_001063.2 | AV656085.1 | EST | 1 |
| 857 | 5627.002.1-B_at | −0.60134 | 0.6013408 | 7.218913 | 7E−11 | 5627.002. | NM_000313.1 | CQ731592.1 | GENBANK_PATENT | 1 |
| 858 | 57447.037.1-F_at | −0.60118 | 0.60117663 | 7.215826 | 7E−11 | 57447.037 | NM_201535.1 | BF793156.1 | EST | 1 |
| 859 | 4147.005.2-D_at | −0.60084 | 0.60084391 | 7.209576 | 8E−11 | 4147.005. | NM_002380.3 | CQ716197.1 | GENBANK_PATENT | 1 |
| 860 | 8404.023.1-T_at | −0.60074 | 0.6007351 | 7.207533 | 8E−11 | 8404.023. | NM_004684.2 | BX463355.2 | EST | 1 |
| 861 | 3872.006.1-D_at | −0.60063 | 0.60063372 | 7.20563 | 8E−11 | 3872.006. | NM_000422.1 | BM017443.1 | EST | 1 |
| 862 | 399687.001.1-C | −0.60061 | 0.60060752 | 7.205138 | 8E−11 | 399687.00 | NM_078471.3 | BM922301.1 | EST | 2 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 863 | 3815.002.4-D_at | −0.60047 | 0.6004748 | 7.202648 | 8E-11 | 3815.002. | NM_000222.1 | CQ719901.1 | GENBANK_PATENT | 1 |
| 864 | 59.034.2-B_at | −0.60033 | 0.60033475 | 7.200021 | 8E-11 | 59.034.2 | — | — | — | 1 |
| 865 | 8404.035.1-T_at | −0.60027 | 0.60026583 | 7.198729 | 8E-11 | 8404.035. | NM_004684.2 | BG716198.1 | EST | 1 |
| 866 | 8404.030.1-T_at | −0.60022 | 0.60021743 | 7.197822 | 8E-11 | 8404.030. | NM_004684.2 | CD357736.1 | EST | 1 |
| 867 | 54997.002.2-T_at | −0.60016 | 0.60015635 | 7.196677 | 8E-11 | 54997.002 | NM_017899.1 | CQ729176.1 | GENBANK_PATENT | 1 |
| 868 | 57561.001.1-F_at | −0.6001 | 0.60010368 | 7.19569 | 8E-11 | 57561.001 | NM_020801.1 | BQ428039.1 | EST | 1 |
| 869 | 8404.031.1-T_at | −0.6 | 0.59999606 | 7.193674 | 8E-11 | 8404.031. | NM_004684.2 | BP327616.1 | EST | 1 |
| 870 | 2.025.1-E_at | 0.599999 | 0.59998752 | 7.193514 | 8E-11 | 2.025.1 | NM_000014.4 | DB288732.1 | EST | 1 |
| 871 | 699.002.1-F_at | 0.599982 | 0.59998236 | 7.193417 | 8E-11 | 699.002.1 | NM_004336.2 | CQ715813.1 | GENBANK_PATENT | 1 |
| 872 | 57447.041.1-F_at | −0.59992 | 0.59999151 | 7.192157 | 8E-11 | 57447.041 | NM_201535.1 | DA295124.1 | EST | 1 |
| 873 | 9055.013.1-D_at | 0.59986 | 0.59986038 | 7.191132 | 8E-11 | 9055.013. | NM_003981.2 | CN348395.1 | EST | 1 |
| 874 | 8404.008.1-D_at | −0.59979 | 0.5997907 | 7.189828 | 8E-11 | 8404.008. | NM_004684.2 | DA342341.1 | EST | 1 |
| 875 | 7018.028.1-T_at | −0.59975 | 0.59975341 | 7.189129 | 8E-11 | 7018.028. | NM_001063.2 | BX537660.1 | mRNA | 1 |
| 876 | 2568.005.1-T_at | −0.59968 | 0.59967705 | 7.1877 | 8E-11 | 2568.005. | NM_014211.1 | AK055205.1 | mRNA | 11 |
| 877 | 10051.005.3-T_at | −0.59953 | 0.59953164 | 7.184979 | 8E-11 | 10051.005 | NM_001002799. | BU183025.1 | EST | 1 |
| 878 | 2568.002.2-T_at | −0.59944 | 0.59943802 | 7.183228 | 9E-11 | 2568.002. | NM_014211.1 | DB235581.1 | EST | 1 |
| 879 | 4147.004.1-F_at | −0.59921 | 0.59921316 | 7.179023 | 9E-11 | 4147.004. | NM_002380.3 | AX675291.1 | GENBANK_PATENT | 1 |
| 880 | 2938.001.1-T_at | −0.59919 | 0.59919321 | 7.17865 | 9E-11 | 2938.001. | NM_145740.2 | AV683456.1 | EST | 1 |
| 881 | 1308.007.1-E_at | −0.59902 | 0.59902115 | 7.175435 | 9E-11 | 1308.007. | NM_130778.1 | BF916393.1 | EST | 1 |
| 882 | 2982.012.1-T_at | −0.59882 | 0.59881603 | 7.171604 | 1E-10 | 2982.012. | NM_000856.2 | BC012627.1 | mRNA | 2 |
| 883 | 8404.028.1-D_at | −0.59877 | 0.5987733 | 7.170806 | 1E-10 | 8404.028. | NM_004684.2 | CQ727530.1 | GENBANK_PATENT | 1 |
| 884 | 7373.001.2-B_at | −0.5986 | 0.598602 | 7.167609 | 1E-10 | 7373.001. | NM_021110.1 | DB089175.1 | EST | 1 |
| 885 | 2893.002.2-B_at | −0.59834 | 0.59834456 | 7.162807 | 1E-10 | 2893.002. | NM_000829.1 | DA365406.1 | EST | 1 |
| 886 | 116369.006.4-C | −0.59832 | 0.59831944 | 7.162338 | 1E-10 | 116369.00 | NM_052961.2 | AX480884.1 | GENBANK_PATENT | 1 |
| 887 | 6304.007.1-T_at | −0.59819 | 0.59819347 | 7.15999 | 1E-10 | 6304.007. | NM_002971.2 | DB141052.1 | EST | 1 |
| 888 | 2335.035.1-T_at | 0.597963 | 0.5979628 | 7.155692 | 1E-10 | 2335.035. | NM_212482.1 | CX755647.1 | EST | 1 |
| 889 | 4751.002.1-T_at | 0.597837 | 0.59783662 | 7.153342 | 1E-10 | 4751.002. | NM_002497.2 | BI464450.1 | EST | 1 |
| 890 | 64151.001.2-T_at | 0.597704 | 0.59770416 | 7.150876 | 1E-10 | 64151.001 | NM_022346.3 | CQ729716.1 | GENBANK_PATENT | 2 |
| 891 | 29089.003.1-T_at | 0.597695 | 0.59769515 | 7.150708 | 1E-10 | 29089.003 | NM_014176.1 | AV740591.1 | EST | 1 |
| 892 | 59.031.1-B_at | −0.59762 | 0.59761835 | 7.149279 | 1E-10 | 59.031.1 | NM_001613.1 | BG197213.1 | EST | 19 |
| 893 | 7018.025.1-T_at | −0.59758 | 0.59757801 | 7.148528 | 1E-10 | 7018.025. | NM_001063.2 | BE971065.1 | EST | 1 |
| 894 | 3860.008.1-T_at | −0.59747 | 0.5974712 | 7.146341 | 1E-10 | 3860.008. | NM_153490.1 | DA668693.1 | EST | 1 |
| 895 | 5858.003.3-F_at | −0.59734 | 0.5973382 | 7.144067 | 1E-10 | 5858.003. | NM_002864.1 | AX512279.1 | GENBANK_PATENT | 2 |
| 896 | 8404.009.1-C_at | −0.59725 | 0.59725088 | 7.142444 | 1E-10 | 8404.009. | NM_004684.2 | BP258993.1 | EST | 1 |
| 897 | 7169.022.1-T_at | −0.59719 | 0.59718906 | 7.141295 | 1E-10 | 7169.022. | NM_213674.1 | BG385598.1 | EST | 1 |
| 898 | 25925.006.1-T_at | 0.597714 | 0.59714283 | 7.140436 | 1E-10 | 25925.006 | NM_022346.3 | DB276803.1 | EST | 1 |
| 899 | 59.049.1-F_at | −0.59713 | 0.59712525 | 7.140109 | 1E-10 | 59.049.1 | — | — | — | — |
| 900 | 5284.003.1-T_at | −0.59709 | 0.59708796 | 7.139416 | 1E-10 | 5284.003. | NM_002644.2 | BP220016.1 | EST | 1 |
| 901 | 2982.002.1-F_at | −0.59705 | 0.59705092 | 7.138728 | 1E-10 | 2982.002. | NM_000856.2 | BP199345.1 | EST | 1 |
| 902 | 2568.002.1-T_at | −0.59693 | 0.59693461 | 7.136567 | 1E-10 | 2568.002. | NM_014211.1 | DB235581.1 | EST | 1 |
| 903 | 301.004.1-B_at | −0.59688 | 0.59688305 | 7.135609 | 1E-10 | 301.004.1 | NM_000700.1 | DB194639.1 | EST | 1 |
| 904 | 25925.011.1-F_at | −0.59665 | 0.59664856 | 7.131256 | 1E-10 | 25925.011 | NM_015461.1 | DA105762.1 | EST | 1 |
| 905 | 59.004.1-F_at | −0.59647 | 0.59647098 | 7.127961 | 1E-10 | 59.004.1 | NM_001613.1 | CQ696293.1 | GENBANK_PATENT | 1 |
| 906 | 6289.002.1-B_at | −0.59635 | 0.59634661 | 7.125655 | 1E-10 | 6289.002. | NM_030754.2 | AA345111.1 | EST | 1 |
| 907 | 244.003.1-C_at | −0.59612 | 0.59612161 | 7.121484 | 1E-10 | 244.003.1 | NM_001630.1 | BM809869.1 | EST | 1 |
| 908 | 11065.008.1-C_at | 0.595877 | 0.59587676 | 7.116948 | 1E-10 | 11065.008 | NM_181802.1 | NM_181800.1 | REFSEQ | 5 |
| 909 | 7091.006.1-T_at | −0.59586 | 0.59586302 | 7.116693 | 1E-10 | 7091.006. | NM_007005.3 | AK057236.1 | mRNA | 1 |
| 910 | 79608.009.1-F_at | −0.59581 | 0.59580998 | 7.115711 | 1E-10 | 79608.009 | NM_024557.2 | CA406619.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 911 | 9413.002.1-T_at | −0.5958 | 0.5958106 | 7.115546 | 1E−10 | 9413.002. | NM_004816.2 | AW779892.1 | EST | 1 |
| 912 | 7431.064.1-C_at | −0.59575 | 0.59575257 | 7.114648 | 1E−10 | 7431.064. | NM_003380.2 | BE728213.1 | EST | 1 |
| 913 | 8404.029.1-E_at | −0.5957 | 0.59569505 | 7.113583 | 1E−10 | 8404.029. | NM_004684.2 | AA384658.1 | EST | 1 |
| 914 | 6876.020.1-T_at | −0.59541 | 0.59541268 | 7.108359 | 1E−10 | 6876.020. | NM_001001522. | BM921237.1 | EST | 1 |
| 915 | 301.005.1-T_at | −0.59539 | 0.59538592 | 7.107864 | 1E−10 | 301.005.1 | NM_000700.1 | AU139656.1 | EST | 7 |
| 916 | 9055.014.1-T_at | −0.59529 | 0.59528897 | 7.106085 | 1E−10 | 9055.014. | NM_003981.2 | BE300335.1 | EST | 1 |
| 917 | 4281.023.1-T_at | −0.5952 | 0.59520125 | 7.104449 | 1E−10 | 4281.023. | NM_033290.1 | AY539976.1 | mRNA | 1 |
| 918 | 3868.005.1-D_at | −0.59519 | 0.59519189 | 7.104276 | 1E−10 | 3868.005. | NM_005557.2 | BG682632.1 | EST | 1 |
| 919 | 1062.001.6-B_at | 0.595002 | 0.59500239 | 7.100775 | 1E−10 | 1062.001. | NM_001813.2 | CQ715352.1 | GENBANK_PATENT | 1 |
| 920 | 5858.005.1-T_at | −0.59493 | 0.5949259 | 7.099362 | 1E−10 | 5858.005. | NM_002864.1 | DB040351.1 | EST | 1 |
| 921 | 51201.007.1-F_at | −0.59491 | 0.59490972 | 7.099063 | 1E−10 | 51201.007 | NM_016353.2 | BF541714.1 | EST | 1 |
| 922 | 4240.001.1-B_at | −0.59478 | 0.59477936 | 7.096655 | 1E−10 | 4240.001. | NM_005928.1 | BF525404.1 | EST | 1 |
| 923 | 8404.029.1-T_at | −0.59477 | 0.59477341 | 7.096546 | 1E−10 | 8404.029. | NM_004684.2 | AA384658.1 | EST | 1 |
| 924 | 9413.001.1-T_at | −0.59469 | 0.59468964 | 7.094999 | 1E−10 | 9413.001. | NM_004816.2 | DA824091.1 | EST | 1 |
| 925 | 9768.005.1-T_at | −0.59458 | 0.59458041 | 7.092983 | 1E−10 | 9768.005. | NM_014736.4 | BG529193.1 | EST | 13 |
| 926 | 11197.001.1-T_at | −0.59454 | 0.59454222 | 7.092279 | 1E−10 | 11197.001 | NM_007191.2 | W37154.1 | EST | 1 |
| 927 | 6285.002.1-T_at | −0.59451 | 0.59450684 | 7.091626 | 1E−10 | 6285.002. | NM_006272.1 | BQ435930.1 | EST | 1 |
| 928 | 2335.006.2-F_at | 0.594359 | 0.59435947 | 7.088907 | 1E−10 | 2335.006. | NM_212482.1 | CX785805.1 | EST | 1 |
| 929 | 7169.001.1-C_at | −0.59424 | 0.59424202 | 7.086742 | 1E−10 | 7169.001. | NM_213674.1 | BM809268.1 | EST | 4 |
| 930 | 9493.004.1-T_at | −0.59408 | 0.59410838 | 7.084278 | 1E−10 | 9493.004. | NM_138555.1 | BM792243.1 | EST | 1 |
| 931 | 4601.014.1-T_at | −0.59408 | 0.59408377 | 7.083825 | 1E−10 | 4601.014. | NM_130439.3 | AX885544.1 | GENBANK_PATENT | 1 |
| 932 | 51203.002.2-F_at | 0.593876 | 0.59387576 | 7.079993 | 1E−10 | 51203.002 | NM_016359.2 | AL561514.3 | EST | 1 |
| 933 | 7018.022.1-F_at | 0.59374 | 0.593741 | 7.077512 | 1E−10 | 7018.022. | NM_001063.2 | T74625.1 | EST | 1 |
| 934 | 4288.009.1-F_at | 0.593675 | 0.59367472 | 7.076291 | 1E−10 | 4288.009. | NM_002417.2 | BG106198.1 | EST | 1 |
| 935 | 8321.004.1-D_at | 0.59365 | 0.59365154 | 7.075865 | 1E−10 | 8321.004. | NM_003505.1 | AA249884.1 | EST | 1 |
| 936 | 8564.004.1-E_at | −0.59345 | 0.59344954 | 7.072148 | 1E−10 | 8564.004. | NM_003679.2 | AV646525.1 | EST | 3 |
| 937 | 7169.022.1-C_at | −0.59343 | 0.59343079 | 7.071803 | 1E−10 | 7169.022. | NM_213674.1 | BG385598.1 | EST | 1 |
| 938 | 29127.013.1-T_at | 0.593386 | 0.59338577 | 7.070975 | 1E−10 | 29127.013 | NM_013277.2 | DA812983.1 | EST | 1 |
| 939 | 2.018.1-B_at | −0.59317 | 0.59316746 | 7.066961 | 1E−10 | 2.018.1 | NM_000014.4 | DB090657.1 | EST | 1 |
| 940 | 2.005.1-D_at | −0.59314 | 0.59313787 | 7.066417 | 1E−10 | 2.005.1 | NM_000014.4 | BI493707.1 | EST | 1 |
| 941 | 1058.004.2-T_at | 0.5931 | 0.593110026 | 7.065726 | 2E−10 | 1058.004. | NM_001809.2 | AL555851.3 | EST | 1 |
| 942 | 2232.014.1-C_at | −0.59284 | 0.59284081 | 7.060959 | 2E−10 | 2232.014. | NM_044110.2 | DB052280.1 | EST | 1 |
| 943 | 23650.005.1-E_at | −0.59283 | 0.59282614 | 7.06069 | 2E−10 | 23650.005 | NM_058193.1 | DB116882.1 | EST | 1 |
| 944 | 5621.002.2-T_at | −0.59271 | 0.59270593 | 7.058482 | 2E−10 | 5621.002. | NM_000311.2 | DA151722.1 | EST | 1 |
| 945 | 51201.005.1-B_at | −0.5927 | 0.59270147 | 7.058401 | 2E−10 | 51201.005 | NM_016353.2 | DA655803.1 | EST | 1 |
| 946 | 667.022.1-F_at | −0.59265 | 0.59265274 | 7.057506 | 2E−10 | 667.022.1 | NM_183380.1 | AX683196.1 | GENBANK_PATENT | 1 |
| 947 | 54443.012.1-C_at | 0.592546 | 0.59254619 | 7.055551 | 2E−10 | 54443.012 | NM_018685.2 | BG167656.1 | EST | 1 |
| 948 | 25802.003.1-C_at | −0.59251 | 0.59250565 | 7.054807 | 2E−10 | 25802.003 | NM_012134.1 | BC001755.1 | mRNA | 1 |
| 949 | 3479.003.1-T_at | −0.59248 | 0.59247776 | 7.054295 | 2E−10 | 3479.003. | NM_000618.2 | U40870.1 | mRNA | 4 |
| 950 | 94274.003.1-D_at | −0.59243 | 0.59242603 | 7.053346 | 2E−10 | 94274.003 | NM_033256.1 | AB056509.1 | mRNA | 1 |
| 951 | 84668.003.1-T_at | −0.59229 | 0.5922945 | 7.050934 | 2E−10 | 84668.003 | NM_032581.2 | CQ727246.1 | GENBANK_PATENT | 1 |
| 952 | 22974.008.1-E_at | 0.592131 | 0.59213066 | 7.04793 | 2E−10 | 22974.008 | NM_012112.4 | CQ727779.1 | GENBANK_PATENT | 1 |
| 953 | 55656.007.3-B_at | 0.592104 | 0.59210361 | 7.047434 | 2E−10 | 55656.007 | NM_017864.2 | CQ715091.1 | GENBANK_PATENT | 1 |
| 954 | 29127.002.1-T_at | 0.591958 | 0.59195836 | 7.044773 | 2E−10 | 29127.002 | NM_013277.2 | AB030251.1 | mRNA | 44 |
| 955 | 4281.012.2-T_at | −0.59195 | 0.59194704 | 7.044565 | 2E−10 | 4281.012. | NM_033290.1 | CN298826.1 | EST | 1 |
| 956 | 2335.013.1-B_at | 0.591874 | 0.59187364 | 7.043221 | 2E−10 | 2335.013. | NM_212482.1 | AL551632.3 | EST | 2 |
| 957 | 79627.003.1-B_at | −0.59185 | 0.59184571 | 7.042709 | 2E−10 | 79627.003 | NM_024576.3 | CQ725357.1 | GENBANK_PATENT | 1 |
| 958 | 2982.014.1-T_at | −0.5918 | 0.5918033 | 7.041932 | 2E−10 | 2982.014. | NM_000856.2 | BM469193.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 959 | 2335.053.1-T_at | 0.591795 | 0.5917954 | 7.041788 | 2E-10 | 2335.053. | NM_212482.1 | BX380854.2 | EST | 1 |
| 960 | 667.001.1-F_at | -0.59167 | 0.5916653 | 7.039406 | 2E-10 | 667.001.1 | NM_183380.1 | BG387402.1 | EST | 2 |
| 961 | 8404.030.1-B_at | -0.59165 | 0.59165467 | 7.039211 | 2E-10 | 8404.030. | NM_004684.2 | CD357736.1 | EST | 1 |
| 962 | 2335.025.1-C_at | 0.591645 | 0.59164549 | 7.039043 | 2E-10 | 2335.025. | NM_212482.1 | CQ715726.1 | GENBANK_PATENT | 3 |
| 963 | 140885.010.3-D | -0.59164 | 0.59164248 | 7.038988 | 2E-10 | 140885.01 | NM_080792.2 | CQ728313.1 | GENBANK_PATENT | 1 |
| 964 | 55366.001.2-F_at | -0.59159 | 0.59158568 | 7.037948 | 2E-10 | 55366.001 | NM_018490.1 | CQ722924.1 | GENBANK_PATENT | 1 |
| 965 | 7169.015.1-D_at | 0.591548 | 0.59147642 | 7.035949 | 2E-10 | 7169.015. | NM_213674.1 | DB291177.1 | EST | 1 |
| 966 | 57447.002.1-B_at | -0.59141 | 0.59140949 | 7.034725 | 2E-10 | 57447.002 | NM_201535.1 | BF526188.1 | EST | 1 |
| 967 | 22974.008.1-T_at | 0.591372 | 0.59137204 | 7.034039 | 2E-10 | 22974.008 | NM_012112.4 | CQ727779.1 | GENBANK_PATENT | 1 |
| 968 | 6876.011.1-C_at | -0.59135 | 0.59135455 | 7.033719 | 2E-10 | 6876.011. | NM_001001522. | AW956430.1 | EST | 1 |
| 969 | 4281.008.2-D_at | -0.59123 | 0.591231 | 7.03146 | 2E-10 | 4281.008. | NM_033290.1 | AY539984.1 | mRNA | 1 |
| 970 | 59.008.1-T_at | -0.59118 | 0.59117565 | 7.030448 | 2E-10 | 59.008.1 | NM_001613.1 | BP373197.1 | EST | 1 |
| 971 | 23266.008.1-F_at | -0.59109 | 0.59109236 | 7.028926 | 2E-10 | 23266.008 | NM_012302.2 | CQ799210.1 | GENBANK_PATENT | 1 |
| 972 | 2568.003.2-T_at | -0.59089 | 0.59089352 | 7.025292 | 2E-10 | 2568.003. | NM_014211.1 | CD696885.1 | EST | 1 |
| 973 | 5311.003.1-T_at | -0.59073 | 0.59073163 | 7.022336 | 2E-10 | 5311.003. | NM_000297.2 | DA153606.1 | EST | 1 |
| 974 | 6304.011.1-T_at | -0.59052 | 0.59052216 | 7.018512 | 2E-10 | 6304.011. | NM_002971.2 | BP359118.1 | EST | 1 |
| 975 | 3861.008.1-B_at | -0.59048 | 0.59048159 | 7.017772 | 2E-10 | 3861.008. | NM_000526.3 | BE184532.1 | EST | 1 |
| 976 | 7018.013.1-B_at | -0.59035 | 0.59035214 | 7.01541 | 2E-10 | 7018.013. | NM_001063.2 | AX147484.1 | GENBANK_PATENT | 1 |
| 977 | 8404.005.1-F_at | -0.59023 | 0.59022734 | 7.013134 | 2E-10 | 8404.005. | NM_004684.2 | DA763956.1 | EST | 1 |
| 978 | 7170.027.1-C_at | 0.590216 | 0.59021624 | 7.012932 | 2E-10 | 7170.027. | NM_153649.2 | BQ959117.1 | EST | 1 |
| 979 | 8404.023.1-C_at | -0.59009 | 0.59009089 | 7.010646 | 2E-10 | 8404.023. | NM_004684.2 | BX463355.2 | EST | 1 |
| 980 | 7373.007.1-C_at | -0.59009 | 0.59009037 | 7.010637 | 2E-10 | 7373.007. | NM_021110.1 | Y11710.1 | mRNA | 2 |
| 981 | 1410.009.1-T_at | -0.5899 | 0.5898986 | 7.007142 | 2E-10 | 1410.009. | NM_001885. | BQ437433.1 | EST | 3 |
| 982 | 79745.004.3-D_at | -0.58947 | 0.58947272 | 6.999388 | 2E-10 | 79745.004 | NM_024692.3 | AK057267.1 | mRNA | 1 |
| 983 | 24137.004.1-T_at | -0.58944 | 0.5894492 | 6.99896 | 2E-10 | 24137.004 | NM_012310.2 | BQ055679.1 | EST | 1 |
| 984 | 6241.013.1-B_at | -0.58941 | 0.58941768 | 6.998387 | 2E-10 | 6241.013. | NM_001034.1 | BG261296.1 | EST | 1 |
| 985 | 1410.001.1-T_at | -0.5894 | 0.58939515 | 6.997977 | 2E-10 | 1410.001. | NM_001885. | W40377.1 | EST | 1 |
| 986 | 4781.015.2-B_at | -0.58938 | 0.5893752 | 6.997614 | 2E-10 | 4781.015. | NM_005596.1 | DN995118.1 | EST | 1 |
| 987 | 72.002.1-T_at | -0.58937 | 0.58936787 | 6.99748 | 2E-10 | 72.002.1 | NM_001615.3 | BP372072.1 | EST | 2 |
| 988 | 4833.004.1-D_at | 0.589279 | 0.58927851 | 6.995855 | 2E-10 | 4833.004. | NM_005009.2 | BG478602.1 | EST | 8 |
| 989 | 57447.024.1-D_at | -0.58924 | 0.58924443 | 6.995235 | 2E-10 | 57447.024 | NM_201535.1 | DA566498.1 | EST | 1 |
| 990 | 2982.013.2-T_at | -0.5892 | 0.58920321 | 6.994486 | 2E-10 | 2982.013. | NM_000856.2 | CF594362.1 | EST | 1 |
| 991 | 79971.012.1-T_at | -0.58907 | 0.5890694 | 6.992053 | 2E-10 | 79971.012 | NM_001002292. | BG702604.1 | EST | 1 |
| 992 | 8404.028.3-C_at | -0.589 | 0.58899948 | 6.990782 | 2E-10 | 8404.028. | NM_004684.2 | CQ727530.1 | GENBANK_PATENT | 1 |
| 993 | 4638.011.1-E_at | -0.58897 | 0.58897325 | 6.990305 | 2E-10 | 4638.011. | NM_053025.2 | DB267860.1 | EST | 1 |
| 994 | 7169.004.1-C_at | -0.58895 | 0.58894617 | 6.989813 | 2E-10 | 7169.004. | NM_213674.1 | BG027526.1 | EST | 1 |
| 995 | 4288.004.1-F_at | -0.58788 | 0.58878813 | 6.986942 | 2E-10 | 4288.004. | NM_002417.2 | BP232141.1 | EST | 1 |
| 996 | 59.012.2-C_at | -0.58875 | 0.58875113 | 6.98627 | 2E-10 | 59.012.2 | NM_001613.1 | AL546033.3 | EST | 1 |
| 997 | 301.008.1-B_at | -0.5887 | 0.58869814 | 6.985308 | 2E-10 | 301.008.1 | NM_000700.1 | CD688703.1 | EST | 1 |
| 998 | 4281.012.1-T_at | -0.58864 | 0.58863805 | 6.984217 | 2E-10 | 4281.012. | NM_033290.1 | CN298826.1 | EST | 1 |
| 999 | 2335.016.1-F_at | 0.58863 | 0.58863031 | 6.984076 | 2E-10 | 2335.016. | NM_212482.1 | CQ875357.1 | GENBANK_PATENT | 281 |
| 1000 | 259266.003.1-C | 0.588552 | 0.58855227 | 6.98266 | 2E-10 | 259266.00 | NM_018136.2 | CB217235.1 | EST | 1 |
| 1001 | 9055.020.1-T_at | 0.588545 | 0.58854487 | 6.982525 | 2E-10 | 9055.020. | NM_003981.2 | BP363287.1 | EST | 1 |
| 1002 | 7091.016.1-T_at | -0.58837 | 0.58836788 | 6.979313 | 2E-10 | 7091.016. | NM_007005.3 | DA323941.1 | EST | 1 |
| 1003 | 59.023.1-T_at | -0.5882 | 0.58819673 | 6.976209 | 2E-10 | 59.023.1 | NM_001613.1 | DB248573.1 | EST | 1 |
| 1004 | 57162.010.1-B_at | -0.58814 | 0.58813698 | 6.975125 | 2E-10 | 57162.010 | NM_020651.2 | DB241492.1 | EST | 1 |
| 1005 | 4781.002.2-D_at | -0.58809 | 0.58808634 | 6.974207 | 2E-10 | 4781.002. | NM_005596.1 | BF688131.1 | EST | 2 |
| 1006 | 6122.037.1-T_at | -0.58806 | 0.58805933 | 6.973718 | 2E-10 | 6122.037. | NM_000967.3 | BP417473.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1007 | 4240.015.1-B_at | −0.58803 | 0.58803047 | 6.973195 | 2E-10 | 4240.015. | NM_005928.1 | AA021047.1 | EST | 1 |
| 1008 | 59.034.1-T_at | −0.58783 | 0.58782732 | 6.969513 | 2E-10 | 59.034.1 | — | — | — | — |
| 1009 | 8404.004.2-D_at | −0.58782 | 0.58782345 | 6.969443 | 2E-10 | 8404.004. | NM_004684.2 | DA589023.1 | EST | 1 |
| 1010 | 9413.001.2-T_at | −0.58777 | 0.5877726 | 6.968522 | 2E-10 | 9413.001. | NM_004816.2 | DA824091.1 | EST | 1 |
| 1011 | 2.005.1-F_at | −0.58772 | 0.58771984 | 6.967566 | 2E-10 | 2.005.1 | NM_000014.4 | BI493707.1 | EST | 1 |
| 1012 | 6304.002.1-T_at | −0.58771 | 0.58770553 | 6.967307 | 2E-10 | 6304.002. | NM_002971.2 | BC001744.1 | mRNA | 33 |
| 1013 | 3852.005.1-C_at | −0.58768 | 0.58768033 | 6.966851 | 2E-10 | 3852.005. | NM_000424.2 | R47851.1 | EST | 1 |
| 1014 | 7170.027.1-B_at | −0.587642 | 0.58764175 | 6.966152 | 2E-10 | 7170.027. | NM_153649.2 | BQ959117.1 | EST | 1 |
| 1015 | 301.013.1-T_at | −0.5873 | 0.58729565 | 6.959888 | 2E-10 | 301.013.1 | NM_000700.1 | BF130804.1 | EST | 1 |
| 1016 | 6304.012.1-F_at | −0.58724 | 0.58724193 | 6.958916 | 2E-10 | 6304.012. | NM_002971.2 | BP359502.1 | EST | 1 |
| 1017 | 57447.051.2-T_at | −0.58722 | 0.58721828 | 6.958489 | 2E-10 | 57447.051 | NM_201535.1 | BX460053.2 | GENBANK_PATENT | 1 |
| 1018 | 11065.005.1-C_at | −0.587192 | 0.58719194 | 6.958012 | 2E-10 | 11065.005 | NM_181802.1 | CS138820.1 | GENBANK_PATENT | 2 |
| 1019 | 6422.002.1-F_at | −0.58719 | 0.58719017 | 6.95798 | 2E-10 | 6422.002. | NM_003012.3 | AX565729.1 | GENBANK_PATENT | 3 |
| 1020 | 6241.013.1-F_at | −0.587043 | 0.58704329 | 6.955324 | 3E-10 | 6241.013. | NM_001034.1 | BG261296.1 | EST | 1 |
| 1021 | 2335.032.1-T_at | −0.58699 | 0.58699048 | 6.95437 | 3E-10 | 2335.032. | NM_212482.1 | DA647475.1 | EST | 1 |
| 1022 | 11065.005.2-T_at | −0.586925 | 0.5869248 | 6.953183 | 3E-10 | 11065.005 | NM_181802.1 | CS138820.1 | GENBANK_PATENT | 2 |
| 1023 | 2335.028.1-D_at | −0.586789 | 0.58678853 | 6.95072 | 3E-10 | 2335.028. | NM_212482.1 | AJ320525.1 | mRNA | 1 |
| 1024 | 29997.016.1-F_at | −0.58672 | 0.58671564 | 6.949404 | 3E-10 | 29997.016 | NM_015710.3 | BF686243.1 | EST | 1 |
| 1025 | 7018.014.1-T_at | −0.58659 | 0.58658835 | 6.947105 | 3E-10 | 7018.014. | NM_001063.3 | AX147483.1 | GENBANK_PATENT | 1 |
| 1026 | 1410.011.1-E_at | −0.58657 | 0.58657023 | 6.946778 | 3E-10 | 1410.011. | NM_001885.1 | BI561839.1 | EST | 1 |
| 1027 | 7170.040.1-E_at | −0.586568 | 0.58656826 | 6.946742 | 3E-10 | 7170.040. | NM_153649.2 | BG283654.1 | EST | 1 |
| 1028 | 6289.002.2-F_at | −0.5864 | 0.58639668 | 6.943645 | 3E-10 | 6289.002. | NM_030754.2 | AA345111.1 | EST | 1 |
| 1029 | 7373.003.4-C_at | −0.58637 | 0.58636622 | 6.943095 | 3E-10 | 7373.003. | NM_021110.1 | CQ716670.1 | GENBANK_PATENT | 1 |
| 1030 | 7170.041.1-F_at | −0.58605 | 0.58604991 | 6.93739 | 3E-10 | 7170.041. | NM_153649.2 | BF967161.1 | EST | 4 |
| 1031 | 128553.003.1-B | −0.586 | 0.58599544 | 6.936408 | 3E-10 | 128553.00 | NM_173485.2 | BP394387.1 | EST | 1 |
| 1032 | 4094.002.1-D_at | −0.58596 | 0.58595549 | 6.935688 | 3E-10 | 4094.002. | NM_001031804. | BI458211.1 | EST | 1 |
| 1033 | 7113.011.1-T_at | −0.5859 | 0.58589757 | 6.934644 | 3E-10 | 7113.011. | NM_056656.2 | DA868984.1 | EST | 2 |
| 1034 | 7170.002.1-C_at | −0.585876 | 0.58587638 | 6.934262 | 3E-10 | 7170.002. | NM_153649.2 | AL547448.3 | EST | 2 |
| 1035 | 8404.017.2-T_at | −0.58585 | 0.58584564 | 6.933708 | 3E-10 | 8404.017. | NM_004684.2 | CD001002.1 | EST | 1 |
| 1036 | 59.029.1-T_at | −0.58564 | 0.58563959 | 6.929996 | 3E-10 | 59.029.1 | NM_001613.1 | AL540709.3 | EST | 1 |
| 1037 | 29089.001.1-T_at | −0.585601 | 0.58560082 | 6.929298 | 3E-10 | 29089.001 | NM_014176.1 | CA495294.1 | EST | 2 |
| 1038 | 358.012.1-T_at | −0.5856 | 0.58559702 | 6.929229 | 3E-10 | 358.012.1 | NM_198098.1 | AX397685.1 | GENBANK_PATENT | 1 |
| 1039 | 9134.001.1-B_at | 0.585561 | 0.58556099 | 6.92858 | 3E-10 | 9134.001. | NM_057749.1 | BC007015.1 | mRNA | 1 |
| 1040 | 2335.013.1-C_at | 0.583476 | 0.58547585 | 6.927047 | 3E-10 | 2335.013. | NM_212482.1 | AL551632.3 | EST | 2 |
| 1041 | 1410.010.1-F_at | −0.58543 | 0.58542981 | 6.926219 | 3E-10 | 1410.010. | NM_001885.1 | AJ710474.1 | EST | 2 |
| 1042 | 2327.003.4-F_at | −0.58542 | 0.58541593 | 6.925969 | 3E-10 | 2327.003. | NM_001460.2 | AI223310.1 | EST | 1 |
| 1043 | 59.042.1-T_at | −0.58536 | 0.58536256 | 6.925008 | 3E-10 | 59.042.1 | NM_001613.1 | EH_001613.8 | PREDICTED | 1 |
| 1044 | 6304.007.2-T_at | −0.58518 | 0.58517695 | 6.921669 | 3E-10 | 6304.007. | NM_002971.2 | DB141052.1 | EST | 1 |
| 1045 | 8404.031.1-B_at | −0.58502 | 0.5850183 | 6.918815 | 3E-10 | 8404.031. | NM_004684.2 | BP327616.1 | EST | 1 |
| 1046 | 6289.001.1-F_at | −0.58499 | 0.58499281 | 6.918357 | 3E-10 | 6289.001. | NM_030754.2 | CR744712.1 | EST | 1 |
| 1047 | 1410.006.1-T_at | −0.58487 | 0.58487369 | 6.916216 | 3E-10 | 1410.006. | NM_001885.1 | BF670917.1 | EST | 1 |
| 1048 | 80034.004.1-T_at | −0.58483 | 0.58482793 | 6.915393 | 3E-10 | 80034.004 | NM_024969.2 | DA786544.1 | EST | 1 |
| 1049 | 1410.008.1-T_at | −0.58477 | 0.58476949 | 6.914343 | 3E-10 | 1410.008. | NM_001885.1 | R68496.1 | EST | 1 |
| 1050 | 57447.051.2-D_at | −0.5847 | 0.58469568 | 6.913017 | 3E-10 | 57447.051 | NM_201535.1 | BX460053.2 | GENBANK_PATENT | 1 |
| 1051 | 7170.016.3-B_at | 0.58466 | 0.58466041 | 6.912384 | 3E-10 | 7170.016. | NM_153649.2 | BF575596.1 | EST | 1 |
| 1052 | 4240.001.1-C_at | −0.58464 | 0.58463983 | 6.912014 | 3E-10 | 4240.001. | NM_005928.1 | BF525404.1 | EST | 1 |
| 1053 | 6288.001.1-T_at | −0.58463 | 0.58462773 | 6.911797 | 3E-10 | 6288.001. | NM_199161.1 | AX899121.1 | GENBANK_PATENT | 2 |
| 1054 | 7018.014.1-C_at | −0.58462 | 0.58461793 | 6.911621 | 3E-10 | 7018.014. | NM_001063.2 | AX147483.1 | GENBANK_PATENT | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1055 | 8404.020.1-T_at | −0.58456 | 0.58455592 | 6.910507 | 3E-10 | 8404.020. | NM_004684.2 | DA298626.1 | EST | 1 |
| 1056 | 6289.001.2-F_at | −0.58442 | 0.58441549 | 6.907986 | 3E-10 | 6289.001. | NM_030754.2 | CR744712.1 | EST | 1 |
| 1057 | 6876.011.1-F_at | −0.58434 | 0.58433766 | 6.906588 | 3E-10 | 6876.011. | NM_001001522. | AW956430.1 | EST | 1 |
| 1058 | 8404.031.1-C_at | −0.5841 | 0.58410499 | 6.902414 | 3E-10 | 8404.031. | NM_004684.2 | BP327616.1 | EST | 1 |
| 1059 | 57447.010.1-T_at | −0.58408 | 0.5840791 | 6.90195 | 3E-10 | 57447.010 | NM_201535.1 | BP349691.1 | EST | 1 |
| 1060 | 1410.007.2-C_at | −0.58404 | 0.58404076 | 6.901262 | 3E-10 | 1410.007. | NM_001885.1 | BI548180.1 | EST | 1 |
| 1061 | 59.012.2-B_at | −0.58397 | 0.58396561 | 6.899914 | 3E-10 | 59.012.2 | NM_001613.1 | AL546033.3 | EST | 1 |
| 1062 | 3459.005.1-T_at | −0.58389 | 0.58388527 | 6.898474 | 3E-10 | 3459.005. | NM_000416.1 | BP259682.1 | EST | 1 |
| 1063 | 301.013.1-C_at | −0.58378 | 0.58377547 | 6.896506 | 3E-10 | 301.013.1 | NM_000700.1 | BF130804.1 | EST | 1 |
| 1064 | 83539.001.1-D_at | −0.58353 | 0.58353306 | 6.892163 | 3E-10 | 83539.001 | NM_031422.1 | BM919514.1 | EST | 3 |
| 1065 | 6288.004.1-F_at | −0.58351 | 0.58351232 | 6.891792 | 3E-10 | 6288.004. | NM_199161.1 | BG367754.1 | EST | 1 |
| 1066 | 4781.016.1-E_at | −0.58347 | 0.58347336 | 6.891094 | 3E-10 | 4781.016. | NM_005596.1 | DA518562.1 | EST | 1 |
| 1067 | 29997.012.1-E_at | −0.58343 | 0.58343189 | 6.890351 | 3E-10 | 29997.012 | NM_015710.3 | BG746448.1 | EST | 1 |
| 1068 | 57447.021.1-T_at | −0.5834 | 0.58339709 | 6.889728 | 3E-10 | 57447.021 | NM_201535.1 | BQ954948.1 | EST | 28 |
| 1069 | 3426.002.1-C_at | −0.58304 | 0.58304119 | 6.88336 | 3E-10 | 3426.002. | NM_000204.1 | CQ718881.1 | GENBANK_PATENT | 1 |
| 1070 | 53829.001.2-T_at | −0.58296 | 0.58295977 | 6.881904 | 4E-10 | 53829.001 | NM_023914.2 | NM_176894.1 | REFSEQ | 12 |
| 1071 | 2115.001.2-B_at | −0.58274 | 0.58274226 | 6.878015 | 4E-10 | 2115.001. | NM_004956.3 | X87175.1 | mRNA | 1 |
| 1072 | 10051.008.1-T_at | −0.58274 | 0.58274024 | 6.877979 | 4E-10 | 10051.008 | NM_001002799. | DA436898.1 | EST | 1 |
| 1073 | 1033.002.1-T_at | 0.582723 | 0.58272336 | 6.877677 | 4E-10 | 1033.002. | NM_005192.2 | BG771524.1 | EST | 1 |
| 1074 | 2335.005.1-D_at | 0.582597 | 0.58259651 | 6.875411 | 4E-10 | 2335.005. | NM_212482.1 | BX417388.2 | EST | 1 |
| 1075 | 7113.009.1-T_at | −0.58253 | 0.58252547 | 6.874142 | 4E-10 | 7113.009. | NM_005656.2 | DA873416.1 | EST | 1 |
| 1076 | 3866.002.1-B_at | −0.58251 | 0.58251356 | 6.873929 | 4E-10 | 3866.002. | NM_002275.2 | BG990007.1 | EST | 1 |
| 1077 | 140885.014.1-D | −0.58226 | 0.58225938 | 6.869391 | 4E-10 | 140885.01 | NM_080792.2 | DR423079.1 | EST | 1 |
| 1078 | 7168.003.1-T_at | −0.58216 | 0.58215776 | 6.867577 | 4E-10 | 7168.003. | NM_001018020. | AK092051.1 | mRNA | 25 |
| 1079 | 79608.001.1-F_at | −0.58215 | 0.58214776 | 6.867399 | 4E-10 | 79608.001 | NM_024557.2 | CQ739424.1 | GENBANK_PATENT | 1 |
| 1080 | 79608.008.2-F_at | −0.58205 | 0.58205249 | 6.865699 | 4E-10 | 79608.008 | NM_024557.2 | DA748988.1 | EST | 2 |
| 1081 | 1410.001.1-B_at | −0.58186 | 0.58185842 | 6.862238 | 4E-10 | 1410.001. | NM_001885.1 | W40377.1 | EST | 1 |
| 1082 | 7113.010.1-T_at | −0.5816 | 0.5816021 | 6.857669 | 4E-10 | 7113.010. | NM_005656.2 | DA460061.1 | EST | 1 |
| 1083 | 4781.014.2-B_at | −0.5816 | 0.58160201 | 6.857667 | 4E-10 | 4781.014. | NM_005596.1 | DN918235.1 | EST | 1 |
| 1084 | 2335.016.1-E_at | 0.581544 | 0.58154398 | 6.856633 | 4E-10 | 2335.016. | NM_212482.1 | CQ875357.1 | GENBANK_PATENT | 281 |
| 1085 | 11065.003.1-F_at | 0.581391 | 0.58139079 | 6.853905 | 4E-10 | 11065.003 | NM_181802.1 | CS138819.1 | GENBANK_PATENT | 5 |
| 1086 | 3872.006.1-T_at | −0.58132 | 0.58131729 | 6.852596 | 4E-10 | 3872.006. | NM_000422.1 | BM017443.1 | EST | 1 |
| 1087 | 3084.005.1-F_at | −0.58129 | 0.58128817 | 6.852078 | 4E-10 | 3084.005. | NM_013957.1 | NM_013960.1 | REFSEQ | 2 |
| 1088 | 6285.003.1-E_at | −0.5812 | 0.58120469 | 6.850591 | 4E-10 | 6285.003. | NM_006272.1 | BG765453.1 | EST | 2 |
| 1089 | 6876.016.2-F_at | −0.58101 | 0.58100573 | 6.847051 | 4E-10 | 6876.016. | NM_001001522. | AB209555.1 | EST | 2 |
| 1090 | 8404.004.1-T_at | −0.58099 | 0.58098676 | 6.846714 | 4E-10 | 8404.004. | NM_004684.2 | DA589023.1 | EST | 1 |
| 1091 | 54829.001.1-F_at | 0.580792 | 0.58079186 | 6.843247 | 4E-10 | 54829.001 | NM_017680.3 | AK027359.1 | mRNA | 4 |
| 1092 | 8404.001.1-T_at | 0.58046 | 0.58046456 | 6.83743 | 4E-10 | 8404.001. | NM_004684.2 | DA132781.1 | EST | 1 |
| 1093 | 9055.011.1-E_at | 0.580443 | 0.58044278 | 6.837043 | 4E-10 | 9055.011. | NM_003681.1 | CX868839.1 | EST | 1 |
| 1094 | 6289.003.2-F_at | −0.58043 | 0.58043238 | 6.836859 | 4E-10 | 6289.003. | NM_030754.2 | R835510.1 | EST | 1 |
| 1095 | 22974.007.1-T_at | 0.580276 | 0.5802757 | 6.834076 | 4E-10 | 22974.007 | NM_122112.4 | AF287265.1 | mRNA | 213 |
| 1096 | 59.023.2-T_at | 0.58018 | 0.58017715 | 6.832326 | 4E-10 | 59.023.2 | NM_001613.1 | DB248573.1 | EST | 1 |
| 1097 | 7169.015.1-T_at | 0.58013 | 0.58013361 | 6.831554 | 4E-10 | 7169.015. | NM_213674.1 | DB291177.1 | EST | 1 |
| 1098 | 6289.002.1-F_at | −0.58009 | 0.58008892 | 6.83076 | 4E-10 | 6289.002. | NM_030754.2 | AA345111.1 | EST | 1 |
| 1099 | 4288.008.1-B_at | 0.580029 | 0.58002917 | 6.8297 | 4E-10 | 4288.008. | NM_002417.2 | BP235232.1 | EST | 1 |
| 1100 | 4781.007.1-B_at | −0.5799 | 0.57989557 | 6.82733 | 5E-10 | 4781.007. | NM_005596.1 | BP350370.1 | EST | 1 |
| 1101 | 6876.023.1-T_at | −0.57988 | 0.57988374 | 6.82712 | 5E-10 | 6876.023. | NM_001001522. | CN482091.1 | EST | 1 |
| 1102 | 9055.017.1-F_at | 0.579678 | 0.57967782 | 6.823468 | 5E-10 | 9055.017. | NM_003981.2 | DB031145.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1103 | 7170.018.2-D_at | 0.579645 | 0.5796446 | 6.822879 | 5E-10 | 7170.018. | NM_153649.2 | DB037267.1 | EST | 1 |
| 1104 | 4781.014.2-D_at | -0.57948 | 0.57948256 | 6.820008 | 5E-10 | 4781.014. | NM_005596.1 | DN918235.1 | EST | 1 |
| 1105 | 7170.025.1-T_at | -0.579385 | 0.5793851 | 6.818281 | 5E-10 | 7170.025. | NM_153649.2 | BE208737.1 | EST | 1 |
| 1106 | 7018.025.1-B_at | -0.57934 | 0.57934031 | 6.817488 | 5E-10 | 7018.025. | NM_001063.2 | BE971065.1 | EST | 1 |
| 1107 | 10253.003.1-T_at | -0.57928 | 0.5792786 | 6.816395 | 5E-10 | 10253.003 | NM_005842.2 | DA345721.1 | EST | 1 |
| 1108 | 57447.039.1-D_at | -0.57924 | 0.57923531 | 6.815628 | 5E-10 | 57447.039 | NM_201535.1 | DA356658.1 | EST | 1 |
| 1109 | 59.022.1-T_at | -0.5792 | 0.57920027 | 6.815007 | 5E-10 | 59.022.1 | NM_001613.1 | BQ881176.1 | EST | 6 |
| 1110 | 2982.015.1-F_at | -0.57917 | 0.57917337 | 6.814531 | 5E-10 | 2982.015. | NM_000856.2 | CB049566.1 | EST | 1 |
| 1111 | 10124.004.2-F_at | -0.57893 | 0.57892871 | 6.810201 | 5E-10 | 10124.004 | NM_001037164. | BU661374.1 | EST | 12 |
| 1112 | 6289.001.1-B_at | -0.57871 | 0.57871022 | 6.806336 | 5E-10 | 6289.001. | NM_030754.2 | CR744712.1 | EST | 1 |
| 1113 | 7091.005.1-F_at | -0.57865 | 0.57864807 | 6.805237 | 5E-10 | 7091.005. | NM_007005.3 | BC059405.1 | mRNA | 1 |
| 1114 | 501.006.1-B_at | -0.57847 | 0.57847445 | 6.802168 | 5E-10 | 501.006.1 | NM_001182.2 | AI142140.1 | EST | 1 |
| 1115 | 1410.001.1-C_at | -0.57836 | 0.57835697 | 6.800092 | 5E-10 | 1410.001. | NM_001885.1 | W40377.1 | EST | 1 |
| 1116 | 57447.021.1-C_at | -0.57826 | 0.57825824 | 6.798348 | 5E-10 | 57447.021 | NM_201535.1 | BQ954948.1 | EST | 28 |
| 1117 | 244.012.1-B_at | -0.57821 | 0.57821349 | 6.797558 | 5E-10 | 244.012.1 | NM_001630.1 | DA445163.1 | EST | 1 |
| 1118 | 7018.026.1-F_at | -0.57794 | 0.57793533 | 6.792647 | 5E-10 | 7018.026. | NM_001063.2 | BM690655.1 | EST | 1 |
| 1119 | 3872.018.1-T_at | -0.57791 | 0.57790767 | 6.792159 | 5E-10 | 3872.018. | NM_000422.1 | BP226405.1 | EST | 1 |
| 1120 | 10144.017.3-T_at | -0.57781 | 0.57781025 | 6.79044 | 5E-10 | 10144.017 | NM_014883.2 | AX747234.1 | GENBANK_PATENT | 1 |
| 1121 | 11197.001.1-F_at | -0.57764 | 0.57763981 | 6.787434 | 5E-10 | 11197.001 | NM_007191.2 | W37154.1 | EST | 1 |
| 1122 | 29127.007.1-B_at | -0.577519 | 0.57751875 | 6.785299 | 6E-10 | 29127.007 | NM_013277.2 | DA362566.1 | EST | 1 |
| 1123 | 10010.004.1-F_at | -0.57745 | 0.57744716 | 6.784037 | 6E-10 | 10010.004 | NM_004180.2 | BM750784.1 | EST | 1 |
| 1124 | 81704.013.1-C_at | -0.57744 | 0.57744059 | 6.783922 | 6E-10 | 81704.013 | NM_203447.1 | CQ723361.1 | GENBANK_PATENT | 1 |
| 1125 | 4781.006.2-B_at | -0.57742 | 0.57742143 | 6.783584 | 6E-10 | 4781.006. | NM_005596.1 | AK131233.1 | mRNA | 2 |
| 1126 | 7373.003.1-F_at | -0.57736 | 0.57736415 | 6.782575 | 6E-10 | 7373.003. | NM_021110.1 | CQ716670.1 | GENBANK_PATENT | 1 |
| 1127 | 8404.009.1-D_at | -0.57736 | 0.57735822 | 6.78247 | 6E-10 | 8404.009. | NM_004684.2 | BP258993.1 | EST | 1 |
| 1128 | 23092.004.1-D_at | -0.57727 | 0.5772653 | 6.780833 | 6E-10 | 23092.004 | NM_015071.2 | DA211853.1 | EST | 1 |
| 1129 | 2335.002.1-F_at | 0.577229 | 0.57722889 | 6.780192 | 6E-10 | 2335.002. | NM_212482.1 | AU118498.1 | EST | 26 |
| 1130 | 8404.031.1-F_at | -0.5772 | 0.57720205 | 6.779719 | 6E-10 | 8404.031. | NM_004684.2 | BP327616.1 | EST | 1 |
| 1131 | 6304.006.2-T_at | -0.57715 | 0.57714631 | 6.778737 | 6E-10 | 6304.006. | NM_002971.2 | BI462843.1 | EST | 1 |
| 1132 | 1410.008.1-F_at | -0.57711 | 0.57710598 | 6.778027 | 6E-10 | 1410.008. | NM_001885.1 | R68496.1 | EST | 1 |
| 1133 | 9055.019.1-F_at | -0.57707 | 0.57707199 | 6.777428 | 6E-10 | 9055.019. | NM_003981.2 | AL079833.1 | EST | 1 |
| 1134 | 1398.001.1-D_at | -0.5772 | 0.577042 | 6.7769 | 6E-10 | 1398.001. | NM_016823.2 | BE898353.1 | EST | 1 |
| 1135 | 57447.051.1-E_at | -0.57704 | 0.57703991 | 6.776863 | 6E-10 | 57447.051 | NM_201535.1 | BX460053.2 | EST | 5 |
| 1136 | 339965.001.2-B | -0.57702 | 0.57701808 | 6.776479 | 6E-10 | 339965.00 | NM_178555.2 | BC086869.1 | mRNA | 1 |
| 1137 | 7113.001.1-C_at | -0.57697 | 0.57697321 | 6.775689 | 6E-10 | 7113.001. | NM_005656.2 | CQ976407.1 | GENBANK_PATENT | 2 |
| 1138 | 4240.009.1-D_at | -0.57692 | 0.57692271 | 6.7748 | 6E-10 | 4240.009. | NM_005928.1 | BG829936.1 | EST | 114 |
| 1139 | 7153.002.4-B_at | -0.576735 | 0.57673523 | 6.771501 | 6E-10 | 7153.002. | NM_001067.2 | CQ735949.1 | GENBANK_PATENT | 1 |
| 1140 | 7169.004.1-D_at | -0.57658 | 0.57658017 | 6.768774 | 6E-10 | 7169.004. | NM_213674.1 | BG027526.1 | EST | 1 |
| 1141 | 1410.001.1-D_at | -0.57648 | 0.57647869 | 6.766989 | 6E-10 | 1410.001. | NM_001885.1 | W40377.1 | EST | 1 |
| 1142 | 59.015.2-B_at | -0.57634 | 0.57634377 | 6.764618 | 6E-10 | 59.015.2 | NM_001613.1 | BP372009.1 | EST | 1 |
| 1143 | 4833.010.1-T_at | 0.576197 | 0.57619729 | 6.762044 | 6E-10 | 4833.010. | NM_005009.2 | BU532120.1 | EST | 1 |
| 1144 | 7169.022.1-B_at | -0.57611 | 0.57611084 | 6.760525 | 6E-10 | 7169.022. | NM_213674.1 | BG385598.1 | EST | 1 |
| 1145 | 11065.005.1-T_at | 0.576067 | 0.57606684 | 6.759752 | 6E-10 | 11065.005 | NM_181802.1 | CS138820.1 | GENBANK_PATENT | 2 |
| 1146 | 7170.018.2-T_at | -0.575994 | 0.57599361 | 6.758466 | 6E-10 | 7170.018. | NM_153649.2 | DB037267.1 | EST | 1 |
| 1147 | 79971.013.2-F_at | -0.57599 | 0.57598932 | 6.758391 | 6E-10 | 79971.013 | NM_001002292. | DA878291.1 | EST | 1 |
| 1148 | 152015.005.2-F | -0.5759 | 0.57589713 | 6.756772 | 6E-10 | 152015.00 | NM_001012337. | CQ732372.1 | GENBANK_PATENT | 1 |
| 1149 | 4288.005.1-D_at | 0.577849 | 0.57584855 | 6.75592 | 6E-10 | 4288.005. | NM_002417.2 | BM455229.1 | EST | 1 |
| 1150 | 8404.002.1-T_at | -0.57584 | 0.57584028 | 6.755774 | 6E-10 | 8404.002. | NM_004684.2 | BP383384.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1151 | 6441.004.1-E_at | −0.57578 | 0.5757767 | 6.754659 | 6E−10 | 6441.004. | NM_003019.4 | BG542824.1 | EST | 1 |
| 1152 | 6122.046.1-B_at | −0.57577 | 0.57577128 | 6.754563 | 6E−10 | 6122.046. | NM_000967.3 | BM019962.1 | EST | 1 |
| 1153 | 115908.002.1-T | 0.575641 | 0.57564097 | 6.752277 | 6E−10 | 115908.00 | NM_138455.2 | AF395488.1 | mRNA | 1 |
| 1154 | 9481.001.1-F_at | −0.57564 | 0.5756408 | 6.752274 | 6E−10 | 9481.001. | NM_004277.2 | BC033091.1 | mRNA | 2 |
| 1155 | 8404.008.1-T_at | −0.57561 | 0.57561259 | 6.751779 | 6E−10 | 8404.008. | NM_004684.2 | DA342341.1 | EST | 1 |
| 1156 | 1410.007.1-D_at | −0.57559 | 0.57559279 | 6.751432 | 6E−10 | 1410.007. | NM_001885.1 | BI548180.1 | EST | 1 |
| 1157 | 8404.030.1-C_at | −0.57555 | 0.57554678 | 6.750625 | 6E−10 | 8404.030. | NM_004684.2 | CD357736.1 | EST | 1 |
| 1158 | 57447.039.1-T_at | −0.57552 | 0.57551972 | 6.75015 | 6E−10 | 57447.039 | NM_201535.1 | DA356658.1 | EST | 1 |
| 1159 | 4147.004.1-E_at | −0.57546 | 0.57545554 | 6.749025 | 7E−10 | 4147.004. | NM_002380.3 | AX675291.1 | GENBANK_PATENT | 1 |
| 1160 | 2335.024.2-F_at | 0.575372 | 0.57537228 | 6.747565 | 7E−10 | 2335.024. | NM_212482.1 | CQ731573.1 | GENBANK_PATENT | 1 |
| 1161 | 891.007.1-F_at | 0.575369 | 0.57536931 | 6.747513 | 7E−10 | 891.007.1 | NM_031966.2 | BT020128.1 | mRNA | 1 |
| 1162 | 2335.002.1-T_at | 0.575308 | 0.57530785 | 6.746436 | 7E−10 | 2335.002. | NM_212482.1 | AU118498.1 | EST | 26 |
| 1163 | 8404.017.1-T_at | −0.57528 | 0.5752762 | 6.745881 | 7E−10 | 8404.017. | NM_004684.2 | CD001002.1 | EST | 1 |
| 1164 | 57451.004.1-B_at | −0.57522 | 0.57521923 | 6.744883 | 7E−10 | 57451.004 | XM_931456.1 | AK056053.1 | mRNA | 5 |
| 1165 | 8404.001.1-F_at | −0.57518 | 0.57517525 | 6.744112 | 7E−10 | 8404.001. | NM_004684.2 | DA132781.1 | EST | 1 |
| 1166 | 8626.006.2-B_at | −0.57508 | 0.57507892 | 6.742424 | 7E−10 | 8626.006. | NM_003722.3 | CB049427.1 | EST | 1 |
| 1167 | 2335.025.1-T_at | 0.575019 | 0.5750189 | 6.741373 | 7E−10 | 2335.025. | NM_212482.1 | CQ715726.1 | GENBANK_PATENT | 3 |
| 1168 | 6286.001.1-T_at | 0.574986 | 0.57498586 | 6.740794 | 7E−10 | 6286.001. | NM_005980.2 | BM850288.1 | EST | 1 |
| 1169 | 10580.012.1-C_at | 0.57498 | 0.57497814 | 6.740659 | 7E−10 | 10580.012 | NM_015385.2 | AX879149.1 | GENBANK_PATENT | 1 |
| 1170 | 23321.014.1-T_at | 0.57485 | 0.57484627 | 6.73835 | 7E−10 | 23321.014 | NM_015271.2 | CQ723480.1 | GENBANK_PATENT | 1 |
| 1171 | 2824.001.2-B_at | 0.57481 | 0.57480725 | 6.737667 | 7E−10 | 2824.001. | NM_001001994. | CQ717842.1 | GENBANK_PATENT | 1 |
| 1172 | 29127.022.1-T_at | 0.574796 | 0.57479644 | 6.737478 | 7E−10 | 29127.022 | NM_013277.2 | DB065206.1 | EST | 1 |
| 1173 | 6289.003.1-F_at | 0.57455 | 0.57455392 | 6.733234 | 7E−10 | 6289.003. | NM_030754.2 | R83510.1 | EST | 1 |
| 1174 | 7170.005.2-B_at | 0.574471 | 0.57447114 | 6.731785 | 7E−10 | 7170.005. | NM_153649.2 | DA762962.1 | EST | 1 |
| 1175 | 54443.011.1-F_at | 0.574461 | 0.57446085 | 6.731605 | 7E−10 | 54443.011 | NM_018685.2 | DA244113.1 | EST | 1 |
| 1176 | 29127.019.1-T_at | 0.574322 | 0.57432168 | 6.729172 | 7E−10 | 29127.019 | NM_013277.2 | DA779708.1 | EST | 1 |
| 1177 | 6288.004.1-T_at | 0.57432 | 0.57432014 | 6.729145 | 7E−10 | 6288.004. | NM_199161.1 | BG567754.1 | EST | 3 |
| 1178 | 29997.008.1-C_at | 0.57411 | 0.57411065 | 6.725483 | 7E−10 | 29997.008 | NM_015710.3 | BI871613.1 | EST | 1 |
| 1179 | 57447.039.1-B_at | −0.57407 | 0.57406597 | 6.724703 | 7E−10 | 57447.039 | NM_201535.1 | DA356658.1 | EST | 1 |
| 1180 | 3872.007.1-B_at | −0.57388 | 0.573875 | 6.721367 | 7E−10 | 3872.007. | NM_000422.1 | BU155457.1 | EST | 1 |
| 1181 | 57561.002.1-T_at | −0.57383 | 0.57383005 | 6.720582 | 7E−10 | 57561.002 | NM_020801.1 | DB094913.1 | EST | 1 |
| 1182 | 57451.002.3-B_at | 0.57383 | 0.57382775 | 6.720542 | 7E−10 | 57451.002 | XM_931456.1 | AX133821.1 | GENBANK_PATENT | 1 |
| 1183 | 5213.024.1-B_at | −0.57376 | 0.57376229 | 6.719399 | 7E−10 | 5213.024. | NM_000289.3 | CQ723196.1 | GENBANK_PATENT | 1 |
| 1184 | 2.005.1-T_at | −0.57371 | 0.57370601 | 6.718416 | 8E−10 | 2.005.1 | NM_000014.4 | BI493707.1 | EST | 1 |
| 1185 | 11065.004.1-C_at | 0.573605 | 0.57360463 | 6.716647 | 8E−10 | 11065.004 | NM_181803.1 | NM_181803.1 | REFSEQ | 3 |
| 1186 | 1410.006.1-C_at | −0.57357 | 0.57356845 | 6.716015 | 8E−10 | 1410.006. | NM_001885.1 | BF670917.1 | EST | 1 |
| 1187 | 6289.006.1-T_at | −0.57356 | 0.5735557 | 6.715793 | 8E−10 | 6289.006. | NM_030754.2 | BG618255.1 | EST | 3 |
| 1188 | 55366.001.1-T_at | −0.57354 | 0.57353923 | 6.715506 | 8E−10 | 55366.001 | NM_018490.1 | CQ722924.1 | GENBANK_PATENT | 1 |
| 1189 | 23284.007.1-F_at | −0.57343 | 0.57342883 | 6.71358 | 8E−10 | 23284.007 | NM_015236.3 | CX868514.1 | EST | 1 |
| 1190 | 79971.009.1-T_at | −0.57327 | 0.573273 | 6.710862 | 8E−10 | 79971.009 | NM_001002292. | DA264864.1 | EST | 3 |
| 1191 | 6288.004.1-E_at | 0.57316 | 0.57316396 | 6.708961 | 8E−10 | 6288.004. | NM_199161.1 | BG567754.1 | EST | 3 |
| 1192 | 11065.004.1-T_at | 0.573162 | 0.57316172 | 6.708922 | 8E−10 | 11065.004 | NM_181802.1 | NM_181803.1 | REFSEQ | 3 |
| 1193 | 51203.009.1-T_at | −0.57286 | 0.57286422 | 6.703738 | 8E−10 | 51203.009 | NM_016359.2 | AV714397.1 | EST | 1 |
| 1194 | 1410.010.1-E_at | −0.57282 | 0.57282236 | 6.703009 | 8E−10 | 1410.010. | NM_001885.1 | AJ710474.1 | EST | 2 |
| 1195 | 57447.030.1-D_at | −0.57277 | 0.57277435 | 6.702173 | 8E−10 | 57447.030 | NM_201535.1 | BM783465.1 | EST | 5 |
| 1196 | 1308.002.1-T_at | −0.57253 | 0.57252742 | 6.697874 | 8E−10 | 1308.002. | NM_130778.1 | BX117940.1 | EST | 2 |
| 1197 | 4288.007.1-C_at | 0.572423 | 0.57242333 | 6.696062 | 8E−10 | 4288.007. | NM_002417.2 | BE840921.1 | EST | 1 |
| 1198 | 244.011.1-T_at | −0.5724 | 0.57240479 | 6.69574 | 8E−10 | 244.011.1 | NM_001630.1 | BX399166.2 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1199 | 94274.003.1-B_at | −0.57238 | 0.57238283 | 6.695358 | 8E-10 | 94274.003 | NM_033256.1 | AB056509.1 | mRNA | 1 |
| 1200 | 3178.003.1-E_at | −0.57235 | 0.5723545 | 6.694865 | 8E-10 | 3178.003. | NM_031157.2 | DA761057.1 | EST | 1 |
| 1201 | 7153.002.4-T_at | 0.572294 | 0.57229362 | 6.693806 | 8E-10 | 7153.002. | NM_001067.2 | CQ735949.1 | GENBANK_PATENT | 114 |
| 1202 | 9055.012.1-D_at | 0.57223 | 0.57222967 | 6.692694 | 8E-10 | 9055.012. | NM_003981.2 | BE298728.1 | EST | 1 |
| 1203 | 9232.001.1-F_at | 0.572158 | 0.57215824 | 6.691452 | 8E-10 | 9232.001. | NM_004219.2 | CN285866.1 | EST | 1 |
| 1204 | 79068.011.2-B_at | −0.57201 | 0.57200741 | 6.68883 | 9E-10 | 79068.011 | XM_051200.8 | CQ733443.1 | GENBANK_PATENT | 1 |
| 1205 | 120.005.2-F_at | −0.57195 | 0.57194991 | 6.687831 | 9E-10 | 120.005.2 | NM_019903.3 | AK223270.1 | mRNA | 78 |
| 1206 | 7534.001.1-C_at | −0.571947 | 0.57194717 | 6.687783 | 9E-10 | 7534.001. | NM_003406.2 | CB051503.1 | EST | 1 |
| 1207 | 120.005.2-T_at | −0.57189 | 0.57188711 | 6.686739 | 9E-10 | 120.005.2 | NM_019903.3 | AK223270.1 | mRNA | 78 |
| 1208 | 7373.003.3-C_at | −0.57177 | 0.57177348 | 6.684765 | 9E-10 | 7373.003. | NM_021170.1 | CQ716670.1 | GENBANK_PATENT | 1 |
| 1209 | 57447.004.2-D_at | −0.57171 | 0.57171371 | 6.683727 | 9E-10 | 57447.004 | NM_201535.1 | CD515320.1 | EST | 2 |
| 1210 | 2568.005.1-F_at | −0.57162 | 0.57161693 | 6.682047 | 9E-10 | 2568.005. | NM_014211.1 | AK055205.1 | mRNA | 11 |
| 1211 | 1308.001.1-E_at | −0.57152 | 0.5715167 | 6.680307 | 9E-10 | 1308.001. | NM_130778.1 | BM773425.1 | EST | 1 |
| 1212 | 6876.020.1-F_at | −0.57133 | 0.5713288 | 6.677046 | 9E-10 | 6876.020. | NM_001001522. | BM921237.1 | EST | 1 |
| 1213 | 79971.014.1-D_at | −0.57124 | 0.57124451 | 6.675583 | 9E-10 | 79971.014 | NM_001002292. | DA776805.1 | EST | 1 |
| 1214 | 5621.008.1-D_at | −0.57121 | 0.57120843 | 6.674957 | 9E-10 | 5621.008. | NM_000311.2 | DA648110.1 | EST | 1 |
| 1215 | 55732.003.2-T_at | 0.571055 | 0.57105463 | 6.67229 | 9E-10 | 55732.003 | NM_018186.2 | DA733233.1 | EST | 2 |
| 1216 | 221120.006.1-D | −0.57094 | 0.57093826 | 6.670273 | 9E-10 | 221120.00 | NM_139178.1 | BE892721.1 | EST | 1 |
| 1217 | 23266.008.1-T_at | −0.57077 | 0.57076776 | 6.667318 | 9E-10 | 23266.008 | NM_012302.2 | CQ799210.1 | GENBANK_PATENT | 1 |
| 1218 | 2335.045.1-F_at | 0.570754 | 0.57075398 | 6.66708 | 1E-09 | 2335.045. | NM_212482.1 | DA989523.1 | EST | 1 |
| 1219 | 7170.007.1-F_at | 0.570733 | 0.57073264 | 6.66671 | 1E-09 | 7170.007. | NM_153649.2 | DA684242.1 | EST | 1 |
| 1220 | 10461.002.1-B_at | −0.57071 | 0.57071065 | 6.666329 | 1E-09 | 10461.002 | NM_006343.2 | CQ725500.1 | GENBANK_PATENT | 1 |
| 1221 | 59.031.2-F_at | −0.57071 | 0.57070847 | 6.666291 | 1E-09 | 59.031.2 | NM_001613.2 | BG197213.1 | EST | 19 |
| 1222 | 9055.010.1-T_at | 0.570674 | 0.5706743 | 6.665699 | 1E-09 | 9055.010. | NM_003981.2 | BU164001.1 | EST | 1 |
| 1223 | 58499.005.2-F_at | 0.5706 | 0.5706034 | 6.664471 | 1E-09 | 58499.005 | NM_021224.3 | BI461756.1 | EST | 1 |
| 1224 | 54443.006.2-F_at | 0.570459 | 0.57045888 | 6.661969 | 1E-09 | 54443.006 | NM_018685.2 | CQ716589.1 | GENBANK_PATENT | 1 |
| 1225 | 59.016.1-B_at | −0.57036 | 0.57035643 | 6.660196 | 1E-09 | 59.016.1 | — | — | — | |
| 1226 | 4288.004.1-C_at | 0.570301 | 0.5703013 | 6.659241 | 1E-09 | 4288.004. | NM_002417.2 | BP232141.1 | EST | 1 |
| 1227 | 7170.014.1-C_at | 0.570269 | 0.57026859 | 6.658675 | 1E-09 | 7170.014. | NM_153649.2 | DA690776.1 | EST | 1 |
| 1228 | 7170.007.1-D_at | 0.570241 | 0.57024107 | 6.658199 | 1E-09 | 7170.007. | NM_153649.2 | DA684242.1 | EST | 1 |
| 1229 | 244.004.2-B_at | 0.56972 | 0.56971798 | 6.649154 | 1E-09 | 244.004.2 | NM_001630.1 | CB115047.1 | EST | 1 |
| 1230 | 59.015.2-D_at | 0.56961 | 0.56961045 | 6.647297 | 1E-09 | 59.015.2 | NM_001613.1 | BP372009.1 | EST | 1 |
| 1231 | 2327.002.1-B_at | −0.56956 | 0.56955941 | 6.646415 | 1E-09 | 2327.002. | NM_001460.2 | CD684429.1 | EST | 1 |
| 1232 | 79068.011.2-C_at | −0.56954 | 0.5695389 | 6.646061 | 1E-09 | 79068.011 | XM_051200.8 | CQ733443.1 | GENBANK_PATENT | 1 |
| 1233 | 23266.006.1-T_at | −0.56936 | 0.56936191 | 6.643005 | 1E-09 | 23266.006 | NM_012302.2 | DR005890.1 | EST | 1 |
| 1234 | 4288.007.1-B_at | 0.56932 | 0.56931985 | 6.642278 | 1E-09 | 4288.007. | NM_002417.2 | BE840921.1 | EST | 1 |
| 1235 | 301.008.1-T_at | 0.5693 | 0.56929536 | 6.641856 | 1E-09 | 301.008.1 | NM_000700.1 | CD68703.1 | EST | 1 |
| 1236 | 5156.003.1-T_at | 0.56918 | 0.56918229 | 6.639904 | 1E-09 | 5156.003. | NM_006206.3 | BP321319.1 | EST | 1 |
| 1237 | 4781.001.1-F_at | 0.56917 | 0.56917015 | 6.639695 | 1E-09 | 4781.001. | NM_005596.1 | BF541662.1 | EST | 1 |
| 1238 | 4281.016.1-E_at | 0.56916 | 0.56915511 | 6.639435 | 1E-09 | 4281.016. | NM_033290.1 | AY540010.1 | mRNA | 1 |
| 1239 | 72.004.1-T_at | 0.5691 | 0.56910279 | 6.638533 | 1E-09 | 72.004.1 | NM_001615.3 | BF680547.1 | EST | 1 |
| 1240 | 57447.029.1-B_at | −0.56896 | 0.56895732 | 6.636023 | 1E-09 | 57447.029 | NM_201535.1 | BX354120.2 | EST | 6 |
| 1241 | 79971.006.2-T_at | −0.56871 | 0.56870809 | 6.631726 | 1E-09 | 79971.006 | NM_001002292. | DA048370.1 | EST | 1 |
| 1242 | 2327.003.2-F_at | −0.56867 | 0.56866928 | 6.631058 | 1E-09 | 2327.003. | NM_001460.2 | AI223310.1 | EST | 1 |
| 1243 | 166824.001.2-F | −0.56859 | 0.56858745 | 6.629647 | 1E-09 | 166824.00 | NM_201431.1 | CQ492114.1 | GENBANK_PATENT | 4 |
| 1244 | 29997.010.1-F_at | −0.56857 | 0.56856635 | 6.629284 | 1E-09 | 29997.010 | NM_015710.3 | BG120545.1 | EST | 1 |
| 1245 | 57447.024.1-C_at | −0.56853 | 0.56852805 | 6.628624 | 1E-09 | 57447.024 | NM_201535.1 | DA566498.1 | EST | 1 |
| 1246 | 4781.007.1-F_at | −0.56839 | 0.56838621 | 6.626181 | 1E-09 | 4781.007. | NM_005596.1 | BP350370.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1247 | 4306.001.1-C_at | −0.5682 | 0.56819649 | 6.622914 | 1E−09 | 4306.001. | NM_000901.1 | AJ315514.1 | mRNA | 5 |
| 1248 | 137682.002.2-T | 0.568182 | 0.56818211 | 6.622667 | 1E−09 | 137682.00 | NM_152416.1 | BX375940.2 | EST | 1 |
| 1249 | 24137.002.1-F_at | 0.568153 | 0.56815265 | 6.62216 | 1E−09 | 24137.002 | NM_012310.2 | BC050548.1 | mRNA | 1 |
| 1250 | 79971.006.1-T_at | −0.56815 | 0.5681458 | 6.622042 | 1E−09 | 79971.006 | NM_001002292. | DA048370.1 | EST | 3 |
| 1251 | 7168.004.1-F_at | −0.56797 | 0.56796804 | 6.618983 | 1E−09 | 7168.004. | NM_001018020. | BX438993.2 | EST | 1 |
| 1252 | 79068.011.1-T_at | −0.56789 | 0.56788757 | 6.617599 | 1E−09 | 79068.011 | XM_051200.8 | CQ733443.1 | GENBANK_PATENT | 1 |
| 1253 | 4781.009.1-T_at | −0.56772 | 0.56772333 | 6.614775 | 1E−09 | 4781.009. | NM_005596.1 | CQ732556.1 | GENBANK_PATENT | 1 |
| 1254 | 5608.003.1-T_at | −0.56753 | 0.56752894 | 6.611433 | 1E−09 | 5608.003. | NM_002758.2 | BP220368.1 | EST | 1 |
| 1255 | 9055.014.1-D_at | −0.56752 | 0.56752001 | 6.61128 | 1E−09 | 9055.014. | NM_003981.2 | BE300335.1 | EST | 1 |
| 1256 | 5156.009.1-F_at | −0.56751 | 0.56750707 | 6.611058 | 1E−09 | 5156.009. | NM_006206.3 | L25829.1 | mRNA | 3 |
| 1257 | 9055.018.2-F_at | 0.567502 | 0.56750204 | 6.610971 | 1E−09 | 9055.018. | NM_003981.2 | DA033856.1 | EST | 1 |
| 1258 | 92241.002.1-D_at | −0.5675 | 0.56749779 | 6.610898 | 1E−09 | 92241.002 | NM_052862.2 | CQ730679.1 | GENBANK_PATENT | 5 |
| 1259 | 5010.007.1-B_at | −0.56735 | 0.56734864 | 6.608336 | 1E−09 | 5010.007. | NM_005602.4 | BQ067107.1 | EST | 1 |
| 1260 | 25862.005.1-E_at | 0.567345 | 0.56734544 | 6.608281 | 1E−09 | 25862.005 | NM_212482.1 | AJ320525.1 | mRNA | 1 |
| 1261 | 7113.006.1-E_at | −0.56728 | 0.56728076 | 6.60717 | 1E−09 | 7113.006. | NM_005656.2 | DA874671.1 | EST | 1 |
| 1262 | 1756.024.1-B_at | −0.56726 | 0.5672562 | 6.606748 | 1E−09 | 1756.024. | NM_000109.2 | CD299688.1 | EST | 1 |
| 1263 | 79971.008.2-T_at | −0.56716 | 0.56716259 | 6.605141 | 1E−09 | 79971.008 | NM_001002292. | DA711278.1 | EST | 1 |
| 1264 | 7169.001.1-F_at | −0.56705 | 0.56704888 | 6.603189 | 1E−09 | 7169.001. | NM_213674.1 | BM809268.1 | EST | 4 |
| 1265 | 2.022.1-D_at | −0.56703 | 0.56702777 | 6.602826 | 1E−09 | 2.022.1 | NM_000014.4 | BP343424.1 | EST | 1 |
| 1266 | 6876.020.1-D_at | −0.56697 | 0.56697169 | 6.601864 | 1E−09 | 6876.020. | NM_001001522. | BM921237.1 | EST | 1 |
| 1267 | 301.011.1-T_at | −0.56692 | 0.56691975 | 6.600973 | 1E−09 | 301.011.1 | NM_000700.1 | BG435248.1 | EST | 5 |
| 1268 | 25862.005.1-E_at | −0.56682 | 0.5668213 | 6.599284 | 1E−09 | 25862.005 | NM_018561.3 | DR003626.1 | EST | 1 |
| 1269 | 7170.047.2-D_at | 0.566775 | 0.56677489 | 6.598488 | 1E−09 | 7170.047. | NM_153649.2 | BF693459.1 | EST | 1 |
| 1270 | 4281.0101.1-T_at | −0.56677 | 0.56677057 | 6.598413 | 1E−09 | 4281.010. | NM_033290.1 | AY540016.1 | mRNA | 5 |
| 1271 | 57447.020.1-T_at | −0.56666 | 0.56665556 | 6.596441 | 1E−09 | 57447.020 | NM_201535.1 | BX461883.2 | EST | 1 |
| 1272 | 7170.035.2-D_at | 0.566638 | 0.5666377 | 6.596136 | 1E−09 | 7170.035. | NM_153649.2 | BF575164.1 | EST | 1 |
| 1273 | 10124.005.1-T_at | −0.56646 | 0.56645955 | 6.593081 | 1E−09 | 10124.005 | NM_001037164. | BU661565.1 | EST | 1 |
| 1274 | 9055.018.1-C_at | 0.566425 | 0.56642488 | 6.592487 | 1E−09 | 9055.018. | NM_003981.2 | DA033856.1 | EST | 1 |
| 1275 | 59.038.1-T_at | −0.56631 | 0.5663098 | 6.590515 | 1E−09 | 59.038.1 | NM_001613.1 | EH_001613.2 | PREDICTED | 1 |
| 1276 | 4288.009.1-B_at | 0.566296 | 0.56629606 | 6.59028 | 1E−09 | 4288.009. | NM_002417.2 | BG106198.1 | EST | 1 |
| 1277 | 57561.004.1-E_at | −0.5662 | 0.56620405 | 6.588704 | 1E−09 | 57561.004 | NM_020801.1 | DB046772.1 | EST | 1 |
| 1278 | 2568.003.2-B_at | −0.56616 | 0.56615719 | 6.587901 | 1E−09 | 2568.003. | NM_014211.1 | CD696885.1 | EST | 1 |
| 1279 | 55713.004.1-T_at | −0.56607 | 0.56607498 | 6.586493 | 1E−09 | 55713.004 | NM_018102.3 | AL833936.1 | mRNA | 1 |
| 1280 | 2335.026.3-F_at | 0.565913 | 0.56591326 | 6.583725 | 1E−09 | 2335.026. | NM_212482.1 | BX641150.1 | mRNA | 43 |
| 1281 | 7168.010.1-C_at | −0.56585 | 0.56585375 | 6.582706 | 1E−09 | 7168.010. | NM_001018020. | CD556048.1 | EST | 1 |
| 1282 | 1959.002.1-T_at | −0.56583 | 0.56583226 | 6.582339 | 1E−09 | 1959.002. | NM_000399.2 | DB264199.1 | EST | 5 |
| 1283 | 259266.002.2-F | 0.565786 | 0.56578622 | 6.581551 | 1E−09 | 259266.00 | NM_018136.2 | CQ729660.1 | GENBANK_PATENT | 1 |
| 1284 | 57447.010.3-C_at | −0.56578 | 0.56578285 | 6.581493 | 1E−09 | 57447.010 | NM_201535.1 | BP349691.1 | EST | 1 |
| 1285 | 59.026.2-D_at | −0.56573 | 0.56573398 | 6.580657 | 1E−09 | 59.026.2 | — | — | — | |
| 1286 | 5156.002.1-B_at | −0.56572 | 0.56571946 | 6.580409 | 1E−09 | 5156.002. | NM_006206.3 | DB259428.1 | EST | 1 |
| 1287 | 10124.003.1-F_at | −0.56572 | 0.56571682 | 6.580364 | 1E−09 | 10124.003 | NM_001037164. | BU664973.1 | EST | 1 |
| 1288 | 4240.007.1-T_at | −0.56557 | 0.56556799 | 6.577818 | 1E−09 | 4240.007. | NM_005928.1 | CN485231.1 | EST | 1 |
| 1289 | 4931.007.1-F_at | 0.565418 | 0.56541793 | 6.575252 | 1E−09 | 4931.007. | NM_002533.2 | CQ731324.1 | GENBANK_PATENT | 1 |
| 1290 | 57447.039.1-C_at | −0.5653 | 0.56530385 | 6.573303 | 1E−09 | 57447.039 | NM_201535.1 | DA356658.1 | EST | 1 |
| 1291 | 57561.001.1-T_at | −0.56529 | 0.56529076 | 6.573079 | 1E−09 | 57561.001 | NM_020801.1 | BQ428339.1 | EST | 1 |
| 1292 | 57447.002.1-D_at | −0.56527 | 0.56526525 | 6.572643 | 1E−09 | 57447.002 | NM_201535.1 | BF526188.1 | EST | 1 |
| 1293 | 4094.001. | −0.56526 | 0.56525669 | 6.572497 | 1E−09 | 4094.001. | NM_001031804. | NM_005360.3 | REFSEQ | 17 |
| 1294 | 59.041.2-T_at | −0.56524 | 0.56524383 | 6.572277 | 1E−09 | 59.041.2 | NM_001613.1 | AL540709.3 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1295 | 137682.004.2-T | 0.565172 | 0.56517245 | 6.571058 | 1E-09 | 137682.00 | NM_152416.1 | BI670491.1 | EST | 1 |
| 1296 | 4931.011.2-T_at | 0.565117 | 0.56511747 | 6.570118 | 1E-09 | 4931.011. | NM_002533.2 | BU170621.1 | EST | 1 |
| 1297 | 79971.010.2-T_at | -0.56505 | 0.56505357 | 6.569027 | 1E-09 | 79971.010 | NM_001002292. | CB368343.1 | EST | 1 |
| 1298 | 29127.009.1-T_at | 0.564971 | 0.56497093 | 6.567616 | 1E-09 | 29127.009 | NM_013277.2 | BX421176.2 | EST | 1 |
| 1299 | 2770.004.1-T_at | 0.56473 | 0.56473004 | 6.563504 | 2E-09 | 2770.004. | NM_002069.4 | DA801873.1 | EST | 1 |
| 1300 | 59.015.2-F_at | -0.56468 | 0.56468244 | 6.562692 | 2E-09 | 59.015.2 | NM_001613.1 | BP372009.1 | EST | 1 |
| 1301 | 2335.032.1-B_at | 0.564674 | 0.56467386 | 6.562545 | 2E-09 | 2335.032. | NM_212482.1 | DA647475.1 | EST | 1 |
| 1302 | 1410.006.1-B_at | -0.56446 | 0.56446046 | 6.558905 | 2E-09 | 1410.006. | NM_001885.1 | BF670917.1 | EST | 1 |
| 1303 | 79971.004.1-B_at | -0.56442 | 0.56442019 | 6.558218 | 2E-09 | 79971.004 | NM_001002292. | BX648748.1 | mRNA | 2 |
| 1304 | 94274.003.1-T_at | -0.56432 | 0.56432491 | 6.556594 | 2E-09 | 94274.003 | NM_033256.1 | AB056509.1 | mRNA | 1 |
| 1305 | 2335.005.1-T_at | 0.564117 | 0.5641167 | 6.553045 | 2E-09 | 2335.005. | NM_212482.1 | BX417388.2 | EST | 3 |
| 1306 | 966.004.2-B_at | -0.56412 | 0.56411646 | 6.553041 | 2E-09 | 966.004.2 | NM_203330.1 | AU117114.1 | EST | 1 |
| 1307 | 79780.006.1-B_at | -0.56406 | 0.5640582 | 6.552049 | 2E-09 | 79780.006 | NM_024725.2 | BG570666.1 | EST | 1 |
| 1308 | 57561.003.1-T_at | -0.56392 | 0.56392094 | 6.549711 | 2E-09 | 57561.003 | NM_020801.1 | DA797962.1 | EST | 1 |
| 1309 | 9073.002.1-B_at | 0.56389 | 0.56389001 | 6.549184 | 2E-09 | 9073.002. | NM_199328.1 | BP277133.1 | EST | 1 |
| 1310 | 55656.014.2-F_at | 0.56379 | 0.56378984 | 6.547479 | 2E-09 | 55656.014 | NM_017864.2 | BF770934.1 | EST | 1 |
| 1311 | 2335.035.1-B_at | 0.563724 | 0.56372399 | 6.546357 | 2E-09 | 2335.035. | NM_212482.1 | CX755647.1 | EST | 1 |
| 1312 | 3161.005.1-T_at | 0.563648 | 0.56364847 | 6.545072 | 2E-09 | 3161.005. | NM_012484.1 | AX675838.1 | GENBANK_PATENT | 1 |
| 1313 | 57451.006.1-B_at | -0.56362 | 0.56362219 | 6.544625 | 2E-09 | 57451.006 | XM_931456.1 | AL598057.1 | EST | 1 |
| 1314 | 2568.004.1-T_at | -0.56349 | 0.56348518 | 6.542294 | 2E-09 | 2568.004. | NM_014211.1 | BP342098.1 | EST | 1 |
| 1315 | 440073.003.1-E | -0.56329 | 0.56329195 | 6.539007 | 2E-09 | 440073.00 | NM_015232.1 | BX110676.1 | EST | 1 |
| 1316 | 2335.006.1-T_at | 0.563204 | 0.56320431 | 6.537517 | 2E-09 | 2335.006. | NM_212482.1 | CX785805.1 | EST | 1 |
| 1317 | 10051.011.2-T_at | 0.563182 | 0.56318212 | 6.53714 | 2E-09 | 10051.011 | NM_001002799, | BG776861.1 | EST | 4 |
| 1318 | 55784.003.1-T_at | -0.56304 | 0.56303549 | 6.534648 | 2E-09 | 55784.003 | NM_018349.2 | BC025708.1 | mRNA | 2 |
| 1319 | 3860.010.1-T_at | -0.56302 | 0.56302355 | 6.534445 | 2E-09 | 3860.010. | NM_153490.1 | DA441591.1 | EST | 1 |
| 1320 | 5284.001.1-B_at | -0.56297 | 0.56297106 | 6.533553 | 2E-09 | 5284.001. | NM_002644.2 | AX012182.1 | GENBANK_PATENT | 1 |
| 1321 | 301.003.1-T_at | -0.56291 | 0.56291408 | 6.532585 | 2E-09 | 301.003.1 | NM_000700.1 | CB124198.1 | EST | 1 |
| 1322 | 4240.007.1-F_at | -0.5629 | 0.56290348 | 6.532405 | 2E-09 | 4240.007. | NM_005928.1 | CN485231.1 | EST | 1 |
| 1323 | 4240.007.1-B_at | -0.56283 | 0.56283211 | 6.531193 | 2E-09 | 4240.007. | NM_005928.1 | CN485231.1 | EST | 1 |
| 1324 | 4781.015.2-D_at | -0.56272 | 0.56272205 | 6.529324 | 2E-09 | 4781.015. | NM_005596.1 | DN995118.1 | EST | 1 |
| 1325 | 10124.001.1-T_at | -0.56261 | 0.56260672 | 6.527366 | 2E-09 | 10124.001 | NM_001037164. | BX354322.2 | EST | 87 |
| 1326 | 57561.004.1-T_at | 0.56258 | 0.56258399 | 6.52698 | 2E-09 | 57561.004 | NM_020801.1 | DB046772.1 | EST | 1 |
| 1327 | 29127.022.2-T_at | 0.562515 | 0.56251532 | 6.525814 | 2E-09 | 29127.022 | NM_013277.2 | DB065206.1 | EST | 1 |
| 1328 | 10461.002.2-T_at | -0.56243 | 0.56242806 | 6.524333 | 2E-09 | 10461.002 | NM_006343.2 | CQ725500.1 | GENBANK_PATENT | 1 |
| 1329 | 7168.039.1-B_at | -0.56237 | 0.56236838 | 6.523321 | 2E-09 | 7168.039. | NM_001018020. | AA096317.1 | EST | 1 |
| 1330 | 90293.004.2-T_at | 0.56231 | 0.56231454 | 6.522407 | 2E-09 | 90293.004 | NM_033495.2 | AL591986.1 | mRNA | 38 |
| 1331 | 1410.006.1-D_at | -0.56207 | 0.56206646 | 6.518201 | 2E-09 | 1410.006. | NM_001885.1 | BF670917.1 | EST | 1 |
| 1332 | 7113.010.1-E_at | -0.56205 | 0.56205065 | 6.517933 | 2E-09 | 7113.010. | NM_005656.2 | DA460061.1 | EST | 1 |
| 1333 | 8404.025.1-T_at | -0.562 | 0.56200329 | 6.51713 | 2E-09 | 8404.025. | NM_004684.2 | DB086831.1 | EST | 1 |
| 1334 | 79971.008.1-T_at | 0.56198 | 0.56198359 | 6.516796 | 2E-09 | 79971.008 | NM_001002292. | DA711278.1 | EST | 1 |
| 1335 | 4240.005.1-T_at | 0.56194 | 0.5619438 | 6.516122 | 2E-09 | 4240.005. | NM_005928.1 | BX341151.2 | EST | 1 |
| 1336 | 10051.007.1-T_at | 0.561888 | 0.56188758 | 6.515169 | 2E-09 | 10051.007 | NM_001002799. | CS161896.1 | GENBANK_PATENT | 13 |
| 1337 | 2.002.1-F_at | -0.56186 | 0.56185527 | 6.51462 | 2E-09 | 2.002.1 | NM_000014.4 | CQ672194.1 | GENBANK_PATENT | 1 |
| 1338 | 29997.021.1-E_at | -0.56185 | 0.56185259 | 6.514576 | 2E-09 | 29997.021 | NM_015710.3 | CN353870.1 | EST | 1 |
| 1339 | 1410.011.1-T_at | -0.56169 | 0.56168682 | 6.511768 | 2E-09 | 1410.011. | NM_001885.1 | BI561839.1 | EST | 1 |
| 1340 | 4601.009.2-F_at | -0.56154 | 0.5615434 | 6.509339 | 2E-09 | 4601.009. | NM_130439.3 | BE789186.1 | EST | 1 |
| 1341 | 1959.001.1-T_at | -0.56154 | 0.56153623 | 6.509218 | 2E-09 | 1959.001. | NM_000399.2 | DB086600.1 | EST | 1 |
| 1342 | 2335.026.3-T_at | 0.561472 | 0.56147179 | 6.508127 | 2E-09 | 2335.026. | NM_212482.1 | BX641150.1 | mRNA | 43 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1343 | 55107.001.1-F_at | -0.56145 | 0.56144879 | 6.507738 | 2E-09 | 55107.001 | NM_018043.4 | AY728143.1 | mRNA | 30 |
| 1344 | 1062.001.1-B_at | 0.561342 | 0.56134161 | 6.505924 | 2E-09 | 1062.001. | NM_001813.2 | CQ715352.1 | GENBANK_PATENT | 1 |
| 1345 | 6876.002.1-B_at | -0.56132 | 0.56132281 | 6.505606 | 2E-09 | 6876.002. | NM_001001522. | DB262921.1 | EST | 1 |
| 1346 | 358.018.1-D_at | -0.56116 | 0.56116002 | 6.502851 | 2E-09 | 358.018.1 | NM_198098.1 | BI765065.1 | EST | 1 |
| 1347 | 4781.004.1-F_at | -0.5611 | 0.56110421 | 6.501907 | 2E-09 | 4781.004. | NM_005596.1 | BG742798.1 | EST | 4 |
| 1348 | 8404.028.3-F_at | -0.56107 | 0.56107051 | 6.501338 | 2E-09 | 8404.028. | NM_004684.2 | CQ727530.1 | GENBANK_PATENT | 1 |
| 1349 | 11130.004.1-T_at | 0.561027 | 0.56102703 | 6.500602 | 2E-09 | 11130.004 | NM_001005414. | BQ065119.1 | EST | 1 |
| 1350 | 2568.002.2-B_at | 0.56101 | 0.56100825 | 6.500285 | 2E-09 | 2568.002. | NM_014211.1 | DB235581.1 | EST | 1 |
| 1351 | 29089.004.1-T_at | 0.560878 | 0.56087834 | 6.498089 | 2E-09 | 29089.004 | NM_014176.1 | AV727151.1 | EST | 1 |
| 1352 | 57685.005.1-B_at | -0.5608 | 0.56079992 | 6.496763 | 2E-09 | 57685.005 | NM_020925.1 | CQ721664.1 | GENBANK_PATENT | 1 |
| 1353 | 7170.016.3-T_at | 0.560753 | 0.56075324 | 6.495974 | 2E-09 | 7170.016. | NM_153649.2 | BF575596.1 | EST | 1 |
| 1354 | 10440.003.1-T_at | 0.560736 | 0.56073635 | 6.495689 | 2E-09 | 10440.003 | NM_066335.1 | BG449850.1 | EST | 1 |
| 1355 | 2335.017.1-F_at | 0.560696 | 0.56069643 | 6.495015 | 2E-09 | 2335.017. | NM_212482.1 | CQ896577.1 | GENBANK_PATENT | 4 |
| 1356 | 2.002.1-D_at | -0.56056 | 0.56056211 | 6.492745 | 2E-09 | 2.002.1 | NM_000014.4 | CQ672194.1 | GENBANK_PATENT | 1 |
| 1357 | 9055.018.1-D_at | 0.56056 | 0.56056001 | 6.49271 | 2E-09 | 9055.018. | NM_003981.2 | DA033856.1 | EST | 1 |
| 1358 | 64151.003.1-T_at | 0.56055 | 0.56055011 | 6.492543 | 2E-09 | 64151.003 | NM_022346.3 | BG202075.1 | EST | 1 |
| 1359 | 59342.002.1-B_at | 0.56049 | 0.56049557 | 6.491622 | 2E-09 | 59342.002 | NM_021626.1 | BP338281.1 | EST | 1 |
| 1360 | 7169.007.1-F_at | -0.56034 | 0.56033824 | 6.488965 | 2E-09 | 7169.007. | NM_213674.1 | BQ923578.1 | EST | 67 |
| 1361 | 7170.026.1-C_at | 0.560224 | 0.5602241 | 6.487039 | 2E-09 | 7170.026. | NM_153649.2 | BQ933569.1 | EST | 1 |
| 1362 | 667.010.1-B_at | -0.56012 | 0.56011837 | 6.485255 | 2E-09 | 667.010.1 | NM_183380.1 | DA361412.1 | EST | 1 |
| 1363 | 4781.010.1-F_at | -0.56006 | 0.56006097 | 6.484286 | 2E-09 | 4781.010. | NM_005596.1 | BX648845.1 | mRNA | 3 |
| 1364 | 10051.001.1-T_at | 0.560051 | 0.56005099 | 6.484118 | 2E-09 | 10051.001 | NM_001002799. | BC106033.1 | mRNA | 52 |
| 1365 | 7113.004.1-C_at | -0.56001 | 0.56001252 | 6.483469 | 2E-09 | 7113.004. | NM_005656.2 | CQ976405.1 | GENBANK_PATENT | 2 |
| 1366 | 140885.010.2-F | -0.55988 | 0.55988455 | 6.481311 | 2E-09 | 140885.01 | NM_080792.2 | CQ728313.1 | GENBANK_PATENT | 1 |
| 1367 | 29997.019.1-F_at | -0.55983 | 0.55982573 | 6.480319 | 2E-09 | 29997.019 | NM_015710.3 | BF771953.1 | EST | 1 |
| 1368 | 2335.013.1-T_at | -0.55975 | 0.55975189 | 6.479074 | 2E-09 | 2335.013. | NM_212482.1 | AL551632.3 | EST | 2 |
| 1369 | 7170.017.1-D_at | 0.55967 | 0.55967009 | 6.477696 | 2E-09 | 7170.017. | NM_153649.2 | BF574676.1 | EST | 1 |
| 1370 | 219972.004.1-F | -0.55958 | 0.55957847 | 6.476152 | 2E-09 | 219972.00 | XM_166227.6 | DA946058.1 | EST | 1 |
| 1371 | 22974.010.1-E_at | 0.559421 | 0.55942061 | 6.473493 | 2E-09 | 22974.010 | NM_012112.4 | DB096591.1 | EST | 1 |
| 1372 | 2982.011.1-T_at | -0.55932 | 0.55932229 | 6.471837 | 2E-09 | 2982.011. | NM_000856.2 | BX649180.1 | mRNA | 10 |
| 1373 | 152015.005.1-F | -0.55929 | 0.55929021 | 6.471297 | 2E-09 | 152015.00 | NM_001012337. | CQ732372.1 | GENBANK_PATENT | 1 |
| 1374 | 3914.001.1-C_at | -0.5592 | 0.55919902 | 6.469761 | 2E-09 | 3914.001. | NM_000228.2 | CQ921791.1 | GENBANK_PATENT | 2 |
| 1375 | 7168.012.2-B_at | -0.55912 | 0.55911961 | 6.468425 | 2E-09 | 7168.012. | NM_001018020. | AK129882.1 | mRNA | 2 |
| 1376 | 1938.024.1-C_at | -0.55904 | 0.55903817 | 6.467054 | 2E-09 | 1938.024. | NM_001961.3 | BE747136.1 | EST | 1 |
| 1377 | 10051.004.1-T_at | 0.559001 | 0.55900072 | 6.466424 | 2E-09 | 10051.004 | NM_001002799. | DB144219.1 | EST | 1 |
| 1378 | 2335.006.1-B_at | 0.55897 | 0.55897034 | 6.465913 | 2E-09 | 2335.006. | NM_212482.1 | CX785805.1 | EST | 1 |
| 1379 | 57447.028.1-E_at | -0.55892 | 0.55891938 | 6.465056 | 2E-09 | 57447.028 | NM_2015355.1 | DA205446.1 | EST | 1 |
| 1380 | 2893.001.1-T_at | 0.5589 | 0.55890095 | 6.464746 | 2E-09 | 2893.001. | NM_000829.1 | DA258118.1 | EST | 1 |
| 1381 | 4288.005.1-F_at | 0.558883 | 0.55888308 | 6.464445 | 2E-09 | 4288.005. | NM_002417.2 | BM455229.1 | EST | 1 |
| 1382 | 2938.007.1-T_at | -0.55888 | 0.55887858 | 6.464369 | 2E-09 | 2938.007. | NM_145740.2 | AX477713.1 | GENBANK_PATENT | 1 |
| 1383 | 29127.020.1-T_at | -0.55848 | 0.55884819 | 6.463858 | 2E-09 | 29127.020 | NM_013277.2 | DB089267.1 | EST | 1 |
| 1384 | 154810.002.1-T | -0.55861 | 0.55861375 | 6.459916 | 2E-09 | 154810.00 | NM_130847.1 | AX886249.1 | GENBANK_PATENT | 1 |
| 1385 | 9232.001.1-T_at | 0.558605 | 0.55860527 | 6.459774 | 2E-09 | 9232.001. | NM_004219.2 | CN285866.1 | EST | 1 |
| 1386 | 55214.004.1-T_at | -0.55803 | 0.55802814 | 6.450079 | 2E-09 | 55214.004 | NM_018192.2 | DA953365.1 | EST | 1 |
| 1387 | 79971.002.1-B_at | -0.55798 | 0.55797779 | 6.449236 | 3E-09 | 79971.002 | NM_001002292. | CQ720425.1 | GENBANK_PATENT | 1 |
| 1388 | 3977.002.1-T_at | -0.55793 | 0.55793279 | 6.448479 | 3E-09 | 3977.002. | NM_002310.3 | DR005799.1 | EST | 1 |
| 1389 | 7170.028.1-F_at | 0.557857 | 0.5578569 | 6.447206 | 3E-09 | 7170.028. | NM_153649.2 | BQ220396.1 | EST | 2 |
| 1390 | 1410.009.1-E_at | -0.55785 | 0.55784993 | 6.447089 | 3E-09 | 1410.009. | NM_001885.1 | BQ437433.1 | EST | 2 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1391 | 4781.004.1-T_at | -0.55762 | 0.55762387 | 6.443297 | 3E-09 | 4781.004. | NM_005596.1 | BG742798.1 | EST | 4 |
| 1392 | 9413.002.2-T_at | -0.55755 | 0.5575481 | 6.442026 | 3E-09 | 9413.002. | NM_004816.2 | AW779892.1 | EST | 1 |
| 1393 | 25925.005.1-T_at | -0.55744 | 0.55744483 | 6.440295 | 3E-09 | 25925.005 | NM_015461.1 | DB285938.1 | EST | 1 |
| 1394 | 55366.002.1-T_at | -0.55743 | 0.55743398 | 6.440113 | 3E-09 | 55366.002 | NM_018490.1 | BC033039.2 | mRNA | 3 |
| 1395 | 6288.001.1-F_at | -0.55742 | 0.55742086 | 6.439893 | 3E-09 | 6288.001. | NM_199161.1 | AX899121.1 | GENBANK_PATENT | 2 |
| 1396 | 2335.025.2-C_at | 0.557411 | 0.55741092 | 6.439727 | 3E-09 | 2335.025. | NM_212482.1 | CQ715726.1 | GENBANK_PATENT | 3 |
| 1397 | 2335.004.1-F_at | 0.557345 | 0.55734468 | 6.438616 | 3E-09 | 2335.004. | NM_212482.1 | AU139388.1 | EST | 1 |
| 1398 | 7170.038.1-F_at | 0.557344 | 0.55734423 | 6.438609 | 3E-09 | 7170.038. | NM_153649.2 | BG425254.1 | EST | 2 |
| 1399 | 7373.003.3-B_at | -0.55728 | 0.55728249 | 6.437574 | 3E-09 | 7373.003. | NM_021110.1 | CQ716670.1 | GENBANK_PATENT | 1 |
| 1400 | 5744.003.2-B_at | -0.55713 | 0.55713472 | 6.435099 | 3E-09 | 5744.003. | NM_198955.1 | BG680355.1 | EST | 1 |
| 1401 | 1164.001.1-F_at | 0.556978 | 0.5569777 | 6.432469 | 3E-09 | 1164.001. | NM_001827.1 | AX971617.1 | GENBANK_PATENT | 1 |
| 1402 | 23266.005.1-T_at | -0.55685 | 0.55685184 | 6.430362 | 3E-09 | 23266.005 | NM_012302.2 | DA764511.1 | EST | 1 |
| 1403 | 4601.015.2-F_at | -0.55673 | 0.55673111 | 6.428342 | 3E-09 | 4601.015. | NM_130439.3 | DA279837.1 | EST | 1 |
| 1404 | 23092.009.1-D_at | -0.55669 | 0.55668653 | 6.427596 | 3E-09 | 23092.009 | NM_015071.2 | BM045740.1 | EST | 1 |
| 1405 | 83699.004.1-T_at | -0.55668 | 0.55667613 | 6.427422 | 3E-09 | 83699.004 | NM_031469.1 | AX980231.1 | GENBANK_PATENT | 1 |
| 1406 | 2982.013.1-T_at | -0.55666 | 0.55665713 | 6.427104 | 3E-09 | 2982.013. | NM_000856.2 | CF594362.1 | EST | 1 |
| 1407 | 26289.013.1-F_at | -0.55662 | 0.55662356 | 6.426543 | 3E-09 | 26289.013 | NM_174858.1 | CK024190.1 | EST | 1 |
| 1408 | 7113.003.1-F_at | -0.55657 | 0.5565676 | 6.425607 | 3E-09 | 7113.003. | NM_005656.2 | CQ976404.1 | GENBANK_PATENT | 2 |
| 1409 | 390.003.1-T_at | -0.55648 | 0.55648155 | 6.424167 | 3E-09 | 390.003.1 | NM_005168.3 | DA532407.1 | EST | 1 |
| 1410 | 6304.002.2-T_at | -0.55641 | 0.55641323 | 6.423025 | 3E-09 | 6304.002. | NM_002971.2 | BC001744.1 | mRNA | 33 |
| 1411 | 6304.009.2-T_at | -0.55633 | 0.55633335 | 6.42169 | 3E-09 | 6304.009. | NM_002971.2 | DA497369.1 | EST | 1 |
| 1412 | 3872.017.1-T_at | -0.55631 | 0.55631309 | 6.421351 | 3E-09 | 3872.017. | NM_000422.1 | BX378477.2 | EST | 1 |
| 1413 | 2335.013.1-D_at | 0.556298 | 0.55629818 | 6.421102 | 3E-09 | 2335.013. | NM_212482.1 | AL551632.3 | EST | 2 |
| 1414 | 6790.001.1-T_at | -0.55629 | 0.55629311 | 6.421017 | 3E-09 | 6790.001. | NM_198436.1 | D84212.1 | mRNA | 8 |
| 1415 | 51201.007.1-B_at | -0.55615 | 0.55614867 | 6.418603 | 3E-09 | 51201.007 | NM_016353.2 | BF541714.1 | EST | 1 |
| 1416 | 54443.009.1-T_at | -0.55614 | 0.5561397 | 6.418453 | 3E-09 | 54443.009 | NM_018685.2 | DA242046.1 | EST | 1 |
| 1417 | 54443.012.1-T_at | 0.556003 | 0.55600288 | 6.416167 | 3E-09 | 54443.012 | NM_018685.2 | BG167656.1 | EST | 1 |
| 1418 | 5608.003.1-D_at | -0.55592 | 0.55592463 | 6.41486 | 3E-09 | 5608.003. | NM_002758.2 | BP220368.1 | EST | 1 |
| 1419 | 2.005.1-B_at | -0.55591 | 0.55590928 | 6.414604 | 3E-09 | 2.005.1 | NM_000014.4 | BI493707.1 | REFSEQ | 1 |
| 1420 | 23015.010.2-F_at | -0.55591 | 0.55590628 | 6.414554 | 3E-09 | 23015.010 | NM_181076.2 | XM_497449.1 | GENBANK_PATENT | 114 |
| 1421 | 25925.010.1-T_at | -0.55586 | 0.55586644 | 6.413722 | 3E-09 | 25925.010 | NM_015461.1 | DA215395.1 | EST | 1 |
| 1422 | 79745.002.2-T_at | -0.55584 | 0.55584433 | 6.413519 | 3E-09 | 79745.002 | NM_024692.3 | DB034631.1 | EST | 2 |
| 1423 | 23650.007.1-E_at | -0.55581 | 0.55580568 | 6.412874 | 3E-09 | 23650.007 | NM_058193.1 | BX395679.2 | EST | 1 |
| 1424 | 953.013.1-B_at | -0.55579 | 0.55578981 | 6.412609 | 3E-09 | 953.013.1 | NM_001776.3 | CQ721824.1 | GENBANK_PATENT | 1 |
| 1425 | 7153.002.5-C_at | -0.55574 | 0.55574323 | 6.411832 | 3E-09 | 7153.002. | NM_001067.2 | CQ735949.1 | GENBANK_PATENT | 1 |
| 1426 | 4240.001.1-T_at | -0.55574 | 0.55573744 | 6.411735 | 3E-09 | 4240.001. | NM_005928.1 | BF525404.1 | EST | 1 |
| 1427 | 58499.005.1-T_at | -0.55571 | 0.55571242 | 6.411317 | 3E-09 | 58499.005 | NM_021224.3 | BI461756.1 | EST | 1 |
| 1428 | 7168.026.1-C_at | -0.55559 | 0.55558644 | 6.409271 | 3E-09 | 7168.026. | NM_001018020. | CV810859.1 | EST | 1 |
| 1429 | 8404.026.1-T_at | -0.55559 | 0.55558982 | 6.406658 | 3E-09 | 8404.026. | NM_004684.2 | BX647713.1 | mRNA | 141 |
| 1430 | 94274.002.1-D_at | -0.55558 | 0.55558292 | 6.409156 | 3E-09 | 94274.002 | NM_033256.1 | CQ730829.1 | GENBANK_PATENT | 1 |
| 1431 | 301.008.1-C_at | -0.55557 | 0.55557226 | 6.408978 | 3E-09 | 301.008.1 | NM_000700.1 | CD688703.1 | EST | 1 |
| 1432 | 3426.001.1-C_at | -0.55554 | 0.55553521 | 6.40836 | 3E-09 | 3426.001. | NM_000204.1 | BC020718.1 | mRNA | 165 |
| 1433 | 2938.007.2-B_at | -0.55549 | 0.55548513 | 6.407525 | 3E-09 | 2938.007. | NM_145740.2 | AX477713.1 | GENBANK_PATENT | 1 |
| 1434 | 7373.003.5-C_at | -0.55543 | 0.55543318 | 6.406658 | 3E-09 | 7373.003. | NM_021110.1 | CQ716670.1 | GENBANK_PATENT | 1 |
| 1435 | 7169.001.2-F_at | -0.55538 | 0.55537917 | 6.405757 | 3E-09 | 7169.001. | NM_213674.1 | BM809268.1 | mRNA | 4 |
| 1436 | 2119.007.1-F_at | -0.55536 | 0.55535866 | 6.405415 | 3E-09 | 2119.007. | NM_004454.1 | BE408130.1 | EST | 1 |
|      |              | -0.55522 | 0.5552225  | 6.403145 |        |          |                                  |                                |                                |            |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1437 | 1959.001.2-T_at | −0.55498 | 0.55498357 | 6.399162 | 3E-09 | 1959.001. | NM_000399.2 | DB086600.1 | EST | 1 |
| 1438 | 9824.006.1-T_at | 0.55476 | 0.55475962 | 6.395432 | 3E-09 | 9824.006. | NM_014783.2 | CK903028.1 | EST | 2 |
| 1439 | 301.013.1-B_at | −0.55475 | 0.55475105 | 6.395289 | 3E-09 | 301.013.1 | NM_000700.1 | BF130804.1 | EST | 1 |
| 1440 | 10124.004.1-B_at | −0.55458 | 0.55458304 | 6.392491 | 3E-09 | 10124.004 | NM_001037164. | BU61374.1 | EST | 12 |
| 1441 | 140885.010.3-F | −0.55438 | 0.55438483 | 6.389193 | 3E-09 | 140885.01 | NM_080792.2 | CQ728313.1 | GENBANK_PATENT | 1 |
| 1442 | 54443.012.1-B_at | 0.554381 | 0.5543815 | 6.389137 | 3E-09 | 54443.012 | NM_018685.2 | BG167656.1 | EST | 1 |
| 1443 | 29997.008.1-F_at | −0.55437 | 0.554365 | 6.388863 | 3E-09 | 29997.008 | NM_015710.3 | BI871613.1 | EST | 1 |
| 1444 | 23092.002.1-T_at | −0.55436 | 0.55435963 | 6.388774 | 3E-09 | 23092.002 | NM_015071.2 | CQ732129.1 | GENBANK_PATENT | 1 |
| 1445 | 1308.009.1-E_at | −0.55427 | 0.55427197 | 6.387315 | 3E-09 | 1308.009. | NM_130778.1 | DA425187.1 | EST | 1 |
| 1446 | 1308.004.1-C_at | −0.55418 | 0.55418499 | 6.385868 | 3E-09 | 1308.004. | NM_130778.1 | BE615666.1 | EST | 1 |
| 1447 | 59342.003.1-B_at | −0.55416 | 0.55416164 | 6.38548 | 3E-09 | 59342.003 | NM_021626.1 | DA821057.1 | EST | 1 |
| 1448 | 2119.006.1-F_at | −0.55414 | 0.55413804 | 6.385088 | 3E-09 | 2119.006. | NM_004454.1 | DB094869.1 | EST | 1 |
| 1449 | 6304.011.2-T_at | −0.55412 | 0.55411832 | 6.38476 | 3E-09 | 6304.011. | NM_002971.2 | BP359118.1 | EST | 1 |
| 1450 | 4288.006.2-D_at | 0.553943 | 0.5539433 | 6.38185 | 3E-09 | 4288.006. | NM_002417.2 | BP363635.1 | EST | 1 |
| 1451 | 358.017.1-D_at | −0.55393 | 0.5539341 | 6.381697 | 3E-09 | 358.017.1 | NM_198098.1 | AY312580.1 | mRNA | 1 |
| 1452 | 29994.009.1-D_at | −0.55389 | 0.55388615 | 6.380901 | 4E-09 | 29994.009 | NM_013450.1 | DA218896.1 | EST | 1 |
| 1453 | 23650.006.1-T_at | −0.55388 | 0.55387924 | 6.380786 | 4E-09 | 23650.006 | NM_058193.1 | BE304682.1 | EST | 1 |
| 1454 | 3945.024.1-T_at | −0.5538 | 0.55379733 | 6.379425 | 4E-09 | 3945.024. | NM_002300.3 | BF127786.1 | EST | 1 |
| 1455 | 9073.003.1-T_at | −0.55367 | 0.55367412 | 6.377378 | 4E-09 | 9073.003. | NM_199328.1 | BP276390.1 | EST | 1 |
| 1456 | 55165.004.1-B_at | 0.553669 | 0.55366932 | 6.377298 | 4E-09 | 55165.004 | NM_018131.3 | BX416068.2 | EST | 1 |
| 1457 | 54928.003.1-C_at | −0.55352 | 0.55352466 | 6.374896 | 4E-09 | 54928.003 | NM_017813.2 | DB283344.1 | EST | 1 |
| 1458 | 489.006.1-T_at | −0.55341 | 0.55340971 | 6.372987 | 4E-09 | 489.006.1 | NM_174958.1 | CV379840.1 | EST | 1 |
| 1459 | 6122.030.1-F_at | −0.55337 | 0.55337311 | 6.37238 | 4E-09 | 6122.030. | NM_000967.3 | BF315041.1 | EST | 1 |
| 1460 | 4781.014.2-T_at | −0.55315 | 0.55315167 | 6.368705 | 4E-09 | 4781.014. | NM_005596.1 | DN918235.1 | EST | 1 |
| 1461 | 7168.014.3-B_at | −0.55307 | 0.55307042 | 6.367357 | 4E-09 | 7168.014. | NM_001018020. | BP257563.1 | EST | 1 |
| 1462 | 4147.003.1-F_at | −0.55281 | 0.55280885 | 6.36302 | 4E-09 | 4147.003. | NM_002380.3 | AY358895.1 | mRNA | 81 |
| 1463 | 57451.001.3-B_at | −0.55273 | 0.55273245 | 6.361754 | 4E-09 | 57451.001 | XM_931456.1 | CS188752.1 | GENBANK_PATENT | 1 |
| 1464 | 9055.018.1-T_at | 0.552521 | 0.55252074 | 6.358246 | 4E-09 | 9055.018. | NM_003981.2 | DA033856.1 | EST | 1 |
| 1465 | 4931.013.1-T_at | 0.552443 | 0.552443 | 6.356958 | 4E-09 | 4931.013. | NM_002533.2 | BG771162.1 | EST | 1 |
| 1466 | 7169.001.1-T_at | −0.55242 | 0.55241607 | 6.356513 | 4E-09 | 7169.001. | NM_213674.1 | BM809268.1 | EST | 4 |
| 1467 | 2568.005.1-B_at | −0.55241 | 0.55241426 | 6.356483 | 4E-09 | 2568.005. | NM_014211.1 | AK055205.1 | mRNA | 11 |
| 1468 | 4435.001.1-T_at | −0.5524 | 0.55240125 | 6.356267 | 4E-09 | 4435.001. | NM_004143.2 | AA317379.1 | EST | 1 |
| 1469 | 2335.006.1-F_at | 0.552355 | 0.55235498 | 6.355501 | 4E-09 | 2335.006. | NM_212482.1 | CX785805.1 | EST | 1 |
| 1470 | 55294.007.1-T_at | −0.55234 | 0.55234085 | 6.355267 | 4E-09 | 55294.007 | NM_033632.2 | BF380630.1 | EST | 1 |
| 1471 | 4288.006.2-B_at | 0.55233 | 0.55233026 | 6.355092 | 4E-09 | 4288.006. | NM_002417.2 | BP363635.1 | EST | 1 |
| 1472 | 29089.003.1-F_at | 0.552316 | 0.55231581 | 6.354852 | 4E-09 | 29089.003 | NM_014176.1 | AV740591.1 | EST | 1 |
| 1473 | 2335.032.1-F_at | 0.55229 | 0.55228962 | 6.354419 | 4E-09 | 2335.032. | NM_212482.1 | DA647475.1 | EST | 1 |
| 1474 | 57162.003.1-T_at | −0.55221 | 0.55220544 | 6.353025 | 4E-09 | 57162.003 | NM_020651.2 | BX380539.2 | EST | 3 |
| 1475 | 4288.005.1-B_at | 0.552168 | 0.5521684 | 6.352412 | 4E-09 | 4288.005. | NM_002417.2 | BM455229.1 | EST | 1 |
| 1476 | 3860.004.1-T_at | −0.55215 | 0.5521477 | 6.35207 | 4E-09 | 3860.004. | NM_153490.1 | DA763721.1 | EST | 1 |
| 1477 | 2.018.1-F_at | −0.55206 | 0.55205696 | 6.350568 | 4E-09 | 2.018.1 | NM_000014.4 | DB090657.1 | EST | 1 |
| 1478 | 23015.010.2-C_at | −0.55198 | 0.55198079 | 6.349308 | 4E-09 | 23015.010 | NM_181076.2 | XM_497449.1 | REFSEQ | 1 |
| 1479 | 6122.029.1-F_at | −0.55188 | 0.55188275 | 6.347686 | 4E-09 | 6122.029. | NM_009967.3 | BG547902.1 | EST | 1 |
| 1480 | 7113.007.1-E_at | −0.55181 | 0.55181118 | 6.346503 | 4E-09 | 7113.007. | NM_005656.2 | DR005196.1 | EST | 1 |
| 1481 | 2982.001.1-T_at | −0.55178 | 0.55177855 | 6.345963 | 4E-09 | 2982.001. | NM_000856.2 | DA793192.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1482 | 56999.003.1-C_at | −0.55176 | 0.55175685 | 6.345604 | 4E-09 | 56999.003 | NM_182920.1 | CQ721254.1 | GENBANK_PATENT | 1 |
| 1483 | 152015.005.1-B | −0.55166 | 0.55165647 | 6.343945 | 4E-09 | 152015.00 | NM_001012337. | CQ732372.1 | GENBANK_PATENT | 1 |
| 1484 | 1410.002.1-T_at | −0.55165 | 0.55165464 | 6.343914 | 4E-09 | 1410.002. | NM_001885.1 | AX899073.1 | GENBANK_PATENT | 4 |
| 1485 | 7373.004.1-B_at | −0.55161 | 0.55160828 | 6.343148 | 4E-09 | 7373.004. | NM_021110.1 | M64109.1 | mRNA | 1 |
| 1486 | 492304.010.1-T | −0.5516 | 0.55160004 | 6.343012 | 4E-09 | 492304.01 | — | — | — | — |
| 1487 | 80034.003.2-T_at | −0.55149 | 0.55148932 | 6.341182 | 4E-09 | 80034.003 | NM_024969.2 | CQ733306.1 | GENBANK_PATENT | 1 |
| 1488 | 4281.009.1-F_at | −0.55134 | 0.55133895 | 6.338698 | 4E-09 | 4281.009. | NM_033290.1 | AY540014.1 | mRNA | |
| 1489 | 301.011.1-B_at | −0.5513 | 0.55130021 | 6.338058 | 4E-09 | 301.011.1 | NM_000700.1 | BG435248.1 | EST | 1 |
| 1490 | 90293.002.2-T_at | −0.55112 | 0.55112335 | 6.335138 | 4E-09 | 90293.002 | NM_033495.2 | BP360232.1 | EST | 1 |
| 1491 | 800.013.1-C_at | −0.55112 | 0.55112102 | 6.335099 | 4E-09 | 800.013.1 | NM_033138.2 | NM_033157.2 | REFSEQ | 151 |
| 1492 | 142.011.1-T_at | 0.550921 | 0.55092062 | 6.331791 | 4E-09 | 142.011.1 | NM_001618.2 | DA757025.1 | EST | 1 |
| 1493 | 6876.017.1-T_at | −0.55079 | 0.55078992 | 6.329635 | 4E-09 | 6876.017. | NM_001001522. | BX428130.2 | EST | 1 |
| 1494 | 825.021.1-D_at | −0.55076 | 0.55076446 | 6.329215 | 4E-09 | 825.021.1 | NM_212464.1 | AV645796.1 | EST | 1 |
| 1495 | 714.002.1-F_at | −0.5507 | 0.55069829 | 6.328124 | 4E-09 | 714.002.1 | NM_172369.2 | AX894785.1 | GENBANK_PATENT | 2 |
| 1496 | 2335.039.1-C_at | 0.550688 | 0.55068782 | 6.327951 | 4E-09 | 2335.039. | NM_212482.1 | BP288118.1 | EST | 1 |
| 1497 | 2.024.2-D_at | −0.55068 | 0.55068374 | 6.327884 | 4E-09 | 2.024.2 | NM_000014.4 | DB286897.1 | EST | 1 |
| 1498 | 9037.004.2-T_at | −0.55067 | 0.55066904 | 6.327641 | 4E-09 | 9037.004. | NM_003966.1 | BF923022.1 | EST | 1 |
| 1499 | 4781.006.2-D_at | −0.55052 | 0.55051889 | 6.325165 | 5E-09 | 4781.006. | NM_005596.1 | AK131233.1 | mRNA | 2 |
| 1500 | 4601.012.1-T_at | −0.55051 | 0.55051321 | 6.325072 | 5E-09 | 4601.012. | NM_130439.3 | DA746301.1 | EST | 1 |
| 1501 | 4781.009.2-B_at | −0.55048 | 0.55048372 | 6.324586 | 5E-09 | 4781.009. | NM_005596.1 | CQ733556.1 | GENBANK_PATENT | 1 |
| 1502 | 7169.004.1-F_at | −0.55041 | 0.55041381 | 6.323433 | 5E-09 | 7169.004. | NM_213674.1 | BG027526.1 | EST | 1 |
| 1503 | 54443.010.1-C_at | 0.550402 | 0.55040232 | 6.323244 | 5E-09 | 54443.010 | NM_018685.2 | DA196444.1 | EST | 1 |
| 1504 | 7818.023.1-F_at | 0.550382 | 0.55038162 | 6.322903 | 5E-09 | 7818.023. | NM_004632.2 | BQ424083.1 | EST | 1 |
| 1505 | 79971.009.2-T_at | −0.55036 | 0.5503562 | 6.322484 | 5E-09 | 79971.009 | NM_001002292. | DA264864.1 | EST | 1 |
| 1506 | 4601.007.1-T_at | −0.55036 | 0.5503552 | 6.322467 | 5E-09 | 4601.007. | NM_130439.3 | DA009519.1 | EST | 1 |
| 1507 | 7113.011.2-D_at | −0.55032 | 0.55031657 | 6.321831 | 5E-09 | 7113.011. | NM_005656.2 | DA868984.1 | EST | 1 |
| 1508 | 54443.008.1-B_at | 0.550158 | 0.5501582 | 6.319222 | 5E-09 | 54443.008 | NM_018685.2 | DB172145.1 | EST | 1 |
| 1509 | 23092.009.2-D_at | −0.55009 | 0.5500931 | 6.318149 | 5E-09 | 23092.009 | NM_015071.2 | BM045740.1 | EST | 1 |
| 1510 | 57447.006.1-E_at | −0.55005 | 0.55004557 | 6.317367 | 5E-09 | 57447.006 | NM_201535.1 | DA283861.1 | EST | 4 |
| 1511 | 7170.035.2-B_at | −0.54938 | 0.54938028 | 6.30642 | 5E-09 | 7170.035. | NM_153649.2 | BF575164.1 | EST | 1 |
| 1512 | 79971.010.1-T_at | −0.54937 | 0.54936792 | 6.306216 | 5E-09 | 79971.010 | NM_001002292. | CB268343.1 | EST | 1 |
| 1513 | 4288.004.1-T_at | −0.54933 | 0.54932704 | 6.305544 | 5E-09 | 4288.004. | NM_002417.2 | BP232141.1 | EST | 1 |
| 1514 | 59342.006.1-T_at | −0.54953 | 0.54953056 | 6.314367 | 5E-09 | 59342.006 | NM_021626.1 | BP196952.1 | EST | 1 |
| 1515 | 4781.017.1-B_at | 0.548993 | 0.54899327 | 6.30006 | 5E-09 | 4781.017. | NM_005596.1 | DR002043.1 | EST | 1 |
| 1516 | 4781.013.2-B_at | −0.54894 | 0.54894022 | 6.299188 | 5E-09 | 4781.013. | NM_005596.1 | DA750893.1 | EST | 1 |
| 1517 | 23015.010.3-E_at | −0.5488 | 0.54880253 | 6.296927 | 5E-09 | 23015.010 | NM_181076.2 | XM_497449.1 | REFSEQ | 1 |
| 1518 | 9055.013.1-B_at | 0.548622 | 0.54862189 | 6.293962 | 5E-09 | 9055.013. | NM_003981.2 | CN348395.1 | EST | 1 |
| 1519 | 5621.003.1-T_at | −0.54841 | 0.548412 | 6.290518 | 5E-09 | 5621.003. | NM_000311.2 | BP218622.1 | EST | 1 |
| 1520 | 2893.006.1-T_at | −0.54819 | 0.54819208 | 6.286911 | 5E-09 | 2893.006. | NM_000829.1 | BF669210.1 | EST | 1 |
| 1521 | 3161.007.1-F_at | −0.54812 | 0.54812393 | 6.285794 | 5E-09 | 3161.007. | NM_012484.1 | BG198860.1 | EST | 1 |
| 1522 | 55107.001.1-T_at | −0.54801 | 0.54801484 | 6.284006 | 5E-09 | 55107.001 | NM_018043.4 | AY728143.1 | mRNA | 30 |
| 1523 | 2327.002.1-C_at | −0.54819 | 0.54819208 | 6.286911 | 5E-09 | 2327.002. | NM_001460.2 | CD684429.1 | EST | 1 |
| 1524 | 3945.014.1-B_at | −0.54812 | 0.54812393 | 6.285794 | 5E-09 | 3945.014. | NM_002300.3 | BG402389.1 | EST | 1 |
| 1525 | 151438.003.1-C | −0.54801 | 0.54801484 | 6.284006 | 5E-09 | 151438.00 | AK058877.1 | DB124570.1 | EST | 2 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1526 | 7113.013.1-F_at | −0.54795 | 0.54795303 | 6.282993 | 5E-09 | 7113.013. | NM_005656.2 | DA627080.1 | EST | 1 |
| 1527 | 441417.001.1-B | −0.54784 | 0.54783722 | 6.281095 | 5E-09 | 441417.00 | XM_497039.2 | XM_933326.1 | REFSEQ | 3 |
| 1528 | 2982.012.1-F_at | −0.54781 | 0.54781217 | 6.280685 | 6E-09 | 2982.012. | NM_000856.2 | BC012627.1 | mRNA | 2 |
| 1529 | 7168.005.3-E_at | −0.54767 | 0.54766942 | 6.278347 | 6E-09 | 7168.005. | NM_001018020. | BP373012.1 | EST | 1 |
| 1530 | 27338.001.1-B_at | 0.547668 | 0.54766773 | 6.27832 | 6E-09 | 27338.001 | NM_014501.1 | BI198504.1 | EST | 3 |
| 1531 | 8404.028.1-B_at | −0.54766 | 0.54766289 | 6.27824 | 6E-09 | 8404.028. | NM_004684.2 | CQ727530.1 | GENBANK_PATENT | 1 |
| 1532 | 4601.019.1-F_at | −0.54764 | 0.54764478 | 6.277944 | 6E-09 | 4601.019. | NM_130439.3 | BQ425277.1 | EST | 1 |
| 1533 | 8404.008.1-B_at | −0.54752 | 0.54751598 | 6.275835 | 6E-09 | 8404.008. | NM_004684.2 | DA342341.1 | EST | 1 |
| 1534 | 23266.008.3-F_at | −0.54739 | 0.54739477 | 6.273851 | 6E-09 | 23266.008 | NM_012302.2 | CQ799210.1 | GENBANK_PATENT | 1 |
| 1535 | 4931.012.1-F_at | 0.547302 | 0.54730211 | 6.272335 | 6E-09 | 4931.012. | NM_002533.2 | BQ930348.1 | EST | 1 |
| 1536 | 10010.007.1-E_at | −0.54712 | 0.54711818 | 6.269326 | 6E-09 | 10010.007 | NM_004180.2 | AI525053.1 | EST | 1 |
| 1537 | 11065.003.1-B_at | 0.54698 | 0.54697977 | 6.267063 | 6E-09 | 11065.003 | NM_181802.1 | CS138819.1 | GENBANK_PATENT | 5 |
| 1538 | 3925.016.1-C_at | 0.546859 | 0.5468594 | 6.265095 | 6E-09 | 3925.016. | NM_203399.1 | BE888426.1 | EST | 1 |
| 1539 | 7170.017.1-C_at | 0.546805 | 0.54680477 | 6.264203 | 6E-09 | 7170.017. | NM_153649.2 | BF574676.1 | EST | 1 |
| 1540 | 301.011.1-F_at | −0.54668 | 0.54668114 | 6.262183 | 6E-09 | 301.011.1. | NM_000700.1 | BG435248.1 | EST | 1 |
| 1541 | 57685.005.2-T_at | −0.54663 | 0.54663145 | 6.261371 | 6E-09 | 57685.005 | NM_020925.1 | CQ721664.1 | GENBANK_PATENT | 1 |
| 1542 | 23015.014.1-T_at | −0.54659 | 0.54658979 | 6.26069 | 6E-09 | 23015.014 | NM_181076.2 | DA928720.1 | EST | 1 |
| 1543 | 7153.002.3-T_at | 0.546559 | 0.54655896 | 6.260187 | 6E-09 | 7153.002. | NM_001067.2 | CQ735949.1 | GENBANK_PATENT | 114 |
| 1544 | 2568.005.2-D_at | −0.5465 | 0.5464996 | 6.259217 | 6E-09 | 2568.005. | NM_014211.1 | AK055205.1 | mRNA | 11 |
| 1545 | 2335.039.1-F_at | 0.546413 | 0.5464132 | 6.257806 | 6E-09 | 2335.039. | NM_212482.1 | BP288118.1 | EST | 1 |
| 1546 | 10124.002.1-F_at | −0.5464 | 0.54640453 | 6.257665 | 6E-09 | 10124.002 | NM_001037164. | BG178114.1 | EST | 6 |
| 1547 | 28299.003.1-D | −0.54611 | 0.54610398 | 6.252759 | 6E-09 | 28299.00 | XM_498506.1 | XM_932188.1 | REFSEQ | 1 |
| 1548 | 4781.013.1-T_at | −0.54585 | 0.54585341 | 6.248672 | 6E-09 | 4781.013. | NM_005596.1 | DA750893.1 | EST | 1 |
| 1549 | 7170.012.2-D_at | 0.545774 | 0.545774 | 6.247378 | 6E-09 | 7170.012. | NM_153649.2 | DA893534.1 | EST | 1 |
| 1550 | 667.014.1-T_at | −0.54573 | 0.54572906 | 6.246645 | 6E-09 | 667.014.1. | NM_183380.1 | CQ851391.1 | GENBANK_PATENT | 1 |
| 1551 | 4781.009.2-D_at | −0.54569 | 0.54568951 | 6.246 | 6E-09 | 4781.009. | NM_005596.1 | CQ732556.1 | GENBANK_PATENT | 1 |
| 1552 | 7169.001.1-D_at | −0.54565 | 0.54565203 | 6.24539 | 6E-09 | 7169.001. | NM_213674.1 | BM809268.1 | EST | 4 |
| 1553 | 2161.001.1-T_at | 0.545644 | 0.54564352 | 6.245251 | 6E-09 | 2161.001. | NM_000505.2 | AX147449.1 | GENBANK_PATENT | 30 |
| 1554 | 1308.001.1-F_at | −0.5456 | 0.54560226 | 6.244578 | 6E-09 | 1308.001. | NM_130778.1 | BM773425.1 | EST | 1 |
| 1555 | 7168.012.2-F_at | −0.54541 | 0.54540889 | 6.241428 | 7E-09 | 7168.012. | NM_001018020. | AK129882.1 | mRNA | 2 |
| 1556 | 10010.004.1-E_at | −0.54541 | 0.54540884 | 6.241427 | 7E-09 | 10010.004 | NM_004180.2 | BM750784.1 | EST | 1 |
| 1557 | 54443.009.1-D_at | 0.545394 | 0.54539371 | 6.241181 | 7E-09 | 54443.009 | NM_018685.2 | DA242046.1 | EST | 1 |
| 1558 | 7039.002.1-D_at | −0.54538 | 0.54537813 | 6.240927 | 7E-09 | 7039.002. | NM_003236.1 | AF149096.1 | mRNA | 2 |
| 1559 | 57447.041.1-B_at | −0.54524 | 0.54523712 | 6.23863 | 7E-09 | 57447.041 | NM_201535.1 | DA295124.1 | EST | 1 |
| 1560 | 4281.007.1-B_at | −0.54521 | 0.54521491 | 6.238269 | 7E-09 | 4281.007. | NM_033290.1 | AY540023.1 | mRNA | 1 |
| 1561 | 301.009.1-T_at | −0.54517 | 0.54516544 | 6.237463 | 7E-09 | 301.009.1. | NM_000700.1 | CD357777.1 | EST | 1 |
| 1562 | 9055.014.1-F_at | 0.545101 | 0.54510063 | 6.236408 | 7E-09 | 9055.014. | NM_003981.2 | BE300335.1 | EST | 2 |
| 1563 | 79971.013.1-C_at | −0.54495 | 0.54494911 | 6.233942 | 7E-09 | 79971.013 | NM_001002292. | DA878291.1 | EST | 1 |
| 1564 | 11065.003.2-T_at | 0.544945 | 0.5449453 | 6.23388 | 7E-09 | 11065.003 | NM_181802.1 | CS138819.1 | GENBANK_PATENT | 5 |
| 1565 | 7113.009.1-E_at | −0.54493 | 0.54493426 | 6.233701 | 7E-09 | 7113.009. | NM_005656.2 | DA873416.1 | EST | 1 |
| 1566 | 51203.002.2-T_at | 0.544867 | 0.54486653 | 6.232599 | 7E-09 | 51203.002 | NM_016359.2 | AL561514.3 | EST | 1 |
| 1567 | 7170.006.1-B_at | 0.54486 | 0.54486029 | 6.232497 | 7E-09 | 7170.006. | NM_153649.2 | DB003864.1 | EST | 2 |
| 1568 | 80034.002.1-T_at | 0.54484 | 0.54484345 | 6.232223 | 7E-09 | 80034.002 | NM_024969.2 | DA769284.1 | EST | 1 |
| 1569 | 1345.012.1-D_at | 0.544806 | 0.54480624 | 6.231618 | 7E-09 | 1345.012. | NM_004374.2 | DB564533.1 | EST | 1 |
| 1570 | 8321.004.1-T_at | −0.54478 | 0.54477916 | 6.231178 | 7E-09 | 8321.004. | NM_003505.1 | AA249884.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1571 | 10461.001.1-T_at | -0.54469 | 0.54468608 | 6.229664 | 7E-09 | 10461.001 | NM_006343.2 | CQ760423.1 | GENBANK_PATENT | 4 |
| 1572 | 4601.010.1-T_at | -0.54466 | 0.54466418 | 6.229308 | 7E-09 | 4601.010. | NM_130439.3 | CS031066.1 | GENBANK_PATENT | 3 |
| 1573 | 3709.004.1-E_at | -0.54444 | 0.54444277 | 6.225708 | 7E-09 | 3709.004. | NM_002223.1 | BP364657.1 | EST | 1 |
| 1574 | 4781.017.2-T_at | -0.5444 | 0.5444035 | 6.225019 | 7E-09 | 4781.017. | NM_005596.1 | DR002043.1 | EST | 1 |
| 1575 | 5621.010.1-B_at | -0.54431 | 0.54431029 | 6.223555 | 7E-09 | 5621.010. | NM_000311.2 | DA174560.1 | EST | 1 |
| 1576 | 54763.001.1-T_at | -0.54431 | 0.54430594 | 6.223485 | 7E-09 | 54763.001 | NM_017578.2 | BI465233.1 | EST | 4 |
| 1577 | 306.003.1-B_at | -0.54429 | 0.54428587 | 6.223159 | 7E-09 | 306.003.1 | NM_005139.1 | CQ721707.1 | GENBANK_PATENT | 1 |
| 1578 | 2335.035.1-C_at | 0.544238 | 0.54423813 | 6.222383 | 7E-09 | 2335.035. | NM_212482.1 | CX755647.1 | EST | 1 |
| 1579 | 4601.015.1-T_at | -0.54414 | 0.54413917 | 6.220776 | 7E-09 | 4601.015. | NM_130439.3 | DA279837.1 | EST | 1 |
| 1580 | 7168.038.1-D_at | -0.54409 | 0.54408836 | 6.219951 | 7E-09 | 7168.038. | NM_001018020. | AK092573.1 | mRNA | 5 |
| 1581 | 55732.003.1-T_at | 0.543852 | 0.54385205 | 6.216114 | 7E-09 | 55732.003 | NM_018186.2 | DA733233.1 | EST | 2 |
| 1582 | 23266.001.1-T_at | -0.54381 | 0.54380864 | 6.21541 | 7E-09 | 23266.001 | NM_012302.2 | AK123422.1 | mRNA | 2 |
| 1583 | 4288.006.2-E_at | 0.543777 | 0.54377742 | 6.214903 | 7E-09 | 4288.006. | NM_002417.2 | BP363635.1 | EST | 1 |
| 1584 | 4781.013.2-D_at | -0.54375 | 0.54374747 | 6.214417 | 7E-09 | 4781.013. | NM_005596.1 | DA750893.1 | EST | 1 |
| 1585 | 259266.001.1-B | 0.543672 | 0.54367202 | 6.213193 | 7E-09 | 259266.00 | NM_018136.2 | BC034607.1 | mRNA | 7 |
| 1586 | 7170.029.1-F_at | 0.543574 | 0.54357435 | 6.211608 | 7E-09 | 7170.029. | NM_153649.2 | BM011010.1 | EST | 1 |
| 1587 | 51201.007.1-T_at | -0.54346 | 0.5434567 | 6.2097 | 8E-09 | 51201.007 | NM_016353.2 | BF541714.1 | EST | 1 |
| 1588 | 7169.002.1-F_at | -0.54328 | 0.54327991 | 6.206834 | 8E-09 | 7169.002. | NM_213674.1 | AL555921.3 | EST | 1 |
| 1589 | 8404.028.1-T_at | -0.54323 | 0.5432313 | 6.206046 | 8E-09 | 8404.028. | NM_004684.2 | CQ727530.1 | GENBANK_PATENT | 1 |
| 1590 | 4781.015.1-T_at | -0.54315 | 0.54314788 | 6.204695 | 8E-09 | 4781.015. | NM_005596.1 | DN995118.1 | EST | 1 |
| 1591 | 9055.012.1-T_at | 0.543077 | 0.54307679 | 6.203543 | 8E-09 | 9055.012. | NM_003981.2 | BE298728.1 | EST | 1 |
| 1592 | 2893.004.1-T_at | -0.5429 | 0.54289557 | 6.200829 | 8E-09 | 2893.004. | NM_000829.1 | DA066848.1 | EST | 1 |
| 1593 | 91653.015.1-T_at | -0.54284 | 0.54283984 | 6.199705 | 8E-09 | 91653.015 | NM_033254.2 | R75666.1 | EST | 1 |
| 1594 | 10010.001.1-T_at | -0.54281 | 0.54280637 | 6.199163 | 8E-09 | 10010.001 | NM_004180.2 | DA670701.1 | EST | 6 |
| 1595 | 1410.003.2-T_at | -0.54281 | 0.54280581 | 6.199154 | 8E-09 | 1410.003. | NM_001885.1 | AX899079.1 | GENBANK_PATENT | 1 |
| 1596 | 6595.013.1-B_at | -0.54268 | 0.54268082 | 6.19713 | 8E-09 | 6595.013. | NM_003070.3 | DA825858.1 | EST | 1 |
| 1597 | 4601.009.1-T_at | -0.54264 | 0.54264498 | 6.19655 | 8E-09 | 4601.009. | NM_130439.3 | BE789186.1 | EST | 1 |
| 1598 | 23015.009.1-E_at | 0.542456 | 0.5424498 | 6.193392 | 8E-09 | 23015.009 | NM_181076.2 | CA943083.1 | EST | 1 |
| 1599 | 2335.024.1-T_at | 0.542425 | 0.54242468 | 6.192986 | 8E-09 | 2335.024. | NM_212482.1 | CQ731573.1 | GENBANK_PATENT | 1 |
| 1600 | 23650.009.1-F_at | -0.54242 | 0.54242338 | 6.192965 | 8E-09 | 23650.009 | NM_058193.1 | BF836741.1 | EST | 1 |
| 1601 | 11254.001.1-F_at | -0.54238 | 0.54237719 | 6.192217 | 8E-09 | 11254.001 | NM_007231.1 | BE819593.1 | EST | 1 |
| 1602 | 7286.002.1-T_at | 0.542342 | 0.5423416 | 6.191642 | 8E-09 | 7286.002. | NM_020127.1 | BP315579.1 | EST | 1 |
| 1603 | 4931.004.1-T_at | 0.5424 | 0.54223963 | 6.189993 | 8E-09 | 4931.004. | NM_002533.2 | BM693264.1 | GENBANK_PATENT | 1 |
| 1604 | 7113.005.1-E_at | -0.54224 | 0.5422385 | 6.189974 | 8E-09 | 7113.005. | NM_005656.2 | DA865300.1 | EST | 1 |
| 1605 | 150572.009.1-F_at | -0.54223 | 0.54222998 | 6.189837 | 8E-09 | 150572.00 | NM_198274.2 | BF790590.1 | EST | 1 |
| 1606 | 57447.002.1-C_at | -0.54216 | 0.54215776 | 6.188669 | 8E-09 | 57447.002 | NM_201535.1 | BF526188.1 | EST | 1 |
| 1607 | 1410.002.2-T_at | -0.54199 | 0.54198899 | 6.185941 | 9E-09 | 1410.002. | NM_001885.1 | AX899073.1 | GENBANK_PATENT | 4 |
| 1608 | 4316.001.1-F_at | -0.54197 | 0.54197342 | 6.185689 | 9E-09 | 4316.001. | NM_002423.3 | CQ733055.1 | GENBANK_PATENT | 1 |
| 1609 | 254042.002.1-E | -0.54193 | 0.54192668 | 6.184934 | 9E-09 | 254042.00 | NM_199227.1 | AX188221.1 | GENBANK_PATENT | 7 |
| 1610 | 79971.006.2-B_at | -0.54193 | 0.54192511 | 6.184909 | 9E-09 | 79971.006 | NM_001002292. | DA048370.1 | EST | 1 |
| 1611 | 1396.001.1-T_at | 0.54189 | 0.54189009 | 6.184343 | 9E-09 | 1396.001. | NM_001311.3 | N46592.1 | EST | 2 |
| 1612 | 7153.002.3-D_at | 0.541626 | 0.54162631 | 6.180082 | 9E-09 | 7153.002. | NM_001067.2 | CQ735949.1 | GENBANK_PATENT | 114 |
| 1613 | 54443.001.1-F_at | 0.541435 | 0.54143463 | 6.176988 | 9E-09 | 54443.001 | NM_018685.2 | BC070066.1 | mRNA | 10 |
| 1614 | 142.012.1-F_at | 0.541335 | 0.54133459 | 6.175374 | 9E-09 | 142.012.1 | NM_001618.2 | BG900662.1 | EST | 1 |

TABLE 3-continued

Polynucleotides probe sets that harbor different values between malignant and benign tumors.

| No | Probeset_ID | correl | abs_correl | tstat | pvalue | Event_ID | reference_representative_accession | variant_representative_accession | variant_representative_database | variant nb |
|---|---|---|---|---|---|---|---|---|---|---|
| 1615 | 301.013.1-F_at | −0.54115 | 0.54115484 | 6.172474 | 9E-09 | 301.013.1 | NM_000700.1 | BF130804.1 | EST | 1 |
| 1616 | 152015.004.1-E | −0.54097 | 0.54096565 | 6.169423 | 9E-09 | 152015.00 | NM_001012337. | BC015413.1 | mRNA | 2 |
| 1617 | 8857.001.1-F_at | −0.54089 | 0.54089094 | 6.168218 | 9E-09 | 8857.001. | NM_003890.1 | CQ730859.1 | GENBANK_PATENT | 1 |
| 1618 | 6203.002.1-B_at | −0.54088 | 0.54087544 | 6.167968 | 9E-09 | 6203.002. | NM_001013.3 | AX969894.1 | GENBANK_PATENT | 1 |
| 1619 | 7168.010.1-D_at | −0.54079 | 0.54078858 | 6.166568 | 9E-09 | 7168.010. | NM_001018020. | CD556048.1 | EST | 1 |
| 1620 | 57447.051.2-C_at | −0.54076 | 0.54076391 | 6.166171 | 9E-09 | 57447.051 | NM_201535.1 | BX460053.2 | EST | 1 |
| 1621 | 4288.006.1-T_at | 0.540756 | 0.54075554 | 6.166036 | 9E-09 | 4288.006. | NM_002417.2 | BP363635.1 | EST | 1 |
| 1622 | 54443.013.1-T_at | 0.54066 | 0.54065959 | 6.16449 | 9E-09 | 54443.013 | NM_018685.2 | BX410228.2 | EST | 1 |
| 1623 | 9055.017.1-E_at | 0.540557 | 0.54055744 | 6.162844 | 9E-09 | 9055.017. | NM_003981.2 | DB031145.1 | EST | 1 |
| 1624 | 55732.004.1-T_at | 0.540487 | 0.54048721 | 6.161713 | 9E-09 | 55732.004 | NM_018186.2 | BF216714.1 | EST | 1 |
| 1625 | 9413.003.2-F_at | −0.54047 | 0.5404689 | 6.161418 | 9E-09 | 9413.003. | NM_004816.2 | BX641153.1 | mRNA | 10 |
| 1626 | 4629.015.1-B_at | −0.54046 | 0.5404569 | 6.161225 | 9E-09 | 4629.015. | NM_022844.1 | DB284318.1 | EST | 1 |
| 1627 | 84766.002.2-C_at | −0.54045 | 0.54045424 | 6.161182 | 9E-09 | 84766.002 | NM_032680.2 | XM_498532.1 | REFSEQ | 1 |
| 1628 | 11065.008.1-T_at | 0.540347 | 0.5403468 | 6.159452 | 9E-09 | 11065.008 | NM_181802.1 | NM_181800.1 | REFSEQ | 5 |
| 1629 | 81704.013.8-F_at | −0.54034 | 0.5403434 | 6.159398 | 9E-09 | 81704.013 | NM_203447.1 | CQ723361.1 | GENBANK_PATENT | 1 |
| 1630 | 667.016.1-T_at | −0.54033 | 0.54032607 | 6.159119 | 9E-09 | 667.016.1 | NM_183380.1 | DB013737.1 | EST | 1 |
| 1631 | 29997.004.1-F_at | 0.5403 | 0.54030048 | 6.158707 | 1E-08 | 29997.004 | NM_015710.3 | BU154441.1 | EST | 1 |
| 1632 | 2824.001.3-B_at | −0.5403 | 0.54029788 | 6.158665 | 1E-08 | 2824.001. | NM_001001994. | CQ717842.1 | GENBANK_PATENT | 1 |
| 1633 | 57447.004.1-B_at | −0.54026 | 0.54025744 | 6.158014 | 1E-08 | 57447.004 | NM_201535.1 | CD515320.1 | EST | 2 |
| 1634 | 2982.003.1-T_at | −0.54014 | 0.54014125 | 6.156144 | 1E-08 | 2982.003. | NM_000856.2 | DB179470.1 | EST | 1 |
| 1635 | 4288.005.1-T_at | 0.539862 | 0.53986198 | 6.151651 | 1E-08 | 4288.005. | NM_002417.2 | BM455229.1 | EST | 1 |
| 1636 | 10957.018.1-F_at | −0.53982 | 0.53982225 | 6.151012 | 1E-08 | 10957.018 | NM_006813.1 | AI547283.1 | EST | 1 |
| 1637 | 2568.006.2-B_at | −0.53981 | 0.53980996 | 6.150815 | 1E-08 | 2568.006. | NM_014211.1 | CD385249.1 | EST | 1 |
| 1638 | 10051.015.2-F_at | 0.539796 | 0.53979645 | 6.150597 | 1E-08 | 10051.015 | NM_001002799. | BM010546.1 | EST | 1 |
| 1639 | 2.007.1-F_at | −0.53972 | 0.53972151 | 6.149392 | 1E-08 | 2.007.1 | NM_000014.4 | BG547500.1 | EST | 1 |
| 1640 | 5803.003.1-T_at | −0.53965 | 0.53964973 | 6.148239 | 1E-08 | 5803.003. | NM_002851.1 | CD672822.1 | EST | 1 |

In order to find subsets of smaller amounts of polynucleotide probe sets to be used for classifying the benign or malignant status of tissues, prediction rules were constructed using the top 50, top 100, top 150 and top 200 polynucleotide probe sets of Table 4 (with identifiers no 1 to no 50, no 1 to no 100, no 1 to no 150 and no 1 to no 200). The estimated prediction accuracies by leave-one-out crossvalidation were as follows:

using the top 50 polynucleotide probe sets: 1 out of 24 patients with benign status were misclassified and 7 out of 70 patients with malignant status.
using the top 100 polynucleotide probe sets: 1 out of 24 patients with benign status were misclassified and 5 out of 70 patients with malignant status.
using the top 150 polynucleotide probe sets: 0 out of 24 patients with benign status were misclassified and 6 out of 70 patients with malignant status.
using the top 200 polynucleotide probe sets: 0 out of 24 patients with benign status were misclassified and 4 out of 70 patients with malignant status.

Table 5 contains the average profiles of the preferred 1,228 signature polynucleotide probe sets with $p<10e-9$ measured on the 24 benign and 70 malignant tissues of the training set.

Thus, the preferred set of probes to be used for predicting the malignant status of a tissue of a future patient is reported here.

An additional 100 patients referred at the Institut Gustave Roussy for a clinical or radiological breast lesion in 2006-2007 for which a FNA was performed to assess the diagnosis of the breast lesion has been analyzed by exon profiling. The prediction rule using the preferred 1228 signature polynucleotide probe sets has been applied to this independent validation set.

The inventors have developed an optimal prediction rule based on the methodology reported previously. The preferred p-value threshold for defining signature genes was $p<10e-9$. When using leave-one-out cross-validation to estimate the prediction accuracy of the prediction rule with this particular threshold, the inventors accurately classified all the samples as shown in FIG. 4. This corresponds to a sensitivity of 100% and a specificity of 100%. Table 5 contains the average profiles of the preferred 1228 signature probe sets with $p<10e-9$ measured on the 20 benign and 74 malignant tissues of the training set. The probes with positive correlation are those which have increased expression in malignant tissues, those with negative correlation have increased expression in the benign tissues.

TABLE 4

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 1 | 1756.022.2-C_at | DMD | NM_000109 | Xp21.2 | 1756.022.2 | 10010.002.1 | 1756.22 | 1756.22 |
| 2 | 1756.029.1-D_at | DMD | NM_000110 | Xp21.2 | 1756.029.1 | 10010.004.1 | 1756.29 | 1756.29 |
| 3 | 1756.026.1-C_at | DMD | NM_000111 | Xp21.2 | 1756.026.1 | 10051.005.3 | 1756.26 | 1756.26 |
| 4 | 1756.022.4-T_at | DMD | NM_000112 | Xp21.2 | 1756.022.4 | 10051.008.1 | 1756.22 | 1756.22 |
| 5 | 1756.011.1-B_at | DMD | NM_000113 | Xp21.2 | 1756.011.1 | 10051.016.1 | 1756.11 | 1756.11 |
| 6 | 1308.008.1-C_at | COL17A1 | NM_000494 | 10q24.3 | 1308.008.1 | 10124.002.1 | 1308.8 | 1308.8 |
| 7 | 1756.022.3-F_at | DMD | NM_000114 | Xp21.2 | 1756.022.3 | 10124.003.1 | 1756.22 | 3861.20 |
| 8 | 3861.020.1-D_at | KRT14 | NM_000526 | 17q12-q21 | 3861.020.1 | 10124.004.2 | 3861.20 | 4629.7 |
| 9 | 1756.011.1-F_at | DMD | NM_000115 | Xp21.2 | 1756.011.1 | 10144.017.3 | 1756.11 | 1756.24 |
| 10 | 4629.007.1-F_at | MYH11 | NM_001040113 | 16p13.11 | 4629.007.1 | 10144.020.2 | 4629.7 | 3861.19 |
| 11 | 1756.022.4-B_at | DMD | NM_000116 | Xp21.2 | 1756.022.4 | 10144.021.1 | 1756.22 | 3861.1 |
| 12 | 1756.024.1-F_at | DMD | NM_000117 | Xp21.2 | 1756.024.1 | 10253.001.1 | 1756.24 | 4629.20 |
| 13 | 3861.019.1-T_at | KRT14 | NM_000526 | 17q12-q21 | 3861.019.1 | 10253.003.1 | 3861.19 | 1756.27 |
| 14 | 1756.026.1-T_at | DMD | NM_000118 | Xp21.2 | 1756.026.1 | 10253.004.1 | 1756.26 | 3861.13 |
| 15 | 1756.022.1-B_at | DMD | NM_000119 | Xp21.2 | 1756.022.1 | 1033.002.1 | 1756.22 | 3861.22 |
| 16 | 3861.001.1-T_at | KRT14 | NM_000526 | 17q12-q21 | 3861.001.1 | 10461.002.1 | 3861.1 | 3868.4 |
| 17 | 1308.008.1-T_at | COL17A1 | NM_000495 | 10q24.3 | 1308.008.1 | 10461.002.2 | 1308.8 | 4629.15 |
| 18 | 4629.020.1-C_at | MYH11 | NM_001040114 | 16p13.11 | 4629.020.1 | 1058.004.2 | 4629.20 | 6422.2 |
| 19 | 1756.027.1-T_at | DMD | NM_000120 | Xp21.2 | 1756.027.1 | 10580.012.1 | 1756.27 | 1308.3 |
| 20 | 3861.013.1-T_at | KRT14 | NM_000526 | 17q12-q21 | 3861.013.1 | 1062.001.6 | 3861.13 | 3868.5 |
| 21 | 4629.020.1-F_at | MYH11 | NM_001040115 | 16p13.11 | 4629.020.1 | 1063.001.1 | 4629.20 | 1308.7 |
| 22 | 3861.001.1-B_at | KRT14 | NM_000526 | 17q12-q21 | 3861.001.1 | 1063.002.1 | 3861.1 | 1308.9 |
| 23 | 1756.022.4-F_at | DMD | NM_000121 | Xp21.2 | 1756.022.4 | 11065.003.1 | 1756.22 | 3861.7 |
| 24 | 1756.026.1-F_at | DMD | NM_000122 | Xp21.2 | 1756.026.1 | 11065.004.1 | 1756.26 | 4629.16 |
| 25 | 1756.022.2-T_at | DMD | NM_000123 | Xp21.2 | 1756.022.2 | 11065.005.1 | 1756.22 | 3084.7 |
| 26 | 1756.022.2-F_at | DMD | NM_000124 | Xp21.2 | 1756.022.2 | 11065.005.2 | 1756.22 | 26289.3 |
| 27 | 3861.022.1-B_at | KRT14 | NM_000526 | 17q12-q21 | 3861.022.1 | 11065.008.1 | 3861.22 | 1756.28 |
| 28 | 3868.004.1-D_at | KRT16 | NM_005557 | 17q12-q21 | 3868.004.1 | 11065.009.1 | 3868.4 | 4629.21 |
| 29 | 4629.015.1-C_at | MYH11 | NM_001040116 | 16p13.11 | 4629.015.1 | 11197.001.1 | 4629.15 | 5764.1 |
| 30 | 6422.002.1-E_at | SFRP1 | NM_003012 | 8p12-p11.1 | 6422.002.1 | 115207.002.1 | 6422.2 | 3815.2 |
| 31 | 3861.001.1-D_at | KRT14 | NM_000526 | 17q12-q21 | 3861.001.1 | 115908.002.1 | 3861.1 | 3852.20 |
| 32 | 1756.022.1-F_at | DMD | NM_000125 | Xp21.2 | 1756.022.1 | 116369.006.4 | 1756.22 | 128553.3 |
| 33 | 1308.003.1-T_at | COL17A1 | NM_000496 | 10q24.3 | 1308.003.1 | 120.005.2 | 1308.3 | 4629.5 |
| 34 | 3868.005.1-B_at | KRT16 | NM_005557 | 17q12-q21 | 3868.005.1 | 1264.003.1 | 3868.5 | 4629.10 |
| 35 | 1308.007.1-F_at | COL17A1 | NM_000497 | 10q24.3 | 1308.007.1 | 1264.006.1 | 1308.7 | 6422.1 |
| 36 | 1308.009.1-F_at | COL17A1 | NM_000498 | 10q24.3 | 1308.009.1 | 1264.007.1 | 1308.9 | 3861.8 |
| 37 | 3861.007.1-E_at | KRT14 | NM_000526 | 17q12-q21 | 3861.007.1 | 128553.003.1 | 3861.7 | 1756.30 |
| 38 | 4629.016.1-D_at | MYH11 | NM_001040117 | 16p13.11 | 4629.016.1 | 130497.001.2 | 4629.16 | 3084.9 |
| 39 | 3084.007.1-F_at | NRG1 | NM_004495 | 8p12 | 3084.007.1 | 1308.001.1 | 3084.7 | 26289.2 |
| 40 | 3861.007.1-F_at | KRT14 | NM_000526 | 17q12-q21 | 3861.007.1 | 1308.002.1 | 3861.7 | 23336.1 |
| 41 | 26289.003.1-E_at | AK5 | NM_012093 | 1p31 | 26289.003.1 | 1308.003.1 | 26289.3 | 3852.12 |
| 42 | 1756.028.1-T_at | DMD | NM_000126 | Xp21.2 | 1756.028.1 | 1308.004.1 | 1756.28 | 26289.12 |
| 43 | 4629.021.1-E_at | MYH11 | NM_001040118 | 16p13.11 | 4629.021.1 | 1308.007.1 | 4629.21 | 23336.3 |
| 44 | 4629.020.1-D_at | MYH11 | NM_001040119 | 16p13.11 | 4629.020.1 | 1308.008.1 | 4629.20 | 26289.7 |
| 45 | 5764.001.1-F_at | PTN | NM_002825 | 7q33-q34 | 5764.001.1 | 1308.009.1 | 5764.1 | 84417.1 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 46 | 3815.002.3-F_at | KIT | NM_000222 | 4q11-q12 | 3815.002.3 | 1398.001.1 | 3815.2 | 3861.18 |
| 47 | 3852.020.1-T_at | KRT5 | NM_000424 | 12q12-q13 | 3852.020.1 | 140446.004.1 | 3852.20 | 3852.4 |
| 48 | 4629.007.1-E_at | MYH11 | NM_001040120 | 16p13.11 | 4629.007.1 | 140807.003.1 | 4629.7 | 90865.6 |
| 49 | 128553.003.1-F | TSHZ2 | NM_173485 | 20q13.2 | 128553.003.1 | 140885.010.1 | 128553.3 | 1264.3 |
| 50 | 26289.003.1-F_at | AK5 | NM_012094 | 1p31 | 26289.003.1 | 140885.010.2 | 26289.3 | 26289.10 |
| 51 | 3815.002.2-F_at | KIT | NM_000223 | 4q11-q12 | 3815.002.2 | 140885.010.3 | 3815.2 | 1908.2 |
| 52 | 1756.029.1-B_at | DMD | NM_000127 | Xp21.2 | 1756.029.1 | 140885.011.1 | 1756.29 | 3852.8 |
| 53 | 4629.005.1-E_at | MYH11 | NM_001040121 | 16p13.11 | 4629.005.1 | 140885.013.1 | 4629.5 | 4915.11 |
| 54 | 4629.010.1-B_at | MYH11 | NM_001040122 | 16p13.11 | 4629.010.1 | 140885.014.1 | 4629.10 | 5288.1 |
| 55 | 6422.001.1-T_at | SFRP1 | NM_003012 | 8p12-p11.1 | 6422.001.1 | 1410.001.1 | 6422.1 | 3852.6 |
| 56 | 5764.001.1-E_at | PTN | NM_002825 | 7q33-q34 | 5764.001.1 | 1410.002.2 | 5764.1 | 9413.3 |
| 57 | 3861.008.1-F_at | KRT14 | NM_000526 | 17q12-q21 | 3861.008.1 | 1410.003.2 | 3861.8 | 3815.1 |
| 58 | 1756.030.2-T_at | DMD | NM_000128 | Xp21.2 | 1756.030.2 | 1410.004.2 | 1756.30 | 79937.1 |
| 59 | 3084.009.1-B_at | NRG1 | NM_004496 | 8p12 | 3084.009.1 | 1410.005.1 | 3084.9 | 4915.12 |
| 60 | 26289.002.1-T_at | AK5 | NM_012095 | 1p31 | 26289.002.1 | 1410.006.1 | 26289.2 | 26289.5 |
| 61 | 1756.022.5-B_at | DMD | NM_000129 | Xp21.2 | 1756.022.5 | 1410.007.1 | 1756.22 | 4311.9 |
| 62 | 4629.007.1-D_at | MYH11 | NM_001040123 | 16p13.11 | 4629.007.1 | 1410.007.2 | 4629.7 | 26289.6 |
| 63 | 23336.001.1-C_at | DMN | NM_015286 | 15q26.3 | 23336.001.1 | 1410.008.1 | 23336.1 | 5288.3 |
| 64 | 1308.003.1-D_at | COL17A1 | NM_000499 | 10q24.3 | 1308.003.1 | 1410.009.1 | 1308.3 | 26289.4 |
| 65 | 1756.022.3-T_at | DMD | NM_000130 | Xp21.2 | 1756.022.3 | 1410.010.1 | 1756.22 | 79192.2 |
| 66 | 3861.020.1-T_at | KRT14 | NM_000526 | 17q12-q21 | 3861.020.1 | 1410.011.1 | 3861.20 | 4638.6 |
| 67 | 3861.022.1-C_at | KRT14 | NM_000526 | 17q12-q21 | 3861.022.1 | 147495.005.1 | 3861.22 | 3084.8 |
| 68 | 3852.012.2-B_at | KRT5 | NM_000424 | 12q12-q13 | 3852.012.2 | 147495.006.1 | 3852.12 | 4311.1 |
| 69 | 26289.012.1-E_at | AK5 | NM_012096 | 1p31 | 26289.012.1 | 147495.008.1 | 26289.12 | 3852.22 |
| 70 | 23336.003.1-T_at | DMN | NM_015287 | 15q26.3 | 23336.003.1 | 147495.009.1 | 23336.3 | 23194.3 |
| 71 | 26289.007.1-B_at | AK5 | NM_012097 | 1p31 | 26289.007.1 | 147804.004.1 | 26289.7 | 65983.9 |
| 72 | 84417.001.1-T_at | C2orf40 | NM_032411 | 2q12.2 | 84417.001.1 | 152015.004.1 | 84417.1 | 1410.7 |
| 73 | 3861.018.1-D_at | KRT14 | NM_000526 | 17q12-q21 | 3861.018.1 | 152015.005.2 | 3861.18 | 7373.3 |
| 74 | 3852.004.1-B_at | KRT5 | NM_000424 | 12q12-q13 | 3852.004.1 | 162605.001.4 | 3852.4 | 10010.2 |
| 75 | 90865.006.1-B_at | IL33 | NM_033439 | 9p24.1 | 90865.006.1 | 1717.007.1 | 90865.6 | 59.26 |
| 76 | 4629.021.1-F_at | MYH11 | NM_001040124 | 16p13.11 | 4629.021.1 | 1717.009.2 | 4629.21 | 3872.7 |
| 77 | 3861.018.1-T_at | KRT14 | NM_000526 | 17q12-q21 | 3861.018.1 | 1756.002.2 | 3861.18 | 84668.2 |
| 78 | 1756.022.1-T_at | DMD | NM_000131 | Xp21.2 | 1756.022.1 | 1756.003.1 | 1756.22 | 1756.2 |
| 79 | 1264.003.1-B_at | CNN1 | NM_001299 | 19p13.2-p13.1 | 1264.003.1 | 1756.009.1 | 1264.3 | 57447.33 |
| 80 | 26289.010.1-E_at | AK5 | NM_012098 | 1p31 | 26289.010.1 | 1756.011.1 | 26289.10 | 26289.9 |
| 81 | 3861.001.1-F_at | KRT14 | NM_000526 | 17q12-q21 | 3861.001.1 | 1756.013.1 | 3861.1 | 3872.6 |
| 82 | 1908.002.1-T_at | EDN3 | NM_001729 | 20q13.2-q13.3 | 1908.002.1 | 1756.022.1 | 1908.2 | 667.21 |
| 83 | 4629.007.1-C_at | MYH11 | NM_001040125 | 16p13.11 | 4629.007.1 | 1756.022.2 | 4629.7 | 57447.27 |
| 84 | 1756.022.5-T_at | DMD | NM_000132 | Xp21.2 | 1756.022.5 | 1756.022.3 | 1756.22 | 56477.1 |
| 85 | 3815.002.4-B_at | KIT | NM_000224 | 4q11-q12 | 3815.002.4 | 1756.022.4 | 3815.2 | 26289.8 |
| 86 | 1756.022.2-B_at | DMD | NM_000133 | Xp21.2 | 1756.022.2 | 1756.022.5 | 1756.22 | 59.24 |
| 87 | 1756.027.1-B_at | DMD | NM_000134 | Xp21.2 | 1756.027.1 | 1756.024.1 | 1756.27 | 3084.4 |
| 88 | 3852.008.2-T_at | KRT5 | NM_000424 | 12q12-q13 | 3852.008.2 | 1756.026.1 | 3852.8 | 27122.14 |
| 89 | 6422.001.1-E_at | SFRP1 | NM_003012 | 8p12-p11.1 | 6422.001.1 | 1756.027.1 | 6422.1 | 286887.3 |
| 90 | 3861.022.1-F_at | KRT14 | NM_000526 | 17q12-q21 | 3861.022.1 | 1756.028.1 | 3861.22 | 3872.9 |
| 91 | 4915.011.1-D_at | NTRK2 | NM_001007097 | 9q22.1 | 4915.011.1 | 1756.029.1 | 4915.11 | 59.14 |
| 92 | 5288.001.1-F_at | PIK3C2G | NM_004570 | 12p12 | 5288.001.1 | 1756.030.2 | 5288.1 | 403340.1 |
| 93 | 3861.007.1-F_at | KRT14 | NM_000526 | 17q12-q21 | 3861.007.1 | 1908.001.1 | 3861.7 | 3852.14 |
| 94 | 3852.006.1-C_at | KRT5 | NM_000424 | 12q12-q13 | 3852.006.1 | 1908.002.1 | 3852.6 | 27122.1 |
| 95 | 9413.003.1-T_at | C9orf61 | NM_004816 | 9q21 | 9413.003.1 | 1959.002.1 | 9413.3 | 8626.5 |
| 96 | 3861.020.1-C_at | KRT14 | NM_000526 | 17q12-q21 | 3861.020.1 | 1959.003.1 | 3861.20 | 84668.4 |
| 97 | 1308.008.1-D_at | COL17A1 | NM_000500 | 10q24.3 | 1308.008.1 | 2.002.1 | 1308.8 | 57447.31 |
| 98 | 23336.001.1-T_at | DMN | NM_015288 | 15q26.3 | 23336.001.1 | 2.005.1 | 23336.1 | 3084.12 |
| 99 | 3815.001.1-F_at | KIT | NM_000225 | 4q11-q12 | 3815.001.1 | 2.013.1 | 3815.1 | 3852.5 |
| 100 | 1756.022.5-F_at | DMD | NM_000135 | Xp21.2 | 1756.022.5 | 2.018.1 | 1756.22 | 3866.3 |
| 101 | 79937.001.1-T_at | CNTNAP3 | NM_033655 | 9p13.1 | 79937.001.1 | 2.022.1 | 79937.1 | 3866.8 |
| 102 | 4915.012.1-E_at | NTRK2 | NM_001007098 | 9q22.1 | 4915.012.1 | 2.024.1 | 4915.12 | 3852.9 |
| 103 | 3861.022.1-T_at | KRT14 | NM_000526 | 17q12-q21 | 3861.022.1 | 2.025.1 | 3861.22 | 59.15 |
| 104 | 26289.005.1-T_at | AK5 | NM_012099 | 1p31 | 26289.005.1 | 2115.001.2 | 26289.5 | 79937.2 |
| 105 | 3815.002.3-B_at | KIT | NM_000226 | 4q11-q12 | 3815.002.3 | 2115.003.1 | 3815.2 | 7153.2 |
| 106 | 4311.009.1-F_at | MME | NM_000902 | 3q25.1-q25.2 | 4311.009.1 | 2115.006.1 | 4311.9 | 4281.10 |
| 107 | 26289.006.1-T_at | AK5 | NM_012100 | 1p31 | 26289.006.1 | 2115.007.1 | 26289.6 | 59.8 |
| 108 | 5288.003.1-F_at | PIK3C2G | NM_004570 | 12p12 | 5288.003.1 | 2115.008.1 | 5288.3 | 1264.7 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 109 | 4629.020.1-B_at | MYH11 | NM_001040126 | 16p13.11 | 4629.020.1 | 2115.011.1 | 4629.20 | 3084.2 |
| 110 | 26289.007.1-D_at | AK5 | NM_012101 | 1p31 | 26289.007.1 | 2115.012.1 | 26289.7 | 5137.4 |
| 111 | 3815.002.1-B_at | KIT | NM_000227 | 4q11-q12 | 3815.002.1 | 2115.014.1 | 3815.2 | 4629.22 |
| 112 | 26289.004.1-T_at | AK5 | NM_012102 | 1p31 | 26289.004.1 | 2115.015.1 | 26289.4 | 3852.13 |
| 113 | 79192.002.2-T_at | IRX1 | NM_024337 | 5p15.3 | 79192.002.2 | 2119.005.1 | 79192.2 | 59.12 |
| 114 | 4638.006.1-D_at | MYLK | NM_005965 | 3q21 | 4638.006.1 | 2119.006.1 | 4638.6 | 23336.2 |
| 115 | 3084.008.1-F_at | NRG1 | NM_004497 | 8p12 | 3084.008.1 | 221120.006.1 | 3084.8 | 3866.11 |
| 116 | 4311.001.2-T_at | MME | NM_000903 | 3q25.1-q25.2 | 4311.001.2 | 2232.014.1 | 4311.1 | 59.31 |
| 117 | 3815.002.1-D_at | KIT | NM_000228 | 4q11-q12 | 3815.002.1 | 22974.007.1 | 3815.2 | 57447.30 |
| 118 | 4629.020.1-T_at | MYH11 | NM_001040127 | 16p13.11 | 4629.020.1 | 22974.008.1 | 4629.20 | 1410.3 |
| 119 | 1756.026.1-B_at | DMD | NM_000136 | Xp21.2 | 1756.026.1 | 23092.004.1 | 1756.26 | 3866.9 |
| 120 | 3852.022.1-T_at | KRT5 | NM_000424 | 12q12-q13 | 3852.022.1 | 23194.003.1 | 3852.22 | 440421.1 |
| 121 | 4629.015.1-D_at | MYH11 | NM_001040128 | 16p13.11 | 4629.015.1 | 23266.001.3 | 4629.15 | 57447.41 |
| 122 | 26289.007.1-C_at | AK5 | NM_012103 | 1p31 | 26289.007.1 | 23266.008.1 | 26289.7 | 3872.10 |
| 123 | 23194.003.1-C_at | FBXL7 | NM_012304 | 5p15.1 | 23194.003.1 | 23266.008.2 | 23194.3 | 4629.6 |
| 124 | 3815.002.1-F_at | KIT | NM_000229 | 4q11-q12 | 3815.002.1 | 2327.002.1 | 3815.2 | 3866.12 |
| 125 | 26289.007.1-T_at | AK5 | NM_012104 | 1p31 | 26289.007.1 | 2327.002.2 | 26289.7 | 57447.21 |
| 126 | 65983.009.1-B_at | GRAMD3 | NM_023927 | 5q23.2 | 65983.009.1 | 2327.003.4 | 65983.9 | 8626.7 |
| 127 | 23336.001.1-F_at | DMN | NM_015289 | 15q26.3 | 23336.001.1 | 23284.007.1 | 23336.1 | 72.1 |
| 128 | 1410.007.2-B_at | CRYAB | NM_001885 | 11q22.3-q23.1 | 1410.007.2 | 23321.014.1 | 1410.7 | 3866.6 |
| 129 | 1756.029.1-F_at | DMD | NM_000137 | Xp21.2 | 1756.029.1 | 23336.001.1 | 1756.29 | 65983.8 |
| 130 | 7373.003.6-C_at | COL14A1 | NM_021110 | 8q23 | 7373.003.6 | 23336.002.1 | 7373.3 | 65983.13 |
| 131 | 10010.002.1-E_at | TANK | NM_004180 | 2q24-q31 | 10010.002.1 | 23336.003.1 | 10010.2 | 27122.7 |
| 132 | 59.026.1-B_at | ACTA2 | NM_001613 | 10q23.3 | 59.026.1 | 2335.002.1 | 59.26 | 59.9 |
| 133 | 4915.011.1-F_at | NTRK2 | NM_001007099 | 9q22.1 | 4915.011.1 | 2335.005.1 | 4915.11 | 59.23 |
| 134 | 3872.007.1-D_at | KRT17 | NM_000422 | 17q12-q21 | 3872.007.1 | 2335.006.1 | 3872.7 | 1908.1 |
| 135 | 26289.002.1-D_at | AK5 | NM_012105 | 1p31 | 26289.002.1 | 2335.006.2 | 26289.2 | 4915.8 |
| 136 | 84668.002.1-C_at | FAM126A | NM_032581 | 7p15.3 | 84668.002.1 | 2335.009.1 | 84668.2 | 57447.35 |
| 137 | 1756.002.2-T_at | DMD | NM_000138 | Xp21.2 | 1756.002.2 | 2335.013.1 | 1756.2 | 667.22 |
| 138 | 57447.033.1-C_at | NDRG2 | NM_016250 | 14q11.2 | 57447.033.1 | 2335.016.1 | 57447.33 | 2115.1 |
| 139 | 26289.009.1-E_at | AK5 | NM_012106 | 1p31 | 26289.009.1 | 2335.017.1 | 26289.9 | 27303.4 |
| 140 | 3872.006.1-F_at | KRT17 | NM_000422 | 17q12-q21 | 3872.006.1 | 2335.024.2 | 3872.6 | 59.3 |
| 141 | 3861.022.1-D_at | KRT14 | NM_000526 | 17q12-q21 | 3861.022.1 | 2335.025.1 | 3861.22 | 65983.4 |
| 142 | 3861.020.1-B_at | KRT14 | NM_000526 | 17q12-q21 | 3861.020.1 | 2335.025.3 | 3861.20 | 26289.13 |
| 143 | 667.021.1-B_at | DST | NM_001723 | 6p12.1 | 667.021.1 | 2335.027.1 | 667.21 | 3866.4 |
| 144 | 57447.027.1-F_at | NDRG2 | NM_016251 | 14q11.2 | 57447.027.1 | 2335.028.1 | 57447.27 | 57447.37 |
| 145 | 56477.001.1-D_at | CCL28 | NM_148672 | 5p12 | 56477.001.1 | 2335.032.1 | 56477.1 | 59.22 |
| 146 | 26289.008.1-F_at | AK5 | NM_012107 | 1p31 | 26289.008.1 | 2335.035.1 | 26289.8 | 147495.8 |
| 147 | 59.024.2-D_at | ACTA2 | NM_001613 | 10q23.3 | 59.024.2 | 2335.045.1 | 59.24 | 2.18 |
| 148 | 4629.005.1-T_at | MYH11 | NM_001040129 | 16p13.11 | 4629.005.1 | 2335.053.1 | 4629.5 | 140807.3 |
| 149 | 3815.002.1-T_at | KIT | NM_000230 | 4q11-q12 | 3815.002.1 | 23650.003.1 | 3815.2 | 2115.8 |
| 150 | 23336.001.1-B_at | DMN | NM_015290 | 15q26.3 | 23336.001.1 | 23650.005.1 | 23336.1 | 57447.34 |
| 151 | 3084.004.2-F_at | NRG1 | NM_004498 | 8p12 | 3084.004.2 | 23650.011.1 | 3084.4 | 3866.1 |
| 152 | 27122.014.2-T_at | DKK3 | NM_001018057 | 11p15.2 | 27122.014.2 | 23650.011.2 | 27122.14 | 1959.3 |
| 153 | 26289.008.1-C_at | AK5 | NM_012108 | 1p31 | 26289.008.1 | 23650.019.1 | 26289.8 | 389432.2 |
| 154 | 286887.003.2-B | KRT6C | NM_173086 | 12q13.13 | 286887.003.2 | 23650.020.1 | 286887.3 | 389734.1 |
| 155 | 4629.005.1-F_at | MYH11 | NM_001040130 | 16p13.11 | 4629.005.1 | 24137.004.1 | 4629.5 | 3855.1 |
| 156 | 3872.009.1-T_at | KRT17 | NM_000422 | 17q12-q21 | 3872.009.1 | 244.003.1 | 3872.9 | 3084.6 |
| 157 | 59.014.2-D_at | ACTA2 | NM_001613 | 10q23.3 | 59.014.2 | 244.011.1 | 59.14 | 2115.11 |
| 158 | 403340.001.2-B | MGC70870 | NM_203481 | — | 403340.001.2 | 244.012.1 | 403340.1 | 65983.5 |
| 159 | 3852.014.1-F_at | KRT5 | NM_000424 | 12q12-q13 | 3852.014.1 | 2487.001.1 | 3852.14 | 2119.6 |
| 160 | 27122.001.1-T_at | DKK3 | NM_001018058 | 11p15.2 | 27122.001.1 | 2568.001.1 | 27122.1 | 3866.7 |
| 161 | 3815.002.3-T_at | KIT | NM_000231 | 4q11-q12 | 3815.002.3 | 2568.001.2 | 3815.2 | 3866.13 |
| 162 | 3852.008.1-E_at | KRT5 | NM_000424 | 12q12-q13 | 3852.008.1 | 2568.002.1 | 3852.8 | 27122.13 |
| 163 | 26289.012.1-T_at | AK5 | NM_012109 | 1p31 | 26289.012.1 | 2568.002.2 | 26289.12 | 27122.6 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 164 | 26289.007.1-F_at | AK5 | NM_012110 | 1p31 | 26289.007.1 | 2568.003.1 | 26289.7 | 4240.4 |
| 165 | 4638.006.1-T_at | MYLK | NM_005966 | 3q21 | 4638.006.1 | 2568.003.2 | 4638.6 | 3866.10 |
| 166 | 8626.005.1-B_at | TP63 | NM_003722 | 3q28 | 8626.005.1 | 2568.005.1 | 8626.5 | 7018.29 |
| 167 | 3815.002.4-T_at | KIT | NM_000232 | 4q11-q12 | 3815.002.4 | 2568.005.2 | 3815.2 | 1410.2 |
| 168 | 84668.004.1-F_at | FAM126A | NM_032581 | 7p15.3 | 84668.004.1 | 2568.006.1 | 84668.4 | 59.34 |
| 169 | 3872.007.1-F_at | KRT17 | NM_000422 | 17q12-q21 | 3872.007.1 | 25802.003.1 | 3872.7 | 27122.19 |
| 170 | 57447.031.1-E_at | NDRG2 | NM_016252 | 14q11.2 | 57447.031.1 | 25802.004.1 | 57447.31 | 5156.1 |
| 171 | 3084.012.3-T_at | NRG1 | NM_004499 | 8p12 | 3084.012.3 | 25802.008.1 | 3084.12 | 57447.10 |
| 172 | 3852.005.1-T_at | KRT5 | NM_000424 | 12q12-q13 | 3852.005.1 | 2582.007.2 | 3852.5 | 358.18 |
| 173 | 84417.001.2-T_at | C2orf40 | NM_032411 | 2q12.2 | 84417.001.2 | 25925.001.1 | 84417.1 | 7373.1 |
| 174 | 3866.003.2-T_at | KRT15 | NM_002275 | 17q21.2 | 3866.003.2 | 25925.006.1 | 3866.3 | 57447.29 |
| 175 | 3866.008.1-C_at | KRT15 | NM_002275 | 17q21.2 | 3866.008.1 | 25925.007.1 | 3866.8 | 79068.10 |
| 176 | 3852.009.1-F_at | KRT5 | NM_000424 | 12q12-q13 | 3852.009.1 | 25925.008.1 | 3852.9 | 59.4 |
| 177 | 59.015.1-B_at | ACTA2 | NM_001613 | 10q23.3 | 59.015.1 | 25925.009.1 | 59.15 | 2115.12 |
| 178 | 79937.002.1-F_at | CNTNAP3 | NM_033655 | 9p13.1 | 79937.002.1 | 25925.011.1 | 79937.2 | 2115.7 |
| 179 | 7153.002.6-F_at | TOP2A | NM_001067 | 17q21-q22 | 7153.002.6 | 259266.003.1 | 7153.2 | 59.40 |
| 180 | 4281.010.1-B_at | MID1 | NM_000381 | Xp22 | 4281.010.1 | 26289.002.1 | 4281.10 | 130497.1 |
| 181 | 59.008.1-B_at | ACTA2 | NM_001613 | 10q23.3 | 59.008.1 | 26289.003.1 | 59.8 | 140885.14 |
| 182 | 1264.007.1-T_at | CNN1 | NM_001299 | 19p13.2-p13.1 | 1264.007.1 | 26289.004.1 | 1264.7 | 3866.5 |
| 183 | 3868.004.1-T_at | KRT16 | NM_005557 | 17q12-q21 | 3868.004.1 | 26289.005.1 | 3868.4 | 8404.28 |
| 184 | 3084.002.1-F_at | NRG1 | NM_004500 | 8p12 | 3084.002.1 | 26289.006.1 | 3084.2 | 3860.7 |
| 185 | 5137.004.2-T_at | PDE1C | NM_005020 | 7p15.1-p14.3 | 5137.004.2 | 26289.007.1 | 5137.4 | 4638.3 |
| 186 | 4629.022.1-T_at | MYH11 | NM_001040131 | 16p13.11 | 4629.022.1 | 26289.008.1 | 4629.22 | 25925.8 |
| 187 | 4915.011.1-T_at | NTRK2 | NM_001007100 | 9q22.1 | 4915.011.1 | 26289.009.1 | 4915.11 | 23650.11 |
| 188 | 3852.013.1-E_at | KRT5 | NM_000424 | 12q12-q13 | 3852.013.1 | 26289.010.1 | 3852.13 | 3852.17 |
| 189 | 59.012.2-T_at | ACTA2 | NM_001613 | 10q23.3 | 59.012.2 | 26289.012.1 | 59.12 | 4915.5 |
| 190 | 59.015.1-F_at | ACTA2 | NM_001613 | 10q23.3 | 59.015.1 | 26289.013.1 | 59.15 | 1756.3 |
| 191 | 4638.006.2-T_at | MYLK | NM_005967 | 3q21 | 4638.006.2 | 2707.002.1 | 4638.6 | 4638.14 |
| 192 | 23336.002.1-B_at | DMN | NM_015291 | 15q26.3 | 23336.002.1 | 27122.001.1 | 23336.2 | 2707.2 |
| 193 | 3868.005.1-C_at | KRT16 | NM_005557 | 17q12-q21 | 3868.005.1 | 27122.002.1 | 3868.5 | 4638.11 |
| 194 | 3866.011.2-D_at | KRT15 | NM_002275 | 17q21.2 | 3866.011.2 | 27122.006.1 | 3866.11 | 7373.2 |
| 195 | 56477.001.1-T_at | CCL28 | NM_148672 | 5p12 | 56477.001.1 | 27122.006.2 | 56477.1 | 5608.2 |
| 196 | 3815.001.1-T_at | KIT | NM_000233 | 4q11-q12 | 3815.001.1 | 27122.007.1 | 3815.1 | 1756.13 |
| 197 | 4311.001.1-T_at | MME | NM_000904 | 3q25.1-q25.2 | 4311.001.1 | 27122.013.1 | 4311.1 | 2115.6 |
| 198 | 1264.003.1-D_at | CNN1 | NM_001299 | 19p13.2-p13.1 | 1264.003.1 | 27122.014.1 | 1264.3 | 6376.1 |
| 199 | 59.031.1-T_at | ACTA2 | NM_001613 | 10q23.3 | 59.031.1 | 27122.014.2 | 59.31 | 8404.2 |
| 200 | 57447.030.1-B_at | NDRG2 | NM_016253 | 14q11.2 | 57447.030.1 | 27122.016.1 | 57447.30 | 1264.6 |
| 201 | 1410.003.2-B_at | CRYAB | NM_001885 | 11q22.3-q23.1 | 1410.003.2 | 27122.017.1 | 1410.3 | 25925.1 |
| 202 | 3866.009.2-D_at | KRT15 | NM_002275 | 17q21.2 | 3866.009.2 | 27122.018.1 | 3866.9 | 8404.35 |
| 203 | 59.026.1-T_at | ACTA2 | NM_001613 | 10q23.3 | 59.026.1 | 27122.019.1 | 59.26 | 2.22 |
| 204 | 440421.001.1-T | | | | 440421.001.1 | 27303.004.1 | 440421.1 | 27122.16 |
| 205 | 1756.022.4-D_at | DMD | NM_000139 | Xp21.2 | 1756.022.4 | 2824.001.2 | 1756.22 | 57447.25 |
| 206 | 65983.009.1-D_at | GRAMD3 | NM_023927 | 5q23.2 | 65983.009.1 | 285203.001.2 | 65983.9 | 1717.7 |
| 207 | 57447.041.1-T_at | NDRG2 | NM_016254 | 14q11.2 | 57447.041.1 | 286887.003.2 | 57447.41 | 9768.4 |
| 208 | 3872.010.2-D_at | KRT17 | NM_000422 | 17q12-q21 | 3872.010.2 | 2893.002.2 | 3872.10 | 1410.4 |
| 209 | 4629.006.2-T_at | MYH11 | NM_001040132 | 16p13.11 | 4629.006.2 | 2893.006.2 | 4629.6 | 2327.2 |
| 210 | 3861.018.1-F_at | KRT14 | NM_000526 | 17q12-q21 | 3861.018.1 | 29089.001.1 | 3861.18 | 1308.4 |
| 211 | 3815.002.2-T_at | KIT | NM_000234 | 4q11-q12 | 3815.002.2 | 29089.003.1 | 3815.2 | 2568.5 |
| 212 | 3866.012.2-D_at | KRT15 | NM_002275 | 17q21.2 | 3866.012.2 | 29127.002.1 | 3866.12 | 2568.1 |
| 213 | 57447.021.1-D_at | NDRG2 | NM_016255 | 14q11.2 | 57447.021.1 | 29127.007.1 | 57447.21 | 2893.6 |
| 214 | 59.015.1-T_at | ACTA2 | NM_001613 | 10q23.3 | 59.015.1 | 29127.013.1 | 59.15 | 3872.16 |
| 215 | 8626.007.1-F_at | TP63 | NM_003722 | 3q28 | 8626.007.1 | 29127.019.1 | 8626.7 | 9413.6 |
| 216 | 5288.001.1-B_at | PIK3C2G | NM_004570 | 12p12 | 5288.001.1 | 29127.019.2 | 5288.1 | 72.5 |
| 217 | 72.001.1-B_at | ACTG2 | NM_001615 | 2p13.1 | 72.001.1 | 29127.022.1 | 72.1 | 27122.18 |
| 218 | 3866.006.2-D_at | KRT15 | NM_002275 | 17q21.2 | 3866.006.2 | 2938.001.1 | 3866.6 | 7153.5 |
| 219 | 3852.004.1-T_at | KRT5 | NM_000424 | 12q12-q13 | 3852.004.1 | 2982.002.1 | 3852.4 | 7018.26 |
| 220 | 4629.016.1-F_at | MYH11 | NM_001040133 | 16p13.11 | 4629.016.1 | 2982.012.1 | 4629.16 | 7402.14 |
| 221 | 4629.007.1-T_at | MYH11 | NM_001040134 | 16p13.11 | 4629.007.1 | 2982.013.2 | 4629.7 | 140446.4 |
| 222 | 65983.008.1-T_at | GRAMD3 | NM_023927 | 5q23.2 | 65983.008.1 | 2982.014.1 | 65983.8 | 59.38 |
| 223 | 65983.013.1-F_at | GRAMD3 | NM_023927 | 5q23.2 | 65983.013.1 | 2982.015.1 | 65983.13 | 4240.9 |
| 224 | 3084.004.1-F_at | NRG1 | NM_004501 | 8p12 | 3084.004.1 | 2995.001.1 | 3084.4 | 57447.8 |
| 225 | 27122.007.1-F_at | DKK3 | NM_001018059 | 11p15.2 | 27122.007.1 | 29997.008.1 | 27122.7 | 2582.7 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 226 | 3866.008.1-D_at | KRT15 | NM_002275 | 17q21.2 | 3866.008.1 | 29997.012.1 | 3866.8 | 4638.9 |
| 227 | 26289.009.1-T_at | AK5 | NM_012111 | 1p31 | 26289.009.1 | 29997.016.1 | 26289.9 | 3861.23 |
| 228 | 59.009.1-B_at | ACTA2 | NM_001613 | 10q23.3 | 59.009.1 | 301.004.1 | 59.9 | 5858.3 |
| 229 | 4629.010.1-D_at | MYH11 | NM_001040135 | 16p13.11 | 4629.010.1 | 301.005.1 | 4629.10 | 147495.5 |
| 230 | 59.023.1-B_at | ACTA2 | NM_001613 | 10q23.3 | 59.023.1 | 301.008.1 | 59.23 | 4915.4 |
| 231 | 26289.002.1-F_at | AK5 | NM_012112 | 1p31 | 26289.002.1 | 301.013.1 | 26289.2 | 8626.2 |
| 232 | 1908.001.1-T_at | EDN3 | NM_001730 | 20q13.2-q13.3 | 1908.001.1 | 301.015.1 | 1908.1 | 59.42 |
| 233 | 4915.008.1-F_at | NTRK2 | NM_001007101 | 9q22.1 | 4915.008.1 | 3084.002.1 | 4915.8 | 4833.4 |
| 234 | 23336.002.1-T_at | DMN | NM_015292 | 15q26.3 | 23336.002.1 | 3084.004.1 | 23336.2 | 2568.6 |
| 235 | 3861.008.1-C_at | KRT14 | NM_000526 | 17q12-q21 | 3861.008.1 | 3084.004.2 | 3861.8 | 57447.4 |
| 236 | 3861.008.1-D_at | KRT14 | NM_000526 | 17q12-q21 | 3861.008.1 | 3084.005.1 | 3861.8 | 27122.17 |
| 237 | 57447.035.1-E_at | NDRG2 | NM_016256 | 14q11.2 | 57447.035.1 | 3084.006.1 | 57447.35 | 59.33 |
| 238 | 3861.018.1-C_at | KRT14 | NM_000526 | 17q12-q21 | 3861.018.1 | 3084.007.1 | 3861.18 | 27122.2 |
| 239 | 1308.003.1-B_at | COL17A1 | NM_000501 | 10q24.3 | 1308.003.1 | 3084.008.1 | 1308.3 | 3880.11 |
| 240 | 667.022.1-B_at | DST | NM_001724 | 6p12.1 | 667.022.1 | 3084.009.1 | 667.22 | 3872.14 |
| 241 | 3866.011.2-T_at | KRT15 | NM_002275 | 17q21.2 | 3866.011.2 | 3084.010.1 | 3866.11 | 162605.1 |
| 242 | 2115.001.2-F_at | ETV1 | NM_004956 | 7p21.3 | 2115.001.2 | 3084.011.1 | 2115.1 | 5858.1 |
| 243 | 3866.011.2-B_at | KRT15 | NM_002275 | 17q21.2 | 3866.011.2 | 3084.012.1 | 3866.11 | 65983.10 |
| 244 | 26289.010.1-T_at | AK5 | NM_012113 | 1p31 | 26289.010.1 | 3084.012.2 | 26289.10 | 8404.5 |
| 245 | 27303.004.1-E_at | RBMS3 | NM_001003792 | 3p24-p23 | 27303.004.1 | 3084.012.3 | 27303.4 | 2487.1 |
| 246 | 59.003.1-B_at | ACTA2 | NM_001613 | 10q23.3 | 59.003.1 | 3178.003.1 | 59.3 | 147495.9 |
| 247 | 4311.009.1-C_at | MME | NM_000905 | 3q25.1-q25.2 | 4311.009.1 | 3204.001.1 | 4311.9 | 65983.3 |
| 248 | 7373.003.6-B_at | COL14A1 | NM_021110 | 8q23 | 7373.003.6 | 338707.006.1 | 7373.3 | 1717.9 |
| 249 | 65983.004.1-T_at | GRAMD3 | NM_023927 | 5q23.2 | 65983.004.1 | 339965.001.2 | 65983.4 | 140885.11 |
| 250 | 26289.013.1-D_at | AK5 | NM_012114 | 1p31 | 26289.013.1 | 3426.001.1 | 26289.13 | 3832.2 |
| 251 | 3866.004.1-F_at | KRT15 | NM_002275 | 17q21.2 | 3866.004.1 | 3426.002.1 | 3866.4 | 3880.5 |
| 252 | 56477.001.1-F_at | CCL28 | NM_148672 | 5p12 | 56477.001.1 | 3426.002.2 | 56477.1 | 6595.12 |
| 253 | 57447.037.1-F_at | NDRG2 | NM_016257 | 14q11.2 | 57447.037.1 | 3459.005.1 | 57447.37 | 9768.5 |
| 254 | 59.022.2-T_at | ACTA2 | NM_001613 | 10q23.3 | 59.022.2 | 3479.003.1 | 59.22 | 285203.1 |
| 255 | 147495.008.1-F | APCDD1 | NM_153000 | 18p11.22 | 147495.008.1 | 358.012.1 | 147495.8 | 147495.6 |
| 256 | 2.018.1-T_at | A2M | NM_000014 | 12p13.3-p12.3 | 2.018.1 | 358.018.1 | 2.18 | 1959.2 |
| 257 | 140807.003.1-E | KRT72 | NM_080747 | 12q13.13 | 140807.003.1 | 3815.001.1 | 140807.3 | 7018.14 |
| 258 | 65983.009.1-T_at | GRAMD3 | NM_023927 | 5q23.2 | 65983.009.1 | 3815.002.1 | 65983.9 | 5858.4 |
| 259 | 84668.002.1-F_at | FAM126A | NM_032581 | 7p15.3 | 84668.002.1 | 3815.002.2 | 84668.2 | 8404.8 |
| 260 | 3872.007.1-C_at | KRT17 | NM_000422 | 17q12-q21 | 3872.007.1 | 3815.002.3 | 3872.7 | 4240.11 |
| 261 | 2115.008.1-T_at | ETV1 | NM_004956 | 7p21.3 | 2115.008.1 | 3815.002.4 | 2115.8 | 94274.2 |
| 262 | 65983.004.2-T_at | GRAMD3 | NM_023927 | 5q23.2 | 65983.004.2 | 3832.002.1 | 65983.4 | 4638.15 |
| 263 | 57447.034.1-D_at | NDRG2 | NM_016258 | 14q11.2 | 57447.034.1 | 3852.004.1 | 57447.34 | 57447.43 |
| 264 | 3866.001.1-F_at | KRT15 | NM_002275 | 17q21.2 | 3866.001.1 | 3852.005.1 | 3866.1 | 59.39 |
| 265 | 3866.008.1-T_at | KRT15 | NM_002275 | 17q21.2 | 3866.008.1 | 3852.006.1 | 3866.8 | 25802.3 |
| 266 | 1959.003.1-C_at | EGR2 | NM_000399 | 10q21.1 | 1959.003.1 | 3852.008.1 | 1959.3 | 57447.17 |
| 267 | 389432.002.1-T | SAMD5 | NM_001030060 | 6q24.3 | 389432.002.1 | 3852.008.2 | 389432.2 | 7018.28 |
| 268 | 389734.001.1-T | | | | 389734.001.1 | 3852.009.1 | 389734.1 | 57447.12 |
| 269 | 3855.001.2-D_at | KRT7 | NM_005556 | 12q12-q13 | 3855.001.2 | 3852.012.2 | 3855.1 | 57447.6 |
| 270 | 3866.003.1-T_at | KRT15 | NM_002275 | 17q21.2 | 3866.003.1 | 3852.013.1 | 3866.3 | 9493.6 |
| 271 | 3084.006.1-F_at | NRG1 | NM_004502 | 8p12 | 3084.006.1 | 3852.014.1 | 3084.6 | 9493.4 |
| 272 | 4915.008.1-B_at | NTRK2 | NM_001007102 | 9q22.1 | 4915.008.1 | 3852.017.1 | 4915.8 | 7169.15 |
| 273 | 2115.011.1-T_at | ETV1 | NM_004956 | 7p21.3 | 2115.011.1 | 3852.020.1 | 2115.11 | 57451.1 |
| 274 | 65983.005.1-T_at | GRAMD3 | NM_023927 | 5q23.2 | 65983.005.1 | 3852.021.1 | 65983.5 | 8404.4 |
| 275 | 84668.004.1-T_at | FAM126A | NM_032581 | 7p15.3 | 84668.004.1 | 3852.022.1 | 84668.4 | 3855.4 |
| 276 | 59.015.2-T_at | ACTA2 | NM_001613 | 10q23.3 | 59.015.2 | 3852.023.1 | 59.15 | 9452.1 |
| 277 | 2119.006.1-B_at | ETV5 | NM_004454 | 3q28 | 2119.006.1 | 3855.001.2 | 2119.6 | 57447.40 |
| 278 | 4638.006.2-F_at | MYLK | NM_005968 | 3q21 | 4638.006.2 | 3855.004.2 | 4638.6 | 3426.1 |
| 279 | 3866.007.2-D_at | KRT15 | NM_002275 | 17q21.2 | 3866.007.2 | 3860.007.1 | 3866.7 | 10253.1 |
| 280 | 59.014.1-T_at | ACTA2 | NM_001613 | 10q23.3 | 59.014.1 | 3860.008.1 | 59.14 | 9073.1 |
| 281 | 3866.001.2-F_at | KRT15 | NM_002275 | 17q21.2 | 3866.001.2 | 3861.001.1 | 3866.1 | 51201.5 |
| 282 | 1308.008.1-B_at | COL17A1 | NM_000502 | 10q24.3 | 1308.008.1 | 3861.007.1 | 1308.8 | 9477.6 |
| 283 | 59.026.1-F_at | ACTA2 | NM_001613 | 10q23.3 | 59.026.1 | 3861.008.1 | 59.26 | 57447.28 |
| 284 | 3866.013.1-T_at | KRT15 | NM_002275 | 17q21.2 | 3866.013.1 | 3861.013.1 | 3866.13 | 25925.7 |
| 285 | 1264.007.1-F_at | CNN1 | NM_001299 | 19p13.2-p13.1 | 1264.007.1 | 3861.018.1 | 1264.7 | 4281.8 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 286 | 3866.007.2-T_at | KRT15 | NM_002275 | 17q21.2 | 3866.007.2 | 3861.019.1 | 3866.7 | 90231.1 |
| 287 | 27122.013.1-T_at | DKK3 | NM_001018060 | 11p15.2 | 27122.013.1 | 3861.020.1 | 27122.13 | 358.12 |
| 288 | 27122.006.2-T_at | DKK3 | NM_001018061 | 11p15.2 | 27122.006.2 | 3861.022.1 | 27122.6 | 3852.21 |
| 289 | 3866.006.2-T_at | KRT15 | NM_002275 | 17q21.2 | 3866.006.2 | 3861.023.1 | 3866.6 | 57447.48 |
| 290 | 3866.009.2-T_at | KRT15 | NM_002275 | 17q21.2 | 3866.009.2 | 3866.001.1 | 3866.9 | 7018.25 |
| 291 | 4240.004.1-D_at | MFGE8 | NM_005928 | 15q25 | 4240.004.1 | 3866.001.2 | 4240.4 | 5608.4 |
| 292 | 3866.010.1-C_at | KRT15 | NM_002275 | 17q21.2 | 3866.010.1 | 3866.002.1 | 3866.10 | 4306.2 |
| 293 | 3866.009.2-B_at | KRT15 | NM_002275 | 17q21.2 | 3866.009.2 | 3866.003.1 | 3866.9 | 4288.4 |
| 294 | 3866.009.1-T_at | KRT15 | NM_002275 | 17q21.2 | 3866.009.1 | 3866.003.2 | 3866.9 | 57447.2 |
| 295 | 4629.006.1-T_at | MYH11 | NM_001040136 | 16p13.11 | 4629.006.1 | 3866.004.1 | 4629.6 | 4281.18 |
| 296 | 7018.029.1-B_at | TF | NM_001063 | 3q22.1 | 7018.029.1 | 3866.005.1 | 7018.29 | 10144.20 |
| 297 | 1410.002.2-B_at | CRYAB | NM_001885 | 11q22.3-q23.1 | 1410.002.2 | 3866.006.1 | 1410.2 | 6876.16 |
| 298 | 3866.012.1-T_at | KRT15 | NM_002275 | 17q21.2 | 3866.012.1 | 3866.006.2 | 3866.12 | 51203.4 |
| 299 | 59.034.2-D_at | ACTA2 | NM_001613 | 10q23.3 | 59.034.2 | 3866.007.1 | 59.34 | 2335.28 |
| 300 | 27122.019.1-F_at | DKK3 | NM_001018062 | 11p15.2 | 27122.019.1 | 3866.007.2 | 27122.19 | 81557.6 |
| 301 | 5156.001.1-T_at | PDGFRA | NM_006206 | 4q11-q13 | 5156.001.1 | 3866.008.1 | 5156.1 | 3866.2 |
| 302 | 389734.001.2-T | | | | 389734.001.2 | 3866.009.1 | 389734.1 | 55107.6 |
| 303 | 27122.014.1-T_at | DKK3 | NM_001018063 | 11p15.2 | 27122.014.1 | 3866.009.2 | 27122.14 | 57447.9 |
| 304 | 57447.010.3-T_at | NDRG2 | NM_016259 | 14q11.2 | 57447.010.3 | 3866.010.1 | 57447.10 | 2115.15 |
| 305 | 358.018.1-F_at | AQP1 | NM_198098 | 7p14 | 358.018.1 | 3866.011.1 | 358.18 | 8404.1 |
| 306 | 3866.006.1-T_at | KRT15 | NM_002275 | 17q21.2 | 3866.006.1 | 3866.011.2 | 3866.6 | 57447.24 |
| 307 | 7373.001.1-T_at | COL14A1 | NM_021110 | 8q23 | 7373.001.1 | 3866.012.1 | 7373.1 | 79608.2 |
| 308 | 26289.012.1-B_at | AK5 | NM_012115 | 1p31 | 26289.012.1 | 3866.012.2 | 26289.12 | 8404.23 |
| 309 | 57447.029.1-T_at | NDRG2 | NM_016260 | 14q11.2 | 57447.029.1 | 3866.013.1 | 57447.29 | 3426.2 |
| 310 | 358.018.1-B_at | AQP1 | NM_198098 | 7p14 | 358.018.1 | 3868.004.1 | 358.18 | 2335.27 |
| 311 | 79068.010.1-B_at | FTO | NM_001080432 | 16q12.2 | 79068.010.1 | 3868.005.1 | 79068.10 | 11065.9 |
| 312 | 59.024.1-B_at | ACTA2 | NM_001613 | 10q23.3 | 59.024.1 | 3872.005.1 | 59.24 | 140885.13 |
| 313 | 59.004.1-B_at | ACTA2 | NM_001613 | 10q23.3 | 59.004.1 | 3872.006.1 | 59.4 | 25802.4 |
| 314 | 3866.011.1-T_at | KRT15 | NM_002275 | 17q21.2 | 3866.011.1 | 3872.007.1 | 3866.11 | 5156.5 |
| 315 | 3866.013.1-E_at | KRT15 | NM_002275 | 17q21.2 | 3866.013.1 | 3872.009.1 | 3866.13 | 25802.8 |
| 316 | 3866.010.1-D_at | KRT15 | NM_002275 | 17q21.2 | 3866.010.1 | 3872.010.2 | 3866.10 | 7169.22 |
| 317 | 59.004.1-T_at | ACTA2 | NM_001613 | 10q23.3 | 59.004.1 | 3872.014.1 | 59.4 | 23266.1 |
| 318 | 2115.012.1-T_at | ETV1 | NM_004956 | 7p21.3 | 2115.012.1 | 3872.016.1 | 2115.12 | 29127.19 |
| 319 | 2.018.1-D_at | A2M | NM_000014 | 12p13.3-p12.3 | 2.018.1 | 3872.018.1 | 2.18 | 10253.4 |
| 320 | 2115.007.1-T_at | ETV1 | NM_004956 | 7p21.3 | 2115.007.1 | 3880.005.1 | 2115.7 | 10124.2 |
| 321 | 59.040.1-T_at | ACTA2 | NM_001613 | 10q23.3 | 59.040.1 | 3880.011.1 | 59.40 | 8404.32 |
| 322 | 130497.001.2-T | OSR1 | NM_145260 | 2p24.1 | 130497.001.2 | 389432.002.1 | 130497.1 | 84441.2 |
| 323 | 140885.014.1-T | SIRPA | NM_001040022 | 20p15 | 140885.014.1 | 389734.001.1 | 140885.14 | 2.13 |
| 324 | 3866.005.1-F_at | KRT15 | NM_002275 | 17q21.2 | 3866.005.1 | 389734.002.1 | 3866.5 | 2.24 |
| 325 | 7373.003.3-F_at | COL14A1 | NM_021110 | 8q23 | 7373.003.3 | 399687.001.1 | 7373.3 | 1756.9 |
| 326 | 8404.028.1-F_at | SPARCL1 | NM_004684 | 4q22.1 | 8404.028.1 | 403340.001.2 | 8404.28 | 7091.14 |
| 327 | 3860.007.1-D_at | KRT13 | NM_002274 | 17q12-q21.2 | 3860.007.1 | 4094.001.1 | 3860.7 | 115207.2 |
| 328 | 4638.003.1-C_at | MYLK | NM_005969 | 3q21 | 4638.003.1 | 4094.002.1 | 4638.3 | 4281.1 |
| 329 | 3872.009.1-E_at | KRT17 | NM_000422 | 17q12-q21 | 3872.009.1 | 4147.004.1 | 3872.9 | 57447.44 |
| 330 | 59.004.2-T_at | ACTA2 | NM_001613 | 10q23.3 | 59.004.2 | 4147.005.2 | 59.4 | 8626.6 |
| 331 | 3872.006.1-C_at | KRT17 | NM_000422 | 17q12-q21 | 3872.006.1 | 4147.011.1 | 3872.6 | 57447.51 |
| 332 | 3866.005.1-C_at | KRT15 | NM_002275 | 17q21.2 | 3866.005.1 | 4147.012.1 | 3866.5 | 1063.1 |
| 333 | 25925.008.1-T_at | ZNF521 | NM_015461 | 18q11.2 | 25925.008.1 | 4240.001.1 | 25925.8 | 1308.1 |
| 334 | 23650.011.2-T_at | TRIM29 | NM_012101 | 11q22-q23 | 23650.011.2 | 4240.004.1 | 23650.11 | 2115.14 |
| 335 | 3866.012.2-T_at | KRT15 | NM_002275 | 17q21.2 | 3866.012.2 | 4240.009.1 | 3866.12 | 5284.4 |
| 336 | 3852.017.1-D_at | KRT5 | NM_000424 | 12q12-q13 | 3852.017.1 | 4240.011.1 | 3852.17 | 2982.2 |
| 337 | 4915.005.1-T_at | NTRK2 | NM_001007103 | 9q22.1 | 4915.005.1 | 4240.011.3 | 4915.5 | 57447.47 |
| 338 | 4638.003.1-B_at | MYLK | NM_005970 | 3q21 | 4638.003.1 | 4240.015.1 | 4638.3 | 5803.6 |
| 339 | 1756.003.1-B_at | DMD | NM_000140 | Xp21.2 | 1756.003.1 | 4281.001.1 | 1756.3 | 57447.39 |
| 340 | 4638.006.1-F_at | MYLK | NM_005971 | 3q21 | 4638.006.1 | 4281.008.2 | 4638.6 | 6876.11 |
| 341 | 57447.035.1-F_at | NDRG2 | NM_016261 | 14q11.2 | 57447.035.1 | 4281.009.1 | 57447.35 | 9768.2 |
| 342 | 4638.014.1-T_at | MYLK | NM_005972 | 3q21 | 4638.014.1 | 4281.010.1 | 4638.14 | 140885.10 |
| 343 | 7373.003.4-T_at | COL14A1 | NM_021110 | 8q23 | 7373.003.4 | 4281.012.1 | 7373.3 | 4638.20 |
| 344 | 27122.014.2-D_at | DKK3 | NM_001018064 | 11p15.2 | 27122.014.2 | 4281.012.2 | 27122.14 | 7373.4 |
| 345 | 3866.007.1-T_at | KRT15 | NM_002275 | 17q21.2 | 3866.007.1 | 4281.014.1 | 3866.7 | 4281.15 |
| 346 | 2707.002.1-E_at | GJB3 | NM_001005752 | 1p34 | 2707.002.1 | 4281.015.1 | 2707.2 | 8404.13 |
| 347 | 59.024.1-T_at | ACTA2 | NM_001613 | 10q23.3 | 59.024.1 | 4281.018.1 | 59.24 | 90293.1 |
| 348 | 23650.011.1-T_at | TRIM29 | NM_012101 | 11q22-q23 | 23650.011.1 | 4281.023.1 | 23650.11 | 2335.6 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 349 | 4638.011.1-F_at | MYLK | NM_005973 | 3q21 | 4638.011.1 | 4288.004.1 | 4638.11 | 57447.22 |
| 350 | 7373.002.1-F_at | COL14A1 | NM_021110 | 8q23 | 7373.002.1 | 4288.005.1 | 7373.2 | 8404.30 |
| 351 | 3866.013.1-F_at | KRT15 | NM_002275 | 17q21.2 | 3866.013.1 | 4288.006.1 | 3866.13 | 5803.2 |
| 352 | 5608.002.1-T_at | MAP2K6 | NM_002758 | 17q24.3 | 5608.002.1 | 4288.006.2 | 5608.2 | 84441.5 |
| 353 | 3866.001.1-C_at | KRT15 | NM_002275 | 17q21.2 | 3866.001.1 | 4288.007.1 | 3866.1 | 7091.15 |
| 354 | 1756.013.1-B_at | DMD | NM_000141 | Xp21.2 | 1756.013.1 | 4288.008.1 | 1756.13 | 2119.5 |
| 355 | 2115.006.1-E_at | ETV1 | NM_004956 | 7p21.3 | 2115.006.1 | 4288.009.1 | 2115.6 | 79608.8 |
| 356 | 6376.001.2-F_at | CX3CL1 | NM_002996 | 16q13 | 6376.001.2 | 4306.002.1 | 6376.1 | 8404.22 |
| 357 | 3084.004.1-B_at | NRG1 | NM_004503 | 8p12 | 3084.004.1 | 4311.001.1 | 3084.4 | 8404.34 |
| 358 | 3815.002.4-F_at | KIT | NM_000235 | 4q11-q12 | 3815.002.4 | 4311.001.2 | 3815.2 | 57447.49 |
| 359 | 8404.002.1-D_at | SPARCL1 | NM_004684 | 4q22.1 | 8404.002.1 | 4311.009.1 | 8404.2 | 5311.2 |
| 360 | 1264.006.1-T_at | CNN1 | NM_001299 | 19p13.2-p13.1 | 1264.006.1 | 440421.001.1 | 1264.6 | 2335.25 |
| 361 | 59.022.2-D_at | ACTA2 | NM_001613 | 10q23.3 | 59.022.2 | 4601.014.1 | 59.22 | 4147.12 |
| 362 | 25925.001.1-T_at | ZNF521 | NM_015461 | 18q11.2 | 25925.001.1 | 4629.005.1 | 25925.1 | 301.15 |
| 363 | 4638.006.2-B_at | MYLK | NM_005974 | 3q21 | 4638.006.2 | 4629.006.1 | 4638.6 | 301.4 |
| 364 | 7373.003.5-B_at | COL14A1 | NM_021110 | 8q23 | 7373.003.5 | 4629.006.2 | 7373.3 | 7091.1 |
| 365 | 8404.035.1-B_at | SPARCL1 | NM_004684 | 4q22.1 | 8404.035.1 | 4629.007.1 | 8404.35 | 8404.21 |
| 366 | 59.012.1-T_at | ACTA2 | NM_001613 | 10q23.3 | 59.012.1 | 4629.010.1 | 59.12 | 53335.2 |
| 367 | 3852.017.1-T_at | KRT5 | NM_000424 | 12q12-q13 | 3852.017.1 | 4629.015.1 | 3852.17 | 5284.3 |
| 368 | 3866.012.1-B_at | KRT15 | NM_002275 | 17q21.2 | 3866.012.1 | 4629.016.1 | 3866.12 | 23650.20 |
| 369 | 2.022.1-B_at | A2M | NM_000014 | 12p13.3-p12.3 | 2.022.1 | 4629.020.1 | 2.22 | 57447.42 |
| 370 | 27122.016.1-F_at | DKK3 | NM_001018065 | 11p15.2 | 27122.016.1 | 4629.021.1 | 27122.16 | 6876.23 |
| 371 | 4311.009.1-B_at | MME | NM_000906 | 3q25.1-q25.2 | 4311.009.1 | 4629.022.1 | 4311.9 | 6876.2 |
| 372 | 59.031.2-T_at | ACTA2 | NM_001613 | 10q23.3 | 59.031.2 | 4638.003.1 | 59.31 | 65983.7 |
| 373 | 4311.009.1-T_at | MME | NM_000907 | 3q25.1-q25.2 | 4311.009.1 | 4638.006.1 | 4311.9 | 152015.4 |
| 374 | 3866.006.2-B_at | KRT15 | NM_002275 | 17q21.2 | 3866.006.2 | 4638.006.2 | 3866.6 | 6285.1 |
| 375 | 57447.025.2-T_at | NDRG2 | NM_016262 | 14q11.2 | 57447.025.2 | 4638.009.1 | 57447.25 | 6289.5 |
| 376 | 1717.007.1-F_at | DHCR7 | NM_001360 | 11q13.2-q13.5 | 1717.007.1 | 4638.011.1 | 1717.7 | 9232.2 |
| 377 | 59.004.2-D_at | ACTA2 | NM_001613 | 10q23.3 | 59.004.2 | 4638.014.1 | 59.4 | 3084.11 |
| 378 | 3866.007.2-B_at | KRT15 | NM_002275 | 17q21.2 | 3866.007.2 | 4638.015.1 | 3866.7 | 3872.5 |
| 379 | 3866.010.1-F_at | KRT15 | NM_002275 | 17q21.2 | 3866.010.1 | 4638.020.1 | 3866.10 | 81704.8 |
| 380 | 9768.004.1-D_at | KIAA0101 | NM_001029989 | 15q22.31 | 9768.004.1 | 4744.004.1 | 9768.4 | 338707.6 |
| 381 | 3084.012.2-T_at | NRG1 | NM_004504 | 8p12 | 3084.012.2 | 4751.002.1 | 3084.12 | 23266.8 |
| 382 | 1410.004.2-B_at | CRYAB | NM_001885 | 11q22.3-q23.1 | 1410.004.2 | 4781.002.2 | 1410.4 | 120.5 |
| 383 | 59.008.1-D_at | ACTA2 | NM_001613 | 10q23.3 | 59.008.1 | 4781.006.2 | 59.8 | 4281.9 |
| 384 | 57447.030.1-C_at | NDRG2 | NM_016263 | 14q11.2 | 57447.030.1 | 4781.007.1 | 57447.30 | 4094.1 |
| 385 | 2327.002.1-D_at | FMO2 | NM_001460 | 1q23-q25 | 2327.002.1 | 4781.014.2 | 2327.2 | 2995.1 |
| 386 | 1308.004.1-B_at | COL17A1 | NM_000503 | 10q24.3 | 1308.004.1 | 4781.015.2 | 1308.4 | 2335.17 |
| 387 | 2568.005.2-B_at | GABRP | NM_014211 | 5q33-q34 | 2568.005.2 | 4781.016.1 | 2568.5 | 5284.1 |
| 388 | 2568.001.1-T_at | GABRP | NM_014211 | 5q33-q34 | 2568.001.1 | 4833.004.1 | 2568.1 | 8404.26 |
| 389 | 3084.004.2-T_at | NRG1 | NM_004505 | 8p12 | 3084.004.2 | 4833.010.1 | 3084.4 | 2335.9 |
| 390 | 7373.003.4-B_at | COL14A1 | NM_021110 | 8q23 | 7373.003.4 | 4915.004.1 | 7373.3 | 10461.2 |
| 391 | 7153.002.2-D_at | TOP2A | NM_001067 | 17q21-q22 | 7153.002.2 | 4915.005.1 | 7153.2 | 7091.10 |
| 392 | 2893.006.2-T_at | GRIA4 | NM_000829 | 11q22 | 2893.006.2 | 4915.008.1 | 2893.6 | 79895.1 |
| 393 | 3872.016.1-D_at | KRT17 | NM_000422 | 17q12-q21 | 3872.016.1 | 4915.011.1 | 3872.16 | 57447.38 |
| 394 | 9413.006.1-F_at | C9orf61 | NM_004816 | 9q13-q21 | 9413.006.1 | 4915.012.1 | 9413.6 | 7373.8 |
| 395 | 59.023.2-B_at | ACTA2 | NM_001613 | 10q23.3 | 59.023.2 | 501.006.1 | 59.23 | 4744.4 |
| 396 | 72.005.1-B_at | ACTG2 | NM_001615 | 2p13.1 | 72.005.1 | 51062.008.1 | 72.5 | 8404.15 |
| 397 | 4915.011.1-C_at | NTRK2 | NM_001007104 | 9q22.1 | 4915.011.1 | 51201.005.1 | 4915.11 | 4281.14 |
| 398 | 27122.018.1-F_at | DKK3 | NM_001018066 | 11p15.2 | 27122.018.1 | 51201.007.1 | 27122.18 | 4288.6 |
| 399 | 3852.006.1-B_at | KRT5 | NM_000424 | 12q12-q13 | 3852.006.1 | 51203.002.2 | 3852.6 | 25925.9 |
| 400 | 4638.006.2-D_at | MYLK | NM_005975 | 3q21 | 4638.006.2 | 51203.003.1 | 4638.6 | 667.10 |
| 401 | 7153.005.1-E_at | TOP2A | NM_001067 | 17q21-q22 | 7153.005.1 | 51203.004.1 | 7153.5 | 57447.11 |
| 402 | 7373.001.2-T_at | COL14A1 | NM_021110 | 8q23 | 7373.001.2 | 51203.009.1 | 7373.1 | 8404.24 |
| 403 | 7018.026.1-B_at | TF | NM_001063 | 3q22.1 | 7018.026.1 | 5137.004.2 | 7018.26 | 57447.32 |
| 404 | 7402.014.1-B_at | UTRN | NM_007124 | 6q24 | 7402.014.1 | 5156.001.1 | 7402.14 | 51062.8 |
| 405 | 57447.010.3-D_at | NDRG2 | NM_016264 | 14q11.2 | 57447.010.3 | 5156.005.1 | 57447.10 | 2335.13 |
| 406 | 140446.004.1-T | | | | 140446.004.1 | 5213.024.1 | 140446.4 | 7170.5 |
| 407 | 59.026.2-T_at | ACTA2 | NM_001613 | 10q23.3 | 59.026.2 | 5284.001.1 | 59.26 | 2568.3 |
| 408 | 59.038.1-B_at | ACTA2 | NM_001613 | 10q23.3 | 59.038.1 | 5284.003.1 | 59.38 | 9898.15 |
| 409 | 4240.009.1-C_at | MFGE8 | NM_005928 | 15q25 | 4240.009.1 | 5284.003.2 | 4240.9 | 7018.13 |
| 410 | 57447.030.1-F_at | NDRG2 | NM_016265 | 14q11.2 | 57447.030.1 | 5284.004.1 | 57447.30 | 7170.34 |
| 411 | 9768.004.1-B_at | KIAA0101 | NM_001029990 | 15q22.31 | 9768.004.1 | 5288.001.1 | 9768.4 | 2.2 |
| 412 | 57447.008.1-T_at | NDRG2 | NM_016266 | 14q11.2 | 57447.008.1 | 5288.001.2 | 57447.8 | 57447.50 |
| 413 | 59.014.2-T_at | ACTA2 | NM_001613 | 10q23.3 | 59.014.2 | 5288.001.3 | 59.14 | 2335.32 |
| 414 | 4915.012.1-T_at | NTRK2 | NM_001007105 | 9q22.1 | 4915.012.1 | 5288.003.1 | 4915.12 | 51203.3 |
| 415 | 3866.004.1-T_at | KRT15 | NM_002275 | 17q21.2 | 3866.004.1 | 5311.002.1 | 3866.4 | 9493.1 |
| 416 | 2582.007.2-C_at | GALE | NM_000403 | 1p36-p35 | 2582.007.2 | 5311.003.1 | 2582.7 | 80034.3 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 417 | 7153.002.5-T_at | TOP2A | NM_001067 | 17q21-q22 | 7153.002.5 | 53335.002.1 | 7153.2 | 7170.16 |
| 418 | 4638.009.1-T_at | MYLK | NM_005976 | 3q21 | 4638.009.1 | 53829.001.2 | 4638.9 | 57447.26 |
| 419 | 3861.023.1-T_at | KRT14 | NM_000526 | 17q12-q21 | 3861.023.1 | 54443.006.2 | 3861.23 | 301.8 |
| 420 | 5858.003.3-C_at | PZP | NM_002864 | 12p13-p12.2 | 5858.003.3 | 54443.011.1 | 5858.3 | 80034.2 |
| 421 | 3861.020.1-F_at | KRT14 | NM_000526 | 17q12-q21 | 3861.020.1 | 54443.012.1 | 3861.20 | 3852.23 |
| 422 | 147495.005.1-T | APCDD1 | NM_153000 | 18p11.22 | 147495.005.1 | 54443.013.1 | 147495.5 | 10124.3 |
| 423 | 4638.006.2-C_at | MYLK | NM_005977 | 3q21 | 4638.006.2 | 54829.001.1 | 4638.6 | 23650.19 |
| 424 | 1308.004.1-F_at | COL17A1 | NM_000504 | 10q24.3 | 1308.004.1 | 54928.003.1 | 1308.4 | 7170.27 |
| 425 | 4915.004.1-F_at | NTRK2 | NM_001007106 | 9q22.1 | 4915.004.1 | 54997.002.1 | 4915.4 | 54928.3 |
| 426 | 3866.008.1-B_at | KRT15 | NM_002275 | 17q21.2 | 3866.008.1 | 55107.006.2 | 3866.8 | 3084.10 |
| 427 | 8626.002.1-E_at | TP63 | NM_003722 | 3q28 | 8626.002.1 | 55366.001.1 | 8626.2 | 2115.3 |
| 428 | 1264.003.1-T_at | CNN1 | NM_001299 | 19p13.2-p13.1 | 1264.003.1 | 55366.001.2 | 1264.3 | 8404.9 |
| 429 | 59.042.1-F_at | ACTA2 | NM_001613 | 10q23.3 | 59.042.1 | 55656.007.3 | 59.42 | 6289.3 |
| 430 | 4833.004.1-C_at | NME4 | NM_005009 | 16p13.3 | 4833.004.1 | 55732.003.2 | 4833.4 | 7170.25 |
| 431 | 2568.006.1-B_at | GABRP | NM_014211 | 5q33-q34 | 2568.006.1 | 5608.002.1 | 2568.6 | 22974.7 |
| 432 | 57447.004.2-T_at | NDRG2 | NM_016267 | 14q11.2 | 57447.004.2 | 5608.004.1 | 57447.4 | 4147.11 |
| 433 | 59.014.2-B_at | ACTA2 | NM_001613 | 10q23.3 | 59.014.2 | 5621.002.2 | 59.14 | 23650.3 |
| 434 | 3084.012.1-T_at | NRG1 | NM_004506 | 8p12 | 3084.012.1 | 5621.008.1 | 3084.12 | 64168.10 |
| 435 | 27122.017.1-T_at | DKK3 | NM_001018067 | 11p15.2 | 27122.017.1 | 5627.002.1 | 27122.17 | 25925.11 |
| 436 | 3852.012.2-T_at | KRT5 | NM_000424 | 12q12-q13 | 3852.012.2 | 56477.001.1 | 3852.12 | 9232.4 |
| 437 | 59.033.1-T_at | ACTA2 | NM_001613 | 10q23.3 | 59.033.1 | 57162.010.1 | 59.33 | 4147.5 |
| 438 | 27122.002.1-C_at | DKK3 | NM_001018068 | 11p15.2 | 27122.002.1 | 57447.002.1 | 27122.2 | 147804.4 |
| 439 | 3880.011.1-B_at | KRT19 | NM_002276 | 17q21.2 | 3880.011.1 | 57447.004.1 | 3880.11 | 81704.13 |
| 440 | 65983.013.1-T_at | GRAMD3 | NM_023927 | 5q23.2 | 65983.013.1 | 57447.004.2 | 65983.13 | 54443.13 |
| 441 | 3872.014.1-T_at | KRT17 | NM_000422 | 17q12-q21 | 3872.014.1 | 57447.006.1 | 3872.14 | 1410.5 |
| 442 | 162605.001.4-C | KRT28 | NM_181535 | 17q21.2 | 162605.001.4 | 57447.008.1 | 162605.1 | 3204.1 |
| 443 | 59.031.2-B_at | ACTA2 | NM_001613 | 10q23.3 | 59.031.2 | 57447.008.2 | 59.31 | 29997.12 |
| 444 | 3084.012.2-B_at | NRG1 | NM_004507 | 8p12 | 3084.012.2 | 57447.009.1 | 3084.12 | 2.5 |
| 445 | 5858.001.2-C_at | PZP | NM_002864 | 12p13-p12.2 | 5858.001.2 | 57447.010.1 | 5858.1 | 1063.2 |
| 446 | 65983.010.1-T_at | GRAMD3 | NM_023927 | 5q23.2 | 65983.010.1 | 57447.010.2 | 65983.10 | 10144.21 |
| 447 | 7373.003.5-F_at | COL14A1 | NM_021110 | 8q23 | 7373.003.5 | 57447.010.3 | 7373.3 | 8404.25 |
| 448 | 3866.010.1-T_at | KRT15 | NM_002275 | 17q21.2 | 3866.010.1 | 57447.011.1 | 3866.10 | 6876.20 |
| 449 | 8404.005.1-B_at | SPARCL1 | NM_004684 | 4q22.1 | 8404.005.1 | 57447.012.1 | 8404.5 | 7170.6 |
| 450 | 3866.005.1-T_at | KRT15 | NM_002275 | 17q21.2 | 3866.005.1 | 57447.012.2 | 3866.5 | 10051.16 |
| 451 | 59.003.1-F_at | ACTA2 | NM_001613 | 10q23.3 | 59.003.1 | 57447.017.1 | 59.3 | 5627.2 |
| 452 | 7153.002.5-F_at | TOP2A | NM_001067 | 17q21-q22 | 7153.002.5 | 57447.021.1 | 7153.2 | 399687.1 |
| 453 | 2487.001.1-T_at | FRZB | NM_001463 | 2qter | 2487.001.1 | 57447.022.1 | 2487.1 | 54997.2 |
| 454 | 3866.010.1-B_at | KRT15 | NM_002275 | 17q21.2 | 3866.010.1 | 57447.024.1 | 3866.10 | 57561.1 |
| 455 | 147495.009.1-T | APCDD1 | NM_153000 | 18p11.22 | 147495.009.1 | 57447.025.1 | 147495.9 | 8404.31 |
| 456 | 65983.003.2-T_at | GRAMD3 | NM_023927 | 5q23.2 | 65983.003.2 | 57447.025.2 | 65983.3 | 2.25 |
| 457 | 59.040.1-D_at | ACTA2 | NM_001613 | 10q23.3 | 59.040.1 | 57447.026.1 | 59.40 | 699.2 |
| 458 | 59.024.2-T_at | ACTA2 | NM_001613 | 10q23.3 | 59.024.2 | 57447.027.1 | 59.24 | 9055.13 |
| 459 | 1717.009.2-B_at | DHCR7 | NM_001360 | 11q13.2-q13.5 | 1717.009.2 | 57447.028.1 | 1717.9 | 10051.5 |
| 460 | 1756.027.1-F_at | DMD | NM_000142 | Xp21.2 | 1756.027.1 | 57447.029.1 | 1756.27 | 2568.2 |
| 461 | 59.042.1-B_at | ACTA2 | NM_001613 | 10q23.3 | 59.042.1 | 57447.030.1 | 59.42 | 4147.4 |
| 462 | 7153.002.5-D_at | TOP2A | NM_001067 | 17q21-q22 | 7153.002.5 | 57447.031.1 | 7153.2 | 2938.1 |
| 463 | 57447.031.1-F_at | NDRG2 | NM_016268 | 14q11.2 | 57447.031.1 | 57447.032.1 | 57447.31 | 2982.12 |
| 464 | 140885.011.1-C | SIRPA | NM_001040023 | 20p13 | 140885.011.1 | 57447.033.1 | 140885.11 | 2893.2 |
| 465 | 59.003.1-T_at | ACTA2 | NM_001613 | 10q23.3 | 59.003.1 | 57447.034.1 | 59.3 | 116369.6 |
| 466 | 3832.002.1-D_at | KIF11 | NM_004523 | 10q24.1 | 3832.002.1 | 57447.035.1 | 3832.2 | 6304.7 |
| 467 | 3880.005.1-D_at | KRT19 | NM_002276 | 17q21.2 | 3880.005.1 | 57447.037.1 | 3880.5 | 2335.35 |
| 468 | 3084.012.1-F_at | NRG1 | NM_004508 | 8p12 | 3084.012.1 | 57447.038.1 | 3084.12 | 4751.2 |
| 469 | 6595.012.1-B_at | SMARCA2 | NM_003070 | 9p22.3 | 6595.012.1 | 57447.039.1 | 6595.12 | 64151.1 |
| 470 | 59.012.2-D_at | ACTA2 | NM_001613 | 10q23.3 | 59.012.2 | 57447.040.1 | 59.12 | 29089.3 |
| 471 | 57447.034.1-C_at | NDRG2 | NM_016269 | 14q11.2 | 57447.034.1 | 57447.041.1 | 57447.34 | 3860.8 |
| 472 | 56477.001.1-B_at | CCL28 | NM_148672 | 5p12 | 56477.001.1 | 57447.042.1 | 56477.1 | 25925.6 |
| 473 | 57447.041.1-D_at | NDRG2 | NM_016270 | 14q11.2 | 57447.041.1 | 57447.043.1 | 57447.41 | 59.49 |
| 474 | 9768.005.1-B_at | KIAA0101 | NM_001029991 | 15q22.31 | 9768.005.1 | 57447.044.1 | 9768.5 | 6289.2 |
| 475 | 285203.001.2-C | C3orf64 | NM_173654 | 3p14.1 | 285203.001.2 | 57447.047.1 | 285203.1 | 244.3 |
| 476 | 147495.006.1-B | APCDD1 | NM_153000 | 18p11.22 | 147495.006.1 | 57447.048.1 | 147495.6 | 11065.8 |
| 477 | 7018.029.1-D_at | TF | NM_001063 | 3q22.1 | 7018.029.1 | 57447.048.2 | 7018.29 | 7091.6 |
| 478 | 3852.009.1-T_at | KRT5 | NM_000424 | 12q12-q13 | 3852.009.1 | 57447.049.1 | 3852.9 | 79608.9 |
| 479 | 59.023.2-D_at | ACTA2 | NM_001613 | 10q23.3 | 59.023.2 | 57447.050.1 | 59.23 | 9413.2 |
| 480 | 1959.002.1-D_at | EGR2 | NM_000399 | 10q21.1 | 1959.002.1 | 57447.051.1 | 1959.2 | 7431.64 |
| 481 | 7018.014.1-D_at | TF | NM_001063 | 3q22.1 | 7018.014.1 | 57447.051.2 | 7018.14 | 8404.29 |
| 482 | 5858.004.1-F_at | PZP | NM_002864 | 12p13-p12.2 | 5858.004.1 | 57451.001.3 | 5858.4 | 301.5 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 483 | 79192.002.2-D_at | IRX1 | NM_024337 | 5p15.3 | 79192.002.2 | 57451.002.3 | 79192.2 | 9055.14 |
| 484 | 59.008.2-B_at | ACTA2 | NM_001613 | 10q23.3 | 59.008.2 | 57451.004.1 | 59.8 | 4281.23 |
| 485 | 8404.008.1-E_at | SPARCL1 | NM_004684 | 4q22.1 | 8404.008.1 | 57561.001.1 | 8404.8 | 1062.1 |
| 486 | 59.008.1-F_at | ACTA2 | NM_001613 | 10q23.3 | 59.008.1 | 57561.002.1 | 59.8 | 5858.5 |
| 487 | 4240.011.1-B_at | MFGE8 | NM_005928 | 15q25 | 4240.011.1 | 5764.001.1 | 4240.11 | 51201.7 |
| 488 | 94274.002.1-C_at | PPP1R14A | NM_033256 | 19q13.1 | 94274.002.1 | 5803.002.1 | 94274.2 | 4240.1 |
| 489 | 4638.015.1-T_at | MYLK | NM_005978 | 3q21 | 4638.015.1 | 5803.002.2 | 4638.15 | 9413.1 |
| 490 | 6376.001.1-T_at | CX3CL1 | NM_002996 | 16q13 | 6376.001.1 | 5803.006.1 | 6376.1 | 11197.1 |
| 491 | 57447.043.1-F_at | NDRG2 | NM_016271 | 14q11.2 | 57447.043.1 | 58499.005.2 | 57447.43 | 6285.2 |
| 492 | 59.039.1-T_at | ACTA2 | NM_001613 | 10q23.3 | 59.039.1 | 5858.001.2 | 59.39 | 7169.1 |
| 493 | 4638.006.1-B_at | MYLK | NM_005979 | 3q21 | 4638.006.1 | 5858.003.3 | 4638.6 | 4601.14 |
| 494 | 25802.003.1-F_at | LMOD1 | NM_012134 | 1q32 | 25802.003.1 | 5858.004.1 | 25802.3 | 51203.2 |
| 495 | 57447.025.1-T_at | NDRG2 | NM_016272 | 14q11.2 | 57447.025.1 | 5858.005.1 | 57447.25 | 7018.22 |
| 496 | 57447.017.1-T_at | NDRG2 | NM_016273 | 14q11.2 | 57447.017.1 | 59.003.1 | 57447.17 | 4288.9 |
| 497 | 7018.026.1-C_at | TF | NM_001063 | 3q22.1 | 7018.026.1 | 59.004.1 | 7018.26 | 8321.4 |
| 498 | 7018.028.1-E_at | TF | NM_001063 | 3q22.1 | 7018.028.1 | 59.004.2 | 7018.28 | 8564.4 |
| 499 | 4915.008.1-C_at | NTRK2 | NM_001007107 | 9q22.1 | 4915.008.1 | 59.008.1 | 4915.8 | 29127.13 |
| 500 | 358.018.1-C_at | AQP1 | NM_198098 | 7p14 | 358.018.1 | 59.008.2 | 358.18 | 1058.4 |
| 501 | 7153.002.6-B_at | TOP2A | NM_001067 | 17q21-q22 | 7153.002.6 | 59.009.1 | 7153.2 | 2232.14 |
| 502 | 57447.012.1-T_at | NDRG2 | NM_016274 | 14q11.2 | 57447.012.1 | 59.012.1 | 57447.12 | 23650.5 |
| 503 | 59.040.1-B_at | ACTA2 | NM_001613 | 10q23.3 | 59.040.1 | 59.012.2 | 59.40 | 5621.2 |
| 504 | 57447.006.1-T_at | NDRG2 | NM_016275 | 14q11.2 | 57447.006.1 | 59.014.1 | 57447.6 | 54443.12 |
| 505 | 9493.006.1-F_at | KIF23 | NM_004856 | 15q23 | 9493.006.1 | 59.014.2 | 9493.6 | 3479.3 |
| 506 | 57447.004.1-T_at | NDRG2 | NM_016276 | 14q11.2 | 57447.004.1 | 59.015.1 | 57447.4 | 94274.3 |
| 507 | 57447.004.2-B_at | NDRG2 | NM_016277 | 14q11.2 | 57447.004.2 | 59.015.2 | 57447.4 | 84668.3 |
| 508 | 7373.001.2-D_at | COL14A1 | NM_021110 | 8q23 | 7373.001.2 | 59.016.1 | 7373.1 | 22974.8 |
| 509 | 9493.004.1-B_at | KIF23 | NM_004856 | 15q23 | 9493.004.1 | 59.022.1 | 9493.4 | 55656.7 |
| 510 | 2568.005.2-C_at | GABRP | NM_014211 | 5q33-q34 | 2568.005.2 | 59.022.2 | 2568.5 | 29127.2 |
| 511 | 7018.029.1-F_at | TF | NM_001063 | 3q22.1 | 7018.029.1 | 59.023.1 | 7018.29 | 4281.12 |
| 512 | 26289.013.1-B_at | AK5 | NM_012116 | 1p31 | 26289.013.1 | 59.023.2 | 26289.13 | 79627.3 |
| 513 | 7169.015.1-B_at | TPM2 | NM_003289 | 9p13.2-p13.1 | 7169.015.1 | 59.024.1 | 7169.15 | 2982.14 |
| 514 | 57451.001.3-F_at | ODZ2 | NM_001080428 | 5q34-q35.1 | 57451.001.3 | 59.024.2 | 57451.1 | 2335.53 |
| 515 | 2568.005.2-F_at | GABRP | NM_014211 | 5q33-q34 | 2568.005.2 | 59.026.1 | 2568.5 | 667.1 |
| 516 | 57447.004.2-F_at | NDRG2 | NM_016278 | 14q11.2 | 57447.004.2 | 59.026.2 | 57447.4 | 55366.1 |
| 517 | 8404.004.1-D_at | SPARCL1 | NM_004684 | 4q22.1 | 8404.004.1 | 59.029.1 | 8404.4 | 5311.3 |
| 518 | 3855.004.2-D_at | KRT7 | NM_005556 | 12q12-q13 | 3855.004.2 | 59.031.1 | 3855.4 | 6304.11 |
| 519 | 3872.014.1-F_at | KRT17 | NM_000422 | 17q12-q21 | 3872.014.1 | 59.031.2 | 3872.14 | 7373.7 |
| 520 | 57447.033.1-F_at | NDRG2 | NM_016279 | 14q11.2 | 57447.033.1 | 59.033.1 | 57447.33 | 1410.9 |
| 521 | 9452.001.1-T_at | ITM2A | NM_004867 | Xq13.3-Xq21.2 | 9452.001.1 | 59.033.2 | 9452.1 | 79745.4 |
| 522 | 59.033.2-T_at | ACTA2 | NM_001613 | 10q23.3 | 59.033.2 | 59.034.1 | 59.33 | 24137.4 |
| 523 | 3084.009.1-T_at | NRG1 | NM_004509 | 8p12 | 3084.009.1 | 59.034.2 | 3084.9 | 6241.13 |
| 524 | 57447.040.1-T_at | NDRG2 | NM_016280 | 14q11.2 | 57447.040.1 | 59.038.1 | 57447.40 | 1410.1 |
| 525 | 4833.004.1-T_at | NME4 | NM_005009 | 16p13.3 | 4833.004.1 | 59.039.1 | 4833.4 | 4781.15 |
| 526 | 3426.001.1-F_at | CFI | NM_000204 | 4q25 | 3426.001.1 | 59.040.1 | 3426.1 | 72.2 |
| 527 | 59.034.1-B_at | ACTA2 | NM_001613 | 10q23.3 | 59.034.1 | 59.042.1 | 59.34 | 2982.13 |
| 528 | 10253.001.1-E_at | SPRY2 | NM_005842 | 13q31.1 | 10253.001.1 | 59.049.1 | 10253.1 | 79971.12 |
| 529 | 9073.001.1-C_at | CLDN8 | NM_199328 | 21q22.11 | 9073.001.1 | 6122.037.1 | 9073.1 | 7169.4 |
| 530 | 51201.005.1-T_at | ZDHHC2 | NM_016353 | 8p21.3-p22 | 51201.005.1 | 6122.046.1 | 51201.5 | 2335.16 |
| 531 | 9477.006.1-C_at | MED20 | NM_004275 | 6p21.1 | 9477.006.1 | 6241.013.1 | 9477.6 | 259266.3 |
| 532 | 57447.028.1-T_at | NDRG2 | NM_016281 | 14q11.2 | 57447.028.1 | 6285.001.1 | 57447.28 | 9055.20 |
| 533 | 25925.007.1-T_at | ZNF521 | NM_015461 | 18q11.2 | 25925.007.1 | 6285.002.1 | 25925.7 | 7091.16 |
| 534 | 59.024.2-B_at | ACTA2 | NM_001613 | 10q23.3 | 59.024.2 | 6285.003.1 | 59.24 | 57162.10 |
| 535 | 2.022.1-T_at | A2M | NM_000014 | 12p13.3-p12.3 | 2.022.1 | 6286.001.1 | 2.22 | 4781.2 |
| 536 | 4281.008.2-B_at | MID1 | NM_000382 | Xp22 | 4281.008.2 | 6288.001.1 | 4281.8 | 6122.37 |
| 537 | 90231.001.1-C_at | KIAA2013 | NM_138346 | 1p36.22 | 90231.001.1 | 6288.004.1 | 90231.1 | 4240.15 |
| 538 | 358.012.1-D_at | AQP1 | NM_198098 | 7p14 | 358.012.1 | 6289.001.1 | 358.12 | 6304.2 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 539 | 3852.021.1-T_at | KRT5 | NM_000424 | 12q12-q13 | 3852.021.1 | 6289.001.2 | 3852.21 | 301.13 |
| 540 | 7373.003.4-D_at | COL14A1 | NM_021110 | 8q23 | 7373.003.4 | 6289.002.1 | 7373.3 | 6304.12 |
| 541 | 57447.048.1-T_at | NDRG2 | NM_016282 | 14q11.2 | 57447.048.1 | 6289.002.2 | 57447.48 | 11065.5 |
| 542 | 358.012.1-B_at | AQP1 | NM_198098 | 7p14 | 358.012.1 | 6289.003.1 | 358.12 | 29997.16 |
| 543 | 7018.025.1-C_at | TF | NM_001063 | 3q22.1 | 7018.025.1 | 6289.003.2 | 7018.25 | 1410.11 |
| 544 | 5608.004.1-T_at | MAP2K6 | NM_002758 | 17q24.3 | 5608.004.1 | 6289.005.1 | 5608.4 | 7170.40 |
| 545 | 3084.012.2-F_at | NRG1 | NM_004510 | 8p12 | 3084.012.2 | 6289.006.1 | 3084.12 | 7170.41 |
| 546 | 4306.002.1-C_at | NR3C2 | NM_000901 | 4q31.1 | 4306.002.1 | 6304.002.1 | 4306.2 | 4094.2 |
| 547 | 4288.004.1-D_at | MKI67 | NM_002417 | 10q25-qter | 4288.004.1 | 6304.006.2 | 4288.4 | 7113.11 |
| 548 | 57447.002.1-F_at | NDRG2 | NM_016283 | 14q11.2 | 57447.002.1 | 6304.007.1 | 57447.2 | 7170.2 |
| 549 | 4281.018.1-T_at | MID1 | NM_000383 | Xp22 | 4281.018.1 | 6304.007.2 | 4281.18 | 8404.17 |
| 550 | 10144.020.2-B_at | FAM13A1 | NM_001015045 | 4q22.1 | 10144.020.2 | 6304.011.1 | 10144.20 | 59.29 |
| 551 | 6876.016.1-E_at | TAGLN | NM_001001522 | 11q23.2 | 6876.016.1 | 6304.012.1 | 6876.16 | 29089.1 |
| 552 | 57447.008.2-T_at | NDRG2 | NM_016284 | 14q11.2 | 57447.008.2 | 6376.001.1 | 57447.8 | 9134.1 |
| 553 | 51203.004.1-T_at | NUSAP1 | NM_016359 | 15q15.1 | 51203.004.1 | 6376.001.2 | 51203.4 | 1410.10 |
| 554 | 2335.028.1-B_at | FN1 | NM_002026 | 2q34 | 2335.028.1 | 64151.001.2 | 2335.28 | 2327.3 |
| 555 | 7018.028.1-F_at | TF | NM_001063 | 3q22.1 | 7018.028.1 | 64168.010.1 | 7018.28 | 6289.1 |
| 556 | 7373.003.5-T_at | COL14A1 | NM_021110 | 8q23 | 7373.003.5 | 6422.001.1 | 7373.3 | 1410.6 |
| 557 | 81557.006.1-C_at | MAGED4B | NM_030801 | — | 81557.006.1 | 6422.002.1 | 81557.6 | 80034.4 |
| 558 | 3866.002.1-D_at | KRT15 | NM_002275 | 17q21.2 | 3866.002.1 | 6441.004.1 | 3866.2 | 1410.8 |
| 559 | 3866.001.1-B_at | KRT15 | NM_002275 | 17q21.2 | 3866.001.1 | 6595.012.1 | 3866.1 | 6288.1 |
| 560 | 55107.006.2-T_at | TMEM16A | NM_018043 | 11q13.3 | 55107.006.2 | 65983.003.1 | 55107.6 | 8404.20 |
| 561 | 79068.010.1-D_at | FTO | NM_001080432 | 16q12.2 | 79068.010.1 | 65983.003.2 | 79068.10 | 3459.5 |
| 562 | 57447.009.1-T_at | NDRG2 | NM_016285 | 14q11.2 | 57447.009.1 | 65983.004.1 | 57447.9 | 83539.1 |
| 563 | 2115.015.1-T_at | ETV1 | NM_004956 | 7p21.3 | 2115.015.1 | 65983.004.2 | 2115.15 | 6288.4 |
| 564 | 1756.013.1-C_at | DMD | NM_000143 | Xp21.2 | 1756.013.1 | 65983.005.1 | 1756.13 | 4781.16 |
| 565 | 7169.015.1-F_at | TPM2 | NM_003290 | 9p13.2-p13.1 | 7169.015.1 | 65983.007.1 | 7169.15 | 53829.1 |
| 566 | 65983.013.2-F_at | GRAMD3 | NM_023927 | 5q23.2 | 65983.013.2 | 65983.008.1 | 65983.13 | 10051.8 |
| 567 | 8404.001.1-B_at | SPARCL1 | NM_004684 | 4q22.1 | 8404.001.1 | 65983.009.1 | 8404.1 | 1033.2 |
| 568 | 4240.004.1-B_at | MFGE8 | NM_005928 | 15q25 | 4240.004.1 | 65983.010.1 | 4240.4 | 2335.5 |
| 569 | 57447.012.2-T_at | NDRG2 | NM_016286 | 14q11.2 | 57447.012.2 | 65983.013.1 | 57447.12 | 7113.9 |
| 570 | 57447.024.1-F_at | NDRG2 | NM_016287 | 14q11.2 | 57447.024.1 | 65983.013.2 | 57447.24 | 7168.3 |
| 571 | 358.018.1-T_at | AQP1 | NM_198098 | 7p14 | 358.018.1 | 667.001.1 | 358.18 | 79608.1 |
| 572 | 57447.048.2-T_at | NDRG2 | NM_016288 | 14q11.2 | 57447.048.2 | 667.010.1 | 57447.48 | 7113.10 |
| 573 | 59.031.1-C_at | ACTA2 | NM_001613 | 10q23.3 | 59.031.1 | 667.021.1 | 59.31 | 4781.14 |
| 574 | 3860.007.1-F_at | KRT13 | NM_002275 | 17q12-q21.2 | 3860.007.1 | 667.022.1 | 3860.7 | 11065.3 |
| 575 | 8404.028.1-C_at | SPARCL1 | NM_004684 | 4q22.1 | 8404.028.1 | 6876.002.1 | 8404.28 | 3084.5 |
| 576 | 4240.011.3-E_at | MFGE8 | NM_005928 | 15q25 | 4240.011.3 | 6876.011.1 | 4240.11 | 6285.3 |
| 577 | 59.022.2-B_at | ACTA2 | NM_001613 | 10q23.3 | 59.022.2 | 6876.016.1 | 59.22 | 54829.1 |
| 578 | 3866.002.1-F_at | KRT15 | NM_002275 | 17q21.2 | 3866.002.1 | 6876.016.2 | 3866.2 | 9055.11 |
| 579 | 3866.002.1-T_at | KRT15 | NM_002275 | 17q21.2 | 3866.002.1 | 6876.020.1 | 3866.2 | 4288.8 |
| 580 | 4915.005.1-B_at | NTRK2 | NM_001007108 | 9q22.1 | 4915.005.1 | 6876.023.1 | 4915.5 | 4781.7 |
| 581 | 8404.008.1-F_at | SPARCL1 | NM_004684 | 4q22.1 | 8404.008.1 | 699.002.1 | 8404.8 | 9055.17 |
| 582 | 79608.002.1-F_at | RIC3 | NM_024557 | 11p15.4 | 79608.002.1 | 7018.013.1 | 79608.2 | 7170.18 |
| 583 | 8404.023.1-D_at | SPARCL1 | NM_004684 | 4q22.1 | 8404.023.1 | 7018.014.1 | 8404.23 | 10253.3 |
| 584 | 3426.002.1-D_at | CFI | NM_000204 | 4q25 | 3426.002.1 | 7018.022.1 | 3426.2 | 2982.15 |
| 585 | 2335.027.1-T_at | FN1 | NM_002027 | 2q34 | 2335.027.1 | 7018.025.1 | 2335.27 | 10124.4 |
| 586 | 11065.009.1-T_at | UBE2C | NM_007019 | 20q13.12 | 11065.009.1 | 7018.026.1 | 11065.9 | 7091.5 |
| 587 | 140885.013.1-F | SIRPA | NM_001040024 | 20p13 | 140885.013.1 | 7018.028.1 | 140885.13 | 501.6 |
| 588 | 57447.021.1-B_at | NDRG2 | NM_016289 | 14q11.2 | 57447.021.1 | 7018.029.1 | 57447.21 | 244.12 |
| 589 | 25802.004.1-C_at | LMOD1 | NM_012134 | 1q32 | 25802.004.1 | 7091.001.1 | 25802.4 | 3872.18 |
| 590 | 4638.014.1-F_at | MYLK | NM_005980 | 3q21 | 4638.014.1 | 7091.005.1 | 4638.14 | 10144.17 |
| 591 | 9493.004.1-F_at | KIF23 | NM_004856 | 15q23 | 9493.004.1 | 7091.006.1 | 9493.4 | 29127.7 |
| 592 | 8404.004.1-B_at | SPARCL1 | NM_004684 | 4q22.1 | 8404.004.1 | 7091.010.1 | 8404.4 | 10010.4 |
| 593 | 8404.004.2-T_at | SPARCL1 | NM_004684 | 4q22.1 | 8404.004.2 | 7091.014.1 | 8404.4 | 4781.6 |
| 594 | 57447.010.2-T_at | NDRG2 | NM_016290 | 14q11.2 | 57447.010.2 | 7091.015.1 | 57447.10 | 23092.4 |
| 595 | 57447.010.3-B_at | NDRG2 | NM_016291 | 14q11.2 | 57447.010.3 | 7091.016.1 | 57447.10 | 2335.2 |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 596 | 27122.006.1-T_at | DKK3 | NM_001018069 | 11p15.2 | 27122.006.1 | 7113.001.1 | 27122.6 | 6304.6 |
| 597 | 5156.005.1-T_at | PDGFRA | NM_006206 | 4q11-q13 | 5156.005.1 | 7113.009.1 | 5156.5 | 9055.19 |
| 598 | 5858.004.1-E_at | PZP | NM_002864 | 12p13-p12.2 | 5858.004.1 | 7113.010.1 | 5858.4 | 1398.1 |
| 599 | 25802.008.1-D_at | LMOD1 | NM_012134 | 1q32 | 25802.008.1 | 7113.011.1 | 25802.8 | 339965.1 |
| 600 | 2327.002.2-T_at | FMO2 | NM_001460 | 1q23-q25 | 2327.002.2 | 7153.002.2 | 2327.2 | 7113.1 |
| 601 | 3852.004.1-C_at | KRT5 | NM_000424 | 12q12-q13 | 3852.004.1 | 7153.002.3 | 3852.4 | 4833.10 |
| 602 | 59.026.2-F_at | ACTA2 | NM_001613 | 10q23.3 | 59.026.2 | 7153.002.4 | 59.26 | 79971.13 |
| 603 | 57447.029.1-C_at | NDRG2 | NM_016292 | 14q11.2 | 57447.029.1 | 7153.002.5 | 57447.29 | 152015.5 |
| 604 | 7169.022.1-D_at | TPM2 | NM_003291 | 9p13.2-p13.1 | 7169.022.1 | 7153.002.6 | 7169.22 | 4288.5 |
| 605 | 23266.001.3-B_at | LPHN2 | NM_012302 | 1p31.1 | 23266.001.3 | 7153.005.1 | 23266.1 | 6441.4 |
| 606 | 3084.012.1-B_at | NRG1 | NM_004511 | 8p12 | 3084.012.1 | 7168.003.1 | 3084.12 | 6122.46 |
| 607 | 29127.019.2-T_at | RACGAP1 | NM_013277 | 12q13.13 | 29127.019.2 | 7169.001.1 | 29127.19 | 115908.2 |
| 608 | 10253.004.1-T_at | SPRY2 | NM_005842 | 13q31.1 | 10253.004.1 | 7169.004.1 | 10253.4 | 9481.1 |
| 609 | 10124.002.1-D_at | ARL4A | NM_001037164 | 7p21-p15.3 | 10124.002.1 | 7169.015.1 | 10124.2 | 2335.24 |
| 610 | 3861.013.1-D_at | KRT14 | NM_000526 | 17q12-q21 | 3861.013.1 | 7169.022.1 | 3861.13 | 891.7 |
| 611 | 8404.032.1-T_at | SPARCL1 | NM_004684 | 4q22.1 | 8404.032.1 | 7170.002.1 | 8404.32 | 57451.4 |
| 612 | 84441.002.1-E_at | MAML2 | NM_032427 | 11q21 | 84441.002.1 | 7170.005.2 | 84441.2 | 6286.1 |
| 613 | 2.013.1-E_at | A2M | NM_000014 | 12p13.3-p12.3 | 2.013.1 | 7170.006.1 | 2.13 | 10580.12 |
| 614 | 3084.004.1-T_at | NRG1 | NM_004512 | 8p12 | 3084.004.1 | 7170.007.1 | 3084.4 | 23321.14 |
| 615 | 5288.001.2-F_at | PIK3C2G | NM_004570 | 12p12 | 5288.001.2 | 7170.014.1 | 5288.1 | 2824.1 |
| 616 | 57447.017.1-F_at | NDRG2 | NM_016293 | 14q11.2 | 57447.017.1 | 7170.016.3 | 57447.17 | 29127.22 |
| 617 | 3084.006.1-T_at | NRG1 | NM_004513 | 8p12 | 3084.006.1 | 7170.018.2 | 3084.6 | 54443.11 |
| 618 | 59.039.1-F_at | ACTA2 | NM_001613 | 10q23.3 | 59.039.1 | 7170.025.1 | 59.39 | 29997.8 |
| 619 | 2.024.1-T_at | A2M | NM_000014 | 12p13.3-p12.3 | 2.024.1 | 7170.027.1 | 2.24 | 57561.2 |
| 620 | 3815.002.2-E_at | KIT | NM_000236 | 4q11-q12 | 3815.002.2 | 7170.034.2 | 3815.2 | 57451.2 |
| 621 | 1756.009.1-D_at | DMD | NM_000144 | Xp21.2 | 1756.009.1 | 7170.040.1 | 1756.9 | 5213.24 |
| 622 | 7091.014.1-B_at | TLE4 | NM_007005 | 9q21.31 | 7091.014.1 | 7170.041.1 | 7091.14 | 11065.4 |
| 623 | 4629.015.1-F_at | MYH11 | NM_001040137 | 16p13.11 | 4629.015.1 | 72.001.1 | 4629.15 | 6289.6 |
| 624 | 59.008.2-F_at | ACTA2 | NM_001613 | 10q23.3 | 59.008.2 | 72.002.1 | 59.8 | 23284.7 |
| 625 | 2568.005.2-T_at | GABRP | NM_014211 | 5q33-q34 | 2568.005.2 | 72.005.1 | 2568.5 | 79971.9 |
| 626 | 115207.002.1-T | KCTD12 | NM_138444 | 13q22.3 | 115207.002.1 | 7373.001.1 | 115207.2 | 51203.9 |
| 627 | 4281.001.1-T_at | MID1 | NM_000384 | Xp22 | 4281.001.1 | 7373.001.2 | 4281.1 | 1308.2 |
| 628 | 84668.002.2-T_at | FAM126A | NM_032581 | 7p15.3 | 84668.002.2 | 7373.002.1 | 84668.2 | 4288.7 |
| 629 | 4240.004.1-F_at | MFGE8 | NM_005928 | 15q25 | 4240.004.1 | 7373.003.1 | 4240.4 | 244.11 |
| 630 | 8404.005.1-D_at | SPARCL1 | NM_004684 | 4q22.1 | 8404.005.1 | 7373.003.2 | 8404.5 | 3178.3 |
| 631 | 8404.032.1-B_at | SPARCL1 | NM_004684 | 4q22.1 | 8404.032.1 | 7373.003.3 | 8404.32 | 9055.12 |
| 632 | 57447.044.1-E_at | NDRG2 | NM_016294 | 14q11.2 | 57447.044.1 | 7373.003.4 | 57447.44 | 9232.1 |
| 633 | 8626.006.2-F_at | TP63 | NM_003722 | 3q28 | 8626.006.2 | 7373.003.5 | 8626.6 | 79068.11 |
| 634 | 57447.051.2-B_at | NDRG2 | NM_016295 | 14q11.2 | 57447.051.2 | 7373.003.6 | 57447.51 | 7534.1 |
| 635 | 1063.001.1-T_at | CENPF | NM_016343 | 1q32-q41 | 1063.001.1 | 7373.004.1 | 1063.1 | 79971.14 |
| 636 | 3426.002.1-T_at | CFI | NM_000204 | 4q25 | 3426.002.1 | 7373.007.1 | 3426.2 | 5621.8 |
| 637 | 1308.001.1-T_at | COL17A1 | NM_000505 | 10q24.3 | 1308.001.1 | 7373.008.1 | 1308.1 | 55732.3 |
| 638 | 389432.002.1-F | SAMD5 | NM_001030060 | 6q24.3 | 389432.002.1 | 7402.014.1 | 389432.2 | 221120.6 |
| 639 | 57447.017.1-B_at | NDRG2 | NM_016296 | 14q11.2 | 57447.017.1 | 7431.064.1 | 57447.17 | 2335.45 |
| 640 | 2115.014.1-F_at | ETV1 | NM_004956 | 7p21.3 | 2115.014.1 | 7534.001.1 | 2115.14 | 7170.7 |
| 641 | 5284.004.1-T_at | PIGR | NM_002644 | 1q31-q41 | 5284.004.1 | 79068.010.1 | 5284.4 | 9055.10 |
| 642 | 57447.029.1-F_at | NDRG2 | NM_016297 | 14q11.2 | 57447.029.1 | 79068.011.2 | 57447.29 | 58499.5 |
| 643 | 8626.006.1-F_at | TP63 | NM_003722 | 3q28 | 8626.006.1 | 79192.002.2 | 8626.6 | 54443.6 |
| 644 | 2982.002.1-C_at | GUCY1A3 | NM_000856 | 4q31.3-q33\| 4q31.1-q31.2 | 2982.002.1 | 79608.001.1 | 2982.2 | 59.16 |
| 645 | 57447.047.1-T_at | NDRG2 | NM_016298 | 14q11.2 | 57447.047.1 | 79608.002.1 | 57447.47 | 7170.14 |
| 646 | 5803.006.1-E_at | PTPRZ1 | NM_002851 | 7q31.3 | 5803.006.1 | 79608.008.1 | 5803.6 | |
| 647 | 57447.021.1-F_at | NDRG2 | NM_016299 | 14q11.2 | 57447.021.1 | 79608.008.2 | 57447.21 | |
| 648 | 57447.039.1-F_at | NDRG2 | NM_016300 | 14q11.2 | 57447.039.1 | 79608.009.1 | 57447.39 | 205 genes |
| 649 | 4281.008.2-F_at | MID1 | NM_000385 | Xp22 | 4281.008.2 | 79627.003.1 | 4281.8 | 645 transcrits |
| 650 | 57447.029.1-D_at | NDRG2 | NM_016301 | 14q11.2 | 57447.029.1 | 79745.004.3 | 57447.29 | 1228 probesets |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 651 | 65983.013.1-B_at | GRAMD3 | NM_023927 | 5q23.2 | 65983.013.1 | 79895.001.1 | 65983.13 | |
| 652 | 5284.004.1-E_at | PIGR | NM_002644 | 1q31-q41 | 5284.004.1 | 79937.001.1 | 5284.4 | |
| 653 | 4240.011.1-D_at | MFGE8 | NM_005928 | 15q25 | 4240.011.1 | 79937.002.1 | 4240.11 | |
| 654 | 57447.024.1-T_at | NDRG2 | NM_016302 | 14q11.2 | 57447.024.1 | 79971.009.1 | 57447.24 | |
| 655 | 6876.011.1-B_at | TAGLN | NM_001001523 | 11q23.2 | 6876.011.1 | 79971.012.1 | 6876.11 | |
| 656 | 7373.003.2-T_at | COL14A1 | NM_021110 | 8q23 | 7373.003.2 | 79971.013.2 | 7373.3 | |
| 657 | 3852.014.1-D_at | KRT5 | NM_000424 | 12q12-q13 | 3852.014.1 | 79971.014.1 | 3852.14 | |
| 658 | 4915.005.1-D_at | NTRK2 | NM_001007109 | 9q22.1 | 4915.005.1 | 80034.002.2 | 4915.5 | |
| 659 | 9768.002.2-B_at | KIAA0101 | NM_001029992 | 15q22.31 | 9768.002.2 | 80034.003.4 | 9768.2 | |
| 660 | 140885.010.1-D | SIRPA | NM_001040025 | 20p13 | 140885.010.1 | 80034.004.1 | 140885.10 | |
| 661 | 4638.020.1-E_at | MYLK | NM_005981 | 3q21 | 4638.020.1 | 81557.006.1 | 4638.20 | |
| 662 | 57447.017.1-C_at | NDRG2 | NM_016303 | 14q11.2 | 57447.017.1 | 81704.008.1 | 57447.17 | |
| 663 | 7373.004.1-T_at | COL14A1 | NM_021110 | 8q23 | 7373.004.1 | 81704.013.1 | 7373.4 | |
| 664 | 3852.008.2-E_at | KRT5 | NM_000424 | 12q12-q13 | 3852.008.2 | 8321.004.1 | 3852.8 | |
| 665 | 4281.015.1-E_at | MID1 | NM_000386 | Xp22 | 4281.015.1 | 83539.001.1 | 4281.15 | |
| 666 | 8404.013.1-C_at | SPARCL1 | NM_004684 | 4q22.1 | 8404.013.1 | 8404.001.1 | 8404.13 | |
| 667 | 90293.001.3-T_at | KLHL13 | NM_033495 | Xq23-q24 | 90293.001.3 | 8404.002.1 | 90293.1 | |
| 668 | 57447.044.1-T_at | NDRG2 | NM_016304 | 14q11.2 | 57447.044.1 | 8404.004.1 | 57447.44 | |
| 669 | 23650.011.2-D_at | TRIM29 | NM_012101 | 11q22-q23 | 23650.011.2 | 8404.004.2 | 23650.11 | |
| 670 | 2335.006.1-D_at | FN1 | NM_002028 | 2q34 | 2335.006.1 | 8404.005.1 | 2335.6 | |
| 671 | 57447.022.1-T_at | NDRG2 | NM_016305 | 14q11.2 | 57447.022.1 | 8404.008.1 | 57447.22 | |
| 672 | 8404.032.1-D_at | SPARCL1 | NM_004684 | 4q22.1 | 8404.032.1 | 8404.009.1 | 8404.32 | |
| 673 | 8404.030.1-F_at | SPARCL1 | NM_004684 | 4q22.1 | 8404.030.1 | 8404.013.1 | 8404.30 | |
| 674 | 5803.002.2-T_at | PTPRZ1 | NM_002851 | 7q31.3 | 5803.002.2 | 8404.015.1 | 5803.2 | |
| 675 | 8404.004.2-C_at | SPARCL1 | NM_004684 | 4q22.1 | 8404.004.2 | 8404.017.1 | 8404.4 | |
| 676 | 84441.005.1-C_at | MAML2 | NM_032427 | 11q21 | 84441.005.1 | 8404.017.2 | 84441.5 | |
| 677 | 7091.015.1-F_at | TLE4 | NM_007005 | 9q21.31 | 7091.015.1 | 8404.020.1 | 7091.15 | |
| 678 | 2119.005.1-D_at | ETV5 | NM_004454 | 3q28 | 2119.005.1 | 8404.021.1 | 2119.5 | |
| 679 | 7373.003.6-F_at | COL14A1 | NM_021110 | 8q23 | 7373.003.6 | 8404.022.1 | 7373.3 | |
| 680 | 79608.008.1-T_at | RIC3 | NM_024557 | 11p15.4 | 79608.008.1 | 8404.023.1 | 79608.8 | |
| 681 | 3852.008.1-T_at | KRT5 | NM_000424 | 12q12-q13 | 3852.008.1 | 8404.024.1 | 3852.8 | |
| 682 | 8626.007.1-T_at | TP63 | NM_003722 | 3q28 | 8626.007.1 | 8404.025.1 | 8626.7 | |
| 683 | 8404.022.1-T_at | SPARCL1 | NM_004684 | 4q22.1 | 8404.022.1 | 8404.026.1 | 8404.22 | |
| 684 | 8404.034.1-T_at | SPARCL1 | NM_004684 | 4q22.1 | 8404.034.1 | 8404.028.1 | 8404.34 | |
| 685 | 57447.049.1-T_at | NDRG2 | NM_016306 | 14q11.2 | 57447.049.1 | 8404.028.3 | 57447.49 | |
| 686 | 5311.002.1-B_at | PKD2 | NM_000297 | 4q21-q23 | 5311.002.1 | 8404.029.1 | 5311.2 | |
| 687 | 2335.025.3-T_at | FN1 | NM_002029 | 2q34 | 2335.025.3 | 8404.030.1 | 2335.25 | |
| 688 | 4147.012.1-T_at | MATN2 | NM_002380 | 8q22 | 4147.012.1 | 8404.031.1 | 4147.12 | |
| 689 | 301.015.1-T_at | ANXA1 | NM_000700 | 9q12-q21.2\|9q12-q21.2 | 301.015.1 | 8404.032.1 | 301.15 | |
| 690 | 301.004.1-T_at | ANXA1 | NM_000700 | 9q12-q21.2\|9q12-q21.2 | 301.004.1 | 8404.034.1 | 301.4 | |
| 691 | 3426.002.2-F_at | CFI | NM_000204 | 4q25 | 3426.002.2 | 8404.035.1 | 3426.2 | |
| 692 | 7091.001.1-C_at | TLE4 | NM_007005 | 9q21.31 | 7091.001.1 | 84417.001.1 | 7091.1 | |
| 693 | 8404.021.1-D_at | SPARCL1 | NM_004684 | 4q22.1 | 8404.021.1 | 84417.001.2 | 8404.21 | |
| 694 | 7153.002.3-B_at | TOP2A | NM_001067 | 17q21-q22 | 7153.002.3 | 84441.002.1 | 7153.2 | |
| 695 | 53335.002.1-E_at | BCL11A | NM_018014 | 2p16.1 | 53335.002.1 | 84441.005.1 | 53335.2 | |
| 696 | 5284.003.2-T_at | PIGR | NM_002644 | 1q31-q41 | 5284.003.2 | 84668.002.1 | 5284.3 | |
| 697 | 4306.002.1-F_at | NR3C2 | NM_000901 | 4q31.1 | 4306.002.1 | 84668.002.2 | 4306.2 | |
| 698 | 5284.003.2-D_at | PIGR | NM_002644 | 1q31-q41 | 5284.003.2 | 84668.003.1 | 5284.3 | |
| 699 | 5803.002.1-T_at | PTPRZ1 | NM_002851 | 7q31.3 | 5803.002.1 | 84668.004.1 | 5803.2 | |
| 700 | 10253.004.1-E_at | SPRY2 | NM_005842 | 13q31.1 | 10253.004.1 | 8564.004.1 | 10253.4 | |
| 701 | 23650.020.1-T_at | TRIM29 | NM_012101 | 11q22-q23 | 23650.020.1 | 8626.002.1 | 23650.20 | |
| 702 | 57447.042.1-T_at | NDRG2 | NM_016307 | 14q11.2 | 57447.042.1 | 8626.005.1 | 57447.42 | |
| 703 | 6876.023.1-F_at | TAGLN | NM_001001524 | 11q23.2 | 6876.023.1 | 8626.006.1 | 6876.23 | |
| 704 | 7169.015.1-C_at | TPM2 | NM_003292 | 9p13.2-p13.1 | 7169.015.1 | 8626.006.2 | 7169.15 | |
| 705 | 7153.002.4-F_at | TOP2A | NM_001067 | 17q21-q22 | 7153.002.4 | 8626.007.1 | 7153.2 | |
| 706 | 4629.016.1-B_at | MYH11 | NM_001040138 | 16p13.11 | 4629.016.1 | 891.007.1 | 4629.16 | |
| 707 | 6876.002.1-C_at | TAGLN | NM_001001525 | 11q23.2 | 6876.002.1 | 90231.001.1 | 6876.2 | |
| 708 | 65983.007.1-T_at | GRAMD3 | NM_023927 | 5q23.2 | 65983.007.1 | 90293.001.3 | 65983.7 | |
| 709 | 7373.003.2-F_at | COL14A1 | NM_021110 | 8q23 | 7373.003.2 | 9055.010.1 | 7373.3 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 710 | 152015.004.1-T | ROPN1B | NM_001012337 | 3q21.2 | 152015.004.1 | 9055.011.1 | 152015.4 | |
| 711 | 8404.004.2-B_at | SPARCL1 | NM_004684 | 4q22.1 | 8404.004.2 | 9055.012.1 | 8404.4 | |
| 712 | 6285.001.1-B_at | S100B | NM_006272 | 21q22.3 | 6285.001.1 | 9055.013.1 | 6285.1 | |
| 713 | 2115.007.1-E_at | ETV1 | NM_004956 | 7p21.3 | 2115.007.1 | 9055.014.1 | 2115.7 | |
| 714 | 2.013.1-T_at | A2M | NM_000014 | 12p13.3-p12.3 | 2.013.1 | 9055.017.1 | 2.13 | |
| 715 | 6289.005.1-T_at | SAA2 | NM_030754 | 11p15.1-p14 | 6289.005.1 | 9055.019.1 | 6289.5 | |
| 716 | 9232.002.1-T_at | PTTG1 | NM_004219 | 5q35.1 | 9232.002.1 | 9055.020.1 | 9232.2 | |
| 717 | 59.014.1-B_at | ACTA2 | NM_001613 | 10q23.3 | 59.014.1 | 9073.001.1 | 59.14 | |
| 718 | 59.031.1-F_at | ACTA2 | NM_001613 | 10q23.3 | 59.031.1 | 90865.006.1 | 59.31 | |
| 719 | 3084.011.1-T_at | NRG1 | NM_004514 | 8p12 | 3084.011.1 | 9134.001.1 | 3084.11 | |
| 720 | 3872.005.1-F_at | KRT17 | NM_000422 | 17q12-q21 | 3872.005.1 | 9232.001.1 | 3872.5 | |
| 721 | 3084.012.3-F_at | NRG1 | NM_004515 | 8p12 | 3084.012.3 | 9232.002.1 | 3084.12 | |
| 722 | 81704.008.1-F_at | DOCK8 | NM_203447 | 9p24.3 | 81704.008.1 | 9232.004.1 | 81704.8 | |
| 723 | 140885.010.2-C | SIRPA | NM_001040026 | 20p13 | 140885.010.2 | 9413.001.1 | 140885.10 | |
| 724 | 338707.006.1-E | B4GALNT4 | NM_178537 | 11p15.5 | 338707.006.1 | 9413.001.2 | 338707.6 | |
| 725 | 23266.008.2-T_at | LPHN2 | NM_012302 | 1p31.1 | 23266.008.2 | 9413.002.1 | 23266.8 | |
| 726 | 120.005.2-E_at | ADD3 | NM_001121 | 10q24.2-q24.3 | 120.005.2 | 9413.003.1 | 120.5 | |
| 727 | 4281.009.1-E_at | MID1 | NM_000387 | Xp22 | 4281.009.1 | 9413.006.1 | 4281.9 | |
| 728 | 4094.001.1-T_at | MAF | NM_001031804 | 16q22-q23 | 4094.001.1 | 94274.002.1 | 4094.1 | |
| 729 | 2995.001.1-T_at | GYPC | NM_002101 | 2q14-q21 | 2995.001.1 | 94274.003.1 | 2995.1 | |
| 730 | 4638.011.1-T_at | MYLK | NM_005982 | 3q21 | 4638.011.1 | 9452.001.1 | 4638.11 | |
| 731 | 2335.017.1-T_at | FN1 | NM_002030 | 2q34 | 2335.017.1 | 9477.006.1 | 2335.17 | |
| 732 | 5284.001.1-F_at | PIGR | NM_002644 | 1q31-q41 | 5284.001.1 | 9481.001.1 | 5284.1 | |
| 733 | 8404.026.1-D_at | SPARCL1 | NM_004684 | 4q22.1 | 8404.026.1 | 9493.001.1 | 8404.26 | |
| 734 | 2335.009.1-D_at | FN1 | NM_002031 | 2q34 | 2335.009.1 | 9493.004.1 | 2335.9 | |
| 735 | 10461.002.2-F_at | MERTK | NM_006343 | 2q14.1 | 10461.002.2 | 9493.006.1 | 10461.2 | |
| 736 | 84441.002.1-T_at | MAML2 | NM_032427 | 11q21 | 84441.002.1 | 9768.002.2 | 84441.2 | |
| 737 | 147495.006.1-T | APCDD1 | NM_153000 | 18p11.22 | 147495.006.1 | 9768.004.1 | 147495.6 | |
| 738 | 7091.010.1-B_at | TLE4 | NM_007005 | 9q21.31 | 7091.010.1 | 9768.005.1 | 7091.10 | |
| 739 | 8404.008.1-C_at | SPARCL1 | NM_004684 | 4q22.1 | 8404.008.1 | 9898.015.2 | 8404.8 | |
| 740 | 6376.001.2-C_at | CX3CL1 | NM_002996 | 16q13 | 6376.001.2 | | 6376.1 | |
| 741 | 3832.002.1-B_at | KIF11 | NM_004523 | 10q24.1 | 3832.002.1 | | 3832.2 | |
| 742 | 59.034.2-T_at | ACTA2 | NM_001613 | 10q23.3 | 59.034.2 | | 59.34 | |
| 743 | 147495.005.1-B | APCDD1 | NM_153000 | 18p11.22 | 147495.005.1 | | 147495.5 | |
| 744 | 3872.005.1-T_at | KRT17 | NM_000422 | 17q12-q21 | 3872.005.1 | | 3872.5 | |
| 745 | 79895.001.1-D_at | ATP8B4 | NM_024837 | 15q21.2 | 79895.001.1 | | 79895.1 | |
| 746 | 57447.038.1-T_at | NDRG2 | NM_016308 | 14q11.2 | 57447.038.1 | | 57447.38 | |
| 747 | 7373.008.1-T_at | COL14A1 | NM_021110 | 8q23 | 7373.008.1 | | 7373.8 | |
| 748 | 4744.004.1-C_at | NEFH | NM_021076 | 22q12.2 | 4744.004.1 | | 4744.4 | |
| 749 | 140885.010.1-T | SIRPA | NM_001040027 | 20p13 | 140885.010.1 | | 140885.10 | |
| 750 | 6876.016.2-E_at | TAGLN | NM_001001526 | 11q23.2 | 6876.016.2 | | 6876.16 | |
| 751 | 8404.015.1-T_at | SPARCL1 | NM_004684 | 4q22.1 | 8404.015.1 | | 8404.15 | |
| 752 | 4281.014.1-T_at | MID1 | NM_000388 | Xp22 | 4281.014.1 | | 4281.14 | |
| 753 | 4288.006.1-F_at | MKI67 | NM_002417 | 10q25-qter | 4288.006.1 | | 4288.6 | |
| 754 | 25925.009.1-E_at | ZNF521 | NM_015461 | 18q11.2 | 25925.009.1 | | 25925.9 | |
| 755 | 4240.009.1-B_at | MFGE8 | NM_005928 | 15q25 | 4240.009.1 | | 4240.9 | |
| 756 | 667.010.1-E_at | DST | NM_001725 | 6p12.1 | 667.010.1 | | 667.10 | |
| 757 | 3866.005.1-B_at | KRT15 | NM_002275 | 17q21.2 | 3866.005.1 | | 3866.5 | |
| 758 | 57447.011.1-T_at | NDRG2 | NM_016309 | 14q11.2 | 57447.011.1 | | 57447.11 | |
| 759 | 57447.034.1-B_at | NDRG2 | NM_016310 | 14q11.2 | 57447.034.1 | | 57447.34 | |
| 760 | 25802.004.1-B_at | LMOD1 | NM_012134 | 1q32 | 25802.004.1 | | 25802.4 | |
| 761 | 8404.024.1-T_at | SPARCL1 | NM_004684 | 4q22.1 | 8404.024.1 | | 8404.24 | |
| 762 | 57447.032.1-T_at | NDRG2 | NM_016311 | 14q11.2 | 57447.032.1 | | 57447.32 | |
| 763 | 667.021.1-F_at | DST | NM_001726 | 6p12.1 | 667.021.1 | | 667.21 | |
| 764 | 5858.001.2-F_at | PZP | NM_002864 | 12p13-p12.2 | 5858.001.2 | | 5858.1 | |
| 765 | 51062.008.1-T_at | SPG3A | NM_015915 | 14q22.1 | 51062.008.1 | | 51062.8 | |
| 766 | 2335.013.1-F_at | FN1 | NM_002032 | 2q34 | 2335.013.1 | | 2335.13 | |
| 767 | 2568.001.2-T_at | GABRP | NM_014211 | 5q33-q34 | 2568.001.2 | | 2568.1 | |
| 768 | 7170.005.2-D_at | TPM3 | NM_001043351 | 1q21.2 | 7170.005.2 | | 7170.5 | |
| 769 | 57447.034.1-F_at | NDRG2 | NM_016312 | 14q11.2 | 57447.034.1 | | 57447.34 | |
| 770 | 7153.002.6-C_at | TOP2A | NM_001067 | 17q21-q22 | 7153.002.6 | | 7153.2 | |
| 771 | 2568.003.1-T_at | GABRP | NM_014211 | 5q33-q34 | 2568.003.1 | | 2568.3 | |
| 772 | 59.008.2-T_at | ACTA2 | NM_001613 | 10q23.3 | 59.008.2 | | 59.8 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 773 | 9898.015.2-B_at | UBAP2L | NM_014847 | 1q21.3 | 9898.015.2 | | 9898.15 | |
| 774 | 7018.013.1-T_at | TF | NM_001063 | 3q22.1 | 7018.013.1 | | 7018.13 | |
| 775 | 7170.034.2-D_at | TPM3 | NM_001043352 | 1q21.2 | 7170.034.2 | | 7170.34 | |
| 776 | 3866.004.1-E_at | KRT15 | NM_002275 | 17q21.2 | 3866.004.1 | | 3866.4 | |
| 777 | 5284.001.1-T_at | PIGR | NM_002644 | 1q31-q41 | 5284.001.1 | | 5284.1 | |
| 778 | 2.002.1-C_at | A2M | NM_000014 | 12p13.3-p12.3 | 2.002.1 | | 2.2 | |
| 779 | 57447.050.1-T_at | NDRG2 | NM_016313 | 14q11.2 | 57447.050.1 | | 57447.50 | |
| 780 | 7018.014.1-F_at | TF | NM_001063 | 3q22.1 | 7018.014.1 | | 7018.14 | |
| 781 | 2335.032.1-D_at | FN1 | NM_002033 | 2q34 | 2335.032.1 | | 2335.32 | |
| 782 | 3866.002.1-C_at | KRT15 | NM_002275 | 17q21.2 | 3866.002.1 | | 3866.2 | |
| 783 | 57447.043.1-T_at | NDRG2 | NM_016314 | 14q11.2 | 57447.043.1 | | 57447.43 | |
| 784 | 51201.005.1-D_at | ZDHHC2 | NM_016353 | 8p21.3-p22 | 51201.005.1 | | 51201.5 | |
| 785 | 51203.003.1-T_at | NUSAP1 | NM_016360 | 15q15.1 | 51203.003.1 | | 51203.3 | |
| 786 | 9493.001.1-F_at | KIF23 | NM_004856 | 15q23 | 9493.001.1 | | 9493.1 | |
| 787 | 57447.024.1-B_at | NDRG2 | NM_016315 | 14q11.2 | 57447.024.1 | | 57447.24 | |
| 788 | 80034.003.4-B_at | FAM130A2 | NM_024969 | 2q24.3 | 80034.003.4 | | 80034.3 | |
| 789 | 7170.016.3-C_at | TPM3 | NM_001043353 | 1q21.2 | 7170.016.3 | | 7170.16 | |
| 790 | 65983.003.1-T_at | GRAMD3 | NM_023927 | 5q23.2 | 65983.003.1 | | 65983.3 | |
| 791 | 57447.026.1-T_at | NDRG2 | NM_016316 | 14q11.2 | 57447.026.1 | | 57447.26 | |
| 792 | 440421.001.1-F | | | | 440421.001.1 | | 440421.1 | |
| 793 | 301.008.1-D_at | ANXA1 | NM_000700 | 9q12-q21.2\|9q12-q21.2 | 301.008.1 | | 301.8 | |
| 794 | 80034.002.2-T_at | FAM130A2 | NM_024969 | 2q24.3 | 80034.002.2 | | 80034.2 | |
| 795 | 7153.002.5-B_at | TOP2A | NM_001067 | 17q21-q22 | 7153.002.5 | | 7153.2 | |
| 796 | 3852.023.1-T_at | KRT5 | NM_000424 | 12q12-q13 | 3852.023.1 | | 3852.23 | |
| 797 | 8404.013.1-F_at | SPARCL1 | NM_004684 | 4q22.1 | 8404.013.1 | | 8404.13 | |
| 798 | 2.018.1-C_at | A2M | NM_000014 | 12p13.3-p12.3 | 2.018.1 | | 2.18 | |
| 799 | 10124.003.1-B_at | ARL4A | NM_001037165 | 7p21-p15.3 | 10124.003.1 | | 10124.3 | |
| 800 | 3852.008.2-F_at | KRT5 | NM_000424 | 12q12-q13 | 3852.008.2 | | 3852.8 | |
| 801 | 4288.006.2-T_at | MKI67 | NM_002417 | 10q25-qter | 4288.006.2 | | 4288.6 | |
| 802 | 8404.026.1-C_at | SPARCL1 | NM_004684 | 4q22.1 | 8404.026.1 | | 8404.26 | |
| 803 | 23650.019.1-C_at | TRIM29 | NM_012101 | 11q22-q23 | 23650.019.1 | | 23650.19 | |
| 804 | 7170.027.1-T_at | TPM3 | NM_001043354 | 1q21.2 | 7170.027.1 | | 7170.27 | |
| 805 | 54928.003.1-E_at | IMPAD1 | NM_017813 | 8q12.1 | 54928.003.1 | | 54928.3 | |
| 806 | 2335.025.1-B_at | FN1 | NM_002034 | 2q34 | 2335.025.1 | | 2335.25 | |
| 807 | 3084.010.1-T_at | NRG1 | NM_004516 | 8p12 | 3084.010.1 | | 3084.10 | |
| 808 | 57447.051.1-T_at | NDRG2 | NM_016317 | 14q11.2 | 57447.051.1 | | 57447.51 | |
| 809 | 80034.003.4-T_at | FAM130A2 | NM_024969 | 2q24.3 | 80034.003.4 | | 80034.3 | |
| 810 | 2568.005.1-D_at | GABRP | NM_014211 | 5q33-q34 | 2568.005.1 | | 2568.5 | |
| 811 | 8404.032.1-F_at | SPARCL1 | NM_004684 | 4q22.1 | 8404.032.1 | | 8404.32 | |
| 812 | 2115.003.1-E_at | ETV1 | NM_004956 | 7p21.3 | 2115.003.1 | | 2115.3 | |
| 813 | 57447.035.1-T_at | NDRG2 | NM_016318 | 14q11.2 | 57447.035.1 | | 57447.35 | |
| 814 | 8404.009.1-T_at | SPARCL1 | NM_004684 | 4q22.1 | 8404.009.1 | | 8404.9 | |
| 815 | 8404.028.3-B_at | SPARCL1 | NM_004684 | 4q22.1 | 8404.028.3 | | 8404.28 | |
| 816 | 6289.003.1-B_at | SAA2 | NM_030754 | 11p15.1-p14 | 6289.003.1 | | 6289.3 | |
| 817 | 7170.025.1-F_at | TPM3 | NM_001043355 | 1q21.2 | 7170.025.1 | | 7170.25 | |
| 818 | 8404.030.1-D_at | SPARCL1 | NM_004684 | 4q22.1 | 8404.030.1 | | 8404.30 | |
| 819 | 8404.009.1-F_at | SPARCL1 | NM_004684 | 4q22.1 | 8404.009.1 | | 8404.9 | |
| 820 | 2335.009.1-T_at | FN1 | NM_002035 | 2q34 | 2335.009.1 | | 2335.9 | |
| 821 | 22974.007.1-F_at | TPX2 | NM_012112 | 20q11.2 | 22974.007.1 | | 22974.7 | |
| 822 | 3426.002.1-B_at | CFI | NM_000204 | 4q25 | 3426.002.1 | | 3426.2 | |
| 823 | 4638.003.1-D_at | MYLK | NM_005983 | 3q21 | 4638.003.1 | | 4638.3 | |
| 824 | 4147.011.1-T_at | MATN2 | NM_002381 | 8q22 | 4147.011.1 | | 4147.11 | |
| 825 | 6876.016.2-T_at | TAGLN | NM_001001527 | 11q23.2 | 6876.016.2 | | 6876.16 | |
| 826 | 23650.003.1-F_at | TRIM29 | NM_012101 | 11q22-q23 | 23650.003.1 | | 23650.3 | |
| 827 | 4744.004.1-E_at | NEFH | NM_021076 | 22q12.2 | 4744.004.1 | | 4744.4 | |
| 828 | 64168.010.1-F_at | EFCBP1 | NM_022351 | 8q21.3 | 64168.010.1 | | 64168.10 | |
| 829 | 9073.001.1-F_at | CLDN8 | NM_199328 | 21q22.11 | 9073.001.1 | | 9073.1 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 830 | 5288.001.3-B_at | PIK3C2G | NM_004570 | 12p12 | 5288.001.3 | | 5288.1 | |
| 831 | 3866.005.1-D_at | KRT15 | NM_002275 | 17q21.2 | 3866.005.1 | | 3866.5 | |
| 832 | 8404.021.1-T_at | SPARCL1 | NM_004684 | 4q22.1 | 8404.021.1 | | 8404.21 | |
| 833 | 25925.011.1-E_at | ZNF521 | NM_015461 | 18q11.2 | 25925.011.1 | | 25925.11 | |
| 834 | 23266.001.3-F_at | LPHN2 | NM_012302 | 1p31.1 | 23266.001.3 | | 23266.1 | |
| 835 | 9232.004.1-F_at | PTTG1 | NM_004219 | 5q35.1 | 9232.004.1 | | 9232.4 | |
| 836 | 4147.005.2-F_at | MATN2 | NM_002382 | 8q22 | 4147.005.2 | | 4147.5 | |
| 837 | 2335.025.3-B_at | FN1 | NM_002036 | 2q34 | 2335.025.3 | | 2335.25 | |
| 838 | 4638.006.1-C_at | MYLK | NM_005984 | 3q21 | 4638.006.1 | | 4638.6 | |
| 839 | 147804.004.1-T | LOC147804 | NM_001010856 | 19q13.41 | 147804.004.1 | | 147804.4 | |
| 840 | 81704.013.1-D_at | DOCK8 | NM_203447 | 9p24.3 | 81704.013.1 | | 81704.13 | |
| 841 | 54443.013.1-B_at | ANLN | NM_018685 | 7p15-p14 | 54443.013.1 | | 54443.13 | |
| 842 | 1410.005.1-T_at | CRYAB | NM_001885 | 11q22.3-q23.1 | 1410.005.1 | | 1410.5 | |
| 843 | 25925.009.1-T_at | ZNF521 | NM_015461 | 18q11.2 | 25925.009.1 | | 25925.9 | |
| 844 | 3204.001.1-T_at | HOXA7 | NM_006896 | 7p15-p14 | 3204.001.1 | | 3204.1 | |
| 845 | 29997.012.1-F_at | GLTSCR2 | NM_015710 | 19q13.3 | 29997.012.1 | | 29997.12 | |
| 846 | 2.005.1-C_at | A2M | NM_000014 | 12p13.3-p12.3 | 2.005.1 | | 2.5 | |
| 847 | 140885.011.1-F | SIRPA | NM_001040028 | 20p13 | 140885.011.1 | | 140885.11 | |
| 848 | 7153.002.3-F_at | TOP2A | NM_001067 | 17q21-q22 | 7153.002.3 | | 7153.2 | |
| 849 | 1063.002.1-F_at | CENPF | NM_016343 | 1q32-q41 | 1063.002.1 | | 1063.2 | |
| 850 | 10144.021.1-F_at | FAM13A1 | NM_001015046 | 4q22.1 | 10144.021.1 | | 10144.21 | |
| 851 | 8404.025.1-E_at | SPARCL1 | NM_004684 | 4q22.1 | 8404.025.1 | | 8404.25 | |
| 852 | 6876.020.1-B_at | TAGLN | NM_001001528 | 11q23.2 | 6876.020.1 | | 6876.20 | |
| 853 | 7170.006.1-C_at | TPM3 | NM_001043356 | 1q21.2 | 7170.006.1 | | 7170.6 | |
| 854 | 10051.016.1-T_at | SMC4 | NM_001002799 | 3q26.1 | 10051.016.1 | | 10051.16 | |
| 855 | 5288.001.2-D_at | PIK3C2G | NM_004570 | 12p12 | 5288.001.2 | | 5288.1 | |
| 856 | 7018.029.1-T_at | TF | NM_001063 | 3q22.1 | 7018.029.1 | | 7018.29 | |
| 857 | 5627.002.1-B_at | PROS1 | NM_000313 | 3q11.2 | 5627.002.1 | | 5627.2 | |
| 858 | 57447.037.1-T_at | NDRG2 | NM_016319 | 14q11.2 | 57447.037.1 | | 57447.37 | |
| 859 | 4147.005.2-D_at | MATN2 | NM_002383 | 8q22 | 4147.005.2 | | 4147.5 | |
| 860 | 8404.023.1-T_at | SPARCL1 | NM_004684 | 4q22.1 | 8404.023.1 | | 8404.23 | |
| 861 | 3872.006.1-D_at | KRT17 | NM_000422 | 17q12-q21 | 3872.006.1 | | 3872.6 | |
| 862 | 399687.001.1-C | MYO18A | NM_078471 | 17q11.2 | 399687.001.1 | | 399687.1 | |
| 863 | 3815.002.4-D_at | KIT | NM_000237 | 4q11-q12 | 3815.002.4 | | 3815.2 | |
| 864 | 59.034.2-B_at | ACTA2 | NM_001613 | 10q23.3 | 59.034.2 | | 59.34 | |
| 865 | 8404.035.1-T_at | SPARCL1 | NM_004684 | 4q22.1 | 8404.035.1 | | 8404.35 | |
| 866 | 8404.030.1-T_at | SPARCL1 | NM_004684 | 4q22.1 | 8404.030.1 | | 8404.30 | |
| 867 | 5997.002.2-T_at | TESC | NM_017899 | 12q24.22 | 54997.002.2 | | 54997.2 | |
| 868 | 57561.001.1-F_at | ARRDC3 | NM_020801 | 5q14.3 | 57561.001.1 | | 57561.1 | |
| 869 | 8404.031.1-T_at | SPARCL1 | NM_004684 | 4q22.1 | 8404.031.1 | | 8404.31 | |
| 870 | 2.025.1-E_at | A2M | NM_000014 | 12p13.3-p12.3 | 2.025.1 | | 2.25 | |
| 871 | 699.002.1-F_at | BUB1 | NM_004336 | 2q14 | 699.002.1 | | 699.2 | |
| 872 | 57447.041.1-F_at | NDRG2 | NM_016320 | 14q11.2 | 57447.041.1 | | 57447.41 | |
| 873 | 9055.013.1-D_at | PRC1 | NM_003981 | 15q26.1 | 9055.013.1 | | 9055.13 | |
| 874 | 8404.008.1-D_at | SPARCL1 | NM_004684 | 4q22.1 | 8404.008.1 | | 8404.8 | |
| 875 | 7018.028.1-T_at | TF | NM_001063 | 3q22.1 | 7018.028.1 | | 7018.28 | |
| 876 | 2568.005.1-T_at | GABRP | NM_014211 | 5q33-q34 | 2568.005.1 | | 2568.5 | |
| 877 | 10051.005.3-T_at | SMC4 | NM_001002800 | 3q26.1 | 10051.005.3 | | 10051.5 | |
| 878 | 2568.002.2-T_at | GABRP | NM_014211 | 5q33-q34 | 2568.002.2 | | 2568.2 | |
| 879 | 4147.004.1-F_at | MATN2 | NM_002384 | 8q22 | 4147.004.1 | | 4147.4 | |
| 880 | 2938.001.1-T_at | GSTA1 | NM_145740 | 6p12.1 | 2938.001.1 | | 2938.1 | |
| 881 | 1308.007.1-E_at | COL17A1 | NM_000506 | 10q24.3 | 1308.007.1 | | 1308.7 | |
| 882 | 2982.012.1-T_at | GUCY1A3 | NM_000856 | 4q31.3-q33\| 4q31.1-q31.2 | 2982.012.1 | | 2982.12 | |
| 883 | 8404.028.1-D_at | SPARCL1 | NM_004684 | 4q22.1 | 8404.028.1 | | 8404.28 | |
| 884 | 7373.001.2-B_at | COL14A1 | NM_021110 | 8q23 | 7373.001.2 | | 7373.1 | |
| 885 | 2893.002.2-B_at | GRIA4 | NM_000829 | 11q22 | 2893.002.2 | | 2893.2 | |
| 886 | 116369.006.4-C | SLC26A8 | NM_052961 | 6p21 | 116369.006.4 | | 116369.6 | |
| 887 | 6304.007.1-T_at | SATB1 | NM_002971 | 3p23 | 6304.007.1 | | 6304.7 | |
| 888 | 2335.035.1-T_at | FN1 | NM_002037 | 2q34 | 2335.035.1 | | 2335.35 | |
| 889 | 4751.002.1-T_at | NEK2 | NM_002497 | 1q32.2-q41 | 4751.002.1 | | 4751.2 | |
| 890 | 64151.001.2-T_at | NCAPG | NM_022346 | 4p15.33 | 64151.001.2 | | 64151.1 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 891 | 29089.003.1-T_at | UBE2T | NM_014176 | 1q32.1 | 29089.003.1 | | 29089.3 | |
| 892 | 59.031.1-B_at | ACTA2 | NM_001613 | 10q23.3 | 59.031.1 | | 59.31 | |
| 893 | 7018.025.1-T_at | TF | NM_001063 | 3q22.1 | 7018.025.1 | | 7018.25 | |
| 894 | 3860.008.1-T_at | KRT13 | NM_002276 | 17q12-q21.2 | 3860.008.1 | | 3860.8 | |
| 895 | 5858.003.3-F_at | PZP | NM_002864 | 12p13-p12.2 | 5858.003.3 | | 5858.3 | |
| 896 | 8404.009.1-C_at | SPARCL1 | NM_004684 | 4q22.1 | 8404.009.1 | | 8404.9 | |
| 897 | 7169.022.1-T_at | TPM2 | NM_003293 | 9p13.2-p13.1 | 7169.022.1 | | 7169.22 | |
| 898 | 25925.006.1-T_at | ZNF521 | NM_015461 | 18q11.2 | 25925.006.1 | | 25925.6 | |
| 899 | 59.049.1-F_at | ACTA2 | NM_001613 | 10q23.3 | 59.049.1 | | 59.49 | |
| 900 | 5284.003.1-T_at | PIGR | NM_002644 | 1q31-q41 | 5284.003.1 | | 5284.3 | |
| 901 | 2982.002.1-F_at | GUCY1A3 | NM_000856 | 4q31.3-q33\|4q31.1-q31.2 | 2982.002.1 | | 2982.2 | |
| 902 | 2568.002.1-T_at | GABRP | NM_014211 | 5q33-q34 | 2568.002.1 | | 2568.2 | |
| 903 | 301.004.1-B_at | ANXA1 | NM_000700 | 9q12-q21.2\|9q12-q21.2 | 301.004.1 | | 301.4 | |
| 904 | 25925.011.1-F_at | ZNF521 | NM_015461 | 18q11.2 | 25925.011.1 | | 25925.11 | |
| 905 | 59.004.1-F_at | ACTA2 | NM_001613 | 10q23.3 | 59.004.1 | | 59.4 | |
| 906 | 6289.002.1-B_at | SAA2 | NM_030754 | 11p15.1-p14 | 6289.002.1 | | 6289.2 | |
| 907 | 244.003.1-C_at | ANXA8L2 | NM_001630 | 10q11.22 | 244.003.1 | | 244.3 | |
| 908 | 11065.008.1-C_at | UBE2C | NM_007020 | 20q13.12 | 11065.008.1 | | 11065.8 | |
| 909 | 7091.006.1-T_at | TLE4 | NM_007005 | 9q21.31 | 7091.006.1 | | 7091.6 | |
| 910 | 79608.009.1-F_at | RIC3 | NM_024557 | 11p15.4 | 79608.009.1 | | 79608.9 | |
| 911 | 9413.002.1-T_at | C9orf61 | NM_004816 | 9q13-q21 | 9413.002.1 | | 9413.2 | |
| 912 | 7431.064.1-C_at | VIM | NM_003380 | 10p13 | 7431.064.1 | | 7431.64 | |
| 913 | 8404.029.1-E_at | SPARCL1 | NM_004684 | 4q22.1 | 8404.029.1 | | 8404.29 | |
| 914 | 6876.020.1-T_at | TAGLN | NM_001001529 | 11q23.2 | 6876.020.1 | | 6876.20 | |
| 915 | 301.005.1-T_at | ANXA1 | NM_000700 | 9q12-q21.2\|9q12-q21.2 | 301.005.1 | | 301.5 | |
| 916 | 9055.014.1-T_at | PRC1 | NM_003982 | 15q26.1 | 9055.014.1 | | 9055.14 | |
| 917 | 4281.023.1-T_at | MID1 | NM_000389 | Xp22 | 4281.023.1 | | 4281.23 | |
| 918 | 3868.005.1-D_at | KRT16 | NM_005557 | 17q12-q21 | 3868.005.1 | | 3868.5 | |
| 919 | 1062.001.6-B_at | CENPE | NM_001813 | 4q24-q25 | 1062.001.6 | | 1062.1 | |
| 920 | 5858.005.1-T_at | PZP | NM_002864 | 12p13-p12.2 | 5858.005.1 | | 5858.5 | |
| 921 | 51201.007.1-F_at | ZDHHC2 | NM_016353 | 8p21.3-p22 | 51201.007.1 | | 51201.7 | |
| 922 | 4240.001.1-B_at | MFGE8 | NM_005928 | 15q25 | 4240.001.1 | | 4240.1 | |
| 923 | 8404.029.1-T_at | SPARCL1 | NM_004684 | 4q22.1 | 8404.029.1 | | 8404.29 | |
| 924 | 9413.001.1-T_at | C9orf61 | NM_004816 | 9q13-q21 | 9413.001.1 | | 9413.1 | |
| 925 | 9768.005.1-T_at | KIAA0101 | NM_001029993 | 15q22.31 | 9768.005.1 | | 9768.5 | |
| 926 | 11197.001.1-T_at | WIF1 | NM_007191 | 12q14.3 | 11197.001.1 | | 11197.1 | |
| 927 | 6285.002.1-T_at | S100B | NM_006272 | 21q22.3 | 6285.002.1 | | 6285.2 | |
| 928 | 2335.006.2-F_at | FN1 | NM_002038 | 2q34 | 2335.006.2 | | 2335.6 | |
| 929 | 7169.001.1-C_at | TPM2 | NM_003294 | 9p13.2-p13.1 | 7169.001.1 | | 7169.1 | |
| 930 | 9493.004.1-T_at | KIF23 | NM_004856 | 15q23 | 9493.004.1 | | 9493.4 | |
| 931 | 4601.014.1-T_at | MXI1 | NM_001008541 | 10q24-q25 | 4601.014.1 | | 4601.14 | |
| 932 | 51203.002.2-F_at | NUSAP1 | NM_016361 | 15q15.1 | 51203.002.2 | | 51203.2 | |
| 933 | 7018.022.1-F_at | TF | NM_001063 | 3q22.1 | 7018.022.1 | | 7018.22 | |
| 934 | 4288.009.1-F_at | MKI67 | NM_002417 | 10q25-qter | 4288.009.1 | | 4288.9 | |
| 935 | 8321.004.1-D_at | FZD1 | NM_003505 | 7q21 | 8321.004.1 | | 8321.4 | |
| 936 | 8564.004.1-E_at | KMO | NM_003679 | 1q42-q44 | 8564.004.1 | | 8564.4 | |
| 937 | 7169.022.1-C_at | TPM2 | NM_003295 | 9p13.2-p13.1 | 7169.022.1 | | 7169.22 | |
| 938 | 29127.013.1-T_at | RACGAP1 | NM_013277 | 12q13.13 | 29127.013.1 | | 29127.13 | |
| 939 | 2.018.1-B_at | A2M | NM_000014 | 12p13.3-p12.3 | 2.018.1 | | 2.18 | |
| 940 | 2.005.1-D_at | A2M | NM_000014 | 12p13.3-p12.3 | 2.005.1 | | 2.5 | |
| 941 | 1058.004.2-T_at | CENPA | NM_001042426 | 2p24-p21 | 1058.004.2 | | 1058.4 | |
| 942 | 2232.014.1-C_at | FDXR | NM_004110 | 17q24-q25 | 2232.014.1 | | 2232.14 | |
| 943 | 23650.005.1-E_at | TRIM29 | NM_012101 | 11q22-q23 | 23650.005.1 | | 23650.5 | |
| 944 | 5621.002.2-T_at | PRNP | NM_000311 | 20p13 | 5621.002.2 | | 5621.2 | |
| 945 | 51201.005.1-B_at | ZDHHC2 | NM_016353 | 8p21.3-p22 | 51201.005.1 | | 51201.5 | |
| 946 | 667.022.1-F_at | DST | NM_001727 | 6p12.1 | 667.022.1 | | 667.22 | |
| 947 | 54443.012.1-C_at | ANLN | NM_018685 | 7p15-p14 | 54443.012.1 | | 54443.12 | |
| 948 | 25802.003.1-C_at | LMOD1 | NM_012134 | 1q32 | 25802.003.1 | | 25802.3 | |
| 949 | 3479.003.1-T_at | IGF1 | NM_000618 | 12q22-q23 | 3479.003.1 | | 3479.3 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 950 | 94274.003.1-D_at | PPP1R14A | NM_033256 | 19q13.1 | 94274.003.1 | | 94274.3 | |
| 951 | 84668.003.1-T_at | FAM126A | NM_032581 | 7p15.3 | 84668.003.1 | | 84668.3 | |
| 952 | 22974.008.1-E_at | TPX2 | NM_012112 | 20q11.2 | 22974.008.1 | | 22974.8 | |
| 953 | 55656.007.3-B_at | INTS8 | NM_017864 | 8q22.1 | 55656.007.3 | | 55656.7 | |
| 954 | 29127.002.1-T_at | RACGAP1 | NM_013277 | 12q13.13 | 29127.002.1 | | 29127.2 | |
| 955 | 4281.012.2-T_at | MID1 | NM_000390 | Xp22 | 4281.012.2 | | 4281.12 | |
| 956 | 2335.013.1-B_at | FN1 | NM_002039 | 2q34 | 2335.013.1 | | 2335.13 | |
| 957 | 79627.003.1-B_at | OGFRL1 | NM_024576 | 6q13 | 79627.003.1 | | 79627.3 | |
| 958 | 2982.014.1-T_at | GUCY1A3 | NM_000856 | 4q31.3-q33\|4q31.1-q31.2 | 2982.014.1 | | 2982.14 | |
| 959 | 2335.053.1-T_at | FN1 | NM_002040 | 2q34 | 2335.053.1 | | 2335.53 | |
| 960 | 667.001.1-F_at | DST | NM_001728 | 6p12.1 | 667.001.1 | | 667.1 | |
| 961 | 8404.030.1-B_at | SPARCL1 | NM_004684 | 4q22.1 | 8404.030.1 | | 8404.30 | |
| 962 | 2335.025.1-C_at | FN1 | NM_002041 | 2q34 | 2335.025.1 | | 2335.25 | |
| 963 | 140885.010.3-D | SIRPA | NM_001040029 | 20p13 | 140885.010.3 | | 140885.10 | |
| 964 | 55366.001.2-F_at | LGR4 | NM_018490 | 11p14-p13 | 55366.001.2 | | 55366.1 | |
| 965 | 7169.015.1-D_at | TPM2 | NM_003296 | 9p13.2-p13.1 | 7169.015.1 | | 7169.15 | |
| 966 | 57447.002.1-B_at | NDRG2 | NM_016321 | 14q11.2 | 57447.002.1 | | 57447.2 | |
| 967 | 22974.008.1-T_at | TPX2 | NM_012112 | 20q11.2 | 22974.008.1 | | 22974.8 | |
| 968 | 6876.011.1-C_at | TAGLN | NM_001001530 | 11q23.2 | 6876.011.1 | | 6876.11 | |
| 969 | 4281.008.2-D_at | MID1 | NM_000391 | Xp22 | 4281.008.2 | | 4281.8 | |
| 970 | 59.008.1-T_at | ACTA2 | NM_001613 | 10q23.3 | 59.008.1 | | 59.8 | |
| 971 | 23266.008.1-F_at | LPHN2 | NM_012302 | 1p31.1 | 23266.008.1 | | 23266.8 | |
| 972 | 2568.003.2-T_at | GABRP | NM_014211 | 5q33-q34 | 2568.003.2 | | 2568.3 | |
| 973 | 5311.003.1-T_at | PKD2 | NM_000297 | 4q21-q23 | 5311.003.1 | | 5311.3 | |
| 974 | 6304.011.1-T_at | SATB1 | NM_002971 | 3p23 | 6304.011.1 | | 6304.11 | |
| 975 | 3861.008.1-B_at | KRT14 | NM_000526 | 17q12-q21 | 3861.008.1 | | 3861.8 | |
| 976 | 7018.013.1-B_at | TF | NM_001063 | 3q22.1 | 7018.013.1 | | 7018.13 | |
| 977 | 8404.005.1-F_at | SPARCL1 | NM_004684 | 4q22.1 | 8404.005.1 | | 8404.5 | |
| 978 | 7170.027.1-C_at | TPM3 | NM_001043357 | 1q21.2 | 7170.027.1 | | 7170.27 | |
| 979 | 8404.023.1-C_at | SPARCL1 | NM_004684 | 4q22.1 | 8404.023.1 | | 8404.23 | |
| 980 | 7373.007.1-C_at | COL14A1 | NM_021110 | 8q23 | 7373.007.1 | | 7373.7 | |
| 981 | 1410.009.1-T_at | CRYAB | NM_001885 | 11q22.3-q23.1 | 1410.009.1 | | 1410.9 | |
| 982 | 79745.004.3-D_at | CLIP4 | NM_024692 | 2p23.2 | 79745.004.3 | | 79745.4 | |
| 983 | 24137.004.1-T_at | KIF4A | NM_012310 | Xq13.1 | 24137.004.1 | | 24137.4 | |
| 984 | 6241.013.1-B_at | RRM2 | NM_001034 | 2p25-p24 | 6241.013.1 | | 6241.13 | |
| 985 | 1410.001.1-T_at | CRYAB | NM_001885 | 11q22.3-q23.1 | 1410.001.1 | | 1410.1 | |
| 986 | 4781.015.2-B_at | NFIB | NM_005596 | 9p24.1 | 4781.015.2 | | 4781.15 | |
| 987 | 72.002.1-T_at | ACTG2 | NM_001615 | 2p13.1 | 72.002.1 | | 72.2 | |
| 988 | 4833.004.1-D_at | NME4 | NM_005009 | 16p13.3 | 4833.004.1 | | 4833.4 | |
| 989 | 57447.024.1-D_at | NDRG2 | NM_016322 | 14q11.2 | 57447.024.1 | | 57447.24 | |
| 990 | 2982.013.2-T_at | GUCY1A3 | NM_000856 | 4q31.3-q33\|4q31.1-q31.2 | 2982.013.2 | | 2982.13 | |
| 991 | 79971.012.1-T_at | GPR177 | NM_001002292 | 1p31.3 | 79971.012.1 | | 79971.12 | |
| 992 | 8404.028.3-C_at | SPARCL1 | NM_004684 | 4q22.1 | 8404.028.3 | | 8404.28 | |
| 993 | 4638.011.1-E_at | MYLK | NM_005985 | 3q21 | 4638.011.1 | | 4638.11 | |
| 994 | 7169.004.1-C_at | TPM2 | NM_003297 | 9p13.2-p13.1 | 7169.004.1 | | 7169.4 | |
| 995 | 4288.004.1-F_at | MKI67 | NM_002417 | 10q25-qter | 4288.004.1 | | 4288.4 | |
| 996 | 59.012.2-C_at | ACTA2 | NM_001613 | 10q23.3 | 59.012.2 | | 59.12 | |
| 997 | 301.008.1-B_at | ANXA1 | NM_000700 | 9q12-q21.2\|9q12-q21.2 | 301.008.1 | | 301.8 | |
| 998 | 4281.012.1-T_at | MID1 | NM_000381; | Xp22 | 4281.012.1 | | 4281.12 | |
| 999 | 2335.016.1-F_at | FN1 | NM_002042 | 2q34 | 2335.016.1 | | 2335.16 | |
| 1000 | 259266.003.1-C | ASPM | NM_018136 | 1q31 | 259266.003.1 | | 259266.3 | |
| 1001 | 9055.020.1-T_at | PRC1 | NM_003983 | 15q26.1 | 9055.020.1 | | 9055.20 | |
| 1002 | 7091.016.1-T_at | TLE4 | NM_007005 | 9q21.31 | 7091.016.1 | | 7091.16 | |
| 1003 | 59.023.1-T_at | ACTA2 | NM_001613 | 10q23.3 | 59.023.1 | | 59.23 | |
| 1004 | 57162.010.1-B_at | PELI1 | NM_020651 | 2p13.3 | 57162.010.1 | | 57162.10 | |
| 1005 | 4781.002.2-D_at | NFIB | NM_005596 | 9p24.1 | 4781.002.2 | | 4781.2 | |
| 1006 | 6122.037.1-T_at | RPL3 | NM_000967 | 22q13 | 6122.037.1 | | 6122.37 | |
| 1007 | 4240.015.1-B_at | MFGE8 | NM_005928 | 15q25 | 4240.015.1 | | 4240.15 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 1008 | 59.034.1-T_at | ACTA2 | NM_001613 | 10q23.3 | 59.034.1 | | 59.34 | |
| 1009 | 8404.004.2-D_at | SPARCL1 | NM_004684 | 4q22.1 | 8404.004.2 | | 8404.4 | |
| 1010 | 9413.001.2-T_at | C9orf61 | NM_004816 | 9q13-q21 | 9413.001.2 | | 9413.1 | |
| 1011 | 2.005.1-F_at | A2M | NM_000014 | 12p13.3-p12.3 | 2.005.1 | | 2.5 | |
| 1012 | 6304.002.1-T_at | SATB1 | NM_002971 | 3p23 | 6304.002.1 | | 6304.2 | |
| 1013 | 3852.005.1-C_at | KRT5 | NM_000424 | 12q12-q13 | 3852.005.1 | | 3852.5 | |
| 1014 | 7170.027.1-B_at | TPM3 | NM_001043358 | 1q21.2 | 7170.027.1 | | 7170.27 | |
| 1015 | 301.013.1-T_at | ANXA1 | NM_000700 | 9q12-q21.2\|9q12-q21.2 | 301.013.1 | | 301.13 | |
| 1016 | 6304.012.1-F_at | SATB1 | NM_002971 | 3p23 | 6304.012.1 | | 6304.12 | |
| 1017 | 57447.051.2-T_at | NDRG2 | NM_016323 | 14q11.2 | 57447.051.2 | | 57447.51 | |
| 1018 | 11065.005.1-C_at | UBE2C | NM_007021 | 20q13.12 | 11065.005.1 | | 11065.5 | |
| 1019 | 6422.002.1-F_at | SFRP1 | NM_003012 | 8p12-p11.1 | 6422.002.1 | | 6422.2 | |
| 1020 | 6241.013.1-F_at | RRM2 | NM_001034 | 2p25-p24 | 6241.013.1 | | 6241.13 | |
| 1021 | 2335.032.1-T_at | FN1 | NM_002043 | 2q34 | 2335.032.1 | | 2335.32 | |
| 1022 | 11065.005.2-T_at | UBE2C | NM_007022 | 20q13.12 | 11065.005.2 | | 11065.5 | |
| 1023 | 2335.028.1-D_at | FN1 | NM_002044 | 2q34 | 2335.028.1 | | 2335.28 | |
| 1024 | 29997.016.1-F_at | GLTSCR2 | NM_015710 | 19q13.3 | 29997.016.1 | | 29997.16 | |
| 1025 | 7018.014.1-T_at | TF | NM_001063 | 3q22.1 | 7018.014.1 | | 7018.14 | |
| 1026 | 1410.011.1-E_at | CRYAB | NM_001885 | 11q22.3-q23.1 | 1410.011.1 | | 1410.11 | |
| 1027 | 7170.040.1-E_at | TPM3 | NM_001043359 | 1q21.2 | 7170.040.1 | | 7170.40 | |
| 1028 | 6289.002.2-F_at | SAA2 | NM_030754 | 11p15.1-p14 | 6289.002.2 | | 6289.2 | |
| 1029 | 7373.003.4-C_at | COL14A1 | NM_021110 | 8q23 | 7373.003.4 | | 7373.3 | |
| 1030 | 7170.041.1-E_at | TPM3 | NM_001043360 | 1q21.2 | 7170.041.1 | | 7170.41 | |
| 1031 | 128553.003.1-B | TSHZ2 | NM_173485 | 20q13.2 | 128553.003.1 | | 128553.3 | |
| 1032 | 4094.002.1-D_at | MAF | NM_001031805 | 16q22-q23 | 4094.002.1 | | 4094.2 | |
| 1033 | 7113.011.1-T_at | TMPRSS2 | NM_005656 | 21q22.3 | 7113.011.1 | | 7113.11 | |
| 1034 | 7170.002.1-C_at | TPM3 | NM_001043361 | 1q21.2 | 7170.002.1 | | 7170.2 | |
| 1035 | 8404.017.2-T_at | SPARCL1 | NM_004684 | 4q22.1 | 8404.017.2 | | 8404.17 | |
| 1036 | 59.029.1-T_at | ACTA2 | NM_001613 | 10q23.3 | 59.029.1 | | 59.29 | |
| 1037 | 29089.001.1-T_at | UBE2T | NM_014176 | 1q32.1 | 29089.001.1 | | 29089.1 | |
| 1038 | 358.012.1-T_at | AQP1 | NM_198098 | 7p14 | 358.012.1 | | 358.12 | |
| 1039 | 9134.001.1-B_at | CCNE2 | NM_057735 | 8q22.1 | 9134.001.1 | | 9134.1 | |
| 1040 | 2335.013.1-C_at | FN1 | NM_002045 | 2q34 | 2335.013.1 | | 2335.13 | |
| 1041 | 1410.010.1-T_at | CRYAB | NM_001885 | 11q22.3-q23.1 | 1410.010.1 | | 1410.10 | |
| 1042 | 2327.003.4-F_at | FMO2 | NM_001460 | 1q23-q25 | 2327.003.4 | | 2327.3 | |
| 1043 | 59.042.1-T_at | ACTA2 | NM_001613 | 10q23.3 | 59.042.1 | | 59.42 | |
| 1044 | 6304.007.2-T_at | SATB1 | NM_002971 | 3p23 | 6304.007.2 | | 6304.7 | |
| 1045 | 8404.031.1-B_at | SPARCL1 | NM_004684 | 4q22.1 | 8404.031.1 | | 8404.31 | |
| 1046 | 6289.001.1-F_at | SAA2 | NM_030754 | 11p15.1-p14 | 6289.001.1 | | 6289.1 | |
| 1047 | 1410.006.1-T_at | CRYAB | NM_001885 | 11q22.3-q23.1 | 1410.006.1 | | 1410.6 | |
| 1048 | 80034.004.1-T_at | FAM130A2 | NM_024969 | 2q24.3 | 80034.004.1 | | 80034.4 | |
| 1049 | 1410.008.1-T_at | CRYAB | NM_001885 | 11q22.3-q23.1 | 1410.008.1 | | 1410.8 | |
| 1050 | 57447.051.2-D_at | NDRG2 | NM_016324 | 14q11.2 | 57447.051.2 | | 57447.51 | |
| 1051 | 7170.016.3-B_at | TPM3 | NM_001043362 | 1q21.2 | 7170.016.3 | | 7170.16 | |
| 1052 | 4240.001.1-C_at | MFGE8 | NM_005928 | 15q25 | 4240.001.1 | | 4240.1 | |
| 1053 | 6288.001.1-T_at | SAA1 | NM_000331 | 11p15.1 | 6288.001.1 | | 6288.1 | |
| 1054 | 7018.014.1-C_at | TF | NM_001063 | 3q22.1 | 7018.014.1 | | 7018.14 | |
| 1055 | 8404.020.1-T_at | SPARCL1 | NM_004684 | 4q22.1 | 8404.020.1 | | 8404.20 | |
| 1056 | 6289.001.2-F_at | SAA2 | NM_030754 | 11p15.1-p14 | 6289.001.2 | | 6289.1 | |
| 1057 | 6876.011.1-F_at | TAGLN | NM_001001531 | 11q23.2 | 6876.011.1 | | 6876.11 | |
| 1058 | 8404.031.1-C_at | SPARCL1 | NM_004684 | 4q22.1 | 8404.031.1 | | 8404.31 | |
| 1059 | 57447.010.1-T_at | NDRG2 | NM_016325 | 14q11.2 | 57447.010.1 | | 57447.10 | |
| 1060 | 1410.007.2-C_at | CRYAB | NM_001885 | 11q22.3-q23.1 | 1410.007.2 | | 1410.7 | |
| 1061 | 59.012.2-B_at | ACTA2 | NM_001613 | 10q23.3 | 59.012.2 | | 59.12 | |
| 1062 | 3459.005.1-T_at | IFNGR1 | NM_000416 | 6q23-q24 | 3459.005.1 | | 3459.5 | |
| 1063 | 301.013.1-C_at | ANXA1 | NM_000700 | 9q12-q21.2\|9q12-q21.2 | 301.013.1 | | 301.13 | |
| 1064 | 83539.001.1-D_at | CHST9 | NM_031422 | 18q11.2 | 83539.001.1 | | 83539.1 | |
| 1065 | 6288.004.1-F_at | SAA1 | NM_000332 | 11p15.1 | 6288.004.1 | | 6288.4 | |
| 1066 | 4781.016.1-E_at | NFIB | NM_005596 | 9p24.1 | 4781.016.1 | | 4781.16 | |
| 1067 | 29997.012.1-E_at | GLTSCR2 | NM_015710 | 19q13.3 | 29997.012.1 | | 29997.12 | |
| 1068 | 57447.021.1-T_at | NDRG2 | NM_016326 | 14q11.2 | 57447.021.1 | | 57447.21 | |
| 1069 | 3426.002.1-C_at | CFI | NM_000204 | 4q25 | 3426.002.1 | | 3426.2 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 1070 | 53829.001.2-T_at | P2RY13 | NM_023914 | 3q24 | 53829.001.2 | | 53829.1 | |
| 1071 | 2115.001.2-B_at | ETV1 | NM_004956 | 7p21.3 | 2115.001.2 | | 2115.1 | |
| 1072 | 10051.008.1-T_at | SMC4 | NM_001002801 | 3q26.1 | 10051.008.1 | | 10051.8 | |
| 1073 | 1033.002.1-T_at | CDKN3 | NM_005192 | 14q22 | 1033.002.1 | | 1033.2 | |
| 1074 | 2335.005.1-D_at | FN1 | NM_002046 | 2q34 | 2335.005.1 | | 2335.5 | |
| 1075 | 7113.009.1-T_at | TMPRSS2 | NM_005656 | 21q22.3 | 7113.009.1 | | 7113.9 | |
| 1076 | 3866.002.1-B_at | KRT15 | NM_002275 | 17q21.2 | 3866.002.1 | | 3866.2 | |
| 1077 | 140885.014.1-D | SIRPA | NM_001040030 | 20p13 | 140885.014.1 | | 140885.14 | |
| 1078 | 7168.003.1-T_at | TPM1 | NM_000366 | 15q22.1 | 7168.003.1 | | 7168.3 | |
| 1079 | 79608.001.1-T_at | RIC3 | NM_024557 | 11p15.4 | 79608.001.1 | | 79608.1 | |
| 1080 | 79608.008.2-F_at | RIC3 | NM_024557 | 11p15.4 | 79608.008.2 | | 79608.8 | |
| 1081 | 1410.001.1-B_at | CRYAB | NM_001885 | 11q22.3-q23.1 | 1410.001.1 | | 1410.1 | |
| 1082 | 7113.010.1-T_at | TMPRSS2 | NM_005656 | 21q22.3 | 7113.010.1 | | 7113.10 | |
| 1083 | 4781.014.2-B_at | NFIB | NM_005596 | 9p24.1 | 4781.014.2 | | 4781.14 | |
| 1084 | 2335.016.1-E_at | FN1 | NM_002047 | 2q34 | 2335.016.1 | | 2335.16 | |
| 1085 | 11065.003.1-T_at | UBE2C | NM_007023 | 20q13.12 | 11065.003.1 | | 11065.3 | |
| 1086 | 3872.006.1-T_at | KRT17 | NM_000422 | 17q12-q21 | 3872.006.1 | | 3872.6 | |
| 1087 | 3084.005.1-F_at | NRG1 | NM_004517 | 8p12 | 3084.005.1 | | 3084.5 | |
| 1088 | 6285.003.1-T_at | S100B | NM_006272 | 21q22.3 | 6285.003.1 | | 6285.3 | |
| 1089 | 6876.016.2-F_at | TAGLN | NM_001001532 | 11q23.2 | 6876.016.2 | | 6876.16 | |
| 1090 | 8404.004.1-T_at | SPARCL1 | NM_004684 | 4q22.1 | 8404.004.1 | | 8404.4 | |
| 1091 | 54829.001.1-F_at | ASPN | NM_017680 | 9q22 | 54829.001.1 | | 54829.1 | |
| 1092 | 8404.001.1-T_at | SPARCL1 | NM_004684 | 4q22.1 | 8404.001.1 | | 8404.1 | |
| 1093 | 9055.011.1-E_at | PRC1 | NM_003984 | 15q26.1 | 9055.011.1 | | 9055.11 | |
| 1094 | 6289.003.2-F_at | SAA2 | NM_030754 | 11p15.1-p14 | 6289.003.2 | | 6289.3 | |
| 1095 | 22974.007.1-T_at | TPX2 | NM_012112 | 20q11.2 | 22974.007.1 | | 22974.7 | |
| 1096 | 59.023.2-T_at | ACTA2 | NM_001613 | 10q23.3 | 59.023.2 | | 59.23 | |
| 1097 | 7169.015.1-T_at | TPM2 | NM_003298 | 9p13.2-p13.1 | 7169.015.1 | | 7169.15 | |
| 1098 | 6289.002.1-F_at | SAA2 | NM_030754 | 11p15.1-p14 | 6289.002.1 | | 6289.2 | |
| 1099 | 4288.008.1-B_at | MKI67 | NM_002417 | 10q25-qter | 4288.008.1 | | 4288.8 | |
| 1100 | 4781.007.1-B_at | NFIB | NM_005596 | 9p24.1 | 4781.007.1 | | 4781.7 | |
| 1101 | 6876.023.1-T_at | TAGLN | NM_001001533 | 11q23.2 | 6876.023.1 | | 6876.23 | |
| 1102 | 9055.017.1-F_at | PRC1 | NM_003985 | 15q26.1 | 9055.017.1 | | 9055.17 | |
| 1103 | 7170.018.2-D_at | TPM3 | NM_001043363 | 1q21.2 | 7170.018.2 | | 7170.18 | |
| 1104 | 4781.014.2-D_at | NFIB | NM_005596 | 9p24.1 | 4781.014.2 | | 4781.14 | |
| 1105 | 7170.025.1-T_at | TPM3 | NM_001043364 | 1q21.2 | 7170.025.1 | | 7170.25 | |
| 1106 | 7018.025.1-B_at | TF | NM_001063 | 3q22.1 | 7018.025.1 | | 7018.25 | |
| 1107 | 10253.003.1-T_at | SPRY2 | NM_005842 | 13q31.1 | 10253.003.1 | | 10253.3 | |
| 1108 | 57447.039.1-D_at | NDRG2 | NM_016327 | 14q11.2 | 57447.039.1 | | 57447.39 | |
| 1109 | 59.022.1-T_at | ACTA2 | NM_001613 | 10q23.3 | 59.022.1 | | 59.22 | |
| 1110 | 2982.015.1-F_at | GUCY1A3 | NM_000856 | 4q31.3-q33\|4q31.1-q31.2 | 2982.015.1 | | 2982.15 | |
| 1111 | 10124.004.2-F_at | ARL4A | NM_001037166 | 7p21-p15.3 | 10124.004.2 | | 10124.4 | |
| 1112 | 6289.001.1-B_at | SAA2 | NM_030754 | 11p15.1-p14 | 6289.001.1 | | 6289.1 | |
| 1113 | 7091.005.1-F_at | TLE4 | NM_007005 | 9q21.31 | 7091.005.1 | | 7091.5 | |
| 1114 | 501.006.1-B_at | ALDH7A1 | NM_001182 | 5q31 | 501.006.1 | | 501.6 | |
| 1115 | 1410.001.1-C_at | CRYAB | NM_001885 | 11q22.3-q23.1 | 1410.001.1 | | 1410.1 | |
| 1116 | 57447.021.1-C_at | NDRG2 | NM_016328 | 14q11.2 | 57447.021.1 | | 57447.21 | |
| 1117 | 244.012.1-B_at | ANXA8L2 | NM_001630 | 10q11.22 | 244.012.1 | | 244.12 | |
| 1118 | 7018.026.1-F_at | TF | NM_001063 | 3q22.1 | 7018.026.1 | | 7018.26 | |
| 1119 | 3872.018.1-T_at | KRT17 | NM_000422 | 17q12-q21 | 3872.018.1 | | 3872.18 | |
| 1120 | 10144.017.3-T_at | FAM13A1 | NM_001015047 | 4q22.1 | 10144.017.3 | | 10144.17 | |
| 1121 | 11197.001.1-F_at | WIF1 | NM_007191 | 12q14.3 | 11197.001.1 | | 11197.1 | |
| 1122 | 29127.007.1-B_at | RACGAP1 | NM_013277 | 12q13.13 | 29127.007.1 | | 29127.7 | |
| 1123 | 10010.004.1-F_at | TANK | NM_004181 | 2q24-q31 | 10010.004.1 | | 10010.4 | |
| 1124 | 81704.013.1-C_at | DOCK8 | NM_203447 | 9p24.3 | 81704.013.1 | | 81704.13 | |
| 1125 | 4781.006.2-B_at | NFIB | NM_005596 | 9p24.1 | 4781.006.2 | | 4781.6 | |
| 1126 | 7373.003.1-F_at | COL14A1 | NM_021110 | 8q23 | 7373.003.1 | | 7373.3 | |
| 1127 | 8404.009.1-D_at | SPARCL1 | NM_004684 | 4q22.1 | 8404.009.1 | | 8404.9 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 1128 | 23092.004.1-T_at | ARHGAP26 | NM_015071 | 5q31 | 23092.004.1 | | 23092.4 | |
| 1129 | 2335.002.1-F_at | FN1 | NM_002048 | 2q34 | 2335.002.1 | | 2335.2 | |
| 1130 | 8404.031.1-F_at | SPARCL1 | NM_004684 | 4q22.1 | 8404.031.1 | | 8404.31 | |
| 1131 | 6304.006.2-T_at | SATB1 | NM_002971 | 3p23 | 6304.006.2 | | 6304.6 | |
| 1132 | 1410.008.1-E_at | CRYAB | NM_001885 | 11q22.3-q23.1 | 1410.008.1 | | 1410.8 | |
| 1133 | 9055.019.1-F_at | PRC1 | NM_003986 | 15q26.1 | 9055.019.1 | | 9055.19 | |
| 1134 | 1398.001.1-D_at | CRK | NM_000509 | 17p13.3 | 1398.001.1 | | 1398.1 | |
| 1135 | 57447.051.1-E_at | NDRG2 | NM_016329 | 14q11.2 | 57447.051.1 | | 57447.51 | |
| 1136 | 339965.001.2-B | FLJ25770 | NM_001042784 | 4q21.1 | 339965.001.2 | | 339965.1 | |
| 1137 | 7113.001.1-C_at | TMPRSS2 | NM_005656 | 21q22.3 | 7113.001.1 | | 7113.1 | |
| 1138 | 4240.009.1-D_at | MFGE8 | NM_005928 | 15q25 | 4240.009.1 | | 4240.9 | |
| 1139 | 7153.002.4-B_at | TOP2A | NM_001067 | 17q21-q22 | 7153.002.4 | | 7153.2 | |
| 1140 | 7169.004.1-D_at | TPM2 | NM_003299 | 9p13.2-p13.1 | 7169.004.1 | | 7169.4 | |
| 1141 | 1410.001.1-D_at | CRYAB | NM_001885 | 11q22.3-q23.1 | 1410.001.1 | | 1410.1 | |
| 1142 | 59.015.2-B_at | ACTA2 | NM_001613 | 10q23.3 | 59.015.2 | | 59.15 | |
| 1143 | 4833.010.1-T_at | NME4 | NM_005009 | 16p13.3 | 4833.010.1 | | 4833.10 | |
| 1144 | 7169.022.1-B_at | TPM2 | NM_003300 | 9p13.2-p13.1 | 7169.022.1 | | 7169.22 | |
| 1145 | 11065.005.1-T_at | UBE2C | NM_007024 | 20q13.12 | 11065.005.1 | | 11065.5 | |
| 1146 | 7170.018.2-T_at | TPM3 | NM_001043365 | 1q21.2 | 7170.018.2 | | 7170.18 | |
| 1147 | 79971.013.2-F_at | GPR177 | NM_001002293 | 1p31.3 | 79971.013.2 | | 79971.13 | |
| 1148 | 152015.005.2-F | ROPN1B | NM_001012337 | 3q21.2 | 152015.005.2 | | 152015.5 | |
| 1149 | 4288.005.1-D_at | MKI67 | NM_002417 | 10q25-qter | 4288.005.1 | | 4288.5 | |
| 1150 | 8404.002.1-T_at | SPARCL1 | NM_004684 | 4q22.1 | 8404.002.1 | | 8404.2 | |
| 1151 | 6441.004.1-E_at | SFTPD | NM_003019 | 10q22.2-q23.1 | 6441.004.1 | | 6441.4 | |
| 1152 | 6122.046.1-B_at | RPL3 | NM_000967 | 22q13 | 6122.046.1 | | 6122.46 | |
| 1153 | 115908.002.1-T | CTHRC1 | NM_138455 | 8q22.3 | 115908.002.1 | | 115908.2 | |
| 1154 | 9481.001.1-F_at | SLC25A27 | NM_004277 | 6p11.2-q12 | 9481.001.1 | | 9481.1 | |
| 1155 | 8404.008.1-T_at | SPARCL1 | NM_004684 | 4q22.1 | 8404.008.1 | | 8404.8 | |
| 1156 | 1410.007.1-D_at | CRYAB | NM_001885 | 11q22.3-q23.1 | 1410.007.1 | | 1410.7 | |
| 1157 | 8404.030.1-C_at | SPARCL1 | NM_004684 | 4q22.1 | 8404.030.1 | | 8404.30 | |
| 1158 | 57447.039.1-T_at | NDRG2 | NM_016330 | 14q11.2 | 57447.039.1 | | 57447.39 | |
| 1159 | 4147.004.1-E_at | MATN2 | NM_002385 | 8q22 | 4147.004.1 | | 4147.4 | |
| 1160 | 2335.024.2-F_at | FN1 | NM_002049 | 2q34 | 2335.024.2 | | 2335.24 | |
| 1161 | 891.007.1-T_at | CCNB1 | NM_031966 | 5q12 | 891.007.1 | | 891.7 | |
| 1162 | 2335.002.1-T_at | FN1 | NM_002050 | 2q34 | 2335.002.1 | | 2335.2 | |
| 1163 | 8404.017.1-T_at | SPARCL1 | NM_004684 | 4q22.1 | 8404.017.1 | | 8404.17 | |
| 1164 | 57451.004.1-B_at | ODZ2 | NM_001080428 | 5q34-q35.1 | 57451.004.1 | | 57451.4 | |
| 1165 | 8404.001.1-F_at | SPARCL1 | NM_004684 | 4q22.1 | 8404.001.1 | | 8404.1 | |
| 1166 | 8626.006.2-B_at | TP63 | NM_003722 | 3q28 | 8626.006.2 | | 8626.6 | |
| 1167 | 2335.025.1-T_at | FN1 | NM_002051 | 2q34 | 2335.025.1 | | 2335.25 | |
| 1168 | 6286.001.1-T_at | S100P | NM_005980 | 4p16 | 6286.001.1 | | 6286.1 | |
| 1169 | 10580.012.1-C_at | SORBS1 | NM_001034954 | 10q23.3-q24.1 | 10580.012.1 | | 10580.12 | |
| 1170 | 23321.014.1-T_at | TRIM2 | NM_015271 | 4q31.3 | 23321.014.1 | | 23321.14 | |
| 1171 | 2824.001.2-B_at | GPM6B | NM_001001994 | Xp22.2 | 2824.001.2 | | 2824.1 | |
| 1172 | 29127.022.1-T_at | RACGAP1 | NM_013277 | 12q13.13 | 29127.022.1 | | 29127.22 | |
| 1173 | 6289.003.1-F_at | SAA2 | NM_030754 | 11p15.1-p14 | 6289.003.1 | | 6289.3 | |
| 1174 | 7170.005.2-B_at | TPM3 | NM_001043366 | 1q21.2 | 7170.005.2 | | 7170.5 | |
| 1175 | 54443.011.1-F_at | ANLN | NM_018685 | 7p15-p14 | 54443.011.1 | | 54443.11 | |
| 1176 | 29127.019.1-T_at | RACGAP1 | NM_013277 | 12q13.13 | 29127.019.1 | | 29127.19 | |
| 1177 | 6288.004.1-T_at | SAA1 | NM_000333 | 11p15.1 | 6288.004.1 | | 6288.4 | |
| 1178 | 29997.008.1-C_at | GLTSCR2 | NM_015710 | 19q13.3 | 29997.008.1 | | 29997.8 | |
| 1179 | 57447.039.1-B_at | NDRG2 | NM_016331 | 14q11.2 | 57447.039.1 | | 57447.39 | |
| 1180 | 3872.007.1-B_at | KRT17 | NM_000422 | 17q12-q21 | 3872.007.1 | | 3872.7 | |
| 1181 | 57561.002.1-T_at | ARRDC3 | NM_020801 | 5q14.3 | 57561.002.1 | | 57561.2 | |
| 1182 | 57451.002.3-B_at | ODZ2 | NM_001080428 | 5q34-q35.1 | 57451.002.3 | | 57451.2 | |
| 1183 | 5213.024.1-B_at | PFKM | NM_000289 | 12q13.3 | 5213.024.1 | | 5213.24 | |
| 1184 | 2.005.1-T_at | A2M | NM_000014 | 12p13.3-p12.3 | 2.005.1 | | 2.5 | |
| 1185 | 11065.004.1-C_at | UBE2C | NM_007025 | 20q13.12 | 11065.004.1 | | 11065.4 | |
| 1186 | 1410.006.1-C_at | CRYAB | NM_001885 | 11q22.3-q23.1 | 1410.006.1 | | 1410.6 | |
| 1187 | 6289.006.1-T_at | SAA2 | NM_030754 | 11p15.1-p14 | 6289.006.1 | | 6289.6 | |

TABLE 4-continued

Probe sets used to construct molecular predictor (n = 1228).

| NO | Probeset_Id | Symbol | RefSeq | Location | Transcrit | Transcrit | Transcrit2 | Transcrit2 |
|---|---|---|---|---|---|---|---|---|
| 1188 | 55366.001.1-T_at | LGR4 | NM_018490 | 11p14-p13 | 55366.001.1 | | 55366.1 | |
| 1189 | 23284.007.1-F_at | LPHN3 | NM_015236 | 4q13.1 | 23284.007.1 | | 23284.7 | |
| 1190 | 79971.009.1-T_at | GPR177 | NM_001002294 | 1p31.3 | 79971.009.1 | | 79971.9 | |
| 1191 | 6288.004.1-E_at | SAA1 | NM_000334 | 11p15.1 | 6288.004.1 | | 6288.4 | |
| 1192 | 11065.004.1-T_at | UBE2C | NM_007026 | 20q13.12 | 11065.004.1 | | 11065.4 | |
| 1193 | 51203.009.1-T_at | NUSAP1 | NM_016362 | 15q15.1 | 51203.009.1 | | 51203.9 | |
| 1194 | 1410.010.1-E_at | CRYAB | NM_001885 | 11q22.3-q23.1 | 1410.010.1 | | 1410.10 | |
| 1195 | 57447.030.1-D_at | NDRG2 | NM_016332 | 14q11.2 | 57447.030.1 | | 57447.30 | |
| 1196 | 1308.002.1-T_at | COL17A1 | NM_000507 | 10q24.3 | 1308.002.1 | | 1308.2 | |
| 1197 | 4288.007.1-C_at | MKI67 | NM_002417 | 10q25-qter | 4288.007.1 | | 4288.7 | |
| 1198 | 244.011.1-T_at | ANXA8L2 | NM_001630 | 10q11.22 | 244.011.1 | | 244.11 | |
| 1199 | 94274.003.1-B_at | PPP1R14A | NM_033256 | 19q13.1 | 94274.003.1 | | 94274.3 | |
| 1200 | 3178.003.1-E_at | HNRNPA1 | NM_002136 | 12q13.1 | 3178.003.1 | | 3178.3 | |
| 1201 | 7153.002.4-T_at | TOP2A | NM_001067 | 17q21-q22 | 7153.002.4 | | 7153.2 | |
| 1202 | 9055.012.1-D_at | PRC1 | NM_003987 | 15q26.1 | 9055.012.1 | | 9055.12 | |
| 1203 | 9232.001.1-E_at | PTTG1 | NM_004219 | 5q35.1 | 9232.001.1 | | 9232.1 | |
| 1204 | 79068.011.2-B_at | FTO | NM_001080432 | 16q12.2 | 79068.011.2 | | 79068.11 | |
| 1205 | 120.005.2-F_at | ADD3 | NM_001122 | 10q24.2-q24.3 | 120.005.2 | | 120.5 | |
| 1206 | 7534.001.1-C_at | YWHAZ | NM_003406 | 8q23.1 | 7534.001.1 | | 7534.1 | |
| 1207 | 120.005.2-T_at | ADD3 | NM_001123 | 10q24.2-q24.3 | 120.005.2 | | 120.5 | |
| 1208 | 7373.003.3-C_at | COL14A1 | NM_021110 | 8q23 | 7373.003.3 | | 7373.3 | |
| 1209 | 57447.004.2-D_at | NDRG2 | NM_016333 | 14q11.2 | 57447.004.2 | | 57447.4 | |
| 1210 | 2568.005.1-F_at | GABRP | NM_014211 | 5q33-q34 | 2568.005.1 | | 2568.5 | |
| 1211 | 1308.001.1-E_at | COL17A1 | NM_000508 | 10q24.3 | 1308.001.1 | | 1308.1 | |
| 1212 | 6876.020.1-F_at | TAGLN | NM_001001534 | 11q23.2 | 6876.020.1 | | 6876.20 | |
| 1213 | 79971.014.1-D_at | GPR177 | NM_001002295 | 1p31.3 | 79971.014.1 | | 79971.14 | |
| 1214 | 5621.008.1-D_at | PRNP | NM_000312 | 20p13 | 5621.008.1 | | 5621.8 | |
| 1215 | 55732.003.2-T_at | C1orf112 | NM_018186 | 1q24.2 | 55732.003.2 | | 55732.3 | |
| 1216 | 221120.006.1-D | ALKBH3 | NM_139178 | 11p11.2 | 221120.006.1 | | 221120.6 | |
| 1217 | 23266.008.1-T_at | LPHN2 | NM_012302 | 1p31.1 | 23266.008.1 | | 23266.8 | |
| 1218 | 2335.045.1-F_at | FN1 | NM_002052 | 2q34 | 2335.045.1 | | 2335.45 | |
| 1219 | 7170.007.1-F_at | TPM3 | NM_001043367 | 1q21.2 | 7170.007.1 | | 7170.7 | |
| 1220 | 10461.002.1-B_at | MERTK | NM_006343 | 2q14.1 | 10461.002.1 | | 10461.2 | |
| 1221 | 59.031.2-F_at | ACTA2 | NM_001613 | 10q23.3 | 59.031.2 | | 59.31 | |
| 1222 | 9055.010.1-T_at | PRC1 | NM_003988 | 15q26.1 | 9055.010.1 | | 9055.10 | |
| 1223 | 58499.005.2-F_at | ZNF462 | NM_021224 | 9q31.2 | 58499.005.2 | | 58499.5 | |
| 1224 | 54443.006.2-F_at | ANLN | NM_018685 | 7p15-p14 | 54443.006.2 | | 54443.6 | |
| 1225 | 59.016.1-B_at | ACTA2 | NM_001613 | 10q23.3 | 59.016.1 | | 59.16 | |
| 1226 | 4288.004.1-C_at | MKI67 | NM_002417 | 10q25-qter | 4288.004.1 | | 4288.4 | |
| 1227 | 7170.014.1-C_at | TPM3 | NM_001043368 | 1q21.2 | 7170.014.1 | | 7170.14 | |
| 1228 | 7170.007.1-D_at | TPM3 | NM_001043369 | 1q21.2 | 7170.007.1 | | 7170.7 | |

TABLE 5

Table 5. Average profiles of the preferred 1,228 signature probe set on the 24 benign and 70 malignant tissues of the training set.

| NO | Probeset_Id | benign profile | malignant profile |
|---|---|---|---|
| 1 | 1756.022.2-C_at | 7.77577583 | 3.59039694 |
| 2 | 1756.029.1-D_at | 7.04295703 | 3.513387741 |
| 3 | 1756.026.1-C_at | 6.95161337 | 3.464276589 |
| 4 | 1756.022.4-T_at | 6.48188081 | 3.420868252 |
| 5 | 1756.011.1-B_at | 6.86417826 | 3.496864254 |
| 6 | 1308.008.1-C_at | 7.57956334 | 3.687873002 |
| 7 | 1756.022.3-F_at | 6.51097796 | 3.58405119 |
| 8 | 3861.020.1-D_at | 6.22316661 | 3.499798722 |
| 9 | 1756.011.1-F_at | 6.46286419 | 3.439670248 |
| 10 | 4629.007.1-F_at | 7.83187958 | 4.047826786 |
| 11 | 1756.022.4-B_at | 5.66870747 | 3.376207029 |
| 12 | 1756.024.1-F_at | 5.6343038 | 3.538881886 |
| 13 | 3861.019.1-T_at | 6.68378293 | 3.662794206 |
| 14 | 1756.026.1-T_at | 5.75006153 | 3.403683849 |
| 15 | 1756.022.1-B_at | 5.5659674 | 3.347255374 |
| 16 | 3861.001.1-T_at | 8.03618493 | 4.233009236 |
| 17 | 1308.008.1-T_at | 7.11931893 | 3.582324909 |
| 18 | 4629.020.1-C_at | 5.83439993 | 3.404790946 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 19 | 1756.027.1-T_at | 5.61961823 | 3.38354471 |
| 20 | 3861.013.1-T_at | 6.54371337 | 3.606451019 |
| 21 | 4629.020.1-F_at | 8.29507715 | 4.572815098 |
| 22 | 3861.001.1-B_at | 6.22211499 | 3.452593672 |
| 23 | 1756.022.4-F_at | 5.86145739 | 3.406465282 |
| 24 | 1756.026.1-F_at | 5.60288028 | 3.360497686 |
| 25 | 1756.022.2-T_at | 5.58253289 | 3.54186397 |
| 26 | 1756.022.2-F_at | 5.61962239 | 3.502994928 |
| 27 | 3861.022.1-B_at | 7.02845041 | 3.87855387 |
| 28 | 3868.004.1-D_at | 7.74158414 | 4.319798082 |
| 29 | 4629.015.1-C_at | 7.25657837 | 3.723809766 |
| 30 | 6422.002.1-E_at | 8.94850792 | 4.159424522 |
| 31 | 3861.001.1-D_at | 6.09123229 | 3.432322015 |
| 32 | 1756.022.1-F_at | 5.69246198 | 3.544494185 |
| 33 | 1308.003.1-T_at | 7.94010542 | 4.370493824 |
| 34 | 3868.005.1-B_at | 8.74334588 | 5.189519553 |
| 35 | 1308.007.1-F_at | 6.53872712 | 4.045429995 |
| 36 | 1308.009.1-F_at | 6.89532626 | 4.071167435 |
| 37 | 3861.007.1-E_at | 6.32900696 | 3.492862508 |
| 38 | 4629.016.1-D_at | 6.54432919 | 3.640775643 |
| 39 | 3084.007.1-F_at | 5.24077491 | 3.36157297 |
| 40 | 3861.007.1-F_at | 8.80010947 | 5.27987695 |
| 41 | 26289.003.1-E_at | 5.86287574 | 3.533159027 |
| 42 | 1756.028.1-T_at | 5.51782565 | 3.40968711 |
| 43 | 4629.021.1-E_at | 5.66627575 | 3.423025757 |
| 44 | 4629.020.1-D_at | 6.44086194 | 3.546901356 |
| 45 | 5764.001.1-F_at | 8.69561376 | 4.488059326 |
| 46 | 3815.002.3-F_at | 7.51289238 | 3.849064631 |
| 47 | 3852.020.1-T_at | 6.42797621 | 4.732898695 |
| 48 | 4629.007.1-E_at | 6.02756027 | 3.473012819 |
| 49 | 128553.003.1-F | 5.53321089 | 3.635562107 |
| 50 | 26289.003.1-F_at | 7.91558754 | 4.209493355 |
| 51 | 3815.002.2-F_at | 7.57464628 | 4.354458317 |
| 52 | 1756.029.1-B_at | 5.14699565 | 3.349809112 |
| 53 | 4629.005.1-E_at | 7.84091036 | 4.284271836 |
| 54 | 4629.010.1-B_at | 6.24893878 | 4.055036115 |
| 55 | 6422.001.1-T_at | 7.16633034 | 3.787746012 |
| 56 | 5764.001.1-E_at | 7.41150914 | 3.725088834 |
| 57 | 3861.008.1-F_at | 7.02710456 | 4.066582177 |
| 58 | 1756.030.2-T_at | 4.94195769 | 3.327396148 |
| 59 | 3084.009.1-B_at | 5.68938525 | 3.45247142 |
| 60 | 26289.002.1-T_at | 7.40948494 | 4.099092499 |
| 61 | 1756.022.5-B_at | 5.43279988 | 3.481330797 |
| 62 | 4629.007.1-D_at | 6.12853852 | 3.536108886 |
| 63 | 23336.001.1-C_at | 6.64495461 | 3.668475185 |
| 64 | 1308.003.1-D_at | 5.60928126 | 3.379520915 |
| 65 | 1756.022.3-T_at | 5.52680369 | 3.62832307 |
| 66 | 3861.020.1-T_at | 7.58427914 | 5.411375294 |
| 67 | 3861.022.1-C_at | 5.51190841 | 3.385538085 |
| 68 | 3852.012.2-B_at | 8.68398341 | 6.89513729 |
| 69 | 26289.012.1-E_at | 7.90570335 | 4.172489159 |
| 70 | 23336.003.1-T_at | 7.08201667 | 4.814503945 |
| 71 | 26289.007.1-B_at | 7.72470925 | 4.152306769 |
| 72 | 84417.001.1-T_at | 5.09011844 | 3.400475459 |
| 73 | 3861.018.1-D_at | 5.42966542 | 3.382067375 |
| 74 | 3852.004.1-B_at | 6.45366587 | 4.048382242 |
| 75 | 90865.006.1-B_at | 6.73968166 | 3.990889311 |
| 76 | 4629.021.1-F_at | 7.91177883 | 2.2531203 |
| 77 | 3861.018.1-T_at | 6.93768003 | 4.389579877 |
| 78 | 1756.022.1-T_at | 5.49427991 | 3.678236167 |
| 79 | 1264.003.1-B_at | 6.59427618 | 3.644806029 |
| 80 | 26289.010.1-E_at | 7.89895995 | 4.173752776 |
| 81 | 3861.001.1-F_at | 8.22227254 | 5.365451942 |
| 82 | 1908.002.1-T_at | 5.89142159 | 3.76026543 |
| 83 | 4629.007.1-C_at | 5.95159281 | 3.449026103 |
| 84 | 1756.022.5-T_at | 7.41985492 | 5.430396438 |
| 85 | 3815.002.4-B_at | 6.82005827 | 3.837481838 |
| 86 | 1756.022.2-B_at | 5.20019167 | 3.394669911 |
| 87 | 1756.027.1-B_at | 4.8537932 | 3.389107204 |
| 88 | 3852.008.2-T_at | 6.48445207 | 3.985807972 |
| 89 | 6422.001.1-E_at | 7.27907161 | 3.874506745 |
| 90 | 3861.022.1-F_at | 6.81336417 | 5.057032572 |
| 91 | 4915.011.1-D_at | 5.90431076 | 3.64199141 |
| 92 | 5288.001.1-F_at | 5.44594693 | 3.485884155 |
| 93 | 3861.007.1-T_at | 7.95368914 | 5.49032736 |
| 94 | 3852.006.1-C_at | 6.13678531 | 3.559093796 |
| 95 | 9413.003.1-T_at | 5.34538697 | 3.552156816 |
| 96 | 3861.020.1-C_at | 5.55692471 | 3.41004352 |
| 97 | 1308.008.1-D_at | 5.59542139 | 3.406938539 |
| 98 | 23336.001.1-T_at | 6.50954711 | 4.440969009 |
| 99 | 3815.001.1-F_at | 7.00089122 | 3.951400817 |
| 100 | 1756.022.5-F_at | 6.87448959 | 4.663598998 |
| 101 | 79937.001.1-T_at | 6.15393538 | 4.110481521 |
| 102 | 4915.012.1-E_at | 8.0872096 | 4.146795298 |
| 103 | 3861.022.1-T_at | 6.45943061 | 3.91885164 |
| 104 | 26289.005.1-T_at | 6.42663922 | 4.148293882 |
| 105 | 3815.002.3-B_at | 5.54627639 | 3.429691278 |
| 106 | 4311.009.1-F_at | 7.16081204 | 4.100265304 |
| 107 | 26289.006.1-T_at | 8.56062669 | 4.815103599 |
| 108 | 5288.003.1-F_at | 5.50819433 | 3.507713463 |
| 109 | 4629.020.1-B_at | 5.84433404 | 3.602970173 |
| 110 | 26289.007.1-D_at | 8.97225664 | 4.739722032 |
| 111 | 3815.002.1-B_at | 6.95057351 | 3.834713723 |
| 112 | 26289.004.1-T_at | 6.34773713 | 4.19513007 |
| 113 | 79192.002.2-T_at | 6.05826364 | 3.842242343 |
| 114 | 4638.006.1-D_at | 7.26387248 | 4.23337548 |
| 115 | 3084.008.1-F_at | 4.91747714 | 3.337620462 |
| 116 | 4311.001.2-T_at | 7.0894017 | 4.083336035 |
| 117 | 3815.002.1-D_at | 5.62489378 | 3.413633401 |
| 118 | 4629.020.1-T_at | 6.54528254 | 4.292670552 |
| 119 | 1756.026.1-B_at | 5.04408715 | 3.401481888 |
| 120 | 3852.022.1-T_at | 6.17920917 | 3.949400375 |
| 121 | 4629.015.1-D_at | 6.8794921 | 4.903440037 |
| 122 | 26289.007.1-C_at | 7.11737708 | 3.991072006 |
| 123 | 23194.003.1-C_at | 6.62756369 | 4.216361434 |
| 124 | 3815.002.1-F_at | 5.96350065 | 3.577775017 |
| 125 | 26289.007.1-T_at | 9.05284176 | 5.053614074 |
| 126 | 65983.009.1-B_at | 4.92316734 | 3.543080498 |
| 127 | 23336.001.1-F_at | 6.76043292 | 4.496928377 |
| 128 | 1410.007.2-B_at | 6.13154201 | 3.800315965 |
| 129 | 1756.029.1-F_at | 4.74778319 | 3.336087634 |
| 130 | 7373.003.6-C_at | 6.42568489 | 3.893070602 |
| 131 | 10010.002.1-E_at | 4.95595545 | 3.398356655 |
| 132 | 59.026.1-B_at | 5.82098007 | 3.829661839 |
| 133 | 4915.011.1-F_at | 6.93603667 | 3.88986704 |
| 134 | 3872.007.1-F_at | 6.20605492 | 3.672782211 |
| 135 | 26289.002.1-D_at | 4.95771354 | 3.437272763 |
| 136 | 84668.002.1-C_at | 7.73745334 | 4.885593169 |
| 137 | 1756.002.2-T_at | 7.42432799 | 4.334919851 |
| 138 | 57447.033.1-C_at | 6.98508503 | 4.791930475 |
| 139 | 26289.009.1-E_at | 8.95673913 | 4.746268267 |
| 140 | 3872.006.1-F_at | 8.33069501 | 5.239623762 |
| 141 | 3861.022.1-D_at | 4.91710968 | 3.325488578 |
| 142 | 3815.002.1-E_at | 5.32314912 | 3.412709023 |
| 143 | 667.021.1-B_at | 6.18631919 | 3.841433137 |
| 144 | 57447.027.1-F_at | 7.08539045 | 4.241139039 |
| 145 | 56477.001.1-D_at | 6.55969728 | 3.814097685 |
| 146 | 26289.008.1-F_at | 8.97978495 | 4.925626071 |
| 147 | 59.024.2-D_at | 7.22299753 | 4.423928704 |
| 148 | 4629.005.1-T_at | 8.60305039 | 5.554148468 |
| 149 | 3815.002.1-T_at | 8.34708459 | 4.557379602 |
| 150 | 23336.001.1-B_at | 7.9283908 | 5.377785469 |
| 151 | 3084.004.2-F_at | 4.90868361 | 3.371411318 |
| 152 | 27122.014.2-T_at | 5.66296874 | 3.671915992 |
| 153 | 26289.008.1-C_at | 6.19905784 | 3.792605417 |
| 154 | 286887.003.2-B | 6.65960082 | 4.217906735 |
| 155 | 4629.005.1-F_at | 7.92220509 | 5.827308726 |
| 156 | 3872.009.1-T_at | 8.11749997 | 4.97186016 |
| 157 | 59.014.2-D_at | 7.2803688 | 4.475411666 |
| 158 | 403340.001.2-B | 6.5225278 | 3.953645308 |
| 159 | 3852.014.1-F_at | 6.65504418 | 4.502352655 |
| 160 | 27122.001.1-T_at | 6.70494956 | 4.219728495 |
| 161 | 3815.002.3-T_at | 5.79983719 | 3.546807083 |
| 162 | 3852.008.1-E_at | 7.70698375 | 4.778195426 |
| 163 | 27122.012.1-T_at | 6.44372459 | 3.808594574 |
| 164 | 26289.007.1-F_at | 6.33764826 | 3.835752254 |
| 165 | 4638.006.1-T_at | 7.48416583 | 4.880628209 |
| 166 | 8626.005.1-B_at | 6.0506832 | 3.689171001 |
| 167 | 3815.002.4-T_at | 7.18867318 | 3.947318855 |
| 168 | 84668.004.1-F_at | 6.36068084 | 4.024117755 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 169 | 3872.007.1-F_at | 8.15990919 | 5.039544664 |
| 170 | 57447.031.1-E_at | 6.98413461 | 4.847264949 |
| 171 | 3084.012.3-T_at | 5.1724186 | 3.372130258 |
| 172 | 3852.005.1-T_at | 6.15177089 | 3.953202014 |
| 173 | 84417.001.2-T_at | 4.88905487 | 3.400666252 |
| 174 | 3866.003.2-T_at | 7.33197079 | 4.76008241 |
| 175 | 3866.008.1-C_at | 6.52361561 | 3.762190903 |
| 176 | 3852.009.1-F_at | 7.29388376 | 4.138971389 |
| 177 | 59.015.1-B_at | 5.98286286 | 3.912382525 |
| 178 | 79937.002.1-F_at | 4.55998542 | 3.353847089 |
| 179 | 7153.002.6-F_at | 5.25845229 | 8.105836861 |
| 180 | 4281.010.1-B_at | 5.89302118 | 3.740600544 |
| 181 | 59.008.1-B_at | 5.76124199 | 3.852970764 |
| 182 | 1264.007.1-T_at | 5.63801742 | 3.838276262 |
| 183 | 3868.004.1-T_at | 5.66410876 | 3.79017218 |
| 184 | 3084.002.1-F_at | 4.98674566 | 3.360938629 |
| 185 | 5137.004.2-T_at | 4.64089266 | 3.34890403 |
| 186 | 4629.022.1-T_at | 4.75765246 | 3.480568786 |
| 187 | 4915.011.1-T_at | 6.94354411 | 3.915112838 |
| 188 | 3852.013.1-E_at | 6.01894366 | 3.617314683 |
| 189 | 59.012.2-T_at | 8.08522667 | 5.172148648 |
| 190 | 59.015.1-F_at | 6.50494881 | 4.765128611 |
| 191 | 4638.006.2-T_at | 7.26086954 | 4.714147988 |
| 192 | 23336.002.1-B_at | 5.95183375 | 3.957277561 |
| 193 | 3868.005.1-C_at | 8.63446621 | 7.297975458 |
| 194 | 3866.011.2-D_at | 8.77838405 | 4.522564109 |
| 195 | 56477.001.1-T_at | 8.14939865 | 5.06922736 |
| 196 | 3815.001.1-F_at | 6.03901568 | 3.756819456 |
| 197 | 4311.001.1-T_at | 7.11420453 | 4.238075405 |
| 198 | 1264.003.1-D_at | 5.1912565 | 3.354675255 |
| 199 | 59.031.1-T_at | 7.4628458 | 4.949828067 |
| 200 | 57447.030.1-B_at | 6.45843286 | 3.891549539 |
| 201 | 1410.003.2-B_at | 6.05784067 | 3.779422009 |
| 202 | 3866.009.2-D_at | 8.80361998 | 4.576378265 |
| 203 | 59.026.1-T_at | 7.29639751 | 4.650053313 |
| 204 | 440421.001.1-T | 9.24293713 | 6.596812139 |
| 205 | 1756.022.4-D_at | 5.07768477 | 3.476314006 |
| 206 | 65983.009.1-D_at | 6.39596028 | 4.086911291 |
| 207 | 57447.041.1-T_at | 6.95593663 | 4.149259947 |
| 208 | 3872.010.2-D_at | 8.56203536 | 5.425416269 |
| 209 | 4629.006.2-T_at | 8.90925918 | 6.221775982 |
| 210 | 3861.018.1-F_at | 6.8430596 | 5.185870988 |
| 211 | 3815.002.2-T_at | 5.28733127 | 3.421518659 |
| 212 | 3866.012.2-D_at | 8.67083494 | 4.478603969 |
| 213 | 57447.021.1-D_at | 6.98727375 | 4.930757851 |
| 214 | 59.015.1-T_at | 7.34935329 | 4.513251269 |
| 215 | 8626.007.1-F_at | 7.17503293 | 5.028534466 |
| 216 | 5288.001.1-B_at | 5.02652959 | 3.42608729 |
| 217 | 72.001.1-B_at | 6.05804544 | 3.853258443 |
| 218 | 3866.006.2-D_at | 8.65913916 | 4.490509023 |
| 219 | 3852.004.1-T_at | 6.78881411 | 4.012650025 |
| 220 | 4629.016.1-F_at | 5.16326314 | 3.700432446 |
| 221 | 4629.007.1-T_at | 5.80150326 | 4.040994731 |
| 222 | 65983.008.1-T_at | 6.32502917 | 4.219582217 |
| 223 | 65983.013.1-F_at | 5.56252368 | 3.731459395 |
| 224 | 3084.004.1-F_at | 4.93700193 | 3.399738343 |
| 225 | 27122.007.1-F_at | 6.83642294 | 4.356100082 |
| 226 | 3866.008.1-D_at | 8.70576582 | 4.517001787 |
| 227 | 26289.009.1-T_at | 8.23631259 | 5.882347434 |
| 228 | 59.009.1-B_at | 7.1080566 | 4.810790662 |
| 229 | 4629.010.1-D_at | 5.14795762 | 3.377019173 |
| 230 | 59.023.1-B_at | 5.9667058 | 4.241472412 |
| 231 | 26289.002.1-F_at | 6.02532667 | 4.093116116 |
| 232 | 1908.001.1-T_at | 5.67746805 | 3.733518249 |
| 233 | 4915.008.1-F_at | 7.26142834 | 4.642285716 |
| 234 | 23336.002.1-T_at | 6.49776495 | 4.343732056 |
| 235 | 3861.008.1-C_at | 5.95153563 | 3.602851161 |
| 236 | 3861.008.1-D_at | 5.29062466 | 3.396003998 |
| 237 | 57447.035.1-E_at | 6.91652713 | 4.662107171 |
| 238 | 3861.018.1-C_at | 5.20378802 | 3.40238733 |
| 239 | 1308.003.1-B_at | 6.04491667 | 4.20754377 |
| 240 | 667.022.1-B_at | 9.21855078 | 6.264675763 |
| 241 | 3866.011.2-T_at | 9.26272502 | 4.964885149 |
| 242 | 2115.001.2-F_at | 4.89563967 | 3.419126266 |
| 243 | 3866.011.2-B_at | 8.90774202 | 5.955221725 |
| 244 | 26289.010.1-T_at | 6.53182588 | 3.913556066 |
| 245 | 27303.004.1-E_at | 5.37295265 | 3.543582523 |
| 246 | 59.003.1-B_at | 7.93270751 | 4.980983024 |
| 247 | 4311.009.1-C_at | 5.83645359 | 3.593262545 |
| 248 | 7373.003.6-B_at | 5.10650551 | 3.591717587 |
| 249 | 65983.004.1-T_at | 6.08803336 | 4.309048954 |
| 250 | 26289.013.1-D_at | 6.4702967 | 4.168098993 |
| 251 | 3866.004.1-F_at | 8.69085999 | 5.161823428 |
| 252 | 56477.001.1-F_at | 6.84530786 | 4.144567561 |
| 253 | 57447.037.1-F_at | 6.50794623 | 4.008371243 |
| 254 | 59.022.2-T_at | 8.05648541 | 5.423260634 |
| 255 | 147495.008.1-F | 4.79759981 | 3.504777229 |
| 256 | 2.018.1-T_at | 6.94869173 | 4.521707124 |
| 257 | 140807.003.1-E | 7.78013704 | 4.939516908 |
| 258 | 65983.009.1-T_at | 5.82469201 | 4.038349093 |
| 259 | 84668.002.1-F_at | 6.10679619 | 3.911726506 |
| 260 | 3872.007.1-C_at | 6.89188543 | 4.236245481 |
| 261 | 2115.008.1-T_at | 4.99544075 | 3.646690809 |
| 262 | 65983.004.2-T_at | 6.08050374 | 4.312433521 |
| 263 | 57447.034.1-D_at | 6.936035 | 4.801981821 |
| 264 | 3866.001.1-F_at | 9.09052167 | 5.099093334 |
| 265 | 3866.008.1-T_at | 9.07318081 | 5.048805174 |
| 266 | 1959.003.1-C_at | 5.09323093 | 3.511681612 |
| 267 | 389432.002.1-T | 5.08376017 | 3.428817257 |
| 268 | 389734.001.1-T | 5.43078503 | 3.868151914 |
| 269 | 3855.001.2-D_at | 7.00167453 | 4.478486691 |
| 270 | 3866.003.1-T_at | 7.28560994 | 4.919439752 |
| 271 | 3084.006.1-F_at | 4.88762029 | 3.435292071 |
| 272 | 4915.008.1-B_at | 9.33812372 | 6.600441272 |
| 273 | 2115.011.1-T_at | 4.96772945 | 3.573388451 |
| 274 | 65983.005.1-T_at | 5.18666491 | 3.68451349 |
| 275 | 84668.004.1-T_at | 5.6127121 | 3.643748216 |
| 276 | 59.015.2-T_at | 7.37091506 | 4.589962999 |
| 277 | 2119.006.1-B_at | 5.29804773 | 3.689885023 |
| 278 | 4638.006.2-F_at | 6.94711133 | 4.982563544 |
| 279 | 3866.007.2-D_at | 8.65600661 | 4.653097355 |
| 280 | 59.014.1-T_at | 6.68646455 | 4.640934588 |
| 281 | 3866.001.2-F_at | 8.99732872 | 5.069416275 |
| 282 | 1308.008.1-B_at | 5.17775427 | 3.436187546 |
| 283 | 59.026.1-F_at | 6.20953542 | 4.590760008 |
| 284 | 3866.013.1-F_at | 8.10955622 | 4.736748894 |
| 285 | 1264.007.1-F_at | 4.75311015 | 3.431422638 |
| 286 | 3866.007.2-F_at | 9.11439411 | 5.094569305 |
| 287 | 27122.013.1-T_at | 6.62548583 | 4.301605936 |
| 288 | 27122.006.2-F_at | 6.55351463 | 4.265429835 |
| 289 | 3866.006.2-T_at | 9.06546704 | 5.104948803 |
| 290 | 3866.009.2-T_at | 9.95142456 | 5.435454431 |
| 291 | 4240.004.1-D_at | 6.56591292 | 3.971193091 |
| 292 | 3866.010.1-F_at | 9.93993743 | 5.314895513 |
| 293 | 3866.009.2-B_at | 8.95840788 | 6.023022151 |
| 294 | 3866.009.1-T_at | 9.94526994 | 5.403869315 |
| 295 | 4629.006.1-T_at | 8.84832501 | 6.182536282 |
| 296 | 7018.029.1-B_at | 7.60030878 | 4.306073488 |
| 297 | 1410.002.2-B_at | 5.81431314 | 3.745409488 |
| 298 | 3866.012.1-T_at | 9.90206544 | 5.308091577 |
| 299 | 59.034.2-D_at | 7.86477089 | 5.080775226 |
| 300 | 27122.019.1-F_at | 6.89881084 | 4.480037843 |
| 301 | 5156.001.1-T_at | 4.81097854 | 3.473046125 |
| 302 | 389734.001.2-T | 5.40328573 | 3.837281942 |
| 303 | 27122.014.1-T_at | 5.51451528 | 3.660985743 |
| 304 | 57447.010.3-T_at | 7.75144798 | 5.575239001 |
| 305 | 358.018.1-F_at | 5.42702744 | 3.627847604 |
| 306 | 3866.006.1-T_at | 9.0668668 | 5.139316838 |
| 307 | 7373.001.1-T_at | 4.83532429 | 3.464644018 |
| 308 | 26289.012.1-B_at | 6.41666504 | 4.261745027 |
| 309 | 57447.029.1-T_at | 6.56314208 | 4.648604292 |
| 310 | 358.018.1-B_at | 6.41651654 | 4.110814767 |
| 311 | 79068.010.1-B_at | 5.46560699 | 3.70220541 |
| 312 | 59.024.1-B_at | 5.86685124 | 4.334726645 |
| 313 | 59.004.1-B_at | 7.7789734 | 4.946058533 |
| 314 | 3866.011.1-T_at | 9.18073541 | 5.037406823 |
| 315 | 3866.013.1-E_at | 9.93641299 | 5.489343529 |
| 316 | 3866.010.1-D_at | 7.92735291 | 4.325351254 |
| 317 | 59.004.1-T_at | 6.80411249 | 4.752679161 |
| 318 | 2115.012.1-T_at | 4.90559701 | 3.671185668 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 319 | 2.018.1-D_at | 7.56738794 | 4.906078362 |
| 320 | 2115.007.1-T_at | 4.92205691 | 3.509530779 |
| 321 | 59.040.1-T_at | 7.92500959 | 5.05284254 |
| 322 | 130497.001.2-T | 5.99836959 | 4.482736911 |
| 323 | 140885.014.1-T | 6.11906211 | 4.162154943 |
| 324 | 3866.005.1-F_at | 10.0863709 | 6.759928131 |
| 325 | 7373.003.3-F_at | 5.33919182 | 3.590603587 |
| 326 | 8404.028.1-F_at | 7.04051836 | 4.637927072 |
| 327 | 3860.007.1-D_at | 6.74551501 | 4.619163344 |
| 328 | 4638.003.1-C_at | 6.92132293 | 4.308398188 |
| 329 | 3872.009.1-E_at | 6.06310081 | 3.900207749 |
| 330 | 59.004.2-T_at | 6.8944992 | 4.903788058 |
| 331 | 3872.006.1-C_at | 5.96674849 | 3.642756113 |
| 332 | 3866.005.1-C_at | 9.92269961 | 5.465682846 |
| 333 | 25925.008.1-T_at | 5.69718285 | 3.927983551 |
| 334 | 23650.011.2-T_at | 7.84409583 | 5.100253551 |
| 335 | 3866.012.2-T_at | 9.91429542 | 5.489051755 |
| 336 | 3852.017.1-D_at | 7.83835576 | 6.280406857 |
| 337 | 4915.005.1-T_at | 6.46700411 | 3.841875247 |
| 338 | 4638.003.1-B_at | 5.77600419 | 3.967963498 |
| 339 | 1756.003.1-B_at | 5.78203385 | 3.613994813 |
| 340 | 4638.006.1-F_at | 6.98679711 | 5.084511181 |
| 341 | 57447.035.1-F_at | 8.86960129 | 6.679175491 |
| 342 | 4638.014.1-T_at | 6.2093321 | 4.224843914 |
| 343 | 7373.003.4-T_at | 5.85405082 | 3.941925452 |
| 344 | 27122.014.2-D_at | 7.20343208 | 5.077601963 |
| 345 | 3866.007.1-T_at | 8.98065251 | 5.096039971 |
| 346 | 2707.002.1-E_at | 5.34630411 | 3.674524536 |
| 347 | 59.024.1-T_at | 6.83542202 | 4.80269153 |
| 348 | 23650.011.1-T_at | 7.77512705 | 5.141458081 |
| 349 | 4638.011.1-F_at | 6.85698752 | 4.967669809 |
| 350 | 7373.002.1-F_at | 5.47015821 | 3.55519593 |
| 351 | 3866.013.1-F_at | 10.0353866 | 5.509128495 |
| 352 | 5608.002.1-T_at | 5.59795956 | 4.054949846 |
| 353 | 3866.001.1-C_at | 8.25309213 | 4.510684041 |
| 354 | 1756.013.1-B_at | 5.65046199 | 3.958957471 |
| 355 | 2115.006.1-E_at | 4.67003702 | 3.398574534 |
| 356 | 6376.001.2-F_at | 6.76738419 | 4.594461954 |
| 357 | 3084.004.1-B_at | 5.38510101 | 3.510068108 |
| 358 | 3815.002.4-F_at | 5.6936983 | 3.530847279 |
| 359 | 8404.002.1-D_at | 5.08914334 | 3.509495218 |
| 360 | 1264.006.1-T_at | 4.78935745 | 3.400776827 |
| 361 | 59.022.2-D_at | 7.5362729 | 4.574317348 |
| 362 | 25925.001.1-T_at | 5.6505549 | 3.971262708 |
| 363 | 4638.006.2-B_at | 10.2697846 | 7.926227045 |
| 364 | 7373.003.5-B_at | 6.13588807 | 3.881763973 |
| 365 | 8404.035.1-B_at | 4.89853755 | 3.542374505 |
| 366 | 59.012.1-T_at | 5.29276653 | 3.730940958 |
| 367 | 3852.017.1-T_at | 5.94439335 | 4.136178865 |
| 368 | 3866.012.2-B_at | 8.89819048 | 6.139221978 |
| 369 | 2.022.1-B_at | 6.71649373 | 4.755989653 |
| 370 | 27122.016.1-F_at | 5.4913787 | 3.685454959 |
| 371 | 4311.009.1-B_at | 5.80492787 | 3.970849589 |
| 372 | 59.031.2-T_at | 7.28741747 | 5.073231596 |
| 373 | 4311.009.1-T_at | 6.04715771 | 3.812370988 |
| 374 | 3866.006.2-B_at | 8.87200336 | 6.165346275 |
| 375 | 57447.025.2-T_at | 7.83901538 | 5.040091008 |
| 376 | 1717.007.1-F_at | 8.47657921 | 6.307092709 |
| 377 | 59.004.2-D_at | 5.77885906 | 4.201996709 |
| 378 | 3866.007.2-B_at | 9.03444459 | 6.541756746 |
| 379 | 3866.010.1-F_at | 10.0841138 | 6.76233538 |
| 380 | 9768.004.1-D_at | 5.61546594 | 8.042566668 |
| 381 | 3084.012.2-T_at | 4.98851121 | 3.374482117 |
| 382 | 1410.004.2-B_at | 5.76955824 | 3.747418029 |
| 383 | 59.008.1-D_at | 7.580525 | 4.705524193 |
| 384 | 57447.030.1-C_at | 6.89544125 | 5.081510062 |
| 385 | 2327.002.1-D_at | 5.9013749 | 3.706350575 |
| 386 | 1308.004.1-B_at | 5.16195304 | 3.553648577 |
| 387 | 2568.005.2-B_at | 6.91662284 | 3.904971891 |
| 388 | 2568.001.1-T_at | 5.88553699 | 3.946862951 |
| 389 | 3084.004.2-T_at | 4.94236295 | 3.3780596 |
| 390 | 7373.003.4-B_at | 5.93233847 | 3.707708869 |
| 391 | 7153.002.2-D_at | 4.68145177 | 7.624764565 |
| 392 | 2893.006.2-T_at | 4.85081759 | 3.447008535 |
| 393 | 3872.016.1-D_at | 11.1567975 | 8.699934006 |
| 394 | 9413.006.1-F_at | 5.72231532 | 3.924184102 |
| 395 | 59.023.2-B_at | 8.07001275 | 5.312063628 |
| 396 | 72.005.1-B_at | 6.00386245 | 3.894301071 |
| 397 | 4915.011.1-C_at | 6.67654504 | 3.909184112 |
| 398 | 27122.018.1-F_at | 6.87829457 | 4.481518888 |
| 399 | 3852.006.1-B_at | 6.41696793 | 4.385795959 |
| 400 | 4638.006.2-D_at | 8.29420831 | 6.32375426 |
| 401 | 7153.005.1-E_at | 4.77417213 | 7.640160109 |
| 402 | 7373.001.2-T_at | 4.90613308 | 3.486605886 |
| 403 | 7018.026.1-B_at | 7.57683708 | 4.643843211 |
| 404 | 7402.014.1-B_at | 4.80489581 | 3.457197254 |
| 405 | 57447.010.3-D_at | 6.06072901 | 3.842292369 |
| 406 | 140446.004.1-T | 6.16231533 | 4.305325034 |
| 407 | 59.026.2-T_at | 7.15005413 | 4.607592814 |
| 408 | 59.038.1-B_at | 5.6494079 | 4.056218565 |
| 409 | 4240.009.1-C_at | 6.78849961 | 4.026127894 |
| 410 | 57447.030.1-F_at | 7.60148038 | 5.351594285 |
| 411 | 9768.004.1-B_at | 8.05212792 | 10.06930458 |
| 412 | 57447.008.1-T_at | 7.31095336 | 4.743544863 |
| 413 | 59.014.2-T_at | 6.61391873 | 4.504144736 |
| 414 | 4915.012.1-T_at | 5.09228311 | 3.51551028 |
| 415 | 3866.004.1-T_at | 8.98279458 | 5.909305497 |
| 416 | 2582.007.2-C_at | 5.8740549 | 3.779098879 |
| 417 | 7153.002.5-T_at | 4.34207016 | 6.815675337 |
| 418 | 4638.009.1-T_at | 6.73711208 | 4.705108768 |
| 419 | 3861.023.1-T_at | 8.54451168 | 7.107258463 |
| 420 | 5858.003.3-C_at | 7.42717125 | 4.805969254 |
| 421 | 3861.020.1-F_at | 6.68913708 | 5.181784732 |
| 422 | 147495.005.1-T | 4.88155983 | 3.636974481 |
| 423 | 4638.006.2-C_at | 6.96393228 | 4.171935351 |
| 424 | 1308.004.1-F_at | 4.77853486 | 3.492851328 |
| 425 | 4915.004.1-F_at | 7.22504252 | 4.799719839 |
| 426 | 3866.008.1-B_at | 10.1199429 | 6.470209973 |
| 427 | 8626.002.1-E_at | 5.06121478 | 3.39085572 |
| 428 | 1264.003.1-T_at | 5.58569266 | 3.581548983 |
| 429 | 59.042.1-F_at | 7.27807331 | 4.623171279 |
| 430 | 4833.004.1-T_at | 9.54827464 | 10.38615702 |
| 431 | 2568.006.1-B_at | 6.6183729 | 3.976037452 |
| 432 | 57447.004.2-T_at | 6.70536079 | 4.18281839 |
| 433 | 59.014.2-B_at | 8.212195 | 5.378024412 |
| 434 | 3084.012.1-T_at | 5.03022579 | 3.397719814 |
| 435 | 27122.017.1-T_at | 6.51481084 | 4.366155325 |
| 436 | 3852.012.2-T_at | 6.92067083 | 5.004410401 |
| 437 | 59.033.1-T_at | 6.06486589 | 4.665665746 |
| 438 | 27122.002.1-C_at | 7.19364005 | 5.202367669 |
| 439 | 3880.011.1-B_at | 10.5071551 | 7.518624838 |
| 440 | 65983.013.1-T_at | 7.70720875 | 5.536789935 |
| 441 | 3872.014.1-T_at | 7.93552665 | 5.762824716 |
| 442 | 162605.001.4-C | 7.30134493 | 4.179141958 |
| 443 | 59.031.2-B_at | 5.4449077 | 3.782243257 |
| 444 | 3084.012.2-B_at | 6.18353868 | 4.174289227 |
| 445 | 5858.001.2-C_at | 7.44400374 | 4.932750742 |
| 446 | 65983.010.1-T_at | 5.57005121 | 3.990871808 |
| 447 | 7373.003.5-F_at | 5.34533867 | 3.627863939 |
| 448 | 3866.010.1-T_at | 9.51219169 | 5.699587788 |
| 449 | 8404.005.1-B_at | 7.38892631 | 4.907319634 |
| 450 | 3866.005.1-T_at | 9.03709767 | 6.030628254 |
| 451 | 59.003.1-F_at | 5.4356104 | 4.096508262 |
| 452 | 7153.002.5-F_at | 5.25391475 | 7.80693684 |
| 453 | 2487.001.1-T_at | 5.33828017 | 3.563654952 |
| 454 | 3866.010.1-B_at | 9.6945434 | 7.292676871 |
| 455 | 147495.009.1-T | 4.85966734 | 3.631522846 |
| 456 | 65983.003.2-T_at | 6.05435123 | 4.377097045 |
| 457 | 59.040.1-D_at | 7.44167751 | 4.584016558 |
| 458 | 59.024.2-T_at | 6.73075195 | 4.593534348 |
| 459 | 1717.009.2-B_at | 8.45360663 | 6.312163684 |
| 460 | 1756.027.1-F_at | 4.75197052 | 3.358719581 |
| 461 | 59.042.1-B_at | 8.72270213 | 5.878159021 |
| 462 | 7153.002.5-D_at | 4.84971619 | 7.17366424 |
| 463 | 57447.031.1-F_at | 6.49415294 | 4.65208765 |
| 464 | 140885.011.1-C | 6.38820366 | 4.253831639 |
| 465 | 59.003.1-T_at | 7.42538834 | 5.15557028 |
| 466 | 3832.002.1-D_at | 3.75527723 | 5.95014323 |
| 467 | 3880.005.1-D_at | 10.9942207 | 8.319628818 |
| 468 | 3084.012.1-F_at | 5.28504089 | 3.485172312 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 469 | 6595.012.1-B_at | 5.31888699 | 3.686393951 |
| 470 | 59.012.2-D_at | 7.44955953 | 4.615757659 |
| 471 | 57447.034.1-C_at | 8.57145373 | 6.706526296 |
| 472 | 56477.001.1-B_at | 7.19333631 | 5.61196287 |
| 473 | 57447.041.1-D_at | 6.52483208 | 4.131433849 |
| 474 | 9768.005.1-B_at | 8.31090623 | 9.919835275 |
| 475 | 285203.001.2-C | 5.76551543 | 4.033568669 |
| 476 | 147495.006.1-B | 4.7178507 | 3.386397601 |
| 477 | 7018.029.1-D_at | 7.49247458 | 4.695975326 |
| 478 | 3852.009.1-T_at | 7.08281122 | 4.869630434 |
| 479 | 59.023.2-D_at | 7.777198 | 5.151112126 |
| 480 | 1959.002.1-D_at | 4.95918444 | 3.503378215 |
| 481 | 7018.014.1-D_at | 7.44352827 | 4.557712011 |
| 482 | 5858.004.1-F_at | 6.76116585 | 4.375553995 |
| 483 | 79192.002.2-D_at | 5.63448533 | 3.51926817 |
| 484 | 59.008.2-B_at | 8.69617919 | 5.779103612 |
| 485 | 8404.008.1-E_at | 5.85502792 | 4.086526269 |
| 486 | 59.008.1-F_at | 6.10922251 | 4.513619758 |
| 487 | 4240.011.1-B_at | 6.01396547 | 3.771634645 |
| 488 | 94274.002.1-C_at | 6.16939359 | 3.837512253 |
| 489 | 4638.015.1-T_at | 5.62349541 | 3.911665402 |
| 490 | 6376.001.1-T_at | 7.28348829 | 5.069341011 |
| 491 | 57447.043.1-F_at | 6.82408835 | 4.362797669 |
| 492 | 59.039.1-T_at | 6.75082374 | 4.916156262 |
| 493 | 4638.006.1-B_at | 5.98299624 | 4.034678304 |
| 494 | 25802.003.1-F_at | 8.44079836 | 5.782396909 |
| 495 | 57447.025.1-T_at | 7.73646375 | 5.084216105 |
| 496 | 57447.017.1-T_at | 6.65771959 | 4.273635182 |
| 497 | 7018.026.1-C_at | 7.45984207 | 4.533286079 |
| 498 | 7018.028.1-E_at | 7.40598333 | 4.550309687 |
| 499 | 4915.008.1-C_at | 5.64881509 | 3.72422841 |
| 500 | 358.018.1-C_at | 5.7267252 | 3.761286452 |
| 501 | 7153.002.6-B_at | 4.11329877 | 6.373276857 |
| 502 | 57447.012.1-T_at | 7.30791833 | 4.819204577 |
| 503 | 59.040.1-B_at | 5.85498792 | 4.104163066 |
| 504 | 57447.006.1-T_at | 7.76068288 | 5.150567998 |
| 505 | 9493.006.1-F_at | 4.10577729 | 6.338245812 |
| 506 | 57447.004.1-T_at | 7.33632129 | 4.896275995 |
| 507 | 57447.004.2-B_at | 8.9127783 | 6.322143899 |
| 508 | 7373.001.2-D_at | 5.3965566 | 3.844531388 |
| 509 | 9493.004.1-B_at | 3.76399079 | 5.935350549 |
| 510 | 2568.005.2-C_at | 6.84549764 | 3.843092863 |
| 511 | 7018.029.1-F_at | 7.12490547 | 4.43476648 |
| 512 | 26289.013.1-B_at | 6.90469249 | 5.370319984 |
| 513 | 7169.015.1-B_at | 6.84318501 | 4.909744137 |
| 514 | 57451.001.3-F_at | 4.90668348 | 3.471308523 |
| 515 | 2568.005.2-F_at | 6.79093209 | 4.252137182 |
| 516 | 57447.004.2-F_at | 8.06429543 | 5.612147867 |
| 517 | 8404.004.1-D_at | 5.17131676 | 3.577119644 |
| 518 | 3855.004.2-D_at | 6.85394835 | 4.458549061 |
| 519 | 3872.014.1-F_at | 6.14273082 | 4.52366007 |
| 520 | 57447.033.1-F_at | 7.64663376 | 5.439828214 |
| 521 | 9452.001.1-T_at | 6.18030538 | 4.323283485 |
| 522 | 59.033.2-T_at | 5.65222584 | 4.220481151 |
| 523 | 3084.009.1-T_at | 5.35152557 | 3.607558469 |
| 524 | 57447.040.1-T_at | 8.2897346 | 6.134921385 |
| 525 | 4833.004.1-T_at | 9.46766291 | 10.42910615 |
| 526 | 3426.001.1-F_at | 6.26649958 | 4.50478468 |
| 527 | 59.034.1-B_at | 5.62313286 | 4.199853557 |
| 528 | 10253.001.1-E_at | 5.11930015 | 3.602200848 |
| 529 | 9073.001.1-C_at | 6.47130665 | 3.903135256 |
| 530 | 51201.005.1-T_at | 6.31581082 | 4.43048891 |
| 531 | 9477.006.1-C_at | 5.53969827 | 4.094283805 |
| 532 | 57447.028.1-T_at | 7.15440543 | 4.718940054 |
| 533 | 25925.007.1-T_at | 5.59498246 | 3.919647944 |
| 534 | 59.024.2-B_at | 8.11536088 | 5.398824045 |
| 535 | 2.022.1-T_at | 6.6607733 | 4.783988683 |
| 536 | 4281.008.2-B_at | 6.31875113 | 4.027809365 |
| 537 | 90231.001.1-C_at | 7.10807035 | 5.499098683 |
| 538 | 358.012.1-D_at | 7.14590494 | 4.561944415 |
| 539 | 3852.021.1-T_at | 6.09796458 | 4.733460989 |
| 540 | 7373.003.4-D_at | 5.31871742 | 3.444341336 |
| 541 | 57447.048.1-T_at | 7.77920047 | 5.301184204 |
| 542 | 358.012.1-B_at | 6.31206962 | 4.291200634 |
| 543 | 7018.025.1-C_at | 6.45586871 | 3.926355221 |
| 544 | 5608.004.1-T_at | 5.49475117 | 4.000756586 |
| 545 | 3084.012.2-F_at | 5.75533986 | 3.729134317 |
| 546 | 4306.002.1-C_at | 4.88461568 | 3.537810553 |
| 547 | 4288.004.1-D_at | 3.93407536 | 6.069531548 |
| 548 | 57447.002.1-F_at | 7.74355125 | 5.160300501 |
| 549 | 4281.018.1-T_at | 5.78771209 | 4.04473446 |
| 550 | 10144.020.2-B_at | 5.47403735 | 3.883269971 |
| 551 | 6876.016.1-E_at | 6.18917118 | 4.18306498 |
| 552 | 57447.008.2-T_at | 7.34801416 | 4.979022114 |
| 553 | 51203.004.1-T_at | 4.78407281 | 7.121996232 |
| 554 | 2335.028.1-B_at | 4.21322617 | 6.985070244 |
| 555 | 7018.028.1-T_at | 7.69070629 | 4.697084965 |
| 556 | 7373.003.5-T_at | 4.92968881 | 3.413713427 |
| 557 | 81557.006.1-C_at | 5.93949691 | 3.8795395 |
| 558 | 3866.002.1-D_at | 8.13043421 | 4.563939496 |
| 559 | 3866.001.1-B_at | 9.58995543 | 5.652717341 |
| 560 | 55107.006.2-T_at | 5.84582122 | 4.291743766 |
| 561 | 79068.010.1-D_at | 5.70046398 | 3.712391955 |
| 562 | 57447.009.1-T_at | 8.2708267 | 6.230837008 |
| 563 | 2115.015.1-E_at | 4.73030559 | 3.529706912 |
| 564 | 1756.013.1-C_at | 5.56755741 | 3.498765701 |
| 565 | 7169.015.1-F_at | 7.18617 | 5.481397093 |
| 566 | 65983.013.2-F_at | 6.02311371 | 4.186716607 |
| 567 | 8404.001.1-B_at | 7.99199458 | 5.467331229 |
| 568 | 4240.004.1-B_at | 5.05165978 | 3.552351613 |
| 569 | 57447.012.2-T_at | 7.26590502 | 4.745539951 |
| 570 | 57447.024.1-F_at | 7.68629251 | 5.418867784 |
| 571 | 358.018.1-T_at | 6.45498824 | 4.241533634 |
| 572 | 57447.048.2-T_at | 7.78420544 | 5.160126545 |
| 573 | 59.031.1-C_at | 7.49205582 | 4.903309981 |
| 574 | 3860.007.1-F_at | 7.96260627 | 7.096659156 |
| 575 | 8404.028.1-C_at | 8.62889588 | 6.246608834 |
| 576 | 4240.011.3-E_at | 6.64966622 | 4.03055242 |
| 577 | 59.022.2-B_at | 6.73772327 | 4.432555365 |
| 578 | 3866.002.1-F_at | 9.25258448 | 5.192570901 |
| 579 | 3866.002.1-T_at | 10.3199488 | 7.640256534 |
| 580 | 4915.005.1-B_at | 5.32094122 | 3.959770809 |
| 581 | 8404.008.1-F_at | 7.59063584 | 4.972790065 |
| 582 | 79608.002.1-F_at | 6.76648623 | 4.436714154 |
| 583 | 8404.023.1-D_at | 5.15683509 | 3.569085706 |
| 584 | 3426.002.1-D_at | 5.89393001 | 3.867643288 |
| 585 | 2335.027.1-T_at | 4.74881131 | 7.635920403 |
| 586 | 11065.009.1-T_at | 4.30670491 | 6.277657291 |
| 587 | 140885.013.1-F | 4.7450748 | 3.529107038 |
| 588 | 57447.021.1-B_at | 8.92169251 | 6.883898006 |
| 589 | 25802.004.1-C_at | 5.57673557 | 3.766890823 |
| 590 | 4638.014.1-F_at | 6.07887669 | 4.28495326 |
| 591 | 9493.004.1-F_at | 4.40101083 | 6.610015234 |
| 592 | 8404.004.1-B_at | 5.26981439 | 3.864868573 |
| 593 | 8404.004.2-T_at | 7.56316749 | 5.288443352 |
| 594 | 57447.010.2-T_at | 8.91041497 | 6.730736236 |
| 595 | 57447.010.3-B_at | 6.48036743 | 4.021664269 |
| 596 | 27122.006.1-T_at | 6.45932378 | 4.338943765 |
| 597 | 5156.005.1-T_at | 6.0454338 | 4.480368629 |
| 598 | 5858.004.1-E_at | 7.37541332 | 5.015122988 |
| 599 | 25802.008.1-D_at | 5.55466297 | 3.708835665 |
| 600 | 2327.002.2-T_at | 5.75006787 | 3.952332834 |
| 601 | 3852.004.1-C_at | 5.36673477 | 3.588173957 |
| 602 | 59.026.2-F_at | 6.23946248 | 4.728060027 |
| 603 | 57447.029.1-C_at | 6.81845329 | 4.22278911 |
| 604 | 7169.022.1-D_at | 7.8722658 | 5.729424902 |
| 605 | 23266.001.3-B_at | 6.46418041 | 4.203358555 |
| 606 | 3084.012.1-B_at | 5.2276441 | 3.451592509 |
| 607 | 29127.019.2-T_at | 4.21990379 | 6.173743362 |
| 608 | 10253.004.1-T_at | 5.1662428 | 3.694488428 |
| 609 | 10124.002.1-D_at | 4.89764097 | 3.541005706 |
| 610 | 3861.013.1-D_at | 9.32851084 | 8.049530881 |
| 611 | 8404.032.1-T_at | 7.52923111 | 5.000568707 |
| 612 | 84441.002.1-E_at | 5.90012193 | 3.970885538 |
| 613 | 2.013.1-E_at | 7.80547535 | 5.549361786 |
| 614 | 3084.004.1-T_at | 4.81080947 | 3.346803546 |
| 615 | 5288.001.2-F_at | 4.76245236 | 3.504782872 |
| 616 | 57447.017.1-F_at | 8.0107637 | 5.541276327 |
| 617 | 3084.006.1-T_at | 4.81532746 | 3.375970424 |
| 618 | 59.039.1-F_at | 6.56572249 | 5.093494374 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 619 | 2.024.1-T_at | 5.21957454 | 3.829912849 |
| 620 | 3815.002.2-E_at | 4.63092258 | 3.36714837 |
| 621 | 1756.009.1-D_at | 4.85499539 | 3.471377655 |
| 622 | 7091.014.1-B_at | 7.40595585 | 5.56221435 |
| 623 | 4629.015.1-F_at | 5.10691679 | 3.491137224 |
| 624 | 59.008.2-F_at | 6.0929029 | 4.444669467 |
| 625 | 2568.005.2-T_at | 8.95422916 | 5.14191273 |
| 626 | 115207.002.1-T | 5.88924208 | 4.419602651 |
| 627 | 4281.001.1-T_at | 5.35086765 | 3.640788304 |
| 628 | 84668.002.2-T_at | 5.15028907 | 3.79042988 |
| 629 | 4240.004.1-F_at | 5.66574104 | 3.720396854 |
| 630 | 8404.005.1-D_at | 6.9401254 | 4.492872909 |
| 631 | 8404.032.1-B_at | 7.44013836 | 5.095849595 |
| 632 | 57447.044.1-E_at | 6.80906698 | 4.217089915 |
| 633 | 8626.006.2-F_at | 7.23333868 | 4.510165054 |
| 634 | 57447.051.2-B_at | 7.98328422 | 5.210860718 |
| 635 | 1063.001.1-T_at | 3.65207754 | 5.460717647 |
| 636 | 3426.002.1-T_at | 6.14481418 | 4.337714037 |
| 637 | 1308.001.1-T_at | 4.49112544 | 3.366968911 |
| 638 | 389432.002.1-F | 4.87416968 | 3.449919343 |
| 639 | 57447.017.1-B_at | 7.4444592 | 4.927207265 |
| 640 | 2115.014.1-F_at | 4.64920074 | 3.393814502 |
| 641 | 5284.004.1-T_at | 5.42573909 | 3.644981157 |
| 642 | 57447.029.1-F_at | 6.90955367 | 4.763872665 |
| 643 | 8626.006.1-F_at | 7.10882986 | 4.577853419 |
| 644 | 2982.002.1-C_at | 5.95650332 | 4.047393285 |
| 645 | 57447.047.1-T_at | 8.49737877 | 6.301927816 |
| 646 | 5803.006.1-E_at | 4.70860909 | 3.460139104 |
| 647 | 57447.021.1-F_at | 6.99463667 | 4.787200512 |
| 648 | 57447.039.1-F_at | 8.6752975 | 7.025558424 |
| 649 | 4281.008.2-F_at | 5.78507528 | 3.786315944 |
| 650 | 57447.029.1-D_at | 7.11241156 | 4.695681706 |
| 651 | 65983.013.1-B_at | 6.06404247 | 4.544332621 |
| 652 | 5284.004.1-E_at | 5.48521773 | 3.473351613 |
| 653 | 4240.011.1-D_at | 6.58817281 | 4.028721269 |
| 654 | 57447.024.1-T_at | 6.74179663 | 4.451590226 |
| 655 | 6876.011.1-B_at | 6.30476658 | 4.18672283 |
| 656 | 7373.003.2-T_at | 4.82544001 | 3.471146792 |
| 657 | 3852.014.1-D_at | 5.18111457 | 3.45188203 |
| 658 | 4915.005.1-D_at | 5.64408415 | 3.959617796 |
| 659 | 9768.002.2-B_at | 5.37116829 | 7.073380688 |
| 660 | 140885.010.1-D | 6.19842073 | 4.31967621 |
| 661 | 4638.020.1-E_at | 5.02985387 | 3.533302553 |
| 662 | 57447.017.1-C_at | 7.71365249 | 6.834906013 |
| 663 | 7373.004.1-T_at | 5.09440176 | 3.576481268 |
| 664 | 3852.008.2-E_at | 5.70467573 | 3.895814365 |
| 665 | 4281.015.1-E_at | 5.86221529 | 3.827749855 |
| 666 | 8404.013.1-C_at | 7.63052911 | 5.806566552 |
| 667 | 90293.001.3-T_at | 5.16415646 | 3.590009024 |
| 668 | 57447.044.1-T_at | 6.3521445 | 4.368444106 |
| 669 | 23650.011.2-D_at | 5.16951309 | 3.620720053 |
| 670 | 2335.006.1-D_at | 5.19038486 | 8.099850829 |
| 671 | 57447.022.1-T_at | 8.16254038 | 6.240130159 |
| 672 | 8404.032.1-D_at | 6.59024869 | 4.387778168 |
| 673 | 8404.030.1-F_at | 6.20905072 | 4.160627809 |
| 674 | 5803.002.2-T_at | 4.56393909 | 3.473197076 |
| 675 | 8404.004.2-C_at | 5.26606619 | 3.620282123 |
| 676 | 84441.005.1-C_at | 4.85915223 | 3.545415518 |
| 677 | 7091.015.1-F_at | 6.21201003 | 4.478013561 |
| 678 | 2119.005.1-D_at | 5.07146093 | 3.567763303 |
| 679 | 7373.003.6-F_at | 6.24165607 | 4.086113068 |
| 680 | 79608.008.1-T_at | 7.43049786 | 5.105020166 |
| 681 | 3852.008.1-T_at | 6.84173919 | 4.788195739 |
| 682 | 8626.007.1-T_at | 5.77669765 | 3.835835567 |
| 683 | 8404.022.1-T_at | 6.96844417 | 4.561425115 |
| 684 | 8404.034.1-T_at | 7.70565001 | 5.437963133 |
| 685 | 57447.049.1-T_at | 8.19539372 | 6.244201139 |
| 686 | 5311.002.1-B_at | 5.23153491 | 3.9379694 |
| 687 | 2335.025.3-T_at | 4.97507454 | 7.552542415 |
| 688 | 4147.012.1-T_at | 6.56476077 | 4.115527169 |
| 689 | 301.015.1-T_at | 7.08671415 | 4.704911993 |
| 690 | 301.004.1-T_at | 5.88285125 | 4.193540097 |
| 691 | 3426.002.2-F_at | 6.42951667 | 4.610291858 |
| 692 | 7091.001.1-C_at | 5.78834657 | 3.99782643 |
| 693 | 8404.021.1-D_at | 7.13632332 | 4.668450897 |
| 694 | 7153.002.3-B_at | 4.32680853 | 6.386139877 |
| 695 | 53335.002.1-E_at | 6.97060249 | 4.349457276 |
| 696 | 5284.003.2-T_at | 5.56357531 | 3.826429145 |
| 697 | 4306.002.1-F_at | 5.12339023 | 3.619119014 |
| 698 | 5284.003.2-D_at | 5.40634511 | 3.413836573 |
| 699 | 5803.002.1-T_at | 4.46452818 | 3.454054461 |
| 700 | 10253.004.1-E_at | 5.04005634 | 3.60976014 |
| 701 | 23650.020.1-T_at | 4.5970193 | 3.540969462 |
| 702 | 57447.042.1-T_at | 8.23732789 | 6.24305985 |
| 703 | 6876.023.1-F_at | 6.0056721 | 4.219933741 |
| 704 | 7169.015.1-C_at | 7.73240413 | 5.633948369 |
| 705 | 7153.002.4-F_at | 4.29974508 | 6.250118979 |
| 706 | 4629.016.1-B_at | 6.78440003 | 5.390110166 |
| 707 | 6876.002.1-C_at | 6.05319952 | 3.996827256 |
| 708 | 65983.007.1-T_at | 5.80300089 | 4.538161738 |
| 709 | 7373.003.2-F_at | 4.94886483 | 3.638149496 |
| 710 | 152015.004.1-T | 7.02090877 | 4.99281238 |
| 711 | 8404.004.2-B_at | 9.10036043 | 6.953060695 |
| 712 | 6285.001.1-B_at | 6.79781208 | 4.254547252 |
| 713 | 2115.007.1-E_at | 4.60359502 | 3.455996501 |
| 714 | 2.013.1-T_at | 7.4129596 | 5.313450804 |
| 715 | 6289.005.1-T_at | 7.97416675 | 5.388443167 |
| 716 | 9232.002.1-T_at | 4.43941526 | 6.671542368 |
| 717 | 59.014.1-B_at | 5.61171235 | 4.093335038 |
| 718 | 59.031.1-F_at | 6.05184505 | 4.804165615 |
| 719 | 3084.011.1-T_at | 4.47393244 | 3.329487007 |
| 720 | 3872.005.1-F_at | 7.08989626 | 4.850069536 |
| 721 | 3084.012.3-F_at | 5.22568038 | 3.554479542 |
| 722 | 81704.008.1-F_at | 6.21408125 | 4.397532613 |
| 723 | 140885.010.2-C | 4.97071116 | 3.671401317 |
| 724 | 338707.006.1-E | 5.98755333 | 4.509773447 |
| 725 | 23266.008.2-T_at | 6.14954287 | 4.054145008 |
| 726 | 120.005.2-E_at | 4.96398804 | 3.493809568 |
| 727 | 4281.009.1-E_at | 5.85541642 | 3.780316615 |
| 728 | 4094.001.1-T_at | 4.9006582 | 3.742133457 |
| 729 | 2995.001.1-T_at | 5.43112669 | 4.074233155 |
| 730 | 4638.011.1-E_at | 5.98438955 | 4.171529554 |
| 731 | 2335.017.1-T_at | 4.62014922 | 7.477442043 |
| 732 | 5284.001.1-F_at | 5.85070156 | 4.156065391 |
| 733 | 8404.026.1-D_at | 5.85230036 | 3.946505653 |
| 734 | 2335.009.1-F_at | 4.30571681 | 7.164817626 |
| 735 | 10461.002.2-F_at | 4.63243519 | 3.535654634 |
| 736 | 84441.002.1-T_at | 5.38195119 | 3.727915338 |
| 737 | 147495.006.1-T | 5.03268944 | 3.722907652 |
| 738 | 7091.010.1-B_at | 7.35452034 | 5.471123192 |
| 739 | 8404.008.1-C_at | 8.16760292 | 5.675687385 |
| 740 | 6376.001.2-C_at | 4.95398073 | 3.657520603 |
| 741 | 3832.002.1-B_at | 5.6547708 | 7.337897553 |
| 742 | 59.034.2-T_at | 7.1564008 | 5.827736739 |
| 743 | 147495.005.1-B | 4.74136095 | 3.469591177 |
| 744 | 3872.005.1-T_at | 7.59194046 | 5.105397146 |
| 745 | 79895.001.1-D_at | 5.67879632 | 4.246832679 |
| 746 | 57447.018.1-T_at | 6.69850781 | 4.473274428 |
| 747 | 7373.008.1-T_at | 5.31202269 | 3.784685566 |
| 748 | 4744.004.1-C_at | 6.56900249 | 4.507168025 |
| 749 | 140885.010.1-T | 5.34750246 | 3.919015769 |
| 750 | 6876.016.2-E_at | 5.93029441 | 3.912787487 |
| 751 | 8404.015.1-T_at | 6.44737359 | 4.403676272 |
| 752 | 4281.014.1-T_at | 5.78461168 | 4.11824695 |
| 753 | 4288.006.1-F_at | 6.66901042 | 8.513403763 |
| 754 | 25925.009.1-E_at | 5.28428858 | 3.73856992 |
| 755 | 4240.009.1-B_at | 5.83089671 | 3.671481622 |
| 756 | 667.010.1-E_at | 6.85392624 | 5.299481091 |
| 757 | 3866.005.1-B_at | 7.15276909 | 4.263334499 |
| 758 | 57447.011.1-T_at | 8.19368289 | 6.289649841 |
| 759 | 57447.034.1-B_at | 5.65705009 | 3.831297336 |
| 760 | 25802.004.1-B_at | 8.21857039 | 6.532464436 |
| 761 | 8404.024.1-T_at | 6.97369157 | 4.587021041 |
| 762 | 57447.032.1-T_at | 7.06280543 | 4.783190929 |
| 763 | 667.021.1-F_at | 8.07963087 | 5.823822156 |
| 764 | 5858.001.2-F_at | 5.1370254 | 3.721747178 |
| 765 | 51062.008.1-T_at | 5.30551619 | 3.890620002 |
| 766 | 2335.013.1-F_at | 6.15540646 | 8.86885363 |
| 767 | 2568.001.2-T_at | 5.68238983 | 3.94629046 |
| 768 | 7170.005.2-D_at | 8.99098118 | 9.775109373 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 769 | 57447.034.1-F_at | 6.98073127 | 5.016025642 |
| 770 | 7153.002.6-C_at | 5.57448334 | 7.592280416 |
| 771 | 2568.003.1-T_at | 5.81249572 | 4.092333465 |
| 772 | 59.008.2-T_at | 8.60581658 | 6.540879986 |
| 773 | 9898.015.2-B_at | 3.9211311 | 5.201936253 |
| 774 | 7018.013.1-T_at | 5.65007058 | 3.778570945 |
| 775 | 7170.034.2-D_at | 9.01623909 | 9.815404878 |
| 776 | 3866.004.1-E_at | 4.83901548 | 3.502240062 |
| 777 | 5284.001.1-T_at | 8.49976792 | 6.07875714 |
| 778 | 2.002.1-C_at | 6.12813044 | 4.193878475 |
| 779 | 57447.050.1-T_at | 8.19795199 | 5.982437202 |
| 780 | 7018.014.1-F_at | 6.97729458 | 4.681227687 |
| 781 | 2335.032.1-D_at | 5.08653484 | 8.031106422 |
| 782 | 3866.002.1-C_at | 6.91504668 | 4.200467449 |
| 783 | 57447.043.1-T_at | 6.56411152 | 4.225208179 |
| 784 | 51201.005.1-D_at | 5.11440976 | 3.64815718 |
| 785 | 51203.003.1-T_at | 4.82041174 | 7.05990414 |
| 786 | 9493.001.1-F_at | 3.98373277 | 6.007980938 |
| 787 | 57447.024.1-B_at | 7.87321828 | 5.204843561 |
| 788 | 80034.003.4-B_at | 5.58242913 | 4.421835696 |
| 789 | 7170.016.3-C_at | 9.01883837 | 9.828229863 |
| 790 | 65983.003.1-T_at | 5.92193731 | 4.324879597 |
| 791 | 57447.026.1-T_at | 8.15874879 | 6.121827399 |
| 792 | 440421.001.1-F | 7.16019583 | 5.432495642 |
| 793 | 301.008.1-D_at | 5.48743448 | 3.703220782 |
| 794 | 80034.002.2-T_at | 4.34845355 | 3.381277916 |
| 795 | 7153.002.5-B_at | 5.10010536 | 7.50996728 |
| 796 | 3852.023.1-T_at | 5.16770498 | 4.068449227 |
| 797 | 8404.013.1-F_at | 6.3516361 | 4.31581135 |
| 798 | 2.018.1-C_at | 4.79949735 | 3.600814702 |
| 799 | 10124.003.1-B_at | 7.77141001 | 5.984762853 |
| 800 | 3852.008.2-F_at | 5.25269037 | 3.555215368 |
| 801 | 4288.006.2-T_at | 4.41269608 | 6.475089289 |
| 802 | 8404.026.1-C_at | 7.87032712 | 5.309471428 |
| 803 | 23650.019.1-C_at | 4.78127834 | 3.449585316 |
| 804 | 7170.027.1-T_at | 10.1785633 | 10.86779555 |
| 805 | 54928.003.1-E_at | 7.95793621 | 6.353966846 |
| 806 | 2335.025.1-B_at | 6.59794162 | 8.83157397 |
| 807 | 3084.010.1-T_at | 4.64480819 | 3.365397857 |
| 808 | 57447.051.1-T_at | 7.94997082 | 5.870179931 |
| 809 | 80034.003.4-T_at | 4.8124569 | 3.414443991 |
| 810 | 2568.005.1-D_at | 5.60503766 | 3.638290306 |
| 811 | 8404.032.1-F_at | 7.82269285 | 5.541014824 |
| 812 | 2115.003.1-E_at | 4.60503701 | 3.463043796 |
| 813 | 57447.035.1-T_at | 6.58609653 | 4.690569876 |
| 814 | 8404.009.1-T_at | 8.30486375 | 5.75977584 |
| 815 | 8404.028.3-B_at | 6.39814918 | 4.353137247 |
| 816 | 6289.003.1-B_at | 8.85424542 | 5.981607568 |
| 817 | 7170.025.1-F_at | 7.37697122 | 8.410726942 |
| 818 | 8404.030.1-D_at | 4.68883661 | 3.480079758 |
| 819 | 8404.009.1-F_at | 6.4288173 | 4.305937183 |
| 820 | 2335.009.1-T_at | 5.3309114 | 8.084486221 |
| 821 | 22974.007.1-F_at | 5.33852227 | 7.851513061 |
| 822 | 3426.002.1-B_at | 5.18878725 | 3.666443854 |
| 823 | 4638.003.1-D_at | 4.80794498 | 3.519315999 |
| 824 | 4147.011.1-T_at | 5.5473121 | 3.770096298 |
| 825 | 6876.016.2-T_at | 6.73562706 | 4.929179325 |
| 826 | 23650.003.1-F_at | 5.36467738 | 3.8134759 |
| 827 | 4744.004.1-E_at | 5.98052533 | 4.025288625 |
| 828 | 64168.010.1-F_at | 4.47544044 | 3.464747266 |
| 829 | 9073.001.1-F_at | 6.32607617 | 3.970691137 |
| 830 | 5288.001.3-F_at | 5.80543381 | 4.395911298 |
| 831 | 3866.005.1-D_at | 4.69976421 | 3.498394825 |
| 832 | 8404.021.1-T_at | 7.61048125 | 5.126133895 |
| 833 | 25925.011.1-E_at | 5.22009218 | 3.770296785 |
| 834 | 23266.001.3-F_at | 6.97341376 | 4.950755879 |
| 835 | 9232.004.1-F_at | 4.54899231 | 6.788996757 |
| 836 | 4147.005.2-F_at | 6.46653951 | 4.116097107 |
| 837 | 2335.025.3-B_at | 4.1218962 | 6.635944112 |
| 838 | 4638.006.1-C_at | 4.60097436 | 3.386710346 |
| 839 | 147804.004.1-T | 8.74204077 | 9.383412702 |
| 840 | 81704.013.1-D_at | 5.74760963 | 4.078176314 |
| 841 | 54443.013.1-B_at | 3.78713573 | 5.832999901 |
| 842 | 1410.005.1-T_at | 7.99587494 | 5.02138884 |
| 843 | 25925.009.1-T_at | 5.84441997 | 4.119796362 |
| 844 | 3204.001.1-T_at | 6.21835333 | 4.25541633 |
| 845 | 29997.012.1-F_at | 9.16397087 | 7.980650261 |
| 846 | 2.005.1-C_at | 9.81288715 | 8.155872692 |
| 847 | 140885.011.1-F | 6.19333879 | 4.903420797 |
| 848 | 7153.002.3-F_at | 3.47065774 | 5.379571026 |
| 849 | 1063.002.1-F_at | 4.818547 | 6.814140949 |
| 850 | 10144.021.1-F_at | 5.41639448 | 3.918615816 |
| 851 | 8404.025.1-E_at | 7.03203124 | 4.624818473 |
| 852 | 6876.020.1-B_at | 6.533895 | 4.437030997 |
| 853 | 7170.006.1-C_at | 9.05537796 | 9.822975281 |
| 854 | 10051.016.1-T_at | 7.11146583 | 8.35678465 |
| 855 | 5288.001.2-D_at | 4.36619367 | 3.362822607 |
| 856 | 7018.029.1-T_at | 6.23394945 | 3.983824938 |
| 857 | 5627.002.1-B_at | 5.10823783 | 3.887587419 |
| 858 | 57447.037.1-T_at | 6.70751747 | 4.463904664 |
| 859 | 4147.005.2-D_at | 6.41967658 | 4.010663201 |
| 860 | 8404.023.1-T_at | 8.96871259 | 6.761468547 |
| 861 | 3872.006.1-D_at | 7.20926464 | 5.468717646 |
| 862 | 399687.001.1-C | 5.1094656 | 3.656879029 |
| 863 | 3815.002.4-D_at | 4.48207839 | 3.345874495 |
| 864 | 59.034.2-B_at | 7.86775534 | 5.305977855 |
| 865 | 8404.035.1-T_at | 7.35557119 | 4.961673356 |
| 866 | 8404.030.1-T_at | 9.22413584 | 7.338140147 |
| 867 | 54997.002.2-T_at | 4.91413205 | 3.541335298 |
| 868 | 57561.001.1-F_at | 7.63984954 | 5.681299176 |
| 869 | 8404.031.1-T_at | 8.83771374 | 6.734753847 |
| 870 | 2.025.1-E_at | 6.76479665 | 4.728179737 |
| 871 | 699.002.1-F_at | 4.23691585 | 6.351343745 |
| 872 | 57447.041.1-F_at | 8.01010166 | 5.655092904 |
| 873 | 9055.013.1-D_at | 3.74232362 | 5.955553435 |
| 874 | 8404.008.1-D_at | 7.31144196 | 4.840262527 |
| 875 | 7018.028.1-T_at | 6.15805126 | 3.968077116 |
| 876 | 2568.005.1-T_at | 5.80411431 | 3.692039293 |
| 877 | 10051.005.3-T_at | 7.06136791 | 8.335822705 |
| 878 | 2568.002.2-T_at | 5.39690112 | 3.699196299 |
| 879 | 4147.004.1-T_at | 6.45719145 | 4.078127629 |
| 880 | 2938.001.1-T_at | 5.28917706 | 3.569952501 |
| 881 | 1308.007.1-E_at | 4.33353721 | 3.32285855 |
| 882 | 2982.012.1-T_at | 6.69749373 | 4.397652902 |
| 883 | 8404.028.1-D_at | 9.17080043 | 6.681120058 |
| 884 | 7373.001.2-B_at | 5.50958781 | 3.91365763 |
| 885 | 2893.002.2-B_at | 4.99194607 | 3.464698996 |
| 886 | 116369.006.4-C | 7.33578706 | 5.780057699 |
| 887 | 6304.007.1-T_at | 6.03651208 | 4.53887378 |
| 888 | 2335.035.1-T_at | 3.84203808 | 6.550409853 |
| 889 | 4751.002.1-T_at | 3.37070549 | 5.029578851 |
| 890 | 64151.001.2-T_at | 4.47557646 | 6.324975406 |
| 891 | 29089.003.1-T_at | 4.48056575 | 6.605198239 |
| 892 | 59.031.1-B_at | 7.22996112 | 4.744191474 |
| 893 | 7018.025.1-T_at | 5.84703558 | 3.746460765 |
| 894 | 3860.008.1-T_at | 5.34250998 | 4.140007902 |
| 895 | 5858.003.3-F_at | 5.09683569 | 3.735471384 |
| 896 | 8404.009.1-C_at | 8.45510904 | 6.045801083 |
| 897 | 7169.022.1-T_at | 6.97482167 | 4.826590592 |
| 898 | 25925.006.1-T_at | 5.34961663 | 3.868058889 |
| 899 | 59.049.1-F_at | 6.6091616 | 5.230817807 |
| 900 | 5284.003.1-T_at | 5.4389606 | 3.820813601 |
| 901 | 2982.002.1-F_at | 6.20754503 | 4.114933269 |
| 902 | 2568.002.1-T_at | 5.18521978 | 3.672133283 |
| 903 | 301.004.1-B_at | 6.4786296 | 4.407193121 |
| 904 | 25925.011.1-F_at | 5.58763288 | 4.002507678 |
| 905 | 59.004.1-F_at | 5.74336584 | 4.280036618 |
| 906 | 6289.002.1-B_at | 8.87204796 | 6.038294234 |
| 907 | 244.003.1-C_at | 5.36729328 | 3.596389122 |
| 908 | 11065.008.1-C_at | 3.66496529 | 5.619449029 |
| 909 | 7091.006.1-T_at | 6.70324989 | 4.896846915 |
| 910 | 79608.009.1-F_at | 6.81856163 | 4.583013558 |
| 911 | 9413.002.1-T_at | 5.78003165 | 4.176180652 |
| 912 | 7431.064.1-C_at | 6.00790783 | 4.318847511 |
| 913 | 8404.029.1-E_at | 7.5152716 | 5.026824891 |
| 914 | 6876.020.1-T_at | 6.73708584 | 4.994785476 |
| 915 | 301.005.1-T_at | 7.12173249 | 4.879038375 |
| 916 | 9055.014.1-T_at | 5.9433395 | 8.161119674 |
| 917 | 4281.023.1-T_at | 5.06611225 | 3.689556134 |
| 918 | 3868.005.1-D_at | 5.81265413 | 4.356646518 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 919 | 1062.001.6-B_at | 4.61979335 | 5.902124565 |
| 920 | 5858.005.1-T_at | 6.62044043 | 5.019290814 |
| 921 | 51201.007.1-F_at | 5.89798751 | 4.556162061 |
| 922 | 4240.001.1-B_at | 7.04315913 | 5.225486532 |
| 923 | 8404.029.1-T_at | 7.19061905 | 4.823349131 |
| 924 | 9413.001.1-T_at | 5.85356534 | 4.184779715 |
| 925 | 9768.005.1-T_at | 4.56065688 | 6.668381892 |
| 926 | 11197.001.1-T_at | 5.497932 | 3.863349343 |
| 927 | 6285.002.1-T_at | 7.15759953 | 4.38354551 |
| 928 | 2335.006.2-F_at | 4.52057793 | 7.007712622 |
| 929 | 7169.001.1-C_at | 9.97986289 | 8.443197393 |
| 930 | 9493.004.1-T_at | 4.12782496 | 5.475321289 |
| 931 | 4601.014.1-T_at | 7.11289499 | 5.834825527 |
| 932 | 51203.002.2-F_at | 3.76957554 | 5.500135903 |
| 933 | 7018.022.1-F_at | 5.24694116 | 3.916461778 |
| 934 | 4288.009.1-F_at | 4.54685294 | 6.450101537 |
| 935 | 8321.004.1-D_at | 5.28227566 | 3.892211156 |
| 936 | 8564.004.1-E_at | 6.48035789 | 5.023116233 |
| 937 | 7169.022.1-C_at | 8.24544042 | 5.873824132 |
| 938 | 29127.013.1-T_at | 4.10561977 | 5.802203111 |
| 939 | 2.018.1-B_at | 7.31981124 | 5.353818042 |
| 940 | 2.005.1-D_at | 8.25561915 | 6.09796658 |
| 941 | 1058.004.2-T_at | 3.7975226 | 5.865920911 |
| 942 | 2232.014.1-C_at | 5.21644948 | 3.868088006 |
| 943 | 23650.005.1-E_at | 6.06219649 | 4.127697497 |
| 944 | 5621.002.2-T_at | 6.01313915 | 4.906824984 |
| 945 | 51201.005.1-B_at | 6.93913414 | 5.202799498 |
| 946 | 667.022.1-F_at | 8.42885166 | 6.36231857 |
| 947 | 54443.012.1-C_at | 3.50725399 | 5.586709148 |
| 948 | 25802.003.1-C_at | 7.43616073 | 5.067395951 |
| 949 | 3479.003.1-T_at | 6.77825963 | 4.651724222 |
| 950 | 94274.003.1-D_at | 5.91050731 | 3.846777655 |
| 951 | 84668.003.1-T_at | 5.22078827 | 3.927647308 |
| 952 | 22974.008.1-E_at | 4.27998201 | 6.244828978 |
| 953 | 55656.007.3-B_at | 5.26745658 | 6.648785128 |
| 954 | 29127.002.1-T_at | 4.18023368 | 5.884883109 |
| 955 | 4281.012.2-T_at | 5.18559903 | 3.709369654 |
| 956 | 2335.013.1-B_at | 4.24843254 | 6.768210889 |
| 957 | 79627.003.1-B_at | 5.80046587 | 4.283731062 |
| 958 | 2982.014.1-T_at | 6.70490207 | 4.400137878 |
| 959 | 2335.053.1-T_at | 5.80672371 | 8.072794315 |
| 960 | 667.001.1-F_at | 5.91836585 | 4.436185766 |
| 961 | 8404.030.1-B_at | 8.7803817 | 6.762729417 |
| 962 | 2335.025.1-C_at | 5.89016354 | 8.340545982 |
| 963 | 140885.010.3-D | 5.64716726 | 3.935175019 |
| 964 | 55366.001.2-F_at | 6.45584577 | 4.52968697 |
| 965 | 7169.015.1-D_at | 9.10850076 | 7.746283286 |
| 966 | 57447.002.1-B_at | 10.5154174 | 8.85406099 |
| 967 | 22974.008.1-T_at | 4.68631855 | 6.537183038 |
| 968 | 6876.011.1-C_at | 6.44837046 | 4.645016388 |
| 969 | 4281.008.2-D_at | 5.85946061 | 3.878305283 |
| 970 | 59.008.1-T_at | 8.48935505 | 6.63847471 |
| 971 | 23266.008.1-F_at | 7.18072955 | 5.133107519 |
| 972 | 2568.003.2-T_at | 5.85722739 | 4.051173411 |
| 973 | 5311.003.1-T_at | 5.37168206 | 4.077343368 |
| 974 | 6304.011.1-T_at | 5.92190291 | 4.37727733 |
| 975 | 3861.008.1-B_at | 7.42551236 | 5.399716053 |
| 976 | 7018.013.1-B_at | 5.26119189 | 3.69876029 |
| 977 | 8404.005.1-F_at | 8.58438422 | 6.423269422 |
| 978 | 7170.027.1-C_at | 9.03620668 | 9.824923692 |
| 979 | 8404.023.1-C_at | 6.96271536 | 4.627460556 |
| 980 | 7373.007.1-C_at | 5.21901652 | 3.512769797 |
| 981 | 1410.009.1-T_at | 8.07507455 | 5.204140322 |
| 982 | 79745.004.3-D_at | 5.57669121 | 4.147896702 |
| 983 | 24137.004.1-T_at | 3.54526583 | 5.143662611 |
| 984 | 6241.013.1-B_at | 5.32142819 | 7.577868116 |
| 985 | 1410.001.1-T_at | 8.89756795 | 5.783554496 |
| 986 | 4781.015.2-B_at | 7.82251501 | 5.588763483 |
| 987 | 72.002.1-T_at | 5.49901408 | 3.657567415 |
| 988 | 4833.004.1-T_at | 7.72478747 | 8.933008875 |
| 989 | 57447.024.1-D_at | 8.39121333 | 5.734774748 |
| 990 | 2982.013.2-T_at | 6.69829498 | 4.788664846 |
| 991 | 79971.012.1-T_at | 7.86816422 | 5.097596928 |
| 992 | 8404.028.3-C_at | 8.43509005 | 5.660339589 |
| 993 | 4638.011.1-E_at | 4.54149983 | 3.401814228 |
| 994 | 7169.004.1-C_at | 9.93319291 | 8.292756224 |
| 995 | 4288.004.1-F_at | 5.48379306 | 7.569481427 |
| 996 | 59.012.2-C_at | 7.35490878 | 6.158197444 |
| 997 | 301.008.1-B_at | 7.75881704 | 5.561554031 |
| 998 | 4281.012.1-T_at | 5.22990892 | 3.775893084 |
| 999 | 2335.016.1-F_at | 5.72062946 | 8.271881228 |
| 1000 | 259266.003.1-C | 3.74524657 | 5.64429601 |
| 1001 | 9055.020.1-T_at | 4.54642664 | 6.710996898 |
| 1002 | 7091.016.1-T_at | 6.32037409 | 4.628367394 |
| 1003 | 59.023.1-T_at | 6.98702578 | 5.652733648 |
| 1004 | 57162.010.1-B_at | 5.51558535 | 4.297033118 |
| 1005 | 4781.002.2-D_at | 4.69751141 | 3.532094277 |
| 1006 | 6122.037.1-T_at | 10.367148 | 9.581841169 |
| 1007 | 4240.015.1-B_at | 5.58448718 | 3.769441906 |
| 1008 | 59.034.1-T_at | 7.30028333 | 5.815069711 |
| 1009 | 8404.004.2-D_at | 6.59680571 | 4.480908858 |
| 1010 | 9413.001.2-T_at | 5.83173699 | 4.199417075 |
| 1011 | 2.005.1-F_at | 9.23135004 | 7.463118008 |
| 1012 | 6304.002.1-F_at | 6.22980998 | 4.691222262 |
| 1013 | 3852.005.1-C_at | 5.1815999 | 3.540371293 |
| 1014 | 7170.027.1-B_at | 8.61016621 | 9.330841255 |
| 1015 | 301.013.1-T_at | 7.9831001 | 5.822883877 |
| 1016 | 6304.012.1-F_at | 5.99863704 | 4.356895672 |
| 1017 | 57447.051.2-T_at | 7.96085286 | 6.017184644 |
| 1018 | 11065.005.1-C_at | 3.70869314 | 5.527276202 |
| 1019 | 6422.002.1-F_at | 5.79053376 | 4.58677324 |
| 1020 | 6241.013.1-F_at | 4.36486456 | 6.707728465 |
| 1021 | 2335.032.1-T_at | 6.09077284 | 8.189655849 |
| 1022 | 11065.005.2-T_at | 4.44502121 | 6.241724709 |
| 1023 | 2335.028.1-D_at | 4.37811935 | 7.181272915 |
| 1024 | 29997.016.1-F_at | 7.01231968 | 5.364391961 |
| 1025 | 7018.014.1-T_at | 5.84447021 | 3.853791495 |
| 1026 | 1410.011.1-E_at | 10.4572153 | 7.631013667 |
| 1027 | 7170.040.1-E_at | 9.04381331 | 9.788601589 |
| 1028 | 6289.002.2-F_at | 7.95331589 | 5.409835249 |
| 1029 | 7373.003.4-C_at | 5.37900799 | 3.668049298 |
| 1030 | 7170.041.1-E_at | 9.0780429 | 9.837001991 |
| 1031 | 128553.003.1-B | 4.33787983 | 3.383127715 |
| 1032 | 4094.002.1-D_at | 5.80489701 | 4.110942964 |
| 1033 | 7113.011.1-T_at | 5.03380702 | 3.77489186 |
| 1034 | 7170.002.1-C_at | 10.3310325 | 11.10058024 |
| 1035 | 8404.017.2-T_at | 7.65991671 | 5.307045406 |
| 1036 | 59.029.1-T_at | 6.00974416 | 4.740356024 |
| 1037 | 29089.001.1-T_at | 4.60079781 | 6.714422405 |
| 1038 | 358.012.1-T_at | 7.75384082 | 5.172139857 |
| 1039 | 9134.001.1-B_at | 3.63113188 | 5.472113919 |
| 1040 | 2335.013.1-C_at | 6.22416658 | 8.858188139 |
| 1041 | 1410.010.1-T_at | 8.00194091 | 5.107287395 |
| 1042 | 2207.003.4-F_at | 5.3147747 | 3.687201869 |
| 1043 | 59.042.1-T_at | 8.33740211 | 6.337284559 |
| 1044 | 6304.007.2-T_at | 6.10850875 | 4.532546697 |
| 1045 | 8404.031.1-B_at | 7.42216219 | 5.19861614 |
| 1046 | 6289.001.1-F_at | 8.9307375 | 6.034635624 |
| 1047 | 1410.006.1-T_at | 9.12745661 | 6.076865916 |
| 1048 | 80034.004.1-T_at | 4.30047326 | 3.355594342 |
| 1049 | 1410.008.1-T_at | 7.99198784 | 5.116495458 |
| 1050 | 57447.051.2-D_at | 6.09844409 | 4.536325155 |
| 1051 | 7170.016.3-B_at | 8.29403671 | 9.288724852 |
| 1052 | 4240.001.1-C_at | 9.00972003 | 7.16992054 |
| 1053 | 6288.001.1-T_at | 8.96603543 | 6.273903027 |
| 1054 | 7018.014.1-C_at | 5.99538964 | 3.822846066 |
| 1055 | 8404.020.1-T_at | 7.54635493 | 5.312082632 |
| 1056 | 6289.001.2-F_at | 8.8100063 | 5.866140365 |
| 1057 | 6876.011.1-F_at | 6.08933324 | 4.374504349 |
| 1058 | 8404.031.1-C_at | 6.08486742 | 4.373738904 |
| 1059 | 57447.010.1-F_at | 8.82775044 | 6.339583859 |
| 1060 | 1410.007.2-C_at | 8.33758962 | 5.131217413 |
| 1061 | 59.012.2-B_at | 6.35775616 | 4.443173526 |
| 1062 | 3459.005.1-T_at | 5.80207334 | 4.471777329 |
| 1063 | 301.017.1-C_at | 4.76677119 | 3.59309712 |
| 1064 | 83539.001.1-D_at | 5.41027098 | 3.741417748 |
| 1065 | 6288.004.1-F_at | 7.89445249 | 5.613330538 |
| 1066 | 4781.016.1-E_at | 6.59597542 | 4.602150459 |
| 1067 | 29997.012.1-E_at | 8.53873537 | 7.295932688 |
| 1068 | 57447.021.1-T_at | 6.81768585 | 5.034847695 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 1069 | 3426.002.1-C_at | 5.23704842 | 3.641068359 |
| 1070 | 53829.001.2-T_at | 5.15275541 | 3.943598064 |
| 1071 | 2115.001.2-B_at | 4.85542703 | 3.530125932 |
| 1072 | 10051.008.1-T_at | 4.4316929 | 5.920843577 |
| 1073 | 1033.002.1-T_at | 3.63139162 | 5.34811339 |
| 1074 | 2335.005.1-D_at | 3.91739921 | 6.295453643 |
| 1075 | 7113.009.1-T_at | 5.43609158 | 3.994720867 |
| 1076 | 3866.002.1-B_at | 9.19732873 | 6.293031612 |
| 1077 | 140885.014.1-D | 7.59348333 | 5.605094004 |
| 1078 | 7168.003.1-T_at | 5.64472419 | 4.457129076 |
| 1079 | 79608.001.1-T_at | 5.30303748 | 3.935571553 |
| 1080 | 79608.008.2-F_at | 6.74835004 | 4.557558664 |
| 1081 | 1410.001.1-B_at | 6.75241131 | 4.22870793 |
| 1082 | 7113.010.1-T_at | 5.85442041 | 4.280294556 |
| 1083 | 4781.014.2-B_at | 7.86598754 | 5.705821081 |
| 1084 | 2335.016.1-E_at | 4.77399968 | 7.375547826 |
| 1085 | 11065.003.1-T_at | 4.37783851 | 6.306175214 |
| 1086 | 3872.006.1-T_at | 7.85482665 | 6.124969921 |
| 1087 | 3084.005.1-F_at | 4.51722715 | 3.439893991 |
| 1088 | 6285.003.1-T_at | 6.40683627 | 4.093334173 |
| 1089 | 6876.016.2-F_at | 6.53765126 | 5.03041211 |
| 1090 | 8404.004.1-T_at | 7.29426573 | 5.24109976 |
| 1091 | 54829.001.1-F_at | 4.55095384 | 7.099570517 |
| 1092 | 8404.001.1-T_at | 8.00106035 | 5.742296291 |
| 1093 | 9055.011.1-E_at | 5.20354473 | 7.152510552 |
| 1094 | 6289.003.2-F_at | 7.95780418 | 5.56331609 |
| 1095 | 22974.007.1-T_at | 4.55846251 | 6.477981817 |
| 1096 | 59.023.2-T_at | 6.91216911 | 5.63439702 |
| 1097 | 7169.015.1-T_at | 10.1958997 | 8.61185317 |
| 1098 | 6289.002.1-F_at | 7.95223459 | 5.506509999 |
| 1099 | 4288.008.1-B_at | 4.4490631 | 6.277435237 |
| 1100 | 4781.007.1-B_at | 6.06074416 | 4.463013886 |
| 1101 | 6876.023.1-T_at | 5.30318153 | 3.837265148 |
| 1102 | 9055.017.1-F_at | 4.93875917 | 6.675610123 |
| 1103 | 7170.018.2-D_at | 8.97464252 | 9.731315695 |
| 1104 | 4781.014.2-D_at | 6.62173963 | 4.59382551 |
| 1105 | 7170.025.1-T_at | 10.1528395 | 10.84778358 |
| 1106 | 7018.025.1-B_at | 5.85576515 | 3.729848132 |
| 1107 | 10253.003.1-T_at | 5.21328569 | 3.796731651 |
| 1108 | 57447.039.1-D_at | 6.20353459 | 4.650979725 |
| 1109 | 59.022.1-T_at | 5.01607936 | 3.66486644 |
| 1110 | 2982.015.1-F_at | 6.52910873 | 4.398315488 |
| 1111 | 10124.004.2-F_at | 5.65171957 | 4.395524581 |
| 1112 | 6289.001.1-B_at | 8.84060005 | 6.026432745 |
| 1113 | 7091.005.1-F_at | 6.22924785 | 4.644117845 |
| 1114 | 501.006.1-B_at | 5.49535249 | 3.832258169 |
| 1115 | 1410.001.1-C_at | 8.37978611 | 5.283357954 |
| 1116 | 57447.021.1-C_at | 6.64989625 | 4.516711936 |
| 1117 | 244.012.1-B_at | 4.57455863 | 3.452384416 |
| 1118 | 7018.026.1-F_at | 7.02591455 | 4.884695118 |
| 1119 | 3872.018.1-T_at | 5.9287371 | 4.536856978 |
| 1120 | 10144.017.3-T_at | 5.24556385 | 3.811639459 |
| 1121 | 11197.001.1-F_at | 5.1313114 | 3.685307479 |
| 1122 | 29127.007.1-B_at | 3.92146605 | 5.671967353 |
| 1123 | 10010.004.1-F_at | 6.85011832 | 5.471009514 |
| 1124 | 81704.013.1-C_at | 7.00929626 | 5.228254202 |
| 1125 | 4781.006.2-B_at | 7.95071123 | 5.849829769 |
| 1126 | 7373.003.1-F_at | 4.96962295 | 3.466223281 |
| 1127 | 8404.009.1-D_at | 7.25304506 | 5.54375843 |
| 1128 | 23092.004.1-T_at | 5.63034915 | 4.135821153 |
| 1129 | 2335.002.1-F_at | 4.95716635 | 7.470035933 |
| 1130 | 8404.031.1-F_at | 8.49473661 | 6.266230481 |
| 1131 | 6304.006.2-T_at | 6.19437915 | 4.664814203 |
| 1132 | 1410.008.1-E_at | 8.35323964 | 5.23093246 |
| 1133 | 9055.019.1-F_at | 5.08438207 | 6.749313988 |
| 1134 | 1398.001.1-D_at | 6.62952 | 5.474846977 |
| 1135 | 57447.051.1-E_at | 7.64975415 | 6.754949154 |
| 1136 | 339965.001.2-B | 6.09281787 | 4.427445717 |
| 1137 | 7113.001.1-C_at | 6.49441996 | 4.364555738 |
| 1138 | 4240.009.1-D_at | 6.92405991 | 4.992040248 |
| 1139 | 7153.002.4-B_at | 3.9192437 | 5.943978275 |
| 1140 | 7169.004.1-D_at | 10.5243791 | 9.455104283 |
| 1141 | 1410.001.1-D_at | 10.4537888 | 7.669238725 |
| 1142 | 59.015.2-B_at | 4.65235051 | 3.439217599 |
| 1143 | 4833.010.1-T_at | 7.67064462 | 8.499214874 |
| 1144 | 7169.022.1-B_at | 8.88810535 | 7.392553599 |
| 1145 | 11065.005.1-T_at | 4.40063594 | 6.264196367 |
| 1146 | 7170.018.2-T_at | 9.1005517 | 9.929531193 |
| 1147 | 79971.013.2-F_at | 7.81954831 | 5.197831093 |
| 1148 | 152015.005.2-F | 5.50228015 | 3.631181096 |
| 1149 | 4288.005.1-D_at | 3.58855622 | 5.41357555 |
| 1150 | 8404.002.1-T_at | 7.82572709 | 5.654573319 |
| 1151 | 6441.004.1-E_at | 7.06431123 | 5.1604289 |
| 1152 | 6122.046.1-B_at | 10.4919703 | 9.7185156 |
| 1153 | 115908.002.1-T | 3.8854167 | 5.716319219 |
| 1154 | 9481.001.1-F_at | 4.56745873 | 3.48672793 |
| 1155 | 8404.008.1-T_at | 7.67594705 | 5.231619593 |
| 1156 | 1410.007.1-D_at | 8.38485465 | 5.254780902 |
| 1157 | 8404.030.1-C_at | 8.36615125 | 6.003710685 |
| 1158 | 57447.039.1-T_at | 6.16284998 | 4.598519131 |
| 1159 | 4147.006.1-E_at | 6.5996408 | 4.306043014 |
| 1160 | 2335.024.2-F_at | 4.14778676 | 6.724104869 |
| 1161 | 891.007.1-T_at | 4.37836908 | 6.277454073 |
| 1162 | 2335.002.1-T_at | 3.69677239 | 5.842235509 |
| 1163 | 8404.017.1-T_at | 7.62129329 | 5.344108953 |
| 1164 | 57451.004.1-B_at | 4.98513349 | 3.645263861 |
| 1165 | 8404.001.1-F_at | 7.80115205 | 5.644594488 |
| 1166 | 8626.006.2-B_at | 4.99013916 | 3.634011318 |
| 1167 | 2335.025.1-T_at | 5.20342277 | 7.312790967 |
| 1168 | 6286.001.1-T_at | 4.37066146 | 7.627611404 |
| 1169 | 10580.012.1-C_at | 5.72236701 | 4.332788093 |
| 1170 | 23321.014.1-T_at | 4.77278608 | 3.653834143 |
| 1171 | 2824.001.2-B_at | 6.86512458 | 5.132614728 |
| 1172 | 29127.022.1-T_at | 4.01626993 | 5.699644246 |
| 1173 | 6289.003.1-F_at | 8.04884622 | 5.558117392 |
| 1174 | 7170.005.2-B_at | 7.21902208 | 8.187290968 |
| 1175 | 54443.011.1-F_at | 3.90847075 | 5.715840566 |
| 1176 | 29127.019.1-T_at | 4.45515346 | 6.238930793 |
| 1177 | 6288.004.1-T_at | 8.9163962 | 6.203405757 |
| 1178 | 29997.008.1-C_at | 8.54806753 | 7.280192975 |
| 1179 | 57447.039.1-B_at | 8.64953038 | 6.241324868 |
| 1180 | 3872.001.1-T_at | 5.78319757 | 3.824950968 |
| 1181 | 57561.002.1-T_at | 7.04642246 | 5.352091902 |
| 1182 | 57451.002.3-B_at | 4.71308984 | 3.460721722 |
| 1183 | 5213.024.1-B_at | 5.69666791 | 4.585191172 |
| 1184 | 2.005.1-T_at | 9.54067496 | 7.938923018 |
| 1185 | 11065.004.1-C_at | 3.58696224 | 5.482200678 |
| 1186 | 1410.006.1-C_at | 8.38947588 | 5.204282844 |
| 1187 | 6289.006.1-T_at | 6.36227497 | 4.331717996 |
| 1188 | 55366.001.1-T_at | 5.81899126 | 4.357905799 |
| 1189 | 23284.007.1-F_at | 5.22440061 | 3.837622352 |
| 1190 | 79971.009.1-T_at | 7.81567707 | 5.261440799 |
| 1191 | 6288.004.1-E_at | 6.55709998 | 4.810646704 |
| 1192 | 11065.004.1-T_at | 4.59241158 | 6.359329521 |
| 1193 | 51203.009.1-T_at | 4.74450869 | 6.362980434 |
| 1194 | 1410.010.1-E_at | 8.32156036 | 5.167245484 |
| 1195 | 57447.030.1-D_at | 7.16110591 | 5.926932144 |
| 1196 | 1308.002.1-T_at | 4.50117394 | 3.487272397 |
| 1197 | 4288.007.1-C_at | 4.97101233 | 7.189192841 |
| 1198 | 244.011.1-T_at | 5.29003948 | 3.948200539 |
| 1199 | 94274.003.1-B_at | 4.42148503 | 3.46060704 |
| 1200 | 3178.003.1-E_at | 6.30358046 | 5.181900836 |
| 1201 | 7153.002.4-T_at | 4.03542364 | 6.008249752 |
| 1202 | 9055.012.1-D_at | 4.02757905 | 6.120371884 |
| 1203 | 9232.001.1-E_at | 5.22181281 | 7.208579638 |
| 1204 | 79068.011.2-B_at | 6.64417255 | 5.308326918 |
| 1205 | 120.005.2-F_at | 9.06074824 | 6.73592483 |
| 1206 | 7534.001.1-C_at | 8.71480548 | 9.492140995 |
| 1207 | 120.005.2-T_at | 8.73626834 | 6.165418999 |
| 1208 | 7373.003.3-C_at | 4.85399243 | 3.462673564 |
| 1209 | 57447.004.2-D_at | 6.16627621 | 4.604091159 |
| 1210 | 2568.005.1-F_at | 4.73444224 | 3.560755491 |
| 1211 | 1308.001.1-E_at | 4.41347272 | 3.418435324 |
| 1212 | 6876.020.1-F_at | 6.2728158 | 4.761356719 |
| 1213 | 79971.014.1-D_at | 6.31129325 | 4.294251993 |
| 1214 | 5621.008.1-D_at | 5.98900704 | 4.179299085 |
| 1215 | 55732.003.2-T_at | 3.81867845 | 5.173615902 |
| 1216 | 221120.006.1-D | 8.08525795 | 7.079961293 |
| 1217 | 23266.008.1-T_at | 6.70366212 | 4.807135334 |
| 1218 | 2335.045.1-F_at | 4.39135516 | 6.494344728 |

TABLE 5-continued

Table 5. Average profiles of the preferred 1,228 signature probe set on the 24 benign and 70 malignant tissues of the training set.

| NO | Probeset_Id | benign profile | malignant profile |
|---|---|---|---|
| 1219 | 7170.007.1-F_at | 7.64167879 | 8.466704716 |
| 1220 | 10461.002.1-B_at | 4.77990896 | 3.622574749 |
| 1221 | 59.031.2-F_at | 5.912075 | 4.730239133 |
| 1222 | 9055.010.1-T_at | 4.95064392 | 6.677393383 |
| 1223 | 58499.005.2-F_at | 5.8908337 | 4.132220814 |
| 1224 | 54443.006.2-F_at | 3.53549616 | 5.526168717 |
| 1225 | 59.016.1-B_at | 5.96979167 | 4.589590519 |
| 1226 | 4288.004.1-C_at | 4.97220803 | 6.791619005 |
| 1227 | 7170.014.1-C_at | 10.3731633 | 11.0837507 |
| 1228 | 7170.007.1-D_at | 10.3462783 | 11.09055128 |

EXAMPLE III

Molecular Prediction for Breast Cancer Diagnosis: Validation Set

A validation set was carried-out that included overall 71 samples. Of these, 21 and 50 were benign lesions and breast cancer respectively. Using this dataset, the inventors assessed the performances of the 1228 signature probes to predict for breast cancer as opposed to benign lesions. Overall 68 out of 71 samples were accurately classified (96%). Sensitivity and specificity of the tests were 96% (95% CI: 90.5-100) and 95% (95% CI: 86.1-100). The correlation of each specimen with the malignant and benign profile is reported in FIG. 6. Of the three misclassified specimen, one corresponded to a benign tumor (inflammatory granulomatosis) classified as malignant, and two were malignant tumors classified as benign by molecular predictor.

The inventors then evaluated the add-value of molecular predictor to cytological exam, and to a model that included classification of American College of Radiology (ACR) and age. Cytological exam failed to provide a definitive diagnosis in 5 out of 71 patients. Four out of these 5 patients were accurately classified by the molecular predictor. The proportion of explained variation (PEV) by Clinical model (age and ACR) was 75%+−8%, while the PEV by molecular predictor was 81% (+/−10%). When clinical model and molecular predictor were combined, the PEV was 87% (+/−7%), suggesting that molecular predictor presented an add-value of 12% (+/−7%) to the clinical model.

Using the top 50 polynucleotide probe sets: 1 out of 21 samples from patients with benign status were misclassified and 8 out of 50 samples from patients with malignant status.

Using the top 100 polynucleotide probe sets: 1 out of 21 samples from patients with benign status were misclassified and 7 out of 50 samples from patients with malignant status.

Using the top 150 polynucleotide probe sets: 1 out of 21 samples from patients with benign status were misclassified and 10 out of 50 samples from patients with malignant status.

Using the top 200 polynucleotide probe sets: 1 out of 21 samples from patients with benign status were misclassified and 7 out of 50 samples from patients with malignant status.

These data demonstrate that top probe set, even if some misclassifications occur, gives a good prognosis for a breast tumor.

Moreover, the use of the 1228, or 1640, polynucleotide probe sets according to the invention allows, without ambiguity, and misclassification, to determine if a breast tumor is benign or malignant.

Discussion

In the present study, the inventors have reported the exonic portrait of breast malignancy. The analysis of differential exonic events between malignant and benign lesions provides a complete picture of genomic anomalies associated with breast malignancy. The present study reveals a high level of genomic dysregulation between malignant and benign breast lesions. The inventors found out that 56652 out of 703680 evidenced probes (8%) were different among the two conditions. When the analysis focused on gene expression level (geo mean of probe sets), 3733 out of 20649 genes (7%) were differentially expressed between malignant and benign lesions. Analysis of gene expression levels revealed overexpression of candidate genes for further investigations. Pituitary Tumor Transforming 1 (PTTG1) has been previously reported to be overexpressed in pituitary tumors, thyroid cancer, colon cancer and glioma and to mediate malignant transformation (Vlotides G, Eigler T, Melmed S. Pituitary tumor-transforming gene: physiology and implications for tumorigenesis. Endocr Rev. 2007 April; 28(2):165-86). Neuroepithelial cell transforming gene 1 (NET1) is a guanine exchange factor that has been reported to mediate oncogenic transformation through activation of RhoA (Chan A M, Takai S, Yamada K, Miki T. Isolation of a novel oncogene, NET1, from neuroepithelioma cells by expression cDNA cloning. Oncogene. 1996 Mar. 21; 12(6):1259-66). Pathway analysis revealed that genes involved in spliceosome assemble were enriched in the malignant condition. Spliceosome mediates alternative splicing, a phenomenon involved in oncogenesis (Lønning P E, Knappskog S, Staalesen V, Chrisanthar R, Lillehaug J R. Breast cancer prognostication and prediction in the postgenomic era. Ann Oncol. 2007 August; 18(8):1293-306; Pajares M J, Ezponda T, Catena R, Calvo A, Pio R, Montuenga L M. Alternative splicing: an emerging topic in molecular and clinical oncology. Lancet Oncol. 2007 April; 8(4):349-57). Present study suggests that alternative splicing could significantly contribute to the molecular profile of breast cancer. Based on this consideration, the inventors further evaluated to what extent analyses at exonic level could provide additional information to the ones provided by analyses at gene expression level.

The inventors identified that 2675 exon-probes that did not belong to genes identified as differentially expressed, actually presented a significantly higher intensity in breast cancer. A high proportion of these 2675 exon-probes presented a significantly increased splice index in breast cancer as compared to benign tumors. These exon-probes were considered to present a higher difference of intensity between cancer and benign lesions, as compared to the one of their relative genes. Several of these exons are located within genes linked to cancer biology (casein kinase 1, delta (Gao Z H, Seeling J M, Hill V, Yochum A, Virshup D M. Casein kinase I phosphorylates and destabilizes the beta-catenin degradation complex. Proc Natl Acad Sci USA. 2002 Feb. 5; 99(3):1182-), retinoblastoma binding protein 9 (Woitach J T, Zhang M, Niu C H, Thorgeirsson S S. A retinoblastoma-binding protein that affects cell-cycle control and confers transforming ability.

Nat Genet. 1998 August; 19(4):371-4) and ERB2 interacting protein (Jaulin-Bastard F, Arsanto J P, Le Bivic A, Navarro C, Vély F, Saito H, Marchetto S, Hatzfeld M, Santoni M J, Birnbaum D, Borg J P. Interaction between Erbin and a Catenin related protein in epithelial cells. J Biol Chem. 2002 Jan. 25; 277(4):2869-75)). These data point out the limits of analyses at gene expression level to define the transcriptional profile of diseases, and suggest that analysis at exon level could capture biological information that is missed by analysis at gene expression level.

Based on the finding that breast cancer presents a widely different exonic profile as compared to benign tumors, the inventors evaluated whether this technology could be used for breast cancer diagnosis. Pathologic exam of tumor biopsy is the gold standard for cancer diagnosis. Nevertheless, such approach presents several limitations including the need for invasive procedures and, in some tumor types, misdiagnosis. In the present study, the inventors have shown that a large scale molecular analysis based on fine needle aspiration could allow breast cancer diagnosis. This finding opens new ways in the field of cancer diagnosis. Applied to breast cancer, it could allow a more effective post-screening pattern of care by increasing the metric performances of fine needle aspiration. Although biopsy is the current gold standard for breast cancer diagnosis, it is associated with both morbidity and treatment delays (Meunier M, Clough K. Fine needle aspiration cytology versus percutaneous biopsy of nonpalpable breast lesions. Eur J Radiol. 2002 April; 42(1):10-6). Fine needle aspiration is a safer and easier approach but is associated with a high rate of false negative results. In the present study, molecular diagnosis by a 1228-probe signature using FNA samples was associated with 100% accuracy in a training set and 96% accuracy in a validation set. Interestingly, molecular classifier provided accurate diagnosis in 4 out of 5 samples for which the cytological exam was not conclusive. Altogether, these data suggested that the 1228-probe signature could be a complementary tool to cytological exam for the breast cancer diagnosis. This tool could allow avoiding biopsies and unnecessary surgery in patients with benign lesions of the breast. At the opposite, for malignant lesions, this approach could speed-up the diagnosis and could allow decreasing time to surgery. The development of molecular assays for cancer diagnosis could be of special interest in other tumor types. As illustration, the benign nature of thyroid nodules is often difficult to be determined preoperatively, leading to unnecessary surgeries (Poller D N, Stelow E B, Yiangou C. Thyroid FNAC cytology: can we do it better? Cytopathology. 2008 February; 19(1):4-10). A molecular assay could dramatically decrease the need for surgery in this setting.

Overall, the present study reports the full description of exons differentially expressed between breast malignant and benign tumors. These data allowed the identification of candidate genes (PTTG1, NET1) for further functional validation in breast cancer. In addition it suggests that alternative splicing significantly contributes the molecular profile of breast cancer, leading to the identification of exons with a significantly higher splice index in cancer, but located within unchanged gene.

Finally, the splice array technology allowed the development of an exon signature for breast cancer diagnosis.

Lengthy table referenced here

US08299233-20121030-T00001

Please refer to the end of the specification for access instructions.

Lengthy table referenced here

US08299233-20121030-T00002

Please refer to the end of the specification for access instructions.

LENGTHY TABLES

The patent contains a lengthy table section. A copy of the table is available in electronic form from the USPTO web site (http://seqdata.uspto.gov/?pageRequest=docDetail&DocID=US08299233B2). An electronic copy of the table will also be available from the USPTO upon request and payment of the fee set forth in 37 CFR 1.19(b)(3).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08299233B2). An electronic copy of the "Sequence Listing" will also be available from the USPTO upon request and payment of the fee set forth in 37 CFR 1.19(b)(3).

The invention claimed is:

1. A combination of 50 polynucleotide probe sets,
said 50 polynucleotide probe sets comprising:
probe set #1 consisting of the nucleic acids consisting of SEQ ID NO: 333, 335 and 334;
probe set #2 consisting of the nucleic acids consisting of SEQ ID NO: 364, 365 and 366;
probe set #3 consisting of the nucleic acids consisting of SEQ ID NO: 364, 366 and 365;
probe set #4 consisting of the nucleic acids consisting of SEQ ID NO: 312, 348 and 313;
probe set #5 consisting of the nucleic acids consisting of SEQ ID NO: 312, 314 and 313;
probe set #6 consisting of the nucleic acids consisting of SEQ ID NO: 171, 172 and 173;
probe set #7 consisting of the nucleic acids consisting of SEQ ID NO: 315, 336 and 331;
probe set #8 consisting of the nucleic acids consisting of SEQ ID NO: 1198, 1199 and 1200;
probe set #9 consisting of the nucleic acids consisting of SEQ ID NO: 315, 317 and 316;
probe set #10 consisting of the nucleic acids consisting of SEQ ID NO: 1522, 1523 and 1524;
probe set #11 consisting of the nucleic acids consisting of SEQ ID NO: 339, 341 and 340;
probe set #12 consisting of the nucleic acids consisting of SEQ ID NO: 353, 361 and 360;
probe set #13 consisting of the nucleic acids consisting of SEQ ID NO: 1185, 1186 and 1194;
probe set #14 consisting of the nucleic acids consisting of SEQ ID NO: 315, 370 and 316;
probe set #15 consisting of the nucleic acids consisting of SEQ ID NO: 324, 326 and 325;
probe set #16 consisting of the nucleic acids consisting of SEQ ID NO: 1165 and 1166;
probe set #17 consisting of the nucleic acid consisting of SEQ ID NO: 177;
probe set #18 consisting of the nucleic acids consisting of SEQ ID NO: 1551, 1552 and 1553;
probe set #19 consisting of the nucleic acids consisting of SEQ ID NO: 315, 316 and 370;
probe set #20 consisting of the nucleic acids consisting of SEQ ID NO: 1185, 1186 and 1194;
probe set #21 consisting of the nucleic acids consisting of SEQ ID NO: 1523, 1524 and 1557;
probe set #22 consisting of the nucleic acid consisting of SEQ ID NO: 1158;
probe set #23 consisting of the nucleic acids consisting of SEQ ID NO: 345, 347 and 346;
probe set #24 consisting of the nucleic acids consisting of SEQ ID NO: 367, 369 and 368;
probe set #25 consisting of the nucleic acids consisting of SEQ ID NO: 315, 331 and 330;
probe set #26 consisting of the nucleic acids consisting of SEQ ID NO: 327, 329 and 328;
probe set #27 consisting of the nucleic acid consisting of SEQ ID NO: 1203;
probe set #28 consisting of the nucleic acids consisting of SEQ ID NO: 1262, 1263 and 1264;
probe set #29 consisting of the nucleic acids consisting of SEQ ID NO: 1534, 1535 and 1536;
probe set #30 consisting of the nucleic acids consisting of SEQ ID NO: 2179, 2180 and 2181;
probe set #31 consisting of the nucleic acids consisting of SEQ ID NO: 1159, 1160 and 1161;
probe set #32 consisting of the nucleic acids consisting of SEQ ID NO: 327, 329 and 328;
probe set #33 consisting of the nucleic acids consisting of SEQ ID NO: 157, 158 and 159;
probe set #34 consisting of the nucleic acids consisting of SEQ ID NO: 1267, 1268 and 1269;
probe set #35 consisting of the nucleic acids consisting of SEQ ID NO: 167, 168 and 169;
probe set #36 consisting of the nucleic acids consisting of SEQ ID NO: 167, 168 and 177;
probe set #37 consisting of the nucleic acids consisting of SEQ ID NO: 1167, 1168 and 1169;
probe set #38 consisting of the nucleic acids consisting of SEQ ID NO: 1544, 1545 and 1546;
probe set #39 consisting of the nucleic acids consisting of SEQ ID NO: 969, 972 and 981;
probe set #40 consisting of the nucleic acids consisting of SEQ ID NO: 1162, 1170 and 1171;
probe set #41 consisting of the nucleic acids consisting of SEQ ID NO: 790, 791 and 792;
probe set #42 consisting of the nucleic acids consisting of SEQ ID NO: 368, 374 and 375;
probe set #43 consisting of the nucleic acids consisting of SEQ ID NO: 1551, 1552 and 1553;
probe set #44 consisting of the nucleic acids consisting of SEQ ID NO: 1554, 1555 and 1556;
probe set #45 consisting of the nucleic acids consisting of SEQ ID NO: 2026, 2027 and 2028;
probe set #46 consisting of the nucleic acids consisting of SEQ ID NO: 1081, 1082 and 1083;
probe set #47 consisting of the nucleic acids consisting of SEQ ID NO: 1129, 1140 and 1141;
probe set #48 consisting of the nucleic acids consisting of SEQ ID NO: 1519, 1520 and 1521;
probe set #49 consisting of the nucleic acids consisting of SEQ ID NO: 136, 137 and 138; and
probe set #50 consisting of the nucleic acids consisting of SEQ ID NO: 793, 794 and 795.

2. The combination according to claim 1, comprising 100 polynucleotide probe sets,
said 100 polynucleotide probe sets comprising probe set #1 to probe set #50, and
probe set #51 consisting of the nucleic acids consisting of SEQ ID NO: 1075; 1076 and 1077;
probe set #52 consisting of the nucleic acids consisting of SEQ ID NO: 369 and 376;
probe set #53 consisting of the nucleic acids consisting of SEQ ID NO: 1509; 1510 and 1511;
probe set #54 consisting of the nucleic acids consisting of SEQ ID NO: 1528 and 1529;
probe set #55 consisting of the nucleic acids consisting of SEQ ID NO: 2176; 2177 and 2178;
probe set #56 consisting of the nucleic acids consisting of SEQ ID NO: 2023; 2024 and 2025;
probe set #57 consisting of the nucleic acids consisting of SEQ ID NO: 1162; 1180 and 1181;
probe set #58 consisting of the nucleic acids consisting of SEQ ID NO: 367 and 378;
probe set #59 consisting of the nucleic acids consisting of SEQ ID NO: 971;
probe set #60 consisting of the nucleic acids consisting of SEQ ID NO: 788 and 789;
probe set #61 consisting of the nucleic acids consisting of SEQ ID NO: 349; 361 and 350;
probe set #62 consisting of the nucleic acids consisting of SEQ ID NO: 1519; 1520 and 1521;

probe set #63 consisting of the nucleic acids consisting of SEQ ID NO: 555; 556 and 557;
probe set #64 consisting of the nucleic acids consisting of SEQ ID NO: 154; 155 and 156;
probe set #65 consisting of the nucleic acids consisting of SEQ ID NO: 317; 338 and 337;
probe set #66 consisting of the nucleic acids consisting of SEQ ID NO: 1201; 1202 and 1203;
probe set #67 consisting of the nucleic acids consisting of SEQ ID NO: 1187; 1188 and 1189;
probe set #68 consisting of the nucleic acids consisting of SEQ ID NO: 1129; 1130 and 1131;
probe set #69 consisting of the nucleic acids consisting of SEQ ID NO: 821; 822 and 823;
probe set #70 consisting of the nucleic acids consisting of SEQ ID NO: 558; 566 and 567;
probe set #71 consisting of the nucleic acids consisting of SEQ ID NO: 800; 801 and 802;
probe set #72 consisting of the nucleic acids consisting of SEQ ID NO: 2762; 2763 and 2764;
probe set #73 consisting of the nucleic acids consisting of SEQ ID NO: 1190; 1191 and 1192;
probe set #74 consisting of the nucleic acids consisting of SEQ ID NO: 1103; 1104 and 1105;
probe set #75 consisting of the nucleic acids consisting of SEQ ID NO: 2860; 2861 and 2862;
probe set #76 consisting of the nucleic acids consisting of SEQ ID NO: 1524; 1561 and 1562;
probe set #77 consisting of the nucleic acids consisting of SEQ ID NO: 1195 and 1196;
probe set #78 consisting of the nucleic acids consisting of SEQ ID NO: 315; 331; 330;
probe set #79 consisting of the nucleic acids consisting of SEQ ID NO: 120;
probe set #80 consisting of the nucleic acids consisting of SEQ ID NO: 821; 822 and 823;
probe set #81 consisting of the nucleic acids consisting of SEQ ID NO: 1162; 1163 and 1164;
probe set #82 consisting of the nucleic acids consisting of SEQ ID NO: 379; 380 and 381;
probe set #83 consisting of the nucleic acids consisting of SEQ ID NO: 1519; 1520 and 1521;
probe set #84 consisting of the nucleic acids consisting of SEQ ID NO: 354; 356 and 355;
probe set #85 consisting of the nucleic acids consisting of SEQ ID NO: 1087; 1088 and 1089;
probe set #86 consisting of the nucleic acids consisting of SEQ ID NO: 332;
probe set #87 consisting of the nucleic acids consisting of SEQ ID NO: 328; 371 and 363;
probe set #88 consisting of the nucleic acids consisting of SEQ ID NO: 1123; 1124 and 1125;
probe set #89 consisting of the nucleic acids consisting of SEQ ID NO: 2173; 2174 and 2175;
probe set #90 consisting of the nucleic acids consisting of SEQ ID NO: 1193; 1194 and 1207;
probe set #91 consisting of the nucleic acids consisting of SEQ ID NO: 1682; 1683 and 1684;
probe set #92 consisting of the nucleic acids consisting of SEQ ID NO: 1776; 1777 and 1778;
probe set #93 consisting of the nucleic acids consisting of SEQ ID NO: 1163; 1164 and 1172;
probe set #94 consisting of the nucleic acids consisting of SEQ ID NO: 1114; 1115 and 1116;
probe set #95 consisting of the nucleic acids consisting of SEQ ID NO: 2883; 2884 and 2885;
probe set #96 consisting of the nucleic acids consisting of SEQ ID NO: 1187; 1188 and 1189;
probe set #97 consisting of the nucleic acids consisting of SEQ ID NO: 174; 175 and 176;
probe set #98 consisting of the nucleic acids consisting of SEQ ID NO: 560; 561 and 562;
probe set #99 consisting of the nucleic acids consisting of SEQ ID NO: 1056; 1057 and 1058; and
probe set #100 consisting of the nucleic acids consisting of SEQ ID NO: 351; 353 and 352.

3. The combination according to claim 2, comprising 150 polynucleotide probe sets, said 150 polynucleotide probe sets comprising probe set #1 to probe set #100, and
probe set #101 consisting of the nucleic acids consisting of SEQ ID NO: 1315; 2599 and 2600;
probe set #102 consisting of the nucleic acids consisting of SEQ ID NO: 1690; 1691 and 1692;
probe set #103 consisting of the nucleic acids consisting of SEQ ID NO: 1199;
probe set #104 consisting of the nucleic acids consisting of SEQ ID NO: 788; 796 and 797;
probe set #105 consisting of the nucleic acids consisting of SEQ ID NO: 1057; 1058 and 1080;
probe set #106 consisting of the nucleic acids consisting of SEQ ID NO: 1469; 1470 and 1471;
probe set #107 consisting of the nucleic acids consisting of SEQ ID NO: 798; 799 and 801;
probe set #108 consisting of the nucleic acids consisting of SEQ ID NO: 1788; 1789 and 1790;
probe set #109 consisting of the nucleic acids consisting of SEQ ID NO: 1550;
probe set #110 consisting of the nucleic acids consisting of SEQ ID NO: 806; 807 and 808;
probe set #111 consisting of the nucleic acids consisting of SEQ ID NO: 1061; 1062 and 1063;
probe set #112 consisting of the nucleic acids consisting of SEQ ID NO: 788; 796 and 797;
probe set #113 consisting of the nucleic acids consisting of SEQ ID NO: 2576; 2577 and 2578;
probe set #114 consisting of the nucleic acids consisting of SEQ ID NO: 1580; 1581 and 1582;
probe set #115 consisting of the nucleic acids consisting of SEQ ID NO: 968; 969 and 970;
probe set #116 consisting of the nucleic acids consisting of SEQ ID NO: 1469; 1470 and 1471;
probe set #117 consisting of the nucleic acids consisting of SEQ ID NO: 1064; 1065 and 1066;
probe set #118 consisting of the nucleic acids consisting of SEQ ID NO: 1558; 1559 and 1560;
probe set #119 consisting of the nucleic acids consisting of SEQ ID NO: 362; 371 and 363;
probe set #120 consisting of the nucleic acids consisting of SEQ ID NO: 197; 1139 and 1141;
probe set #121 consisting of the nucleic acids consisting of SEQ ID NO: 1537; 1538 and 1539;
probe set #122 consisting of the nucleic acids consisting of SEQ ID NO: 803; 804 and 805;
probe set #123 consisting of the nucleic acids consisting of SEQ ID NO: 513; 514 and 515;
probe set #124 consisting of the nucleic acids consisting of SEQ ID NO: 1067; 1068 and 1069;
probe set #125 consisting of the nucleic acids consisting of SEQ ID NO: 812; 813 and 814;
probe set #126 consisting of the nucleic acids consisting of SEQ ID NO: 2196 and 2201;
probe set #127 consisting of the nucleic acids consisting of SEQ ID NO: 558; 559 and 567;

probe set #128 consisting of the nucleic acids consisting of SEQ ID NO: 248; 254 and 255;
probe set #129 consisting of the nucleic acids consisting of SEQ ID NO: 368 and 377;
probe set #130 consisting of the nucleic acids consisting of SEQ ID NO: 2536; 2537 and 2538;
probe set #131 consisting of the nucleic acids consisting of SEQ ID NO: 4; 5 and 6;
probe set #132 consisting of the nucleic acids consisting of SEQ ID NO: 2065; 2067 and 2091;
probe set #133 consisting of the nucleic acids consisting of SEQ ID NO: 1671; 1685 and 1686;
probe set #134 consisting of the nucleic acids consisting of SEQ ID NO: 1174; 1175 and 1176;
probe set #135 consisting of the nucleic acids consisting of SEQ ID NO: 783; 784 and 785;
probe set #136 consisting of the nucleic acids consisting of SEQ ID NO: 2774; 2775 and 2776;
probe set #137 consisting of the nucleic acids consisting of SEQ ID NO: 305; 307 and 306;
probe set #138 consisting of the nucleic acids consisting of SEQ ID NO: 1952; 1953 and 1954;
probe set #139 consisting of the nucleic acids consisting of SEQ ID NO: 806; 807 and 808;
probe set #140 consisting of the nucleic acids consisting of SEQ ID NO: 1162; 1284 and 1285;
probe set #141 consisting of the nucleic acids consisting of SEQ ID NO: 1204; 1205 and 1206;
probe set #142 consisting of the nucleic acids consisting of SEQ ID NO: 1197;
probe set #143 consisting of the nucleic acids consisting of SEQ ID NO: 2229; 2230 and 2231;
probe set #144 consisting of the nucleic acids consisting of SEQ ID NO: 1963;
probe set #145 consisting of the nucleic acids consisting of SEQ ID NO: 1890; 1891 and 1892;
probe set #146 consisting of the nucleic acids consisting of SEQ ID NO: 813; 814 and 818;
probe set #147 consisting of the nucleic acids consisting of SEQ ID NO: 2088; 2089 and 2090;
probe set #148 consisting of the nucleic acids consisting of SEQ ID NO: 1515; 1516 and 1517;
probe set #149 consisting of the nucleic acids consisting of SEQ ID NO: 1056; 1070 and 1071; and
probe set #150 consisting of the nucleic acids consisting of SEQ ID NO: 552; 553 and 554.

4. The combination according to claim 3, comprising 200 polynucleotide probe sets,
said 200 polynucleotide probe sets comprising probe set #1 to probe set #150, and
probe set #151 consisting of the nucleic acids consisting of SEQ ID NO: 972; 973 and 974;
probe set #152 consisting of the nucleic acids consisting of SEQ ID NO: 845; 846 and 847;
probe set #153 consisting of the nucleic acids consisting of SEQ ID NO: 815; 816 and 817;
probe set #154 consisting of the nucleic acids consisting of SEQ ID NO: 195; 196 and 868;
probe set #155 consisting of the nucleic acids consisting of SEQ ID NO: 1512; 1513 and 1514;
probe set #156 consisting of the nucleic acids consisting of SEQ ID NO: 1162; 1284 and 1285;
probe set #157 consisting of the nucleic acids consisting of SEQ ID NO: 2088; 2089 and 2090;
probe set #158 consisting of the nucleic acids consisting of SEQ ID NO: 1335;
probe set #159 consisting of the nucleic acids consisting of SEQ ID NO: 1123; 1124 and 1125;
probe set #160 consisting of the nucleic acids consisting of SEQ ID NO: 840; 841 and 845;
probe set #161 consisting of the nucleic acids consisting of SEQ ID NO: 1084; 1085 and 1086;
probe set #162 consisting of the nucleic acids consisting of SEQ ID NO: 198; 199 and 200;
probe set #163 consisting of the nucleic acids consisting of SEQ ID NO: 824; 825 and 826;
probe set #164 consisting of the nucleic acids consisting of SEQ ID NO: 809; 810 and 811;
probe set #165 consisting of the nucleic acids consisting of SEQ ID NO: 1586; 1587 and 1588;
probe set #166 consisting of the nucleic acids consisting of SEQ ID NO: 2794;
probe set #167 consisting of the nucleic acids consisting of SEQ ID NO: 1094; 1095 and 1096;
probe set #168 consisting of the nucleic acids consisting of SEQ ID NO: 2778; 2779 and 2783;
probe set #169 consisting of the nucleic acids consisting of SEQ ID NO: 1162; 1284 and 1285;
probe set #170 consisting of the nucleic acids consisting of SEQ ID NO: 1952; 1953 and 1954;
probe set #171 consisting of the nucleic acids consisting of SEQ ID NO: 975; 976 and 977;
probe set #172 consisting of the nucleic acids consisting of SEQ ID NO: 1110; 1111 and 1112;
probe set #173 consisting of the nucleic acids consisting of SEQ ID NO: 2762; 2763 and 2764;
probe set #174 consisting of the nucleic acids consisting of SEQ ID NO: 1229; 1230 and 1242;
probe set #175 consisting of the nucleic acids consisting of SEQ ID NO: 1250; 1251 and 1252;
probe set #176 consisting of the nucleic acids consisting of SEQ ID NO: 1126; 1127 and 1128;
probe set #177 consisting of the nucleic acids consisting of SEQ ID NO: 2065; 2067 and 2091;
probe set #178 consisting of the nucleic acids consisting of SEQ ID NO: 2601; 2602 and 2603;
probe set #179 consisting of the nucleic acids consisting of SEQ ID NO: 2381; 2382 and 2383;
probe set #180 consisting of the nucleic acids consisting of SEQ ID NO: 1407 and 1408;
probe set #181 consisting of the nucleic acids consisting of SEQ ID NO: 2065; 2067 and 2068;
probe set #182 consisting of the nucleic acids consisting of SEQ ID NO: 130; 131 and 132;
probe set #183 consisting of the nucleic acids consisting of SEQ ID NO: 1194; 1265 and 1266;
probe set #184 consisting of the nucleic acids consisting of SEQ ID NO: 968; 969 and 970;
probe set #185 consisting of the nucleic acids consisting of SEQ ID NO: 1743; 1744 and 1745;
probe set #186 consisting of the nucleic acids consisting of SEQ ID NO: 1557; 1563 and 1564;
probe set #187 consisting of the nucleic acids consisting of SEQ ID NO: 1687; 1688 and 1689;
probe set #188 consisting of the nucleic acids consisting of SEQ ID NO: 1114; 1115 and 1116;
probe set #189 consisting of the nucleic acids consisting of SEQ ID NO: 2083; 2084 and 2085;
probe set #190 consisting of the nucleic acids consisting of SEQ ID NO: 2072; 2089 and 2092;
probe set #191 consisting of the nucleic acids consisting of SEQ ID NO: 1586; 1587 and 1588;

probe set #192 consisting of the nucleic acids consisting of SEQ ID NO: 563; 564 and 565;
probe set #193 consisting of the nucleic acids consisting of SEQ ID NO: 1270; 1271 and 1272;
probe set #194 consisting of the nucleic acids consisting of SEQ ID NO: 1243; 1244 and 1245;
probe set #195 consisting of the nucleic acids consisting of SEQ ID NO: 1896; 1897 and 1898;
probe set #196 consisting of the nucleic acids consisting of SEQ ID NO: 1059; 1060 and 1085;
probe set #197 consisting of the nucleic acids consisting of SEQ ID NO: 1469; 1470 and 1471;
probe set #198 consisting of the nucleic acids consisting of SEQ ID NO: 121; 122 and 123;
probe set #199 consisting of the nucleic acids consisting of SEQ ID NO: 2061; 2062 and 2063; and
probe set #200 consisting of the nucleic acids consisting of SEQ ID NO: 1974.

5. The combination according to claim 4, comprising 1228 polynucleotide probe sets,
said 1228 polynucleotide probe sets comprising probe set #1 to probe set #200, and
probe set #201 consisting of the nucleic acids consisting of SEQ ID NO: 246; 247 and 248;
probe set #202 consisting of the nucleic acids consisting of SEQ ID NO: 1243; 1244 and 1245;
probe set #203 consisting of the nucleic acids consisting of SEQ ID NO: 2061; 2103 and 2104;
probe set #204 consisting of the nucleic acids consisting of SEQ ID NO: 1284; 1489 and 1490;
probe set #205 consisting of the nucleic acids consisting of SEQ ID NO: 342; 344 and 343;
probe set #206 consisting of the nucleic acids consisting of SEQ ID NO: 2202; 2203 and 2204;
probe set #207 consisting of the nucleic acids consisting of SEQ ID NO: 1931; 1932 and 1971;
probe set #208 consisting of the nucleic acids consisting of SEQ ID NO: 1293; 1294 and 1295;
probe set #209 consisting of the nucleic acids consisting of SEQ ID NO: 1515; 1517 and 1518;
probe set #210 consisting of the nucleic acids consisting of SEQ ID NO: 1193; 1194 and 1207;
probe set #211 consisting of the nucleic acids consisting of SEQ ID NO: 1068; 1078 and 1079;
probe set #212 consisting of the nucleic acids consisting of SEQ ID NO: 1243; 1244 and 1245;
probe set #213 consisting of the nucleic acids consisting of SEQ ID NO: 1952; 1953 and 1954;
probe set #214 consisting of the nucleic acids consisting of SEQ ID NO: 2061; 2062 and 2103;
probe set #215 consisting of the nucleic acids consisting of SEQ ID NO: 2798; 2799 and 2800;
probe set #216 consisting of the nucleic acids consisting of SEQ ID NO: 1773; 1774 and 1775;
probe set #217 consisting of the nucleic acids consisting of SEQ ID NO: 2471; 2472 and 2473;
probe set #218 consisting of the nucleic acids consisting of SEQ ID NO: 1243; 1244 and 1245;
probe set #219 consisting of the nucleic acids consisting of SEQ ID NO: 1109;
probe set #220 consisting of the nucleic acids consisting of SEQ ID NO: 1547; 1548 and 1549;
probe set #221 consisting of the nucleic acids consisting of SEQ ID NO: 1525; 1526 and 1527;
probe set #222 consisting of the nucleic acids consisting of SEQ ID NO: 2193; 2196 and 2200;
probe set #223 consisting of the nucleic acids consisting of SEQ ID NO: 2212 and 2213;
probe set #224 consisting of the nucleic acids consisting of SEQ ID NO: 972; 973 and 974;
probe set #225 consisting of the nucleic acids consisting of SEQ ID NO: 841; 845 and 846;
probe set #226 consisting of the nucleic acids consisting of SEQ ID NO: 1243; 1244 and 1245;
probe set #227 consisting of the nucleic acids consisting of SEQ ID NO: 813; 819 and 820;
probe set #228 consisting of the nucleic acids consisting of SEQ ID NO: 2060; 2077 and 2089;
probe set #229 consisting of the nucleic acids consisting of SEQ ID NO: 1530; 1531 and 1532;
probe set #230 consisting of the nucleic acids consisting of SEQ ID NO: 2060; 2072 and 2097;
probe set #231 consisting of the nucleic acids consisting of SEQ ID NO: 786; 787 and 796;
probe set #232 consisting of the nucleic acids consisting of SEQ ID NO: 379; 380 and 381;
probe set #233 consisting of the nucleic acids consisting of SEQ ID NO: 1662; 1663 and 1664;
probe set #234 consisting of the nucleic acids consisting of SEQ ID NO: 560; 561 and 562;
probe set #235 consisting of the nucleic acids consisting of SEQ ID NO: 1174; 1175 and 1176;
probe set #236 consisting of the nucleic acids consisting of SEQ ID NO: 1177; 1178 and 1179;
probe set #237 consisting of the nucleic acids consisting of SEQ ID NO: 1952; 1953 and 1954;
probe set #238 consisting of the nucleic acids consisting of SEQ ID NO: 1187; 1188 and 1189;
probe set #239 consisting of the nucleic acids consisting of SEQ ID NO: 151; 152 and 153;
probe set #240 consisting of the nucleic acids consisting of SEQ ID NO: 2235; 2236 and 2237;
probe set #241 consisting of the nucleic acids consisting of SEQ ID NO: 1218; 1238 and 1253;
probe set #242 consisting of the nucleic acids consisting of SEQ ID NO: 446; 447 and 454;
probe set #243 consisting of the nucleic acids consisting of SEQ ID NO: 1229; 1242 and 1260;
probe set #244 consisting of the nucleic acids consisting of SEQ ID NO: 824; 825 and 826;
probe set #245 consisting of the nucleic acids consisting of SEQ ID NO: 848; 849 and 850;
probe set #246 consisting of the nucleic acids consisting of SEQ ID NO: 2058; 2059 and 2089;
probe set #247 consisting of the nucleic acids consisting of SEQ ID NO: 1475; 1476 and 1477;
probe set #248 consisting of the nucleic acids consisting of SEQ ID NO: 2533; 2534 and 2535;
probe set #249 consisting of the nucleic acids consisting of SEQ ID NO: 2192; 2193 and 2194;
probe set #250 consisting of the nucleic acids consisting of SEQ ID NO: 832; 833 and 834;
probe set #251 consisting of the nucleic acids consisting of SEQ ID NO: 1234 and 1235;
probe set #252 consisting of the nucleic acids consisting of SEQ ID NO: 1893; 1894 and 1895;
probe set #253 consisting of the nucleic acids consisting of SEQ ID NO: 1932; 1971 and 1987;
probe set #254 consisting of the nucleic acids consisting of SEQ ID NO: 2083; 2084 and 2085;
probe set #255 consisting of the nucleic acids consisting of SEQ ID NO: 264; 273 and 274;

probe set #256 consisting of the nucleic acids consisting of SEQ ID NO: 428;
probe set #257 consisting of the nucleic acids consisting of SEQ ID NO: 198; 199 and 200;
probe set #258 consisting of the nucleic acids consisting of SEQ ID NO: 2200; 2205 and 2206;
probe set #259 consisting of the nucleic acids consisting of SEQ ID NO: 2777; 2778 and 2779;
probe set #260 consisting of the nucleic acids consisting of SEQ ID NO: 1287; 1288 and 1289;
probe set #261 consisting of the nucleic acids consisting of SEQ ID NO: 446; 453 and 454;
probe set #262 consisting of the nucleic acids consisting of SEQ ID NO: 2192; 2193 and 2194;
probe set #263 consisting of the nucleic acids consisting of SEQ ID NO: 1952; 1953 and 1954;
probe set #264 consisting of the nucleic acids consisting of SEQ ID NO: 1216; 1217 and 1218;
probe set #265 consisting of the nucleic acids consisting of SEQ ID NO: 1216; 1217 and 1218;
probe set #266 consisting of the nucleic acids consisting of SEQ ID NO: 388; 389 and 390;
probe set #267 consisting of the nucleic acids consisting of SEQ ID NO: 1310; 1311 and 1312;
probe set #268 consisting of the nucleic acids consisting of SEQ ID NO: 1313; 1314 and 1315;
probe set #269 consisting of the nucleic acids consisting of SEQ ID NO: 1142; 1143 and 1144;
probe set #270 consisting of the nucleic acids consisting of SEQ ID NO: 1229; 1230 and 1242;
probe set #271 consisting of the nucleic acids consisting of SEQ ID NO: 972; 973 and 974;
probe set #272 consisting of the nucleic acids consisting of SEQ ID NO: 1673; 1674 and 1675;
probe set #273 consisting of the nucleic acids consisting of SEQ ID NO: 446; 453 and 454;
probe set #274 consisting of the nucleic acids consisting of SEQ ID NO: 2195; 2196 and 2197;
probe set #275 consisting of the nucleic acids consisting of SEQ ID NO: 2784;
probe set #276 consisting of the nucleic acids consisting of SEQ ID NO: 2061; 2062 and 2103;
probe set #277 consisting of the nucleic acids consisting of SEQ ID NO: 459 and 460;
probe set #278 consisting of the nucleic acids consisting of SEQ ID NO: 1583; 1584 and 1585;
probe set #279 consisting of the nucleic acids consisting of SEQ ID NO: 1246; 1247 and 1248;
probe set #280 consisting of the nucleic acids consisting of SEQ ID NO: 2061; 2063 and 2068;
probe set #281 consisting of the nucleic acids consisting of SEQ ID NO: 1216; 1217 and 1218;
probe set #282 consisting of the nucleic acids consisting of SEQ ID NO: 170;
probe set #283 consisting of the nucleic acids consisting of SEQ ID NO: 2072; 2089 and 2102;
probe set #284 consisting of the nucleic acids consisting of SEQ ID NO: 1216; 1217 and 1238;
probe set #285 consisting of the nucleic acids consisting of SEQ ID NO: 127; 128 and 129;
probe set #286 consisting of the nucleic acids consisting of SEQ ID NO: 1216; 1217 and 1218;
probe set #287 consisting of the nucleic acids consisting of SEQ ID NO: 840; 841 and 845;
probe set #288 consisting of the nucleic acids consisting of SEQ ID NO: 840; 841 and 845;
probe set #289 consisting of the nucleic acids consisting of SEQ ID NO: 1216; 1217 and 1218;
probe set #290 consisting of the nucleic acids consisting of SEQ ID NO: 1218; 1253 and 1254;
probe set #291 consisting of the nucleic acids consisting of SEQ ID NO: 1369; 1370 and 1371;
probe set #292 consisting of the nucleic acids consisting of SEQ ID NO: 1239; 1240 and 1241;
probe set #293 consisting of the nucleic acids consisting of SEQ ID NO: 1229; 1242 and 1260;
probe set #294 consisting of the nucleic acids consisting of SEQ ID NO: 1218; 1253 and 1254;
probe set #295 consisting of the nucleic acids consisting of SEQ ID NO: 1515; 1517 and 1518;
probe set #296 consisting of the nucleic acids consisting of SEQ ID NO: 2307;
probe set #297 consisting of the nucleic acids consisting of SEQ ID NO: 246; 247 and 248;
probe set #298 consisting of the nucleic acids consisting of SEQ ID NO: 1216; 1218 and 1253;
probe set #299 consisting of the nucleic acids consisting of SEQ ID NO: 2059; 2100 and 2101;
probe set #300 consisting of the nucleic acids consisting of SEQ ID NO: 841; 845 and 846;
probe set #301 consisting of the nucleic acids consisting of SEQ ID NO: 1746; 1747 and 1748;
probe set #302 consisting of the nucleic acids consisting of SEQ ID NO: 1313; 1314 and 1315;
probe set #303 consisting of the nucleic acids consisting of SEQ ID NO: 845; 846 and 847;
probe set #304 consisting of the nucleic acids consisting of SEQ ID NO: 1942; 1943 and 1948;
probe set #305 consisting of the nucleic acids consisting of SEQ ID NO: 1047; 1048 and 1049;
probe set #306 consisting of the nucleic acids consisting of SEQ ID NO: 1216; 1217 and 1218;
probe set #307 consisting of the nucleic acids consisting of SEQ ID NO: 2483; 2484 and 2485;
probe set #308 consisting of the nucleic acids consisting of SEQ ID NO: 827 and 828;
probe set #309 consisting of the nucleic acids consisting of SEQ ID NO: 1943; 1948 and 1973;
probe set #310 consisting of the nucleic acids consisting of SEQ ID NO: 1039 and 1040;
probe set #311 consisting of the nucleic acids consisting of SEQ ID NO: 2558; 2559 and 2560;
probe set #312 consisting of the nucleic acids consisting of SEQ ID NO: 2060; 2072 and 2097;
probe set #313 consisting of the nucleic acids consisting of SEQ ID NO: 2058; 2059 and 2089;
probe set #314 consisting of the nucleic acids consisting of SEQ ID NO: 1218; 1238 and 1253;
probe set #315 consisting of the nucleic acids consisting of SEQ ID NO: 1239; 1240 and 1241;
probe set #316 consisting of the nucleic acids consisting of SEQ ID NO: 1256; 1257 and 1258;
probe set #317 consisting of the nucleic acids consisting of SEQ ID NO: 2063; 2068 and 2103;
probe set #318 consisting of the nucleic acids consisting of SEQ ID NO: 446; 453 and 454;
probe set #319 consisting of the nucleic acids consisting of SEQ ID NO: 422; 423 and 424;
probe set #320 consisting of the nucleic acids consisting of SEQ ID NO: 451; 452 and 454;
probe set #321 consisting of the nucleic acids consisting of SEQ ID NO: 2076; 2103 and 2108;

probe set #322 consisting of the nucleic acids consisting of SEQ ID NO: 139; 140 and 141;
probe set #323 consisting of the nucleic acids consisting of SEQ ID NO: 228; 229 and 230;
probe set #324 consisting of the nucleic acids consisting of SEQ ID NO: 1218; 1242 and 1260;
probe set #325 consisting of the nucleic acids consisting of SEQ ID NO: 2510; 2511 and 2512;
probe set #326 consisting of the nucleic acids consisting of SEQ ID NO: 2670; 2723 and 2759;
probe set #327 consisting of the nucleic acids consisting of SEQ ID NO: 1148; 1149 and 1150;
probe set #328 consisting of the nucleic acids consisting of SEQ ID NO: 1568; 1569 and 1570;
probe set #329 consisting of the nucleic acids consisting of SEQ ID NO: 1290; 1291 and 1292;
probe set #330 consisting of the nucleic acids consisting of SEQ ID NO: 2061; 2063 and 2068;
probe set #331 consisting of the nucleic acids consisting of SEQ ID NO: 1174; 1175 and 1176;
probe set #332 consisting of the nucleic acids consisting of SEQ ID NO: 1239; 1240 and 1241;
probe set #333 consisting of the nucleic acids consisting of SEQ ID NO: 761; 762 and 763;
probe set #334 consisting of the nucleic acids consisting of SEQ ID NO: 669; 670 and 671;
probe set #335 consisting of the nucleic acids consisting of SEQ ID NO: 1216; 1218 and 1253;
probe set #336 consisting of the nucleic acids consisting of SEQ ID NO: 1136; 1137 and 1138;
probe set #337 consisting of the nucleic acids consisting of SEQ ID NO: 1671; 1672 and 1685;
probe set #338 consisting of the nucleic acids consisting of SEQ ID NO: 1565; 1566 and 1567;
probe set #339 consisting of the nucleic acids consisting of SEQ ID NO: 308;
probe set #340 consisting of the nucleic acids consisting of SEQ ID NO: 1583; 1584 and 1585;
probe set #341 consisting of the nucleic acids consisting of SEQ ID NO: 1985;
probe set #342 consisting of the nucleic acids consisting of SEQ ID NO: 1583; 1584 and 1600;
probe set #343 consisting of the nucleic acids consisting of SEQ ID NO: 2520; 2521 and 2522;
probe set #344 consisting of the nucleic acids consisting of SEQ ID NO: 842; 843 and 844;
probe set #345 consisting of the nucleic acids consisting of SEQ ID NO: 1216; 1217 and 1218;
probe set #346 consisting of the nucleic acids consisting of SEQ ID NO: 837; 838 and 839;
probe set #347 consisting of the nucleic acids consisting of SEQ ID NO: 2063; 2068 and 2103;
probe set #348 consisting of the nucleic acids consisting of SEQ ID NO: 669; 670 and 671;
probe set #349 consisting of the nucleic acids consisting of SEQ ID NO: 1583; 1584 and 1585;
probe set #350 consisting of the nucleic acids consisting of SEQ ID NO: 2492; 2493 and 2494;
probe set #351 consisting of the nucleic acids consisting of SEQ ID NO: 1218; 1253 and 1261;
probe set #352 consisting of the nucleic acids consisting of SEQ ID NO: 1869; 1870 and 1871;
probe set #353 consisting of the nucleic acids consisting of SEQ ID NO: 1213; 1214 and 1215;
probe set #354 consisting of the nucleic acids consisting of SEQ ID NO: 318; 320 and 319;
probe set #355 consisting of the nucleic acids consisting of SEQ ID NO: 448; 449 and 450;
probe set #356 consisting of the nucleic acids consisting of SEQ ID NO: 2158; 2163 and 2164;
probe set #357 consisting of the nucleic acids consisting of SEQ ID NO: 971;
probe set #358 consisting of the nucleic acids consisting of SEQ ID NO: 1059; 1060 and 1093;
probe set #359 consisting of the nucleic acids consisting of SEQ ID NO: 2662; 2663 and 2664;
probe set #360 consisting of the nucleic acids consisting of SEQ ID NO: 125; 126 and 127;
probe set #361 consisting of the nucleic acids consisting of SEQ ID NO: 2069; 2070 and 2071;
probe set #362 consisting of the nucleic acids consisting of SEQ ID NO: 761; 762 and 763;
probe set #363 consisting of the nucleic acids consisting of SEQ ID NO: 1589; 1590 and 1591;
probe set #364 consisting of the nucleic acids consisting of SEQ ID NO: 2523;
probe set #365 consisting of the nucleic acids consisting of SEQ ID NO: 2760;
probe set #366 consisting of the nucleic acids consisting of SEQ ID NO: 2078 and 2079;
probe set #367 consisting of the nucleic acids consisting of SEQ ID NO: 197; 868 and 1139;
probe set #368 consisting of the nucleic acids consisting of SEQ ID NO: 1229; 1242 and 1260;
probe set #369 consisting of the nucleic acids consisting of SEQ ID NO: 429; 430 and 431;
probe set #370 consisting of the nucleic acids consisting of SEQ ID NO: 845; 846 and 847;
probe set #371 consisting of the nucleic acids consisting of SEQ ID NO: 1472; 1473 and 1474;
probe set #372 consisting of the nucleic acids consisting of SEQ ID NO: 2061; 2062 and 2063;
probe set #373 consisting of the nucleic acids consisting of SEQ ID NO: 1478; 1479 and 1480;
probe set #374 consisting of the nucleic acids consisting of SEQ ID NO: 1229; 1242 and 1260;
probe set #375 consisting of the nucleic acids consisting of SEQ ID NO: 1931; 1932 and 1962;
probe set #376 consisting of the nucleic acids consisting of SEQ ID NO: 304;
probe set #377 consisting of the nucleic acids consisting of SEQ ID NO: 2064; 2065 and 2066;
probe set #378 consisting of the nucleic acids consisting of SEQ ID NO: 1229; 1242 and 1260;
probe set #379 consisting of the nucleic acids consisting of SEQ ID NO: 1218; 1242 and 1260;
probe set #380 consisting of the nucleic acids consisting of SEQ ID NO: 2928; 2929 and 2930;
probe set #381 consisting of the nucleic acids consisting of SEQ ID NO: 975; 976 and 977;
probe set #382 consisting of the nucleic acids consisting of SEQ ID NO: 246; 247 and 248;
probe set #383 consisting of the nucleic acids consisting of SEQ ID NO: 2069; 2070 and 2071;
probe set #384 consisting of the nucleic acids consisting of SEQ ID NO: 1952; 1953 and 1954;
probe set #385 consisting of the nucleic acids consisting of SEQ ID NO: 538; 539 and 540;
probe set #386 consisting of the nucleic acids consisting of SEQ ID NO: 160;
probe set #387 consisting of the nucleic acids consisting of SEQ ID NO: 722; 723 and 724;

probe set #388 consisting of the nucleic acids consisting of SEQ ID NO: 702; 703 and 704;
probe set #389 consisting of the nucleic acids consisting of SEQ ID NO: 975; 976 and 977;
probe set #390 consisting of the nucleic acids consisting of SEQ ID NO: 2513;
probe set #391 consisting of the nucleic acids consisting of SEQ ID NO: 2338; 2339 and 2340;
probe set #392 consisting of the nucleic acids consisting of SEQ ID NO: 869; 873 and 874;
probe set #393 consisting of the nucleic acids consisting of SEQ ID NO: 1299; 1300 and 1301;
probe set #394 consisting of the nucleic acids consisting of SEQ ID NO: 2886; 2887 and 2888;
probe set #395 consisting of the nucleic acids consisting of SEQ ID NO: 2099;
probe set #396 consisting of the nucleic acids consisting of SEQ ID NO: 2471; 2472 and 2473;
probe set #397 consisting of the nucleic acids consisting of SEQ ID NO: 1679; 1680 and 1681;
probe set #398 consisting of the nucleic acids consisting of SEQ ID NO: 841; 845 and 846;
probe set #399 consisting of the nucleic acids consisting of SEQ ID NO: 1113;
probe set #400 consisting of the nucleic acids consisting of SEQ ID NO: 1592; 1593 and 1594;
probe set #401 consisting of the nucleic acids consisting of SEQ ID NO: 2338; 2339 and 2340;
probe set #402 consisting of the nucleic acids consisting of SEQ ID NO: 2483; 2484 and 2485;
probe set #403 consisting of the nucleic acids consisting of SEQ ID NO: 2300; 2301 and 2302;
probe set #404 consisting of the nucleic acids consisting of SEQ ID NO: 2548; 2549 and 2550;
probe set #405 consisting of the nucleic acids consisting of SEQ ID NO: 1939; 1940 and 1941;
probe set #406 consisting of the nucleic acids consisting of SEQ ID NO: 195; 196 and 197;
probe set #407 consisting of the nucleic acids consisting of SEQ ID NO: 2061; 2103 and 2104;
probe set #408 consisting of the nucleic acids consisting of SEQ ID NO: 2060; 2072 and 2097;
probe set #409 consisting of the nucleic acids consisting of SEQ ID NO: 1382; 1383 and 1384;
probe set #410 consisting of the nucleic acids consisting of SEQ ID NO: 1943; 1948 and 1978;
probe set #411 consisting of the nucleic acids consisting of SEQ ID NO: 2927;
probe set #412 consisting of the nucleic acids consisting of SEQ ID NO: 1920 and 1921;
probe set #413 consisting of the nucleic acids consisting of SEQ ID NO: 2061; 2063 and 2068;
probe set #414 consisting of the nucleic acids consisting of SEQ ID NO: 1686; 1693 and 1694;
probe set #415 consisting of the nucleic acids consisting of SEQ ID NO: 1217; 1236 and 1237;
probe set #416 consisting of the nucleic acids consisting of SEQ ID NO: 755; 756 and 757;
probe set #417 consisting of the nucleic acids consisting of SEQ ID NO: 2372; 2373 and 2374;
probe set #418 consisting of the nucleic acids consisting of SEQ ID NO: 1595; 1596 and 1597;
probe set #419 consisting of the nucleic acids consisting of SEQ ID NO: 1193; 1208 and 1209;
probe set #420 consisting of the nucleic acids consisting of SEQ ID NO: 2049; 2050 and 2051;
probe set #421 consisting of the nucleic acids consisting of SEQ ID NO: 1193; 1194 and 1207;
probe set #422 consisting of the nucleic acids consisting of SEQ ID NO: 265; 266 and 267;
probe set #423 consisting of the nucleic acids consisting of SEQ ID NO: 1580; 1581 and 1582;
probe set #424 consisting of the nucleic acids consisting of SEQ ID NO: 146; 147 and 150;
probe set #425 consisting of the nucleic acids consisting of SEQ ID NO: 1662; 1663 and 1664;
probe set #426 consisting of the nucleic acids consisting of SEQ ID NO: 1242; 1249 and 1268;
probe set #427 consisting of the nucleic acids consisting of SEQ ID NO: 2791; 2792 and 2793;
probe set #428 consisting of the nucleic acids consisting of SEQ ID NO: 124;
probe set #429 consisting of the nucleic acids consisting of SEQ ID NO: 2061; 2062 and 2103;
probe set #430 consisting of the nucleic acids consisting of SEQ ID NO: 1649; 1650 and 1651;
probe set #431 consisting of the nucleic acids consisting of SEQ ID NO: 703; 711 and 736;
probe set #432 consisting of the nucleic acids consisting of SEQ ID NO: 1927; 1932 and 1987;
probe set #433 consisting of the nucleic acids consisting of SEQ ID NO: 2086 and 2087;
probe set #434 consisting of the nucleic acids consisting of SEQ ID NO: 975; 976 and 977;
probe set #435 consisting of the nucleic acids consisting of SEQ ID NO: 840; 841 and 845;
probe set #436 consisting of the nucleic acids consisting of SEQ ID NO: 197; 868 and 1132;
probe set #437 consisting of the nucleic acids consisting of SEQ ID NO: 2060; 2065 and 2072;
probe set #438 consisting of the nucleic acids consisting of SEQ ID NO: 842; 843 and 844;
probe set #439 consisting of the nucleic acids consisting of SEQ ID NO: 1306;
probe set #440 consisting of the nucleic acids consisting of SEQ ID NO: 2214 and 2215;
probe set #441 consisting of the nucleic acids consisting of SEQ ID NO: 1284; 1290 and 1489;
probe set #442 consisting of the nucleic acids consisting of SEQ ID NO: 298; 300 and 299;
probe set #443 consisting of the nucleic acids consisting of SEQ ID NO: 2106;
probe set #444 consisting of the nucleic acids consisting of SEQ ID NO: 986;
probe set #445 consisting of the nucleic acids consisting of SEQ ID NO: 2049; 2050 and 2051;
probe set #446 consisting of the nucleic acids consisting of SEQ ID NO: 2206; 2207 and 2208;
probe set #447 consisting of the nucleic acids consisting of SEQ ID NO: 2527; 2528 and 2529;
probe set #448 consisting of the nucleic acids consisting of SEQ ID NO: 1259;
probe set #449 consisting of the nucleic acids consisting of SEQ ID NO: 2677; 2678 and 2708;
probe set #450 consisting of the nucleic acids consisting of SEQ ID NO: 1217; 1236 and 1237;
probe set #451 consisting of the nucleic acids consisting of SEQ ID NO: 2060; 2072 and 2102;
probe set #452 consisting of the nucleic acids consisting of SEQ ID NO: 2369; 2370 and 2371;
probe set #453 consisting of the nucleic acids consisting of SEQ ID NO: 696; 697 and 698;

probe set #454 consisting of the nucleic acids consisting of SEQ ID NO: 1255;
probe set #455 consisting of the nucleic acids consisting of SEQ ID NO: 265; 266 and 267;
probe set #456 consisting of the nucleic acids consisting of SEQ ID NO: 2192; 2193 and 2200;
probe set #457 consisting of the nucleic acids consisting of SEQ ID NO: 2069; 2070 and 2071;
probe set #458 consisting of the nucleic acids consisting of SEQ ID NO: 2063; 2068 and 2103;
probe set #459 consisting of the nucleic acids consisting of SEQ ID NO: 304;
probe set #460 consisting of the nucleic acids consisting of SEQ ID NO: 372 and 373;
probe set #461 consisting of the nucleic acids consisting of SEQ ID NO: 2075; 2076 and 2109;
probe set #462 consisting of the nucleic acids consisting of SEQ ID NO: 2366; 2367 and 2368;
probe set #463 consisting of the nucleic acids consisting of SEQ ID NO: 1948; 1979 and 1980;
probe set #464 consisting of the nucleic acids consisting of SEQ ID NO: 216; 217 and 218;
probe set #465 consisting of the nucleic acids consisting of SEQ ID NO: 2061; 2062 and 2063;
probe set #466 consisting of the nucleic acids consisting of SEQ ID NO: 1100; 1101 and 1102;
probe set #467 consisting of the nucleic acids consisting of SEQ ID NO: 1303; 1304 and 1305;
probe set #468 consisting of the nucleic acids consisting of SEQ ID NO: 985;
probe set #469 consisting of the nucleic acids consisting of SEQ ID NO: 2188; 2189 and 2190;
probe set #470 consisting of the nucleic acids consisting of SEQ ID NO: 2069; 2070 and 2071;
probe set #471 consisting of the nucleic acids consisting of SEQ ID NO: 1982; 1983 and 1984;
probe set #472 consisting of the nucleic acids consisting of SEQ ID NO: 1887; 1888 and 1889;
probe set #473 consisting of the nucleic acids consisting of SEQ ID NO: 1995; 1996 and 1997;
probe set #474 consisting of the nucleic acids consisting of SEQ ID NO: 2931;
probe set #475 consisting of the nucleic acids consisting of SEQ ID NO: 865; 866 and 867;
probe set #476 consisting of the nucleic acids consisting of SEQ ID NO: 268; 269 and 270;
probe set #477 consisting of the nucleic acids consisting of SEQ ID NO: 2286; 2287 and 2288;
probe set #478 consisting of the nucleic acids consisting of SEQ ID NO: 1117; 1118 and 1124;
probe set #479 consisting of the nucleic acids consisting of SEQ ID NO: 2059; 2100 and 2101;
probe set #480 consisting of the nucleic acids consisting of SEQ ID NO: 388; 389 and 390;
probe set #481 consisting of the nucleic acids consisting of SEQ ID NO: 2286; 2287 and 2288;
probe set #482 consisting of the nucleic acids consisting of SEQ ID NO: 2055;
probe set #483 consisting of the nucleic acids consisting of SEQ ID NO: 2573; 2574 and 2575;
probe set #484 consisting of the nucleic acids consisting of SEQ ID NO: 2075 and 2076;
probe set #485 consisting of the nucleic acids consisting of SEQ ID NO: 2689; 2690 and 2691;
probe set #486 consisting of the nucleic acids consisting of SEQ ID NO: 2072; 2089 and 2102;
probe set #487 consisting of the nucleic acids consisting of SEQ ID NO: 1388; 1389 and 1390;
probe set #488 consisting of the nucleic acids consisting of SEQ ID NO: 2889; 2890 and 2891;
probe set #489 consisting of the nucleic acids consisting of SEQ ID NO: 1565; 1599 and 1601;
probe set #490 consisting of the nucleic acids consisting of SEQ ID NO: 2157; 2158 and 2159;
probe set #491 consisting of the nucleic acids consisting of SEQ ID NO: 1931; 1932 and 1987;
probe set #492 consisting of the nucleic acids consisting of SEQ ID NO: 2061; 2063 and 2068;
probe set #493 consisting of the nucleic acids consisting of SEQ ID NO: 1574; 1575 and 1576;
probe set #494 consisting of the nucleic acids consisting of SEQ ID NO: 743; 744 and 745;
probe set #495 consisting of the nucleic acids consisting of SEQ ID NO: 1931; 1932 and 1962;
probe set #496 consisting of the nucleic acids consisting of SEQ ID NO: 1927; 1947 and 1987;
probe set #497 consisting of the nucleic acids consisting of SEQ ID NO: 2286; 2287 and 2288;
probe set #498 consisting of the nucleic acids consisting of SEQ ID NO: 2286; 2287 and 2288;
probe set #499 consisting of the nucleic acids consisting of SEQ ID NO: 1676; 1677 and 1678;
probe set #500 consisting of the nucleic acids consisting of SEQ ID NO: 1041; 1042 and 1043;
probe set #501 consisting of the nucleic acids consisting of SEQ ID NO: 2375; 2376 and 2377;
probe set #502 consisting of the nucleic acids consisting of SEQ ID NO: 1920 and 1921;
probe set #503 consisting of the nucleic acids consisting of SEQ ID NO: 2061; 2093 and 2107;
probe set #504 consisting of the nucleic acids consisting of SEQ ID NO: 1931; 1932 and 1962;
probe set #505 consisting of the nucleic acids consisting of SEQ ID NO: 2908; 2917 and 2918;
probe set #506 consisting of the nucleic acids consisting of SEQ ID NO: 1920; 1921 and 1922;
probe set #507 consisting of the nucleic acids consisting of SEQ ID NO: 1922;
probe set #508 consisting of the nucleic acids consisting of SEQ ID NO: 2489; 2490 and 2491;
probe set #509 consisting of the nucleic acids consisting of SEQ ID NO: 2909; 2910 and 2917;
probe set #510 consisting of the nucleic acids consisting of SEQ ID NO: 725; 726 and 727;
probe set #511 consisting of the nucleic acids consisting of SEQ ID NO: 2304; 2305 and 2308;
probe set #512 consisting of the nucleic acids consisting of SEQ ID NO: 829; 830 and 831;
probe set #513 consisting of the nucleic acids consisting of SEQ ID NO: 2414; 2415 and 2416;
probe set #514 consisting of the nucleic acids consisting of SEQ ID NO: 2003; 2005 and 2006;
probe set #515 consisting of the nucleic acids consisting of SEQ ID NO: 731; 732 and 736;
probe set #516 consisting of the nucleic acids consisting of SEQ ID NO: 1926 and 1962;
probe set #517 consisting of the nucleic acids consisting of SEQ ID NO: 2662; 2663 and 2664;
probe set #518 consisting of the nucleic acids consisting of SEQ ID NO: 1142; 1143 and 1144;
probe set #519 consisting of the nucleic acids consisting of SEQ ID NO: 1296; 1297 and 1298;

probe set #520 consisting of the nucleic acids consisting of SEQ ID NO: 1943; 1948 and 1978;
probe set #521 consisting of the nucleic acids consisting of SEQ ID NO: 2899; 2900 and 2901;
probe set #522 consisting of the nucleic acids consisting of SEQ ID NO: 2060; 2065 and 2072;
probe set #523 consisting of the nucleic acids consisting of SEQ ID NO: 982;
probe set #524 consisting of the nucleic acids consisting of SEQ ID NO: 1920; 1933 and 1999;
probe set #525 consisting of the nucleic acids consisting of SEQ ID NO: 1655;
probe set #526 consisting of the nucleic acids consisting of SEQ ID NO: 1008; 1009 and 1010;
probe set #527 consisting of the nucleic acids consisting of SEQ ID NO: 2060; 2072 and 2097;
probe set #528 consisting of the nucleic acids consisting of SEQ ID NO: 37; 38 and 39;
probe set #529 consisting of the nucleic acids consisting of SEQ ID NO: 2852; 2853 and 2854;
probe set #530 consisting of the nucleic acids consisting of SEQ ID NO: 1721; 1722 and 1723;
probe set #531 consisting of the nucleic acids consisting of SEQ ID NO: 2902; 2903 and 2904;
probe set #532 consisting of the nucleic acids consisting of SEQ ID NO: 1920 and 1921;
probe set #533 consisting of the nucleic acids consisting of SEQ ID NO: 761; 762 and 765;
probe set #534 consisting of the nucleic acids consisting of SEQ ID NO: 2086 and 2087;
probe set #535 consisting of the nucleic acids consisting of SEQ ID NO: 435; 436 and 437;
probe set #536 consisting of the nucleic acids consisting of SEQ ID NO: 1397; 1398 and 1399;
probe set #537 consisting of the nucleic acids consisting of SEQ ID NO: 2808; 2809 and 2810;
probe set #538 consisting of the nucleic acids consisting of SEQ ID NO: 1032; 1033 and 1034;
probe set #539 consisting of the nucleic acids consisting of SEQ ID NO: 1129; 1140 and 1141;
probe set #540 consisting of the nucleic acids consisting of SEQ ID NO: 2517; 2518 and 2519;
probe set #541 consisting of the nucleic acids consisting of SEQ ID NO: 1931; 1932 and 1962;
probe set #542 consisting of the nucleic acids consisting of SEQ ID NO: 1029; 1030 and 1031;
probe set #543 consisting of the nucleic acids consisting of SEQ ID NO: 2296; 2297 and 2298;
probe set #544 consisting of the nucleic acids consisting of SEQ ID NO: 1869; 1870 and 1871;
probe set #545 consisting of the nucleic acids consisting of SEQ ID NO: 985;
probe set #546 consisting of the nucleic acids consisting of SEQ ID NO: 1464; 1465 and 1466;
probe set #547 consisting of the nucleic acids consisting of SEQ ID NO: 1418; 1419 and 1420;
probe set #548 consisting of the nucleic acids consisting of SEQ ID NO: 1916; 1917 and 1918;
probe set #549 consisting of the nucleic acids consisting of SEQ ID NO: 1406; 1407 and 1413;
probe set #550 consisting of the nucleic acids consisting of SEQ ID NO: 35 and 36;
probe set #551 consisting of the nucleic acids consisting of SEQ ID NO: 2254; 2255 and 2256;
probe set #552 consisting of the nucleic acids consisting of SEQ ID NO: 1920 and 1921;
probe set #553 consisting of the nucleic acids consisting of SEQ ID NO: 1737; 1738 and 1739;
probe set #554 consisting of the nucleic acids consisting of SEQ ID NO: 573; 643 and 644;
probe set #555 consisting of the nucleic acids consisting of SEQ ID NO: 2304; 2305 and 2307;
probe set #556 consisting of the nucleic acids consisting of SEQ ID NO: 2530; 2531 and 2532;
probe set #557 consisting of the nucleic acids consisting of SEQ ID NO: 2628; 2629 and 2630;
probe set #558 consisting of the nucleic acids consisting of SEQ ID NO: 1223; 1224 and 1225;
probe set #559 consisting of the nucleic acids consisting of SEQ ID NO: 1210; 1211 and 1212;
probe set #560 consisting of the nucleic acids consisting of SEQ ID NO: 1839; 1840 and 1841;
probe set #561 consisting of the nucleic acids consisting of SEQ ID NO: 2561; 2562 and 2563;
probe set #562 consisting of the nucleic acids consisting of SEQ ID NO: 1920; 1933 and 1999;
probe set #563 consisting of the nucleic acids consisting of SEQ ID NO: 446; 453 and 454;
probe set #564 consisting of the nucleic acids consisting of SEQ ID NO: 321; 323 and 322;
probe set #565 consisting of the nucleic acids consisting of SEQ ID NO: 2423; 2424 and 2425;
probe set #566 consisting of the nucleic acids consisting of SEQ ID NO: 2216 and 2217;
probe set #567 consisting of the nucleic acids consisting of SEQ ID NO: 2658; 2670 and 2708;
probe set #568 consisting of the nucleic acids consisting of SEQ ID NO: 1366; 1367 and 1368;
probe set #569 consisting of the nucleic acids consisting of SEQ ID NO: 1920 and 1921;
probe set #570 consisting of the nucleic acids consisting of SEQ ID NO: 1926; 1961 and 1962;
probe set #571 consisting of the nucleic acids consisting of SEQ ID NO: 1050; 1051 and 1052;
probe set #572 consisting of the nucleic acids consisting of SEQ ID NO: 1931; 1932 and 1962;
probe set #573 consisting of the nucleic acids consisting of SEQ ID NO: 2100; 2101 and 2105;
probe set #574 consisting of the nucleic acids consisting of SEQ ID NO: 1151; 1152 and 1153;
probe set #575 consisting of the nucleic acids consisting of SEQ ID NO: 2717; 2718 and 2719;
probe set #576 consisting of the nucleic acids consisting of SEQ ID NO: 1382; 1383 and 1384;
probe set #577 consisting of the nucleic acids consisting of SEQ ID NO: 2061;
probe set #578 consisting of the nucleic acids consisting of SEQ ID NO: 1211; 1212 and 1226;
probe set #579 consisting of the nucleic acids consisting of SEQ ID NO: 1227 and 1228;
probe set #580 consisting of the nucleic acids consisting of SEQ ID NO: 1665; 1666 and 1667;
probe set #581 consisting of the nucleic acids consisting of SEQ ID NO: 2659; 2660 and 2709;
probe set #582 consisting of the nucleic acids consisting of SEQ ID NO: 2580; 2581 and 2582;
probe set #583 consisting of the nucleic acids consisting of SEQ ID NO: 2662; 2663 and 2664;
probe set #584 consisting of the nucleic acids consisting of SEQ ID NO: 1017; 1018 and 1019;
probe set #585 consisting of the nucleic acids consisting of SEQ ID NO: 573; 642 and 644;

probe set #586 consisting of the nucleic acids consisting of SEQ ID NO: 80; 81 and 82;
probe set #587 consisting of the nucleic acids consisting of SEQ ID NO: 222; 223 and 224;
probe set #588 consisting of the nucleic acids consisting of SEQ ID NO: 1948;
probe set #589 consisting of the nucleic acids consisting of SEQ ID NO: 749; 750 and 751;
probe set #590 consisting of the nucleic acids consisting of SEQ ID NO: 1565; 1598 and 1599;
probe set #591 consisting of the nucleic acids consisting of SEQ ID NO: 2911; 2912 and 2913;
probe set #592 consisting of the nucleic acids consisting of SEQ ID NO: 2668; 2669 and 2709;
probe set #593 consisting of the nucleic acids consisting of SEQ ID NO: 2670; 2676 and 2759;
probe set #594 consisting of the nucleic acids consisting of SEQ ID NO: 1934;
probe set #595 consisting of the nucleic acids consisting of SEQ ID NO: 1932; 1935 and 1978;
probe set #596 consisting of the nucleic acids consisting of SEQ ID NO: 840; 841 and 845;
probe set #597 consisting of the nucleic acids consisting of SEQ ID NO: 1749; 1750 and 1751;
probe set #598 consisting of the nucleic acids consisting of SEQ ID NO: 2049; 2050 and 2051;
probe set #599 consisting of the nucleic acids consisting of SEQ ID NO: 752; 753 and 754;
probe set #600 consisting of the nucleic acids consisting of SEQ ID NO: 541; 542 and 543;
probe set #601 consisting of the nucleic acids consisting of SEQ ID NO: 1106; 1107 and 1108;
probe set #602 consisting of the nucleic acids consisting of SEQ ID NO: 2072; 2089 and 2102;
probe set #603 consisting of the nucleic acids consisting of SEQ ID NO: 1965; 1966 and 1967;
probe set #604 consisting of the nucleic acids consisting of SEQ ID NO: 2417; 2418 and 2419;
probe set #605 consisting of the nucleic acids consisting of SEQ ID NO: 519; 520 and 521;
probe set #606 consisting of the nucleic acids consisting of SEQ ID NO: 971;
probe set #607 consisting of the nucleic acids consisting of SEQ ID NO: 884 and 888;
probe set #608 consisting of the nucleic acids consisting of SEQ ID NO: 40; 41 and 42;
probe set #609 consisting of the nucleic acids consisting of SEQ ID NO: 24; 25 and 26;
probe set #610 consisting of the nucleic acids consisting of SEQ ID NO: 1182; 1183 and 1184;
probe set #611 consisting of the nucleic acids consisting of SEQ ID NO: 2658; 2676 and 2759;
probe set #612 consisting of the nucleic acids consisting of SEQ ID NO: 2765; 2766 and 2767;
probe set #613 consisting of the nucleic acids consisting of SEQ ID NO: 410; 411 and 412;
probe set #614 consisting of the nucleic acids consisting of SEQ ID NO: 975; 976 and 977;
probe set #615 consisting of the nucleic acids consisting of SEQ ID NO: 1782; 1783 and 1784;
probe set #616 consisting of the nucleic acids consisting of SEQ ID NO: 1926 and 1962;
probe set #617 consisting of the nucleic acids consisting of SEQ ID NO: 975; 976 and 977;
probe set #618 consisting of the nucleic acids consisting of SEQ ID NO: 2072; 2089 and 2092;
probe set #619 consisting of the nucleic acids consisting of SEQ ID NO: 429; 430 and 438;
probe set #620 consisting of the nucleic acids consisting of SEQ ID NO: 1072; 1073 and 1074;
probe set #621 consisting of the nucleic acids consisting of SEQ ID NO: 309; 311 and 310;
probe set #622 consisting of the nucleic acids consisting of SEQ ID NO: 2321; 2322 and 2323;
probe set #623 consisting of the nucleic acids consisting of SEQ ID NO: 1540;
probe set #624 consisting of the nucleic acids consisting of SEQ ID NO: 2072; 2089 and 2102;
probe set #625 consisting of the nucleic acids consisting of SEQ ID NO: 733; 734 and 735;
probe set #626 consisting of the nucleic acids consisting of SEQ ID NO: 99; 100 and 101;
probe set #627 consisting of the nucleic acids consisting of SEQ ID NO: 1394;
probe set #628 consisting of the nucleic acids consisting of SEQ ID NO: 2780; 2781 and 2782;
probe set #629 consisting of the nucleic acids consisting of SEQ ID NO: 1372; 1373 and 1374;
probe set #630 consisting of the nucleic acids consisting of SEQ ID NO: 2679; 2680 and 2681;
probe set #631 consisting of the nucleic acids consisting of SEQ ID NO: 2670; 2708 and 2754;
probe set #632 consisting of the nucleic acids consisting of SEQ ID NO: 1965; 1966 and 1967;
probe set #633 consisting of the nucleic acids consisting of SEQ ID NO: 2795;
probe set #634 consisting of the nucleic acids consisting of SEQ ID NO: 2002;
probe set #635 consisting of the nucleic acids consisting of SEQ ID NO: 68; 69 and 70;
probe set #636 consisting of the nucleic acids consisting of SEQ ID NO: 1020; 1021 and 1022;
probe set #637 consisting of the nucleic acids consisting of SEQ ID NO: 148; 149 and 150;
probe set #638 consisting of the nucleic acids consisting of SEQ ID NO: 1307; 1308 and 1309;
probe set #639 consisting of the nucleic acids consisting of SEQ ID NO: 1944; 1945 and 1946;
probe set #640 consisting of the nucleic acids consisting of SEQ ID NO: 446; 454 and 455;
probe set #641 consisting of the nucleic acids consisting of SEQ ID NO: 1767; 1768 and 1769;
probe set #642 consisting of the nucleic acids consisting of SEQ ID NO: 1971; 1972 and 1987;
probe set #643 consisting of the nucleic acids consisting of SEQ ID NO: 2795;
probe set #644 consisting of the nucleic acids consisting of SEQ ID NO: 899; 900 and 901;
probe set #645 consisting of the nucleic acids consisting of SEQ ID NO: 1962; 1998 and 1999;
probe set #646 consisting of the nucleic acids consisting of SEQ ID NO: 2041; 2042 and 2043;
probe set #647 consisting of the nucleic acids consisting of SEQ ID NO: 1927; 1955 and 1978;
probe set #648 consisting of the nucleic acids consisting of SEQ ID NO: 1990;
probe set #649 consisting of the nucleic acids consisting of SEQ ID NO: 1403; 1404 and 1408;
probe set #650 consisting of the nucleic acids consisting of SEQ ID NO: 1968; 1969 and 1970;
probe set #651 consisting of the nucleic acids consisting of SEQ ID NO: 2209; 2210 and 2211;

probe set #652 consisting of the nucleic acids consisting of SEQ ID NO: 1770; 1771 and 1772;
probe set #653 consisting of the nucleic acids consisting of SEQ ID NO: 1382; 1383 and 1384;
probe set #654 consisting of the nucleic acids consisting of SEQ ID NO: 1927; 1932 and 1987;
probe set #655 consisting of the nucleic acids consisting of SEQ ID NO: 2248;
probe set #656 consisting of the nucleic acids consisting of SEQ ID NO: 2501; 2502 and 2503;
probe set #657 consisting of the nucleic acids consisting of SEQ ID NO: 1133; 1134 and 1135;
probe set #658 consisting of the nucleic acids consisting of SEQ ID NO: 1668; 1669 and 1670;
probe set #659 consisting of the nucleic acids consisting of SEQ ID NO: 2925; 2926 and 2927;
probe set #660 consisting of the nucleic acids consisting of SEQ ID NO: 201; 202 and 203;
probe set #661 consisting of the nucleic acids consisting of SEQ ID NO: 1602; 1603 and 1604;
probe set #662 consisting of the nucleic acids consisting of SEQ ID NO: 1936; 1937 and 1938;
probe set #663 consisting of the nucleic acids consisting of SEQ ID NO: 2504; 2512 and 2543;
probe set #664 consisting of the nucleic acids consisting of SEQ ID NO: 1119; 1120 and 1121;
probe set #665 consisting of the nucleic acids consisting of SEQ ID NO: 1400; 1401 and 1402;
probe set #666 consisting of the nucleic acids consisting of SEQ ID NO: 2700; 2701 and 2702;
probe set #667 consisting of the nucleic acids consisting of SEQ ID NO: 2811; 2812 and 2813;
probe set #668 consisting of the nucleic acids consisting of SEQ ID NO: 1955 and 1964;
probe set #669 consisting of the nucleic acids consisting of SEQ ID NO: 672; 673 and 674;
probe set #670 consisting of the nucleic acids consisting of SEQ ID NO: 582; 583 and 584;
probe set #671 consisting of the nucleic acids consisting of SEQ ID NO: 1920; 1933 and 1999;
probe set #672 consisting of the nucleic acids consisting of SEQ ID NO: 2755; 2756 and 2757;
probe set #673 consisting of the nucleic acids consisting of SEQ ID NO: 2659 and 2746;
probe set #674 consisting of the nucleic acids consisting of SEQ ID NO: 2035; 2036 and 2037;
probe set #675 consisting of the nucleic acids consisting of SEQ ID NO: 2662; 2663 and 2664;
probe set #676 consisting of the nucleic acids consisting of SEQ ID NO: 2771; 2772 and 2773;
probe set #677 consisting of the nucleic acids consisting of SEQ ID NO: 2317; 2318 and 2319;
probe set #678 consisting of the nucleic acids consisting of SEQ ID NO: 456; 457 and 458;
probe set #679 consisting of the nucleic acids consisting of SEQ ID NO: 2539; 2540 and 2541;
probe set #680 consisting of the nucleic acids consisting of SEQ ID NO: 2582; 2583 and 2584;
probe set #681 consisting of the nucleic acids consisting of SEQ ID NO: 868; 1117 and 1118;
probe set #682 consisting of the nucleic acids consisting of SEQ ID NO: 2801;
probe set #683 consisting of the nucleic acids consisting of SEQ ID NO: 2659; 2707 and 2709;
probe set #684 consisting of the nucleic acids consisting of SEQ ID NO: 2659; 2660 and 2709;
probe set #685 consisting of the nucleic acids consisting of SEQ ID NO: 1920; 1933 and 1999;
probe set #686 consisting of the nucleic acids consisting of SEQ ID NO: 1791; 1792 and 1793;
probe set #687 consisting of the nucleic acids consisting of SEQ ID NO: 633; 634 and 635;
probe set #688 consisting of the nucleic acids consisting of SEQ ID NO: 1351; 1352 and 1353;
probe set #689 consisting of the nucleic acids consisting of SEQ ID NO: 934; 935 and 941;
probe set #690 consisting of the nucleic acids consisting of SEQ ID NO: 938; 939 and 940;
probe set #691 consisting of the nucleic acids consisting of SEQ ID NO: 1009; 1023 and 1024;
probe set #692 consisting of the nucleic acids consisting of SEQ ID NO: 2314; 2315 and 2316;
probe set #693 consisting of the nucleic acids consisting of SEQ ID NO: 2704; 2705 and 2706;
probe set #694 consisting of the nucleic acids consisting of SEQ ID NO: 2341; 2342 and 2343;
probe set #695 consisting of the nucleic acids consisting of SEQ ID NO: 1797; 1798 and 1799;
probe set #696 consisting of the nucleic acids consisting of SEQ ID NO: 1767; 1768 and 1769;
probe set #697 consisting of the nucleic acids consisting of SEQ ID NO: 1467 and 1468;
probe set #698 consisting of the nucleic acids consisting of SEQ ID NO: 1770; 1771 and 1772;
probe set #699 consisting of the nucleic acids consisting of SEQ ID NO: 2035; 2036 and 2037;
probe set #700 consisting of the nucleic acids consisting of SEQ ID NO: 37; 38 and 39;
probe set #701 consisting of the nucleic acids consisting of SEQ ID NO: 678; 679 and 680;
probe set #702 consisting of the nucleic acids consisting of SEQ ID NO: 1920; 1933 and 1999;
probe set #703 consisting of the nucleic acids consisting of SEQ ID NO: 2242; 2252 and 2271;
probe set #704 consisting of the nucleic acids consisting of SEQ ID NO: 2417; 2418 and 2419;
probe set #705 consisting of the nucleic acids consisting of SEQ ID NO: 2356; 2357 and 2358;
probe set #706 consisting of the nucleic acids consisting of SEQ ID NO: 1541; 1542 and 1543;
probe set #707 consisting of the nucleic acids consisting of SEQ ID NO: 2245; 2246 and 2247;
probe set #708 consisting of the nucleic acids consisting of SEQ ID NO: 2194; 2198 and 2199;
probe set #709 consisting of the nucleic acids consisting of SEQ ID NO: 2498; 2499 and 2500;
probe set #710 consisting of the nucleic acids consisting of SEQ ID NO: 287; 289 and 288;
probe set #711 consisting of the nucleic acids consisting of SEQ ID NO: 2671; 2672 and 2708;
probe set #712 consisting of the nucleic acids consisting of SEQ ID NO: 2130; 2131 and 2132;
probe set #713 consisting of the nucleic acids consisting of SEQ ID NO: 448; 449 and 450;
probe set #714 consisting of the nucleic acids consisting of SEQ ID NO: 413; 414 and 415;
probe set #715 consisting of the nucleic acids consisting of SEQ ID NO: 2148; 2150 and 2151;
probe set #716 consisting of the nucleic acids consisting of SEQ ID NO: 2875; 2876 and 2877;
probe set #717 consisting of the nucleic acids consisting of SEQ ID NO: 2060; 2072 and 2097;

probe set #718 consisting of the nucleic acids consisting of SEQ ID NO: 2060; 2072 and 2092;
probe set #719 consisting of the nucleic acids consisting of SEQ ID NO: 983; 984 and 985;
probe set #720 consisting of the nucleic acids consisting of SEQ ID NO: 1276; 1277 and 1285;
probe set #721 consisting of the nucleic acids consisting of SEQ ID NO: 985;
probe set #722 consisting of the nucleic acids consisting of SEQ ID NO: 2631; 2632 and 2633;
probe set #723 consisting of the nucleic acids consisting of SEQ ID NO: 207; 208 and 209;
probe set #724 consisting of the nucleic acids consisting of SEQ ID NO: 999; 1000 and 1001;
probe set #725 consisting of the nucleic acids consisting of SEQ ID NO: 521; 527 and 528;
probe set #726 consisting of the nucleic acids consisting of SEQ ID NO: 111; 112 and 113;
probe set #727 consisting of the nucleic acids consisting of SEQ ID NO: 1400; 1401 and 1402;
probe set #728 consisting of the nucleic acids consisting of SEQ ID NO: 1339; 1340 and 1341;
probe set #729 consisting of the nucleic acids consisting of SEQ ID NO: 912; 913 and 914;
probe set #730 consisting of the nucleic acids consisting of SEQ ID NO: 1574; 1575 and 1576;
probe set #731 consisting of the nucleic acids consisting of SEQ ID NO: 573; 614 and 642;
probe set #732 consisting of the nucleic acids consisting of SEQ ID NO: 1761; 1762 and 1763;
probe set #733 consisting of the nucleic acids consisting of SEQ ID NO: 2713; 2714 and 2715;
probe set #734 consisting of the nucleic acids consisting of SEQ ID NO: 589; 590 and 591;
probe set #735 consisting of the nucleic acids consisting of SEQ ID NO: 53; 54 and 55;
probe set #736 consisting of the nucleic acids consisting of SEQ ID NO: 2768; 2769 and 2770;
probe set #737 consisting of the nucleic acids consisting of SEQ ID NO: 264; 271 and 272;
probe set #738 consisting of the nucleic acids consisting of SEQ ID NO: 2321; 2322 and 2323;
probe set #739 consisting of the nucleic acids consisting of SEQ ID NO: 2683; 2684 and 2685;
probe set #740 consisting of the nucleic acids consisting of SEQ ID NO: 2160; 2161 and 2162;
probe set #741 consisting of the nucleic acids consisting of SEQ ID NO: 1097; 1098 and 1099;
probe set #742 consisting of the nucleic acids consisting of SEQ ID NO: 2063; 2065 and 2098;
probe set #743 consisting of the nucleic acids consisting of SEQ ID NO: 263; 264 and 271;
probe set #744 consisting of the nucleic acids consisting of SEQ ID NO: 1278; 1279 and 1280;
probe set #745 consisting of the nucleic acids consisting of SEQ ID NO: 2596; 2597 and 2598;
probe set #746 consisting of the nucleic acids consisting of SEQ ID NO: 1964; 1988 and 1989;
probe set #747 consisting of the nucleic acids consisting of SEQ ID NO: 2547;
probe set #748 consisting of the nucleic acids consisting of SEQ ID NO: 1605; 1606 and 1607;
probe set #749 consisting of the nucleic acids consisting of SEQ ID NO: 204; 205 and 206;
probe set #750 consisting of the nucleic acids consisting of SEQ ID NO: 2245; 2246 and 2247;
probe set #751 consisting of the nucleic acids consisting of SEQ ID NO: 2659; 2703 and 2709;
probe set #752 consisting of the nucleic acids consisting of SEQ ID NO: 1406; 1407 and 1413;
probe set #753 consisting of the nucleic acids consisting of SEQ ID NO: 1435;
probe set #754 consisting of the nucleic acids consisting of SEQ ID NO: 766; 767 and 768;
probe set #755 consisting of the nucleic acids consisting of SEQ ID NO: 1381;
probe set #756 consisting of the nucleic acids consisting of SEQ ID NO: 2222; 2223 and 2224;
probe set #757 consisting of the nucleic acids consisting of SEQ ID NO: 1238;
probe set #758 consisting of the nucleic acids consisting of SEQ ID NO: 1920; 1933 and 1999;
probe set #759 consisting of the nucleic acids consisting of SEQ ID NO: 1981;
probe set #760 consisting of the nucleic acids consisting of SEQ ID NO: 746; 747 and 748;
probe set #761 consisting of the nucleic acids consisting of SEQ ID NO: 2659; 2707 and 2709;
probe set #762 consisting of the nucleic acids consisting of SEQ ID NO: 1927; 1943 and 1978;
probe set #763 consisting of the nucleic acids consisting of SEQ ID NO: 2232; 2233 and 2234;
probe set #764 consisting of the nucleic acids consisting of SEQ ID NO: 2052; 2053 and 2054;
probe set #765 consisting of the nucleic acids consisting of SEQ ID NO: 1713; 1714 and 1715;
probe set #766 consisting of the nucleic acids consisting of SEQ ID NO: 602 and 603;
probe set #767 consisting of the nucleic acids consisting of SEQ ID NO: 702; 703 and 704;
probe set #768 consisting of the nucleic acids consisting of SEQ ID NO: 2438; 2439 and 2440;
probe set #769 consisting of the nucleic acids consisting of SEQ ID NO: 1943; 1955 and 1978;
probe set #770 consisting of the nucleic acids consisting of SEQ ID NO: 2378; 2379 and 2380;
probe set #771 consisting of the nucleic acids consisting of SEQ ID NO: 702; 703 and 704;
probe set #772 consisting of the nucleic acids consisting of SEQ ID NO: 2073; 2074 and 2109;
probe set #773 consisting of the nucleic acids consisting of SEQ ID NO: 2936; 2937 and 2938;
probe set #774 consisting of the nucleic acids consisting of SEQ ID NO: 2280; 2281 and 2282;
probe set #775 consisting of the nucleic acids consisting of SEQ ID NO: 2438; 2439 and 2440;
probe set #776 consisting of the nucleic acids consisting of SEQ ID NO: 1231; 1232 and 1233;
probe set #777 consisting of the nucleic acids consisting of SEQ ID NO: 1764; 1765 and 1766;
probe set #778 consisting of the nucleic acids consisting of SEQ ID NO: 391; 392 and 393;
probe set #779 consisting of the nucleic acids consisting of SEQ ID NO: 1931; 1962 and 1999;
probe set #780 consisting of the nucleic acids consisting of SEQ ID NO: 2282; 2289 and 2305;
probe set #781 consisting of the nucleic acids consisting of SEQ ID NO: 582; 583 and 584;
probe set #782 consisting of the nucleic acids consisting of SEQ ID NO: 1220; 1221 and 1222;
probe set #783 consisting of the nucleic acids consisting of SEQ ID NO: 1935;

probe set #784 consisting of the nucleic acids consisting of SEQ ID NO: 1718; 1719 and 1720;
probe set #785 consisting of the nucleic acids consisting of SEQ ID NO: 1737; 1738 and 1739;
probe set #786 consisting of the nucleic acids consisting of SEQ ID NO: 2908; 2909 and 2917;
probe set #787 consisting of the nucleic acids consisting of SEQ ID NO: 1957;
probe set #788 consisting of the nucleic acids consisting of SEQ ID NO: 2622; 2623 and 2624;
probe set #789 consisting of the nucleic acids consisting of SEQ ID NO: 2438; 2439 and 2440;
probe set #790 consisting of the nucleic acids consisting of SEQ ID NO: 2192; 2193 and 2200;
probe set #791 consisting of the nucleic acids consisting of SEQ ID NO: 1920; 1933 and 1999;
probe set #792 consisting of the nucleic acids consisting of SEQ ID NO: 1296; 1487 and 1488;
probe set #793 consisting of the nucleic acids consisting of SEQ ID NO: 947; 948 and 949;
probe set #794 consisting of the nucleic acids consisting of SEQ ID NO: 2617; 2618 and 2619;
probe set #795 consisting of the nucleic acids consisting of SEQ ID NO: 2362;
probe set #796 consisting of the nucleic acids consisting of SEQ ID NO: 1129; 1139 and 1140;
probe set #797 consisting of the nucleic acids consisting of SEQ ID NO: 2659; 2703 and 2709;
probe set #798 consisting of the nucleic acids consisting of SEQ ID NO: 419; 420 and 421;
probe set #799 consisting of the nucleic acids consisting of SEQ ID NO: 23; 29 and 30;
probe set #800 consisting of the nucleic acids consisting of SEQ ID NO: 1122;
probe set #801 consisting of the nucleic acids consisting of SEQ ID NO: 1423; 1447 and 1448;
probe set #802 consisting of the nucleic acids consisting of SEQ ID NO: 2710; 2711 and 2712;
probe set #803 consisting of the nucleic acids consisting of SEQ ID NO: 675; 676 and 677;
probe set #804 consisting of the nucleic acids consisting of SEQ ID NO: 2458; 2461 and 2462;
probe set #805 consisting of the nucleic acids consisting of SEQ ID NO: 1831; 1832 and 1833;
probe set #806 consisting of the nucleic acids consisting of SEQ ID NO: 618; 619 and 620;
probe set #807 consisting of the nucleic acids consisting of SEQ ID NO: 983; 984 and 985;
probe set #808 consisting of the nucleic acids consisting of SEQ ID NO: 2000 and 2001;
probe set #809 consisting of the nucleic acids consisting of SEQ ID NO: 2625; 2626 and 2627;
probe set #810 consisting of the nucleic acids consisting of SEQ ID NO: 714; 715 and 716;
probe set #811 consisting of the nucleic acids consisting of SEQ ID NO: 2659; 2660 and 2758;
probe set #812 consisting of the nucleic acids consisting of SEQ ID NO: 448; 449 and 450;
probe set #813 consisting of the nucleic acids consisting of SEQ ID NO: 1986;
probe set #814 consisting of the nucleic acids consisting of SEQ ID NO: 2699;
probe set #815 consisting of the nucleic acids consisting of SEQ ID NO: 2726; 2727 and 2728;
probe set #816 consisting of the nucleic acids consisting of SEQ ID NO: 2145; 2146 and 2147;
probe set #817 consisting of the nucleic acids consisting of SEQ ID NO: 2437; 2459 and 2460;
probe set #818 consisting of the nucleic acids consisting of SEQ ID NO: 2743; 2744 and 2745;
probe set #819 consisting of the nucleic acids consisting of SEQ ID NO: 2659; 2703 and 2709;
probe set #820 consisting of the nucleic acids consisting of SEQ ID NO: 592; 593 and 594;
probe set #821 consisting of the nucleic acids consisting of SEQ ID NO: 476; 477 and 478;
probe set #822 consisting of the nucleic acids consisting of SEQ ID NO: 1011; 1012 and 1013;
probe set #823 consisting of the nucleic acids consisting of SEQ ID NO: 1571; 1572 and 1573;
probe set #824 consisting of the nucleic acids consisting of SEQ ID NO: 1345; 1346 and 1347;
probe set #825 consisting of the nucleic acids consisting of SEQ ID NO: 2242; 2252 and 2259;
probe set #826 consisting of the nucleic acids consisting of SEQ ID NO: 661 and 662;
probe set #827 consisting of the nucleic acids consisting of SEQ ID NO: 1608; 1609 and 1610;
probe set #828 consisting of the nucleic acids consisting of SEQ ID NO: 2170; 2171 and 2172;
probe set #829 consisting of the nucleic acids consisting of SEQ ID NO: 2855; 2856 and 2859;
probe set #830 consisting of the nucleic acids consisting of SEQ ID NO: 1785; 1786 and 1787;
probe set #831 consisting of the nucleic acids consisting of SEQ ID NO: 1231; 1232 and 1233;
probe set #832 consisting of the nucleic acids consisting of SEQ ID NO: 2659; 2660 and 2709;
probe set #833 consisting of the nucleic acids consisting of SEQ ID NO: 766; 767 and 768;
probe set #834 consisting of the nucleic acids consisting of SEQ ID NO: 518; 522 and 523;
probe set #835 consisting of the nucleic acids consisting of SEQ ID NO: 2876; 2877 and 2878;
probe set #836 consisting of the nucleic acids consisting of SEQ ID NO: 1351; 1352 and 1353;
probe set #837 consisting of the nucleic acids consisting of SEQ ID NO: 630; 631 and 632;
probe set #838 consisting of the nucleic acids consisting of SEQ ID NO: 1577; 1578 and 1579;
probe set #839 consisting of the nucleic acids consisting of SEQ ID NO: 275; 276 and 277;
probe set #840 consisting of the nucleic acids consisting of SEQ ID NO: 2637; 2638 and 2639;
probe set #841 consisting of the nucleic acids consisting of SEQ ID NO: 1806; 1821 and 1822;
probe set #842 consisting of the nucleic acids consisting of SEQ ID NO: 233; 249 and 250;
probe set #843 consisting of the nucleic acids consisting of SEQ ID NO: 769; 770 and 771;
probe set #844 consisting of the nucleic acids consisting of SEQ ID NO: 996; 997 and 998;
probe set #845 consisting of the nucleic acids consisting of SEQ ID NO: 927; 928 and 929;
probe set #846 consisting of the nucleic acids consisting of SEQ ID NO: 399; 400 and 401;
probe set #847 consisting of the nucleic acids consisting of SEQ ID NO: 219; 220 and 221;
probe set #848 consisting of the nucleic acids consisting of SEQ ID NO: 2347; 2348 and 2349;
probe set #849 consisting of the nucleic acids consisting of SEQ ID NO: 71; 72 and 73;

probe set #850 consisting of the nucleic acids consisting of SEQ ID NO: 35 and 36;
probe set #851 consisting of the nucleic acids consisting of SEQ ID NO: 2704; 2705 and 2706;
probe set #852 consisting of the nucleic acids consisting of SEQ ID NO: 2263;
probe set #853 consisting of the nucleic acids consisting of SEQ ID NO: 2438; 2439 and 2440;
probe set #854 consisting of the nucleic acids consisting of SEQ ID NO: 13; 14 and 16;
probe set #855 consisting of the nucleic acids consisting of SEQ ID NO: 1779; 1780 and 1781;
probe set #856 consisting of the nucleic acids consisting of SEQ ID NO: 2309 and 2310;
probe set #857 consisting of the nucleic acids consisting of SEQ ID NO: 1884; 1885 and 1886;
probe set #858 consisting of the nucleic acids consisting of SEQ ID NO: 1964; 1988 and 1989;
probe set #859 consisting of the nucleic acids consisting of SEQ ID NO: 1354; 1355 and 1356;
probe set #860 consisting of the nucleic acids consisting of SEQ ID NO: 2660; 2672 and 2708;
probe set #861 consisting of the nucleic acids consisting of SEQ ID NO: 1281; 1282 and 1283;
probe set #862 consisting of the nucleic acids consisting of SEQ ID NO: 1332; 1333 and 1334;
probe set #863 consisting of the nucleic acids consisting of SEQ ID NO: 1090; 1091 and 1092;
probe set #864 consisting of the nucleic acids consisting of SEQ ID NO: 2099;
probe set #865 consisting of the nucleic acids consisting of SEQ ID NO: 2659; 2705 and 2761;
probe set #866 consisting of the nucleic acids consisting of SEQ ID NO: 2747; 2748 and 2753;
probe set #867 consisting of the nucleic acids consisting of SEQ ID NO: 1834 and 1835;
probe set #868 consisting of the nucleic acids consisting of SEQ ID NO: 2010; 2011 and 2012;
probe set #869 consisting of the nucleic acids consisting of SEQ ID NO: 2658; 2747 and 2753;
probe set #870 consisting of the nucleic acids consisting of SEQ ID NO: 442; 443 and 444;
probe set #871 consisting of the nucleic acids consisting of SEQ ID NO: 2274; 2275 and 2276;
probe set #872 consisting of the nucleic acids consisting of SEQ ID NO: 1926 and 1962;
probe set #873 consisting of the nucleic acids consisting of SEQ ID NO: 2833; 2834 and 2835;
probe set #874 consisting of the nucleic acids consisting of SEQ ID NO: 2686; 2687 and 2688;
probe set #875 consisting of the nucleic acids consisting of SEQ ID NO: 2300; 2301 and 2306;
probe set #876 consisting of the nucleic acids consisting of SEQ ID NO: 719; 720 and 721;
probe set #877 consisting of the nucleic acids consisting of SEQ ID NO: 13; 14 and 16;
probe set #878 consisting of the nucleic acids consisting of SEQ ID NO: 702; 705 and 709;
probe set #879 consisting of the nucleic acids consisting of SEQ ID NO: 1351; 1352 and 1353;
probe set #880 consisting of the nucleic acids consisting of SEQ ID NO: 889; 890 and 891;
probe set #881 consisting of the nucleic acids consisting of SEQ ID NO: 164; 165 and 166;
probe set #882 consisting of the nucleic acids consisting of SEQ ID NO: 908; 909 and 910;
probe set #883 consisting of the nucleic acids consisting of SEQ ID NO: 2720; 2721 and 2722;
probe set #884 consisting of the nucleic acids consisting of SEQ ID NO: 2486; 2487 and 2488;
probe set #885 consisting of the nucleic acids consisting of SEQ ID NO: 871 and 872;
probe set #886 consisting of the nucleic acids consisting of SEQ ID NO: 105; 106 and 107;
probe set #887 consisting of the nucleic acids consisting of SEQ ID NO: 2153; 2154 and 2155;
probe set #888 consisting of the nucleic acids consisting of SEQ ID NO: 651;
probe set #889 consisting of the nucleic acids consisting of SEQ ID NO: 1611; 1612 and 1613;
probe set #890 consisting of the nucleic acids consisting of SEQ ID NO: 2165; 2166 and 2167;
probe set #891 consisting of the nucleic acids consisting of SEQ ID NO: 875 and 880;
probe set #892 consisting of the nucleic acids consisting of SEQ ID NO: 2089;
probe set #893 consisting of the nucleic acids consisting of SEQ ID NO: 2299;
probe set #894 consisting of the nucleic acids consisting of SEQ ID NO: 1154; 1155 and 1156;
probe set #895 consisting of the nucleic acids consisting of SEQ ID NO: 2052; 2053 and 2054;
probe set #896 consisting of the nucleic acids consisting of SEQ ID NO: 2660; 2694 and 2695;
probe set #897 consisting of the nucleic acids consisting of SEQ ID NO: 2431 and 2432;
probe set #898 consisting of the nucleic acids consisting of SEQ ID NO: 761; 762 and 764;
probe set #899 consisting of the nucleic acids consisting of SEQ ID NO: 2072; 2077 and 2092;
probe set #900 consisting of the nucleic acids consisting of SEQ ID NO: 1767; 1768 and 1769;
probe set #901 consisting of the nucleic acids consisting of SEQ ID NO: 902;
probe set #902 consisting of the nucleic acids consisting of SEQ ID NO: 702; 705 and 709;
probe set #903 consisting of the nucleic acids consisting of SEQ ID NO: 933; 936 and 937;
probe set #904 consisting of the nucleic acids consisting of SEQ ID NO: 762; 765 and 773;
probe set #905 consisting of the nucleic acids consisting of SEQ ID NO: 2060; 2072 and 2097;
probe set #906 consisting of the nucleic acids consisting of SEQ ID NO: 2145; 2146 and 2147;
probe set #907 consisting of the nucleic acids consisting of SEQ ID NO: 687; 688 and 689;
probe set #908 consisting of the nucleic acids consisting of SEQ ID NO: 83; 84 and 85;
probe set #909 consisting of the nucleic acids consisting of SEQ ID NO: 2318; 2319 and 2320;
probe set #910 consisting of the nucleic acids consisting of SEQ ID NO: 2580; 2581 and 2582;
probe set #911 consisting of the nucleic acids consisting of SEQ ID NO: 2879; 2880 and 2882;
probe set #912 consisting of the nucleic acids consisting of SEQ ID NO: 2551; 2552 and 2553;
probe set #913 consisting of the nucleic acids consisting of SEQ ID NO: 2734; 2735 and 2736;
probe set #914 consisting of the nucleic acids consisting of SEQ ID NO: 2268; 2269 and 2270;
probe set #915 consisting of the nucleic acids consisting of SEQ ID NO: 934; 935 and 941;

probe set #916 consisting of the nucleic acids consisting of SEQ ID NO: 2838;
probe set #917 consisting of the nucleic acids consisting of SEQ ID NO: 1412 and 1414;
probe set #918 consisting of the nucleic acids consisting of SEQ ID NO: 1273; 1274 and 1275;
probe set #919 consisting of the nucleic acids consisting of SEQ ID NO: 65; 66 and 67;
probe set #920 consisting of the nucleic acids consisting of SEQ ID NO: 2052; 2056 and 2057;
probe set #921 consisting of the nucleic acids consisting of SEQ ID NO: 1727; 1728 and 1729;
probe set #922 consisting of the nucleic acids consisting of SEQ ID NO: 1357; 1358 and 1359;
probe set #923 consisting of the nucleic acids consisting of SEQ ID NO: 2737; 2738 and 2739;
probe set #924 consisting of the nucleic acids consisting of SEQ ID NO: 2879; 2880 and 2881;
probe set #925 consisting of the nucleic acids consisting of SEQ ID NO: 2932;
probe set #926 consisting of the nucleic acids consisting of SEQ ID NO: 93; 94 and 95;
probe set #927 consisting of the nucleic acids consisting of SEQ ID NO: 2133;
probe set #928 consisting of the nucleic acids consisting of SEQ ID NO: 574; 587 and 588;
probe set #929 consisting of the nucleic acids consisting of SEQ ID NO: 2397; 2398 and 2399;
probe set #930 consisting of the nucleic acids consisting of SEQ ID NO: 2914; 2915 and 2916;
probe set #931 consisting of the nucleic acids consisting of SEQ ID NO: 1496; 1498 and 1506;
probe set #932 consisting of the nucleic acids consisting of SEQ ID NO: 1731; 1732 and 1733;
probe set #933 consisting of the nucleic acids consisting of SEQ ID NO: 2292; 2293 and 2294;
probe set #934 consisting of the nucleic acids consisting of SEQ ID NO: 1461; 1462 and 1463;
probe set #935 consisting of the nucleic acids consisting of SEQ ID NO: 2646; 2647 and 2648;
probe set #936 consisting of the nucleic acids consisting of SEQ ID NO: 2788; 2789 and 2790;
probe set #937 consisting of the nucleic acids consisting of SEQ ID NO: 2428; 2429 and 2430;
probe set #938 consisting of the nucleic acids consisting of SEQ ID NO: 884; 885 and 886;
probe set #939 consisting of the nucleic acids consisting of SEQ ID NO: 416; 417 and 418;
probe set #940 consisting of the nucleic acids consisting of SEQ ID NO: 402; 403 and 404;
probe set #941 consisting of the nucleic acids consisting of SEQ ID NO: 56; 57 and 58;
probe set #942 consisting of the nucleic acids consisting of SEQ ID NO: 473; 474 and 475;
probe set #943 consisting of the nucleic acids consisting of SEQ ID NO: 663; 664 and 665;
probe set #944 consisting of the nucleic acids consisting of SEQ ID NO: 1876; 1877 and 1878;
probe set #945 consisting of the nucleic acids consisting of SEQ ID NO: 1716 and 1717;
probe set #946 consisting of the nucleic acids consisting of SEQ ID NO: 2233; 2234 and 2238;
probe set #947 consisting of the nucleic acids consisting of SEQ ID NO: 1813; 1814 and 1815;
probe set #948 consisting of the nucleic acids consisting of SEQ ID NO: 740; 741 and 742;
probe set #949 consisting of the nucleic acids consisting of SEQ ID NO: 1028;
probe set #950 consisting of the nucleic acids consisting of SEQ ID NO: 2889; 2890 and 2891;
probe set #951 consisting of the nucleic acids consisting of SEQ ID NO: 2780; 2781 and 2782;
probe set #952 consisting of the nucleic acids consisting of SEQ ID NO: 482; 483 and 484;
probe set #953 consisting of the nucleic acids consisting of SEQ ID NO: 1855; 1856 and 1857;
probe set #954 consisting of the nucleic acids consisting of SEQ ID NO: 884; 885 and 886;
probe set #955 consisting of the nucleic acids consisting of SEQ ID NO: 1407; 1412 and 1413;
probe set #956 consisting of the nucleic acids consisting of SEQ ID NO: 595;
probe set #957 consisting of the nucleic acids consisting of SEQ ID NO: 2585; 2586 and 2587;
probe set #958 consisting of the nucleic acids consisting of SEQ ID NO: 908; 909 and 910;
probe set #959 consisting of the nucleic acids consisting of SEQ ID NO: 659; 660 and 661;
probe set #960 consisting of the nucleic acids consisting of SEQ ID NO: 2218; 2219 and 2220;
probe set #961 consisting of the nucleic acids consisting of SEQ ID NO: 2670; 2672 and 2708;
probe set #962 consisting of the nucleic acids consisting of SEQ ID NO: 621; 622 and 623;
probe set #963 consisting of the nucleic acids consisting of SEQ ID NO: 213; 214 and 215;
probe set #964 consisting of the nucleic acids consisting of SEQ ID NO: 1851; 1853 and 1854;
probe set #965 consisting of the nucleic acids consisting of SEQ ID NO: 2420; 2421 and 2422;
probe set #966 consisting of the nucleic acids consisting of SEQ ID NO: 1909;
probe set #967 consisting of the nucleic acids consisting of SEQ ID NO: 485; 486 and 487;
probe set #968 consisting of the nucleic acids consisting of SEQ ID NO: 2249; 2250 and 2251;
probe set #969 consisting of the nucleic acids consisting of SEQ ID NO: 1400; 1401 and 1402;
probe set #970 consisting of the nucleic acids consisting of SEQ ID NO: 2073; 2074 and 2109;
probe set #971 consisting of the nucleic acids consisting of SEQ ID NO: 518; 522 and 523;
probe set #972 consisting of the nucleic acids consisting of SEQ ID NO: 702; 703 and 704;
probe set #973 consisting of the nucleic acids consisting of SEQ ID NO: 1794; 1795 and 1796;
probe set #974 consisting of the nucleic acids consisting of SEQ ID NO: 2153; 2154 and 2155;
probe set #975 consisting of the nucleic acids consisting of SEQ ID NO: 1173;
probe set #976 consisting of the nucleic acids consisting of SEQ ID NO: 2277; 2278 and 2279;
probe set #977 consisting of the nucleic acids consisting of SEQ ID NO: 2659; 2660 and 2672;
probe set #978 consisting of the nucleic acids consisting of SEQ ID NO: 2438; 2439 and 2440;
probe set #979 consisting of the nucleic acids consisting of SEQ ID NO: 2704; 2705 and 2706;
probe set #980 consisting of the nucleic acids consisting of SEQ ID NO: 2544; 2545 and 2546;
probe set #981 consisting of the nucleic acids consisting of SEQ ID NO: 233; 249 and 250;

probe set #982 consisting of the nucleic acids consisting of SEQ ID NO: 2589; 2591 and 2592;
probe set #983 consisting of the nucleic acids consisting of SEQ ID NO: 684; 685 and 686;
probe set #984 consisting of the nucleic acids consisting of SEQ ID NO: 2124; 2125 and 2126;
probe set #985 consisting of the nucleic acids consisting of SEQ ID NO: 240; 241 and 242;
probe set #986 consisting of the nucleic acids consisting of SEQ ID NO: 1624; 1625 and 1626;
probe set #987 consisting of the nucleic acids consisting of SEQ ID NO: 2474; 2475 and 2476;
probe set #988 consisting of the nucleic acids consisting of SEQ ID NO: 1652; 1653 and 1654;
probe set #989 consisting of the nucleic acids consisting of SEQ ID NO: 1958; 1959 and 1960;
probe set #990 consisting of the nucleic acids consisting of SEQ ID NO: 902 and 911;
probe set #991 consisting of the nucleic acids consisting of SEQ ID NO: 2605; 2606 and 2610;
probe set #992 consisting of the nucleic acids consisting of SEQ ID NO: 2729; 2730 and 2731;
probe set #993 consisting of the nucleic acids consisting of SEQ ID NO: 1577; 1578 and 1579;
probe set #994 consisting of the nucleic acids consisting of SEQ ID NO: 2397; 2398 and 2399;
probe set #995 consisting of the nucleic acids consisting of SEQ ID NO: 1421; 1422 and 1423;
probe set #996 consisting of the nucleic acids consisting of SEQ ID NO: 2080; 2081 and 2082;
probe set #997 consisting of the nucleic acids consisting of SEQ ID NO: 941; 942 and 943;
probe set #998 consisting of the nucleic acids consisting of SEQ ID NO: 1407; 1412 and 1413;
probe set #999 consisting of the nucleic acids consisting of SEQ ID NO: 610; 611 and 612;
probe set #1000 consisting of the nucleic acids consisting of SEQ ID NO: 780; 781 and 782;
probe set #1001 consisting of the nucleic acids consisting of SEQ ID NO: 2849; 2850 and 2851;
probe set #1002 consisting of the nucleic acids consisting of SEQ ID NO: 2318; 2319 and 2324;
probe set #1003 consisting of the nucleic acids consisting of SEQ ID NO: 2065; 2068 and 2098;
probe set #1004 consisting of the nucleic acids consisting of SEQ ID NO: 1905; 1906 and 1907;
probe set #1005 consisting of the nucleic acids consisting of SEQ ID NO: 1617; 1618 and 1619;
probe set #1006 consisting of the nucleic acids consisting of SEQ ID NO: 2118 and 2119;
probe set #1007 consisting of the nucleic acids consisting of SEQ ID NO: 1391; 1392 and 1393;
probe set #1008 consisting of the nucleic acids consisting of SEQ ID NO: 2063; 2065 and 2098;
probe set #1009 consisting of the nucleic acids consisting of SEQ ID NO: 2673; 2674 and 2675;
probe set #1010 consisting of the nucleic acids consisting of SEQ ID NO: 2879; 2880 and 2881;
probe set #1011 consisting of the nucleic acids consisting of SEQ ID NO: 405; 406 and 407;
probe set #1012 consisting of the nucleic acids consisting of SEQ ID NO: 2153; 2154 and 2155;
probe set #1013 consisting of the nucleic acids consisting of SEQ ID NO: 1106; 1107 and 1108;
probe set #1014 consisting of the nucleic acids consisting of SEQ ID NO: 2466;
probe set #1015 consisting of the nucleic acids consisting of SEQ ID NO: 964;
probe set #1016 consisting of the nucleic acids consisting of SEQ ID NO: 2153; 2154 and 2156;
probe set #1017 consisting of the nucleic acids consisting of SEQ ID NO: 2000 and 2001;
probe set #1018 consisting of the nucleic acids consisting of SEQ ID NO: 83; 84 and 85;
probe set #1019 consisting of the nucleic acids consisting of SEQ ID NO: 2182; 2183 and 2184;
probe set #1020 consisting of the nucleic acids consisting of SEQ ID NO: 2127; 2128 and 2129;
probe set #1021 consisting of the nucleic acids consisting of SEQ ID NO: 646;
probe set #1022 consisting of the nucleic acids consisting of SEQ ID NO: 80; 81 and 82;
probe set #1023 consisting of the nucleic acids consisting of SEQ ID NO: 589; 590 and 591;
probe set #1024 consisting of the nucleic acids consisting of SEQ ID NO: 930 and 931;
probe set #1025 consisting of the nucleic acids consisting of SEQ ID NO: 2290; 2291 and 2310;
probe set #1026 consisting of the nucleic acids consisting of SEQ ID NO: 237; 238 and 239;
probe set #1027 consisting of the nucleic acids consisting of SEQ ID NO: 2438; 2439 and 2440;
probe set #1028 consisting of the nucleic acids consisting of SEQ ID NO: 2148; 2150 and 2151;
probe set #1029 consisting of the nucleic acids consisting of SEQ ID NO: 2514; 2515 and 2516;
probe set #1030 consisting of the nucleic acids consisting of SEQ ID NO: 2438; 2439 and 2440;
probe set #1031 consisting of the nucleic acids consisting of SEQ ID NO: 133; 134 and 135;
probe set #1032 consisting of the nucleic acids consisting of SEQ ID NO: 1342; 1343 and 1344;
probe set #1033 consisting of the nucleic acids consisting of SEQ ID NO: 2329; 2335 and 2336;
probe set #1034 consisting of the nucleic acids consisting of SEQ ID NO: 2433; 2434 and 2435;
probe set #1035 consisting of the nucleic acids consisting of SEQ ID NO: 2659; 2660 and 2709;
probe set #1036 consisting of the nucleic acids consisting of SEQ ID NO: 2060; 2072 and 2092;
probe set #1037 consisting of the nucleic acids consisting of SEQ ID NO: 875; 876 and 880;
probe set #1038 consisting of the nucleic acids consisting of SEQ ID NO: 1035;
probe set #1039 consisting of the nucleic acids consisting of SEQ ID NO: 2863; 2864 and 2865;
probe set #1040 consisting of the nucleic acids consisting of SEQ ID NO: 596; 597 and 598;
probe set #1041 consisting of the nucleic acids consisting of SEQ ID NO: 233; 249 and 250;
probe set #1042 consisting of the nucleic acids consisting of SEQ ID NO: 544 and 545;
probe set #1043 consisting of the nucleic acids consisting of SEQ ID NO: 2073; 2074 and 2110;
probe set #1044 consisting of the nucleic acids consisting of SEQ ID NO: 2153; 2154 and 2155;
probe set #1045 consisting of the nucleic acids consisting of SEQ ID NO: 2670; 2708 and 2754;
probe set #1046 consisting of the nucleic acids consisting of SEQ ID NO: 2148; 2149 and 2150;
probe set #1047 consisting of the nucleic acids consisting of SEQ ID NO: 251; 252 and 253;

probe set #1048 consisting of the nucleic acids consisting of SEQ ID NO: 2617; 2618 and 2619;
probe set #1049 consisting of the nucleic acids consisting of SEQ ID NO: 233; 249 and 250;
probe set #1050 consisting of the nucleic acids consisting of SEQ ID NO: 1923; 1924 and 1925;
probe set #1051 consisting of the nucleic acids consisting of SEQ ID NO: 2446 and 2447;
probe set #1052 consisting of the nucleic acids consisting of SEQ ID NO: 1360; 1361 and 1362;
probe set #1053 consisting of the nucleic acids consisting of SEQ ID NO: 2141; 2142 and 2143;
probe set #1054 consisting of the nucleic acids consisting of SEQ ID NO: 2283; 2284 and 2285;
probe set #1055 consisting of the nucleic acids consisting of SEQ ID NO: 2659; 2660 and 2709;
probe set #1056 consisting of the nucleic acids consisting of SEQ ID NO: 2148; 2149 and 2150;
probe set #1057 consisting of the nucleic acids consisting of SEQ ID NO: 2242; 2252 and 2253;
probe set #1058 consisting of the nucleic acids consisting of SEQ ID NO: 2749; 2750 and 2751;
probe set #1059 consisting of the nucleic acids consisting of SEQ ID NO: 1934;
probe set #1060 consisting of the nucleic acids consisting of SEQ ID NO: 234; 235 and 236;
probe set #1061 consisting of the nucleic acids consisting of SEQ ID NO: 2061;
probe set #1062 consisting of the nucleic acids consisting of SEQ ID NO: 1025; 1026 and 1027;
probe set #1063 consisting of the nucleic acids consisting of SEQ ID NO: 960; 961 and 962;
probe set #1064 consisting of the nucleic acids consisting of SEQ ID NO: 2652; 2653 and 2654;
probe set #1065 consisting of the nucleic acids consisting of SEQ ID NO: 2144;
probe set #1066 consisting of the nucleic acids consisting of SEQ ID NO: 1627; 1628 and 1629;
probe set #1067 consisting of the nucleic acids consisting of SEQ ID NO: 921; 922 and 923;
probe set #1068 consisting of the nucleic acids consisting of SEQ ID NO: 1956;
probe set #1069 consisting of the nucleic acids consisting of SEQ ID NO: 1014; 1015 and 1016;
probe set #1070 consisting of the nucleic acids consisting of SEQ ID NO: 1800; 1801 and 1802;
probe set #1071 consisting of the nucleic acids consisting of SEQ ID NO: 445;
probe set #1072 consisting of the nucleic acids consisting of SEQ ID NO: 12; 13 and 20;
probe set #1073 consisting of the nucleic acids consisting of SEQ ID NO: 43; 44 and 45;
probe set #1074 consisting of the nucleic acids consisting of SEQ ID NO: 576; 577 and 578;
probe set #1075 consisting of the nucleic acids consisting of SEQ ID NO: 2329; 2334 and 2335;
probe set #1076 consisting of the nucleic acids consisting of SEQ ID NO: 1219;
probe set #1077 consisting of the nucleic acids consisting of SEQ ID NO: 225; 226 and 227;
probe set #1078 consisting of the nucleic acids consisting of SEQ ID NO: 2384; 2385 and 2386;
probe set #1079 consisting of the nucleic acids consisting of SEQ ID NO: 2579 and 2582;
probe set #1080 consisting of the nucleic acids consisting of SEQ ID NO: 2580; 2581 and 2582;
probe set #1081 consisting of the nucleic acids consisting of SEQ ID NO: 231; 232 and 233;
probe set #1082 consisting of the nucleic acids consisting of SEQ ID NO: 2329; 2334 and 2335;
probe set #1083 consisting of the nucleic acids consisting of SEQ ID NO: 1624; 1625 and 1626;
probe set #1084 consisting of the nucleic acids consisting of SEQ ID NO: 607; 608 and 609;
probe set #1085 consisting of the nucleic acids consisting of SEQ ID NO: 80; 81 and 82;
probe set #1086 consisting of the nucleic acids consisting of SEQ ID NO: 1277;
probe set #1087 consisting of the nucleic acids consisting of SEQ ID NO: 978; 979 and 980;
probe set #1088 consisting of the nucleic acids consisting of SEQ ID NO: 2130; 2131 and 2134;
probe set #1089 consisting of the nucleic acids consisting of SEQ ID NO: 2257; 2258 and 2271;
probe set #1090 consisting of the nucleic acids consisting of SEQ ID NO: 2670; 2676 and 2759;
probe set #1091 consisting of the nucleic acids consisting of SEQ ID NO: 1825; 1826 and 1827;
probe set #1092 consisting of the nucleic acids consisting of SEQ ID NO: 2661 and 2748;
probe set #1093 consisting of the nucleic acids consisting of SEQ ID NO: 2823; 2824 and 2825;
probe set #1094 consisting of the nucleic acids consisting of SEQ ID NO: 2148; 2150 and 2151;
probe set #1095 consisting of the nucleic acids consisting of SEQ ID NO: 479; 480 and 481;
probe set #1096 consisting of the nucleic acids consisting of SEQ ID NO: 2065; 2068 and 2098;
probe set #1097 consisting of the nucleic acids consisting of SEQ ID NO: 2411; 2412 and 2426;
probe set #1098 consisting of the nucleic acids consisting of SEQ ID NO: 2148; 2150 and 2151;
probe set #1099 consisting of the nucleic acids consisting of SEQ ID NO: 1455; 1456 and 1457;
probe set #1100 consisting of the nucleic acids consisting of SEQ ID NO: 1630 and 1631;
probe set #1101 consisting of the nucleic acids consisting of SEQ ID NO: 2243; 2272 and 2273;
probe set #1102 consisting of the nucleic acids consisting of SEQ ID NO: 2839; 2840 and 2849;
probe set #1103 consisting of the nucleic acids consisting of SEQ ID NO: 2438; 2439 and 2440;
probe set #1104 consisting of the nucleic acids consisting of SEQ ID NO: 1627; 1628 and 1629;
probe set #1105 consisting of the nucleic acids consisting of SEQ ID NO: 2458; 2461 and 2462;
probe set #1106 consisting of the nucleic acids consisting of SEQ ID NO: 2295;
probe set #1107 consisting of the nucleic acids consisting of SEQ ID NO: 40; 41 and 42;
probe set #1108 consisting of the nucleic acids consisting of SEQ ID NO: 1923; 1924 and 1925;
probe set #1109 consisting of the nucleic acids consisting of SEQ ID NO: 2078 and 2079;
probe set #1110 consisting of the nucleic acids consisting of SEQ ID NO: 908; 909 and 910;
probe set #1111 consisting of the nucleic acids consisting of SEQ ID NO: 21; 22 and 31;
probe set #1112 consisting of the nucleic acids consisting of SEQ ID NO: 2145; 2146 and 2147;
probe set #1113 consisting of the nucleic acids consisting of SEQ ID NO: 2317; 2318 and 2319;

probe set #1114 consisting of the nucleic acids consisting of SEQ ID NO: 1709;
probe set #1115 consisting of the nucleic acids consisting of SEQ ID NO: 234; 235 and 236;
probe set #1116 consisting of the nucleic acids consisting of SEQ ID NO: 1949; 1950 and 1951;
probe set #1117 consisting of the nucleic acids consisting of SEQ ID NO: 693; 694 and 695;
probe set #1118 consisting of the nucleic acids consisting of SEQ ID NO: 2289; 2303 and 2305;
probe set #1119 consisting of the nucleic acids consisting of SEQ ID NO: 1296; 1297 and 1298;
probe set #1120 consisting of the nucleic acids consisting of SEQ ID NO: 32; 33 and 34;
probe set #1121 consisting of the nucleic acids consisting of SEQ ID NO: 90; 91 and 92;
probe set #1122 consisting of the nucleic acids consisting of SEQ ID NO: 885; 886 and 887;
probe set #1123 consisting of the nucleic acids consisting of SEQ ID NO: 2; 10 and 11;
probe set #1124 consisting of the nucleic acids consisting of SEQ ID NO: 2634; 2635 and 2636;
probe set #1125 consisting of the nucleic acids consisting of SEQ ID NO: 1624; 1625 and 1626;
probe set #1126 consisting of the nucleic acids consisting of SEQ ID NO: 2495; 2496 and 2497;
probe set #1127 consisting of the nucleic acids consisting of SEQ ID NO: 2696; 2697 and 2698;
probe set #1128 consisting of the nucleic acids consisting of SEQ ID NO: 504; 505 and 506;
probe set #1129 consisting of the nucleic acids consisting of SEQ ID NO: 568; 569 and 570;
probe set #1130 consisting of the nucleic acids consisting of SEQ ID NO: 2672; 2752 and 2758;
probe set #1131 consisting of the nucleic acids consisting of SEQ ID NO: 2153; 2154 and 2155;
probe set #1132 consisting of the nucleic acids consisting of SEQ ID NO: 234; 235 and 236;
probe set #1133 consisting of the nucleic acids consisting of SEQ ID NO: 2839; 2840 and 2849;
probe set #1134 consisting of the nucleic acids consisting of SEQ ID NO: 192; 193 and 194;
probe set #1135 consisting of the nucleic acids consisting of SEQ ID NO: 1936; 1937 and 1938;
probe set #1136 consisting of the nucleic acids consisting of SEQ ID NO: 1002; 1003 and 1004;
probe set #1137 consisting of the nucleic acids consisting of SEQ ID NO: 2325; 2326 and 2327;
probe set #1138 consisting of the nucleic acids consisting of SEQ ID NO: 1385; 1386 and 1387;
probe set #1139 consisting of the nucleic acids consisting of SEQ ID NO: 2353; 2354 and 2355;
probe set #1140 consisting of the nucleic acids consisting of SEQ ID NO: 2408; 2409 and 2410;
probe set #1141 consisting of the nucleic acids consisting of SEQ ID NO: 237; 238 and 239;
probe set #1142 consisting of the nucleic acids consisting of SEQ ID NO: 2093;
probe set #1143 consisting of the nucleic acids consisting of SEQ ID NO: 1656; 1657 and 1658;
probe set #1144 consisting of the nucleic acids consisting of SEQ ID NO: 2427;
probe set #1145 consisting of the nucleic acids consisting of SEQ ID NO: 80; 81 and 82;
probe set #1146 consisting of the nucleic acids consisting of SEQ ID NO: 2446; 2457 and 2458;
probe set #1147 consisting of the nucleic acids consisting of SEQ ID NO: 2605; 2606 and 2610;
probe set #1148 consisting of the nucleic acids consisting of SEQ ID NO: 289; 294 and 293;
probe set #1149 consisting of the nucleic acids consisting of SEQ ID NO: 1429; 1430; 1431 and 1432
probe set #1150 consisting of the nucleic acids consisting of SEQ ID NO: 2665; 2666 and 2667;
probe set #1151 consisting of the nucleic acids consisting of SEQ ID NO: 2185; 2186 and 2187;
probe set #1152 consisting of the nucleic acids consisting of SEQ ID NO: 2118; 2119 and 2120;
probe set #1153 consisting of the nucleic acids consisting of SEQ ID NO: 102; 103 and 104;
probe set #1154 consisting of the nucleic acids consisting of SEQ ID NO: 2905; 2906 and 2907;
probe set #1155 consisting of the nucleic acids consisting of SEQ ID NO: 2692 and 2693;
probe set #1156 consisting of the nucleic acids consisting of SEQ ID NO: 234; 235 and 236;
probe set #1157 consisting of the nucleic acids consisting of SEQ ID NO: 2740; 2741 and 2742;
probe set #1158 consisting of the nucleic acids consisting of SEQ ID NO: 1991; 1992 and 1993;
probe set #1159 consisting of the nucleic acids consisting of SEQ ID NO: 1348; 1349 and 1350;
probe set #1160 consisting of the nucleic acids consisting of SEQ ID NO: 574; 575 and 587;
probe set #1161 consisting of the nucleic acids consisting of SEQ ID NO: 2805; 2806 and 2807;
probe set #1162 consisting of the nucleic acids consisting of SEQ ID NO: 571; 572 and 573;
probe set #1163 consisting of the nucleic acids consisting of SEQ ID NO: 2659; 2660 and 2709;
probe set #1164 consisting of the nucleic acids consisting of SEQ ID NO: 2003; 2004 and 2008;
probe set #1165 consisting of the nucleic acids consisting of SEQ ID NO: 2659; 2660 and 2758;
probe set #1166 consisting of the nucleic acids consisting of SEQ ID NO: 2796 and 2797;
probe set #1167 consisting of the nucleic acids consisting of SEQ ID NO: 624; 625 and 626;
probe set #1168 consisting of the nucleic acids consisting of SEQ ID NO: 2135; 2136 and 2137;
probe set #1169 consisting of the nucleic acids consisting of SEQ ID NO: 59; 60 and 61;
probe set #1170 consisting of the nucleic acids consisting of SEQ ID NO: 549; 550 and 551;
probe set #1171 consisting of the nucleic acids consisting of SEQ ID NO: 856; 857 and 858;
probe set #1172 consisting of the nucleic acids consisting of SEQ ID NO: 884; 885 and 888;
probe set #1173 consisting of the nucleic acids consisting of SEQ ID NO: 2148; 2150 and 2151;
probe set #1174 consisting of the nucleic acids consisting of SEQ ID NO: 2436; 2437 and 2460;
probe set #1175 consisting of the nucleic acids consisting of SEQ ID NO: 1803; 1804 and 1816;
probe set #1176 consisting of the nucleic acids consisting of SEQ ID NO: 884 and 888;
probe set #1177 consisting of the nucleic acids consisting of SEQ ID NO: 2141; 2142 and 2143;
probe set #1178 consisting of the nucleic acids consisting of SEQ ID NO: 921; 922 and 923;
probe set #1179 consisting of the nucleic acids consisting of SEQ ID NO: 1922;

probe set #1180 consisting of the nucleic acids consisting of SEQ ID NO: 1286;
probe set #1181 consisting of the nucleic acids consisting of SEQ ID NO: 2012; 2016 and 2017;
probe set #1182 consisting of the nucleic acids consisting of SEQ ID NO: 2003; 2004 and 2007;
probe set #1183 consisting of the nucleic acids consisting of SEQ ID NO: 1756 and 1757;
probe set #1184 consisting of the nucleic acids consisting of SEQ ID NO: 408;
probe set #1185 consisting of the nucleic acids consisting of SEQ ID NO: 83; 84 and 85;
probe set #1186 consisting of the nucleic acids consisting of SEQ ID NO: 234; 235 and 236;
probe set #1187 consisting of the nucleic acids consisting of SEQ ID NO: 2150; 2151 and 2152;
probe set #1188 consisting of the nucleic acids consisting of SEQ ID NO: 1851; 1852 and 1854;
probe set #1189 consisting of the nucleic acids consisting of SEQ ID NO: 546; 547 and 548;
probe set #1190 consisting of the nucleic acids consisting of SEQ ID NO: 2605; 2606 and 2610;
probe set #1191 consisting of the nucleic acids consisting of SEQ ID NO: 2138; 2139 and 2140;
probe set #1192 consisting of the nucleic acids consisting of SEQ ID NO: 80; 81 and 82;
probe set #1193 consisting of the nucleic acids consisting of SEQ ID NO: 1740; 1741 and 1742;
probe set #1194 consisting of the nucleic acids consisting of SEQ ID NO: 234; 235 and 236;
probe set #1195 consisting of the nucleic acids consisting of SEQ ID NO: 1975; 1976 and 1977;
probe set #1196 consisting of the nucleic acids consisting of SEQ ID NO: 146; 147 and 150;
probe set #1197 consisting of the nucleic acids consisting of SEQ ID NO: 1452; 1453 and 1454;
probe set #1198 consisting of the nucleic acids consisting of SEQ ID NO: 692; 693 and 695;
probe set #1199 consisting of the nucleic acids consisting of SEQ ID NO: 2895;
probe set #1200 consisting of the nucleic acids consisting of SEQ ID NO: 993; 994 and 995;
probe set #1201 consisting of the nucleic acids consisting of SEQ ID NO: 2359; 2360 and 2361;
probe set #1202 consisting of the nucleic acids consisting of SEQ ID NO: 2826; 2827 and 2828;
probe set #1203 consisting of the nucleic acids consisting of SEQ ID NO: 2872; 2873 and 2878;
probe set #1204 consisting of the nucleic acids consisting of SEQ ID NO: 2567; 2568 and 2569;
probe set #1205 consisting of the nucleic acids consisting of SEQ ID NO: 114; 115 and 116;
probe set #1206 consisting of the nucleic acids consisting of SEQ ID NO: 2554; 2555 and 2556;
probe set #1207 consisting of the nucleic acids consisting of SEQ ID NO: 117; 118 and 119;
probe set #1208 consisting of the nucleic acids consisting of SEQ ID NO: 2507; 2508 and 2509;
probe set #1209 consisting of the nucleic acids consisting of SEQ ID NO: 1923; 1924 and 1925;
probe set #1210 consisting of the nucleic acids consisting of SEQ ID NO: 702; 717 and 718;
probe set #1211 consisting of the nucleic acids consisting of SEQ ID NO: 142; 143 and 144;
probe set #1212 consisting of the nucleic acids consisting of SEQ ID NO: 2242; 2252 and 2267;
probe set #1213 consisting of the nucleic acids consisting of SEQ ID NO: 2611; 2612 and 2613;
probe set #1214 consisting of the nucleic acids consisting of SEQ ID NO: 1881; 1882 and 1883;
probe set #1215 consisting of the nucleic acids consisting of SEQ ID NO: 1862; 1863 and 1864;
probe set #1216 consisting of the nucleic acids consisting of SEQ ID NO: 470; 471 and 472;
probe set #1217 consisting of the nucleic acids consisting of SEQ ID NO: 524; 525 and 526;
probe set #1218 consisting of the nucleic acids consisting of SEQ ID NO: 656; 657 and 658;
probe set #1219 consisting of the nucleic acids consisting of SEQ ID NO: 2444; 2445 and 2446;
probe set #1220 consisting of the nucleic acids consisting of SEQ ID NO: 50; 51 and 52;
probe set #1221 consisting of the nucleic acids consisting of SEQ ID NO: 2060; 2072 and 2092;
probe set #1222 consisting of the nucleic acids consisting of SEQ ID NO: 2820; 2821 and 2822;
probe set #1223 consisting of the nucleic acids consisting of SEQ ID NO: 2046; 2047 and 2048;
probe set #1224 consisting of the nucleic acids consisting of SEQ ID NO: 1806; 1807 and 1808;
probe set #1225 consisting of the nucleic acids consisting of SEQ ID NO: 2060; 2089 and 2092;
probe set #1226 consisting of the nucleic acids consisting of SEQ ID NO: 1415; 1416 and 1417;
probe set #1227 consisting of the nucleic acids consisting of SEQ ID NO: 2433; 2434 and 2435; and
probe set #1228 consisting of the nucleic acids consisting of SEQ ID NO: 2433; 2434 and 2435.

6. The combination according to claim 5, comprising 1640 polynucleotide probe sets,
said 1640 polynucleotide probe sets comprising probe set #1 to probe set #1228, and
probe set #1229 consisting of the nucleic acids consisting of SEQ ID NO: 690 and 691;
probe set #1230 consisting of the nucleic acids consisting of SEQ ID NO: 2094; 2095 and 2096;
probe set #1231 consisting of the nucleic acids consisting of SEQ ID NO: 532; 533 and 534;
probe set #1232 consisting of the nucleic acids consisting of SEQ ID NO: 2570; 2571 and 2572;
probe set #1233 consisting of the nucleic acids consisting of SEQ ID NO: 516; 517 and 518;
probe set #1234 consisting of the nucleic acids consisting of SEQ ID NO: 1449; 1450 and 1451;
probe set #1235 consisting of the nucleic acids consisting of SEQ ID NO: 950; 951 and 952;
probe set #1236 consisting of the nucleic acids consisting of SEQ ID NO: 1749; 1751 and 1752;
probe set #1237 consisting of the nucleic acids consisting of SEQ ID NO: 1614; 1615 and 1616;
probe set #1238 consisting of the nucleic acids consisting of SEQ ID NO: 1400; 1401 and 1402;
probe set #1239 consisting of the nucleic acids consisting of SEQ ID NO: 2477; 2478 and 2479;
probe set #1240 consisting of the nucleic acids consisting of SEQ ID NO: 1964;
probe set #1241 consisting of the nucleic acids consisting of SEQ ID NO: 2607; 2608 and 2609;
probe set #1242 consisting of the nucleic acids consisting of SEQ ID NO: 544; 545 and 544;
probe set #1243 consisting of the nucleic acids consisting of SEQ ID NO: 301; 303 and 302;

probe set #1244 consisting of the nucleic acids consisting of SEQ ID NO: 918; 919 and 920;
probe set #1245 consisting of the nucleic acids consisting of SEQ ID NO: 1923; 1924 and 1925;
probe set #1246 consisting of the nucleic acids consisting of SEQ ID NO: 1620; 1632 and 1633;
probe set #1247 consisting of the nucleic acids consisting of SEQ ID NO: 1464; 1465 and 1466;
probe set #1248 consisting of the nucleic acids consisting of SEQ ID NO: 184; 185 and 186;
probe set #1249 consisting of the nucleic acids consisting of SEQ ID NO: 681; 682 and 683;
probe set #1250 consisting of the nucleic acids consisting of SEQ ID NO: 2607; 2608 and 2609;
probe set #1251 consisting of the nucleic acids consisting of SEQ ID NO: 2384; 2385 and 2387;
probe set #1252 consisting of the nucleic acids consisting of SEQ ID NO: 2564; 2565 and 2566;
probe set #1253 consisting of the nucleic acids consisting of SEQ ID NO: 1634; 1635 and 1636;
probe set #1254 consisting of the nucleic acids consisting of SEQ ID NO: 1875;
probe set #1255 consisting of the nucleic acids consisting of SEQ ID NO: 2833; 2834 and 2835;
probe set #1256 consisting of the nucleic acids consisting of SEQ ID NO: 1753; 1754 and 1755;
probe set #1257 consisting of the nucleic acids consisting of SEQ ID NO: 2830; 2836 and 2837;
probe set #1258 consisting of the nucleic acids consisting of SEQ ID NO: 2869; 2870 and 2871;
probe set #1259 consisting of the nucleic acids consisting of SEQ ID NO: 1710; 1711 and 1712;
probe set #1260 consisting of the nucleic acids consisting of SEQ ID NO: 592; 593 and 594;
probe set #1261 consisting of the nucleic acids consisting of SEQ ID NO: 2331; 2332 and 2333;
probe set #1262 consisting of the nucleic acids consisting of SEQ ID NO: 357; 359 and 358;
probe set #1263 consisting of the nucleic acids consisting of SEQ ID NO: 2605; 2607 and 2610;
probe set #1264 consisting of the nucleic acids consisting of SEQ ID NO: 2403;
probe set #1265 consisting of the nucleic acids consisting of SEQ ID NO: 432; 433 and 434;
probe set #1266 consisting of the nucleic acids consisting of SEQ ID NO: 2264; 2265 and 2266;
probe set #1267 consisting of the nucleic acids consisting of SEQ ID NO: 956; 957 and 958;
probe set #1268 consisting of the nucleic acids consisting of SEQ ID NO: 758; 759 and 760;
probe set #1269 consisting of the nucleic acids consisting of SEQ ID NO: 2438; 2439 and 2440;
probe set #1270 consisting of the nucleic acids consisting of SEQ ID NO: 1409; 1410 and 1411;
probe set #1271 consisting of the nucleic acids consisting of SEQ ID NO: 1920; 1933 and 1999;
probe set #1272 consisting of the nucleic acids consisting of SEQ ID NO: 2438; 2439 and 2440;
probe set #1273 consisting of the nucleic acids consisting of SEQ ID NO: 21; 22 and 23;
probe set #1274 consisting of the nucleic acids consisting of SEQ ID NO: 2841; 2842 and 2843;
probe set #1275 consisting of the nucleic acids consisting of SEQ ID NO: 2063; 2065 and 2068;
probe set #1276 consisting of the nucleic acids consisting of SEQ ID NO: 1458; 1459 and 1460;
probe set #1277 consisting of the nucleic acids consisting of SEQ ID NO: 2019; 2020 and 2021;
probe set #1278 consisting of the nucleic acids consisting of SEQ ID NO: 706; 707 and 708;
probe set #1279 consisting of the nucleic acids consisting of SEQ ID NO: 1859; 1860 and 1861;
probe set #1280 consisting of the nucleic acids consisting of SEQ ID NO: 636; 637 and 638;
probe set #1281 consisting of the nucleic acids consisting of SEQ ID NO: 2388; 2389 and 2390;
probe set #1282 consisting of the nucleic acids consisting of SEQ ID NO: 385; 386 and 387;
probe set #1283 consisting of the nucleic acids consisting of SEQ ID NO: 777; 778 and 779;
probe set #1284 consisting of the nucleic acids consisting of SEQ ID NO: 1936; 1937 and 1938;
probe set #1285 consisting of the nucleic acids consisting of SEQ ID NO: 2094; 2095 and 2096;
probe set #1286 consisting of the nucleic acids consisting of SEQ ID NO: 1749; 1750 and 1752;
probe set #1287 consisting of the nucleic acids consisting of SEQ ID NO: 21; 22 and 31;
probe set #1288 consisting of the nucleic acids consisting of SEQ ID NO: 1366; 1367 and 1380;
probe set #1289 consisting of the nucleic acids consisting of SEQ ID NO: 1701; 1702 and 1703;
probe set #1290 consisting of the nucleic acids consisting of SEQ ID NO: 1936; 1937 and 1938;
probe set #1291 consisting of the nucleic acids consisting of SEQ ID NO: 2013; 2014 and 2015;
probe set #1292 consisting of the nucleic acids consisting of SEQ ID NO: 1913; 1914 and 1915;
probe set #1293 consisting of the nucleic acids consisting of SEQ ID NO: 1336; 1337 and 1338;
probe set #1294 consisting of the nucleic acids consisting of SEQ ID NO: 2060; 2072 and 2092;
probe set #1295 consisting of the nucleic acids consisting of SEQ ID NO: 184; 187 and 188;
probe set #1296 consisting of the nucleic acids consisting of SEQ ID NO: 1702; 1703 and 1704;
probe set #1297 consisting of the nucleic acids consisting of SEQ ID NO: 2605; 2607 and 2610;
probe set #1298 consisting of the nucleic acids consisting of SEQ ID NO: 884; 885 and 886;
probe set #1299 consisting of the nucleic acids consisting of SEQ ID NO: 853; 854 and 855;
probe set #1300 consisting of the nucleic acids consisting of SEQ ID NO: 2072; 2089 and 2092;
probe set #1301 consisting of the nucleic acids consisting of SEQ ID NO: 645;
probe set #1302 consisting of the nucleic acids consisting of SEQ ID NO: 231; 232 and 233;
probe set #1303 consisting of the nucleic acids consisting of SEQ ID NO: 2605; 2606 and 2610;
probe set #1304 consisting of the nucleic acids consisting of SEQ ID NO: 2896; 2897 and 2898;
probe set #1305 consisting of the nucleic acids consisting of SEQ ID NO: 579; 587 and 646;
probe set #1306 consisting of the nucleic acids consisting of SEQ ID NO: 2922; 2923 and 2924;
probe set #1307 consisting of the nucleic acids consisting of SEQ ID NO: 2593; 2594 and 2595;
probe set #1308 consisting of the nucleic acids consisting of SEQ ID NO: 2012 and 2018;
probe set #1309 consisting of the nucleic acids consisting of SEQ ID NO: 2857 and 2858;

probe set #1310 consisting of the nucleic acids consisting of SEQ ID NO: 1855; 1857 and 1858;
probe set #1311 consisting of the nucleic acids consisting of SEQ ID NO: 648; 649 and 650;
probe set #1312 consisting of the nucleic acids consisting of SEQ ID NO: 987; 988 and 989;
probe set #1313 consisting of the nucleic acids consisting of SEQ ID NO: 2003; 2007 and 2009;
probe set #1314 consisting of the nucleic acids consisting of SEQ ID NO: 702; 710 and 717;
probe set #1315 consisting of the nucleic acids consisting of SEQ ID NO: 1484; 1485 and 1486;
probe set #1316 consisting of the nucleic acids consisting of SEQ ID NO: 574; 587 and 647;
probe set #1317 consisting of the nucleic acids consisting of SEQ ID NO: 12; 13 and 20;
probe set #1318 consisting of the nucleic acids consisting of SEQ ID NO: 1868;
probe set #1319 consisting of the nucleic acids consisting of SEQ ID NO: 1157;
probe set #1320 consisting of the nucleic acids consisting of SEQ ID NO: 1758; 1759 and 1760;
probe set #1321 consisting of the nucleic acids consisting of SEQ ID NO: 933; 934 and 935;
probe set #1322 consisting of the nucleic acids consisting of SEQ ID NO: 1372; 1373 and 1379;
probe set #1323 consisting of the nucleic acids consisting of SEQ ID NO: 1378;
probe set #1324 consisting of the nucleic acids consisting of SEQ ID NO: 1627; 1628 and 1629;
probe set #1325 consisting of the nucleic acids consisting of SEQ ID NO: 21; 22 and 23;
probe set #1326 consisting of the nucleic acids consisting of SEQ ID NO: 2012; 2016 and 2022;
probe set #1327 consisting of the nucleic acids consisting of SEQ ID NO: 884; 885 and 888;
probe set #1328 consisting of the nucleic acids consisting of SEQ ID NO: 47; 48 and 49;
probe set #1329 consisting of the nucleic acids consisting of SEQ ID NO: 2396;
probe set #1330 consisting of the nucleic acids consisting of SEQ ID NO: 2814; 2815 and 2816;
probe set #1331 consisting of the nucleic acids consisting of SEQ ID NO: 237; 238 and 239;
probe set #1332 consisting of the nucleic acids consisting of SEQ ID NO: 2331; 2332 and 2333;
probe set #1333 consisting of the nucleic acids consisting of SEQ ID NO: 2709;
probe set #1334 consisting of the nucleic acids consisting of SEQ ID NO: 2605; 2607 and 2610;
probe set #1335 consisting of the nucleic acids consisting of SEQ ID NO: 1375; 1376 and 1377;
probe set #1336 consisting of the nucleic acids consisting of SEQ ID NO: 17; 18 and 19;
probe set #1337 consisting of the nucleic acids consisting of SEQ ID NO: 397;
probe set #1338 consisting of the nucleic acids consisting of SEQ ID NO: 921; 922 and 923;
probe set #1339 consisting of the nucleic acids consisting of SEQ ID NO: 250; 256 and 257;
probe set #1340 consisting of the nucleic acids consisting of SEQ ID NO: 1501; 1502 and 1503;
probe set #1341 consisting of the nucleic acids consisting of SEQ ID NO: 385; 386 and 387;
probe set #1342 consisting of the nucleic acids consisting of SEQ ID NO: 639; 640 and 641;
probe set #1343 consisting of the nucleic acids consisting of SEQ ID NO: 1836; 1837 and 1838;
probe set #1344 consisting of the nucleic acids consisting of SEQ ID NO: 62; 63 and 64;
probe set #1345 consisting of the nucleic acids consisting of SEQ ID NO: 2242; 2243 and 2244;
probe set #1346 consisting of the nucleic acids consisting of SEQ ID NO: 1044; 1045 and 1046;
probe set #1347 consisting of the nucleic acids consisting of SEQ ID NO: 1615; 1616 and 1620;
probe set #1348 consisting of the nucleic acids consisting of SEQ ID NO: 2724; 2732 and 2733;
probe set #1349 consisting of the nucleic acids consisting of SEQ ID NO: 87; 88 and 89;
probe set #1350 consisting of the nucleic acids consisting of SEQ ID NO: 706; 707 and 708;
probe set #1351 consisting of the nucleic acids consisting of SEQ ID NO: 881; 882 and 883;
probe set #1352 consisting of the nucleic acids consisting of SEQ ID NO: 2029; 2030 and 2031;
probe set #1353 consisting of the nucleic acids consisting of SEQ ID NO: 2448; 2449 and 2450;
probe set #1354 consisting of the nucleic acids consisting of SEQ ID NO: 46;
probe set #1355 consisting of the nucleic acids consisting of SEQ ID NO: 574; 575 and 613;
probe set #1356 consisting of the nucleic acids consisting of SEQ ID NO: 394; 395 and 396;
probe set #1357 consisting of the nucleic acids consisting of SEQ ID NO: 2844; 2845 and 2846;
probe set #1358 consisting of the nucleic acids consisting of SEQ ID NO: 2165; 2168 and 2169;
probe set #1359 consisting of the nucleic acids consisting of SEQ ID NO: 2111; 2112 and 2113;
probe set #1360 consisting of the nucleic acids consisting of SEQ ID NO: 2404; 2405 and 2407;
probe set #1361 consisting of the nucleic acids consisting of SEQ ID NO: 2463; 2464 and 2465;
probe set #1362 consisting of the nucleic acids consisting of SEQ ID NO: 2221;
probe set #1363 consisting of the nucleic acids consisting of SEQ ID NO: 1620; 1632 and 1633;
probe set #1364 consisting of the nucleic acids consisting of SEQ ID NO: 12; 13 and 20;
probe set #1365 consisting of the nucleic acids consisting of SEQ ID NO: 2325; 2326 and 2327;
probe set #1366 consisting of the nucleic acids consisting of SEQ ID NO: 210; 211 and 212;
probe set #1367 consisting of the nucleic acids consisting of SEQ ID NO: 918; 927 and 932;
probe set #1368 consisting of the nucleic acids consisting of SEQ ID NO: 604; 605 and 606;
probe set #1369 consisting of the nucleic acids consisting of SEQ ID NO: 2454; 2455 and 2456;
probe set #1370 consisting of the nucleic acids consisting of SEQ ID NO: 467; 468 and 469;
probe set #1371 consisting of the nucleic acids consisting of SEQ ID NO: 488; 489 and 490;
probe set #1372 consisting of the nucleic acids consisting of SEQ ID NO: 904; 905 and 906;
probe set #1373 consisting of the nucleic acids consisting of SEQ ID NO: 289; 294 and 293;
probe set #1374 consisting of the nucleic acids consisting of SEQ ID NO: 1319; 1320 and 1321;
probe set #1375 consisting of the nucleic acids consisting of SEQ ID NO: 2394;

probe set #1376 consisting of the nucleic acids consisting of SEQ ID NO: 382; 383 and 384;
probe set #1377 consisting of the nucleic acids consisting of SEQ ID NO: 14; 15 and 16;
probe set #1378 consisting of the nucleic acids consisting of SEQ ID NO: 580 and 581;
probe set #1379 consisting of the nucleic acids consisting of SEQ ID NO: 1928; 1929 and 1930;
probe set #1380 consisting of the nucleic acids consisting of SEQ ID NO: 869; 870 and 874;
probe set #1381 consisting of the nucleic acids consisting of SEQ ID NO: 1433; 1434 and 1457;
probe set #1382 consisting of the nucleic acids consisting of SEQ ID NO: 892; 893 and 894;
probe set #1383 consisting of the nucleic acids consisting of SEQ ID NO: 884; 885 and 888;
probe set #1384 consisting of the nucleic acids consisting of SEQ ID NO: 295; 297 and 296;
probe set #1385 consisting of the nucleic acids consisting of SEQ ID NO: 2874;
probe set #1386 consisting of the nucleic acids consisting of SEQ ID NO: 1845; 1846 and 1847;
probe set #1387 consisting of the nucleic acids consisting of SEQ ID NO: 2604; 2606 and 2610;
probe set #1388 consisting of the nucleic acids consisting of SEQ ID NO: 1329; 1330 and 1331;
probe set #1389 consisting of the nucleic acids consisting of SEQ ID NO: 2461; 2462 and 2467;
probe set #1390 consisting of the nucleic acids consisting of SEQ ID NO: 234; 235 and 236;
probe set #1391 consisting of the nucleic acids consisting of SEQ ID NO: 1621; 1622 and 1623;
probe set #1392 consisting of the nucleic acids consisting of SEQ ID NO: 2879; 2880 and 2882;
probe set #1393 consisting of the nucleic acids consisting of SEQ ID NO: 761; 762 and 765;
probe set #1394 consisting of the nucleic acids consisting of SEQ ID NO: 1851; 1853 and 1854;
probe set #1395 consisting of the nucleic acids consisting of SEQ ID NO: 2138; 2139 and 2140;
probe set #1396 consisting of the nucleic acids consisting of SEQ ID NO: 627; 628 and 629;
probe set #1397 consisting of the nucleic acids consisting of SEQ ID NO: 574; 575 and 613;
probe set #1398 consisting of the nucleic acids consisting of SEQ ID NO: 2462;
probe set #1399 consisting of the nucleic acids consisting of SEQ ID NO: 2504; 2505 and 2506;
probe set #1400 consisting of the nucleic acids consisting of SEQ ID NO: 1908;
probe set #1401 consisting of the nucleic acids consisting of SEQ ID NO: 108; 109 and 110;
probe set #1402 consisting of the nucleic acids consisting of SEQ ID NO: 516; 517 and 518;
probe set #1403 consisting of the nucleic acids consisting of SEQ ID NO: 1496; 1506 and 1508;
probe set #1404 consisting of the nucleic acids consisting of SEQ ID NO: 507; 508 and 509;
probe set #1405 consisting of the nucleic acids consisting of SEQ ID NO: 2655; 2656 and 2657;
probe set #1406 consisting of the nucleic acids consisting of SEQ ID NO: 902; 911 and 902;
probe set #1407 consisting of the nucleic acids consisting of SEQ ID NO: 835 and 836;
probe set #1408 consisting of the nucleic acids consisting of SEQ ID NO: 2328; 2329 and 2330;
probe set #1409 consisting of the nucleic acids consisting of SEQ ID NO: 1316; 1317 and 1318;
probe set #1410 consisting of the nucleic acids consisting of SEQ ID NO: 2153; 2154 and 2155;
probe set #1411 consisting of the nucleic acids consisting of SEQ ID NO: 2153; 2154 and 2155;
probe set #1412 consisting of the nucleic acids consisting of SEQ ID NO: 1296; 1297 and 1302;
probe set #1413 consisting of the nucleic acids consisting of SEQ ID NO: 599; 600 and 601;
probe set #1414 consisting of the nucleic acids consisting of SEQ ID NO: 2239; 2240 and 2241;
probe set #1415 consisting of the nucleic acids consisting of SEQ ID NO: 1724; 1725 and 1726;
probe set #1416 consisting of the nucleic acids consisting of SEQ ID NO: 1803; 1804 and 1805;
probe set #1417 consisting of the nucleic acids consisting of SEQ ID NO: 1819 and 1820;
probe set #1418 consisting of the nucleic acids consisting of SEQ ID NO: 1872; 1873 and 1874;
probe set #1419 consisting of the nucleic acids consisting of SEQ ID NO: 398;
probe set #1420 consisting of the nucleic acids consisting of SEQ ID NO: 497;
probe set #1421 consisting of the nucleic acids consisting of SEQ ID NO: 770; 771 and 772;
probe set #1422 consisting of the nucleic acids consisting of SEQ ID NO: 2588; 2589 and 2590;
probe set #1423 consisting of the nucleic acids consisting of SEQ ID NO: 663; 664 and 665;
probe set #1424 consisting of the nucleic acids consisting of SEQ ID NO: 2919; 2920 and 2921;
probe set #1425 consisting of the nucleic acids consisting of SEQ ID NO: 2363; 2364 and 2365;
probe set #1426 consisting of the nucleic acids consisting of SEQ ID NO: 1363; 1364 and 1365;
probe set #1427 consisting of the nucleic acids consisting of SEQ ID NO: 2044; 2045 and 2048;
probe set #1428 consisting of the nucleic acids consisting of SEQ ID NO: 2388; 2389 and 2390;
probe set #1429 consisting of the nucleic acids consisting of SEQ ID NO: 2660; 2672 and 2708;
probe set #1430 consisting of the nucleic acids consisting of SEQ ID NO: 2892; 2893 and 2894;
probe set #1431 consisting of the nucleic acids consisting of SEQ ID NO: 944; 945 and 946;
probe set #1432 consisting of the nucleic acids consisting of SEQ ID NO: 1005; 1006 and 1007;
probe set #1433 consisting of the nucleic acids consisting of SEQ ID NO: 889; 895 and 896;
probe set #1434 consisting of the nucleic acids consisting of SEQ ID NO: 2524; 2525 and 2526;
probe set #1435 consisting of the nucleic acids consisting of SEQ ID NO: 2403;
probe set #1436 consisting of the nucleic acids consisting of SEQ ID NO: 461; 462 and 463;
probe set #1437 consisting of the nucleic acids consisting of SEQ ID NO: 385; 386 and 387;
probe set #1438 consisting of the nucleic acids consisting of SEQ ID NO: 2933; 2934 and 2935;
probe set #1439 consisting of the nucleic acids consisting of SEQ ID NO: 960;
probe set #1440 consisting of the nucleic acids consisting of SEQ ID NO: 23; 29 and 30;
probe set #1441 consisting of the nucleic acids consisting of SEQ ID NO: 210; 211 and 212;

probe set #1442 consisting of the nucleic acids consisting of SEQ ID NO: 1817; 1818 and 1821;
probe set #1443 consisting of the nucleic acids consisting of SEQ ID NO: 924; 925 and 926;
probe set #1444 consisting of the nucleic acids consisting of SEQ ID NO: 504; 505 and 506;
probe set #1445 consisting of the nucleic acids consisting of SEQ ID NO: 178; 179 and 180;
probe set #1446 consisting of the nucleic acids consisting of SEQ ID NO: 161; 162 and 163;
probe set #1447 consisting of the nucleic acids consisting of SEQ ID NO: 2114 and 2115;
probe set #1448 consisting of the nucleic acids consisting of SEQ ID NO: 461; 462 and 463;
probe set #1449 consisting of the nucleic acids consisting of SEQ ID NO: 2153; 2154 and 2155;
probe set #1450 consisting of the nucleic acids consisting of SEQ ID NO: 1441; 1442 and 1443;
probe set #1451 consisting of the nucleic acids consisting of SEQ ID NO: 1036; 1037 and 1038;
probe set #1452 consisting of the nucleic acids consisting of SEQ ID NO: 915; 916 and 917;
probe set #1453 consisting of the nucleic acids consisting of SEQ ID NO: 661; 662 and 666;
probe set #1454 consisting of the nucleic acids consisting of SEQ ID NO: 1326; 1327 and 1328;
probe set #1455 consisting of the nucleic acids consisting of SEQ ID NO: 2855; 2858 and 2859;
probe set #1456 consisting of the nucleic acids consisting of SEQ ID NO: 1842; 1843 and 1844;
probe set #1457 consisting of the nucleic acids consisting of SEQ ID NO: 1828; 1829 and 1830;
probe set #1458 consisting of the nucleic acids consisting of SEQ ID NO: 1659; 1660 and 1661;
probe set #1459 consisting of the nucleic acids consisting of SEQ ID NO: 2116; 2117 and 2118;
probe set #1460 consisting of the nucleic acids consisting of SEQ ID NO: 1642; 1643 and 1645;
probe set #1461 consisting of the nucleic acids consisting of SEQ ID NO: 2395;
probe set #1462 consisting of the nucleic acids consisting of SEQ ID NO: 1345; 1346 and 1347;
probe set #1463 consisting of the nucleic acids consisting of SEQ ID NO: 2003; 2004 and 2007;
probe set #1464 consisting of the nucleic acids consisting of SEQ ID NO: 2831; 2847 and 2848;
probe set #1465 consisting of the nucleic acids consisting of SEQ ID NO: 1702; 1703 and 1708;
probe set #1466 consisting of the nucleic acids consisting of SEQ ID NO: 2404; 2405 and 2406;
probe set #1467 consisting of the nucleic acids consisting of SEQ ID NO: 711; 712 and 713;
probe set #1468 consisting of the nucleic acids consisting of SEQ ID NO: 1494 and 1495;
probe set #1469 consisting of the nucleic acids consisting of SEQ ID NO: 570; 585 and 586;
probe set #1470 consisting of the nucleic acids consisting of SEQ ID NO: 1848; 1849 and 1850;
probe set #1471 consisting of the nucleic acids consisting of SEQ ID NO: 1439; 1440 and 1457;
probe set #1472 consisting of the nucleic acids consisting of SEQ ID NO: 877; 878 and 879;
probe set #1473 consisting of the nucleic acids consisting of SEQ ID NO: 568; 569 and 579;
probe set #1474 consisting of the nucleic acids consisting of SEQ ID NO: 1902; 1903 and 1904;
probe set #1475 consisting of the nucleic acids consisting of SEQ ID NO: 1426; 1427 and 1428;
probe set #1476 consisting of the nucleic acids consisting of SEQ ID NO: 1145; 1146 and 1147;
probe set #1477 consisting of the nucleic acids consisting of SEQ ID NO: 425; 426 and 427;
probe set #1478 consisting of the nucleic acids consisting of SEQ ID NO: 494; 495 and 496;
probe set #1479 consisting of the nucleic acids consisting of SEQ ID NO: 2116; 2117 and 2118;
probe set #1480 consisting of the nucleic acids consisting of SEQ ID NO: 2331; 2332 and 2333;
probe set #1481 consisting of the nucleic acids consisting of SEQ ID NO: 897; 902 and 911;
probe set #1482 consisting of the nucleic acids consisting of SEQ ID NO: 1899; 1900 and 1901;
probe set #1483 consisting of the nucleic acids consisting of SEQ ID NO: 290; 292 and 291;
probe set #1484 consisting of the nucleic acids consisting of SEQ ID NO: 243; 244 and 245;
probe set #1485 consisting of the nucleic acids consisting of SEQ ID NO: 2502; 2503 and 2542;
probe set #1486 consisting of the nucleic acids consisting of SEQ ID NO: 1695; 1696 and 1697;
probe set #1487 consisting of the nucleic acids consisting of SEQ ID NO: 2617; 2620 and 2621;
probe set #1488 consisting of the nucleic acids consisting of SEQ ID NO: 1405; 1406 and 1410;
probe set #1489 consisting of the nucleic acids consisting of SEQ ID NO: 941; 954 and 955;
probe set #1490 consisting of the nucleic acids consisting of SEQ ID NO: 2814; 2815 and 2816;
probe set #1491 consisting of the nucleic acids consisting of SEQ ID NO: 2614; 2615 and 2616;
probe set #1492 consisting of the nucleic acids consisting of SEQ ID NO: 258; 259 and 260;
probe set #1493 consisting of the nucleic acids consisting of SEQ ID NO: 2260; 2261 and 2262;
probe set #1494 consisting of the nucleic acids consisting of SEQ ID NO: 2643; 2644 and 2645;
probe set #1495 consisting of the nucleic acids consisting of SEQ ID NO: 2337;
probe set #1496 consisting of the nucleic acids consisting of SEQ ID NO: 652; 653 and 654;
probe set #1497 consisting of the nucleic acids consisting of SEQ ID NO: 439; 440 and 441;
probe set #1498 consisting of the nucleic acids consisting of SEQ ID NO: 2817; 2818 and 2819;
probe set #1499 consisting of the nucleic acids consisting of SEQ ID NO: 1627; 1628 and 1629;
probe set #1500 consisting of the nucleic acids consisting of SEQ ID NO: 1496; 1505 and 1506;
probe set #1501 consisting of the nucleic acids consisting of SEQ ID NO: 1632; 1637 and 1638;
probe set #1502 consisting of the nucleic acids consisting of SEQ ID NO: 2411; 2412 and 2413;
probe set #1503 consisting of the nucleic acids consisting of SEQ ID NO: 1813; 1814 and 1815;
probe set #1504 consisting of the nucleic acids consisting of SEQ ID NO: 2557;
probe set #1505 consisting of the nucleic acids consisting of SEQ ID NO: 2605; 2606 and 2610;
probe set #1506 consisting of the nucleic acids consisting of SEQ ID NO: 1496; 1497 and 1506;
probe set #1507 consisting of the nucleic acids consisting of SEQ ID NO: 2331; 2332 and 2333;

probe set #1508 consisting of the nucleic acids consisting of SEQ ID NO: 1803; 1804 and 1809;
probe set #1509 consisting of the nucleic acids consisting of SEQ ID NO: 510; 511 and 512;
probe set #1510 consisting of the nucleic acids consisting of SEQ ID NO: 1928; 1929 and 1930;
probe set #1511 consisting of the nucleic acids consisting of SEQ ID NO: 2436; 2437 and 2460;
probe set #1512 consisting of the nucleic acids consisting of SEQ ID NO: 2605; 2607 and 2610;
probe set #1513 consisting of the nucleic acids consisting of SEQ ID NO: 1424; 1425 and 1450;
probe set #1514 consisting of the nucleic acids consisting of SEQ ID NO: 2111; 2112 and 2113;
probe set #1515 consisting of the nucleic acids consisting of SEQ ID NO: 1625; 1647 and 1648;
probe set #1516 consisting of the nucleic acids consisting of SEQ ID NO: 1624; 1625 and 1626;
probe set #1517 consisting of the nucleic acids consisting of SEQ ID NO: 498; 499 and 500;
probe set #1518 consisting of the nucleic acids consisting of SEQ ID NO: 2831; 2832 and 2848;
probe set #1519 consisting of the nucleic acids consisting of SEQ ID NO: 1878; 1879 and 1880;
probe set #1520 consisting of the nucleic acids consisting of SEQ ID NO: 869; 873 and 874;
probe set #1521 consisting of the nucleic acids consisting of SEQ ID NO: 990; 991 and 992;
probe set #1522 consisting of the nucleic acids consisting of SEQ ID NO: 1839; 1840 and 1841;
probe set #1523 consisting of the nucleic acids consisting of SEQ ID NO: 535; 536 and 537;
probe set #1524 consisting of the nucleic acids consisting of SEQ ID NO: 1325;
probe set #1525 consisting of the nucleic acids consisting of SEQ ID NO: 281; 283 and 282;
probe set #1526 consisting of the nucleic acids consisting of SEQ ID NO: 2331; 2332 and 2333;
probe set #1527 consisting of the nucleic acids consisting of SEQ ID NO: 1491; 1492 and 1493;
probe set #1528 consisting of the nucleic acids consisting of SEQ ID NO: 897; 903 and 907;
probe set #1529 consisting of the nucleic acids consisting of SEQ ID NO: 2388; 2389 and 2390;
probe set #1530 consisting of the nucleic acids consisting of SEQ ID NO: 851 and 852;
probe set #1531 consisting of the nucleic acids consisting of SEQ ID NO: 2716;
probe set #1532 consisting of the nucleic acids consisting of SEQ ID NO: 1496; 1506 and 1508;
probe set #1533 consisting of the nucleic acids consisting of SEQ ID NO: 2672; 2682 and 2708;
probe set #1534 consisting of the nucleic acids consisting of SEQ ID NO: 529; 530 and 531;
probe set #1535 consisting of the nucleic acids consisting of SEQ ID NO: 1705; 1706 and 1707;
probe set #1536 consisting of the nucleic acids consisting of SEQ ID NO: 7; 8 and 9;
probe set #1537 consisting of the nucleic acids consisting of SEQ ID NO: 77; 78 and 79;
probe set #1538 consisting of the nucleic acids consisting of SEQ ID NO: 1322; 1323 and 1324;
probe set #1539 consisting of the nucleic acids consisting of SEQ ID NO: 2451; 2452 and 2453;
probe set #1540 consisting of the nucleic acids consisting of SEQ ID NO: 935 and 942;
probe set #1541 consisting of the nucleic acids consisting of SEQ ID NO: 2032; 2033 and 2034;
probe set #1542 consisting of the nucleic acids consisting of SEQ ID NO: 501; 502 and 503;
probe set #1543 consisting of the nucleic acids consisting of SEQ ID NO: 2350; 2351 and 2352;
probe set #1544 consisting of the nucleic acids consisting of SEQ ID NO: 728; 729 and 730;
probe set #1545 consisting of the nucleic acids consisting of SEQ ID NO: 610; 611 and 655;
probe set #1546 consisting of the nucleic acids consisting of SEQ ID NO: 22; 27 and 28;
probe set #1547 consisting of the nucleic acids consisting of SEQ ID NO: 862; 863 and 864;
probe set #1548 consisting of the nucleic acids consisting of SEQ ID NO: 1642; 1643 and 1644;
probe set #1549 consisting of the nucleic acids consisting of SEQ ID NO: 2438; 2439 and 2440;
probe set #1550 consisting of the nucleic acids consisting of SEQ ID NO: 2225; 2226 and 2227;
probe set #1551 consisting of the nucleic acids consisting of SEQ ID NO: 1639; 1640 and 1641;
probe set #1552 consisting of the nucleic acids consisting of SEQ ID NO: 2400; 2401 and 2402;
probe set #1553 consisting of the nucleic acids consisting of SEQ ID NO: 464; 465 and 466;
probe set #1554 consisting of the nucleic acids consisting of SEQ ID NO: 145; 146 and 147;
probe set #1555 consisting of the nucleic acids consisting of SEQ ID NO: 2391; 2392 and 2393;
probe set #1556 consisting of the nucleic acids consisting of SEQ ID NO: 7; 8 and 9;
probe set #1557 consisting of the nucleic acids consisting of SEQ ID NO: 1810; 1811 and 1812;
probe set #1558 consisting of the nucleic acids consisting of SEQ ID NO: 2311; 2312 and 2313;
probe set #1559 consisting of the nucleic acids consisting of SEQ ID NO: 1994;
probe set #1560 consisting of the nucleic acids consisting of SEQ ID NO: 1395 and 1396;
probe set #1561 consisting of the nucleic acids consisting of SEQ ID NO: 933; 936 and 953;
probe set #1562 consisting of the nucleic acids consisting of SEQ ID NO: 2830; 2836 and 2837;
probe set #1563 consisting of the nucleic acids consisting of SEQ ID NO: 2605; 2606 and 2610;
probe set #1564 consisting of the nucleic acids consisting of SEQ ID NO: 80; 81 and 82;
probe set #1565 consisting of the nucleic acids consisting of SEQ ID NO: 2331; 2332 and 2333;
probe set #1566 consisting of the nucleic acids consisting of SEQ ID NO: 1734; 1735 and 1736;
probe set #1567 consisting of the nucleic acids consisting of SEQ ID NO: 2441; 2442 and 2443;
probe set #1568 consisting of the nucleic acids consisting of SEQ ID NO: 2617; 2618 and 2619;
probe set #1569 consisting of the nucleic acids consisting of SEQ ID NO: 181; 182 and 183;
probe set #1570 consisting of the nucleic acids consisting of SEQ ID NO: 2649; 2650 and 2651;
probe set #1571 consisting of the nucleic acids consisting of SEQ ID NO: 47; 48 and 49;
probe set #1572 consisting of the nucleic acids consisting of SEQ ID NO: 1504; 1505 and 1506;
probe set #1573 consisting of the nucleic acids consisting of SEQ ID NO: 1053; 1054 and 1055;

probe set #1574 consisting of the nucleic acids consisting of SEQ ID NO: 1625; 1647 and 1648;
probe set #1575 consisting of the nucleic acids consisting of SEQ ID NO: 1878;
probe set #1576 consisting of the nucleic acids consisting of SEQ ID NO: 287; 1823 and 1824;
probe set #1577 consisting of the nucleic acids consisting of SEQ ID NO: 965; 966 and 967;
probe set #1578 consisting of the nucleic acids consisting of SEQ ID NO: 576; 577 and 578;
probe set #1579 consisting of the nucleic acids consisting of SEQ ID NO: 1498; 1499 and 1507;
probe set #1580 consisting of the nucleic acids consisting of SEQ ID NO: 2391; 2392 and 2393;
probe set #1581 consisting of the nucleic acids consisting of SEQ ID NO: 1862; 1863 and 1864;
probe set #1582 consisting of the nucleic acids consisting of SEQ ID NO: 516; 517 and 518;
probe set #1583 consisting of the nucleic acids consisting of SEQ ID NO: 1444; 1445 and 1446;
probe set #1584 consisting of the nucleic acids consisting of SEQ ID NO: 1627; 1628 and 1629;
probe set #1585 consisting of the nucleic acids consisting of SEQ ID NO: 774; 775 and 776;
probe set #1586 consisting of the nucleic acids consisting of SEQ ID NO: 2468; 2469 and 2470;
probe set #1587 consisting of the nucleic acids consisting of SEQ ID NO: 1730;
probe set #1588 consisting of the nucleic acids consisting of SEQ ID NO: 2404; 2405 and 2407;
probe set #1589 consisting of the nucleic acids consisting of SEQ ID NO: 2724; 2725 and 2733;
probe set #1590 consisting of the nucleic acids consisting of SEQ ID NO: 1642; 1644 and 1646;
probe set #1591 consisting of the nucleic acids consisting of SEQ ID NO: 2829; 2830 and 2837;
probe set #1592 consisting of the nucleic acids consisting of SEQ ID NO: 869; 870 and 874;
probe set #1593 consisting of the nucleic acids consisting of SEQ ID NO: 2866; 2867 and 2868;
probe set #1594 consisting of the nucleic acids consisting of SEQ ID NO: 1; 2 and 3;
probe set #1595 consisting of the nucleic acids consisting of SEQ ID NO: 243; 244 and 245;
probe set #1596 consisting of the nucleic acids consisting of SEQ ID NO: 2188; 2190 and 2191;
probe set #1597 consisting of the nucleic acids consisting of SEQ ID NO: 1498; 1499 and 1500;
probe set #1598 consisting of the nucleic acids consisting of SEQ ID NO: 491; 492 and 493;
probe set #1599 consisting of the nucleic acids consisting of SEQ ID NO: 615; 616 and 617;
probe set #1600 consisting of the nucleic acids consisting of SEQ ID NO: 661; 667 and 668;
probe set #1601 consisting of the nucleic acids consisting of SEQ ID NO: 96; 97 and 98;
probe set #1602 consisting of the nucleic acids consisting of SEQ ID NO: 2480; 2481 and 2482;
probe set #1603 consisting of the nucleic acids consisting of SEQ ID NO: 1698; 1699 and 1700;
probe set #1604 consisting of the nucleic acids consisting of SEQ ID NO: 2331; 2332 and 2333;
probe set #1605 consisting of the nucleic acids consisting of SEQ ID NO: 278; 279 and 280;
probe set #1606 consisting of the nucleic acids consisting of SEQ ID NO: 1910; 1911 and 1912;
probe set #1607 consisting of the nucleic acids consisting of SEQ ID NO: 243; 244 and 245;
probe set #1608 consisting of the nucleic acids consisting of SEQ ID NO: 1481; 1482 and 1483;
probe set #1609 consisting of the nucleic acids consisting of SEQ ID NO: 699; 700 and 701;
probe set #1610 consisting of the nucleic acids consisting of SEQ ID NO: 2605; 2606 and 2610;
probe set #1611 consisting of the nucleic acids consisting of SEQ ID NO: 189; 190 and 191;
probe set #1612 consisting of the nucleic acids consisting of SEQ ID NO: 2344; 2345 and 2346;
probe set #1613 consisting of the nucleic acids consisting of SEQ ID NO: 1803; 1804 and 1805;
probe set #1614 consisting of the nucleic acids consisting of SEQ ID NO: 259; 261 and 262;
probe set #1615 consisting of the nucleic acids consisting of SEQ ID NO: 934; 941 and 963;
probe set #1616 consisting of the nucleic acids consisting of SEQ ID NO: 284; 286 and 285;
probe set #1617 consisting of the nucleic acids consisting of SEQ ID NO: 2802; 2803 and 2804;
probe set #1618 consisting of the nucleic acids consisting of SEQ ID NO: 2121; 2122 and 2123;
probe set #1619 consisting of the nucleic acids consisting of SEQ ID NO: 2391; 2392 and 2393;
probe set #1620 consisting of the nucleic acids consisting of SEQ ID NO: 1936; 1937 and 1938;
probe set #1621 consisting of the nucleic acids consisting of SEQ ID NO: 1436; 1437 and 1438;
probe set #1622 consisting of the nucleic acids consisting of SEQ ID NO: 1807;
probe set #1623 consisting of the nucleic acids consisting of SEQ ID NO: 2823; 2824 and 2825;
probe set #1624 consisting of the nucleic acids consisting of SEQ ID NO: 1865; 1866 and 1867;
probe set #1625 consisting of the nucleic acids consisting of SEQ ID NO: 2886; 2887 and 2888;
probe set #1626 consisting of the nucleic acids consisting of SEQ ID NO: 1533;
probe set #1627 consisting of the nucleic acids consisting of SEQ ID NO: 2785; 2786 and 2787;
probe set #1628 consisting of the nucleic acids consisting of SEQ ID NO: 77; 78 and 86;
probe set #1629 consisting of the nucleic acids consisting of SEQ ID NO: 2640; 2641 and 2642;
probe set #1630 consisting of the nucleic acids consisting of SEQ ID NO: 2225; 2226 and 2228;
probe set #1631 consisting of the nucleic acids consisting of SEQ ID NO: 918; 919 and 920;
probe set #1632 consisting of the nucleic acids consisting of SEQ ID NO: 859; 860 and 861;
probe set #1633 consisting of the nucleic acids consisting of SEQ ID NO: 1919;
probe set #1634 consisting of the nucleic acids consisting of SEQ ID NO: 898; 903 and 911;
probe set #1635 consisting of the nucleic acids consisting of SEQ ID NO: 1429;
probe set #1636 consisting of the nucleic acids consisting of SEQ ID NO: 74; 75 and 76;
probe set #1637 consisting of the nucleic acids consisting of SEQ ID NO: 737; 738 and 739;
probe set #1638 consisting of the nucleic acids consisting of SEQ ID NO: 14; 15 and 16;
probe set #1639 consisting of the nucleic acids consisting of SEQ ID NO: 409; and probe set #1640 consisting of the nucleic acids consisting of SEQ ID NO: 2038; 2039 and 2040.

7. A microarray comprising the group of polynucleotide probe sets according to claim 1.

8. A microarray comprising the combination of polynucleotide probe sets according to claim 2.

9. A microarray comprising the combination of polynucleotide probe sets according to claim 3.

10. A microarray comprising the combination of polynucleotide probe sets according to claim 4.

11. A microarray comprising the combination of polynucleotide probe sets according to claim 5.

12. A microarray comprising the combination of polynucleotide probe sets of claim 6.

* * * * *